US012698280B2

(12) United States Patent
Bahmanyar et al.

(10) Patent No.: US 12,698,280 B2
(45) Date of Patent: Aug. 4, 2026

(54) SMALL MOLECULE PROTEIN SYNTHESIS MODULATORS

(71) Applicant: Interdict Bio, Inc., South San Francisco, CA (US)

(72) Inventors: Sogole Sami Bahmanyar, San Francisco, CA (US); Lawrence Hamann, San Francisco, CA (US); Zef Konst, San Francisco, CA (US); David Gygi, San Francisco, CA (US); Margot Meyers, San Francisco, CA (US)

(73) Assignee: Interdict Bio, Inc., South San Francisco, CA (US)

( * ) Notice: Subject to any disclaimer, the term of this patent is extended or adjusted under 35 U.S.C. 154(b) by 0 days.

(21) Appl. No.: 19/353,446

(22) Filed: Oct. 8, 2025

(65) Prior Publication Data

US 2026/0078116 A1 Mar. 19, 2026

Related U.S. Application Data

(63) Continuation of application No. 19/333,657, filed on Sep. 19, 2025.

(60) Provisional application No. 63/774,401, filed on Mar. 19, 2025, provisional application No. 63/696,620, filed on Sep. 19, 2024.

(51) Int. Cl.

| | |
|---|---|
| ***A61K 31/4155*** | (2006.01) |
| ***A61K 31/427*** | (2006.01) |
| ***C07D 403/10*** | (2006.01) |
| ***C07D 417/10*** | (2006.01) |

(52) U.S. Cl.

CPC ........ *C07D 417/10* (2013.01); *A61K 31/4155* (2013.01); *A61K 31/427* (2013.01); *C07D 403/10* (2013.01)

(58) Field of Classification Search

CPC .......................... A61K 31/4155; A61K 31/427

USPC .......................................................... 514/365

See application file for complete search history.

(56) References Cited

U.S. PATENT DOCUMENTS

| | | | | |
|---|---|---|---|---|
| 5,463,078 | A * | 10/1995 | Lino | C07D 207/12 548/541 |
| 8,846,694 | B2 * | 9/2014 | Heinrich | A61P 27/02 514/263.2 |
| 2011/0195929 | A1 * | 8/2011 | De Moor | A61K 31/70 514/315 |
| 2022/0226299 | A1 * | 7/2022 | Zamponi | A61K 31/5377 |
| 2022/0305011 | A1 * | 9/2022 | Philippou | C07D 403/12 |
| 2025/0091989 | A1 | 3/2025 | Gygi et al. | |
| 2025/0129021 | A1 | 4/2025 | Gygi et al. | |

FOREIGN PATENT DOCUMENTS

| | | | |
|---|---|---|---|
| CN | 109513004 | A | 3/2019 |
| WO | WO 2022/160530 | A1 | 8/2022 |
| WO | WO 2024/103178 | A1 | 5/2024 |

OTHER PUBLICATIONS

[No Author Listed], [(2S,3S,4S)-4-hydroxy-2-[(4-methoxyphenyl)methyl]pyrrolidin-3-yl] propanoate Compound Summary, PubChem CID 139583092. PubChem. Nov. 4, 2019. (Year: 2019).*

International Search Report and Written Opinion for Application No. PCT/US2024/047500, mailed Jan. 16, 2025.

Invitation to Pay Additional Fees for Application No. PCT/US2024/047500, mailed Nov. 12, 2024.

International Search Report and Written Opinion for Application No. PCT/US2024/047553, mailed Jan. 23, 2025.

Invitation to Pay Additional Fees for Application No. PCT/US2024/047553, mailed Nov. 12, 2024.

Invitation to Pay Additional Fees for Application No. PCT/US2025/047089, mailed Dec. 30, 2025.

International Search Report and Written Opinion for Application No. PCT/US2025/047089, mailed Feb. 23, 2026.

International Search Report and Written Opinion for Application No. PCT/US2025/047078, mailed Dec. 1, 2025.

[No Author Listed], Anisomycin Compound Summary, PubChem CID 253602. PubChem. Mar. 26, 2005.

[No Author Listed], (2R,3S,4S)-2-benzylpyrrolidine-3,4-diol, Pubchem Cid 15885327. Feb. 12, 2007. Accessed at: https://pubchem.ncbi.nlm.nih.gov/compound/15885327 [last accessed: Nov. 11, 2025].

[No Author Listed], (3R,4R)-4-(4-methoxyphenoxy) pyrrolidin-3-ol, Pubchem Cid 13192214. Feb. 8, 2007. Accessed at: https://pubchem.ncbi.nlm.nih.gov/compound/13192214 [last accessed: Nov. 11, 2025].

[No Author Listed], (3R,4R)-4-pyridin-4-yloxypyrrolidin-3-ol, Pubchem Cid 144223152. Dec. 7, 2019. Accessed at: https://pubchem.ncbi.nlm.nih.gov/compound/1442231521 [last accessed: Nov. 11, 2025].

[No Author Listed], [(2S,3R,4R)-4-hydroxy-2-[(4-methoxyphenyl)methyl]pyrrolidin-3-yl]N-methylcarbamate, PubChem CID 11708931. PubChem. Oct. 26, 2006.

[No Author Listed], 5-(Cyclohexylmethyl)pyrrolidin-3-ol, PubChem CID 80400924. PubChem. Oct. 20, 2014.

[No Author Listed], Pubchem SID 426887815. Aug. 13, 2020. Accessed at: https://pubchem.ncbi.nlm.nih.gov/substance/426887815 [last accessed: Jan. 5, 2026].

Diamond et al., Context-dependent translation inhibition as a novel oncology therapeutic modality. bioRxiv. Jan. 9, 2025. 51 pages. https://doi.org/10.1101/2025.01.09.632223.

(Continued)

*Primary Examiner* — Raymond J Henley, III

(74) *Attorney, Agent, or Firm* — Wolf, Greenfield & Sacks, P.C.

(57) ABSTRACT

The present disclosure provides compounds, and pharmaceutically acceptable salts thereof, which are useful for modulating protein synthesis. The present disclosure also provides pharmaceutical compositions and kits comprising the compounds, or pharmaceutically acceptable salts thereof, and methods of treating or preventing diseases or disorders (e.g., diseases or disorders associated with BCL-2, MYC, CCND1, MCL-1, ALK, KRAS-G12D) by administering to a subject in need thereof the compounds, or pharmaceutically acceptable salts thereof, or pharmaceutical compositions thereof.

21 Claims, No Drawings

(56) References Cited

OTHER PUBLICATIONS

Gu et al., Targeting Molecular Signaling Pathways and Cytokine Responses to Modulate c-MYC in Acute Myeloid Leukemia. Front Biosci (Schol Ed). Sep. 14, 2024;16(3):15. doi: 10.31083/j.fbs1603015.

Seo et al., Anisomycin treatment enhances TRAIL-mediated apoptosis in renal carcinoma cells through the down-regulation of Bcl-2, c-FLIP(L) and Mcl-1. Biochimie. Apr. 2013;95(4):858-65. doi: 10.1016/j.biochi.2012.12.002. Epub Dec. 20, 2012.

Tantawy et al., Targeting MCL-1 protein to treat cancer: opportunities and challenges. Front Oncol. Jul. 31, 2023:13:1226289. doi: 10.3389/fonc.2023.1226289. eCollection 2023.

* cited by examiner

SMALL MOLECULE PROTEIN SYNTHESIS MODULATORS

CROSS-REFERENCE TO RELATED APPLICATIONS

This application is a continuation of and claims priority under 35 U.S.C. § 120 to U.S. patent application Ser. No. 19/333,657, filed Sep. 19, 2025, which claims the benefit of and priority under 35 U.S.C. § 119 (e) to U.S. Provisional Application No. 63/696,620, filed Sep. 19, 2024, and U.S. Provisional Application No. 63/774,401, filed Mar. 19, 2025, the contents of each of which are incorporated herewith by reference in their entireties.

BACKGROUND OF THE INVENTION

Small molecule therapeutics have for decades largely focused on binding to the target protein of interest to inhibit its action, or to induce activation of its function. In the case of inhibition, the net effect of the drug binding to its target is to sequester the target, making it unable to effectively perform its native (or in the case of certain pathologic states, aberrant) function. More recently, small molecule therapeutics have also been developed which alter protein homeostasis. Protein homeostasis refers to the equilibrium between protein synthesis and protein turnover, or degradation. In one instance, the existing pool of a given protein inside the cell may be diminished by accelerating the induction of its degradation. This can be achieved by small molecules that bind to a target and/or an E3 ligase, whereby the net result of binding is the induction of the target's degradation by native cellular machinery, as is the case for both molecular glues and PROteolysis TArgeting ChimeraS (PROTACS).

SUMMARY OF THE INVENTION

The present disclosure relates to small molecules that modulate protein synthesis by inhibiting the translation machinery. These compounds demonstrate therapeutic utility, including but not limited to, in their ability to kill cancer cells.

In one aspect, the present disclosure provides compounds of Formula (I):

(I)

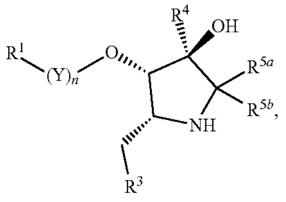

and pharmaceutically acceptable salts thereof, wherein:

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^{1a}$, or —$N(R^{1a})_2$;

each instance of $R^{1a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or two instances of $R^{1a}$ are joined together with their intervening atom to form an optionally substituted heterocyclic ring or optionally substituted heteroaryl ring;

$R^3$ is optionally substituted carbocyclyl, optionally substituted heterocyclyl, optionally substituted aryl, or optionally substituted heteroaryl;

$R^4$ is hydrogen or optionally substituted alkyl;

$R^{5a}$ and $R^{5b}$ are each hydrogen, or $R^{5a}$ and $R^{5b}$ are joined together with their intervening atom to form optionally substituted carbocyclyl;

each instance of Y is independently —$C(R^Y)_2$—, —O—, or —$N(R^{1a})$—, or two instances of Y are taken together to form —$C(R^Y)$=$C(R^Y)$— or —C≡C—;

each instance of $R^Y$ is independently hydrogen or halogen, or two instances of $R^Y$ are taken together to form =O; and n is 0, 1, 2, 3, 4, or 5;

provided that;

if n is 0, then $R^1$ is not optionally substituted aryl, optionally substituted heteroaryl, —$OR^{1a}$, or —$N(R^{1a})_2$;

if n is 1, 2, 3, 4, or 5, the Y attached to the oxygen atom of the moiety

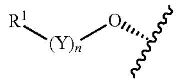

is —$C(R^Y)_2$—; and if $R^1$ is —$OR^{1a}$ or —$N(R^{1a})_2$, then the Y attached to $R^1$ is —$C(R^Y)_2$—.

In another aspect, the present disclosure provides pharmaceutical compositions comprising a compound disclosed herein. In some embodiments, the pharmaceutical composition comprises an excipient.

In another aspect, the present disclosure provides methods of modulating protein synthesis in a subject in need thereof or in a cell, tissue, or biological sample, comprising administering to the subject in need thereof or contacting the cell, tissue, or biological sample with an effective amount of a provided compound, or a pharmaceutical composition thereof.

In another aspect, the present disclosure provides methods of decreasing protein synthesis in a subject in need thereof or in a cell, tissue, or biological sample, comprising administering to the subject in need thereof or contacting the cell, tissue, or biological sample with an effective amount of a provided compound, or a pharmaceutical composition thereof.

In another aspect, the present disclosure provides methods comprising administering to a subject a provided compound, or a pharmaceutical composition thereof.

In another aspect, the present disclosure provides methods of treating or preventing a disease or disorder in a subject in need thereof, comprising administering to the subject in need thereof a therapeutically effective amount of a provided compound, or a pharmaceutical composition thereof.

In another aspect, the present disclosure provides kits comprising a provided compound or pharmaceutical composition and instructions for its use.

It should be appreciated that the foregoing concepts, and the additional concepts discussed below, may be arranged in any suitable combination, as the present disclosure is not limited in this respect. Further, other advantages and novel features of the present disclosure will become apparent from the following detailed description of various non-limiting embodiments.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Michael B. Smith, *March's Advanced Organic Chemistry*, $7^{th}$ Edition, John Wiley & Sons, Inc., New York, 2013; Richard C. Larock, *Comprehensive Organic Transformations*, John Wiley & Sons, Inc., New York, 2018; and Carruthers, Some Modern Methods of Organic Synthesis, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, IN 1972). The present disclosure additionally encompasses compounds as individual isomers substantially free of other isomers, and alternatively, as mixtures of various isomers.

In a formula, the bond 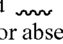 is a single bond, the dashed line - - - is a single bond or absent, and the bond 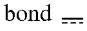 or  is a single or double bond.

Unless otherwise provided, formulae and structures depicted herein include compounds that do not include isotopically enriched atoms, and also include compounds that include isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

When a range of values ("range") is listed, it encompasses each value and sub-range within the range. A range is inclusive of the values at the two ends of the range unless otherwise provided. For example "$C_{1-6}$ alkyl" encompasses, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., $—CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-12}$ alkyl (such as substituted $C_{1-6}$ alkyl, e.g., $—CH_2F$, $—CHF_2$, $—CF_3$, $—CH_2CH_2F$, $—CH_2CHF_2$, $—CH_2CF_3$, or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 20 carbon atoms ("$C_{1-20}$ haloalkyl"). In some embodiments, the haloalkyl moiety has 1 to 10 carbon atoms ("$C_{1-10}$ haloalkyl"). In some embodiments, the haloalkyl moiety has 1 to 9 carbon atoms ("$C_{1-9}$ haloalkyl"). In some embodiments, the haloalkyl moiety has 1 to 8 carbon atoms ("$C_{1-8}$ haloalkyl"). In some embodiments, the haloalkyl moiety has 1 to 7 carbon atoms ("$C_{1-7}$ haloalkyl"). In some embodiments, the haloalkyl moiety has 1 to 6 carbon atoms ("$C_{1-6}$ haloalkyl"). In some embodiments, the haloalkyl moiety has 1 to 5 carbon atoms ("$C_{1-5}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are independently replaced with fluoro to provide a "perfluoroalkyl" group. In some embodiments, all of the haloalkyl hydrogen atoms are independently replaced with chloro to provide a "perchloroalkyl" group. Examples of haloalkyl groups include $—CHF_2$, $—CH_2F$, $—CF_3$, $—CH_2CF_3$, $—CF_2CF_3$, $—CF_2CF_2CF_3$, $—CCl_3$, $—CFCl_2$, $—CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("hetero$C_{1-20}$alkyl"). In certain embodiments, a heteroalkyl group refers to a saturated group having from 1 to 12 carbon atoms and 1 or more heteroatoms within the parent chain ("hetero$C_{1-12}$alkyl"). In some embodiments, a heteroalkyl group is a saturated group having 1 to 11 carbon atoms and 1 or more heteroatoms within the parent chain ("hetero$C_{1-11}$ alkyl"). In some embodiments, a heteroalkyl group is a saturated group having 1 to 10 carbon atoms and 1 or more heteroatoms within the parent chain ("hetero$C_{1-10}$alkyl"). In some embodiments, a heteroalkyl group is a saturated group having 1 to 9 carbon atoms and 1 or more heteroatoms within the parent chain ("hetero$C_{1-9}$alkyl"). In some embodiments, a heteroalkyl group is a saturated group having 1 to 8 carbon atoms and 1 or more heteroatoms within the parent chain ("hetero$C_{1-8}$alkyl"). In some embodiments, a heteroalkyl group is a saturated group having 1 to 7 carbon atoms and 1 or more heteroatoms within the parent chain ("hetero$C_{1-7}$alkyl"). In some embodiments, a heteroalkyl group is a saturated group having 1 to 6 carbon atoms and 1 or more heteroatoms within the parent chain ("hetero$C_{1-6}$alkyl"). In some embodiments, a heteroalkyl group is a saturated group having 1 to 5 carbon atoms and 1 or 2 heteroatoms within the parent chain ("hetero$C_{1-5}$alkyl"). In some embodiments, a heteroalkyl group is a saturated group having 1 to 4 carbon atoms and lor 2 heteroatoms within the parent chain ("hetero$C_{1-4}$alkyl"). In some embodiments, a heteroalkyl group is a saturated group having 1 to 3 carbon atoms and 1 heteroatom within the parent chain ("hetero$C_{1-3}$alkyl"). In some embodiments, a heteroalkyl group is a saturated group having 1 to 2 carbon atoms and 1 heteroatom within the parent chain ("hetero$C_{1-2}$alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-12}$alkyl. In certain embodiments, the heteroalkyl group is a substituted hetero$C_{1-12}$alkyl.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{24}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatricenyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C═C double bond for which the stereochemistry is not specified (e.g., $—CH═CHCH_3$ or

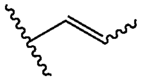

)

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkenyl group refers to a group having from 1 to 20 carbon atoms, at least one double bond, and 1 or more heteroatoms within the parent chain ("hetero$C_{1-20}$alkenyl"). In certain embodiments, a heteroalkenyl group refers to a group having from 1 to 12 carbon atoms, at least one double bond, and 1 or more heteroatoms within the parent chain ("hetero$C_{1-12}$alkenyl"). In certain embodiments, a heteroalkenyl group refers to a group having from 1 to 11 carbon atoms, at least one double bond, and 1 or more heteroatoms within the parent chain ("hetero$C_{1-11}$ alkenyl"). In certain embodiments, a heteroalkenyl group refers to a group having from 1 to 10 carbon atoms, at least one double bond, and 1 or more heteroatoms within the parent chain ("hetero$C_{1-10}$alkenyl"). In some embodiments, a heteroalkenyl group has 1 to 9 carbon atoms at least one double bond, and 1 or more heteroatoms within the parent chain ("hetero$C_{1-9}$alkenyl"). In some embodiments, a heteroalkenyl group has 1 to 8 carbon atoms, at least one double bond, and 1 or more heteroatoms within the parent chain ("hetero$C_{1-8}$alkenyl"). In some embodiments, a heteroalkenyl group has 1 to 7 carbon atoms, at least one double bond, and 1 or more heteroatoms within the parent chain ("hetero$C_{1-7}$alkenyl"). In some embodiments, a heteroalkenyl group has 1 to 6 carbon atoms, at least one double bond, and 1 or more heteroatoms within the parent chain ("hetero$C_{1-6}$alkenyl"). In some embodiments, a heteroalkenyl group has 1 to 5 carbon atoms, at least one double bond, and 1 or 2 heteroatoms within the parent chain ("hetero$C_{1-5}$alkenyl"). In some embodiments, a heteroalkenyl group has 1 to 4 carbon atoms, at least one double bond, and 1 or 2 heteroatoms within the parent chain ("hetero$C_{1-4}$alkenyl"). In some embodiments, a heteroalkenyl group has 1 to 3 carbon atoms, at least one double bond, and 1 heteroatom within the parent chain ("hetero$C_{1-3}$alkenyl"). In some embodiments, a heteroalkenyl group has 1 to 2 carbon atoms, at least one double bond, and 1 heteroatom within the parent chain ("hetero$C_{1-2}$alkenyl"). In some embodiments, a heteroalkenyl group has 1 to 6 carbon atoms, at least one double bond, and 1 or 2 heteroatoms within the parent chain ("hetero$C_{1-6}$alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{1-20}$alkenyl. In certain embodiments, the heteroalkenyl group is a substituted hetero$C_{1-20}$alkenyl.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("$C_{1-20}$ alkynyl"). In some embodiments, an alkynyl group has 1 to 10 carbon atoms ("$C_{1-10}$ alkynyl"). In some embodiments, an alkynyl group has 1 to 9 carbon atoms ("$C_{1-9}$ alkynyl"). In some embodiments, an alkynyl group has 1 to 8 carbon atoms ("$C_{1-8}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in 1-butynyl). Examples of $C_{1-4}$ alkynyl groups include, without limitation, methylidynyl ($C_1$), ethynyl ($C_2$), 1-propynyl ($C_3$), 2-propynyl ($C_3$), 1-butynyl ($C_4$), 2-butynyl ($C_4$), and the like. Examples of $C_{1-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (e.g., inserted between adjacent carbon atoms of) and/or placed at one or more terminal position(s) of the parent chain. In certain embodiments, a heteroalkynyl group refers to a group having from 1 to 20 carbon atoms, at least one triple bond, and 1 or more heteroatoms within the parent chain ("hetero$C_{1-20}$alkynyl"). In certain embodiments, a heteroalkynyl group refers to a group having from 1 to 10 carbon atoms, at least one triple bond, and 1 or more heteroatoms within the parent chain ("hetero$C_{1-10}$alkynyl"). In some embodiments, a heteroalkynyl group has 1 to 9 carbon atoms, at least one triple bond, and 1 or more heteroatoms within the parent chain ("hetero$C_{1-9}$alkynyl"). In some embodiments, a heteroalkynyl group has 1 to 8 carbon atoms, at least one triple bond, and 1 or more heteroatoms within the parent chain ("hetero$C_{1-8}$alkynyl"). In some embodiments, a heteroalkynyl group has 1 to 7 carbon atoms, at least one triple bond, and 1 or more heteroatoms within the parent chain ("hetero$C_{1-7}$alkynyl"). In some embodiments, a heteroalkynyl group has 1 to 6 carbon atoms, at least one triple bond, and 1 or more heteroatoms within the parent chain ("hetero$C_{1-6}$alkynyl"). In some embodiments, a heteroalkynyl group has 1 to 5 carbon atoms, at least one triple bond, and 1 or 2 heteroatoms within the parent chain ("hetero$C_{1-5}$ alkynyl"). In some embodiments, a heteroalkynyl group has 1 to 4 carbon atoms, at least one triple bond, and lor 2 heteroatoms within the parent chain ("hetero$C_{1-4}$alkynyl"). In some embodiments, a heteroalkynyl group has 1 to 3 carbon atoms, at least one triple bond, and 1 heteroatom within the parent chain ("hetero$C_{1-3}$alkynyl"). In some embodiments, a heteroalkynyl group has 1 to 2 carbon atoms, at least one triple bond, and 1 heteroatom within the parent chain ("hetero$C_{1-2}$alkynyl"). In some embodiments, a heteroalkynyl group has 1 to 6 carbon atoms, at least one triple bond, and 1 or 2 heteroatoms within the parent chain ("hetero$C_{1-6}$alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{1-20}$alkynyl. In certain embodiments, the heteroalkynyl group is a substituted hetero$C_{1-20}$alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 14 ring carbon atoms ("$C_{3-14}$ carbocyclyl"). In some embodiments, a carbocyclyl group has 3 to 13 ring carbon atoms ("$C_{3-13}$ carbocyclyl"). In some embodiments, a carbocyclyl group has 3 to 12 ring carbon atoms ("$C_{3-12}$ carbocyclyl"). In some embodiments, a carbocyclyl group has 3 to 11 ring carbon atoms ("$C_{3-11}$ carbocyclyl"). In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like.

Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. Exemplary $C_{3-8}$ carbocyclyl groups include the aforementioned $C_{3-10}$ carbocyclyl groups as well as cycloundecyl ($C_{11}$), spiro[5.5]undecanyl ($C_{11}$), cyclododecyl ($C_{12}$), cyclododecenyl ($C_{12}$), cyclotridecane ($C_{13}$), cyclotetradecane ($C_{14}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydrobenzo-thienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term “aryl” refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system (“$C_{6-14}$ aryl”). In some embodiments, an aryl group has 6 ring carbon atoms (“$C_6$ aryl”; e.g., phenyl). In some embodiments, an aryl group has 10 ring carbon atoms (“$C_{10}$ aryl”; e.g., naphthyl such as 1-naphthyl and 2-naphthyl). In some embodiments, an aryl group has 14 ring carbon atoms (“$C_{14}$ aryl”; e.g., anthracyl). “Aryl” also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an “unsubstituted aryl”) or substituted (a “substituted aryl”) with one or more substituents. In certain embodiments, the aryl group is an unsubstituted $C_{6-14}$ aryl. In certain embodiments, the aryl group is a substituted $C_{6-14}$ aryl.

“Aralkyl” is a subset of “alkyl” and refers to an alkyl group substituted by an aryl group, wherein the point of attachment is on the alkyl moiety.

The term “heteroaryl” refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur (“5-14 membered heteroaryl”). In heteroaryl groups that contain one or more nitrogen atoms, the point of attachment can be a carbon or nitrogen atom, as valency permits. Heteroaryl polycyclic ring systems can include one or more heteroatoms in one or both rings. “Heteroaryl” includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. “Heteroaryl” also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., cither the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur (“5-10 membered heteroaryl”). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur (“5-8 membered heteroaryl”). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur (“5-6 membered heteroaryl”). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an “unsubstituted heteroaryl”) or substituted (a “substituted heteroaryl”) with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

“Heteroaralkyl” is a subset of “alkyl” and refers to an alkyl group substituted by a heteroaryl group, wherein the point of attachment is on the alkyl moiety.

The term “unsaturated bond” refers to a double or triple bond.

The term “unsaturated” or “partially unsaturated” refers to a moiety that includes at least one double or triple bond.

The term “saturated” or “fully saturated” refers to a moiety that does not contain a double or triple bond, e.g., only contains single bonds.

Affixing the suffix “-ene” to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term “optionally substituted” refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. “Optionally substituted” refers to a group which is substituted or unsubstituted (e.g., “substituted” or “unsubstituted” alkyl, “substituted” or “unsubstituted” alkenyl, “substituted” or “unsubstituted” alkynyl, “substituted” or “unsubstituted” heteroalkyl, “substituted” or “unsubstituted” heteroalkenyl, “substituted” or “unsubstituted” heteroalkynyl, “substituted” or “unsubstituted” carbocyclyl, “substituted” or “unsubstituted” heterocyclyl, “substituted” or “unsubstituted” aryl or “substituted” or “unsubstituted” heteroaryl group). In general, the term “substituted” means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a “substituted” group has a substituent at one or more substitutable positions of the group, and when more than one position in any given structure is substituted, the substituent is either the same or different at each position. The term “substituted” is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. The disclosure is not limited in any manner by the exemplary substituents described herein.

Exemplary carbon atom substituents include halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3^+X^-$, $—N(OR^{cc})R^{bb}$, —SH, $—SR^{aa}$, $—SSR^{cc}$, $—C(=O)R^{aa}$, $—CO_2H$, —CHO, $—C(OR^{cc})_2$, $—CO_2R^{aa}$, $—OC(=O)R^{aa}$, $—OCO_2R^{aa}$, $—C(=O)N(R^{bb})_2$, $—OC(=O)N(R^{bb})_2$, $—NR^{bb}C(=O)R^{aa}$, $—NR^{bb}CO_2R^{aa}$, $—NR^{bb}C(=O)N(R^{bb})_2$, $—C(=NR^{bb})R^{aa}$, $—C(=NR^{bb})OR^{aa}$, $—OC(=NR^{bb})R^{aa}$, $—OC(=NR^{bb})OR^{aa}$, $—C(=NR^{bb})N(R^{bb})_2$, $—OC(=NR^{bb})N(R^{bb})_2$, $—NR^{bb}C(=NR^{bb})N(R^{bb})_2$, $—C(=O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(=O)R^{aa}$, $—OS(=O)R^{aa}$, $—Si(R^{aa})_3$, $—OSi(R^{aa})_3$$—C(=S)N(R^{bb})_2$, $—C(=O)SR^{aa}$, $—C(=S)SR^{aa}$, $—SC(=S)SR^{aa}$, $—SC(=O)SR^{aa}$, $—OC(=O)SR^{aa}$, $—SC(=O)OR^{aa}$, $—SC(=O)R^{aa}$, $—P(=O)(R^{aa})_2$, $—P(=O)(OR^{cc})_2$, $—OP(=O)(R^{aa})_2$, $—OP(=O)(OR^{cc})_2$, $—P(=O)(N(R^{bb})_2)_2$, $—OP(=O)(N(R^{bb})_2)_2$, $—NR^{bb}P(=O)(R^{aa})_2$, $—NR^{bb}P(=O)(OR^{cc})_2$, $—NR^{bb}P(=O)(N(R^{bb})_2)_2$, $—P(R^{cc})_2$, $—P(OR^{cc})_2$, $—P(R^{cc})_3^+X^-$, $—P(OR^{cc})_3^+X^-$, $—P(R^{cc})_4$, $—P(OR^{cc})_4$, $—OP(R^{cc})_2$, $—OP(R^{cc})_3^+X^-$, $—OP(OR^{cc})_2$, $—OP(OR^{cc})_3^+X^-$, $—OP(R^{cc})_4$, $—OP(OR^{cc})_4$, $—B(R^{aa})_2$, $—B(OR^{cc})_2$, $—BR^{aa}(OR^{cc})$, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

wherein:

each instance of $R^{aa}$ is, independently, selected from $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each of the alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{3a}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-20}$ alkyl, $C_{1-20}$ perhaloalkyl, $C_{1-20}$ alkenyl, $C_{1-20}$ alkynyl, hetero$C_{1-20}$alkyl, hetero$C_{1-20}$alkenyl, hetero$C_{1-20}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-20}$ alkyl, $C_{1-20}$ perhaloalkyl, $C_{1-20}$ alkenyl, $C_{1-20}$ alkynyl, hetero$C_{1-20}$ alkyl, hetero$C_{1-20}$ alkenyl, hetero$C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3^+$ $X^-$, —N(OR)$R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)N($R^{ff}$)$_2$, —OC(═O)N($R^{ff}$)$_2$, —$NR^{ff}$C(═O)$R^{ee}$, —$NR^{ff}CO_2R^{ee}$, —$NR^{ff}$C(═O)N($R^{ff}$)$_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)N($R^{ff}$)$_2$, —OC(═$NR^{ff}$)N($R^{ff}$)$_2$, —$NR^{ff}$C(═$NR^{ff}$)N($R^{ff}$)$_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —Si($R^{ee}$)$_3$, —OSi($R^{ee}$)$_3$, —C(═S)N($R^{ff}$)$_2$, —C(═O)$SR^{ee}$, —C(═S)$SR^{ee}$, —SC(═S)$SR^{ee}$, —P(═O)($OR^{ee}$)$_2$, —P(═O)($R^{ee}$)$_2$, —OP(═O)($R^{ee}$)$_2$, —OP(═O)($OR^{ee}$)$_2$, $C_{1-10}$ alkyl, $C_{1-10}$ perhaloalkyl, $C_{1-10}$ alkenyl, $C_{1-10}$ alkynyl, hetero-$C_{1-10}$alkyl, hetero$C_{1-10}$alkenyl, hetero$C_{1-10}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents are joined to form ═O or ═S; wherein $X^-$ is a counterion;

each instance of $R^{ee}$ is, independently, selected from $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_3$-10 carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, 3-10 membered heterocyclyl, $C_{6-10}$ aryl, and 5-10 membered heteroaryl, or two R" groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3{}^+X^-$, —NH($C_{1-6}$ alkyl)$_2{}^+X^-$, —$NH_2$($C_{1-6}$ alkyl)+$X^-$, —$NH_3{}^+X^-$, —N($OC_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(═O)($C_{1-6}$ alkyl), —$CO_2H$, —$CO_2$ ($C_{1-6}$ alkyl), —OC(═O)($C_{1-6}$ alkyl), —$OCO_2$ ($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$ ($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH) ($C_{1-6}$ alkyl), —OC(═NH)$OC_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$ ($C_{1-6}$ alkyl), —$SO_2N$($C_{1-6}$ alkyl)$_2$, —$SO_2NH$($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(═S)N($C_{1-6}$ alkyl)$_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)($OC_{1-6}$ alkyl)$_2$, —P(═O)($C_{1-6}$ alkyl)$_2$, —OP(═O)($C_{1-6}$ alkyl)$_2$, —OP(═O)($OC_{1-6}$ alkyl)$_2$, $C_{1-10}$ alkyl, $C_{1-10}$ perhaloalkyl, $C_{1-10}$ alkenyl, $C_{1-10}$ alkynyl, hetero$C_{1-10}$ alkyl, hetero$C_{1-10}$ alkenyl, hetero$C_{1-10}$ alkynyl, $C_{3-10}$ carbocyclyl, $C_{6-10}$ aryl, 3-10 membered heterocyclyl, or 5-10 membered heteroaryl; or two geminal $R^{gg}$ substituents can be joined to form ═O or ═S; and each $X^-$ is a counterion.

In certain embodiments, each carbon atom substituent is independently halogen, substituted (e.g., substituted with one or more halogen) or unsubstituted $C_{1-6}$ alkyl, —$OR^{aa}$, —$SR^{aa}$, —N($R^{bb}$)$_2$, —CN, —SCN, —$NO_2$, —C(═O)$R^{aa}$, —$CO_2R^{aa}$, —C(═O)N($R^{bb}$)$_2$, —OC(═O)$R^{aa}$, —$OCO_2R^{aa}$, —OC(═O)N($R^{bb}$)$_2$, —$NR^{bb}$C(═O)$R^{aa}$, —$NR^{bb}CO_2R^{aa}$, or —$NR^{bb}$C(═O)N($R^{bb}$)$_2$. In certain embodiments, each carbon atom substituent is independently halogen, substituted (e.g., substituted with one or more halogen) or unsubstituted $C_{1-10}$ alkyl, —$OR^{aa}$, —$SR^{aa}$, —N($R^{bb}$)$_2$, —CN, —SCN, —$NO_2$, —C(═O)$R^{aa}$, —$CO_2R^{aa}$, —C(═O)N($R^{bb}$)$_2$, —OC(═O)$R^{aa}$, —$OCO_2R^{aa}$, —OC(═O)N($R^{bb}$)$_2$, —$NR^{bb}$C(═O)$R^{aa}$, —$NR^{bb}CO_2R^{aa}$, or —$NR^{bb}$C(═O)N($R^{bb}$)$_2$, wherein $R^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts). In certain embodiments, each carbon atom substituent is independently halogen, substituted (e.g., substituted with one or more halogen) or unsubstituted $C_{1-6}$ alkyl, —$OR^{aa}$, —$SR^{aa}$, —N($R^{bb}$)$_2$, —CN, —SCN, or —$NO_2$. In certain embodiments, each carbon atom substituent is independently halogen, substituted (e.g., substituted with one or more halogen moieties) or unsubstituted $C_{1-10}$ alkyl, —$OR^{aa}$, —$SR^{aa}$, —N($R^{bb}$)$_2$, —CN, —SCN, or —$NO_2$, wherein $R^{aa}$ is hydrogen, substituted (e.g., substituted with one or more halogen) or unsubstituted $C_{1-10}$ alkyl, an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-10}$ alkyl, or a nitrogen protecting group (e.g., Bn, Boc, Cbz, Fmoc, trifluoroacetyl, triphenylmethyl, acetyl, or Ts).

In certain embodiments, the molecular weight of a carbon atom substituent is lower than 250, lower than 200, lower than 150, lower than 100, or lower than 50 g/mol. In certain embodiments, a carbon atom substituent consists of carbon, hydrogen, fluorine, chlorine, bromine, iodine, oxygen, sulfur, nitrogen, and/or silicon atoms. In certain embodiments, a carbon atom substituent consists of carbon, hydrogen, fluorine, chlorine, bromine, iodine, oxygen, sulfur, and/or nitrogen atoms. In certain embodiments, a carbon atom substituent consists of carbon, hydrogen, fluorine, chlorine, bromine, and/or iodine atoms. In certain embodiments, a carbon atom substituent consists of carbon, hydrogen, fluorine, and/or chlorine atoms.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxy." by extension, refers to a hydroxyl group wherein the oxygen atom directly attached to the parent molecule is substituted with a group other than hydrogen, and includes groups selected from —$OR^{aa}$, —$ON(R^{bb})_2$, —OC(═O)$SR^{aa}$, —OC(═O)$R^{aa}$, —$OCO_2R^{aa}$, —OC(═O)$N(R^{bb})_2$, —OC(═$NR^{bb}$)$R^{aa}$, —OC(═$NR^{bb}$)$OR^{aa}$, —OC(═$NR^{bb}$)N$(R^{bb})_2$, —OS(═O)$R^{aa}$, —$OSO_2R^{aa}$, —$OSi(R^{aa})_3$, —OP$(R^{cc})_2$, —$OP(R^{cc})_3{}^+X^-$, —$OP(OR^{cc})_2$, —$OP(OR^{cc})_3{}^+X^-$, —OP(═O)$(R^{aa})_2$, —OP(═O)$(OR^{cc})_2$, and —OP(═O)(N$(R^{bb}))_2$, wherein $X^-$, $R^{aa}$, $R^{bb}$, and $R^{cc}$ are as defined herein.

The term "alkoxy" as used herein, refers to an alkyl group, as defined herein, appended to the parent molecular moiety through an oxygen atom. Representative examples of alkoxy include, but are not limited to, methoxy, ethoxy, n-propoxy, isopropoxy, n-butoxy and tert-butoxy.

The term "thiol" or "thio" refers to the group —SH. The term "substituted thiol" or "substituted thio." by extension, refers to a thiol group wherein the sulfur atom directly attached to the parent molecule is substituted with a group other than hydrogen, and includes groups selected from —$SR^{aa}$, —S═$SR^{cc}$, —SC(═S)$SR^{aa}$, —SC(═S)$OR^{aa}$, —SC(═S)$N(R^{bb})_2$, —SC(═O)$SR^{aa}$, —SC(═O)$OR^{aa}$, —SC(═O)$N(R^{bb})_2$, and —SC(═O)$R^{aa}$, wherein $R^{aa}$ and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —$NH(R^{bb})$, —NHC(═O)$R^{aa}$, —$NHCO_2R^{aa}$, —NHC(═O)$N(R^{bb})_2$. —NHC(═$NR^{bb}$)$N(R^{bb})_2$, —$NHSO_2R^{aa}$, —NHP(═O)$(OR^{cc})_2$, and —NHP(═O)$(N(R^{bb})_2)_2$, wherein $R^{aa}$, $R^{bb}$ and $R^{cc}$ are as defined herein, and wherein $R^{bb}$ of the group —$NH(R^{bb})$ is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}$C(═O)$R^{aa}$, —$NR^{bb}CO_2R^{aa}$, —$NR^{bb}$C(═O)N$(R^{bb})_2$, —$NR^{bb}$C(═$NR^{bb}$)$N(R^{bb})_2$, —$NR^{bb}SO_2R^{aa}$, —$NR^{bb}$P(═O)$(OR^{cc})_2$, and —$NR^{bb}$P(═O)$(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —$N(R^{bb})$; and —$N(R^{bb})_3{}^+X^-$, wherein $R^{bb}$ and $X^-$ are as defined herein.

The term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

The term "sulfinyl" refers to the group —S(═O)$R^{aa}$, wherein $R^{aa}$ is as defined herein.

The term "acyl" refers to a group having the general formula —C(═O)$R^{X1}$, —C(═O)$OR^{X1}$. —C(═O)—O—C(═O)$R^{X1}$, —C(═O)$SR^{X1}$, —C(═O)$N(R^{X1})_2$, —C(═S)$R^{X1}$, —C(═S)$N(R^{X1})_2$, and —C(═S)S($R^{X1}$), —C(═$NR^{X1}$)$R^{X1}$, —C(═$NR^{X1}$)$OR^{X1}$, —C(═$NR^{X1}$)$SR^{X1}$, and —C(═$NR^{X1}$)$N(R^{X1})_2$, wherein $R^{X1}$ is hydrogen;

halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers to a group wherein the carbon directly attached to the parent molecule is $sp^2$ hybridized, and is substituted with an oxygen, nitrogen or sulfur atom, e.g., a group selected from ketones (—C(═O)$R^{aa}$), carboxylic acids (—$CO_2H$), aldehydes (—CHO), esters (—$CO_2R^{aa}$, —C(═O)$SR^{aa}$, —C(═S)$SR^{aa}$), amides (—C(═O)$N(R^{bb})_2$, —C(═O)$NR^{bb}SO_2R^{aa}$, —C(═S)$N(R^{bb})_2$), and imines (—C(═$NR^{bb}$)$R^{aa}$, —C(═$NR^{bb}$)$OR^{aa}$), —C(═$NR^{bb}$)$N(R^{bb})_2$), wherein $R^{aa}$ and $R^{bb}$ are as defined herein.

The term "silyl" refers to the group —$Si(R^{aa})_3$, wherein $R^{aa}$ is as defined herein.

The term "boronyl" refers to boranes, boronic acids, boronic esters, borinic acids, and borinic esters, e.g., boronyl groups of the formula —$B(R^{aa})_2$, —$B(OR^{cc})_2$, and —$BR^{aa}(OR^{cc})$, wherein $R^{aa}$ and $R^{cc}$ are as defined herein.

The term "phosphino" refers to the group —$P(R^{cc})_2$, wherein $R^{cc}$ is as defined herein.

The term "phosphono" refers to the group —(P═O)$(OR^{cc})_2$, wherein $R^{aa}$ and $R^{cc}$ are as defined herein.

The term "phosphoramido" refers to the group —O(P═O)$(N(R^{bb})_2)_2$, wherein each $R^{bb}$ is as defined herein.

The term "oxo" refers to the group ═O, and the term "thiooxo" refers to the group ═S.

Nitrogen atoms can be substituted or unsubstituted as valency permits, and include primary, secondary, tertiary, and quaternary nitrogen atoms. Exemplary nitrogen atom substituents include hydrogen, —OH, —$OR^{aa}$, —$N(R^{cc})_2$, —CN, —C(=O)$R^{aa}$, —C(=O)$N(R^{cc})_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, —P(=O)$(OR^{cc})_2$, —P(=O)$(R^{aa})_2$, —P(=O)$(N(R^{cc})_2)_2$, $C_{1-20}$ alkyl, $C_{1-20}$ perhaloalkyl, $C_{1-20}$ alkenyl, $C_{1-20}$ alkynyl, hetero $C_{1-20}$ alkyl, hetero $C_{1-20}$ alkenyl, hetero $C_{1-20}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, each nitrogen atom substituent is independently substituted (e.g., substituted with one or more halogen) or unsubstituted $C_{1-6}$ alkyl, —C(=O)$R^{aa}$, —$CO_2R^{aa}$, —C(=O)$N(R^{bb})_2$, or a nitrogen protecting group. In certain embodiments, each nitrogen atom substituent is independently substituted (e.g., substituted with one or more halogen) or unsubstituted $C_{1-10}$ alkyl, —C(=O)$R^{aa}$, —$CO_2R^{aa}$, —C(=O)$N(R^{bb})_2$, or a nitrogen protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each nitrogen atom substituent is independently substituted (e.g., substituted with one or more halogen) or unsubstituted $C_{1-6}$ alkyl or a nitrogen protecting group.

In certain embodiments, the substituent present on the nitrogen atom is a nitrogen protecting group (also referred to herein as an "amino protecting group"). Nitrogen protecting groups include —OH, —$OR^{aa}$, —$N(R^{cc})_2$, —C(=O)$R^{aa}$, —C(=O)$N(R^{cc})_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)$N(R^{cc})_2$, —$SO_2N(R^{cc})_2$, —$SO_2R^{cc}$, —$SO_2OR^{cc}$, —$SOR^{aa}$, —C(=S)$N(R^{cc})_2$, —C(=O)$SR^{cc}$, —C(=S)$SR^{cc}$, $C_{1-10}$ alkyl (e.g., aralkyl, heteroaralkyl), $C_{1-20}$ alkenyl, $C_{1-20}$ alkynyl, hetero $C_{1-20}$ alkyl, hetero $C_{1-20}$ alkenyl, hetero $C_{1-20}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, in certain embodiments, at least one nitrogen protecting group is an amide group (e.g., a moiety that include the nitrogen atom to which the nitrogen protecting groups (e.g., —C(=O)$R^{aa}$) is directly attached). In certain such embodiments, each nitrogen protecting group, together with the nitrogen atom to which the nitrogen protecting group is attached, is independently selected from the group consisting of formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivatives, benzamide, p-phenylbenzamide, o-nitophenylacetamide, o-nitrophenoxyacetamide, acetoacetamide. (N'-dithiobenzyloxyacylamino) acetamide, 3-(p-hydroxyphenyl)propanamide, 3-(0-nitrophenyl)propanamide, 2-methyl-2-(o-nitrophenoxy)propanamide, 2-methyl-2-(0-phenylazophenoxy)propanamide, 4-chlorobutanamide, 3-methyl-3-nitrobutanamide, o-nitrocinnamide, N-acetylmethionine derivatives, o-nitrobenzamide, and o-(benzoyloxymethyl)benzamide.

In certain embodiments, at least one nitrogen protecting group is a carbamate group (e.g., a moiety that include the nitrogen atom to which the nitrogen protecting groups (e.g., C(=O)$OR^{aa}$) is directly attached). In certain such embodiments, each nitrogen protecting group, together with the nitrogen atom to which the nitrogen protecting group is attached, is independently selected from the group consisting of methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)

benzyl carbamate, 2,4,6-tri-t-butylphenyl carbamate, 4-(trimethylammonium)benzyl carbamate, and 2,4,6-trimethylbenzyl carbamate.

In certain embodiments, at least one nitrogen protecting group is a sulfonamide group (e.g., a moiety that include the nitrogen atom to which the nitrogen protecting groups (e.g., —S(═O)$_2$R$^{aa}$) is directly attached). In certain such embodiments, each nitrogen protecting group, together with the nitrogen atom to which the nitrogen protecting group is attached, is independently selected from the group consisting of p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mtc), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

In certain embodiments, each nitrogen protecting group, together with the nitrogen atom to which the nitrogen protecting group is attached, is independently selected from the group consisting of phenothiazinyl-(10)-acyl derivatives, N'-p-toluenesulfonylaminoacyl derivatives, N'-phenylaminothioacyl derivatives, N-benzoylphenylalanyl derivatives, N-acetylmethionine derivatives, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylidencamine, N-p-methoxybenzylideneamine, N-diphenylmethylencamine, N-[(2-pyridyl)mesityl]methylencamine, N—(N',N'-dimethylaminomethylene)amine, N-p-nitrobenzylideneamine, N-salicylidencamine, N-5-chlorosalicylidencamine, N-(5-chloro-2-hydroxyphenyl)phenylmethylencamine, N-cyclohexylidencamine, N-(5,5-dimethyl-3-oxo-1-cyclohexenyl)amine, N-borane derivatives, N-diphenylborinic acid derivatives, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfonamide (Nps), 2,4-dinitrobenzenesulfonamide, pentachlorobenzenesulfonamide, 2-nitro-4-methoxybenzenesulfonamide, triphenylmethylsulfonamide, and 3-nitropyridinesulfonamide (Npys). In some embodiments, two instances of a nitrogen protecting group together with the nitrogen atoms to which the nitrogen protecting groups are attached are N,N'-isopropylidenediamine.

In certain embodiments, at least one nitrogen protecting group is Bn, Boc, Cbz, Fmoc, trifluoroacetyl, triphenylmethyl, acetyl, or Ts.

In certain embodiments, each oxygen atom substituent is independently substituted (e.g., substituted with one or more halogen) or unsubstituted $C_{1-10}$ alkyl, —C(═O)R$^{aa}$, —CO$_2$R$^{aa}$, —C(═O)N(R$^{bb}$)$_2$, or an oxygen protecting group. In certain embodiments, each oxygen atom substituents is independently substituted (e.g., substituted with one or more halogen) or unsubstituted $C_{1-6}$ alkyl, —C(═O)R$^{aa}$, —CO$_2$R$^{aa}$, —C(═O)N(R$^{bb}$)$_2$, or an oxygen protecting group, wherein R$^{aa}$ is hydrogen, substituted (e.g., substituted with one or more halogen) or unsubstituted $C_{1-10}$ alkyl, or an oxygen protecting group when attached to an oxygen atom; and each R$^{bb}$ is independently hydrogen, substituted (e.g., substituted with one or more halogen) or unsubstituted $C_{1-10}$ alkyl, or a nitrogen protecting group. In certain embodiments, each oxygen atom substituent is independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include —R$^{aa}$, —N(R$^{bb}$)$_2$, —C(═O)SR$^{aa}$, —C(═O)R$^{aa}$, —CO$_2$R$^{aa}$, —C(═O)N(R$^{bb}$)$_2$, —C(═NR$^{bb}$)R$^{aa}$, —C(═NR$^{bb}$)OR$^{aa}$, —C(═NR$^{bb}$)N(R$^{bb}$)$_2$, —S(═O)R$^{aa}$, —SO$_2$R$^{aa}$, —Si(R$^{aa}$)$_3$, —P(R$^{cc}$)$_2$, —P(R$^{cc}$)$_3^+$X$^-$, —P(OR$^{cc}$)$_2$, —P(OR$^{cc}$)$_3^+$X$^-$, —P(═O)(R$^{aa}$)$_2$, —P(═O)(OR$^{cc}$)$_2$, and —P(═O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, each oxygen protecting group, together with the oxygen atom to which the oxygen protecting group is attached, is selected from the group consisting of methyl, methoxymethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl (PMB), 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, 4,4'-dimethoxytrityl (4,4'-dimethoxytriphenylmethyl or DMT), α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-Dimethoxy-3'"-[N-(imidazolylmethyl)] trityl Ether (IDTr-OR), 4,4'-Dimethoxy-3'"-[N-(imidazolylethyl) carbamoyl]trityl Ether (IETr-OR), 1,1-bis (4-methoxyphenyl)-1'-pyrenylmethyl, 9-anthryl, 9-(9-phenyl) xanthenyl, 9-(9-phenyl-10-oxo) anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio) pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Pcoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate (MTMEC-OR), 4-(methylthiomethoxy) butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl) phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, at least one oxygen protecting group is silyl, TBDPS, TBDMS, TIPS, TES, TMS, MOM, THP, t-Bu, Bn, allyl, acetyl, pivaloyl, or benzoyl.

In certain embodiments, each sulfur atom substituent is independently substituted (e.g., substituted with one or more halogen) or unsubstituted $C_{1-10}$ alkyl, —C(═O)$R^{aa}$, —$CO_2R^{aa}$, —C(═O)N($R^{bb}$)$_2$, or a sulfur protecting group. In certain embodiments, each sulfur atom substituent is independently substituted (e.g., substituted with one or more halogen) or unsubstituted $C_{1-10}$ alkyl, —C(═O)$R^{aa}$, —$CO_2R^{aa}$, —C(═O)N($R^{bb}$)$_2$, or a sulfur protecting group, wherein $R^{aa}$ is hydrogen, substituted (e.g., substituted with one or more halogen) or unsubstituted $C_{1-10}$ alkyl, or an oxygen protecting group when attached to an oxygen atom; and each $R^{bb}$ is independently hydrogen, substituted (e.g., substituted with one or more halogen) or unsubstituted $C_{1-10}$ alkyl, or a nitrogen protecting group. In certain embodiments, each sulfur atom substituent is independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). In some embodiments, each sulfur protecting group is selected from the group consisting of —$R^{aa}$, —N($R^{bb}$)$_2$, —C(═O)S$R^{aa}$, —C(═O)$R^{aa}$, —$CO_2R^{aa}$, —C(═O)N($R^{bb}$)$_2$, —C(═N$R^{bb}$)$R^{aa}$, —C(═N$R^{bb}$)O$R^{aa}$, —C(═N$R^{bb}$)N($R^{bb}$)$_2$, —S(═O)$R^{aa}$, —$SO_2R^{aa}$, —Si(Ra)$_3$, —P($R^{cc}$)$_2$, —P($R^{cc}$)$_3^+X^-$, —P(O$R^{cc}$)$_2$, —P(O$R^{cc}$)$_3^+X^-$, —P(═O)($R^{aa}$)$_2$, —P(═O)(O$R^{cc}$)$_2$, and —P(═O)(N($R^{bb}$)$_2$)$_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

In certain embodiments, the molecular weight of a substituent is lower than 250, lower than 200, lower than 150, lower than 100, or lower than 50 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, iodine, oxygen, sulfur, and/or nitrogen atoms. In certain embodiments, a substituent consists of carbon, hydrogen, fluorine, chlorine, bromine, and/or iodine atoms. In certain embodiments, a substituent consists of carbon, hydrogen, fluorine, and/or chlorine atoms. In certain embodiments, a substituent comprises 0, 1, 2, or 3 hydrogen bond donors. In certain embodiments, a substituent comprises 0, 1, 2, or 3 hydrogen bond acceptors.

A "counterion" or "anionic counterion" is a negatively charged group associated with a positively charged group in order to maintain electronic neutrality. An anionic counterion may be monovalent (e.g., including one formal negative charge). An anionic counterion may also be multivalent (e.g., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

A "leaving group" (LG) is an art-understood term referring to an atomic or molecular fragment that departs with a pair of electrons in heterolytic bond cleavage, wherein the molecular fragment is an anion or neutral molecule. As used herein, a leaving group can be an atom or a group capable of being displaced by a nucleophile. See e.g., Smith, March Advanced Organic Chemistry 6th ed. (501-502). Exemplary leaving groups include, but are not limited to, halo (e.g., fluoro, chloro, bromo, iodo) and activated substituted hydroxyl groups (e.g., —OC(═O)S$R^{aa}$, —OC(═O)$R^{aa}$, —O$CO_2R^{aa}$, —OC(═O)N($R^{bb}$)$_2$, —OC(═N$R^{bb}$)$R^{aa}$, —OC(═N$R^{bb}$)O$R^{aa}$, —OC(═N$R^{bb}$)N($R^{bb}$)$_2$, —OS(═O)$R^{aa}$, —O$SO_2R^{aa}$, —OP($R^{cc}$)$_2$, —OP($R^{cc}$)$_3$, —OP(═O)$_2R^{aa}$, —OP(═O)($R^{aa}$)$_2$, —OP(═O)(O$R^{cc}$)$_2$, —OP(═O)$_2$N($R^{bb}$)$_2$, and —OP(═O)(N$R^{bb}$)$_2$, wherein $R^{aa}$, $R^{bb}$, and $R^{cc}$ are as defined herein). Additional examples of suitable leaving groups include, but are not limited to, halogen alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some embodiments, the leaving group is a sulfonic acid ester, such as toluenesulfonate (tosylate, —OTs), methanesulfonate (mesylate, —OMs), p-bromobenzenesulfonyloxy (brosylate, —OBs), $—OS(=O)_2(CF_2)_3CF_3$ (nonaflate, —ONf), or trifluoromethanesulfonate (triflate, —OTf). In some embodiments, the leaving group is a brosylate, such as p-bromobenzenesulfonyloxy. In some embodiments, the leaving group is a nosylate, such as 2-nitrobenzenesulfonyloxy. In some embodiments, the leaving group is a sulfonate-containing group. In some embodiments, the leaving group is a tosylate group. In some embodiments, the leaving group is a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

Use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and Claims. The present disclosure is not limited in any manner by the above exemplary listing of substituents.

As used herein, the term "salt" refers to any and all salts, and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of the present disclosure include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and N+ $(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of the present disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N+ $(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THE, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R\cdot0.5H_2O$)), and polyhydrates (x is a number greater than 1, e.g., dihydrates ($R\cdot2H_2O$) and hexahydrates ($R\cdot6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the present disclosure is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering." or "administration" refers to implanting, absorbing, ingesting, injecting, inhaling, or otherwise introducing a compound described herein, or a composition thereof, in or on a subject. Administering a compound described herein encompasses administering the compound, a pharmaceutically acceptable salt thereof, a drug delivery system comprising the compound (e.g., a liposome or lipid nanoparticle (LNP) comprising the compound), or a monovalent form of the compound (e.g., a radical of the compound), which monovalent form may be bonded to a chemical moiety that is cleavable by solvolysis or under physiological conditions (thereby providing a prodrug of the compound), or may be bonded to another agent (e.g., a targeting moiety) via a linker (e.g., a bond or a divalent chemical moiety that is bonded to (i.e., that connects) two separate monovalent chemical moieties). Accordingly, administering a compound described herein encompasses administering the compound, a pharmaceutically acceptable salt thereof, a prodrug, a degrader (e.g., PROTAC), an antibody-drug conjugate (ADC), a liposome or other drug delivery system comprising the compound, and the like. Also contemplated by the disclosure are prodrugs, degraders (e.g., PROTACs), antibody-drug conjugates (ADC), and drug delivery systems comprising a compound provided herein.

The terms "treatment." "treat." and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, severity of side effects, disease, or disorder, the identity, pharmacokinetics, and pharmacodynamics of the particular compound, the condition being treated, the mode, route, and desired or required frequency of administration, the species, age and health or general condition of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses. In certain embodiments, the desired dosage is delivered three times a day, two times a day, once a day, every other day, every third day, every week, every two weeks, every three weeks, or every four weeks. In certain embodiments, the desired dosage is delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human comprises about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the present disclosure are administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is an amount sufficient for modulating protein synthesis (e.g., decreasing protein synthesis). In certain embodiments, a therapeutically effective amount is an amount sufficient for treating a proliferative disease (e.g., cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma)), neurological disease (e.g., cerebellar ataxia, neurodegenerative disease (e.g., Alzheimer's disease, Parkinson's disease, amyotrophic lateral sclerosis, tauopathy (including frontotemporal dementia), Huntington's disease, Friedreich's ataxia)), or immune disorder (e.g., psoriasis, lupus, rheumatoid arthritis). In certain embodiments, a therapeutically effective amount is an amount sufficient for modulating protein synthesis (e.g., decreasing protein synthesis) and a proliferative disease (e.g., cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma)), neurological disease (e.g., cerebellar ataxia, neurodegenerative disease (e.g., Alzheimer's disease, Parkinson's disease, amyotrophic lateral sclerosis, tauopathy (including frontotemporal dementia), Huntington's disease, Friedreich's ataxia)), or immune disorder (e.g., psoriasis, lupus, rheumatoid arthritis).

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for modulating protein synthesis (e.g., decreasing protein synthesis). In certain embodiments, a prophylactically effective amount is an amount sufficient for treating a proliferative disease (e.g., cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma)), neurological disease (e.g., cerebellar ataxia, neurodegenerative disease (e.g., Alzheimer's disease, Parkinson's disease, amyotrophic lateral sclerosis, tauopathy (including frontotemporal dementia), Huntington's disease, Friedreich's ataxia)), or immune disorder (e.g., psoriasis, lupus, rheumatoid arthritis). In certain embodiments, a prophylactically effective amount is an amount sufficient for modulating protein synthesis (e.g., decreasing protein synthesis) and a proliferative disease (e.g., cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma)), neurological disease (e.g., cerebellar ataxia, neurodegenerative disease (e.g., Alzheimer's disease, Parkinson's disease, amyotrophic lateral sclerosis, tauopathy (including frontotemporal dementia), Huntington's disease, Friedreich's ataxia)), or immune disorder (e.g., psoriasis, lupus, rheumatoid arthritis).

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The term "about X," where X is a number or percentage, refers to a number or percentage that is between 99.5% and 100.5%, between 99% and 101%, between 98% and 102%, between 97% and 103%, between 96% and 104%, between 95% and 105%, between 92% and 108%, or between 90% and 110%, inclusive, of X.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant." depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast, triple-negative breast cancer (TNBC)); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis);

muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP—NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The terms "inflammatory disease" and "inflammatory condition" are used interchangeably herein, and refer to a disease or condition caused by, resulting from, or resulting in inflammation. Inflammatory diseases and conditions include those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis. Hashimoto's thyroiditis. Graves' disease. Goodpasture's disease, mixed connective tissue disease, sclerosing cholangitis, inflammatory bowel disease. Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis. Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation. Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

Additional exemplary inflammatory conditions include, but are not limited to, inflammation associated with acne, anemia (e.g., aplastic anemia, hemolytic autoimmune anemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis. Chagas disease, chronic obstructive pulmonary disease, cermatomyositis, diverticulitis, diabetes (e.g., type I diabetes mellitus. Type II diabetes mellitus), a skin condition (e.g., psoriasis, eczema, burns, dermatitis, pruritus (itch)), endometriosis, Guillain-Barre syndrome, infection, ischemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenia purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischemic colitis, diversion colitis. Behcet's syndrome, indeterminate colitis) and inflammatory bowel syndrome (IBS)), lupus, multiple sclerosis, morphea, myasthenia gravis, myocardial ischemia, nephrotic syndrome, pemphigus vulgaris, pernicious anemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, scleroderma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatitis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds disclosed herein may also be useful in treating inflammation associated with cancer.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression. e.g., medications which decrease the immune response. Exemplary autoimmune diseases include, but are not limited to, glomerulonephritis. Goodpasture's syndrome, necrotizing vasculitis, lymphadenitis, peri-arteritis nodosa, systemic lupus erythematosis, rheumatoid arthritis, psoriatic arthritis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia). Huntington's disease, and Friedreich's ataxia. Examples of neurological diseases include, but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; cerebellar ataxia; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis);

lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CL1K1, CL1K1L, CLK1, CLK2, CLK2ps, CLK3, CLK3ps, CLK4, COT, CR1K, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPK2PK2, MAPK2PK3, MAPK2PK5, MAPK2PKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obsen, Obsen2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLKS, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

A "protein." "peptide." or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "inhibition," "inhibiting," "inhibit," or "inhibitor" refer to the ability of a compound to reduce, slow, halt or prevent activity of a particular biological process (e.g., protein activity, protein synthesis) in a cell relative to vehicle.

DETAILED DESCRIPTION OF CERTAIN EMBODIMENTS

The counterbalancing aspect of protein homeostasis relates to modulating the rate of protein synthesis. In this manner, one means to address specific protein targets is to block their synthesis by inhibition of the translation machinery of the cell. Protein synthesis takes place in the ribosome, where a molecule of mRNA encoding for the protein of interest is translated into the protein through a sequence of steps including initiation, elongation, and termination. Small molecules can bind either to elongation or initiation accessory factors to disable proper assembly and operation of the translation machinery or bind directly inside the ribosome to impede translation. In this way, cellular levels of a given protein can be downregulated to ameliorate diseases arising from an overabundance of pathologic proteins. This has broad applications in all therapeutic areas, including, but not limited to oncology, immunology and inflammation, neurodegeneration, cardiovascular and metabolic diseases, rare genetic diseases, and infectious diseases.

The aspects described herein are not limited to specific embodiments, systems, compositions, methods, or configurations, and as such can, of course, vary. The terminology used herein is for the purpose of describing particular aspects only and, unless specifically defined herein, is not intended to be limiting.

Compounds

In one aspect, the present disclosure provides a compound of Formula (I):

(I)

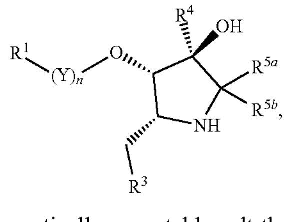

or a pharmaceutically acceptable salt thereof, wherein:

$R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $—OR^{1a}$, or $—N(R^{1a})_2$;

each instance of $R^{1a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or two instances of $R^{1a}$ are joined together with their intervening atom to form an optionally substituted heterocyclic ring or optionally substituted heteroaryl ring;

$R^3$ is optionally substituted carbocyclyl, optionally substituted heterocyclyl, optionally substituted aryl, or optionally substituted heteroaryl;

$R^4$ is hydrogen or optionally substituted alkyl;

$R^{5a}$ and $R^{5b}$ are each hydrogen, or $R^{5a}$ and $R^{5b}$ are joined together with their intervening atom to form optionally substituted carbocyclyl;

each instance of Y is independently $—C(R^Y)_2—$, —O—, or $—N(R^{1a})—$, or two instances of Y are taken together to form $—C(R^Y)═C(R^Y)—$ or —C≡C—;

each instance of $R^Y$ is independently hydrogen or halogen, or two instances of $R^Y$ are taken together to form ═O; and n is 0, 1, 2, 3, 4, or 5;

provided that:

if n is 0, then $R^1$ is not optionally substituted aryl, optionally substituted heteroaryl, $—OR^{1a}$, or $—N(R^{1a})_2$;

if n is 1, 2, 3, 4, or 5, the Y attached to the oxygen atom of the moiety

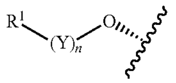

is $—C(R^Y)_2—$; and if $R^1$ is $—OR^{1a}$ or $—N(R^{1a})_2$, then the Y attached to $R^1$ is $—C(R^Y)_2—$.

In some embodiments, if n is 0, then $R^1$ is not optionally substituted aryl. In some embodiments, if n is 0, then $R^1$ is not optionally substituted heteroaryl. In some embodiments, if n is 0, then $R^1$ is not optionally substituted aryl or optionally substituted heteroaryl. In some embodiments, if n is 0, then $R^1$ is not $—OR^{1a}$. In some embodiments, if n is 0, then $R^1$ is not $—N(R^{1a})_2$.

In some embodiments, n is 1, and the Y attached to the oxygen atom of the moiety

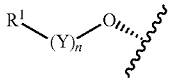

is $—C(R^Y)_2—$. In some embodiments, n is 2, and the Y attached to the oxygen atom of the moiety

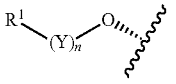

is is-$C(R^Y)_2—$. In some embodiments, n is 3, and the Y attached to the oxygen atom of the moiety is

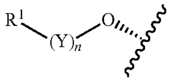

$—C(R^Y)_2—$. In some embodiments, n is 4, and the Y attached to the oxygen atom of the moiety

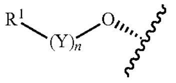

is $—C(R^Y)_2—$. In some embodiments, n is 5, and the Y attached to the oxygen atom of the moiety

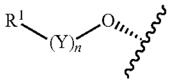

is $—C(R^Y)_2—$.

In some embodiments, if $R^1$ is $—OR^{1a}$, then the Y attached to $R^1$ is $—C(R^Y)_2—$. In some embodiments, if $R^1$ is $—N(R^{1a})_2$, then the Y attached to $R^1$ is $—C(R^Y)_2—$.

$R^1$, $R^{1a}$, Y, $R^Y$, and n

As generally described herein, $R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $—OR^{1a}$, or $—N(R^{1a})_2$; provided that if $R^1$ is $—OR^{1a}$ or $—N(R^{1a})_2$, then the Y attached to $R^1$ is $—C(R^Y)_2—$.

In some embodiments, $R^1$ is hydrogen, halogen, optionally substituted alkyl, optionally substituted alkenyl, optionally substituted alkynyl, optionally substituted carbocyclyl, optionally substituted heterocyclyl, optionally substituted heteroaryl, $—OR^{1a}$, or $—N(R^{1a})_2$. In some embodiments, $R^1$ is hydrogen, halogen, optionally substituted alkyl, optionally substituted alkenyl, optionally substituted alkynyl, optionally substituted carbocyclyl, optionally substituted heterocyclyl, optionally substituted aryl, $—OR^{1a}$, or $—N(R^{1a})_2$. In some embodiments, $R^1$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or $—N(R^{1a})_2$. In some embodiments, $R^1$ is hydrogen, halogen, optionally substituted alkyl, optionally substituted alkenyl, optionally substituted alkynyl, optionally substituted carbocyclyl, optionally substituted heterocyclyl, $—OR^{1a}$, or $—N(R^{1a})_2$. In some embodiments, $R^1$ is hydrogen, halogen, optionally substituted alkyl, optionally substituted alkenyl, optionally substituted alkynyl, optionally substituted carbocyclyl, optionally substituted heterocyclyl, or $—N(R^{1a})_2$.

In some embodiments, $R^1$ is not optionally substituted aryl. In some embodiments, $R^1$ is not optionally substituted heteroaryl. In some embodiments, $R^1$ is not $—OR^{1a}$. In some embodiments, $R^1$ is not $—N(R^{1a})_2$. In some embodiments, $R^1$ is not optionally substituted aryl or optionally substituted heteroaryl. In some embodiments, $R^1$ is not optionally substituted aryl, optionally substituted heteroaryl, $—OR^{1a}$, or $—N(R^{1a})_2$.

In some embodiments, $R^1$ is hydrogen, optionally substituted $C_{1-6}$ alkyl, optionally substituted $C_{2-6}$ alkenyl, or optionally substituted $C_{2-6}$ alkynyl. In some embodiments, $R^1$ is hydrogen, $C_{1-3}$ alkyl, $C_{2-3}$ alkenyl, or $C_{2-3}$ alkynyl, wherein the alkyl, alkenyl, or alkynyl is substituted with 0, 1, 2, or 3 instances of halogen. In some embodiments, $R^1$ is hydrogen, $C_{1-3}$ alkyl, $C_{2-3}$ alkenyl, or $C_{2-3}$ alkynyl, wherein the alkyl, alkenyl, or alkynyl is substituted with 0, 1, 2, or 3 instances of —F. In some embodiments, $R^1$ is: hydrogen, $—CH_3$, $—CH_2CH_3$, $—CF_3$,

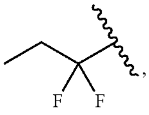, 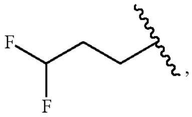, 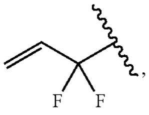 [SMILES: *C(F)(F)C=C], or

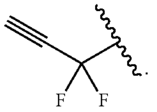 [SMILES: *C(F)(F)C#C].

In some embodiments, $R^1$ is hydrogen.

In some embodiments, $R^1$ is halogen.

In some embodiments, $R^1$ is optionally substituted alkyl. In some embodiments, $R^1$ is optionally substituted $C_{1-6}$ alkyl. In some embodiments, $R^1$ is substituted $C_{1-6}$ alkyl. In some embodiments, $R^1$ is unsubstituted $C_{1-6}$ alkyl. In some embodiments, $R^1$ is optionally substituted $C_{1-3}$ alkyl. In some embodiments, $R^1$ is substituted $C_{1-3}$ alkyl. In some embodiments, $R^1$ is unsubstituted $C_{1-3}$ alkyl. In some embodiments, $R^1$ is $—CH_3$ or $—CH_2CH_3$.

In some embodiments, $R^1$ is $C_{1-3}$ alkyl substituted with 0, 1, 2, or 3 instances of halogen. In some embodiments, $R^1$ is $C_{1-3}$ alkyl substituted with 1, 2, or 3 instances of halogen. In some embodiments, $R^1$ is $C_{1-3}$ alkyl substituted with 1 instance of halogen. In some embodiments, $R^1$ is $C_{1-3}$ alkyl substituted with 2 instances of halogen. In some embodiments, $R^1$ is $C_{1-3}$ alkyl substituted with 3 instances of halogen.

In some embodiments, $R^1$ is $C_{1-3}$ alkyl substituted with 0, 1, 2, or 3 instances of —F. In some embodiments, $R^1$ is $C_{1-3}$ alkyl substituted with 1, 2, or 3 instances of —F. In some embodiments, $R^1$ is $C_{1-3}$ alkyl substituted with 1 instance of —F. In some embodiments, $R^1$ is $C_{1-3}$ alkyl substituted with 2 instances of —F. In some embodiments, $R^1$ is $C_{1-3}$ alkyl substituted with 3 instances of —F. In some embodiments, $R^1$ is $—CF_3$,

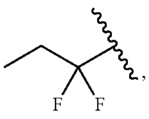, or 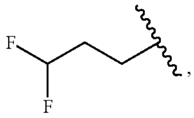,

In some embodiments, $R^1$ is optionally substituted alkenyl. In some embodiments, $R^1$ is optionally substituted $C_{2-6}$ alkenyl. In some embodiments, $R^1$ is substituted $C_{2-6}$ alkenyl. In some embodiments, $R^1$ is unsubstituted $C_{2-6}$ alkenyl. In some embodiments, $R^1$ is optionally substituted $C_{2-3}$ alkenyl. In some embodiments, $R^1$ is substituted $C_{2-3}$ alkenyl. In some embodiments, $R^1$ is unsubstituted $C_{2-3}$ alkenyl.

In some embodiments, $R^1$ is $C_{2-3}$ alkenyl substituted with 0, 1, 2, or 3 instances of halogen. In some embodiments, $R^1$ is $C_{2-3}$ alkenyl substituted with 1, 2, or 3 instances of halogen. In some embodiments, $R^1$ is $C_{2-3}$ alkenyl substituted with 1 instance of halogen. In some embodiments, $R^1$ is $C_{2-3}$ alkenyl substituted with 2 instances of halogen. In some embodiments, $R^1$ is $C_{2-3}$ alkenyl substituted with 3 instances of halogen.

In some embodiments, $R^1$ is $C_{2-3}$ alkenyl substituted with 0, 1, 2, or 3 instances of —F. In some embodiments, $R^1$ is $C_{2-3}$ alkenyl substituted with 1, 2, or 3 instances of —F. In some embodiments, $R^1$ is $C_{2-3}$ alkenyl substituted with 1 instance of —F. In some embodiments, $R^1$ is $C_{2-3}$ alkenyl substituted with 2 instances of —F. In some embodiments, $R^1$ is $C_{2-3}$ alkenyl substituted with 3 instances of —F. In some embodiments, $R^1$ is

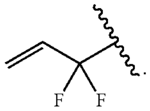.

In some embodiments, $R^1$ is optionally substituted alkynyl. In some embodiments, $R^1$ is optionally substituted $C_{2-6}$ alkynyl. In some embodiments, $R^1$ is substituted $C_{2-6}$ alkynyl. In some embodiments, $R^1$ is unsubstituted $C_{2-6}$ alkynyl. In some embodiments, $R^1$ is optionally substituted $C_{2-3}$ alkynyl. In some embodiments, $R^1$ is substituted $C_{2-3}$ alkynyl. In some embodiments, $R^1$ is unsubstituted $C_{2-3}$ alkynyl.

In some embodiments, $R^1$ is $C_{2-3}$ alkynyl substituted with 0, 1, 2, or 3 instances of halogen. In some embodiments, $R^1$ is $C_{2-3}$ alkynyl substituted with 1, 2, or 3 instances of halogen. In some embodiments, $R^1$ is $C_{2-3}$ alkynyl substituted with 1 instance of halogen. In some embodiments, $R^1$ is $C_{2-3}$ alkynyl substituted with 2 instances of halogen. In some embodiments, $R^1$ is $C_{2-3}$ alkynyl substituted with 3 instances of halogen.

In some embodiments, $R^1$ is $C_{2-3}$ alkynyl substituted with 0, 1, 2, or 3 instances of —F. In some embodiments, $R^1$ is $C_{2-3}$ alkynyl substituted with 1, 2, or 3 instances of —F. In some embodiments, $R^1$ is $C_{2-3}$ alkynyl substituted with 1 instance of —F. In some embodiments, $R^1$ is $C_{2-3}$ alkynyl substituted with 2 instances of —F. In some embodiments, $R^1$ is $C_{2-3}$ alkynyl substituted with 3 instances of —F. In some embodiments, $R^1$ is

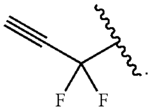.

In some embodiments, $R^1$ is optionally substituted $C_{3-10}$ carbocyclyl, optionally substituted 3-10 membered heterocyclyl, optionally substituted $C_{6-10}$ aryl, or optionally substituted 5-10 membered heteroaryl. In some embodiments, $R^1$ is optionally substituted $C_{3-10}$ carbocyclyl or optionally substituted 3-10 membered heterocyclyl.

In some embodiments, $R^1$ is $C_{3-6}$ carbocyclyl, 4-6 membered heterocyclyl containing 1 ring N atom or 1 ring O atom, 8-10 membered heterocyclyl containing 1 or 2 ring heteroatoms selected from O and N, phenyl, 5-6 membered heteroaryl containing 1, 2, or 3 ring N atoms, or 8-10 membered heteroaryl containing 1, 2, or 3 ring N atoms; wherein the carbocyclyl, heterocyclyl, phenyl, or heteroaryl is substituted with 0, 1, or 2 instances of $R^{1b}$, as valency permits; wherein each instance of $R^{1b}$ is independently halogen, optionally substituted $C_{1-4}$ alkyl, optionally substituted 4-6 membered heterocyclyl, —$OR^{1c}$, —$N(R^{1c})_2$, —CN, —$NO_2$, —C(═O)$R^{1c}$, —C(═O)O$R^{1c}$, —C(═O)N($R^{1c}$)$_2$, —C(═N$R^{1c}$)N($R^{1c}$)$_2$, or —N$R^{1c}$C(═O)$R^{1c}$, or two instances of $R^{1b}$ are taken together to form ═O, as valency permits, or two instances of $R^{1b}$ are joined together with their intervening atoms to form an optionally substituted 5-6 membered heterocyclic ring; and each instance of $R^{1c}$ is independently hydrogen, optionally substituted $C_{1-3}$ alkyl, or optionally substituted 5-6 membered heteroaryl.

In some embodiments, $R^1$ is optionally substituted carbocyclyl. In some embodiments, $R^1$ is optionally substituted $C_{3-10}$ carbocyclyl. In some embodiments, $R^1$ is optionally substituted $C_{3-6}$ carbocyclyl.

In some embodiments, $R^1$ is $C_{3-6}$ carbocyclyl substituted with 0, 1, or 2 instances of $R^{1b}$, as valency permits; wherein each instance of $R^{1b}$ is independently halogen, optionally substituted $C_{1-4}$ alkyl, optionally substituted 4-6 membered heterocyclyl, —$OR^{1c}$, —$N(R^{1c})_2$, —CN, —$NO_2$, —C(═O)$R^{1c}$, —C(═O)O$R^{1c}$, —C(═O)N($R^{1c}$)$_2$, —C(═N$R^{1c}$)N($R^{1c}$)$_2$, or —N$R^{1c}$, (═O)$R^{1c}$, or two instances of $R^{1b}$ are taken together to form ═O, as valency permits, or two instances of $R^{1b}$ are joined together with their intervening atoms to form an optionally substituted 5-6 membered heterocyclic ring; and each instance of $R^{1c}$ is independently hydrogen, optionally substituted $C_{1-3}$ alkyl, or optionally substituted 5-6 membered heteroaryl. In some embodiments, $R^1$ is $C_{3-6}$ carbocyclyl substituted with 0 instances of $R^{1b}$. In some embodiments, $R^1$ is $C_{3-6}$ carbocyclyl substituted with 1 instance of $R^{1b}$, wherein $R^{1b}$ is optionally substituted $C_{1-3}$ alkyl or —N$R^{1c}$C(═O)$R^{1c}$, and each instance of $R^{1c}$ is independently hydrogen or optionally substituted $C_{1-3}$ alkyl. In some embodiments, $R^1$ is $C_{3-6}$ carbocyclyl substituted with 2 instances of $R^{1b}$ joined together with their intervening atoms to form an optionally substituted 5-6 membered heterocyclic ring. In some embodiments, $R^1$ is

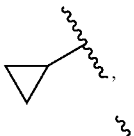
,
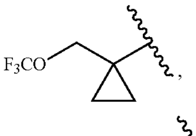
,
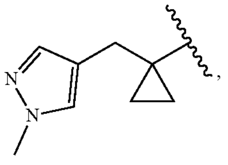
,
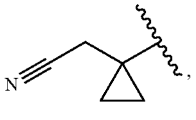
,
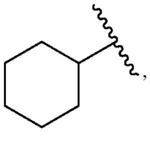
,
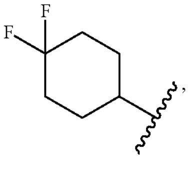
,

-continued

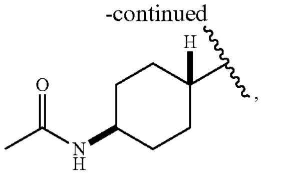
, or
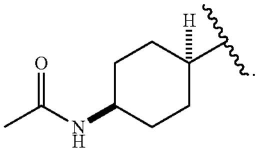
.

In some embodiments, $R^1$ is optionally substituted heterocyclyl. In some embodiments, $R^1$ is optionally substituted 3-10 membered heterocyclyl. In some embodiments, $R^1$ is optionally substituted 4-6 membered heterocyclyl. In some embodiments, $R^1$ is substituted 4-6 membered heterocyclyl. In some embodiments, $R^1$ is unsubstituted 4-6 membered heterocyclyl. In some embodiments, $R^1$ is optionally substituted 4-6 membered heterocyclyl containing 1 ring N atom. In some embodiments, $R^1$ is substituted 4-6 membered heterocyclyl containing 1 ring N atom. In some embodiments, $R^1$ is unsubstituted 4-6 membered heterocyclyl containing 1 ring N atom.

In some embodiments, $R^1$ is 4-6 membered heterocyclyl containing 1 ring N atom, 1 ring O atom, or 1 S atom or 8-10 membered heterocyclyl containing 1 or 2 ring heteroatoms selected from O, N, and S, wherein the heterocyclyl is substituted with 0, 1, or 2 instances of $R^{1b}$, as valency permits; wherein each instance of $R^{1b}$ is independently halogen, optionally substituted $C_{1-4}$ alkyl, optionally substituted 4-6 membered heterocyclyl, —$OR^{1c}$, —$N(R^{1c})_2$, —CN, —$NO_2$, —C(═O)$R^{1c}$, —C(═O)O$R^{1c}$, —C(═O)N($R^{1c}$)$_2$, —C(═N$R^{1c}$)N($R^{1c}$)$_2$, or —N$R^{1c}$C(═O)$R^{1c}$, or two instances of $R^{1b}$ are taken together to form ═O, as valency permits, or two instances of $R^{1b}$ are joined together with their intervening atoms to form an optionally substituted 5-6 membered heterocyclic ring; and each instance of $R^{1c}$ is independently hydrogen, optionally substituted $C_{1-3}$ alkyl, or optionally substituted 5-6 membered heteroaryl. In some embodiments, $R^1$ is 4-6 membered heterocyclyl containing 1 ring N atom, 1 ring O atom, or 1 S atom, wherein the heterocyclyl is substituted with 0 instances of $R^{1b}$. In some embodiments, $R^1$ is 4-6 membered heterocyclyl containing 1 ring N atom, 1 ring O atom, or 1 S atom, wherein the heterocyclyl is substituted with 1 instance of $R^{1b}$. In some embodiments, $R^1$ is 4-6 membered heterocyclyl containing 1 ring N atom, 1 ring O atom, or 1 S atom, wherein the heterocyclyl is substituted with 2 instances of $R^{1b}$. In some embodiments, $R^1$ is 8-10 membered heterocyclyl containing 1 or 2 ring heteroatoms selected from O, N, and S, wherein the heterocyclyl is substituted with 0 instances of $R^{1b}$. In some embodiments, $R^1$ is 8-10 membered heterocyclyl containing 1 or 2 ring heteroatoms selected from O, N, and S, wherein the heterocyclyl is substituted with 1 instance of $R^{1b}$. In some embodiments, $R^1$ is:

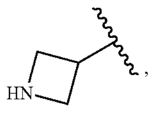
,
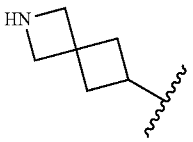
,
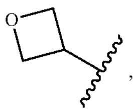
,

-continued

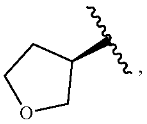, 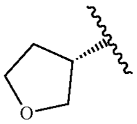, 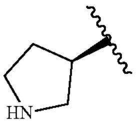,

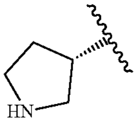, 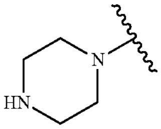, 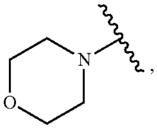,

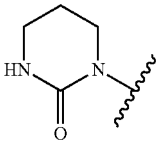, 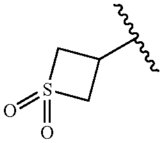, 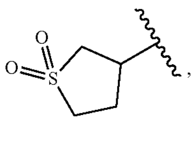,

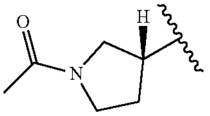, 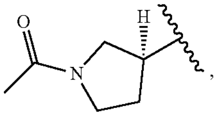,

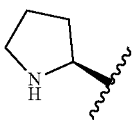, 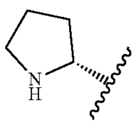, 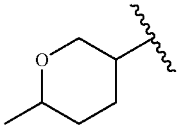,

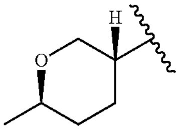, 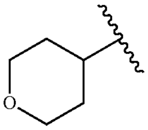,

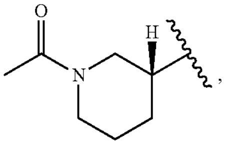, 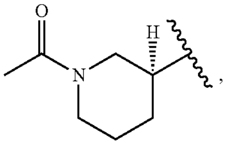,

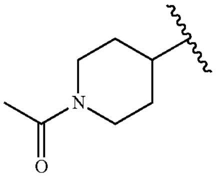, 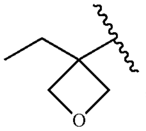,

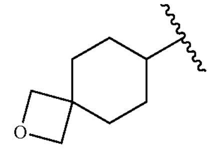, 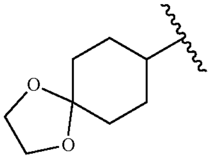, or

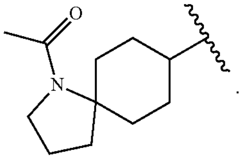.

In some embodiments, $R^1$ is optionally substituted aryl. In some embodiments, $R^1$ is optionally substituted $C_{6-10}$ aryl. In some embodiments, $R^1$ is optionally substituted phenyl. In some embodiments, $R^1$ is substituted phenyl. In some embodiments, $R^1$ is unsubstituted phenyl.

In some embodiments, $R^1$ is phenyl substituted with 0, 1, or 2 instances of $R^{1b}$, as valency permits; wherein each instance of $R^{1b}$ is independently halogen, optionally substituted $C_{1-4}$ alkyl, optionally substituted 4-6 membered heterocyclyl, —$OR^{1c}$, —$N(R^{1c})_2$, —CN, —$NO_2$, —C(=O)$R^{1c}$, —C(=O)$OR^{1c}$, —C(=O)$N(R^{1c})_2$, —C(=$NR^{1c}$)N$(R^{1c})_2$, or —$NR^{1c}$C(=O)$R^{1c}$, or two instances of $R^{1b}$ are joined together with their intervening atoms to form an optionally substituted 5-6 membered heterocyclic ring; and each instance of $R^{1c}$ is independently hydrogen, optionally substituted $C_{1-3}$ alkyl, or optionally substituted 5-6 membered heteroaryl. In some embodiments, $R^1$ is phenyl substituted with 1 instance of $R^{1b}$. In some embodiments, $R^1$ is phenyl substituted with 1 instance of $R^{1b}$, wherein $R^{1b}$ is halogen, optionally substituted 4-6 membered heterocyclyl, or —$OR^{1c}$. In some embodiments, $R^1$ is phenyl substituted with 1 instance of $R^{1b}$, wherein $R^{1b}$ is halogen, optionally substituted 4-6 membered heterocyclyl containing 1 ring N atom, —$OR^{1c}$, wherein $R^{1c}$ is unsubstituted $C_{1-3}$ alkyl or $C_{1-3}$ haloalkyl, —$NO_2$, or C(=$NR^{1c}$)N$(R^{1c})_2$. In some embodiments, $R^1$ is phenyl substituted with 2 instances of $R^{1b}$. In some embodiments, $R^1$ is phenyl substituted with 2 instances of $R^{1b}$ joined together with their intervening atoms to form an optionally substituted 5-6 membered heterocyclic ring. In some embodiments, $R^1$ is phenyl substituted with 2 instances of $R^{1b}$ joined together with their intervening atoms to form an optionally substituted 5-6 membered heterocyclic ring containing 1 ring N atom.

In some embodiments, $R^1$ is:

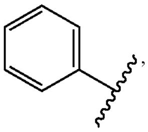, 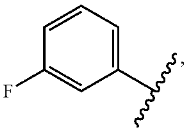,

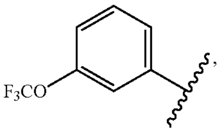, 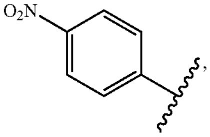,

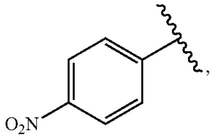, 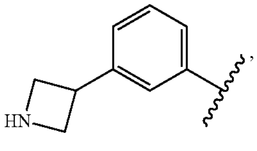,

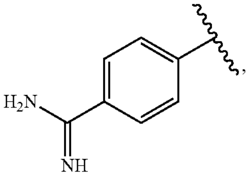, 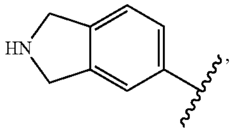, or

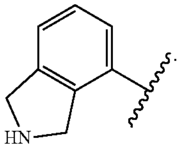.

In some embodiments, $R^1$ is optionally substituted heteroaryl. In some embodiments, $R^1$ is optionally substituted 5-10 membered heteroaryl. In some embodiments, $R^1$ is substituted 5-10 membered heteroaryl. In some embodiments, $R^1$ is unsubstituted 5-10 membered heteroaryl. In some embodiments, $R^1$ is optionally substituted 5-6 membered heteroaryl. In some embodiments, $R^1$ is substituted 5-6 membered heteroaryl. In some embodiments, $R^1$ is unsubstituted 5-6 membered heteroaryl. In some embodiments, $R^1$ is optionally substituted 5-6 membered heteroaryl containing 1, 2, or 3 ring N atoms. In some embodiments, $R^1$ is substituted 5-6 membered heteroaryl containing 1, 2, or 3 ring N atoms. In some embodiments, $R^1$ is unsubstituted 5-6 membered heteroaryl containing 1, 2, or 3 ring N atoms. In some embodiments, $R^1$ is optionally substituted 8-10 membered heteroaryl. In some embodiments, $R^1$ is substituted 8-10 membered heteroaryl. In some embodiments, $R^1$ is unsubstituted 8-10 membered heteroaryl. In some embodiments, $R^1$ is optionally substituted 8-10 membered heteroaryl containing 1, 2, or 3 ring N atoms. In some embodiments, $R^1$ is substituted 8-10 membered heteroaryl containing 1, 2, or 3 ring N atoms. In some embodiments, $R^1$ is unsubstituted 8-10 membered heteroaryl containing 1, 2, or 3 ring N atoms.

In some embodiments, $R^1$ is 5-6 membered heteroaryl containing 1, 2, or 3 ring N atoms or 8-10 membered heteroaryl containing 1, 2, or 3 ring N atoms, wherein the heteroaryl is substituted with 0, 1, or 2 instances of $R^{1b}$, as valency permits; wherein each instance of $R^{1b}$ is independently halogen, optionally substituted $C_{1-4}$ alkyl, optionally substituted 4-6 membered heterocyclyl, —$OR^{1c}$, —$N(R^{1c})_2$, —CN, —C(═O)$R^{1c}$, —C(═O)$OR^{1c}$, —C(═O)$N(R^{1c})_2$, or —$NR^{1c}$C(═O)$R^{1c}$, or two instances of $R^{1b}$ are joined together with their intervening atoms to form an optionally substituted 5-6 membered heterocyclic ring; and each instance of $R^{1c}$ is independently hydrogen, optionally substituted $C_{1-3}$ alkyl, or optionally substituted 5-6 membered heteroaryl.

In some embodiments, $R^1$ is 5-6 membered heteroaryl containing 1, 2, or 3 ring N atoms, wherein the heteroaryl is substituted with 1 instance of $R^{1b}$, as valency permits. In some embodiments, $R^1$ is 5-6 membered heteroaryl containing 1, 2, or 3 ring N atoms, wherein the heteroaryl is substituted with 1 instance of $R^{1b}$, as valency permits, wherein $R^{1b}$ is halogen, optionally substituted $C_{1-4}$ alkyl, optionally substituted 4-6 membered heterocyclyl, —$OR^{1c}$, —$N(R^{1c})_2$, —CN, —$NO_2$, —C(═O)$R^{1c}$, —C(═O)$OR^{1c}$, —C(═O)$N(R^{1c})_2$, —C(═$NR^{1c}$)$N(R^{1c})_2$, or —$NR^{1c}$C(═O)$R^{1c}$. In some embodiments, $R^1$ is 5-6 membered heteroaryl containing 1, 2, or 3 ring N atoms, wherein the heteroaryl is substituted with 1 instance of $R^{1b}$, as valency permits, wherein $R^{1b}$ is optionally substituted $C_{1-4}$ alkyl, optionally substituted 4-6 membered heterocyclyl, —$OR^{1c}$, —$N(R^{1c})_2$, —CN, —C(═O)$OR^{1c}$, or —C(═O)$N(R^{1c})_2$, wherein each instance of $R^{1c}$ is independently hydrogen, optionally substituted $C_{1-3}$ alkyl, or optionally substituted 5-6 membered heteroaryl. In some embodiments, $R^1$ is 5-6 membered heteroaryl containing 1, 2, or 3 ring N atoms, wherein the heteroaryl is substituted with 1 instance of $R^{1b}$, as valency permits, wherein $R^{1b}$ is optionally substituted $C_{1-4}$ alkyl, optionally substituted 4-6 membered heterocyclyl containing 1 ring N atom, —$OR^{1c}$, —$N(R^{1c})_2$, —CN, —C(═O)$OR^{1c}$, or —C(═O)$N(R^{1c})_2$, wherein each instance of $R^{1c}$ is independently hydrogen, optionally substituted $C_{1-3}$ alkyl, or optionally substituted 5-6 membered heteroaryl. In some embodiments, $R^1$ is 5-6 membered heteroaryl containing 1, 2, or 3 ring N atoms, wherein the heteroaryl is substituted with 2 instances of $R^{1b}$, as valency permits. In some embodiments, $R^1$ is 8-10 membered heteroaryl containing 1, 2, or 3 ring N atoms, wherein the heteroaryl is substituted with 0 instances of $R^{1b}$.

In some embodiments, $R^1$ is:

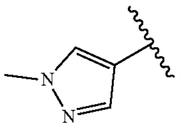,
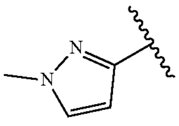,
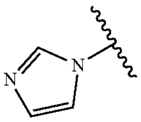,

-continued

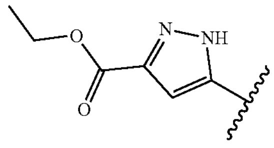,
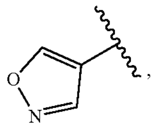,
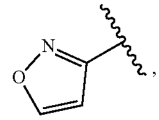,
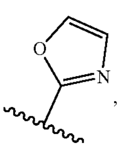,
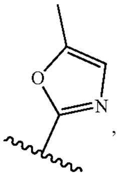,
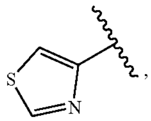,
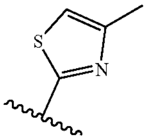,
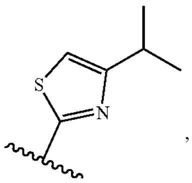,
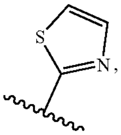,
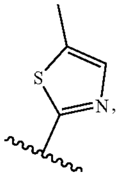,
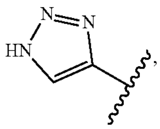,
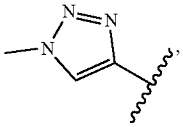,
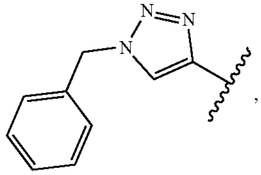,
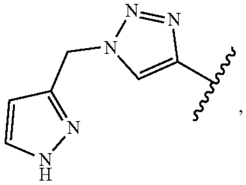,
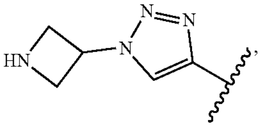,
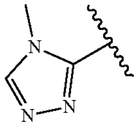,
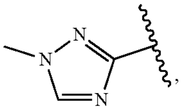,
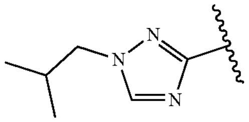,
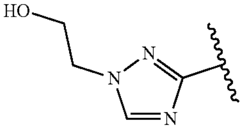,
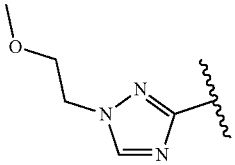,
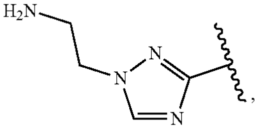,
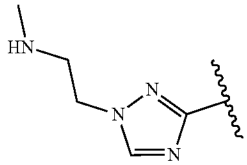,
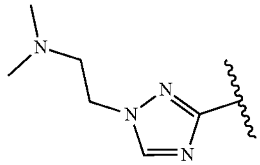, -continued
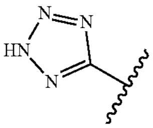,
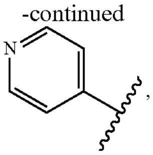,
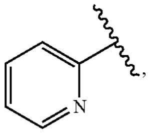,
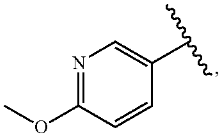,
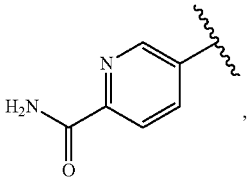,
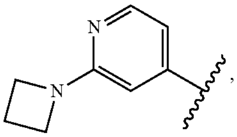,
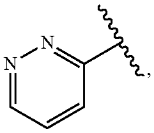,
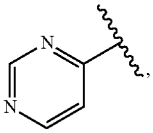,
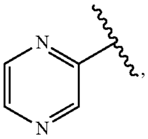,
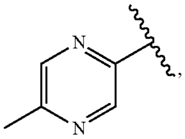,
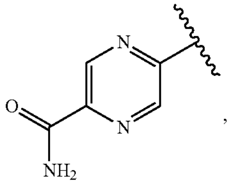,
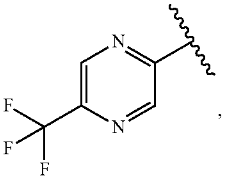,
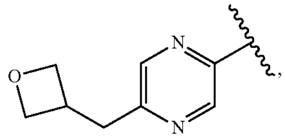,
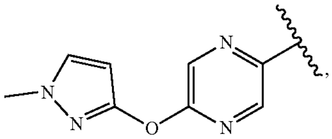,
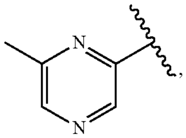,
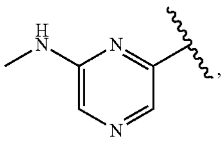,
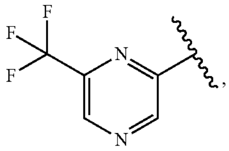,
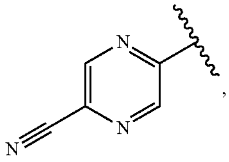,
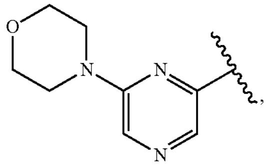,
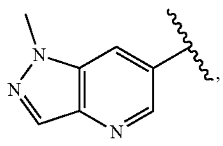,
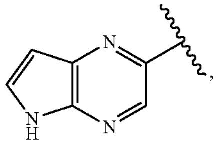,
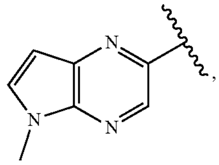,
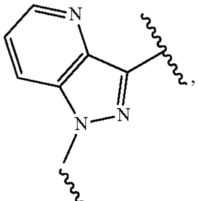, or
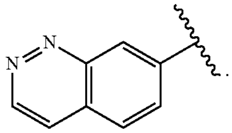.
In some embodiments, $R^1$ is:
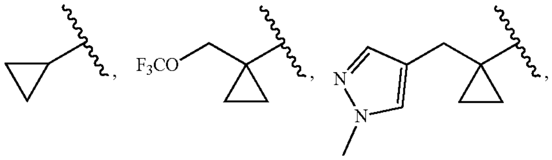
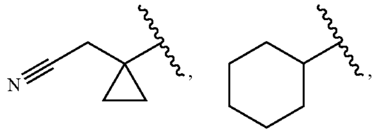
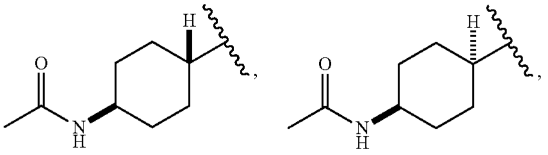
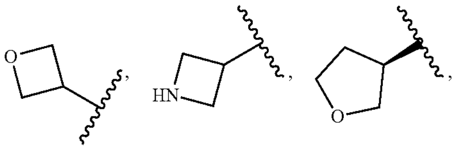
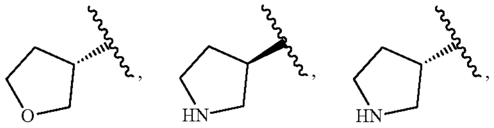
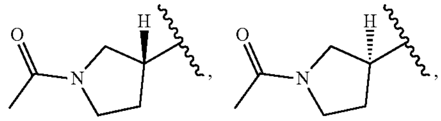
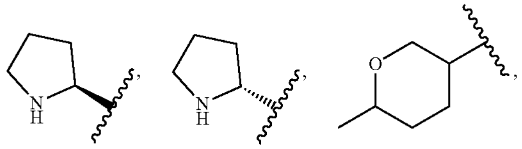
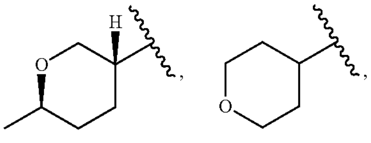
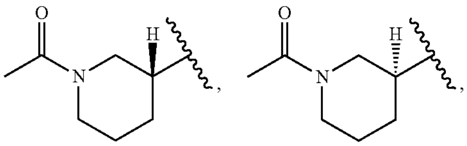
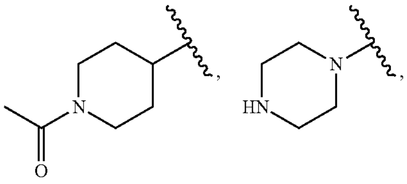
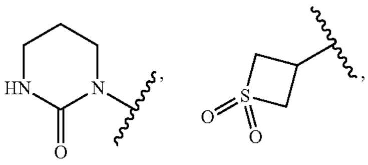

-continued
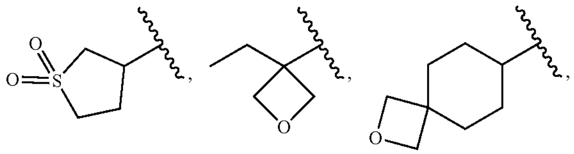
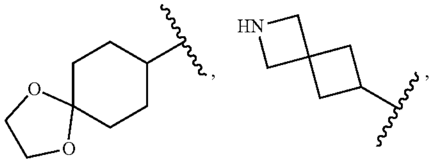
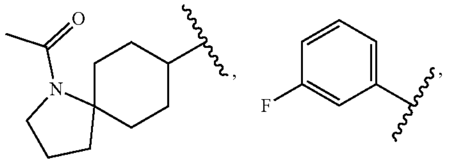
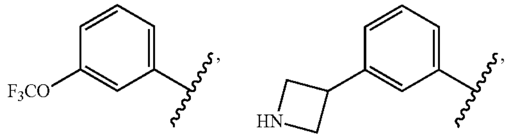
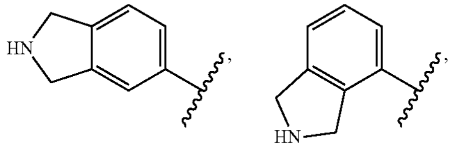
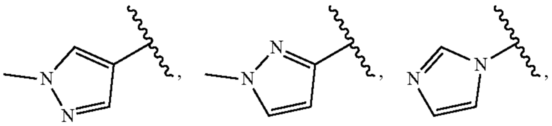
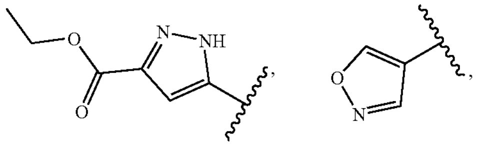
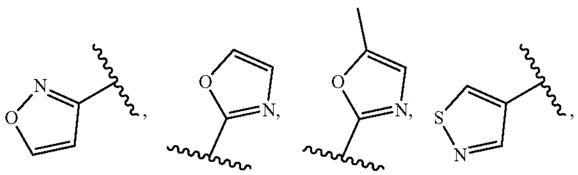
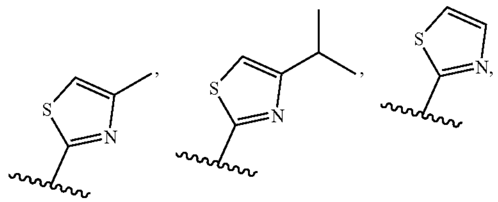
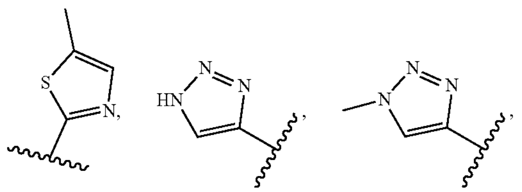
-continued
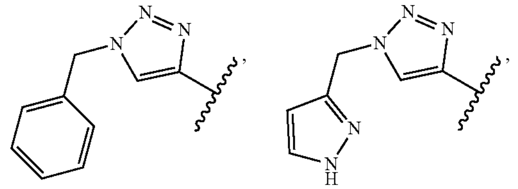
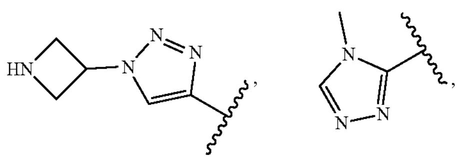
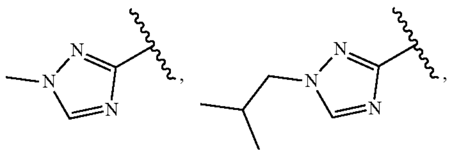
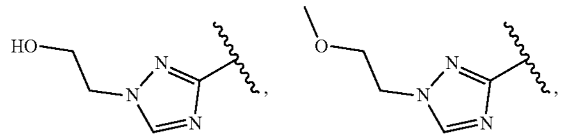
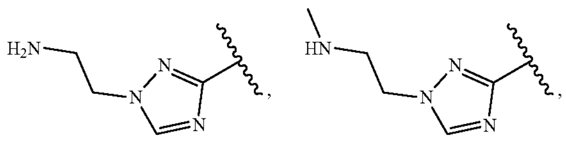
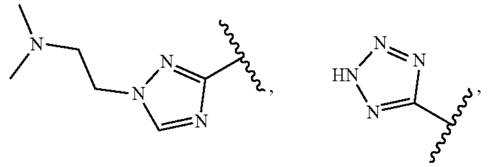
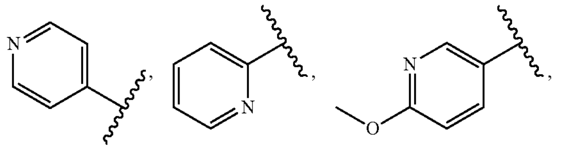
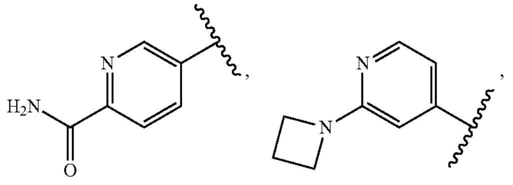
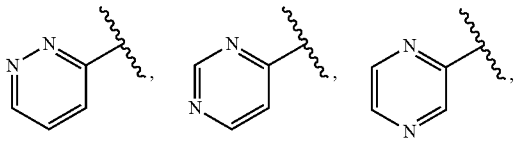
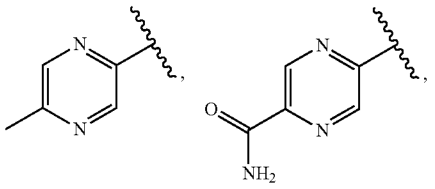

-continued

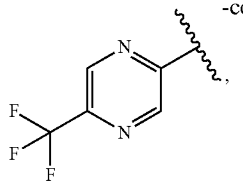,
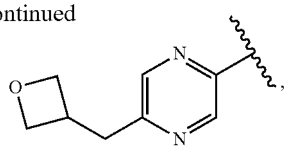,
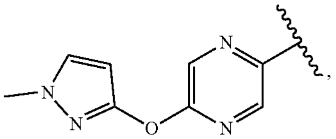,
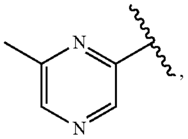,
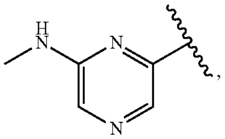,
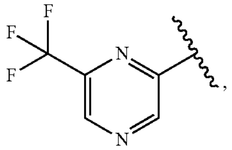,
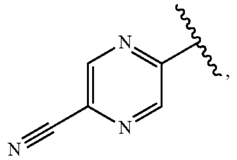,
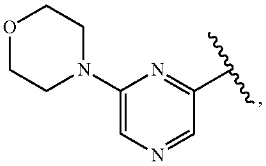,
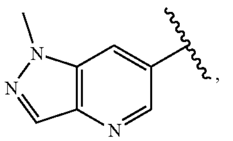,
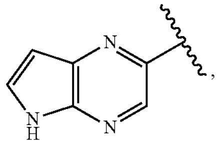,
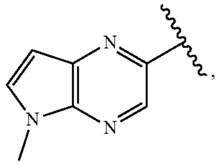,
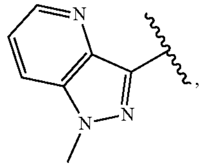, or
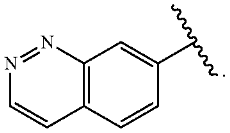.

In some embodiments, $R^1$ is —$OR^{1a}$ or —$N(R^{1a})_2$, wherein each instance of $R^{1a}$ is independently hydrogen, optionally substituted $C_{1-6}$ alkyl, optionally substituted $C_{1-6}$ heteroalkyl, optionally substituted $C_{3-10}$ carbocyclyl, optionally substituted 3-10 membered heterocyclyl, optionally substituted $C_{6-10}$ aryl, or optionally substituted 5-10 membered heteroaryl.

In some embodiments, $R^1$ is —$OR^{1a}$ or —$N(R^{1a})_2$, wherein each instance of $R^{1a}$ is independently hydrogen, $C_{1-3}$ alkyl, $C_{1-3}$ heteroalkyl, $C_{4-6}$ carbocyclyl, 4-6 membered heterocyclyl, $C_6$ aryl, or 5-6 membered heteroaryl, wherein each alkyl, heteroalkyl, carbocyclyl, heterocyclyl, aryl, or heteroaryl is substituted with 0, 1, 2, or 3 instances of halogen.

In some embodiments, $R^1$ is —$OR^{1a}$ or —$N(R^{1a})_2$, wherein each instance of $R^{1a}$ is independently hydrogen, $C_{1-3}$ alkyl, $C_{1-3}$ heteroalkyl, $C_{4-6}$ carbocyclyl, 4-6 membered heterocyclyl, $C_6$ aryl, or 5-6 membered heteroaryl, wherein each alkyl, heteroalkyl, carbocyclyl, heterocyclyl, aryl, or heteroaryl is substituted with 0, 1, 2, or 3 instances of —F.

In some embodiments, $R^1$ is —$OR^{1a}$. In some embodiments, $R^1$ is —$OR^{1a}$, wherein each instance of $R^{1a}$ is independently hydrogen, optionally substituted $C_{1-6}$ alkyl, optionally substituted $C_{1-6}$ heteroalkyl, optionally substituted $C_{3-10}$ carbocyclyl, optionally substituted 3-10 membered heterocyclyl, optionally substituted $C_{6-10}$ aryl, or optionally substituted 5-10 membered heteroaryl. In some embodiments, $R^1$ is —OR 1a, wherein each instance of $R^{1a}$ is independently hydrogen, $C_{1-3}$ alkyl, $C_{1-3}$ heteroalkyl, $C_4$-6 carbocyclyl, 4-6 membered heterocyclyl, $C_6$ aryl, or 5-6 membered heteroaryl, wherein each alkyl, heteroalkyl, carbocyclyl, heterocyclyl, aryl, or heteroaryl is substituted with 0, 1, 2, or 3 instances of halogen. In some embodiments, $R^1$ is —$OR^{1a}$, wherein each instance of $R^{1a}$ is independently hydrogen, $C_{1-3}$ alkyl, $C_{1-3}$ heteroalkyl, $C_{4-6}$ carbocyclyl, 4-6 membered heterocyclyl, $C_6$ aryl, or 5-6 membered heteroaryl, wherein each alkyl, heteroalkyl, carbocyclyl, heterocyclyl, aryl, or heteroaryl is substituted with 0, 1, 2, or 3 instances of —F.

In some embodiments, $R^1$ is —$N(R^{1a})_2$. In some embodiments, $R^1$ is —$NH_2$.

In some embodiments, $R^1$ is: —$NH_2$, —OH, —$OCH_3$, —$OCF_3$,

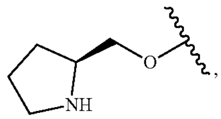, or
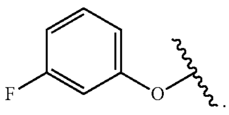.

In some embodiments, $R^1$ is: hydrogen, —$CH_3$, —$CH_2CH_3$, —$CF_3$, —$NH_2$, —OH, —$OCH_3$, —$OCF_3$,

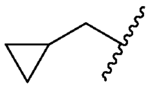,
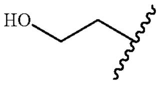,
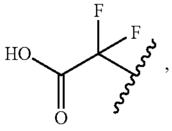,
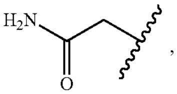,
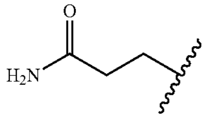,
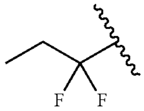,
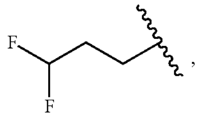,
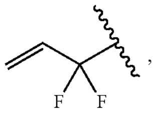,
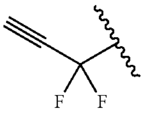,
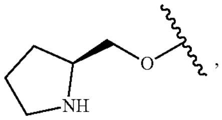,
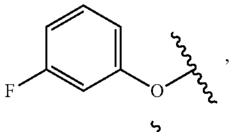,
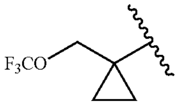,
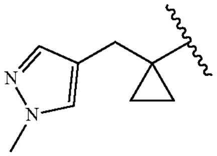,
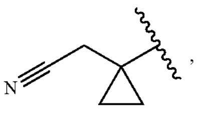,
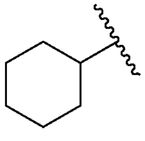,
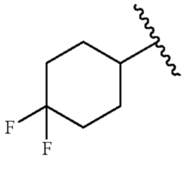, -continued
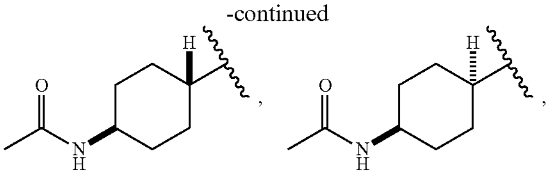
, ,
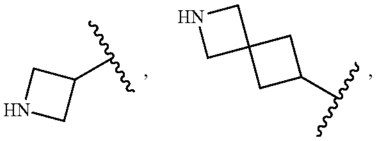
, ,
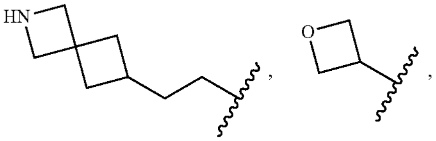
, ,
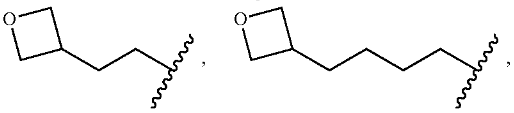
, ,
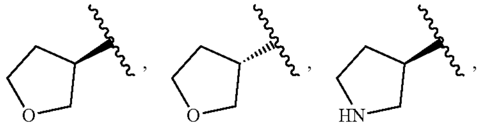
, , ,
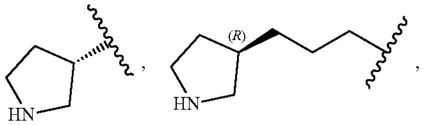
, ,
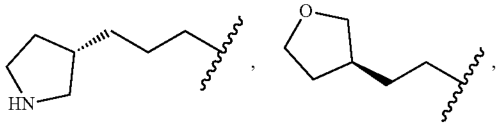
, ,
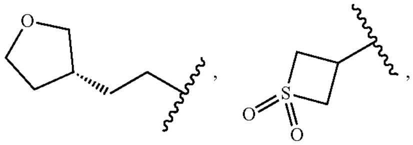
, ,
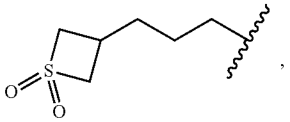
,
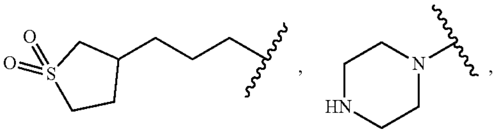
, ,
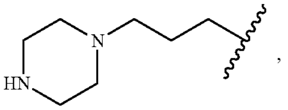
,
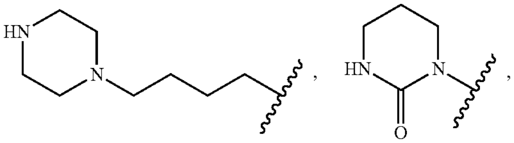
, ,
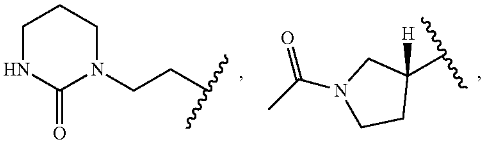
, ,
-continued
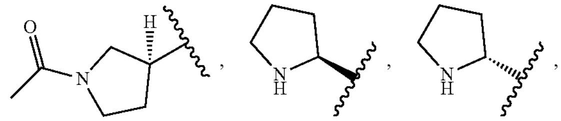
, , ,
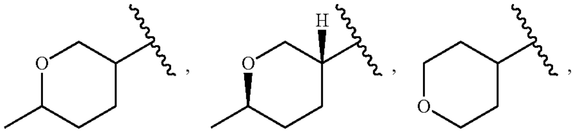
, , ,
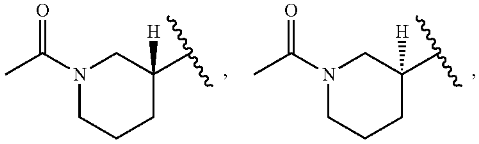
, ,
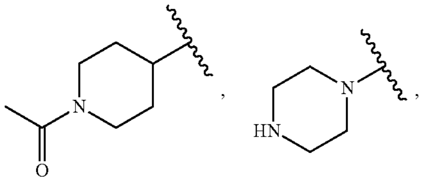
, ,
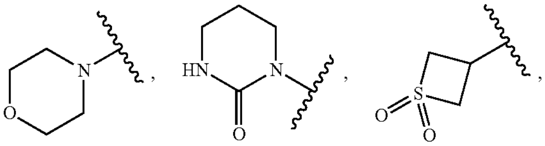
, , ,
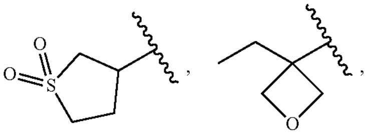
, ,
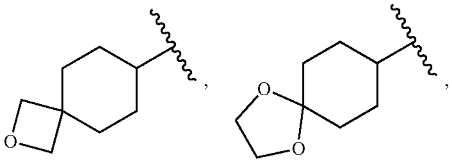
, ,
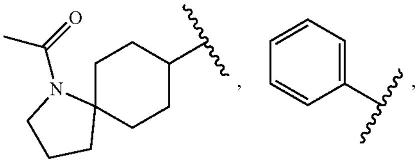
, ,
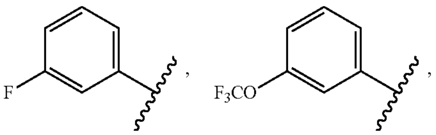
, ,
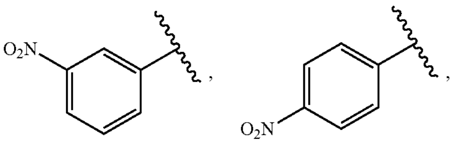
, ,
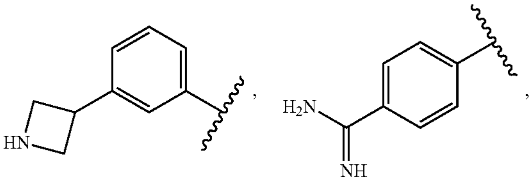
, , -continued
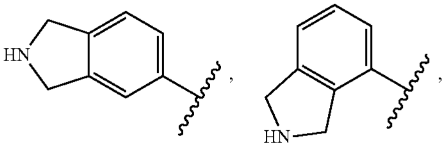
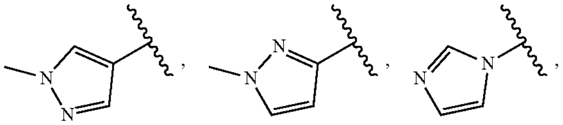
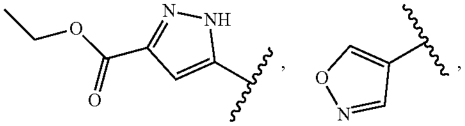
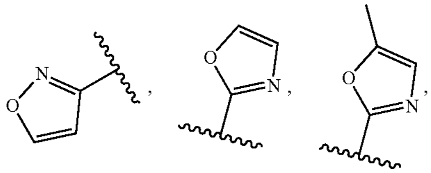
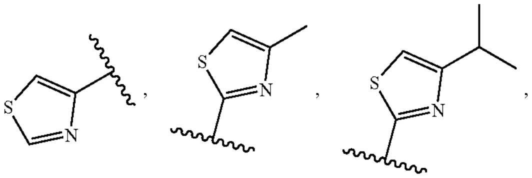
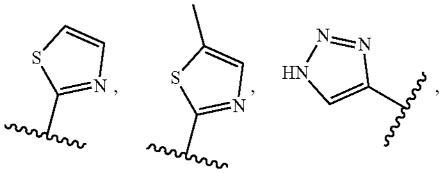
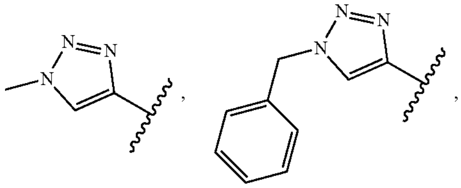
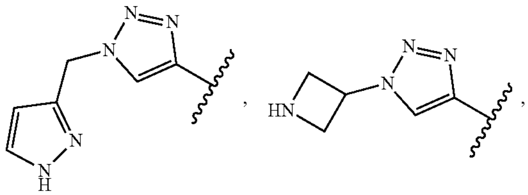
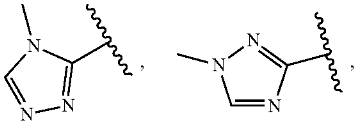
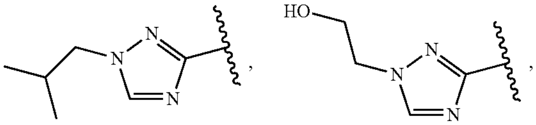
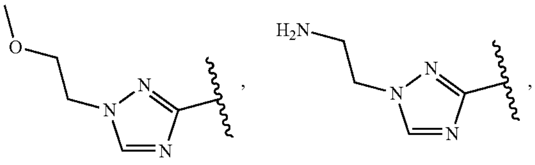
-continued
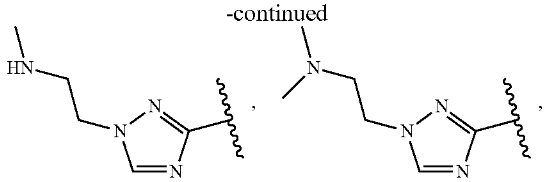
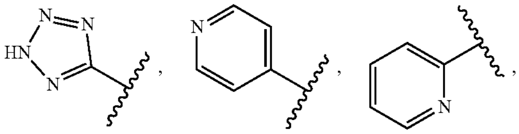
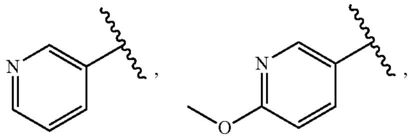
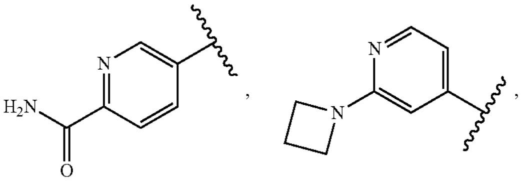
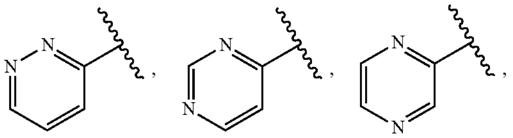
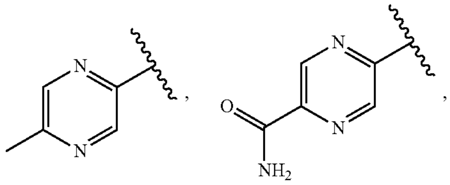
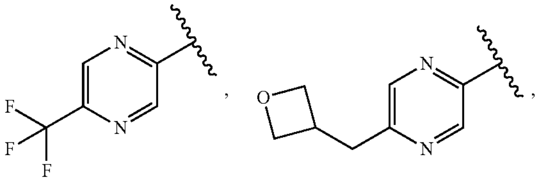
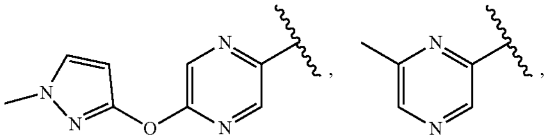
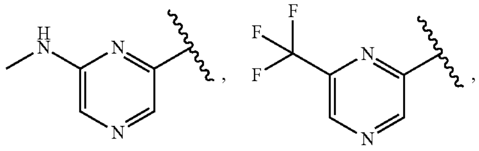
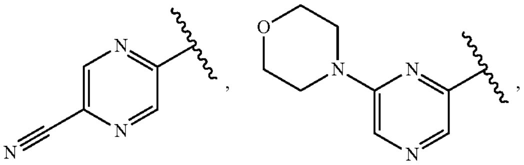
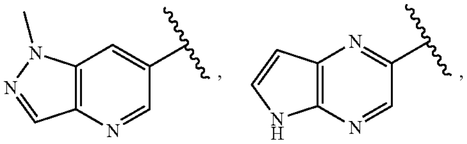

-continued

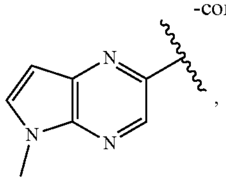

,

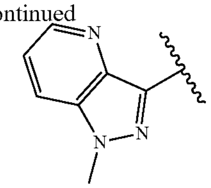

, or

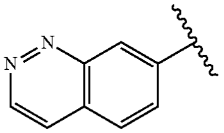

.

As generally described herein, each instance of $R^{1a}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, or an oxygen protecting group when attached to an oxygen atom, or two instances of $R^{1a}$ are joined together with their intervening atom to form an optionally substituted heterocyclic ring or optionally substituted heteroaryl ring.

In some embodiments, at least one instance of $R^{1a}$ is hydrogen.

In some embodiments, at least one instance of $R^{1a}$ is optionally substituted alkyl. In some embodiments, at least one instance of $R^{1a}$ is optionally substituted $C_{1-6}$ alkyl. In some embodiments, at least one instance of $R^{1a}$ is unsubstituted $C_{1-6}$ alkyl. In some embodiments, at least one instance of $R^{1a}$ is substituted $C_{1-6}$ alkyl. In some embodiments, at least one instance of $R^{1a}$ is optionally substituted $C_{1-3}$ alkyl. In some embodiments, at least one instance of $R^{1a}$ is unsubstituted $C_{1-3}$ alkyl. In some embodiments, at least one instance of $R^{1a}$ is substituted $C_{1-3}$ alkyl. In some embodiments, at least one instance of $R^{1a}$ is —$CH_3$, —$CF_3$, or

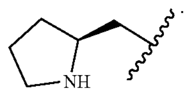 [SMILES: *C[C@@H]1CCCN1]

.

In some embodiments, at least one instance of $R^{1a}$ is optionally substituted alkenyl. In some embodiments, at least one instance of $R^{1a}$ is optionally substituted $C_{2-6}$ alkenyl. In some embodiments, at least one instance of $R^{1a}$ is optionally substituted $C_{2-3}$ alkenyl.

In some embodiments, at least one instance of $R^{1a}$ is optionally substituted alkynyl. In some embodiments, at least one instance of $R^{1a}$ is optionally substituted $C_{2-6}$ alkynyl. In some embodiments, at least one instance of $R^{1a}$ is optionally substituted $C_{2-3}$ alkynyl.

In some embodiments, at least one instance of $R^{1a}$ is optionally substituted carbocyclyl. In some embodiments, at least one instance of $R^{1a}$ is optionally substituted $C_{3-14}$ carbocyclyl. In some embodiments, at least one instance of $R^{1a}$ is optionally substituted $C_{3-6}$ carbocyclyl.

In some embodiments, at least one instance of $R^{1a}$ is optionally substituted membered heterocyclyl. In some embodiments, at least one instance of $R^{1a}$ is optionally substituted 3-10 membered heterocyclyl. In some embodiments, at least one instance of $R^{1a}$ is optionally substituted 4-6 membered heterocyclyl.

In some embodiments, at least one instance of $R^{1a}$ is optionally substituted aryl. In some embodiments, at least one instance of $R^{1a}$ is optionally substituted 6-10 membered aryl. In some embodiments, at least one instance of $R^{1a}$ is optionally substituted phenyl. In some embodiments, at least one instance of $R^{1a}$ is

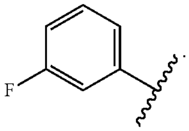 [SMILES: *c1cccc(F)c1]

.

In some embodiments, at least one instance of $R^{1a}$ is optionally substituted membered heteroaryl. In some embodiments, at least one instance of $R^{1a}$ is optionally substituted 5-6 membered heteroaryl.

In some embodiments, at least one instance of $R^{1a}$ is a nitrogen protecting group when attached to a nitrogen atom.

In some embodiments, at least one instance of $R^{1a}$ is an oxygen protecting group when attached to an oxygen atom.

In some embodiments, at least two instances of $R^{1a}$ are joined together with their intervening atom to form an optionally substituted heterocyclic ring or optionally substituted heteroaryl ring. In some embodiments, at least two instances of $R^{1a}$ are joined together with their intervening atom to form an optionally substituted 5-10 membered heterocyclic ring. In some embodiments, at least two instances of $R^{1a}$ are joined together with their intervening atom to form an optionally substituted 5-14 membered heteroaryl ring.

As generally described herein, each instance of $R^{1b}$ is independently halogen, optionally substituted $C_{1-4}$ alkyl, optionally substituted 4-6 membered heterocyclyl, —$OR^{1c}$, —$N(R^{1c})_2$, —CN, —$NO_2$, —C(═O)$R^{1c}$, —C(═O)$OR^{1c}$, —C(═O)$N(R^{1c})_2$, —C(═$NR^{1c}$)$N(R^{1c})_2$, or —$NR^{1c}$C(═O)$R^{1c}$, or two instances of $R^{1b}$ are taken together to form ═O, as valency permits, or two instances of $R^{1b}$ are joined together with their intervening atoms to form an optionally substituted 5-6 membered heterocyclic ring. In some embodiments, each instance of $R^{1b}$ is independently halogen, optionally substituted $C_{1-3}$ alkyl, optionally substituted 4-6 membered heterocyclyl, —$OR^{1c}$, —C(═O)$R^{1c}$, —C(═O)$OR^{1c}$, or —$NR^{1c}$C(═O)$R^{1c}$, or two instances of $R^{1b}$ are joined together with their intervening atoms to form an optionally substituted 5-6 membered heterocyclic ring.

In some embodiments, each instance of $R^{1b}$ is independently halogen, optionally substituted $C_{1-4}$ alkyl, optionally substituted 4-6 membered heterocyclyl, —$OR^{1c}$, —$N(R^{1c})_2$, —CN, —C(═O)$R^{1c}$, —C(═O)$OR^{1c}$, —C(═O)$N(R^{1c})_2$, or —$NR^{1c}$C(═O)$R^{1c}$, or two instances of $R^{1b}$ are joined together with their intervening atoms to form an optionally substituted 5-6 membered heterocyclic ring. In some embodiments, each instance of $R^{1b}$ is independently halogen, optionally substituted $C_{1-3}$ alkyl, optionally substituted 4-6 membered heterocyclyl, —$OR^{1c}$, —C(═O)$R^{1c}$, —C(═O)$OR^{1c}$, or —$NR^{1c}$C(═O)$R^{1c}$, or two instances of $R^{1b}$ are joined together with their intervening atoms to form an optionally substituted 5-6 membered heterocyclic ring.

In some embodiments, at least one instance of $R^{1b}$ is halogen. In some embodiments, at least one instance of $R^{1b}$ is —F.

In some embodiments, at least one instance of $R^{1b}$ is optionally substituted $C_{1-4}$ alkyl. In some embodiments, at least one instance of $R^{1b}$ is —$CH_3$, —$CH_2CH_3$, —$CH_2CH(CH_3)_2$, —$CH_2OCF_3$, —$CH_2CN$,

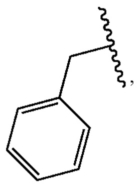,
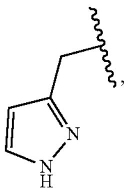, or
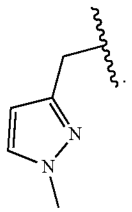.

In some embodiments, at least one instance of $R^{1b}$ is optionally substituted 4-6 membered heterocyclyl. In some embodiments, at least one instance of $R^{1b}$ is

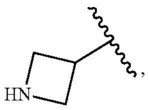,
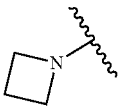, or
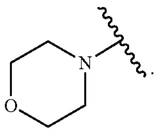.

In some embodiments, at least one instance of $R^{1b}$ is —$OR^{1c}$. In some embodiments, at least one instance of $R^{1b}$ is —$OCF_3$ or

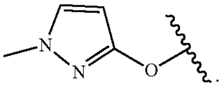 [SMILES: *Oc1ccn(C)n1].

In some embodiments, at least one instance of $R^{1b}$ is —$N(R^{1c})_2$. In some embodiments, at least one instance of $R^{1b}$ is —$NHCH_3$.

In some embodiments, at least one instance of $R^{1b}$ is —CN.

In some embodiments, at least one instance of $R^{1b}$ is —$NO_2$.

In some embodiments, at least one instance of $R^{1b}$ is —C(═O)$R^{1c}$. In some embodiments, at least one instance of $R^{1b}$ is —C(═O) $CH_3$.

In some embodiments, at least one instance of $R^{1b}$ is —C(═O)$OR^{1c}$. In some embodiments, at least one instance of $R^{1b}$ is —C(═O)$OCH_2CH_3$.

In some embodiments, at least one instance of $R^{1b}$ is —C(═O)$N(R^{1c})_2$. In some embodiments, at least one instance of $R^{1b}$ is —C(═O)$NH_2$.

In some embodiments, at least one instance of $R^{1b}$ is —C(═$NR^{1c}$)$N(R^{1c})_2$. In some embodiments, at least one instance of $R^{1b}$ is —C(═NH)$NH_2$.

In some embodiments, at least one instance of $R^{1b}$ is —$NR^{1c}C$(═O)$R^{1c}$. In some embodiments, at least one instance of $R^{1b}$ is —NHC(═O) $CH_3$.

In some embodiments, two instances of $R^{1b}$ are taken together to form ═O, as valency permits.

In some embodiments, two instances of $R^{1b}$ are joined together with their intervening atoms to form an optionally substituted 5-6 membered heterocyclic ring. In some embodiments, two instances of $R^{1b}$ are joined together with their intervening atoms to form

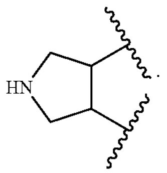 [SMILES: *C1CNCC1*].

As generally described herein, each instance of $R^{1c}$ is independently hydrogen, optionally substituted $C_{1-3}$ alkyl, or optionally substituted 5-6 membered heteroaryl. In some embodiments, each instance of $R^{1c}$ is independently hydrogen or optionally substituted $C_{1-3}$ alkyl.

In some embodiments, at least one instance of $R^{1c}$ is hydrogen. In some embodiments, at least one instance of $R^{1c}$ is optionally substituted $C_{1-3}$ alkyl. In some embodiments, at least one instance of $R^{1c}$ is substituted $C_{1-3}$ alkyl. In some embodiments, at least one instance of $R^{1c}$ is unsubstituted $C_{1-3}$ alkyl. In some embodiments, at least one instance of $R^{1c}$ is —$CH_3$, —$CH_2CH_3$, or —$CF_3$. In some embodiments, at least one instance of $R^{1c}$ is optionally substituted 5-6 membered heteroaryl. In some embodiments, at least one instance of $R^{1c}$ is

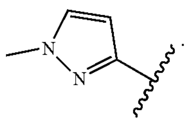 [SMILES: *c1ccn(C)n1].

As generally described herein, each instance of Y is independently —$C(R^Y)_2$—, —O—, or —$N(R^{1a})$—, or two instances of Y are taken together to form —$C(R^Y)$═$C(R^Y)$— or —C≡C—.

In some embodiments, at least one instance of Y is —$C(R^Y)_2$— or —O—, or two instances of Y are taken together to form —$C(R^Y)$═$C(R^Y)$— or —C≡C—. In some embodiments, at least one instance of Y is —$C(R^Y)_2$— or —O—. In some embodiments, at least one instance of Y is —$C(R^Y)_2$—, or two instances of Y are taken together to form —$C(R^Y)$═$C(R^Y)$— or —C≡C—. In some embodiments, at least one instance of Y is —O—, or two instances of Y are taken together to form —$C(R^Y)$═$C(R^Y)$— or —C≡C—. In some embodiments, two instances of Y are taken together to form —$C(R^Y)$═$C(R^Y)$— or —C≡C—.

In some embodiments, at least one instance of Y is —$C(R^Y)_2$—. In some embodiments, at least one instance of Y is —$CH_2$—, —$CF_2$—, or —C(═O)—. In some embodiments, at least one instance of Y is —$CH_2$— or —$CF_2$—.

In some embodiments, at least one instance of Y is —O—. In some embodiments, at least one instance of Y is —$N(R^{1a})$—. In some embodiments, two instances of Y are taken together to form —$C(R^Y)$═$C(R^Y)$—. In some embodiments, two instances of Y are taken together to form —C≡C—.

As generally described herein, each instance of $R^Y$ is independently hydrogen or halogen, or two instances of $R^Y$ are taken together to form ═O.

In some embodiments, at least one instance of $R^Y$ is hydrogen. In some embodiments, at least one instance of $R^Y$ is halogen. In some embodiments, at least one instance of $R^Y$ is —F. In some embodiments, two instances of $R^Y$ are taken together to form ═O.

As generally described herein, n is 0, 1, 2, 3, 4, or 5, provided that: if n is 0, then $R^1$ is not optionally substituted aryl, optionally substituted heteroaryl, —$OR^{1a}$, or —$N(R^{1a})_2$; and if n is 1, 2, 3, 4, or 5, the Y attached to the oxygen atom of the moiety

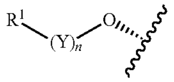

is —$C(R^Y)_2$—.

In some embodiments, n is 0, 1, 2, 3, or 4. In some embodiments, n is 1, 2, 3, or 4. In some embodiments, n is 0, 1, 2, or 3. In some embodiments, n is 0, 1, or 2. In some embodiments, n is 0 or 1. In some embodiments, n is 0. In some embodiments, n is 0, and $R^1$ is not optionally substituted aryl. In some embodiments, n is 0, and $R^1$ is not optionally substituted heteroaryl. In some embodiments, n is 0, and $R^1$ is not optionally substituted aryl or optionally substituted heteroaryl. In some embodiments, n is 0, and $R^1$ is not —$OR^{1a}$. In some embodiments, n is 0, and $R^1$ is not —$N(R^{1a})_2$. In some embodiments, n is 0, and $R^1$ is not optionally substituted aryl, optionally substituted heteroaryl, —$OR^{1a}$, or —$N(R^{1a})_2$. In some embodiments, n is 1. In some embodiments, n is 2. In some embodiments, n is 3. In some embodiments, n is 4. In some embodiments, n is 5.

In some embodiments,

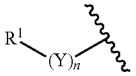

is of formula: —H, —$CH_3$, —$CF_3$, —$CH_2CH_3$,

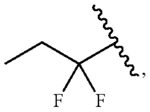, 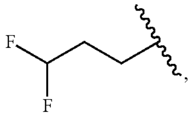, 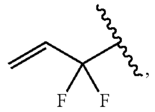,

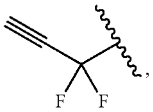, 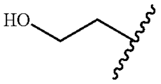, 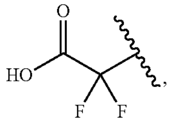,

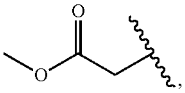, 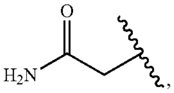,

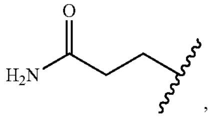, 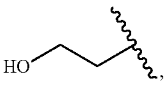,

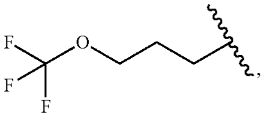, 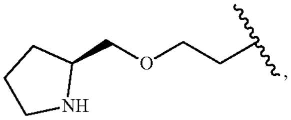,

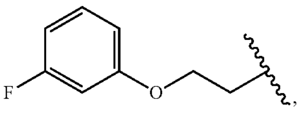, 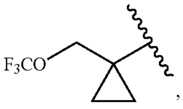,

-continued

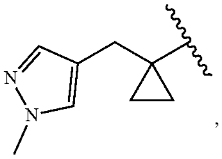, 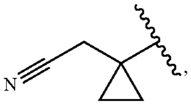,

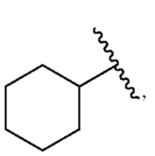, 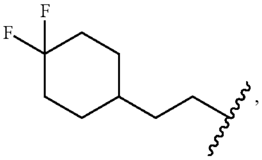,

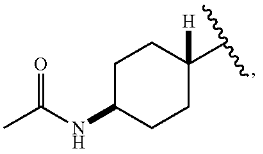, 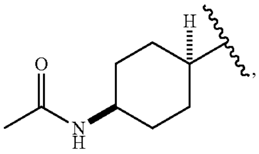,

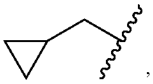, 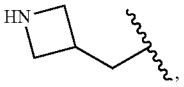,

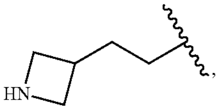, 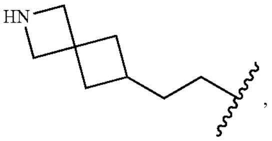,

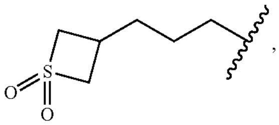, 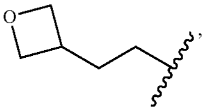,

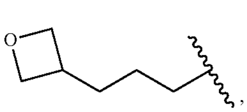, 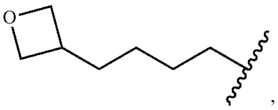,

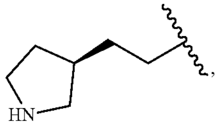, 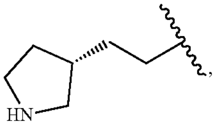,

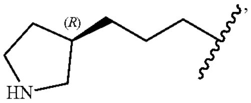, 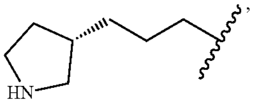,

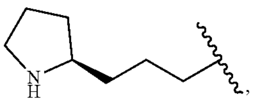, 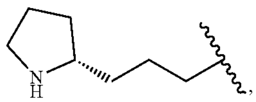,

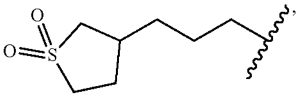,

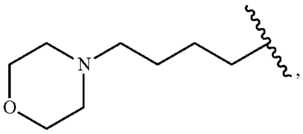,

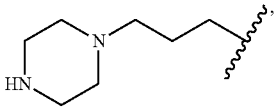,

-continued
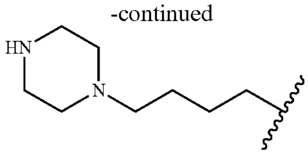,
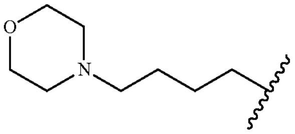,
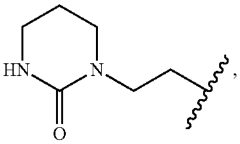, 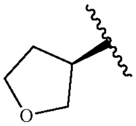, 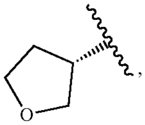,
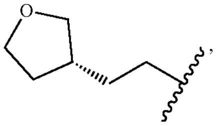, 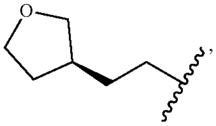,
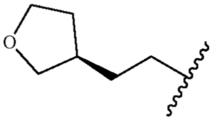, 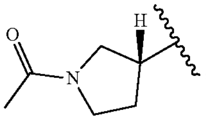,
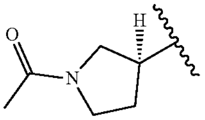, 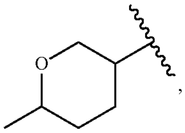,
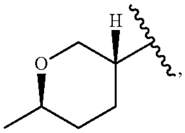, 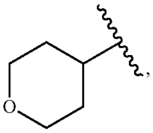,
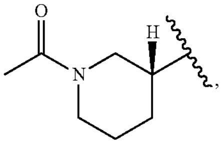, 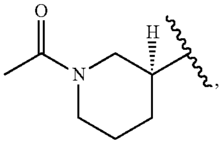,
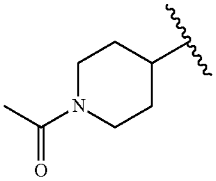, 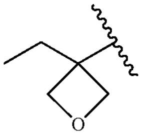,
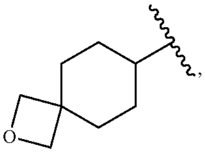, 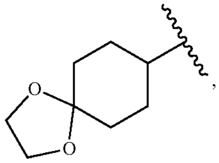,
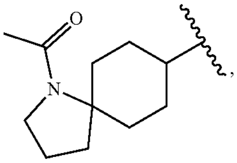, 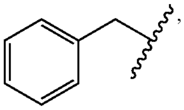,
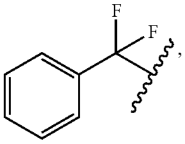, 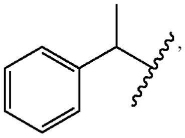,
-continued
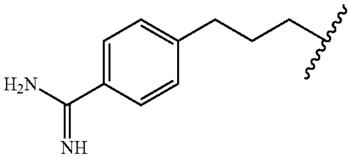,
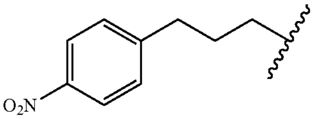,
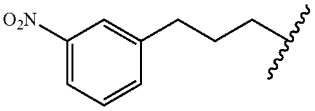,
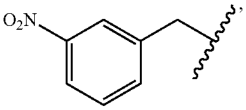, 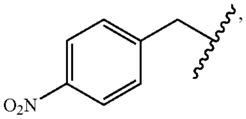,
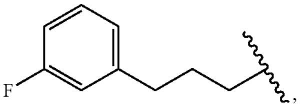,
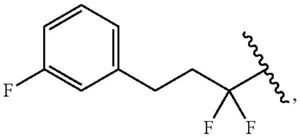,
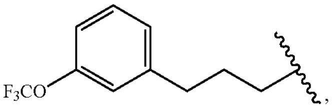,
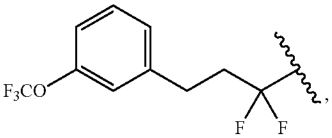,
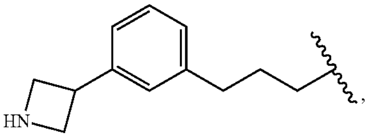,
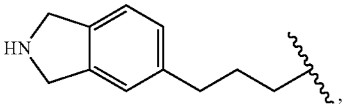,
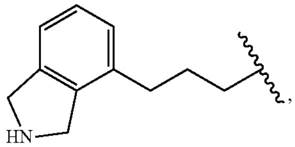,
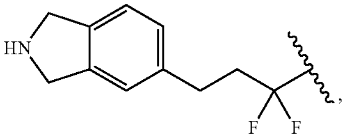,
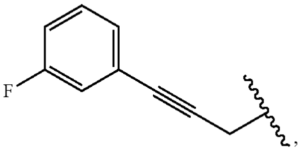 [SMILES: *CC#Cc1cccc(F)c1], 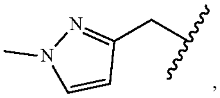, -continued
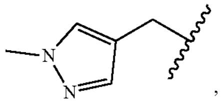,
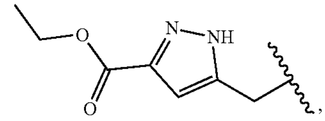,
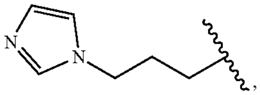,
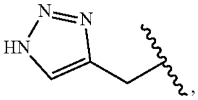,
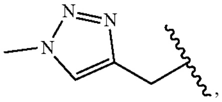,
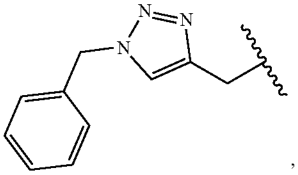,
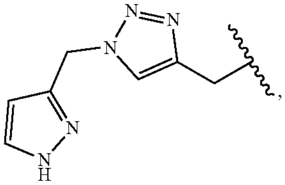,
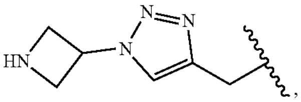,
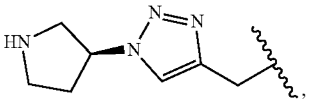,
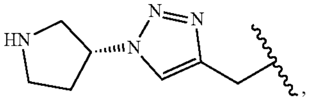,
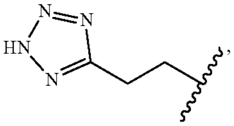,
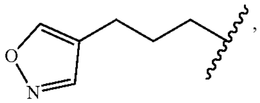,
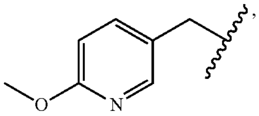,
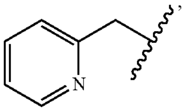,
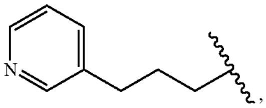,
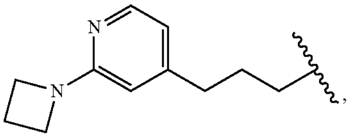,
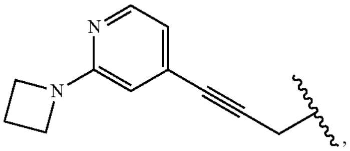,
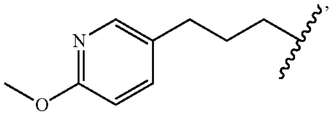, or
-continued
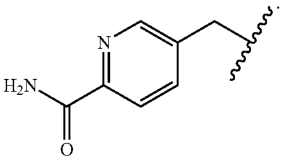 [SMILES: *Cc1ccc(C(N)=O)nc1].
In some embodiments,
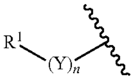
is of formula: —H, —$CH_3$, —$CF_3$, —$CH_2CH_3$,
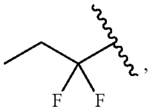,
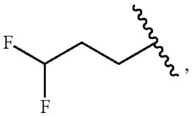,
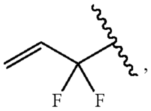,
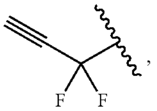,
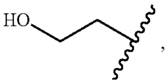,
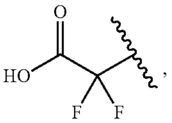,
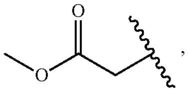,
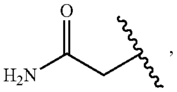,
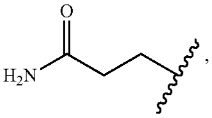,
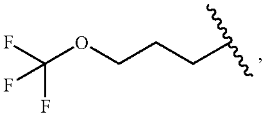,
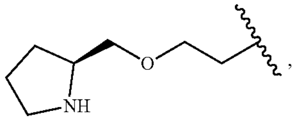,
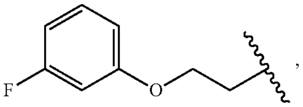,
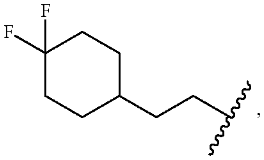,
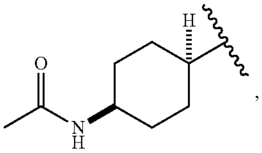,
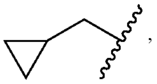,
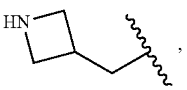,
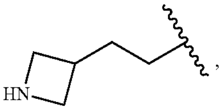,
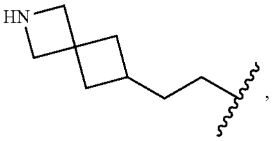,
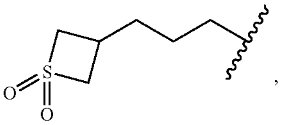,
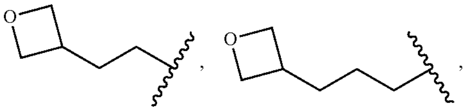, -continued
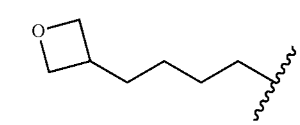, 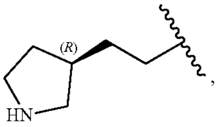,
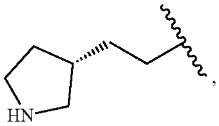, 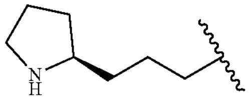,
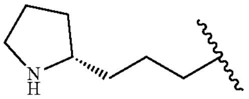, 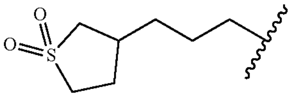,
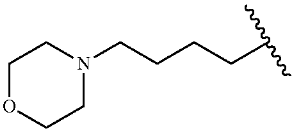,
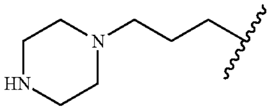,
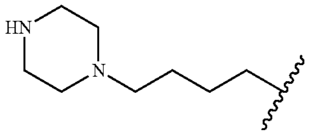,
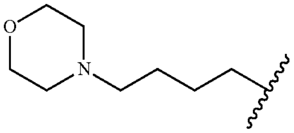, 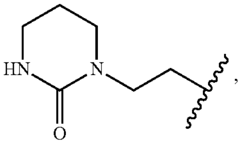,
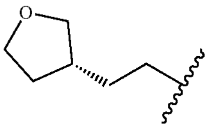, 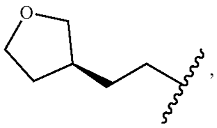, or
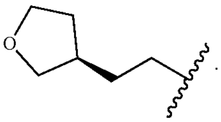.
In some embodiments
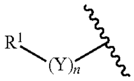
is of formula: —H, —$CH_3$, —$CF_3$, —$CH_2CH_3$,
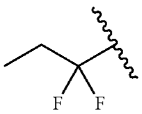, 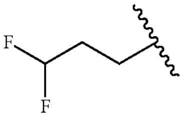, 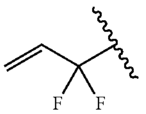,
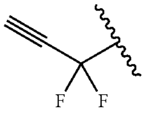, 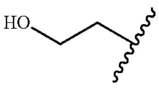, 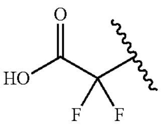,
-continued
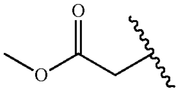, 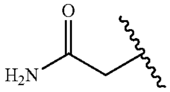,
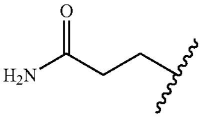, 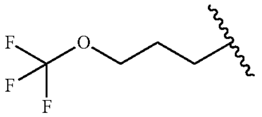.
In some embodiments,
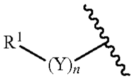
is of formula: —H, —$CH_3$, —$CF_3$, —$CH_2CH_3$,
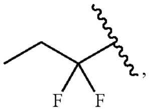, 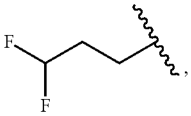, 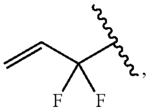, or
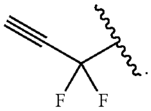.
In some embodiments,
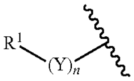
is of formula: —$CH_3$ or —$CH_2CH_3$. In some embodiments,
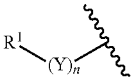
is of formula:
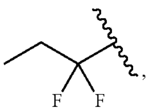, 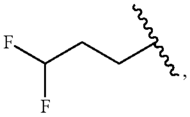, 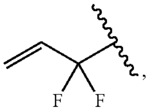, or
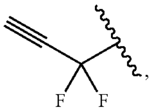,
In some embodiments,
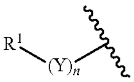

is of formula:
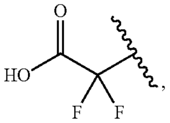,
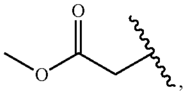,
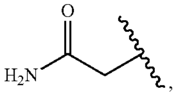,
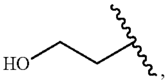, or
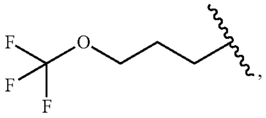,
In some embodiments,
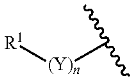
is of formula:
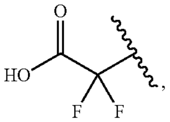,
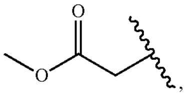,
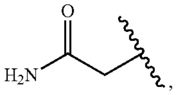,
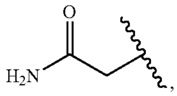, or
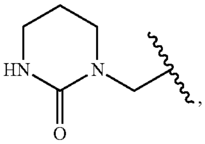,
In some embodiments,
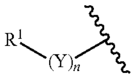
is of formula:
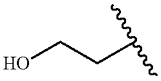 or
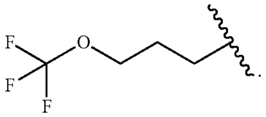.
In some embodiments,
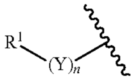
is of formula:
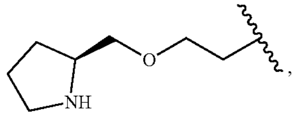,
-continued
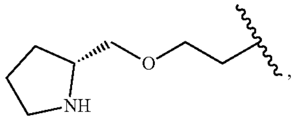, or
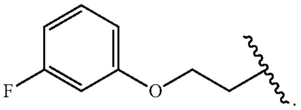.
In some embodiments,
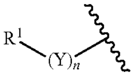
is of formula:
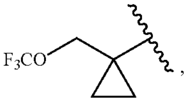,
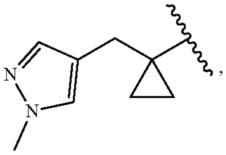,
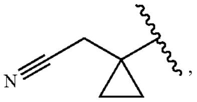,
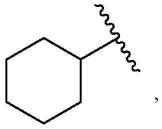,
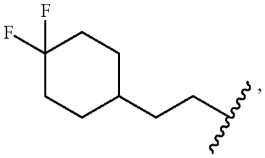,
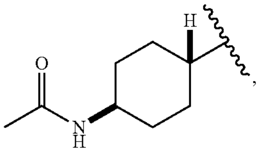,
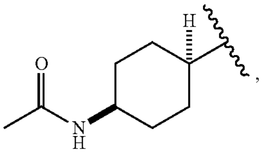,
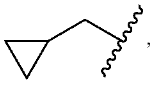,
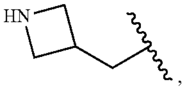,
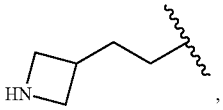,
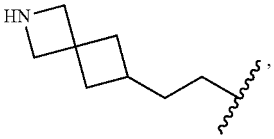,
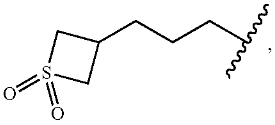,
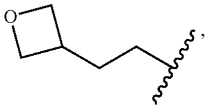,
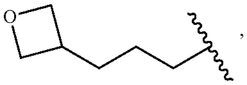,
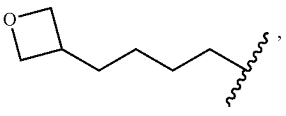,
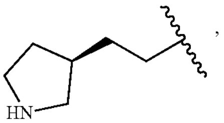, -continued
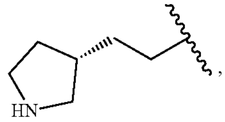, 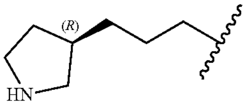,
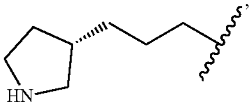, 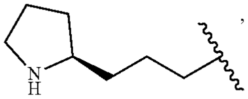,
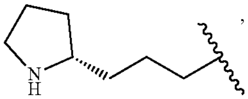,
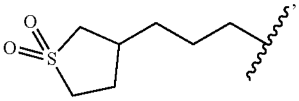,
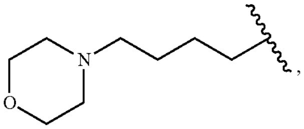,
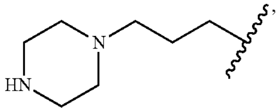,
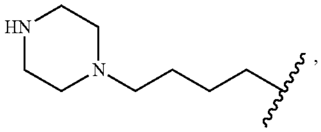,
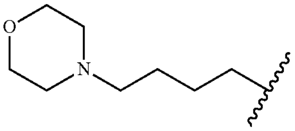, 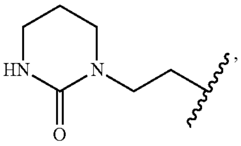,
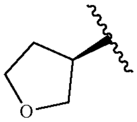, 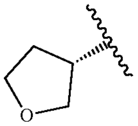, 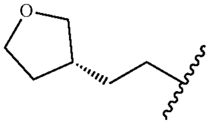,
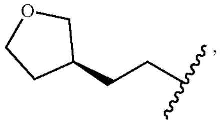, 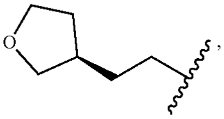,
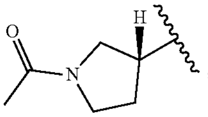, 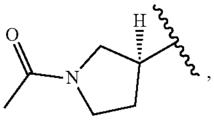,
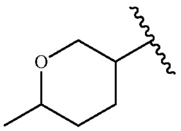, 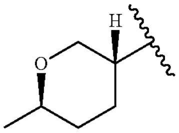, 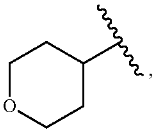,
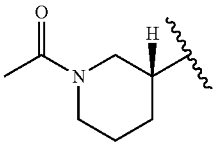, 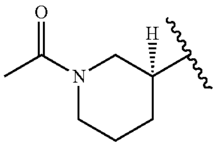,
-continued
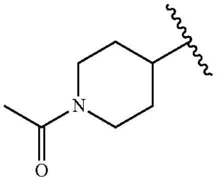, 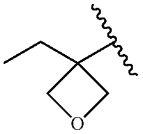,
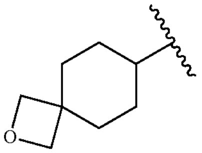, 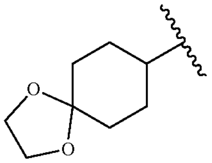,
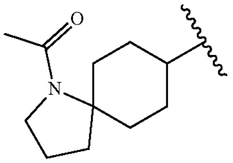, 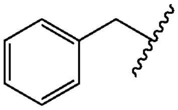,
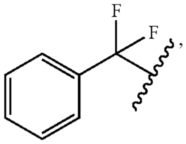, 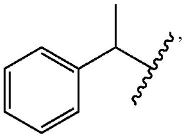,
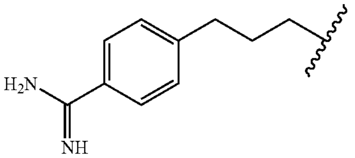,
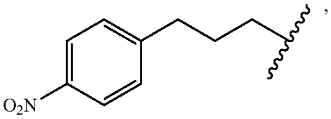,
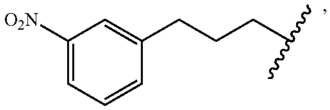,
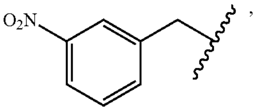, 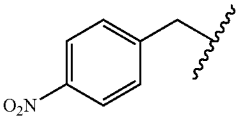,
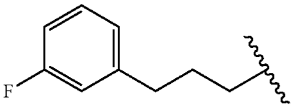,
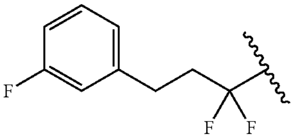,
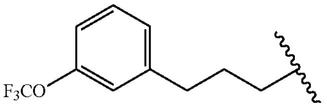,
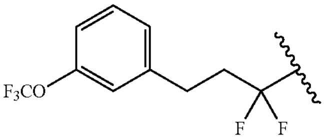, -continued
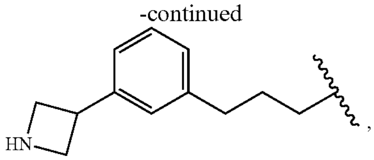
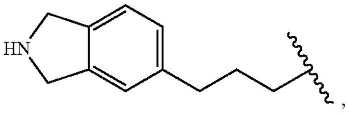
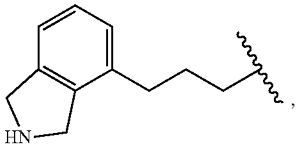
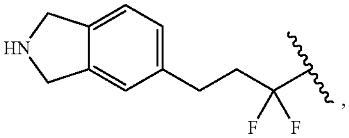
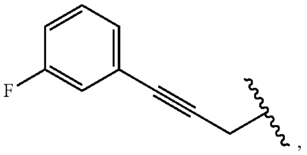
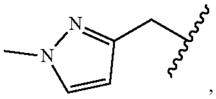
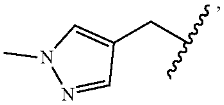
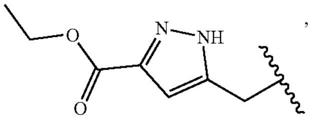
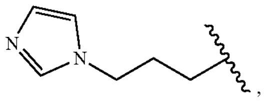
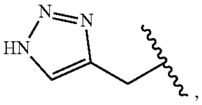
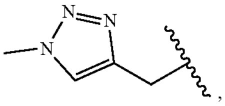
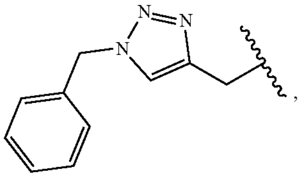
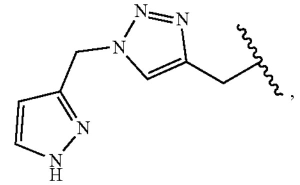
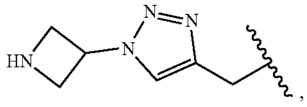
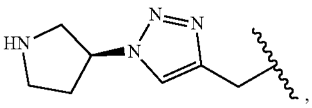
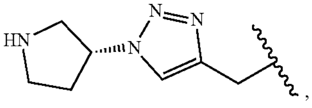
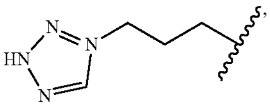
-continued
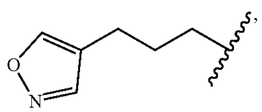
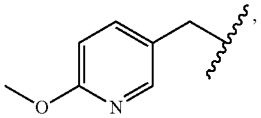
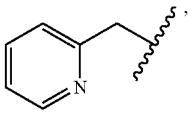
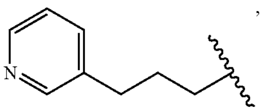
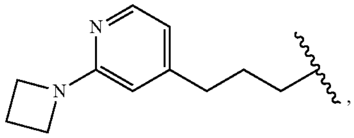
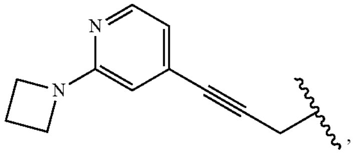
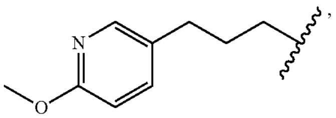
or
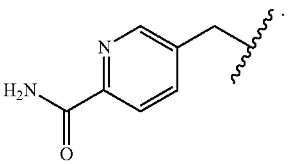
In some embodiments,
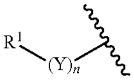
is of formula:
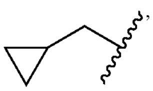
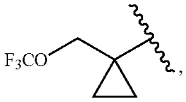
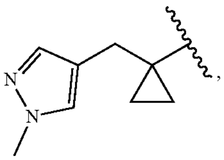
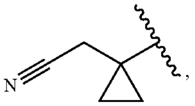
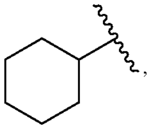
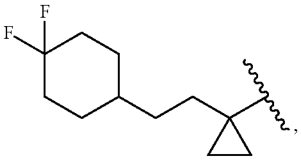

-continued
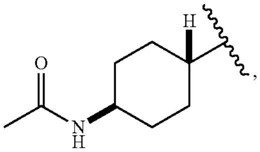
, or
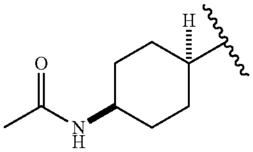
In some embodiments,
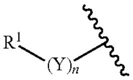
is of formula:
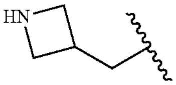
,
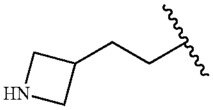
,
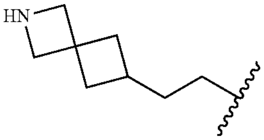
,
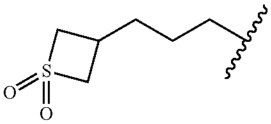
,
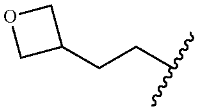
,
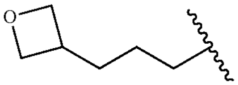
,
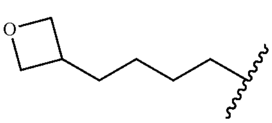
,
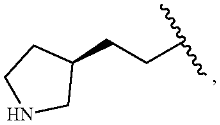
,
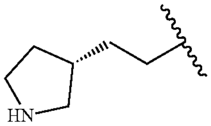
,
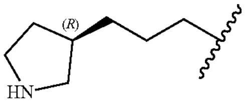
,
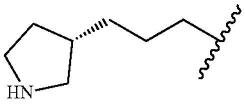
,
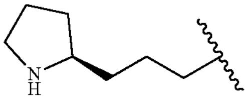
,
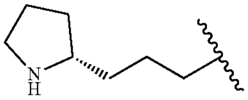
,
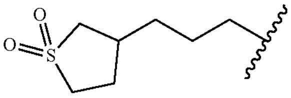
,
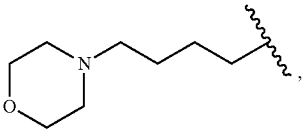
,
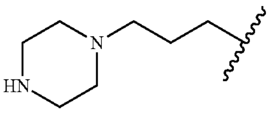
,
-continued
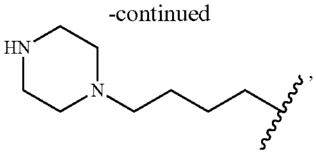
,
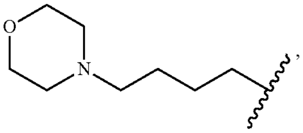
,
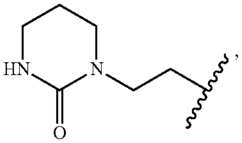
,
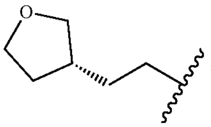
,
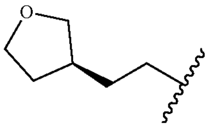
, or
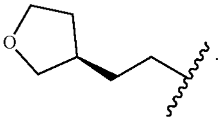
.
In some embodiments,
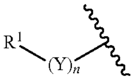
is of formula:
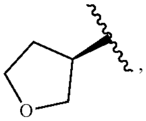
,
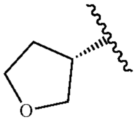
,
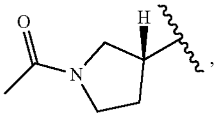
,
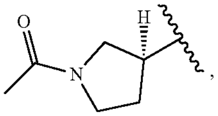
,
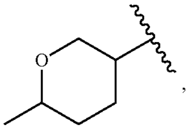
,
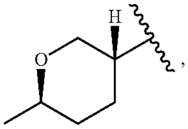
,
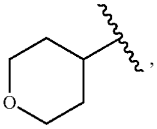
,
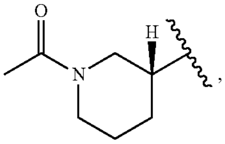
,
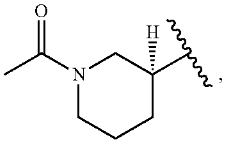
,
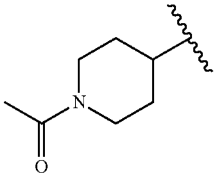
,
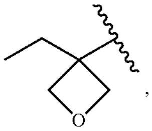
,
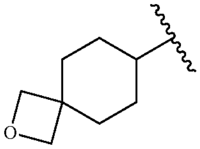
,
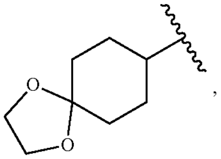
, or -continued
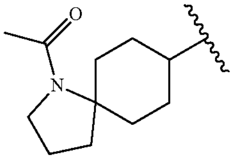
In some embodiments,
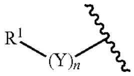
is of formula:
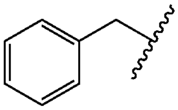,
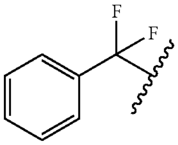,
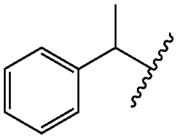,
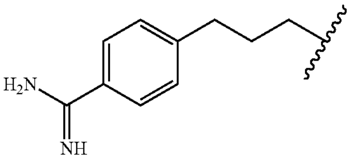,
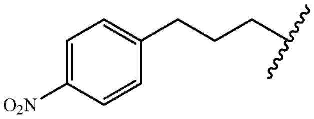,
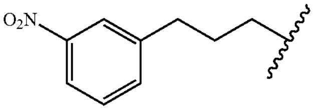,
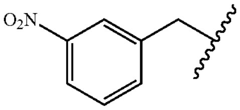,
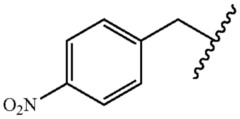,
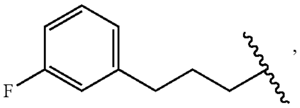,
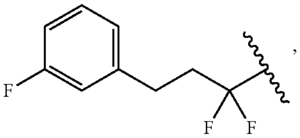,
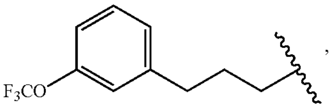,
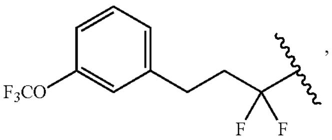,
-continued
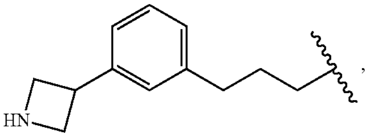,
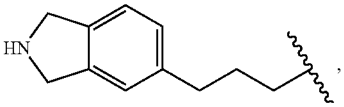,
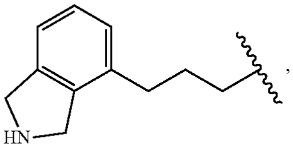,
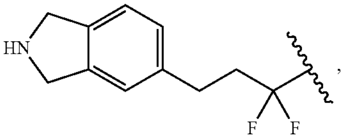, or
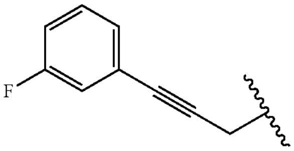.
In some embodiments,
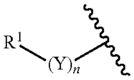
is of formula:
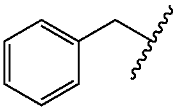,
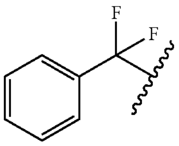,
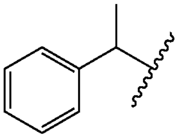,
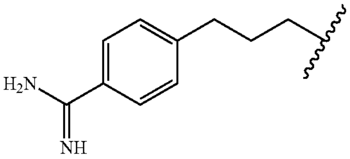,
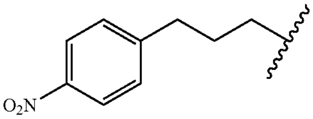,
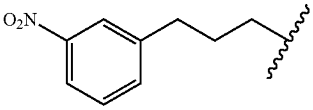,
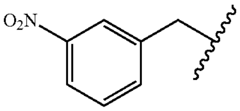,
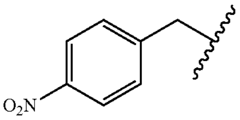, -continued
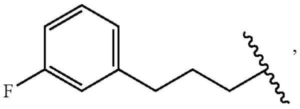,
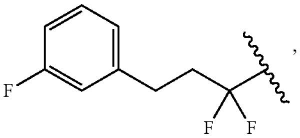,
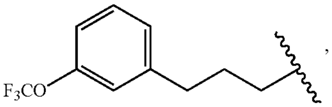,
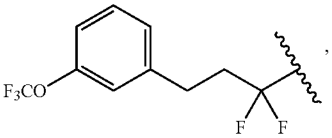,
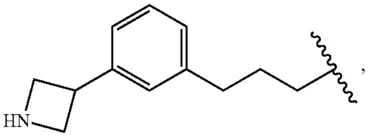, or
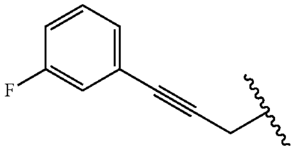..
In some embodiments,
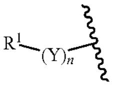
is of formula:
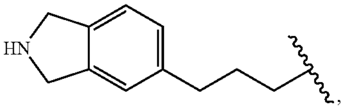,
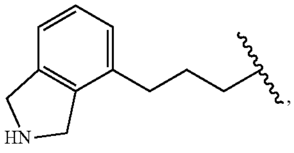, or
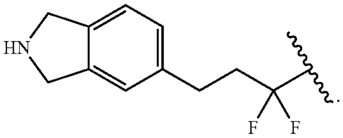.
In some embodiments,
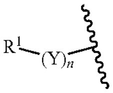
is of formula:
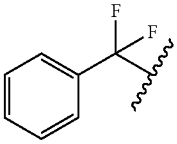,
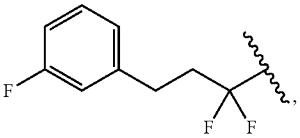,
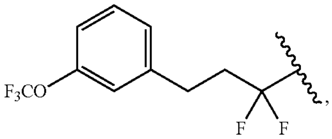, or
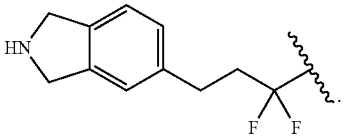.
In some embodiments,
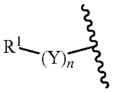
is of formula:
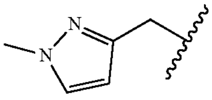,
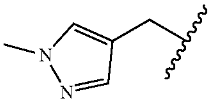,
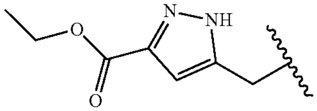,
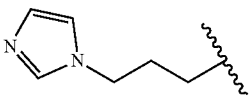,
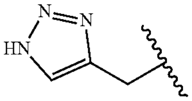,
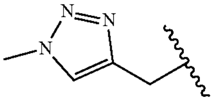,
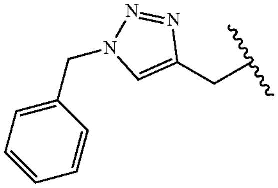,
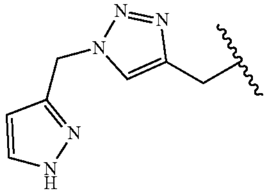, -continued
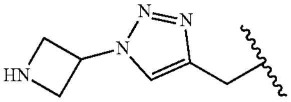,
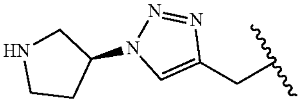,
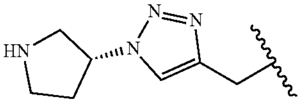, 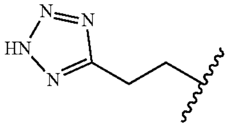,
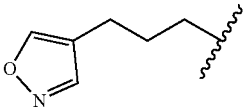, 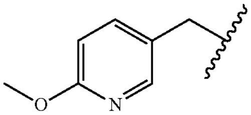,
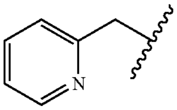, 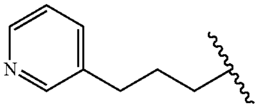,
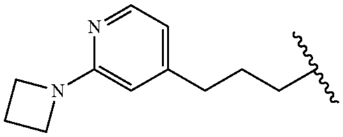,
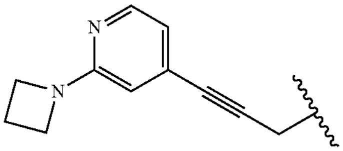,
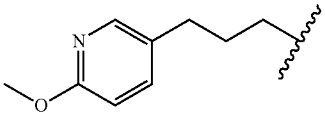, or
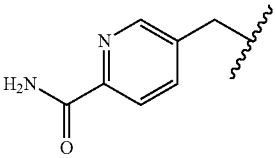.
In some embodiments,
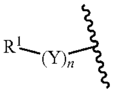
is of formula:
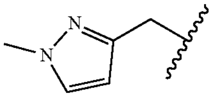, 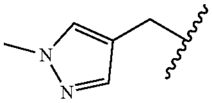,
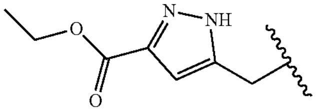,
-continued
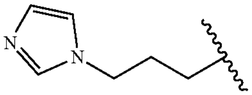, 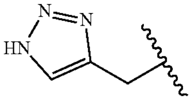,
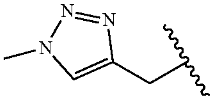, 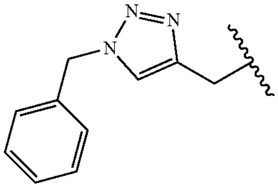,
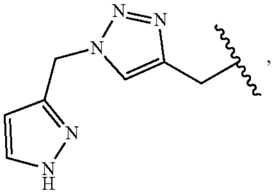,
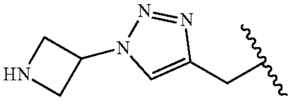,
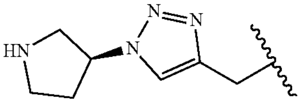,
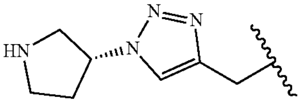,
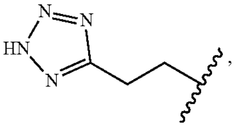, or
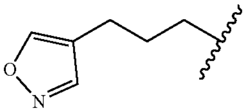.
In some embodiments,
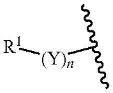
is of formula:
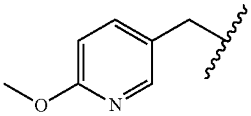, 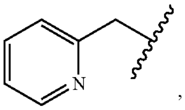,
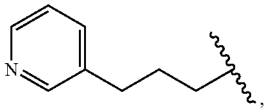,
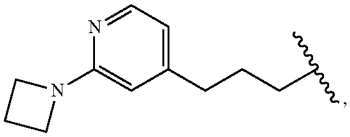, -continued

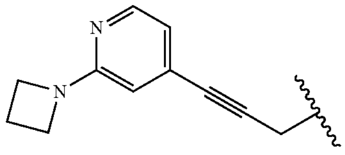

,

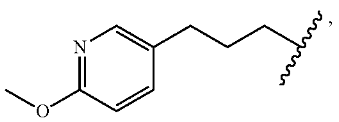

, or

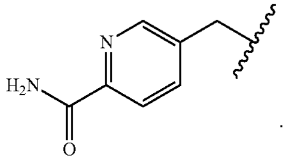

.

In some embodiments,

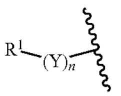

is of formula:

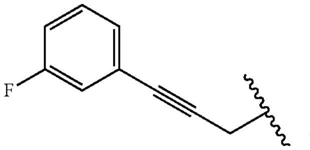

or

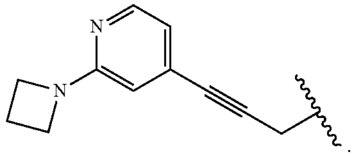

.

$R^3$, $R^{3a}$, $R^A$, and x

As generally described herein, $R^3$ is optionally substituted carbocyclyl, optionally substituted heterocyclyl, optionally substituted aryl, or optionally substituted heteroaryl.

In some embodiments, $R^3$ is optionally substituted $C_{3-10}$ carbocyclyl, optionally substituted 3-10 membered heterocyclyl, optionally substituted $C_{6-10}$ aryl, or optionally substituted 5-10 membered heteroaryl. In some embodiments, $R^3$ is optionally substituted $C_{3-6}$ carbocyclyl, optionally substituted 4-6 membered heterocyclyl, optionally substituted $C_6$ aryl, or optionally substituted 5-6 membered heteroaryl.

In some embodiments, $R^3$ is optionally substituted aryl. In some embodiments, $R^3$ is optionally substituted $C_{6-10}$ aryl. In some embodiments, $R^3$ is optionally substituted phenyl. In some embodiments, $R^3$ is substituted aryl. In some embodiments, $R^3$ is substituted $C_{6-10}$ aryl. In some embodiments, $R^3$ is substituted phenyl. In some embodiments, $R^3$ is unsubstituted aryl. In some embodiments, $R^3$ is unsubstituted $C_{6-10}$ aryl. In some embodiments, $R^3$ is phenyl.

In some embodiments, $R^3$ is of formula:

(A-1)

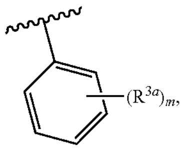

wherein:

each instance of $R^{3a}$ is independently halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —CN, —$OR^A$, —SCN, —$SR^A$, —$SSR^A$, —$N_3$, —NO, —$N(R^A)_2$, —$NO_2$, —C(=O)$R^A$, —C(=O)$OR^A$, —C(=O)$SR^A$, —C(=O)$N(R^A)_2$, —C(=$NR^A$)$R^A$, —C(=$NR^A$)$OR^A$, —C(=$NR^A$)$SR^A$, —C(=$NR^A$)$N(R^A)_2$, —S(=O)$R^A$, —S(=O)$OR^A$, —S(=O)$SR^A$, —S(=O)$N(R^A)_2$, —$S(=O)_2R^A$, —$S(=O)_2OR^A$, —$S(=O)_2SR^A$, —$S(=O)_2N(R^A)_2$, —OC(=O)$R^A$, —OC(=O)$OR^A$, —OC(=O)$SR^A$, —OC(=O)$N(R^A)_2$, —OC(=$NR^A$)$R^A$, —OC(=$NR^A$)$OR^A$, —OC(=$NR^A$)$SR^A$, —OC(=$NR^A$)$N(R^A)_2$, —OS(=O)$R^A$, —OS(=O)$OR^A$, —OS(=O)$SR^A$, —OS(=O)$N(R^A)_2$, —$OS(=O)_2R^A$, —$OS(=O)_2OR^A$, $OS(=O)_2SR^A$, —$OS(=O)_2N(R^A)_2$, —$ON(R^A)_2$, —SC(=O)$R^A$, —SC(=O)$OR^A$, —SC(=O)$SR^A$, —SC(=O)$N(R^A)_2$, —SC(=$NR^A$)$R^A$, —SC(=$NR^A$)$OR^A$, —SC(=$NR^A$)$SR^A$, —SC(=$NR^A$)$N(R^A)_2$, —$NR^A$C(=O)$R^A$, —$NR^A$C(=O)$OR^A$, —$NR^A$C(=O)$SR^A$, —$NR^A$C(=O)$N(R^A)_2$, —$NR^A$C(=$NR^A$)$R^A$, —$NR^A$C(=$NR^A$)$OR^A$, —$NR^A$C(=$NR^A$)$SR^A$, —$NR^A$C(=$NR^A$)$N(R^A)_2$, —$NR^A$S(=O)$R^A$, —$NR^A$S(=O)$OR^A$, —$NR^A$S(=O)$SR^A$, —$NR^A$S(=O)$N(R^A)_2$, —$NR^AS(=O)_2R^A$, —$NR^AS(=O)_2OR^A$, —$NR^AS(=O)_2SR^A$, —$NR^AS(=O)_2N(R^A)_2$, —$Si(R^A)_3$, —$Si(R^A)_2OR^A$, —$Si(R^A)(OR^A)_2$, —$Si(OR^A)_3$, —$OSi(R^A)_3$, —$OSi(R^A)_2OR^A$, —$OSi(R^A)(OR^A)_2$, —$OSi(OR^A)_3$, or —$B(OR^A)_2$;

each instance of $R^A$ is independently hydrogen, optionally substituted acyl, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^A$ are joined together with their intervening atom to form an optionally substituted heterocyclic ring or optionally substituted heteroaryl ring; and m is 0, 1, 2, 3, 4, or 5.

In some embodiments, $R^3$ is of formula (A-1), wherein at least one instance of $R^{3a}$ is halogen, optionally substituted alkyl, optionally substituted alkenyl, optionally substituted alkynyl, —CN, —$NO_2$, —$OR^{1a}$, —$N(R^{1a})_2$, —$NR^{1a}$C(=O)$R^{1a}$, —C(=O)$R^{1a}$, optionally substituted carbocyclyl, optionally substituted heterocyclyl, optionally substituted aryl, or optionally substituted heteroaryl. In some embodiments, $R^3$ is of formula (A-1), wherein at least one instance of $R^{3a}$ is halogen, optionally substituted $C_{1-3}$ alkyl, optionally substituted $C_{2-3}$ alkynyl, —CN, —$NO_2$, —$OR^{1a}$, —$N(R^{1a})_2$, —$NR^{1a}C(=O)R^{1a}$, —$C(=O)R^{1a}$, optionally substituted $C_{3-4}$ carbocyclyl, optionally substituted 3-4 membered heterocyclyl, optionally substituted phenyl, optionally substituted 5-6 membered heteroaryl containing 1, 2, 3, or 4 ring heteroatoms selected from N, O, and S, or optionally substituted 8-10 membered heteroaryl containing 1, 2, 3, or 4 ring heteroatoms selected from N, O, and S. In some embodiments, $R^3$ is of formula (A-1), wherein at least one instance of $R^{3a}$ is —$OR^{1a}$, wherein $R^{1a}$ is unsubstituted $C_{1-3}$ alkyl; —$C(=O)R^{1a}$, wherein $R^{1a}$ is unsubstituted 4-6 membered heterocyclyl containing 1 or 2 ring N atoms; optionally substituted phenyl; optionally substituted 5-6 membered heteroaryl containing 1 ring N atom and 1 ring O atom, 1 ring N atom and 1 ring S atom, or 3 ring N atoms; or optionally substituted 8-10 membered heteroaryl containing 2 ring N atoms and 1 ring S atom.

In some embodiments, $R^3$ of formula (A-1) is of formula:

(A-1a)

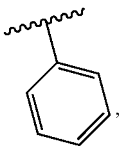

(A-1b)

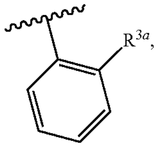

(A-1c)

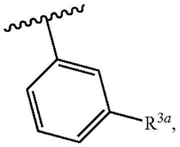

(A-1d)

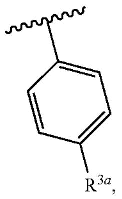

(A-1e)

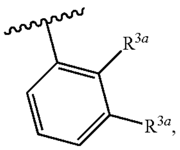

(A-1f)

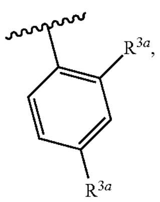

-continued (A-1g)

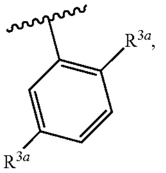

(A-1h)

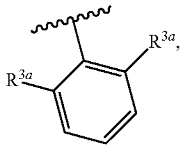

(A-1i)

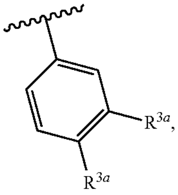

or (A-1j)

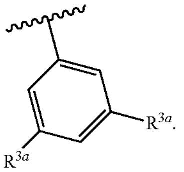

In some embodiments, $R^3$ of formula (A-1) is of formula (A-1a), (A-1c), or (A-1d). In some embodiments, $R^3$ of formula (A-1) is of formula (A-1c) or (A-1d). In some embodiments, $R^3$ of formula (A-1) is of formula (A-1a). In some embodiments, $R^3$ of formula (A-1) is of formula (A-1b). In some embodiments, $R^3$ of formula (A-1) is of formula (A-1c). In some embodiments, $R^3$ of formula (A-1) is of formula (A-1d). In some embodiments, $R^3$ of formula (A-1) is of formula (A-1e). In some embodiments, $R^3$ of formula (A-1) is of formula (A-1f). In some embodiments, $R^3$ of formula (A-1) is of formula (A-1g). In some embodiments, $R^3$ of formula (A-1) is of formula (A-1h). In some embodiments, $R^3$ of formula (A-1) is of formula (A-1i). In some embodiments, $R^3$ of formula (A-1) is of formula (A-1j).

In some embodiments, $R^3$ of formula (A-1) is of formula (A-1c), wherein $R^{3a}$ is optionally substituted heteroaryl. In some embodiments, $R^3$ of formula (A-1) is of formula (A-1c), wherein $R^{3a}$ is optionally substituted 5-6 membered heteroaryl containing 1, 2, 3, or 4 ring heteroatoms selected from N, O, and S. In some embodiments, $R^3$ of formula (A-1) is of formula (A-1c), wherein $R^{3a}$ is optionally substituted 5-6 membered heteroaryl containing 2 ring N atoms, 1 ring N atom and 1 ring O atom, 1 ring N atom and 1 ring S atom, or 3 ring N atoms.

In some embodiments, $R^3$ of formula (A-1) is of formula (A-1d), wherein $R^{3a}$ is halogen, optionally substituted alkyl, optionally substituted alkenyl, optionally substituted alkynyl, —CN, —$NO_2$, —$OR^{1a}$, —$N(R^{1a})_2$, —$NR^{1a}C(=O)R^{1a}$, —$C(=O)R^{1a}$, optionally substituted carbocyclyl, optionally substituted heterocyclyl, optionally substituted aryl, or optionally substituted heteroaryl. In some embodiments, $R^3$ of formula (A-1) is of formula (A-1d), wherein $R^{3a}$ is halogen, optionally substituted $C_{1-3}$ alkyl, optionally substituted $C_{2-3}$ alkynyl, —CN, —$NO_2$, —$OR^{1a}$, —$N(R^{1a})_2$, —$NR^{1a}C(=O)R^{1a}$, —$C(=O)R^{1a}$, optionally substituted $C_{3-4}$ carbocyclyl, optionally substituted 3-4 membered heterocyclyl, optionally substituted phenyl, optionally substituted 5-6 membered heteroaryl containing 1, 2, 3, or 4 ring heteroatoms selected from N, O, and S, or optionally substituted 8-10 membered heteroaryl containing 1, 2, 3, or 4 ring heteroatoms selected from N, O, and S. In some embodiments, $R^3$ of formula (A-1) is of formula (A-1d), wherein $R^{3a}$ is —O-(optionally substituted $C_{1-3}$ alkyl); —C(═O)-(optionally substituted 3-4 membered heterocyclyl); optionally substituted phenyl; optionally substituted 5-6 membered heteroaryl containing 2 ring N atoms, 1 ring N atom and 1 ring O atom, 1 ring N atom and 1 ring S atom, or 3 ring N atoms; or optionally substituted 8-10 membered heteroaryl containing 2 ring N atoms and 1 ring S atom.

In some embodiments, $R^3$ is of formula (A-1), wherein at least one instance of $R^{3a}$ is: —F, —Cl, —Br, —I, $—CH_3$, $—CHF_2$, $—CF_3$, $—CF_2CH_3$, —C≡CH, —CN, $—NO_2$, —OH, $—OCH_3$, $—OCH_2CH_3$, $—OCH_2CH_2CH_3$, $—OCH_2F$, $—OCHF_2$, $—OCF_3$,

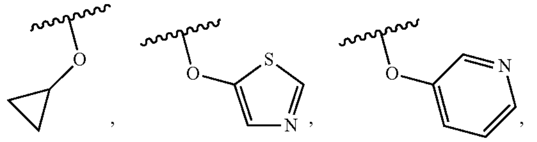 [SMILES: *OC1CC1 ; *Oc1cncs1 ; *Oc1cccnc1]

$—N(CH_3)_2$, —NHC(═O) $CH_3$,

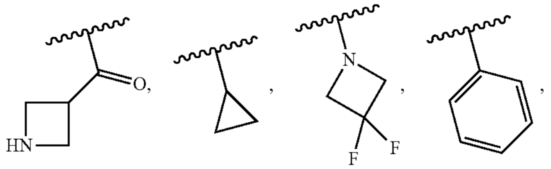

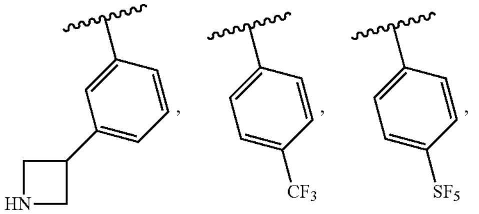

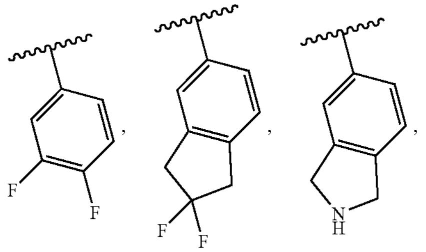

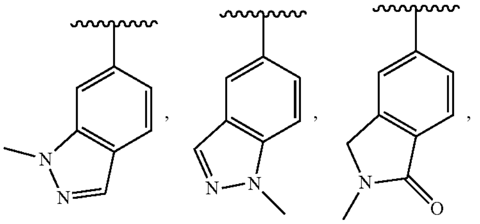

-continued

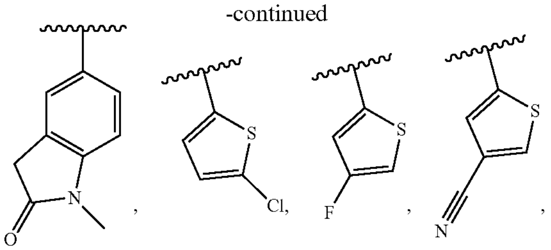

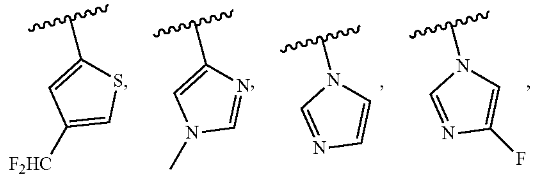

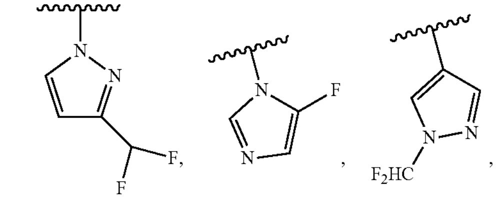

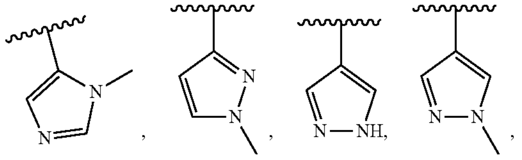

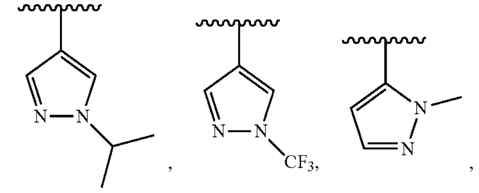

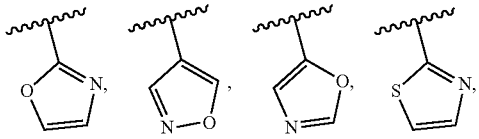

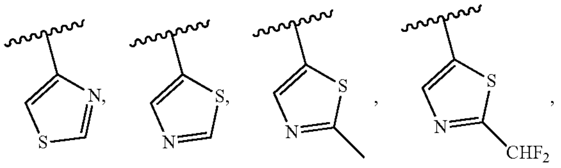

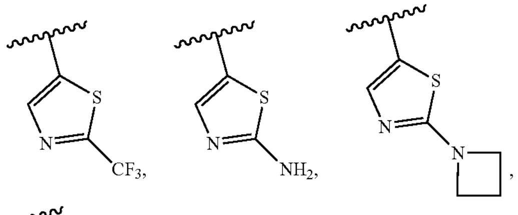

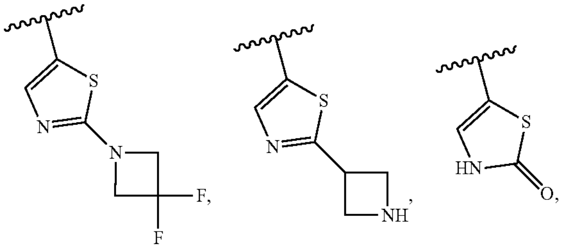

-continued
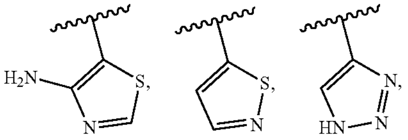
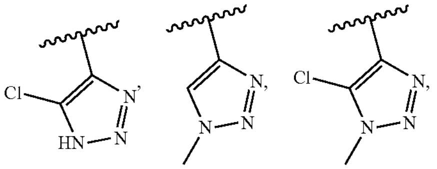
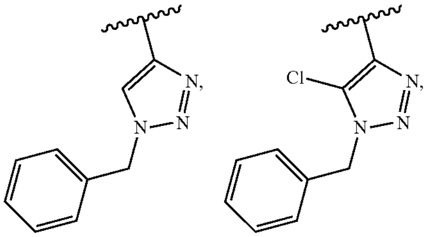
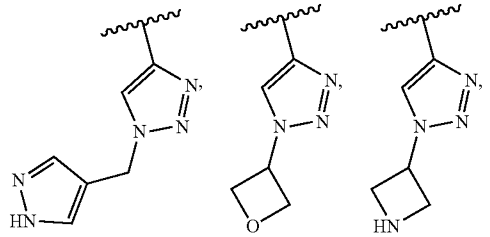
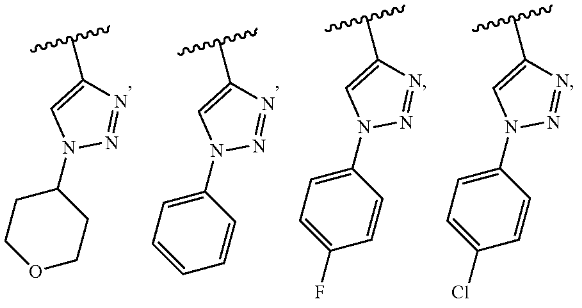
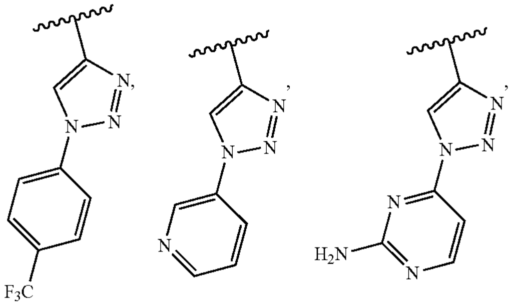
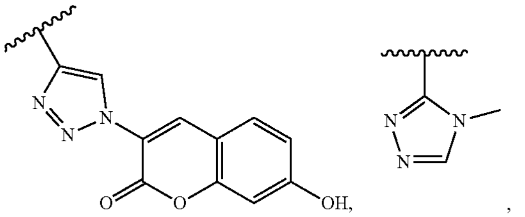
-continued
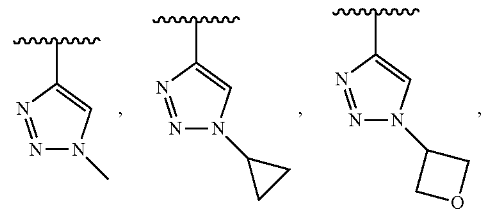
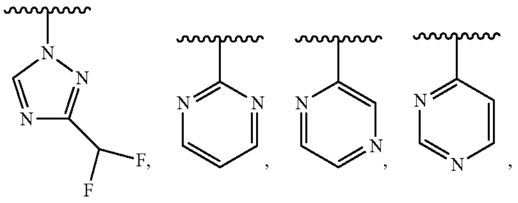
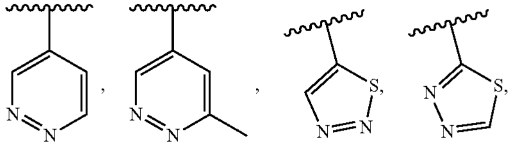
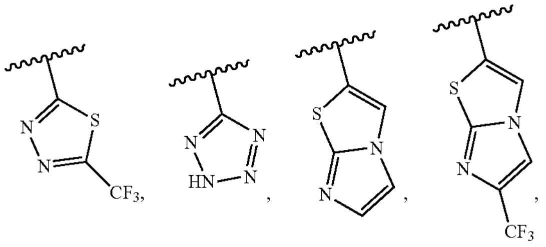
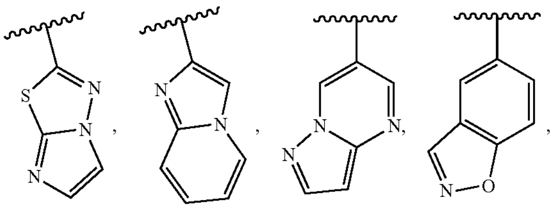
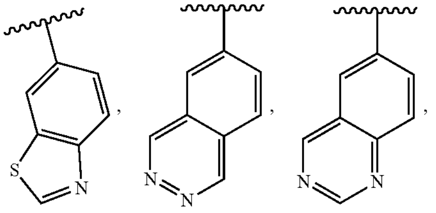
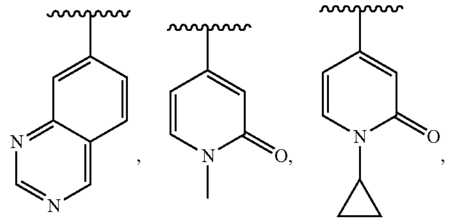
or
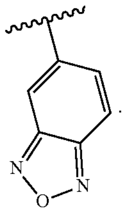

In some embodiments, $R^3$ is of formula (A-1), wherein at least one instance of $R^{3a}$ is:
$-OCH_3$, 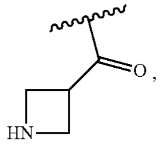, 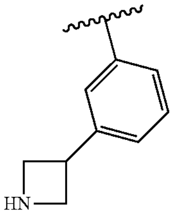,
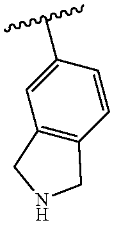, 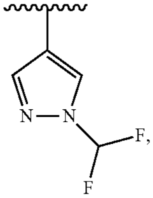 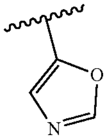, 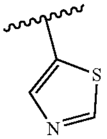,
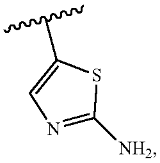 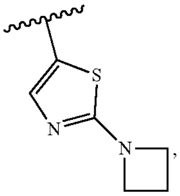, 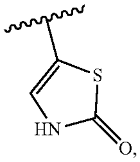
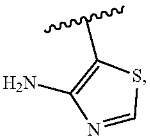 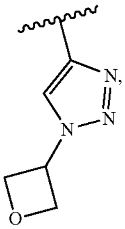 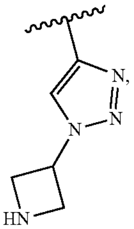
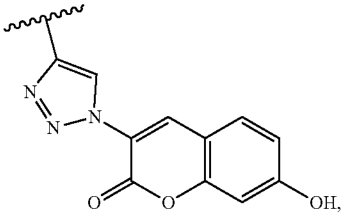 or 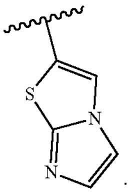.
In some embodiments, $R^3$ is of formula (A-2) to (A-38):
(A-2)
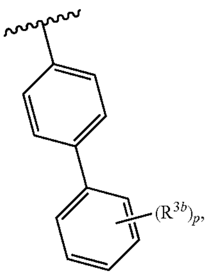
-continued
(A-3)
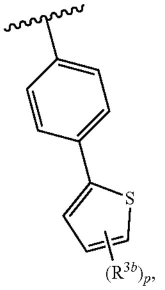
(A-4)
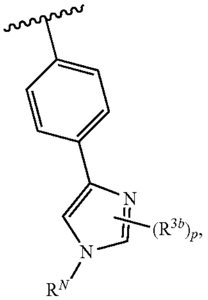
(A-5)
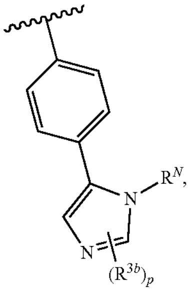
(A-6)
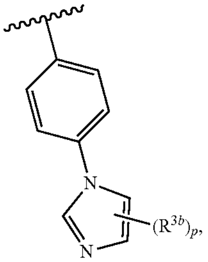
(A-7)
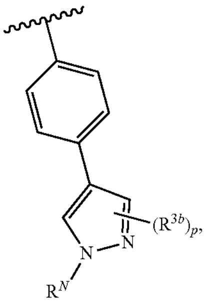

-continued
(A-8)
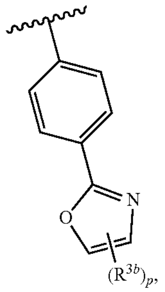
(A-9)
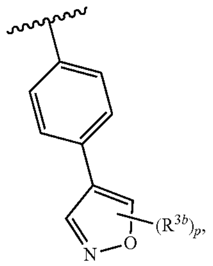
(A-10)
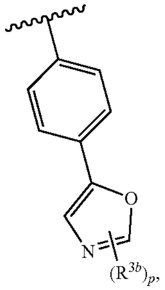
(A-11)
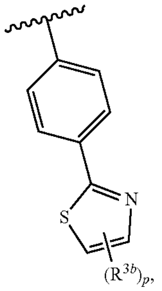
(A-12)
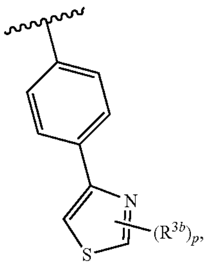
-continued
(A-13)
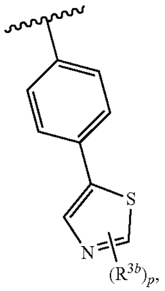
(A-14)
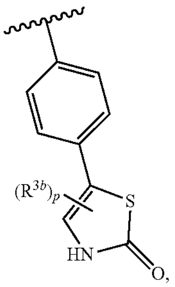
(A-15)
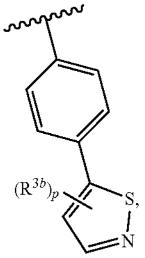
(A-16)
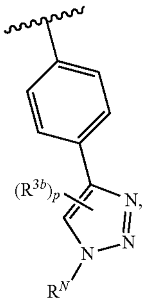
(A-17)
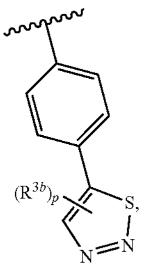

-continued
(A-18)
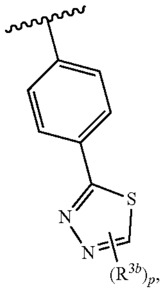
(A-19)
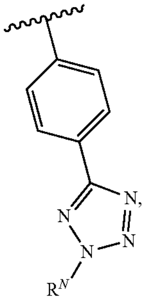
(A-20)
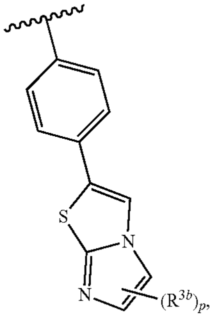
(A-21)
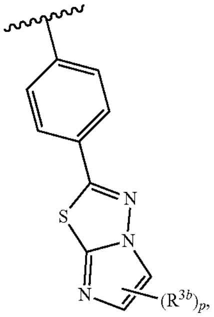
(A-22)
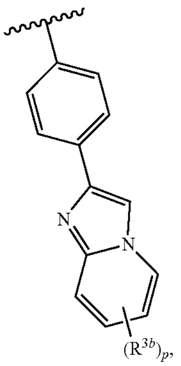
-continued
(A-23)
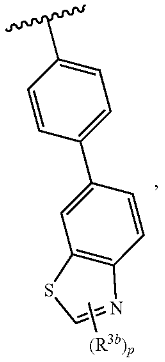
(A-24)
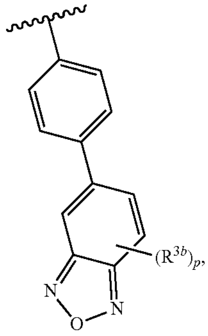
(A-25)
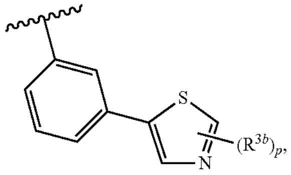
(A-26)
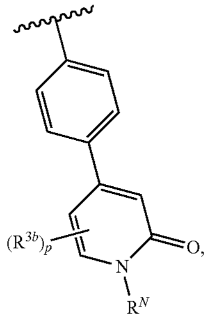
(A-27)
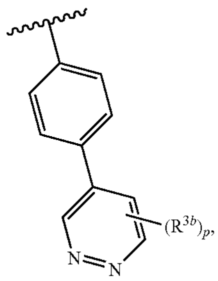

-continued
(A-28)
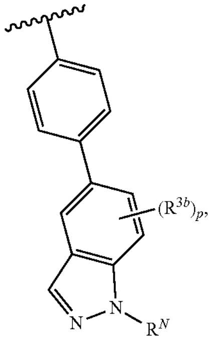
(A-29)
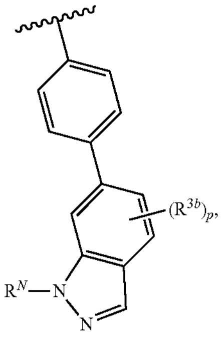
(A-30)
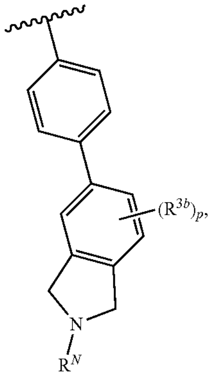
(A-31)
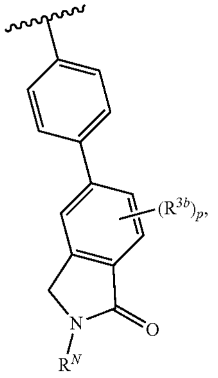
-continued
(A-32)
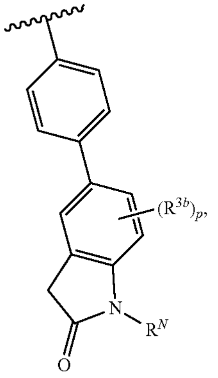
(A-33)
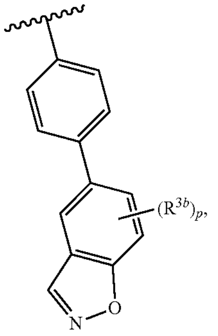
(A-34)
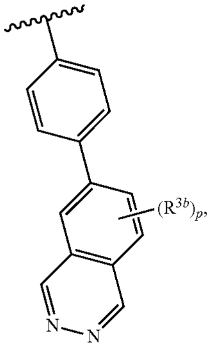
(A-35)
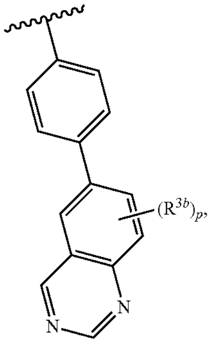

-continued (A-36)

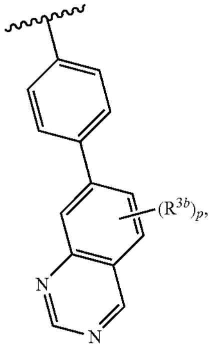

(A-37)

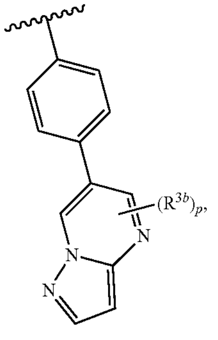

or (A-38)

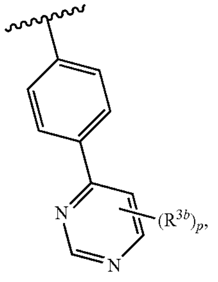

wherein:

each instance of $R^{3b}$ is independently halogen, optionally substituted alkyl, optionally substituted heterocyclyl, —CN, —$N(R^N)_2$, or —$SF_5$, or two instances of $R^{3b}$ are joined together with their intervening atoms to form an optionally substituted carbocyclic ring or optionally substituted heterocyclic ring;

each instance of $R^N$ is independently hydrogen, optionally substituted alkyl, optionally substituted carbocyclyl, optionally substituted heterocyclyl, optionally substituted aryl, optionally substituted heteroaryl, or a nitrogen protecting group, or two instances of $R^N$ are joined together with their intervening nitrogen atom to form an optionally substituted heterocyclic ring; and p is 0, 1, 2, 3, 4, or 5, as valency permits.

In some embodiments, $R^3$ is of formula (A-2). In some embodiments, $R^3$ is of formula (A-3). In some embodiments. $R^3$ is of formula (A-4). In some embodiments, $R^3$ is of formula (A-5). In some embodiments. $R^3$ is of formula (A-6). In some embodiments, $R^3$ is of formula (A-7). In some embodiments. $R^3$ is of formula (A-8). In some embodiments, $R^3$ is of formula (A-9). In some embodiments. $R^3$ is of formula (A-10). In some embodiments, $R^3$ is of formula (A-11). In some embodiments. $R^3$ is of formula (A-12). In some embodiments, $R^3$ is of formula (A-13). In some embodiments. $R^3$ is of formula (A-14). In some embodiments, $R^3$ is of formula (A-15). In some embodiments. $R^3$ is of formula (A-16). In some embodiments, $R^3$ is of formula (A-17). In some embodiments, $R^3$ is of formula (A-18). In some embodiments, $R^3$ is of formula (A-19). In some embodiments. $R^3$ is of formula (A-20). In some embodiments, $R^3$ is of formula (A-21). In some embodiments, $R^3$ is of formula (A-22). In some embodiments, $R^3$ is of formula (A-23). In some embodiments, $R^3$ is of formula (A-24). In some embodiments, $R^3$ is of formula (A-25). In some embodiments, $R^3$ is of formula (A-2) to (A-25). In some embodiments, $R^3$ is of formula (A-26). In some embodiments. $R^3$ is of formula (A-27). In some embodiments, $R^3$ is of formula (A-28). In some embodiments. $R^3$ is of formula (A-29). In some embodiments, $R^3$ is of formula (A-30). In some embodiments, $R^3$ is of formula (A-31). In some embodiments, $R^3$ is of formula (A-32). In some embodiments, $R^3$ is of formula (A-33). In some embodiments, $R^3$ is of formula (A-34). In some embodiments. $R^3$ is of formula (A-35). In some embodiments, $R^3$ is of formula (A-36). In some embodiments, $R^3$ is of formula (A-37). In some embodiments, $R^3$ is of formula (A-38).

In some embodiments, $R^3$ is of formula (A-2), (A-3), (A-4), (A-5), (A-6), (A-7), (A-8), (A-9), (A-10), (A-11), (A-12), (A-13), (A-14), (A-15), (A-16), (A-17), (A-18), (A-19), (A-20), (A-21), (A-22), (A-23), (A-24), (A-25), (A-26), (A-27), (A-28), (A-29), (A-30), (A-31), (A-32), (A-33), (A-34), (A-35), (A-36), (A-37), or (A-38), and p is 0. In some embodiments, $R^3$ is of formula (A-2), (A-3), (A-4), (A-5), (A-6), (A-7), (A-8), (A-9), (A-10), (A-11), (A-12), (A-13), (A-14), (A-15), (A-16), (A-17), (A-18), (A-20), (A-21), (A-22), (A-23), (A-24), (A-25), (A-26), (A-27), (A-28), (A-29), (A-30), (A-31), (A-32), (A-33), (A-34), (A-35), (A-36), (A-37), or (A-38), and p is 1. In some embodiments, $R^3$ is of formula (A-2), (A-3), (A-4), (A-5), (A-6), (A-7), (A-8), (A-9), (A-10), (A-11), (A-12), (A-13), (A-15), (A-20), (A-21), (A-22), (A-23), (A-24), (A-25), (A-26), (A-27), (A-28), (A-29), (A-30), (A-31), (A-32), (A-33), (A-34), (A-35), (A-36), (A-37), or (A-38), and p is 2. In some embodiments, $R^3$ is of formula (A-2), (A-3), (A-6), (A-20), (A-22), (A-23), (A-24), (A-26), (A-27), (A-28), (A-29), (A-30), (A-31), (A-32), (A-33), (A-34), (A-35), (A-36), (A-37), or (A-38), and p is 3. In some embodiments, $R^3$ is of formula (A-2), (A-22), (A-23), (A-28), (A-29), (A-33), (A-34), (A-35), (A-36), or (A-37), and p is 4. In some embodiments, $R^3$ is of formula (A-2), (A-22), (A-34), (A-35), or (A-36), and p is 5.

In some embodiments, $R^3$ of formula (A-2) is of formula:

(A-2a)

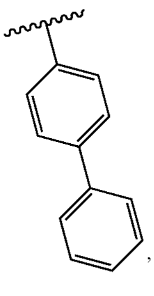

,

-continued (A-2b)

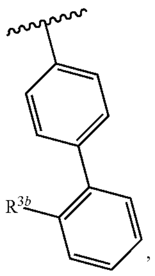

(A-2c)

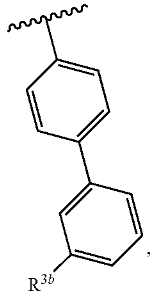

(A-2d)

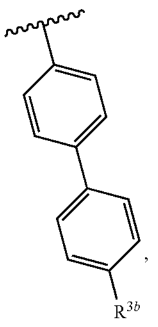

or (A-2e)

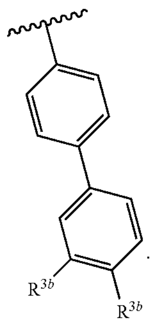

In some embodiments, $R^3$ of formula (A-2) is of formula (A-2a). In some embodiments, $R^3$ of formula (A-2) is of formula (A-2b). In some embodiments, $R^3$ of formula (A-2) is of formula (A-2c). In some embodiments, $R^3$ of formula (A-2) is of formula (A-2d). In some embodiments, $R^3$ of formula (A-2) is of formula (A-2e).

In some embodiments, $R^3$ of formula (A-7) is of formula:

(A-7a)

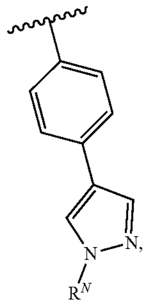

(A-7b)

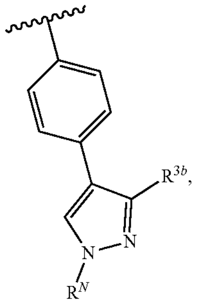

or (A-7c)

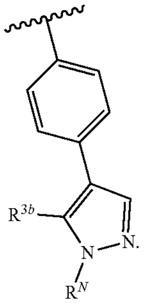

In some embodiments, $R^3$ of formula (A-7) is of formula (A-7a). In some embodiments, $R^3$ of formula (A-7) is of formula (A-7b). In some embodiments, $R^3$ of formula (A-7) is of formula (A-7c).

In some embodiments, $R^3$ of formula (A-10) is of formula:

(A-10a)

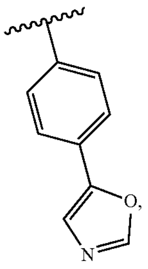

-continued (A-10b)

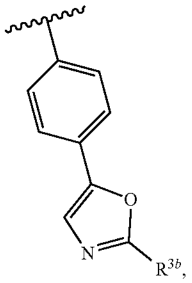

or (A-10c)

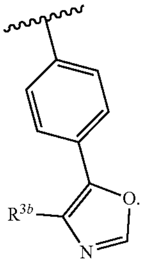

In some embodiments, $R^3$ of formula (A-10) is of formula (A-10a). In some embodiments, $R^3$ of formula (A-10) is of formula (A-10b). In some embodiments, $R^3$ of formula (A-10) is of formula (A-10c).

In some embodiments, $R^3$ of formula (A-13) is of formula:

(A-13a)

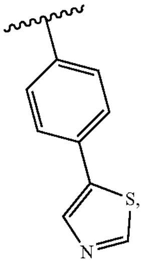

(A-13b)

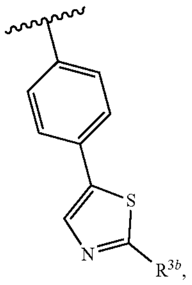

or (A-13c)

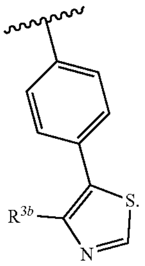

In some embodiments, $R^3$ of formula (A-13) is of formula (A-13a). In some embodiments, $R^3$ of formula (A-13) is of formula (A-13b). In some embodiments, $R^3$ of formula (A-13) is of formula (A-13c).

In some embodiments, $R^3$ of formula (A-14) is of formula:

(A-14a)

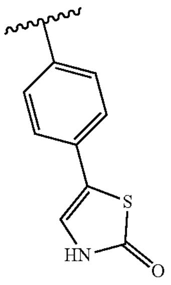

or (A-14b)

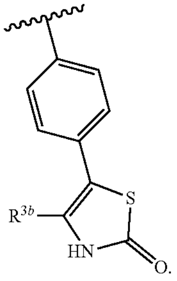

In some embodiments, $R^3$ of formula (A-14) is of formula (A-14a). In some embodiments, $R^3$ of formula (A-14) is of formula (A-14b).

In some embodiments, $R^3$ of formula (A-16) is of formula:

(A-16a)

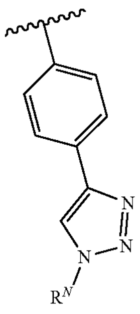

or (A-16b)

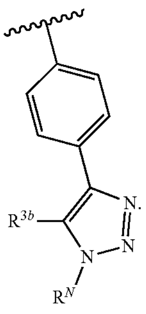

In some embodiments, $R^3$ of formula (A-16) is of formula (A-16a). In some embodiments, $R^3$ of formula (A-16) is of formula (A-16b).

In some embodiments, $R^3$ of formula (A-20) is of formula:

(A-20a)

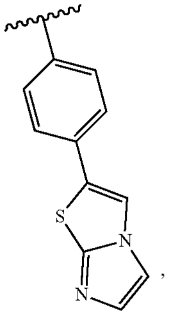

(A-20b)

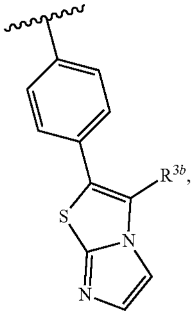

(A-20c)

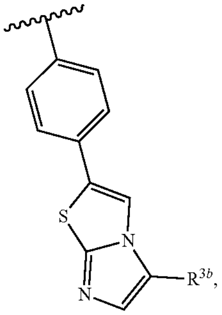

or (A-20d)

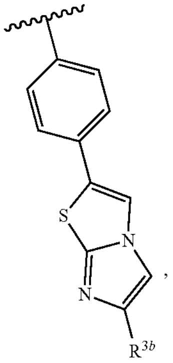

In some embodiments, $R^3$ of formula (A-20) is of formula (A-20a). In some embodiments, $R^3$ of formula (A-20) is of formula (A-20b). In some embodiments, $R^3$ of formula (A-20) is of formula (A-20c). In some embodiments, $R^3$ of formula (A-20) is of formula (A-20d).

In some embodiments, $R^3$ of formula (A-25) is of formula:

(A-25a)

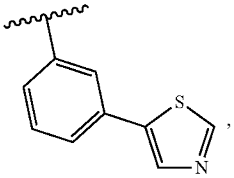

(A-25b)

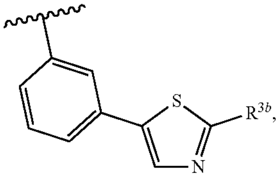

or (A-25c)

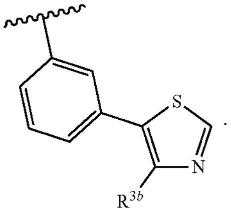

In some embodiments, $R^3$ of formula (A-25) is of formula (A-25a). In some embodiments, $R^3$ of formula (A-25) is of formula (A-25b). In some embodiments, $R^3$ of formula (A-25) is of formula (A-25c).

In some embodiments, $R^3$ of formula (A-26) is of formula:

(A-26a)

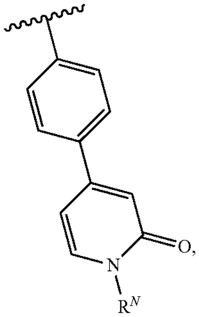

(A-26b)

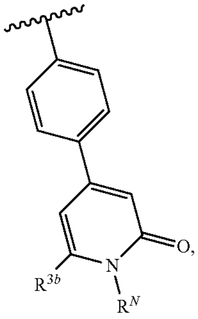

-continued (A-26c)

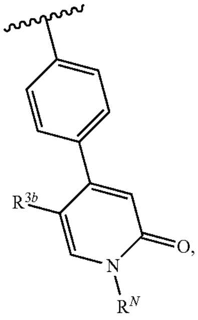

or (A-26d)

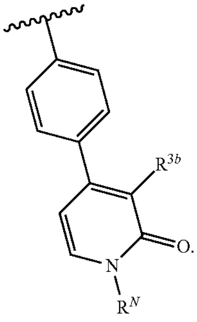

In some embodiments, $R^3$ of formula (A-26) is of formula (A-26a). In some embodiments, $R^3$ of formula (A-26) is of formula (A-26b). In some embodiments, $R^3$ of formula (A-26) is of formula (A-26c). In some embodiments, $R^3$ of formula (A-26) is of formula (A-26d).

In some embodiments, $R^3$ of formula (A-27) is of formula:

(A-27a)

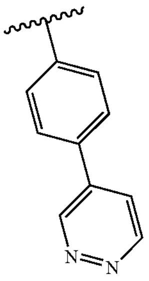

, (A-27b)

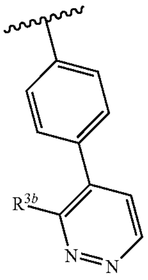

,

-continued (A-27c)

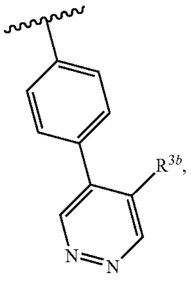

or (A-27d)

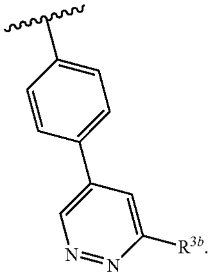

In some embodiments, $R^3$ of formula (A-27) is of formula (A-27a). In some embodiments, $R^3$ of formula (A-27) is of formula (A-27b). In some embodiments, $R^3$ of formula (A-27) is of formula (A-27c). In some embodiments, $R^3$ of formula (A-27) is of formula (A-27d).

In some embodiments, $R^3$ of formula (A-28) is of formula:

(A-28a)

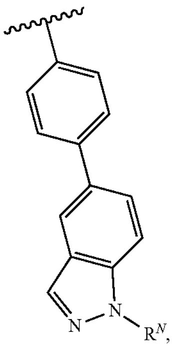

(A-28b)

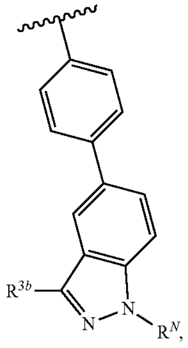

-continued
(A-28c)
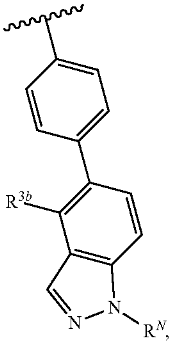
(A-28d)
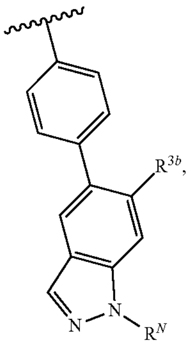
(A-28e)
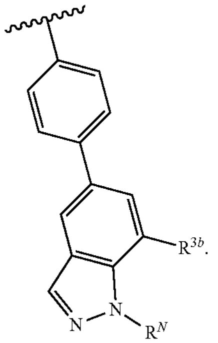
In some embodiments, $R^3$ of formula (A-28) is of formula (A-28a). In some embodiments, $R^3$ of formula (A-28) is of formula (A-28b). In some embodiments, $R^3$ of formula (A-28) is of formula (A-28c). In some embodiments, $R^3$ of formula (A-28) is of formula (A-28d). In some embodiments, $R^3$ of formula (A-28) is of formula (A-28e).
In some embodiments, $R^3$ of formula (A-29) is of formula:
(A-29a)
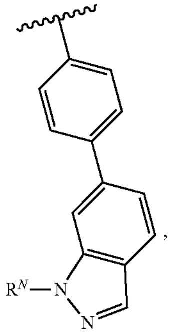
,
(A-29b)
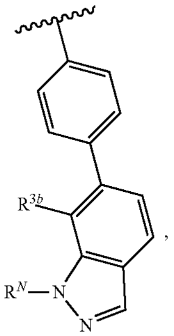
,
(A-29c)
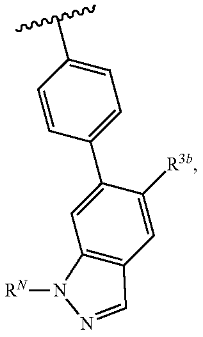
(A-29d)
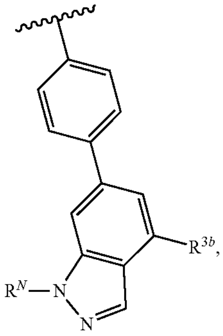
or -continued (A-29e)

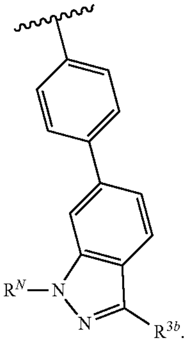

In some embodiments, $R^3$ of formula (A-29) is of formula (A-29a). In some embodiments, $R^3$ of formula (A-29) is of formula (A-29b). In some embodiments, $R^3$ of formula (A-29) is of formula (A-29c). In some embodiments, $R^3$ of formula (A-29) is of formula (A-29d). In some embodiments, $R^3$ of formula (A-29) is of formula (A-29e).

In some embodiments, $R^3$ of formula (A-30) is of formula:

(A-30a)

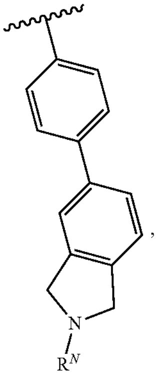

(A-30b)

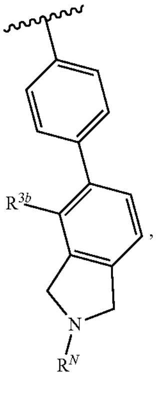

-continued (A-30c)

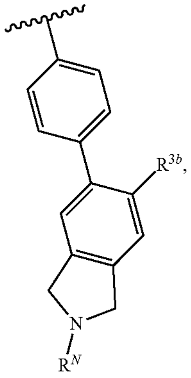

or (A-30d)

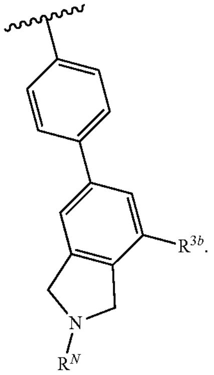

In some embodiments, $R^3$ of formula (A-30) is of formula (A-30a). In some embodiments, $R^3$ of formula (A-30) is of formula (A-30b). In some embodiments, $R^3$ of formula (A-30) is of formula (A-30c). In some embodiments, $R^3$ of formula (A-30) is of formula (A-30d).

In some embodiments, $R^3$ of formula (A-31) is of formula:

(A-31a)

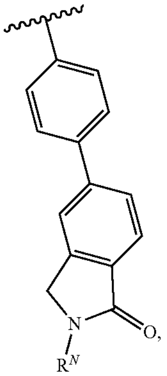

-continued (A-31b)

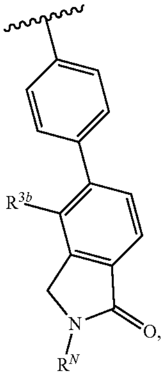

(A-31c)

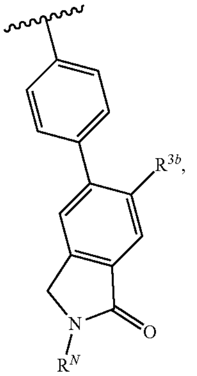

or (A-31d)

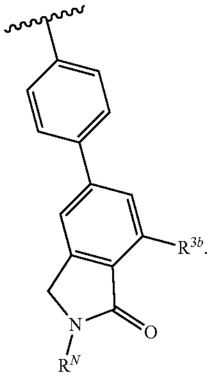

In some embodiments, $R^3$ of formula (A-31) is of formula (A-31a). In some embodiments, $R^3$ of formula (A-31) is of formula (A-31b). In some embodiments, $R^3$ of formula (A-31) is of formula (A-31c). In some embodiments, $R^3$ of formula (A-31) is of formula (A-31d).

In some embodiments, $R^3$ of formula (A-32) is of formula:

(A-32a)

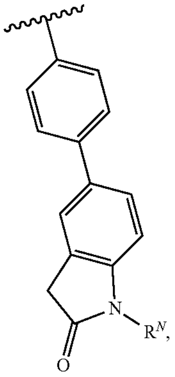

(A-32b)

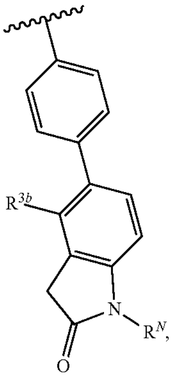

(A-32c)

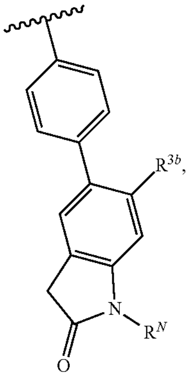

or (A-32d)

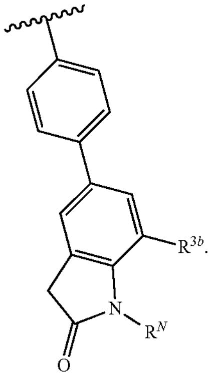

In some embodiments, $R^3$ of formula (A-32) is of formula (A-32a). In some embodiments, $R^3$ of formula (A-32) is of formula (A-32b). In some embodiments, $R^3$ of formula (A-32) is of formula (A-32c). In some embodiments, $R^3$ of formula (A-32) is of formula (A-32d).

In some embodiments, $R^3$ of formula (A-33) is of formula:

(A-33a)

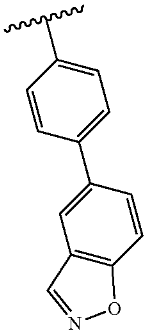

, (A-33b)

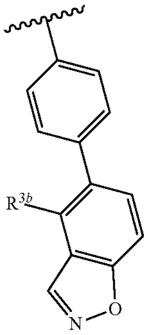

, (A-33c)

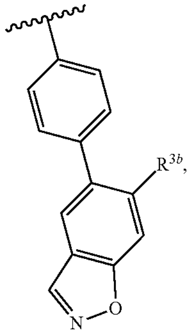

or (A-33d)

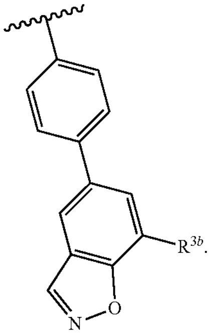

.

In some embodiments, $R^3$ of formula (A-33) is of formula (A-33a). In some embodiments, $R^3$ of formula (A-33) is of formula (A-33b). In some embodiments, $R^3$ of formula (A-33) is of formula (A-33c). In some embodiments, $R^3$ of formula (A-33) is of formula (A-33d).

In some embodiments, $R^3$ of formula (A-34) is of formula:

(A-34a)

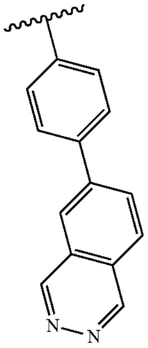

, (A-34b)

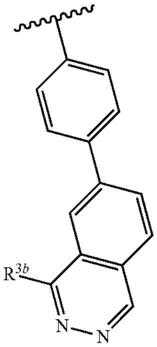

, (A-34c)

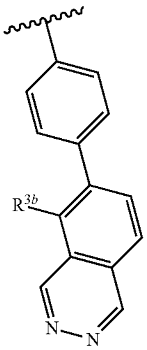

, (A-34d)

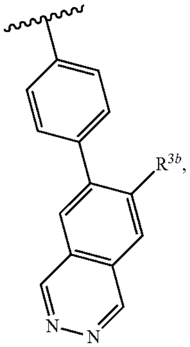

,

-continued (A-34e)

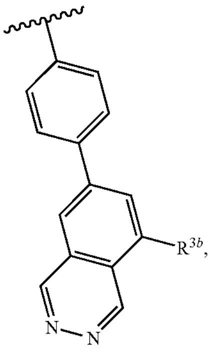

or (A-34f)

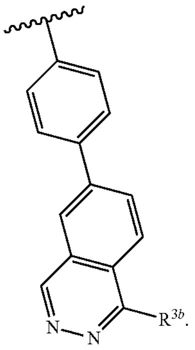

In some embodiments, $R^3$ of formula (A-34) is of formula (A-34a). In some embodiments, $R^3$ of formula (A-34) is of formula (A-34b). In some embodiments, $R^3$ of formula (A-34) is of formula (A-34c). In some embodiments, $R^3$ of formula (A-34) is of formula (A-34d). In some embodiments, $R^3$ of formula (A-34) is of formula (A-34e). In some embodiments, $R^3$ of formula (A-34) is of formula (A-34f).

In some embodiments, $R^3$ of formula (A-35) is of formula:

(A-35a)

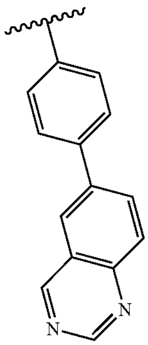

,

-continued (A-35b)

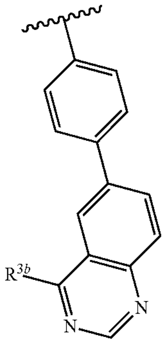

, (A-35c)

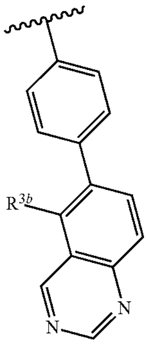

, (A-35d)

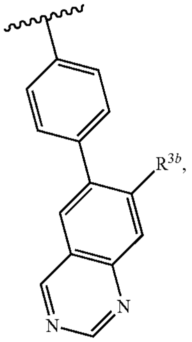

(A-35e)

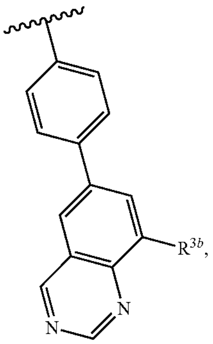

or

-continued (A-35f)

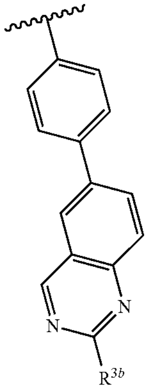

.

In some embodiments, $R^3$ of formula (A-35) is of formula (A-35a). In some embodiments, $R^3$ of formula (A-35) is of formula (A-35b). In some embodiments, $R^3$ of formula (A-35) is of formula (A-35c). In some embodiments, $R^3$ of formula (A-35) is of formula (A-35d). In some embodiments, $R^3$ of formula (A-35) is of formula (A-35e). In some embodiments, $R^3$ of formula (A-35) is of formula (A-35f).

In some embodiments, $R^3$ of formula (A-36) is of formula:

(A-36a)

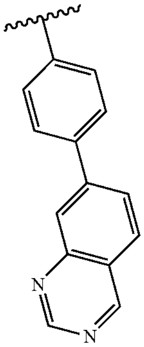

, (A-36b)

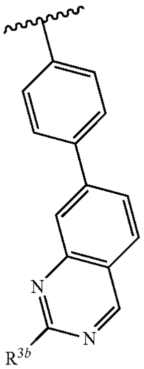

,

-continued (A-36c)

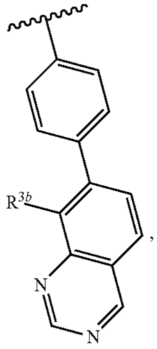

, (A-36d)

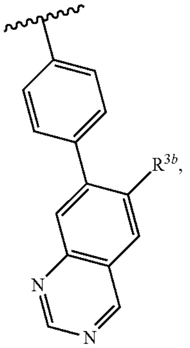

, (A-36e)

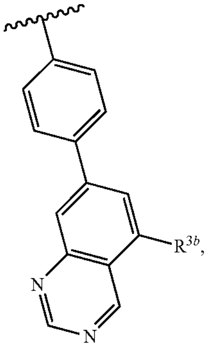

, or (A-36f)

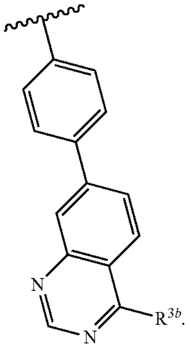

.

In some embodiments, $R^3$ of formula (A-36) is of formula (A-36a). In some embodiments, $R^3$ of formula (A-36) is of formula (A-36b). In some embodiments, $R^3$ of formula (A-36) is of formula (A-36c). In some embodiments, $R^3$ of formula (A-36) is of formula (A-36d). In some embodiments, $R^3$ of formula (A-36) is of formula (A-36e). In some embodiments, $R^3$ of formula (A-36) is of formula (A-36f).

In some embodiments, $R^3$ of formula (A-37) is of formula:

(A-37a)

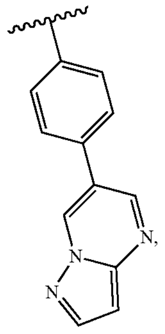

(A-37b)

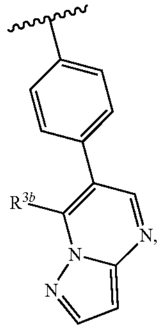

(A-37c)

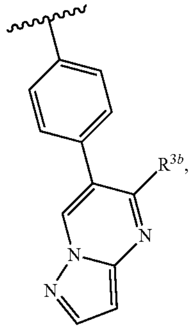

(A-37d)

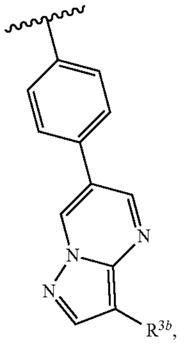

or

-continued (A-37e)

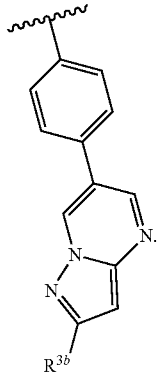

In some embodiments, $R^3$ of formula (A-37) is of formula (A-37a). In some embodiments, $R^3$ of formula (A-37) is of formula (A-37b). In some embodiments, $R^3$ of formula (A-37) is of formula (A-37c). In some embodiments, $R^3$ of formula (A-37) is of formula (A-37d). In some embodiments, $R^3$ of formula (A-37) is of formula (A-37e).

In some embodiments, $R^3$ is of formula (A-2b), (A-2c), (A-2d), (A-7b), (A-7c), (A-10a), (A-10b), (A-10c), (A-13a), (A-13b), (A-13c), (A-14b), (A-16b), (A-20b), (A-20c), (A-20d), (A-25b), or (A-25c), wherein $R^{3b}$ is halogen, unsubstituted $C_{1-3}$ alkyl, $C_{1-3}$ haloalkyl, optionally substituted 4-6 membered heterocyclyl containing 1 or 2 N atoms, —CN, —$N(R^N)_2$, or —$SF_5$. In some embodiments, $R^3$ is of formula (A-2b), (A-2c), (A-2d), (A-7b), (A-7c), (A-10a), (A-10b), (A-10c), (A-13a), (A-13b), (A-13c), (A-14b), (A-16b), (A-20b), (A-20c), (A-20d), (A-25b), or (A-25c), wherein $R^{3b}$ is —F, —Cl, —CN, —$CH_3$, —$CHF_2$, —$CF_3$, —$NH_2$, —$SF_5$,

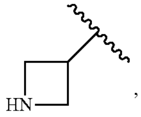

,

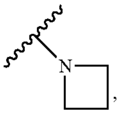

, or

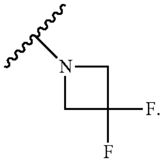

In some embodiments, $R^3$ is of formula (A-2e), wherein two instances of $R^{3b}$ are joined together with their intervening atoms to form an optionally substituted $C_{5-6}$ carbocyclic ring or optionally substituted 5-6 membered heterocyclic ring. In some embodiments, $R^3$ is of formula (A-2e), wherein two instances of $R^{3b}$ are joined together with their intervening atoms to form

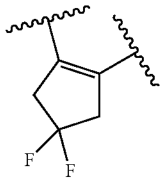

or

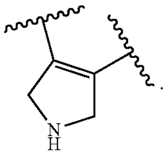

In some embodiments, $R^3$ is of formula (A-7a), (A-7b), (A-7c), (A-16a), (A-16b), (A-26a), (A-28a), (A-29a), (A-31a), or (A-32a), wherein $R^N$ is optionally substituted alkyl. In some embodiments, $R^3$ is of formula (A-7a), (A-7b), (A-7c), (A-16a), (A-16b), (A-26a), (A-28a), (A-29a), (A-31a), or (A-32a), wherein $R^N$ is $C_{1-3}$ alkyl or $C_{1-3}$ haloalkyl. In some embodiments, $R^3$ is of formula (A-7a), (A-7b), (A-7c), (A-16a), (A-16b), (A-26a), (A-28a), (A-29a), (A-31a), or (A-32a), wherein $R^N$ is $—CH_3$ or $—CHF_2$.
In some embodiments, $R^3$ is of formula:
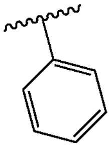,
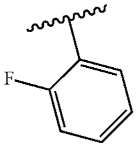,
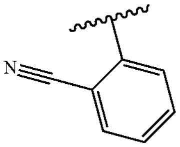,
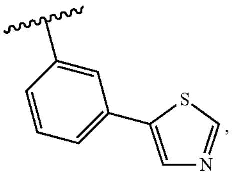,
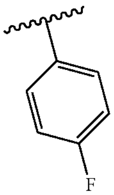,
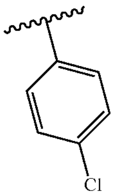,
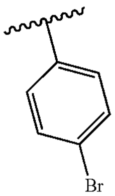,
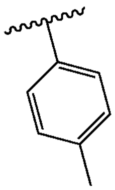,
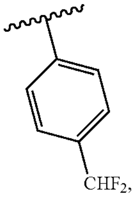,
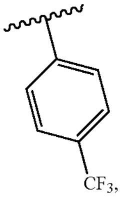,
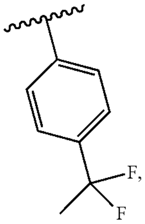,
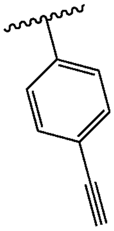,
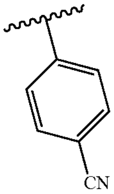,
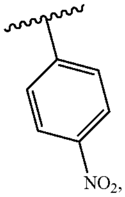,
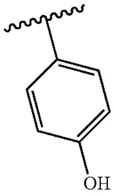,
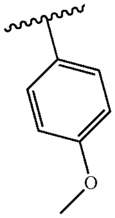,
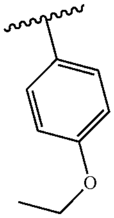,
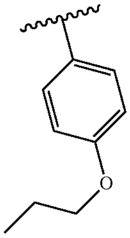,
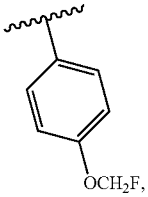,
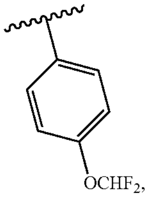,
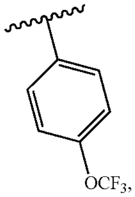,
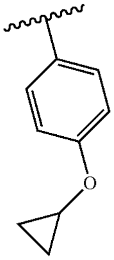,
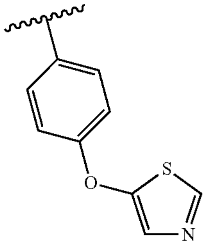,
-continued
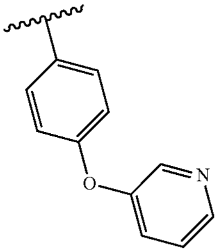,
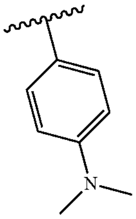,
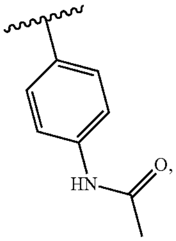,
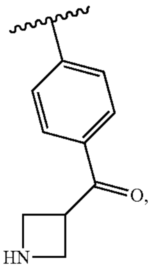,
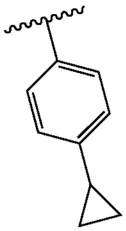,
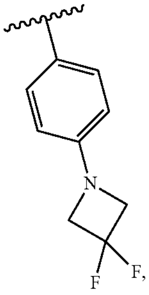,
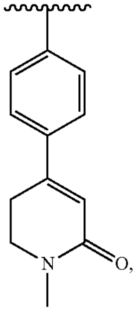,
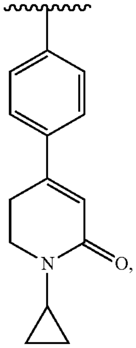,
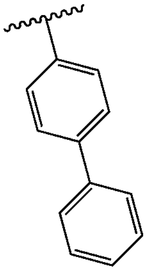,
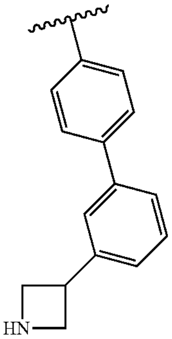,
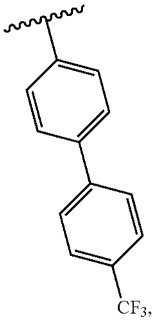,
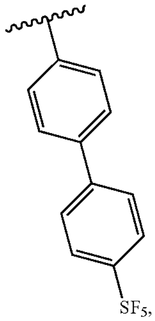,
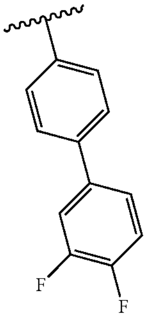,
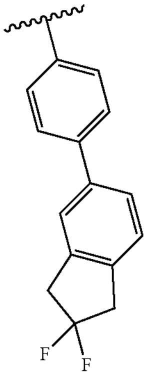,
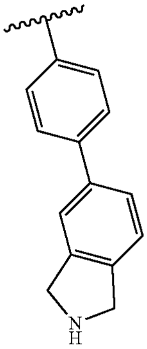, -continued
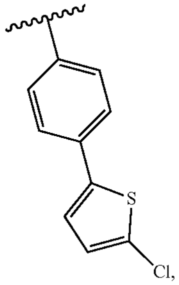
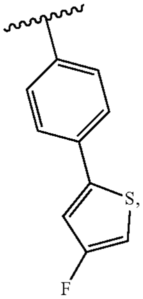
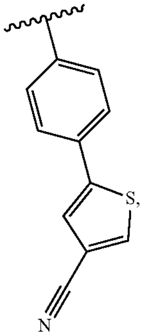
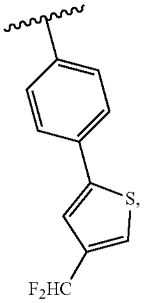
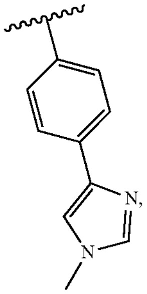
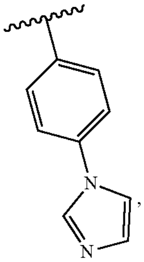
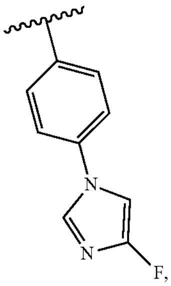
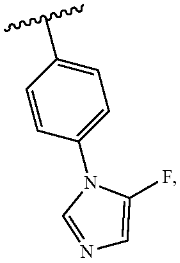
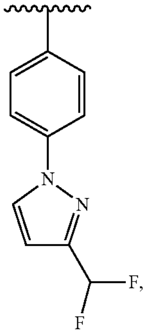
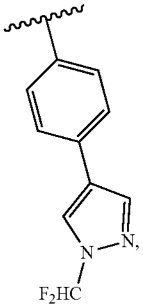
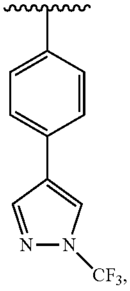
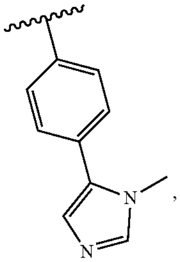
-continued
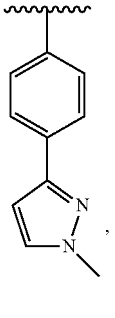
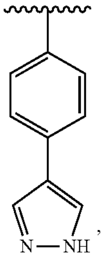
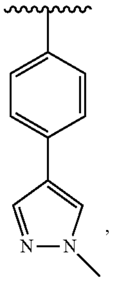
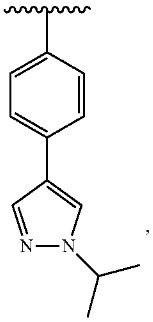
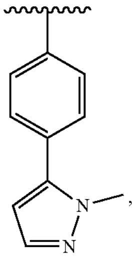
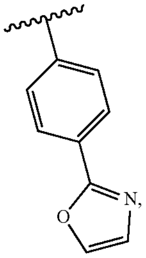
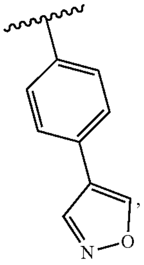
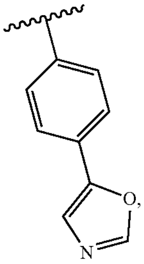
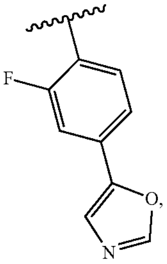
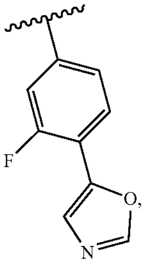
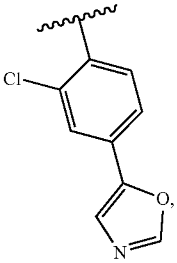
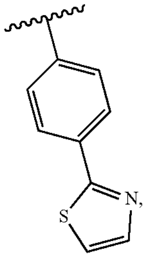
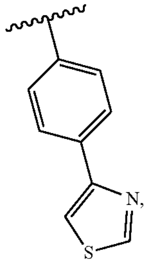
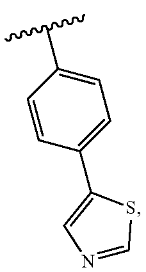
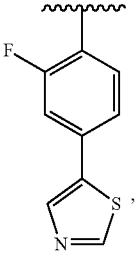
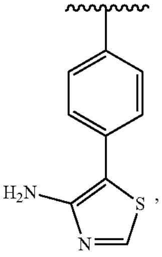
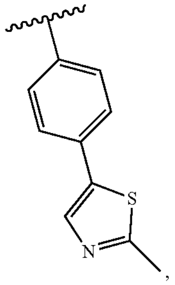
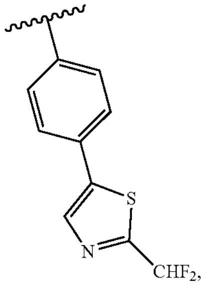

-continued
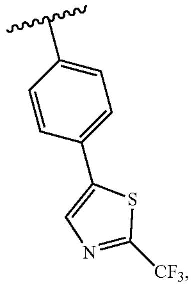
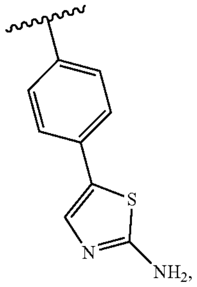
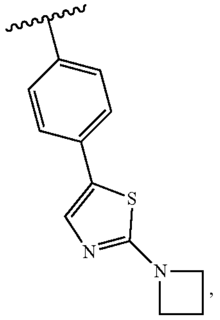
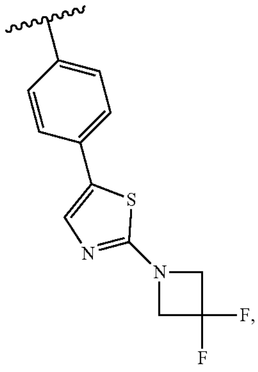
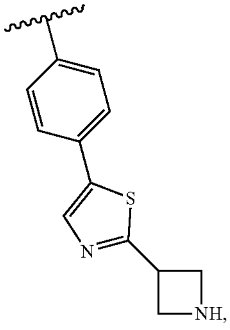
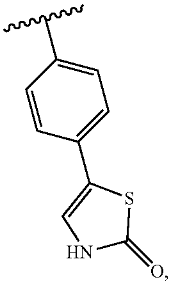
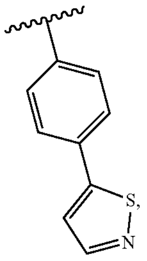
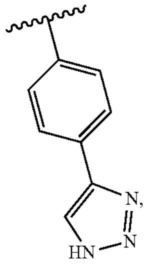
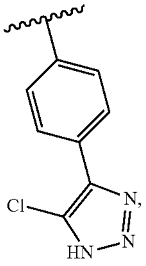
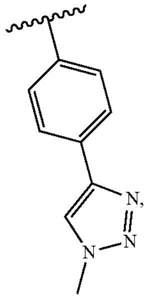
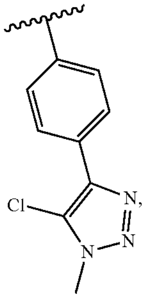
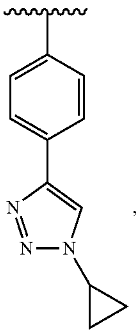
,
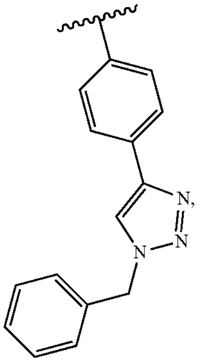
-continued
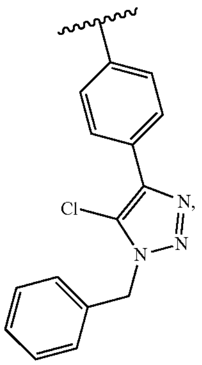
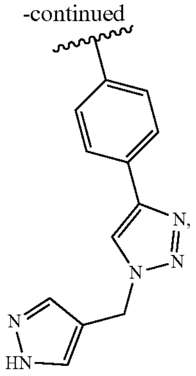
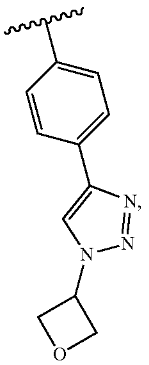
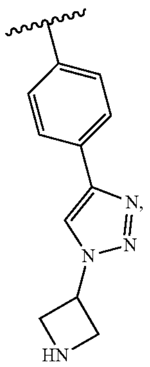
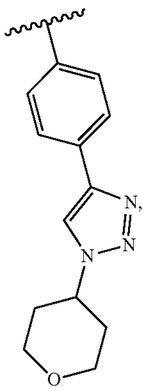
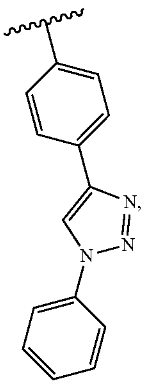
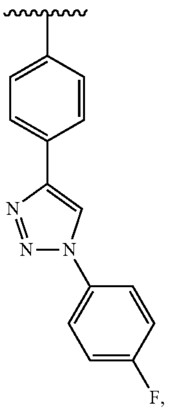
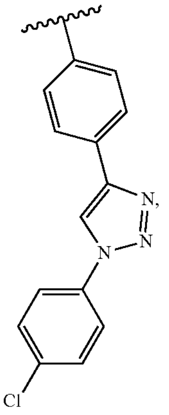
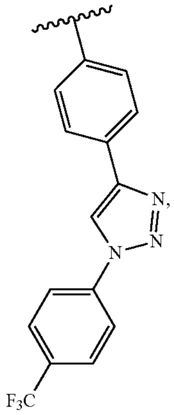
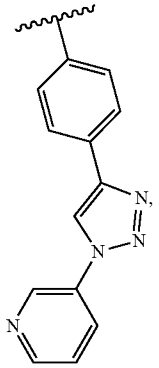
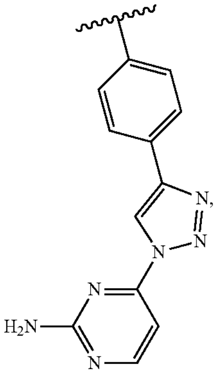

-continued
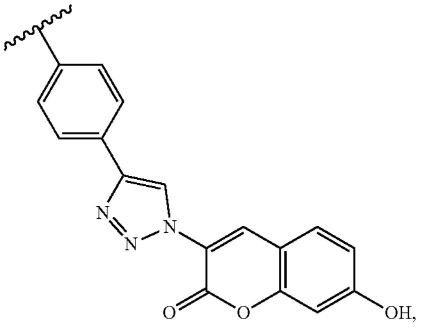
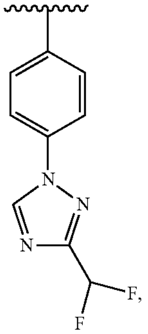
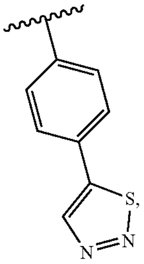
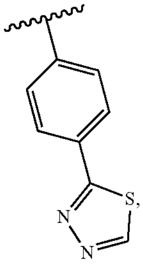
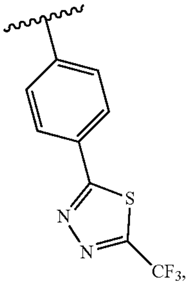
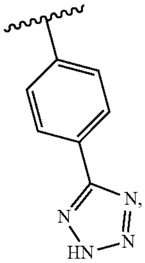
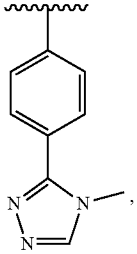
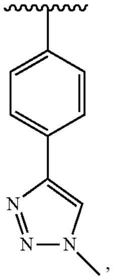
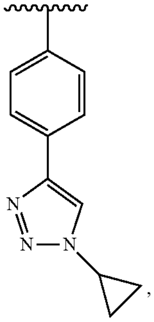
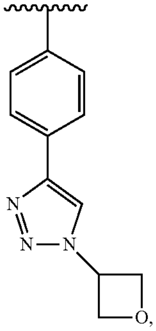
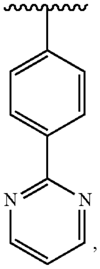
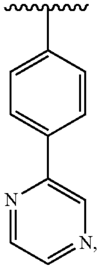
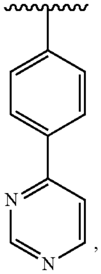
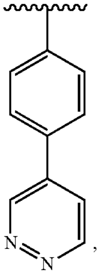
-continued
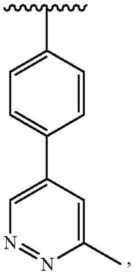
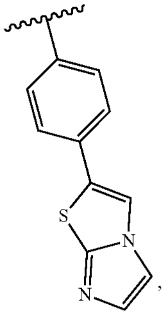
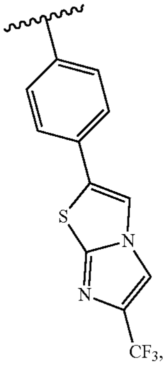
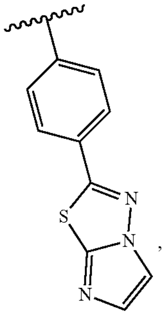
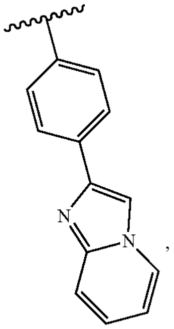
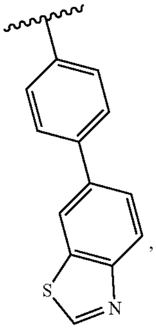
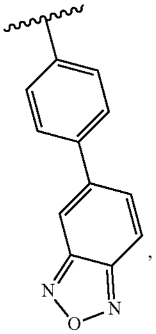
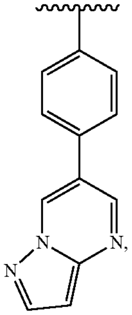
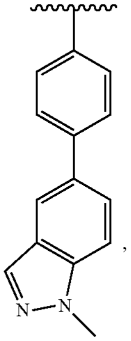
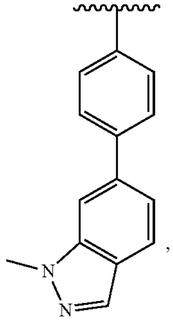
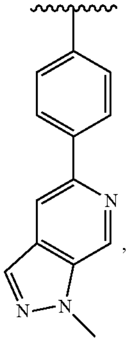
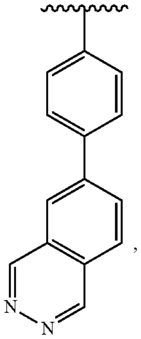

-continued
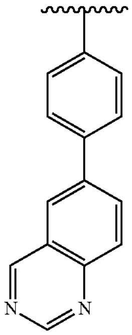, 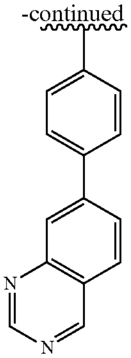, 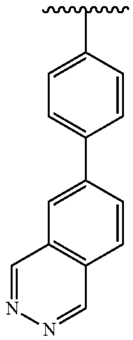,
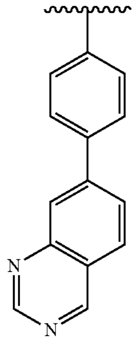, 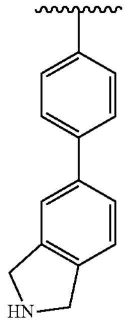, 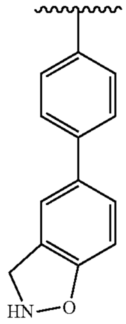,
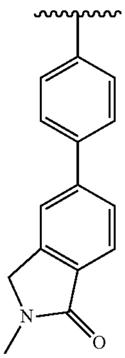, 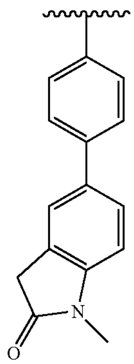, 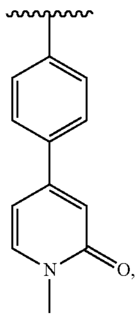
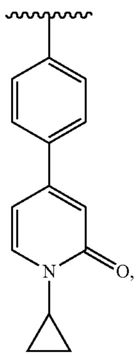 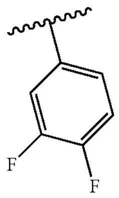, 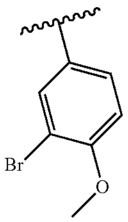,
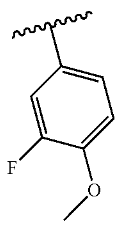, 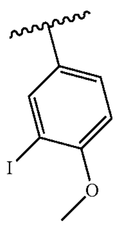, 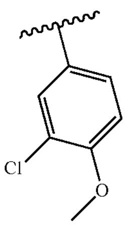,
-continued
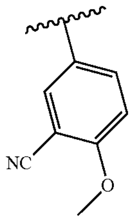, or 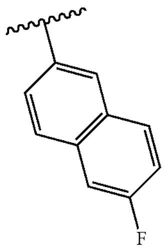.
In some embodiments, $R^3$ is of formula:
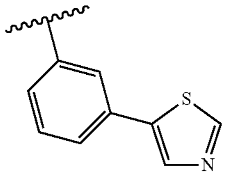, 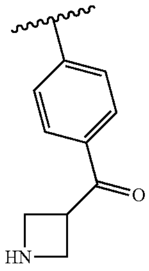, 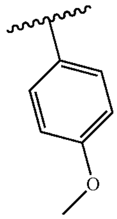,
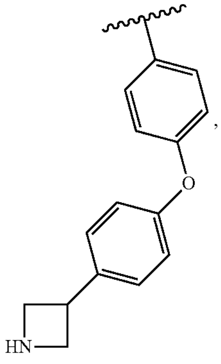, 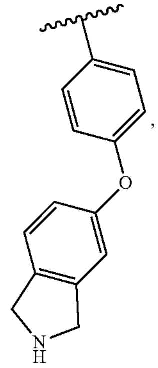, 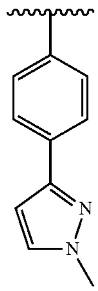,
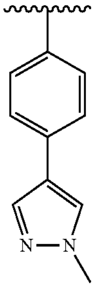, 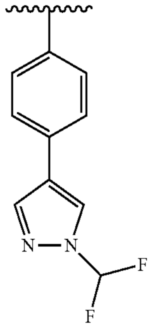, 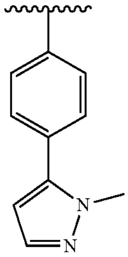,
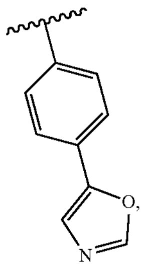 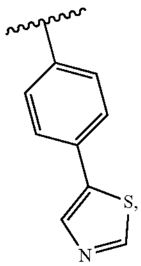 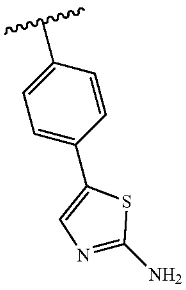, -continued
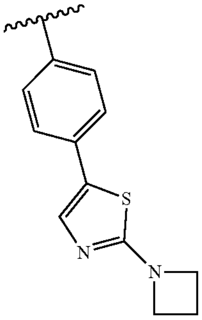
,
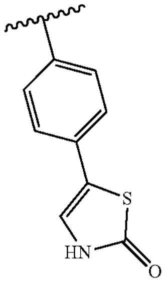
,
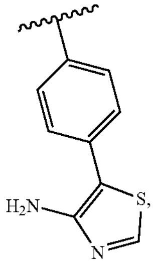
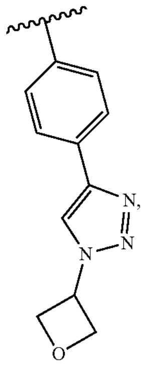
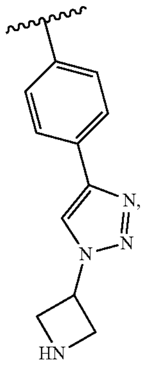
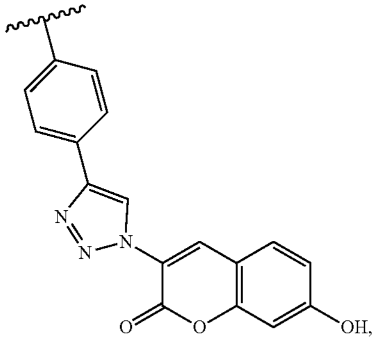
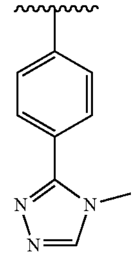
,
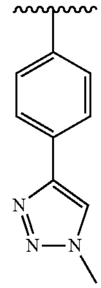
,
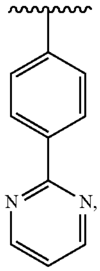
,
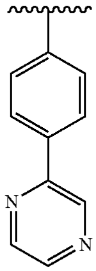
,
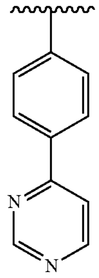
,
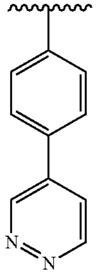
, or
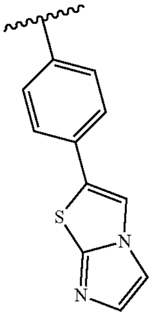
.
In some embodiments, $R^3$ is of formula:
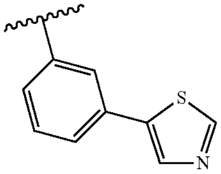
,
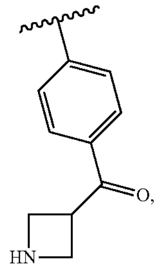
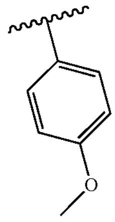
,
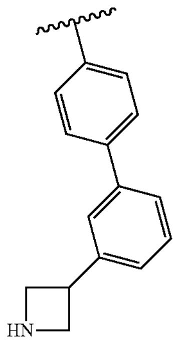
,
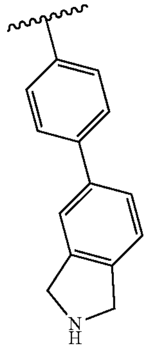
,
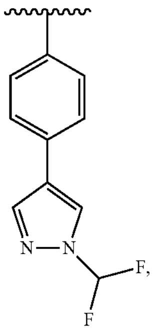
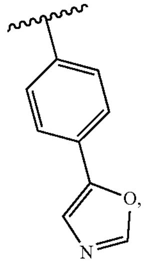
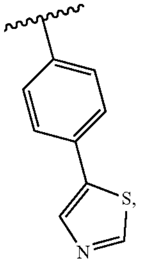
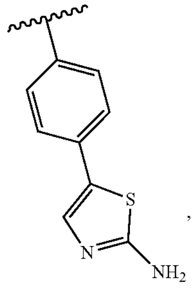
,
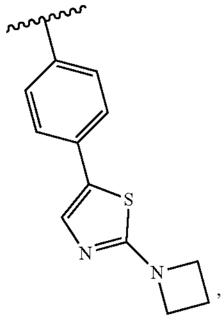
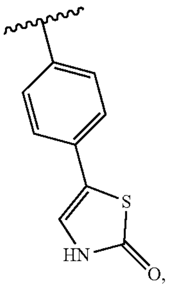
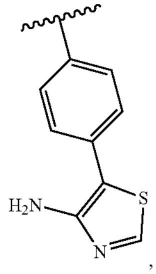
,
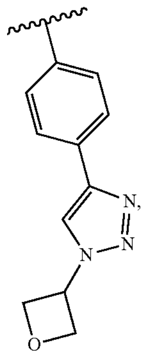
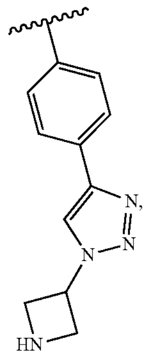

-continued

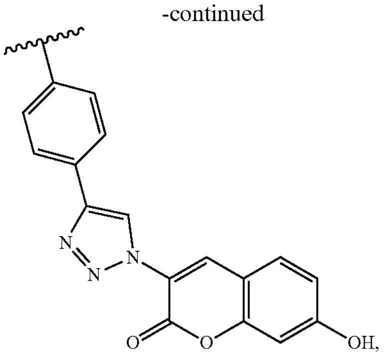

or

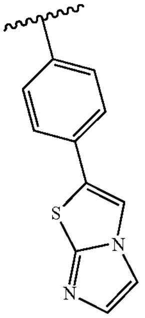

.

In some embodiments, $R^3$ is optionally substituted carbocyclyl. In some embodiments, $R^3$ is optionally substituted $C_{3-10}$ carbocyclyl. In some embodiments, $R^3$ is optionally substituted $C_{3-6}$ carbocyclyl.

In some embodiments, $R^3$ is of formula:

(B-1)

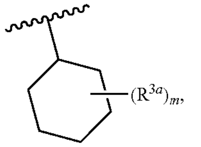

wherein:

each instance of $R^{3a}$ is independently halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —CN, —$OR^A$, —SCN, —$SR^A$, —$SSR^A$, —$N_3$, —NO, —$N(R^A)_2$, —$NO_2$, —C(=O)$R^A$, —C(=O)$OR^A$, —C(=O)$SR^A$, —C(=O)$N(R^A)_2$, —C(=$NR^A$)$R^A$, —C(=$NR^A$)$OR^A$, —C(=$NR^A$)$SR^A$, —C(=$NR^A$)$N(R^A)_2$, —S(=O)$R^A$, —S(=O)$OR^A$, —S(=O)$SR^A$, —S(=O)$N(R^A)_2$, —$S(=O)_2R^A$, —$S(=O)_2OR^A$, —$S(=O)_2SR^A$, —$S(=O)_2N(R^A)_2$, —OC(=O)$R^A$, —OC(=O)$OR^A$, —OC(=O)$SR^A$, —OC(=O)$N(R^A)_2$, —OC(=$NR^A$)$R^A$, —OC(=$NR^A$)$OR^A$, —OC(=$NR^A$)$SR^A$, —OC(=$NR^A$)$N(R^A)_2$, —OS(=O)$R^A$, —OS(=O)$OR^A$, —OS(=O)$SR^A$, —OS(=O)$N(R^A)_2$, —$OS(=O)_2R^A$, —$OS(=O)_2OR^A$, —$OS(=O)_2SR^A$, —$OS(=O)_2N(R^A)_2$, —$ON(R^A)_2$, —SC(=O)$R^A$, —SC(=O)$OR^A$, —SC(=O)$SR^A$, —SC(=O)$N(R^A)_2$, —SC(=$NR^A$)$R^A$, —SC(=$NR^A$)$OR^A$, —SC(=$NR^A$)$SR^A$, —SC(=$NR^A$)$N(R^A)_2$, —$NR^A$C(=O)$R^A$, —$NR^A$C(=O)$OR^A$, —$NR^A$C(=O)$SR^A$, —$NR^A$C(=O)$N(R^A)_2$, —$NR^A$C(=$NR^A$)$R^A$, —$NR^A$C(=$NR^A$)$OR^A$, —$NR^A$C(=$NR^A$)$SR^A$, —$NR^A$C(=$NR^A$)$N(R^A)_2$, —$NR^A$S(=O)$R^A$, —$NR^A$S(=O)$OR^A$, —$NR^A$S(=O)$SR^A$, —$NR^A$S(=O)$N(R^A)_2$, —$NR^AS(=O)_2R^A$, —$NR^AS(=O)_2OR^A$, —$NR^AS(=O)_2SR^A$, —$NR^AS(=O)_2N(R^A)_2$, —$Si(R^A)_3$, —$Si(R^A)_2OR^A$, —$Si(R^A)(OR^A)_2$, —$Si(OR^A)_3$, —$OSi(R^A)_3$, —$OSi(R^A)_2OR^A$, —$OSi(R^A)(OR^A)_2$, —$OSi(OR^A)_3$, or —$B(OR^A)_2$;

each instance of $R^A$ is independently hydrogen, optionally substituted acyl, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^A$ are joined together with their intervening atom to form an optionally substituted heterocyclic ring or optionally substituted heteroaryl ring; and m is 0, 1, 2, 3, 4, or 5.

In some embodiments, $R^3$ is of formula (B-1), wherein at least one instance of $R^{3a}$ is optionally substituted heteroaryl. In some embodiments, $R^3$ is of formula (B-1), wherein at least one instance of $R^{3a}$ is optionally substituted 5-6 membered heteroaryl containing 1, 2, 3, or 4 ring heteroatoms selected from N, O, and S. In some embodiments, $R^3$ is of formula (B-1), wherein at least one instance of $R^{3a}$ is optionally substituted 5-6 membered heteroaryl containing 1 ring N atom and 1 ring O atom, 1 ring N atom and 1 ring S atom, or 3 ring N atoms.

In some embodiments, $R^3$ of formula (B-1) is of formula:

(B-1a)

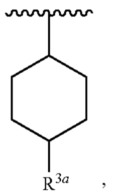

, (B-1b)

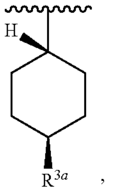

, or (B-1c)

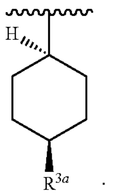

.

In some embodiments, $R^3$ of formula (B-1) is of formula (B-1a). In some embodiments, $R^3$ of formula (B-1) is of formula (B-1b). In some embodiments, $R^3$ of formula (B-1) is of formula (B-1c).

In some embodiments, $R^3$ is

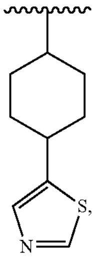, 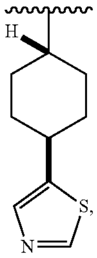, or 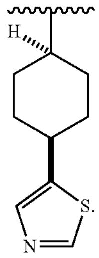.

In some embodiments, $R^3$ is optionally substituted heterocyclyl. In some embodiments, $R^3$ is optionally substituted 3-10 membered heterocyclyl. In some embodiments, $R^3$ is optionally substituted 4-6 membered heterocyclyl. In some embodiments, $R^3$ is optionally substituted 4-6 membered heterocyclyl containing 1 ring N atom.

In some embodiments, $R^3$ is of formula:

(C-1)

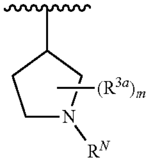 or (C-2)

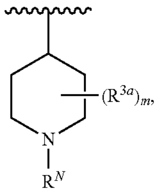, wherein:

each instance of $R^{3a}$ is independently halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, $-CN$, $-OR^A$, $-SCN$, $-SR^A$, $-SSR^A$, $-N_3$, $-NO$, $-N(R^A)_2$, $-NO_2$, $-C(=O)R^A$, $-C(=O)OR^A$, $-C(=O)SR^A$, $-C(=O)N(R^A)_2$, $-C(=NR^A)R^A$, $-C(=NR^A)OR^A$, $-C(=NR^A)SR^A$, $-C(=NR^A)N(R^A)_2$, $-S(=O)R^A$, $-S(=O)OR^A$, $-S(=O)SR^A$, $-S(=O)N(R^A)_2$, $-S(=O)_2R^A$, $-S(=O)_2OR^A$, $-S(=O)_2SR^A$, $-S(=O)_2N(R^A)_2$, $-OC(=O)R^A$, $-OC(=O)OR^A$, $-OC(=O)SR^A$, $-OC(=O)N(R^A)_2$, $-OC(=NR^A)R^A$, $-OC(=NR^A)OR^A$, $-OC(=NR^A)SR^A$, $-OC(=NR^A)N(R^A)_2$, $-OS(=O)R^A$, $-OS(=O)OR^A$, $-OS(=O)SR^A$, $-OS(=O)N(R^A)_2$, $-OS(=O)_2R^A$, $-OS(=O)_2OR^A$, $-OS(=O)_2SR^A$, $-OS(=O)_2N(R^A)_2$, $-ON(R^A)_2$, $-SC(=O)R^A$, $-SC(=O)OR^A$, $-SC(=O)SR^A$, $-SC(=O)N(R^A)_2$, $-SC(=NR^A)R^A$, $-SC(=NR^A)OR^A$, $-SC(=NR^A)SR^A$, $-SC(=NR^A)N(R^A)_2$, $-NR^AC(=O)R^A$, $-NR^AC(=O)OR^A$, $-NR^AC(=O)SR^A$, $-NR^AC(=O)N(R^A)_2$, $-NR^AC(=NR^A)R^A$, $-NR^AC(=NR^A)OR^A$, $-NR^AC(=NR^A)SR^A$, $-NR^AC(=NR^A)N(R^A)_2$, $-NR^AS(=O)R^A$, $-NR^AS(=O)OR^A$, $-NR^AS(=O)SR^A$, $-NR^AS(=O)N(R^A)_2$, $-NR^AS(=O)_2R^A$, $-NR^AS(=O)_2OR^A$, $-NR^AS(=O)_2SR^A$, $-NR^AS(=O)_2N(R^A)_2$, $-Si(R^A)_3$, $-Si(R^A)_2OR^A$, $-Si(R^A)(OR^A)_2$, $-Si(OR^A)_3$, $-OSi(R^A)_3$, $-OSi(R^A)_2OR^A$, $-OSi(R^A)(OR^A)_2$, $-OSi(OR^A)_3$, or $-B(OR^A)_2$;

each instance of $R^A$ is independently hydrogen, optionally substituted acyl, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^A$ are joined together with their intervening atom to form an optionally substituted heterocyclic ring or optionally substituted heteroaryl ring;

$R^N$ is hydrogen, optionally substituted alkyl, optionally substituted carbocyclyl, optionally substituted heterocyclyl, optionally substituted aryl, optionally substituted heteroaryl, or a nitrogen protecting group; and m is 0, 1, 2, 3, 4, or 5.

In some embodiments, $R^3$ is of formula (C-1) or (C-2), wherein at least one instance of $R^{3a}$ is optionally substituted heteroaryl. In some embodiments, $R^3$ is of formula (C-1) or (C-2), wherein at least one instance of $R^{3a}$ is optionally substituted 5-6 membered heteroaryl containing 1, 2, 3, or 4 ring heteroatoms selected from N, O, and S. In some embodiments, $R^3$ is of formula (C-1) or (C-2), wherein at least one instance of $R^{3a}$ is optionally substituted 5-6 membered heteroaryl containing 1 ring N atom and 1 ring O atom, 1 ring N atom and 1 ring S atom, or 3 ring N atoms.

In some embodiments, $R^3$ of formula (C-1) is of formula:

(C-1a)

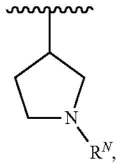, (C-1b)

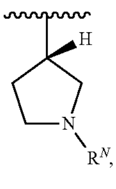, or (C-1c)

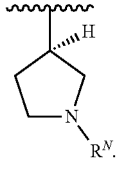.

In some embodiments, $R^3$ of formula (C-1) is of formula (C-1a). In some embodiments, $R^3$ of formula (C-1) is of formula (C-1b). In some embodiments, $R^3$ of formula (C-1) is of formula (C-1c).

In some embodiments, $R^3$ of formula (C-2) is of formula:

(C-2a)

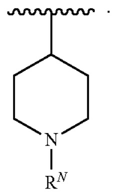

In some embodiments, $R^3$ is

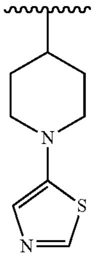
,
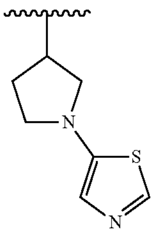
,
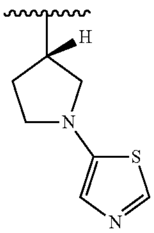
, or
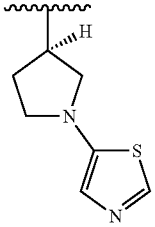
.

In some embodiments, $R^3$ is

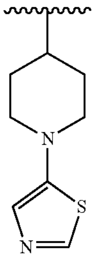
or
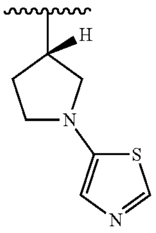
.

In some embodiments, $R^3$ is optionally substituted heteroaryl. In some embodiments, $R^3$ is optionally substituted 5-10 membered heteroaryl. In some embodiments, $R^3$ is optionally substituted 5-6 membered heteroaryl. In some embodiments, $R^3$ is optionally substituted 8-10 membered heteroaryl.

In some embodiments, $R^3$ is of formula:

(D-1)

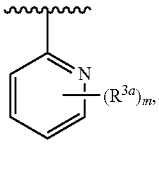

-continued (D-2)

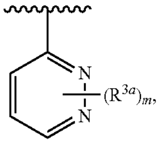

(D-3)

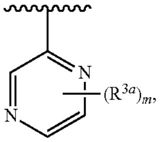

(D-4)

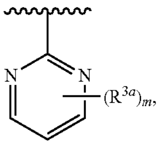

(D-5)

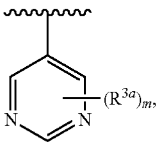

(D-6)

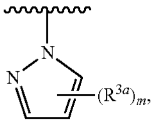

(D-7)

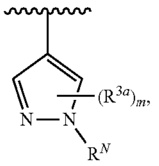
or (D-8)

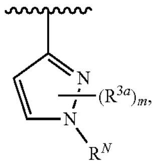

wherein:

each instance of $R^{3a}$ is independently halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —CN, —$OR^A$, —SCN, —$SR^A$, —$SSR^A$, —$N_3$, —NO, —$N(R^A)_2$, —$NO_2$, —C(=O)$R^A$, —C(=O)$OR^A$, —C(=O)$SR^A$, —C(=O)$N(R^A)_2$, —C(=$NR^A$)$R^A$, —C(=$NR^A$)$OR^A$, —C(=$NR^A$)$SR^A$, —C(=$NR^A$)$N(R^A)_2$, —S(=O)$R^A$, —S(=O)$OR^A$, —S(=O)$SR^A$, —S(=O)$N(R^A)_2$, —$S(=O)_2R^A$, —$S(=O)_2OR^A$, —$S(=O)_2SR^A$, —$S(=O)_2N(R^A)_2$, —OC(=O)$R^A$, —OC(=O)$OR^A$, —OC(=O)$SR^A$, —OC(=O)$N(R^A)_2$, —OC(=$NR^A$)$R^A$, —OC(=$NR^A$)$OR^A$, —OC(=$NR^A$)$SR^A$, —OC(=$NR^A$)$N(R^A)_2$, —OS(=O)$R^A$, —OS(=O)$OR^A$, —OS(=O)$SR^A$, —OS(=O)$N(R^A)_2$, —$OS(=O)_2R^A$, —$OS(=O)_2OR^A$, —$OS(=O)_2SR^A$, —$OS(=O)_2N(R^A)_2$, —$ON(R^A)_2$, —SC(═O)$R^A$, —SC(═O)O$R^A$, —SC(═O)S$R^A$, —SC(═O)N$(R^A)_2$, —SC(═N$R^A$)$R^A$, —SC(═N$R^A$)O$R^A$, —SC(═N$R^A$)S$R^A$, —SC(═N$R^A$)N$(R^A)_2$, —N$R^A$C(═O)$R^A$, —N$R^A$C(═O)O$R^A$, —N$R^A$C(═O)S$R^A$, —N$R^A$C(═O)N$(R^A)_2$, —N$R^A$C(═N$R^A$)$R^A$, —N$R^A$C(═N$R^A$)O$R^A$, —N$R^A$C(═N$R^A$)S$R^A$, —N$R^A$C(═N$R^A$)N$(R^A)_2$, —N$R^A$S(═O)$R^A$, —N$R^A$S(═O)O$R^A$, —N$R^A$S(═O)S$R^A$, —N$R^A$S(═O)N$(R^A)_2$, —N$R^A$S$(═O)_2R^A$, —N$R^A$S$(═O)_2$O$R^A$, —N$R^A$S$(═O)_2$S$R^A$, —N$R^A$S$(═O)_2$N$(R^A)_2$, —Si$(R^A)_3$, —Si$(R^A)_2$O$R^A$, —Si$(R^A)$(O$R^A)_2$, —Si$(OR^A)_3$, —OSi$(R^A)_3$, —OSi$(R^A)_2$O$R^A$, —OSi$(R^A)$(O$R^A)_2$, —OSi$(OR^A)_3$, or —B$(OR^A)_2$;

each instance of $R^A$ is independently hydrogen, optionally substituted acyl, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^A$ are joined together with their intervening atom to form an optionally substituted heterocyclic ring or optionally substituted heteroaryl ring;

$R^N$ is hydrogen, optionally substituted alkyl, optionally substituted carbocyclyl, optionally substituted heterocyclyl, optionally substituted aryl, optionally substituted heteroaryl, or a nitrogen protecting group; and m is 0, 1, 2, 3, or 4, as valency permits.

In some embodiments, $R^3$ is of formula (D-1). In some embodiments, $R^3$ is of formula (D-2). In some embodiments. $R^3$ is of formula (D-3). In some embodiments, $R^3$ is of formula (D-4). In some embodiments, $R^3$ is of formula (D-5). In some embodiments, $R^3$ is of formula (D-6). In some embodiments, $R^3$ is of formula (D-7). In some embodiments, $R^3$ is of formula (D-8).

In some embodiments, $R^3$ is of formula (D-1) to (D-6), wherein at least one instance of $R^{3a}$ is optionally substituted heteroaryl. In some embodiments, $R^3$ is of formula (D-1) to (D-6), wherein at least one instance of $R^{3a}$ is optionally substituted 5-6 membered heteroaryl containing 1, 2, 3, or 4 ring heteroatoms selected from N, O, and S. In some embodiments, $R^3$ is of formula (D-1) to (D-6), wherein at least one instance of $R^{3a}$ is optionally substituted 5-6 membered heteroaryl containing 1 ring N atom and 1 ring O atom, 1 ring N atom and 1 ring S atom, or 3 ring N atoms.

In some embodiments, $R^3$ is of formula (D-7) or (D-8), wherein $R^N$ is optionally substituted heteroaryl. In some embodiments, $R^3$ is of formula (D-7) or (D-8), wherein $R^N$ is optionally substituted 5-6 membered heteroaryl containing 1, 2, 3, or 4 ring heteroatoms selected from N, O, and S. In some embodiments, $R^3$ is of formula (D-7) or (D-8), wherein $R^N$ is optionally substituted 5-6 membered heteroaryl containing 1 ring N atom and 1 ring O atom, 1 ring N atom and 1 ring S atom, or 3 ring N atoms.

In some embodiments, $R^3$ of formula (D-1) is of formula:

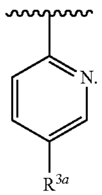

(D-1a)

In some embodiments, $R^3$ of formula (D-2) is of formula:

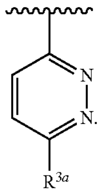

(D-2a)

In some embodiments, $R^3$ of formula (D-3) is of formula:

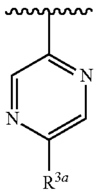

(D-3a)

or

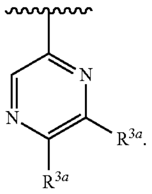

(D-3b)

In some embodiments, $R^3$ of formula (D-3) is of formula (D-3a). In some embodiments, $R^3$ of formula (D-3) is of formula (D-3b).

In some embodiments, $R^3$ of formula (D-4) is of formula:

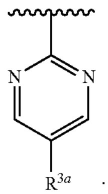

(D-4a)

In some embodiments, $R^3$ of formula (D-5) is of formula:

(D-5a)

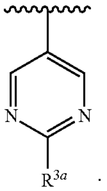

In some embodiments, $R^3$ of formula (D-6) is of formula:

(D-6a)

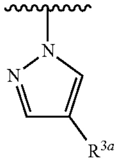

or (D-6b)

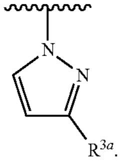

In some embodiments, $R^3$ of formula (D-6) is of formula (D-6a). In some embodiments, $R^3$ of formula (D-6) is of formula (D-6b).

In some embodiments, $R^3$ of formula (D-7) is of formula:

(D-7a)

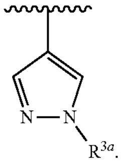

In some embodiments, $R^3$ of formula (D-8) is of formula:

(D-8a)

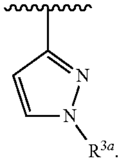

In some embodiments, $R^3$ is:

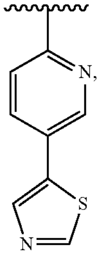 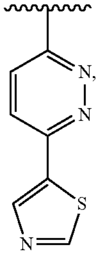 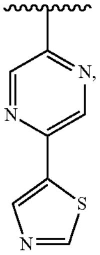 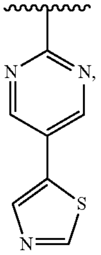

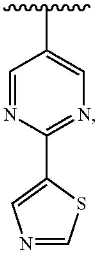 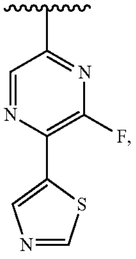 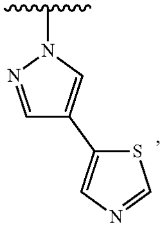

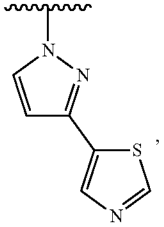 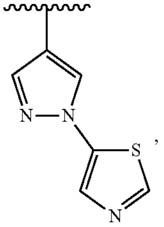 or 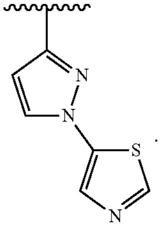

In some embodiments, $R^3$ is

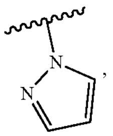 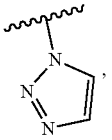 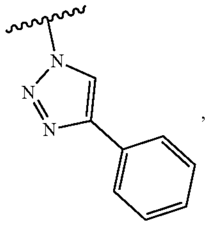

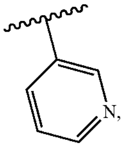 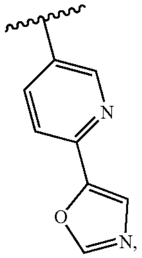

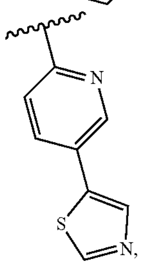 or 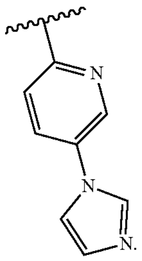

In some embodiments, $R^3$ is

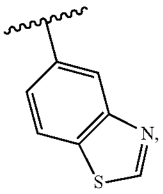

, or

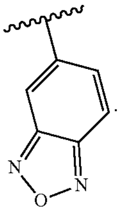

.

As generally described herein, each instance of $R^{3a}$ is independently halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —CN, —$OR^A$, —SCN, —$SR^A$, —$SSR^A$, —$N_3$, —NO, —$N(R^A)_2$, —$NO_2$, —C(═O)$R^A$, —C(═O)$OR^A$, —C(═O)$SR^A$, —C(═O)$N(R^A)_2$, —C(═$NR^A$)$R^A$, —C(═$NR^A$)$OR^A$, —C(═$NR^A$)$SR^A$, —C(═$NR^A$)$N(R^A)_2$, —S(═O)$R^A$, —S(═O)$OR^A$, —S(═O)$SR^A$, —S(═O)$N(R^A)_2$, —$S(═O)_2R^A$, —$S(═O)_2OR^A$, —$S(═O)_2SR^A$, —$S(═O)_2N(R^A)_2$, —OC(═O)$R^A$, —OC(═O)$OR^A$, —OC(═O)$SR^A$, —OC(═O)$N(R^A)_2$, —OC(═$NR^A$)$R^A$, —OC(═$NR^A$)$OR^A$, —OC(═$NR^A$)$SR^A$, —OC(═$NR^A$)$N(R^A)_2$, —OS(═O)$R^A$, —OS(═O)$OR^A$, —OS(═O)$SR^A$, —OS(═O)$N(R^A)_2$, —$OS(═O)_2R^A$, —$OS(═O)_2OR^A$, —$OS(═O)_2SR^A$, —$OS(═O)_2N(R^A)_2$, —$ON(R^A)_2$, —SC(═O)$R^A$, —SC(═O)$OR^A$, —SC(═O)$SR^A$, —SC(═O)$N(R^A)_2$, —SC(═$NR^A$)$R^A$, —SC(═$NR^A$)$OR^A$, —SC(═$NR^A$)$SR^A$, —SC(═$NR^A$)$N(R^A)_2$, —$NR^A$C(═O)$R^A$, —$NR^A$C(═O)$OR^A$, —$NR^A$C(═O)$SR^A$, —$NR^A$C(═O)$N(R^A)_2$, —$NR^A$C(═$NR^A$)$R^A$, —$NR^A$C(═$NR^A$)$OR^A$, —$NR^A$C(═$NR^A$)$SR^A$, —$NR^A$C(═$NR^A$)$N(R^A)_2$, —$NR^A$S(═O)$R^A$, —$NR^A$S(═O)$OR^A$, —$NR^A$S(═O)$SR^A$, —$NR^A$S(═O)$N(R^A)_2$, —$NR^AS(═O)_2R^A$, —$NR^AS(═O)_2OR^A$, —$NR^AS(═O)_2SR^A$, —$NR^AS(═O)_2N(R^A)_2$, —$Si(R^A)_3$, —$Si(R^A)_2OR^A$, —$Si(R^A)(OR^A)_2$, —$Si(OR^A)_3$, —$OSi(R^A)_3$, —$OSi(R^A)_2OR^A$, —$OSi(R^A)(OR^A)_2$, —$OSi(OR^A)_3$, or —$B(OR^A)_2$.

In some embodiments, at least one instance of $R^{3a}$ is halogen, optionally substituted alkyl, optionally substituted alkenyl, optionally substituted alkynyl, —CN, —$NO_2$, —$OR^{1a}$, —$N(R^{1a})_2$, —$NR^{1a}$C(═O)$R^{1a}$, —C(═O)$R^{1a}$, optionally substituted carbocyclyl, optionally substituted heterocyclyl, optionally substituted aryl, or optionally substituted heteroaryl. In some embodiments, at least one instance of $R^{3a}$ is halogen, optionally substituted $C_{1-3}$ alkyl, optionally substituted $C_{2-3}$ alkynyl, —CN, —$NO_2$, —$OR^{1a}$, —$N(R^{1a})_2$, —$NR^{1a}$C(═O)$R^{1a}$, —C(═O)$R^{1a}$, optionally substituted $C_{34}$ carbocyclyl, optionally substituted 3-4 membered heterocyclyl, optionally substituted phenyl, optionally substituted 5-6 membered heteroaryl containing 1, 2, 3, or 4 ring heteroatoms selected from N, O, and S, or optionally substituted 8-10 membered heteroaryl containing 1, 2, 3, or 4 ring heteroatoms selected from N, O, and S. In some embodiments, at least one instance of $R^{3a}$ is —$OR^{1a}$, wherein $R^{1a}$ is unsubstituted $C_{1-3}$ alkyl; —C(═O)$R^{1a}$, wherein $R^{1a}$ is unsubstituted 4-6 membered heterocyclyl containing 1 or 2 ring N atoms; optionally substituted phenyl; optionally substituted 5-6 membered heteroaryl containing 2 ring N atoms, 1 ring N atom and 1 ring O atom, 1 ring N atom and 1 ring S atom, or 3 ring N atoms; or optionally substituted 8-10 membered heteroaryl containing 2 ring N atoms and 1 ring S atom.

In some embodiments, at least one instance of $R^{3a}$ is halogen. In some embodiments, at least one instance of $R^{3a}$ is —F, —Cl, —Br, or —I. In some embodiments, at least one instance of $R^{3a}$ is —Cl or —Br.

In some embodiments, at least one instance of $R^{3a}$ is optionally substituted alkyl. In some embodiments, at least one instance of $R^{3a}$ is optionally substituted $C_{1-6}$ alkyl. In some embodiments, at least one instance of $R^{3a}$ is optionally substituted $C_{1-3}$ alkyl. In some embodiments, at least one instance of $R^{3a}$ is —$CH_3$, —$CHF_2$, —$CF_3$, or —$CF_2CH_3$.

In some embodiments, at least one instance of $R^{3a}$ is optionally substituted alkynyl. In some embodiments, at least one instance of $R^{3a}$ is optionally substituted $C_{2-6}$ alkynyl. In some embodiments, at least one instance of $R^{3a}$ is optionally substituted $C_{2-3}$ alkynyl. In some embodiments, at least one instance of $R^{3a}$ is —C≡CH.

In some embodiments, at least one instance of $R^{3a}$ is —CN.

In some embodiments, at least one instance of $R^{3a}$ is —$NO_2$.

In some embodiments, at least one instance of $R^{3a}$ is —$OR^{1a}$. In some embodiments, at least one instance of $R^{3a}$ is —$OR^{1a}$, wherein $R^{1a}$ is hydrogen, optionally substituted $C_{1-6}$ alkyl, optionally substituted $C_{3-10}$ carbocyclyl, or optionally substituted 5-10 membered heteroaryl. In some embodiments, at least one instance of $R^{3a}$ is —$OR^{1a}$, wherein $R^{1a}$ is hydrogen, optionally substituted $C_{1-3}$ alkyl, optionally substituted $C_{3-6}$ carbocyclyl, or optionally substituted 5-6 membered heteroaryl. In some embodiments, at least one instance of $R^{3a}$ is —$OR^{1a}$, wherein $R^{1a}$ is hydrogen, unsubstituted $C_{1-3}$ alkyl, $C_{1-3}$ haloalkyl, unsubstituted $C_{3-6}$ carbocyclyl, or unsubstituted 5-6 membered heteroaryl. In some embodiments, at least one instance of $R^{3a}$ is —OH, —$OCH_3$, —$OCH_2CH_3$, —$OCH_2CH_2CH_3$, —$OCH_2F$, —$OCHF_2$, —$OCF_3$,

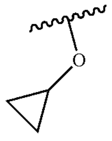

,

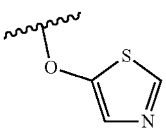

, or

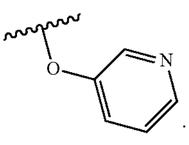

.

In some embodiments, at least one instance of $R^{3a}$ is unsubstituted $C_{1-3}$ alkyl. In some embodiments, at least one instance of $R^{3a}$ is —$OCH_3$.

In some embodiments, at least one instance of $R^{3a}$ is —$N(R^A)_2$. In some embodiments, at least one instance of $R^{3a}$ is —$N(R^A)_2$, wherein each instance of $R^A$ is independently hydrogen or optionally substituted $C_{1-3}$ alkyl. In some embodiments, at least one instance of $R^{3a}$ is —$N(CH_3)_2$.

In some embodiments, at least one instance of $R^{3a}$ is —$NR^A$C(═O)$R^A$. In some embodiments, at least one instance of $R^{3a}$ is —$NR^A$C(═O)$R^A$, wherein each instance of $R^A$ is independently hydrogen or optionally substituted $C_{1-3}$ alkyl. In some embodiments, at least one instance of $R^{3a}$ is —NHC(═O) $CH_3$.

In some embodiments, at least one instance of $R^{3a}$ is —C(═O)$R^{1a}$. In some embodiments, at least one instance of $R^{3a}$ is —C(═O)$R^{1a}$, wherein $R^{1a}$ is optionally substituted 4-6 membered heterocyclyl. In some embodiments, at least one instance of $R^{3a}$ is —C(═O)$R^{1a}$, wherein $R^{1a}$ is unsubstituted 4-6 membered heterocyclyl containing 1 or 2 ring N atoms. In some embodiments, at least one instance of $R^{3a}$ is

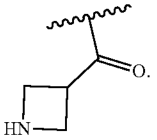

In some embodiments, at least one instance of $R^{3a}$ is optionally substituted carbocyclyl. In some embodiments, at least one instance of $R^{3a}$ is optionally substituted $C_{3-6}$ carbocyclyl. In some embodiments, at least one instance of $R^{3a}$ is unsubstituted $C_{3-6}$ carbocyclyl. In some embodiments, at least one instance of $R^{3a}$ is

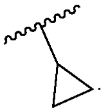 [SMILES: *C1CC1]

In some embodiments, at least one instance of $R^{3a}$ is optionally substituted heterocyclyl. In some embodiments, at least one instance of $R^{3a}$ is optionally substituted 4-6 membered heterocyclyl. In some embodiments, at least one instance of $R^{3a}$ is 4-6 membered heterocyclyl containing 1 or 2 ring N atoms, wherein the heterocyclyl is substituted with 0, 1, or 2-F. In some embodiments, at least one instance of $R^{3a}$ is

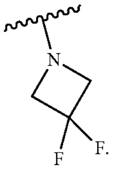 [SMILES: *N1CC(F)(F)C1]

In some embodiments, at least one instance of $R^{3a}$ is optionally substituted aryl. In some embodiments, at least one instance of $R^{3a}$ is optionally substituted phenyl. In some embodiments, at least one instance of $R^{3a}$ is unsubstituted phenyl. In some embodiments, at least one instance of $R^{3a}$ is substituted phenyl. In some embodiments, at least one instance of $R^{3a}$ is

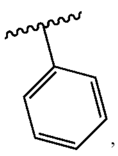,
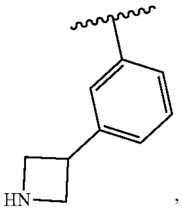,
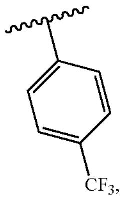
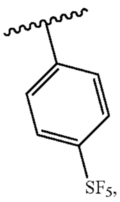
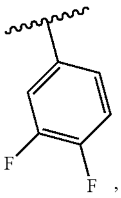,
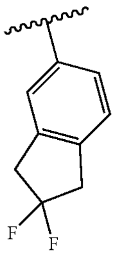, or -continued

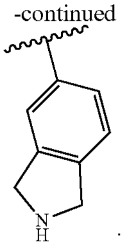.

In some embodiments, at least one instance of $R^{3a}$ is

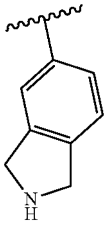.

In some embodiments, at least one instance of $R^{3a}$ is optionally substituted heteroaryl. In some embodiments, at least one instance of $R^{3a}$ is optionally substituted 5-6 membered heteroaryl. In some embodiments, at least one instance of $R^{3a}$ is optionally substituted 5-6 membered heteroaryl containing 1, 2, 3, or 4 ring heteroatoms selected from N, O, and S. In some embodiments, at least one instance of $R^{3a}$ is optionally substituted 5-6 membered heteroaryl containing 1 ring S atom; 2 ring N atoms; 1 ring N atom and 1 ring O atom; 1 ring N atom and 1 ring S atom; 2 ring N atoms and 1 ring S atom; 3 ring N atoms; or 4 ring N atoms. In some embodiments, at least one instance of $R^{3a}$ is optionally substituted 5-6 membered heteroaryl containing 2 ring N atoms, 1 ring N atom and 1 ring O atom, 1 ring N atom and 1 ring S atom, or 3 ring N atoms.

In some embodiments, at least one instance of $R^{3a}$ is optionally substituted 5-6 membered heteroaryl containing 1 ring S atom. In some embodiments, at least one instance of $R^{3a}$ is optionally substituted thiophenyl. In some embodiments, at least one instance of $R^{3a}$ is

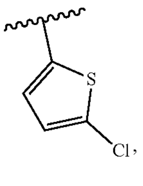
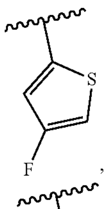,
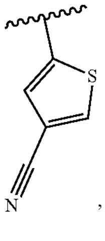, or
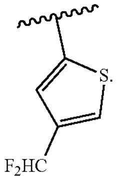

In some embodiments, at least one instance of $R^{3a}$ is optionally substituted 5-6 membered heteroaryl containing 2 ring N atoms. In some embodiments, at least one instance of $R^{3a}$ is optionally substituted pyrazolyl or optionally substituted imidazolyl. In some embodiments, at least one instance of $R^{3a}$ is

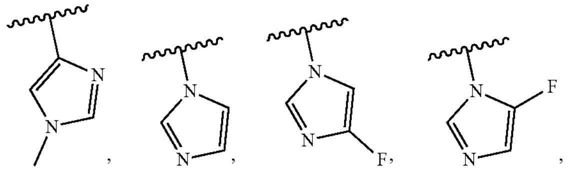
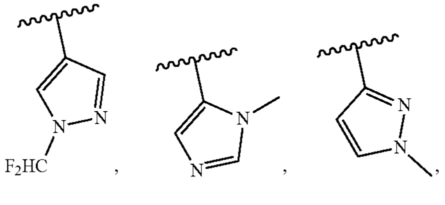
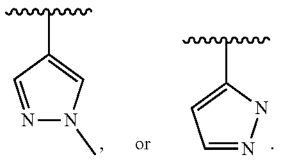
or

In some embodiments, at least one instance of $R^{3a}$ is

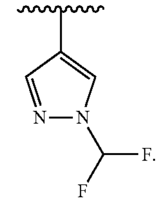 [SMILES: *c1cnn(C(F)F)c1]

In some embodiments, at least one instance of $R^{3a}$ is

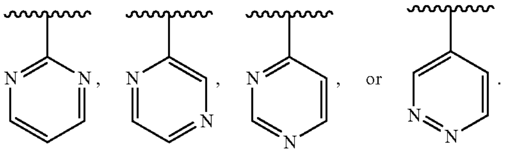
or

In some embodiments, at least one instance of $R^{3a}$ is optionally substituted 5-6 membered heteroaryl containing 1 ring N atom and 1 ring O atom. In some embodiments, at least one instance of $R^{3a}$ is optionally substituted oxazolyl or optionally substituted isoxazolyl. In some embodiments, at least one instance of $R^{3a}$ is

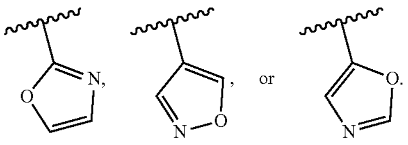 [SMILES: *c1ncco1 ; *c1cnoc1 ; *c1cnco1]
or

In some embodiments, at least one instance of $R^{3a}$ is optionally substituted 5-6 membered heteroaryl containing 1 ring N atom and 1 ring S atom. In some embodiments, at least one instance of $R^{3a}$ is optionally substituted thiazolyl, optionally substituted isothiazolyl, or optionally substituted thiazolonyl. In some embodiments, at least one instance of $R^{3a}$ is

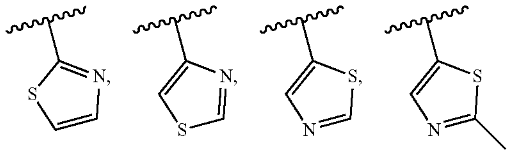
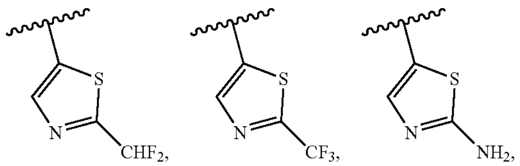
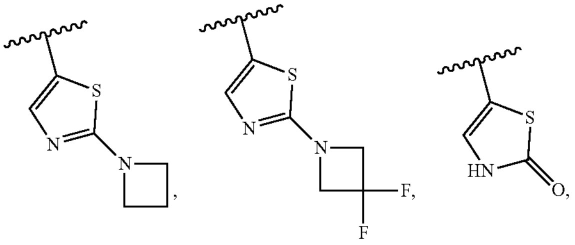
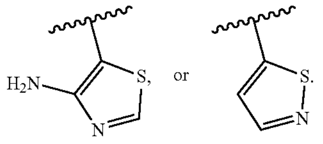
or

In some embodiments, at least one instance of $R^{3a}$ is optionally substituted 5-6 membered heteroaryl containing 2 ring N atoms and 1 ring S atom. In some embodiments, at least one instance of $R^{3a}$ is optionally substituted thiadiazolyl. In some embodiments, at least one instance of $R^{3a}$ is

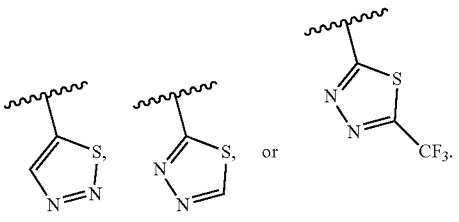 [SMILES: *c1cnns1 ; *c1nncs1 ; *c1nnc(C(F)(F)F)s1]
or

In some embodiments, at least one instance of $R^{3a}$ is optionally substituted 5-6 membered heteroaryl containing 3 ring N atoms. In some embodiments, at least one instance of $R^{3a}$ is optionally substituted triazolyl. In some embodiments, at least one instance of $R^{3a}$ is

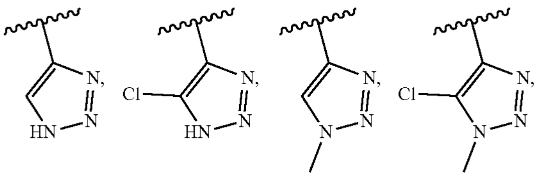

-continued

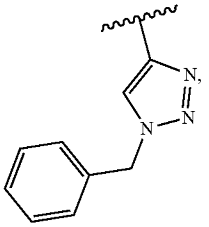 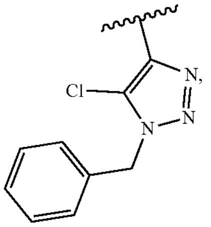

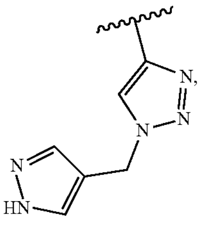 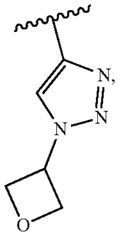 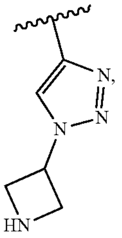

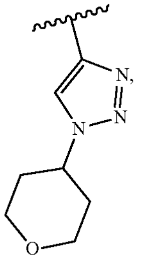 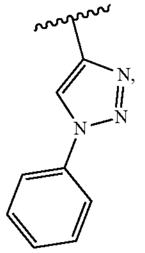 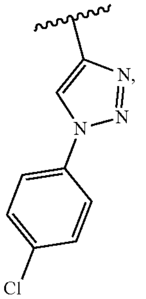

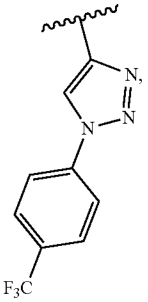 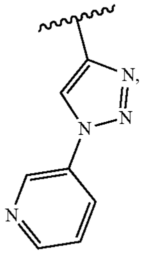 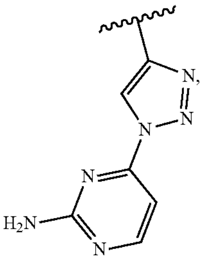 or

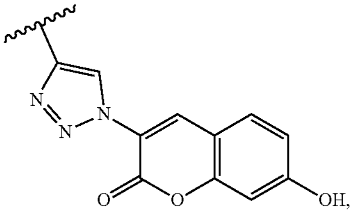 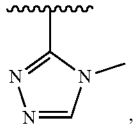 , or

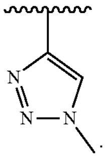

In some embodiments, at least one instance of $R^{3a}$ is optionally substituted 5-6 membered heteroaryl containing 4 ring N atoms. In some embodiments, at least one instance of $R^{3a}$ is optionally substituted tetrazolyl. In some embodiments, at least one instance of $R^{3a}$ is

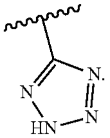

In some embodiments, at least one instance of $R^{3a}$ is optionally substituted 8-10 membered heteroaryl. In some embodiments, at least one instance of $R^{3a}$ is optionally substituted 8-10 membered heteroaryl containing 1, 2, 3, or 4 ring heteroatoms selected from N, O, and S. In some embodiments, at least one instance of $R^{3a}$ is optionally substituted 8-10 membered heteroaryl containing 2 ring N atoms; 1 ring N atom and 1 ring S atom; 2 ring N atoms and 1 ring S atom; 2 ring N atoms and 1 ring O atom; or 3 ring N atoms and 1 ring S atom. In some embodiments, at least one instance of $R^{3a}$ is optionally substituted 8-10 membered heteroaryl containing 2 ring N atoms and 1 ring S atom. In some embodiments, at least one instance of $R^{3a}$ is

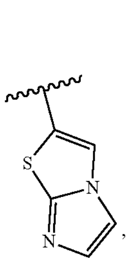 , 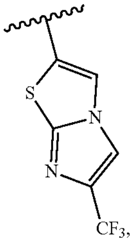 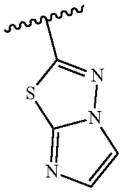 ,

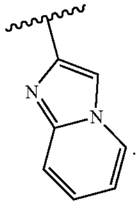 . 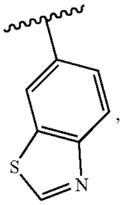 , or 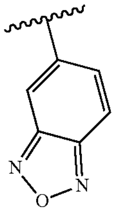 .

In some embodiments, at least one instance of $R^{3a}$ is: —F, —Cl, —Br, —I, —$CH_3$, —$CHF_2$, —$CF_3$, —$CF_2CH_3$, —C≡CH, —CN, —$NO_2$, —OH, —$OCH_3$, —$OCH_2CH_3$, —$OCH_2CH_2CH_3$, —$OCH_2F$, —$OCHF_2$, —$OCF_3$,

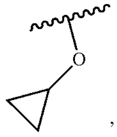 , 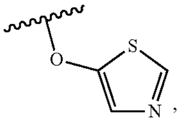 , 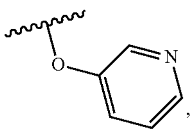 ,

—$N(CH_3)_2$, —NHC(=O) $CH_3$,

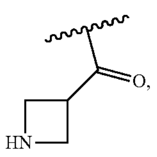 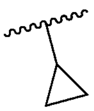 , 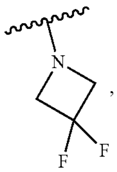 , 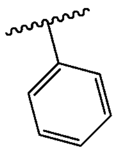 ,

-continued
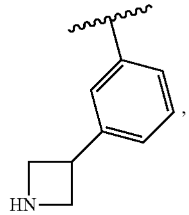 , 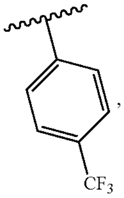 , 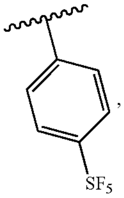 ,
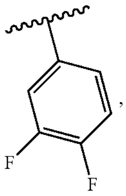 , 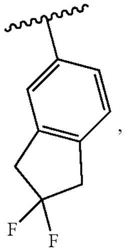 , 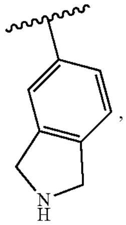 ,
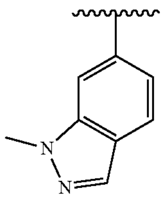 , 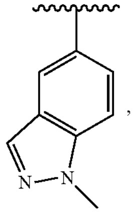 , 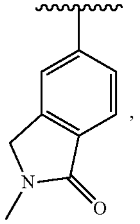 ,
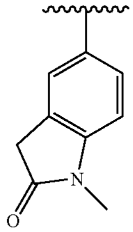 , 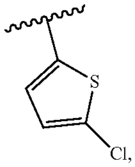 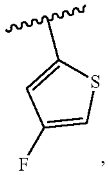 , 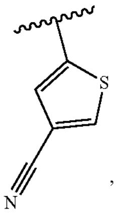 ,
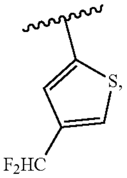 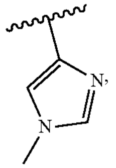 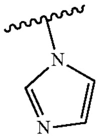 , 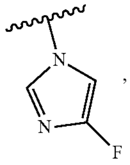 ,
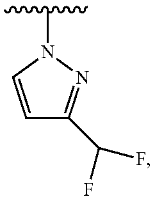 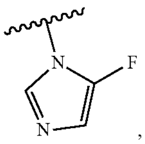 , 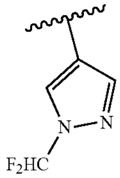 ,
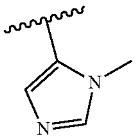 , 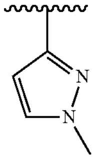 , 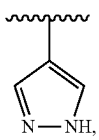 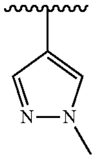 ,
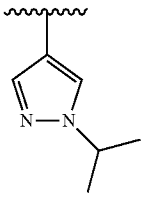 , 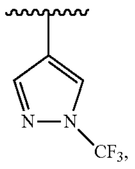 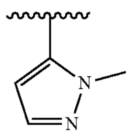 ,
-continued
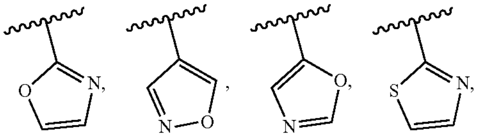
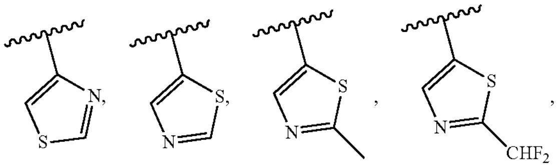
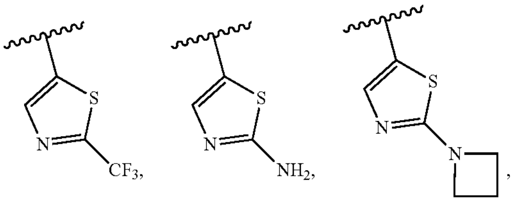
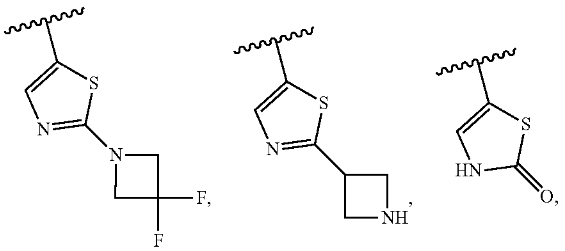
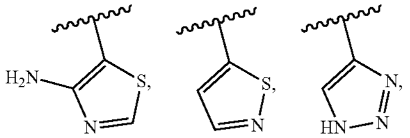
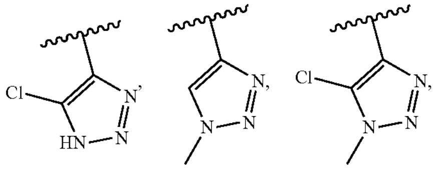
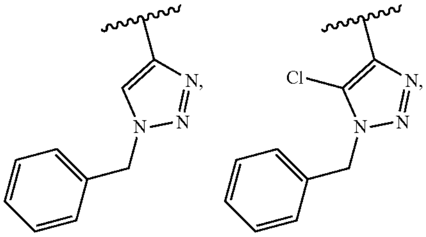
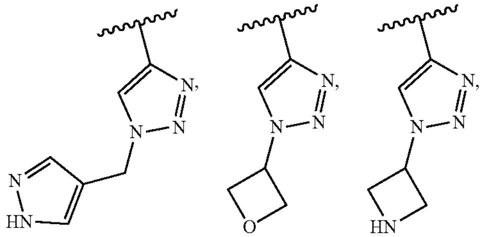

-continued
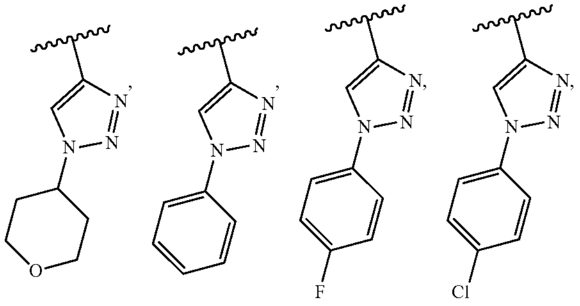
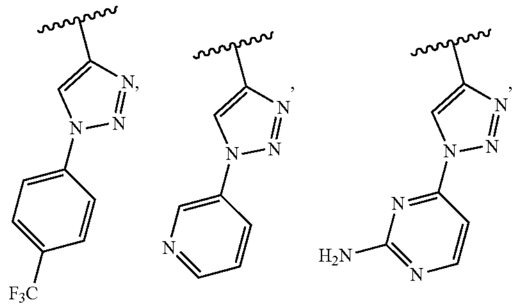
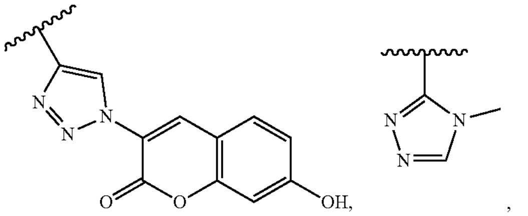
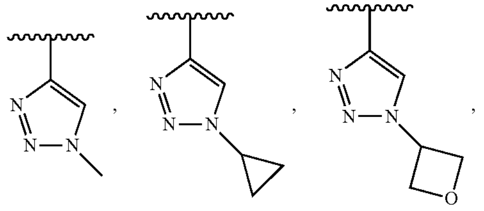
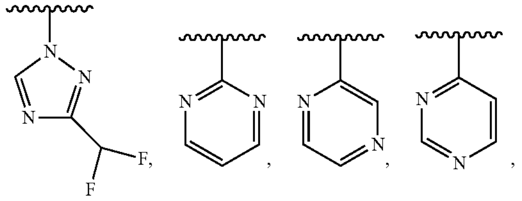
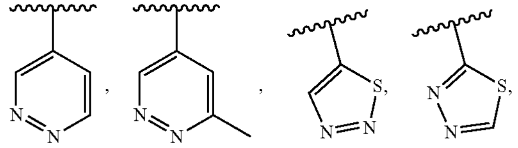
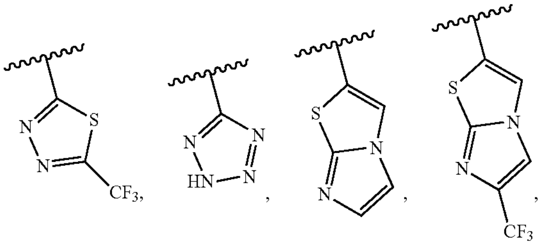
-continued
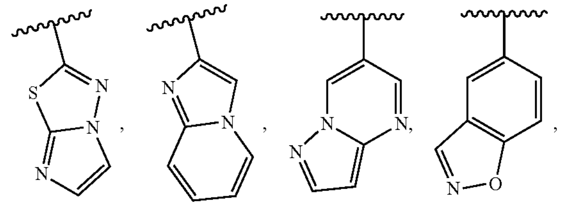
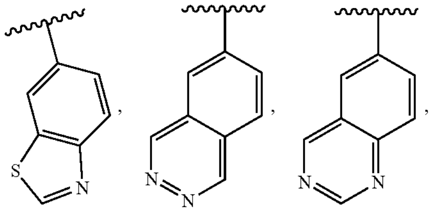
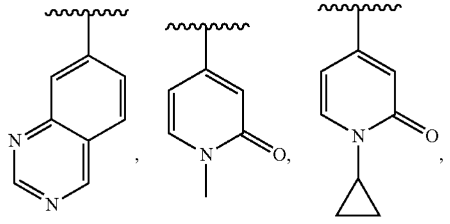
or
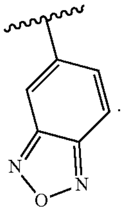
In some embodiments, at least one instance of $R^{3a}$ is:
—$OCH_3$,
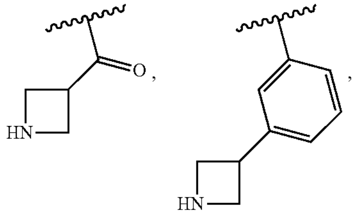
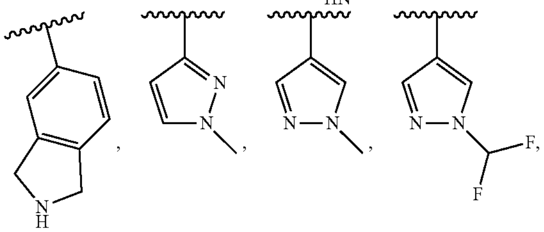
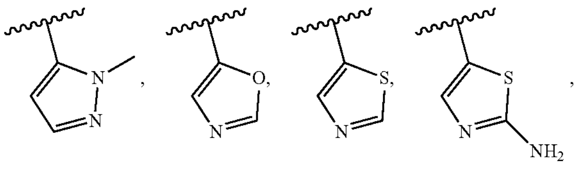

-continued

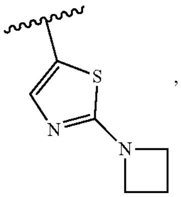,
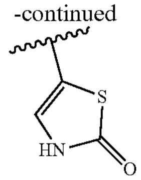,
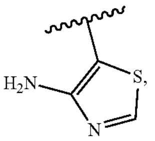

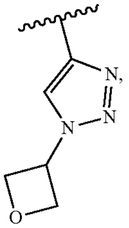
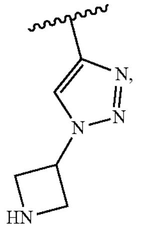

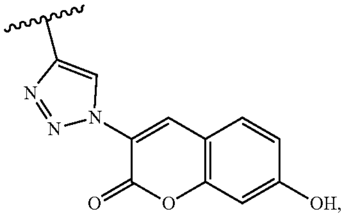
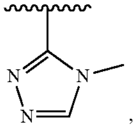,

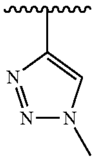,
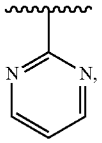
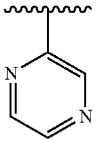,
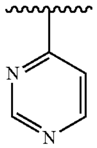,

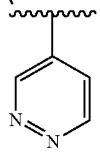, or
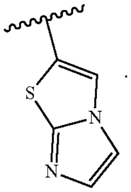.

As generally described herein, each instance of $R^A$ is independently hydrogen, optionally substituted acyl, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^A$ are joined together with their intervening atom to form an optionally substituted heterocyclic ring or optionally substituted heteroaryl ring.

In some embodiments, at least one instance of $R^A$ is hydrogen. In some embodiments, at least one instance of $R^A$ is optionally substituted acyl. In some embodiments, at least one instance of $R^A$ is optionally substituted $C_{1-12}$ alkyl. In some embodiments, at least one instance of $R^A$ is optionally substituted $C_{1-6}$ alkyl. In some embodiments, at least one instance of $R^A$ is unsubstituted $C_{1-6}$ alkyl. In some embodiments, at least one instance of $R^A$ is substituted $C_{1-6}$ alkyl. In some embodiments, at least one instance of $R^A$ is optionally substituted $C_{2-12}$ alkenyl. In some embodiments, at least one instance of $R^A$ is optionally substituted $C_{2-6}$ alkenyl. In some embodiments, at least one instance of $R^A$ is optionally substituted $C_{2-12}$ alkynyl. In some embodiments, at least one instance of $R^A$ is optionally substituted $C_{2-6}$ alkynyl. In some embodiments, at least one instance of $R^A$ is optionally substituted hetero$C_{1-12}$ alkyl. In some embodiments, at least one instance of $R^A$ is optionally substituted hetero$C_{1-6}$ alkyl. In some embodiments, at least one instance of $R^A$ is optionally substituted hetero$C_{1-12}$ alkenyl. In some embodiments, at least one instance of $R^A$ is optionally substituted hetero$C_{1-6}$ alkenyl. In some embodiments, at least one instance of $R^A$ is optionally substituted hetero$C_{1-12}$ alkynyl. In some embodiments, at least one instance of $R^A$ is optionally substituted hetero$C_{1-6}$ alkynyl. In some embodiments, at least one instance of $R^A$ is optionally substituted $C_{3-14}$ cycloalkyl. In some embodiments, at least one instance of $R^A$ is optionally substituted 5-10 membered heterocyclyl. In some embodiments, at least one instance of $R^A$ is optionally substituted 6-14 membered aryl. In some embodiments, at least one instance of $R^A$ is optionally substituted 5-14 membered heteroaryl. In some embodiments, at least one instance of $R^A$ is a nitrogen protecting group when attached to a nitrogen atom. In some embodiments, at least one instance of $R^A$ is an oxygen protecting group when attached to an oxygen atom. In some embodiments, at least one instance of $R^A$ is a sulfur protecting group when attached to a sulfur atom. In some embodiments, at least two instances of $R^A$ are joined together with their intervening atom to form an optionally substituted 5-10 membered heterocyclic ring. In some embodiments, at least two instances of $R^A$ are joined together with their intervening atom to form an optionally substituted 5-14 membered heteroaryl ring.

As generally described herein, m is 0, 1, 2, 3, 4, or 5, as valency permits.

In some embodiments, m is 0, 1, 2, 3, or 4. In some embodiments, m is 0, 1, 2, or 3. In some embodiments, m is 0, 1, or 2. In some embodiments, m is 0 or 1. In some embodiments, m is 0. In some embodiments, m is 1. In some embodiments, m is 2. In some embodiments, m is 3. In some embodiments, m is 4. In some embodiments, m is 5.

As generally described herein, each instance of $R^{3b}$ is independently halogen, optionally substituted alkyl, optionally substituted heterocyclyl, —CN, —$N(R^N)_2$, or —$SF_5$, or two instances of $R^{3b}$ are joined together with their intervening atoms to form an optionally substituted carbocyclic ring or optionally substituted heterocyclic ring.

In some embodiments, at least one instance of $R^{3b}$ is halogen. In some embodiments, at least one instance of $R^{3b}$ is —F or —$C_1$.

In some embodiments, at least one instance of $R^{3b}$ is optionally substituted alkyl. In some embodiments, at least one instance of $R^{3b}$ is unsubstituted $C_{1-3}$ alkyl. In some embodiments, at least one instance of $R^{3b}$ is $C_{1-3}$ haloalkyl. In some embodiments, at least one instance of $R^{3b}$ is —$CH_3$, —$CHF_2$, or —$CF_3$.

In some embodiments, at least one instance of $R^{3b}$ is optionally substituted heterocyclyl. In some embodiments, at least one instance of $R^{3b}$ is optionally substituted 4-6 membered heterocyclyl containing 1 or 2 N atoms. In some embodiments, at least one instance of $R^{3b}$ is

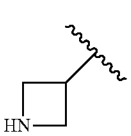,
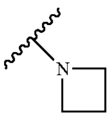, or
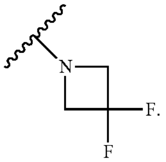

In some embodiments, at least one instance of $R^{3b}$ is —CN.

In some embodiments, at least one instance of $R^{3b}$ is —$N(R^N)_2$. In some embodiments, at least one instance of $R^{3b}$ is —$NH_2$,

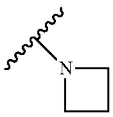

, or

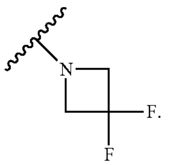

In some embodiments, at least one instance of $R^{3b}$ is —$SF_5$.

In some embodiments, two instances of $R^{3b}$ are joined together with their intervening atoms to form an optionally substituted carbocyclic ring or optionally substituted heterocyclic ring. In some embodiments, two instances of $R^{3b}$ are joined together with their intervening atoms to form an optionally substituted $C_{5-6}$ carbocyclic ring or optionally substituted 5-6 membered heterocyclic ring. In some embodiments, two instances of $R^{3b}$ are joined together with their intervening atoms to form

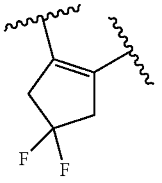

or

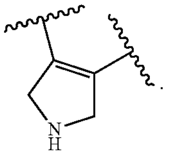

In some embodiments, at least one instance of $R^{3b}$ is —F, —Cl, —CN, —$CH_3$, —$CHF_2$, —$CF_3$, —$NH_2$, —$SF_5$,

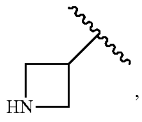

,

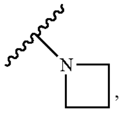

, or

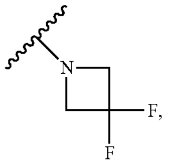

or two instances of $R^{3b}$ are joined together with their intervening atoms to form

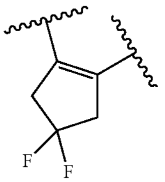

or

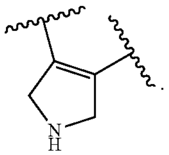

As generally described herein, each instance of $R^N$ is independently hydrogen, optionally substituted alkyl, optionally substituted carbocyclyl, optionally substituted heterocyclyl, optionally substituted aryl, optionally substituted heteroaryl, or a nitrogen protecting group, or two instances of $R^N$ are joined together with their intervening nitrogen atom to form an optionally substituted heterocyclic ring.

In some embodiments, at least one instance of $R^N$ is hydrogen.

In some embodiments, at least one instance of $R^N$ is optionally substituted alkyl. In some embodiments, at least one instance of $R^N$ is optionally substituted $C_{1-3}$ alkyl. In some embodiments, at least one instance of $R^N$ is —$CH_3$,

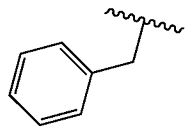

, or

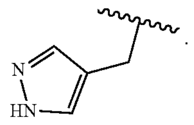

In some embodiments, at least one instance of $R^N$ is $C_{1-3}$ haloalkyl. In some embodiments, at least one instance of $R^N$ is —$CHF_2$.

In some embodiments, at least one instance of $R^N$ is optionally substituted carbocyclyl. In some embodiments, at least one instance of $R^N$ is optionally substituted $C_{3-6}$ heterocyclyl. In some embodiments, at least one instance of $R^N$ is cyclopropyl.

In some embodiments, at least one instance of $R^N$ is optionally substituted heterocyclyl. In some embodiments, at least one instance of $R^N$ is optionally substituted 4-6 membered heterocyclyl containing 1 or 2 ring heteroatoms selected from O and N. In some embodiments, at least one instance of $R^N$ is

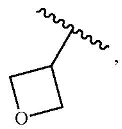

,

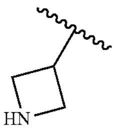

, or

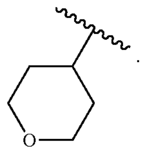

In some embodiments, at least one instance of $R^N$ is optionally substituted aryl. In some embodiments, at least one instance of $R^N$ is optionally substituted phenyl. In some embodiments, at least one instance of $R^N$ is

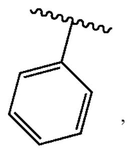

,

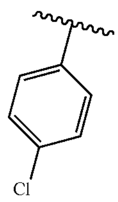

, or

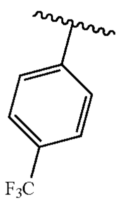

In some embodiments, at least one instance of $R^N$ is optionally substituted heteroaryl. In some embodiments, at least one instance of $R^N$ is optionally substituted 5-10 membered heteroaryl containing 1 or 2 ring heteroatoms selected from O, N, and S. In some embodiments, at least one instance of $R^N$ is

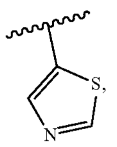

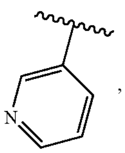

,

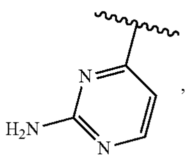

, or

-continued

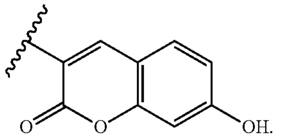

In some embodiments, at least one instance of $R^N$ is a nitrogen protecting group.

In some embodiments, two instances of $R^N$ are joined together with their intervening nitrogen atom to form an optionally substituted heterocyclic ring. In some embodiments, two instances of $R^N$ are joined together with their intervening nitrogen atom to form an optionally substituted 4-6 membered heterocyclyl containing 1 or 2 N atoms. In some embodiments, two instances of $R^N$ are joined together with their intervening nitrogen atom to form

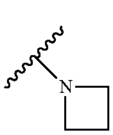 or 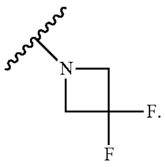

In some embodiments, at least one instance of $R^N$ is hydrogen, —$CH_3$, —$CHF_2$,

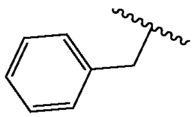, 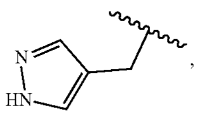, 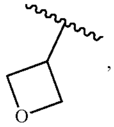, 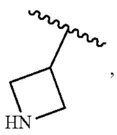, 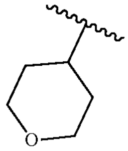, 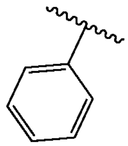, 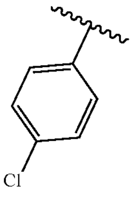, 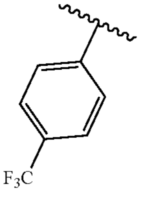, 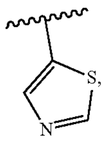 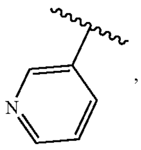, 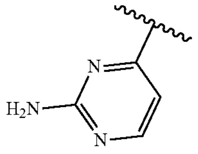, 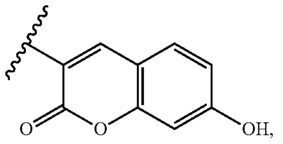

or two instances of $R^N$ are joined together with their intervening nitrogen atom to form

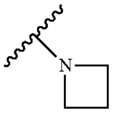 or 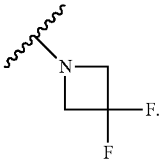

As generally described herein, p is 0, 1, 2, 3, 4, or 5, as valency permits.

In some embodiments, p is 0, 1, 2, 3, or 4. In some embodiments, p is 0, 1, 2, or 3. In some embodiments, p is 0, 1, or 2. In some embodiments, p is 0 or 1. In some embodiments, p is 0. In some embodiments, p is 1. In some embodiments, p is 2. In some embodiments, p is 3. In some embodiments, p is 4. In some embodiments, p is 5.

$R^4$, $R^{5a}$, and $R^{5b}$

As generally described herein, $R^4$ is hydrogen or optionally substituted alkyl.

In some embodiments, $R^4$ is hydrogen.

In some embodiments, $R^4$ is optionally substituted alkyl. In some embodiments, $R^4$ is optionally substituted $C_{1-6}$ alkyl. In some embodiments, $R^4$ is substituted $C_{1-6}$ alkyl. In some embodiments, $R^4$ is substituted methyl, substituted ethyl, substituted n-propyl, substituted isopropyl, substituted n-butyl, substituted tert-butyl, substituted sec-butyl, substituted isobutyl, substituted n-pentyl, substituted 3-pentanyl, substituted amyl, substituted neopentyl, substituted 3-methyl-2-butanyl, substituted tert-amyl, or substituted n-hexyl. In some embodiments, $R^4$ is unsubstituted $C_{1-6}$ alkyl. In some embodiments, $R^4$ is methyl, ethyl, n-propyl, isopropyl, n-butyl, tert-butyl, sec-butyl, isobutyl, n-pentyl, 3-pentanyl, amyl, neopentyl, 3-methyl-2-butanyl, tert-amyl, or n-hexyl.

In some embodiments, $R^4$ is optionally substituted $C_{1-3}$ alkyl. In some embodiments, $R^4$ is substituted $C_{1-3}$ alkyl. In some embodiments, $R^4$ is substituted methyl, substituted ethyl, substituted n-propyl, or substituted isopropyl. In some embodiments, $R^4$ is unsubstituted $C_{1-3}$ alkyl. In some embodiments, $R^4$ is methyl, ethyl, n-propyl, or isopropyl.

In some embodiments, $R^4$ is optionally substituted methyl. In some embodiments, $R^4$ is substituted methyl. In some embodiments, $R^4$ is methyl.

In some embodiments, $R^4$ is hydrogen or optionally substituted $C_{1-6}$ alkyl. In some embodiments, $R^4$ is hydrogen or unsubstituted $C_{1-6}$ alkyl. In some embodiments, $R^4$ is hydrogen or optionally substituted $C_{1-3}$ alkyl. In some embodiments, $R^4$ is hydrogen or unsubstituted $C_{1-3}$ alkyl. In some embodiments, $R^4$ is hydrogen or optionally substituted methyl. In some embodiments, $R^4$ is hydrogen or methyl.

As generally described herein, $R^{5a}$ and $R^{5b}$ are each hydrogen, or $R^{5a}$ and $R^{5b}$ are joined together with their intervening atom to form optionally substituted carbocyclyl.

In some embodiments, $R^{5a}$ and $R^{5b}$ are each hydrogen.

In some embodiments, $R^{5a}$ and $R^{5b}$ are joined together with their intervening atom to form optionally substituted carbocyclyl. In some embodiments, $R^{5a}$ and $R^{5b}$ are joined together with their intervening atom to form optionally substituted $C_{3-10}$ carbocyclyl. In some embodiments, $R^{5a}$ and $R^{5b}$ are joined together with their intervening atom to form optionally substituted $C_{3-6}$ carbocyclyl. In some embodiments. $R^{5a}$ and $R^{5b}$ are joined together with their intervening atom to form substituted $C_{3-6}$ carbocyclyl. In some embodiments, $R^{5a}$ and $R^{5b}$ are joined together with their intervening atom to form unsubstituted $C_{3-6}$ carbocyclyl. In some embodiments, $R^{5a}$ and $R^{5b}$ are joined together with their intervening atom to form optionally substituted cyclopropyl. In some embodiments, $R^{5a}$ and $R^{5b}$ are joined together with their intervening atom to form substituted cyclopropyl. In some embodiments, $R^{5a}$ and $R^{5b}$ are joined together with their intervening atom to form unsubstituted cyclopropyl.

In some embodiments, $R^{5a}$ and $R^{5b}$ are each hydrogen, or $R^{5a}$ and $R^{5b}$ are joined together with their intervening atom to form optionally substituted cyclopropyl. In some embodiments, $R^{5a}$ and $R^{5b}$ are each hydrogen, or $R^{5a}$ and $R^{5b}$ are joined together with their intervening atom to form substituted cyclopropyl. In some embodiments, $R^{5a}$ and $R^{5b}$ are each hydrogen, or $R^{5a}$ and $R^{5b}$ are joined together with their intervening atom to form unsubstituted cyclopropyl.

In some embodiments, $R^4$ is hydrogen, and $R^{5a}$ and $R^{5b}$ are each hydrogen.

Additional Subgeneric Embodiments

In some embodiments, the compound of Formula (I) is of Formula (I-a), (I-b), or (I-c):

(I-a)

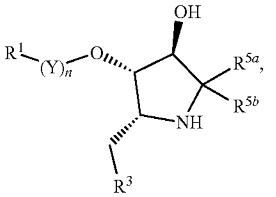

(I-b)

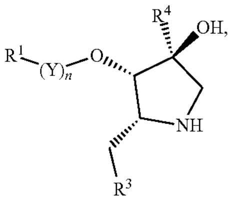

or (I-c)

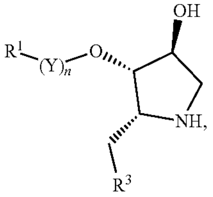

or a pharmaceutically acceptable salt thereof.

In some embodiments, the compound of Formula (I) is of Formula (I-a), or a pharmaceutically acceptable salt thereof. In some embodiments, the compound of Formula (I) is of Formula (I-b), or a pharmaceutically acceptable salt thereof. In some embodiments, the compound of Formula (I) is of Formula (I-c), or a pharmaceutically acceptable salt thereof.

In some embodiments, the compound of Formula (I) is of Formula (I-a), (I-b), or (I-c), or a pharmaceutically acceptable salt thereof, wherein $R^3$ is of formula (A-2), (A-3), (A-4), (A-5), (A-6), (A-7), (A-8), (A-9), (A-10), (A-11), (A-12), (A-13), (A-14), (A-15), (A-16), (A-17), (A-18), (A-19), (A-20), (A-21), (A-22), (A-23), (A-24), (A-25), (A-26), (A-27), (A-28), (A-29), (A-30), (A-31), (A-32), (A-33), (A-34), (A-35), (A-36), (A-37), or (A-38). In some embodiments, the compound of Formula (I) is of Formula (I-a), (I-b), or (I-c), or a pharmaceutically acceptable salt thereof, wherein $R^3$ is of formula (A-2), (A-3), (A-4), (A-5), (A-6), (A-7), (A-8), (A-9), (A-10), (A-11), (A-12), (A-13), (A-14), (A-15), (A-16), (A-17), (A-18), (A-19), (A-20), (A-21), (A-22), (A-23), (A-24), or (A-25).

In some embodiments, the compound of Formula (I) is of Formula (I-a), (I-b), or (I-c), or a pharmaceutically acceptable salt thereof, wherein $R^3$ is of formula (A-2), (A-7), (A-10), (A-13), (A-14), (A-16), (A-20), (A-25), (A-26), (A-28), (A-29), (A-31), or (A-32). In some embodiments, the compound of Formula (I) is of Formula (I-a), (I-b), or (I-c), or a pharmaceutically acceptable salt thereof, wherein $R^3$ is of formula (A-2), (A-7), (A-10), (A-13), (A-14), (A-16), (A-20), or (A-25). In some embodiments, the compound of Formula (I) is of Formula (I-a), (I-b), or (I-c), or a pharmaceutically acceptable salt thereof, wherein $R^3$ is of formula (A-2b), (A-2c), (A-2d), (A-7a), (A-7b), (A-7c), (A-10a), (A-10b), (A-10c), (A-13a), (A-13b), (A-13c), (A-14b), (A-16b), (A-20b), (A-20c), (A-20d), (A-25b), (A-25c), (A-26a), (A-28a), (A-29a), (A-31a), or (A-32a). In some embodiments, the compound of Formula (I) is of Formula (I-a), (I-b), or (I-c), or a pharmaceutically acceptable salt thereof, wherein $R^3$ is of formula (A-2b), (A-2c), (A-2d), (A-7a), (A-7b), (A-7c), (A-10a), (A-10b), (A-10c), (A-13a), (A-13b), (A-13c), (A-14b), (A-16b), (A-20b), (A-20c), (A-20d), (A-25b), or (A-25c).

In some embodiments, the compound of Formula (I) is of Formula (II):

(II)

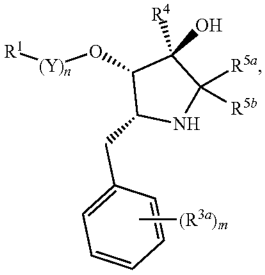

or a pharmaceutically acceptable salt thereof, wherein:

each instance of $R^{3a}$ is independently halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —CN, —$OR^A$, —SCN, —$SR^A$, —$SSR^A$, —$N_3$, —NO, —$N(R^A)_2$, —$NO_2$, —C(=O)$R^A$, —C(=O)$OR^A$, —C(=O)$SR^A$, —C(=O)N$(R^A)_2$. —C(=N$R^A$)$R^A$, —C(=N$R^A$)$OR^A$, —C(=N$R^A$)$SR^A$, —C(=N$R^A$)N$(R^A)_2$, —S(=O)$R^A$, —S(=O)$OR^A$, —S(=O)$SR^A$, —S(=O)N$(R^A)_2$, —$S(=O)_2R^A$, —$S(=O)_2OR^A$, —$S(=O)_2SR^A$, —$S(=O)_2N(R^A)_2$, —OC(=O)$R^A$, —OC(=O)$OR^A$, —OC(=O)$SR^A$, —OC(=O)N$(R^A)_2$, —OC(=N$R^A$)$R^A$, —OC(=N$R^A$)$OR^A$, —OC(=N$R^A$)$SR^A$, —OC(=N$R^A$)N$(R^A)_2$. —OS(=O)$R^A$, —OS(=O)$OR^A$, —OS(=O)$SR^A$, —OS(=O)N$(R^A)_2$, —$OS(=O)_2R^A$, —$OS(=O)_2OR^A$, $OS(=O)_2SR^A$, —$OS(=O)_2N(R^A)_2$, —ON$(R^A)_2$, —SC(=O)$R^A$, —SC(=O)$OR^A$, —SC(=O)$SR^A$, —SC(=O)N$(R^A)_2$, —SC(=N$R^A$)$R^A$, —SC(=N$R^A$)$OR^A$, —SC(=N$R^A$)$SR^A$, —SC(=N$R^A$)N$(R^A)_2$, —$NR^A$C(=O)$R^A$, —NRC(=O)$OR^A$, —$NR^A$C(=O)$SR^A$, —$NR^A$C (=O)N($R^A$)$_2$, —$NR^A$C(=$NR^A$)$R^A$, —$NR^A$C(=$NR^A$)$OR^A$, —$NR^A$C(=$NR^A$)$SR^A$, —$NR^A$C(=$NR^A$)N($R^A$)$_2$, —$NR^A$S(=O)$R^A$, —$NR^A$S(=O)$OR^A$, —$NR^A$S(=O)$SR^A$, —$NR^A$S(=O)N($R^A$)$_2$, —$NR^A$S(=O)$_2R^A$, —$NR^A$S(=O)$_2OR^A$, —$NR^A$S(=O)$_2SR^A$, —$NR^A$S(=O)$_2$N($R^A$)$_2$, —Si($R^A$)$_3$, —Si($R^A$)$_2OR^A$, —Si($R^A$)($OR^A$)$_2$, —Si($OR^A$)$_3$, —OSi($R^A$)$_3$, —OSi($R^A$)$_2OR^A$, —OSi($R^A$)($OR^A$)$_2$, —OSi($OR^A$)$_3$, or —B($OR^A$)$_2$;

each instance of $R^A$ is independently hydrogen, optionally substituted acyl, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^A$ are joined together with their intervening atom to form an optionally substituted heterocyclic ring or optionally substituted heteroaryl ring; and m is 0, 1, 2, 3, 4, or 5.

In some embodiments, the compound of Formula (II) is of Formula (II-a), (II-b), or (II-c):

(II-a)

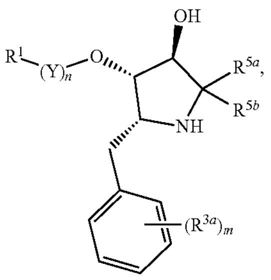

(II-b)

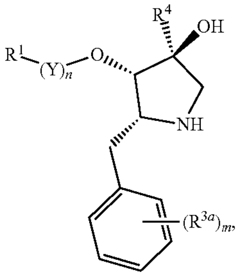

or (II-c)

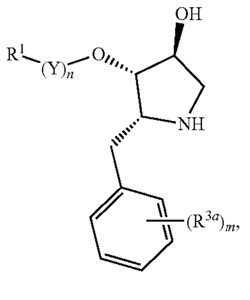

or a pharmaceutically acceptable salt thereof.

In some embodiments, the compound of Formula (II) is of Formula (II-a), or a pharmaceutically acceptable salt thereof. In some embodiments, the compound of Formula (II) is of Formula (II-b), or a pharmaceutically acceptable salt thereof. In some embodiments, the compound of Formula (II) is of Formula (II-c), or a pharmaceutically acceptable salt thereof.

In some embodiments, the compound of Formula (II) is of Formula (II-d-1), (II-d-2), or (II-d-3):

(II-d-1)

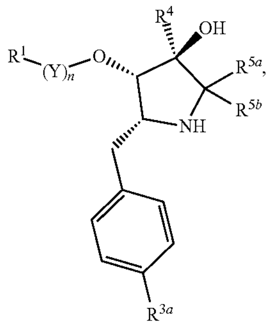

(II-d-2)

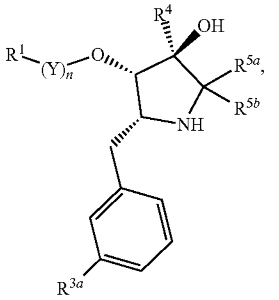

or (II-d-1)

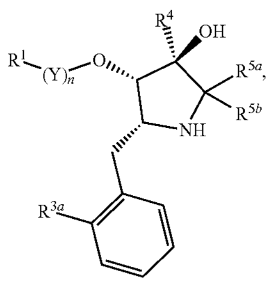

or a pharmaceutically acceptable salt thereof.

In some embodiments, the compound of Formula (II-d) is of Formula (II-d-1), or a pharmaceutically acceptable salt thereof. In some embodiments, the compound of Formula (II-d) is of Formula (II-d-2), or a pharmaceutically acceptable salt thereof. In some embodiments, the compound of Formula (II-d) is of Formula (II-d-3), or a pharmaceutically acceptable salt thereof.

In some embodiments, the compound of Formula (II) is of Formula (II-e-1), (II-e-2), or (II-e-3):

(II-e-1)

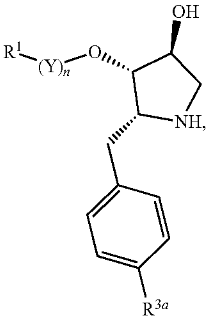

(II-e-2)

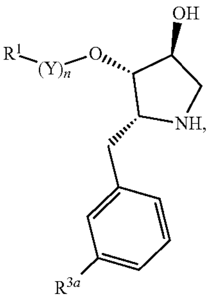

or (II-e-3)

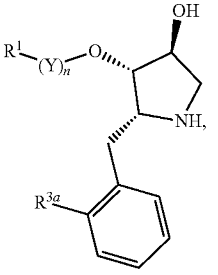

or a pharmaceutically acceptable salt thereof.

In some embodiments, the compound of Formula (II-e) is of Formula (II-e-1), or a pharmaceutically acceptable salt thereof. In some embodiments, the compound of Formula (II-e) is of Formula (II-e-2), or a pharmaceutically acceptable salt thereof. In some embodiments, the compound of Formula (II-e) is of Formula (II-e-3), or a pharmaceutically acceptable salt thereof.

In some embodiments of Formula (II), or a subgenus thereof (e.g., Formula (II-a), (II-b), (II-c), (II-d-1), (II-d-2), (II-d-3), (II-e-1), (II-e-2), or (II-e-3)), or a pharmaceutically acceptable salt thereof, $R^1$ is $C_{3-6}$ carbocyclyl, 4-6 membered heterocyclyl containing 1 ring N atom or 1 ring O atom, 8-10 membered heterocyclyl containing 1 or 2 ring heteroatoms selected from O and N, phenyl, 5-6 membered heteroaryl containing 1, 2, or 3 ring N atoms, or 8-10 membered heteroaryl containing 1, 2, or 3 ring N atoms; wherein the carbocyclyl, heterocyclyl, phenyl, or heteroaryl is substituted with 0, 1, or 2 instances of $R^{1b}$, as valency permits; wherein each instance of $R^{1b}$ is independently halogen, optionally substituted $C_{1-4}$ alkyl, optionally substituted 4-6 membered heterocyclyl, $—OR^{1c}$, $—N(R^{1c})_2$, —CN, $—NO_2$, $—C(=O)R^{1c}$, $—C(=O)OR^{1c}$, $—C(=O)N(R^{1c})_2$, $—C(=NR^{1c})N(R^{1c})_2$, or $—NR^{1c}C(=O)R^{1c}$, or two instances of $R^{1b}$ are taken together to form =O, as valency permits, or two instances of $R^{1b}$ are joined together with their intervening atoms to form an optionally substituted 5-6 membered heterocyclic ring; and each instance of $R^{1c}$ is independently hydrogen, optionally substituted $C_{1-3}$ alkyl, or optionally substituted 5-6 membered heteroaryl; and each instance of $R^{1c}$ is independently hydrogen, optionally substituted $C_{1-3}$ alkyl, or optionally substituted 5-6 membered heteroaryl.

In some embodiments of Formula (II), or a subgenus thereof, or a pharmaceutically acceptable salt thereof, $R^1$ is unsubstituted $C_{1-3}$ alkyl or $C_{1-3}$ haloalkyl, and n is 0. In some embodiments of Formula (II), or a subgenus thereof, or a pharmaceutically acceptable salt thereof, $R^1$ is unsubstituted $C_{1-3}$ alkyl. In some embodiments of Formula (II), or a subgenus thereof, or a pharmaceutically acceptable salt thereof, $R^1$ is $C_{1-3}$ haloalkyl, and n is 0.

In some embodiments of Formula (II), or a subgenus thereof, or a pharmaceutically acceptable salt thereof,

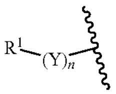

is of formula: —H, $—CH_3$, $—CF_3$, $—CH_2CH_3$,

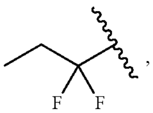, 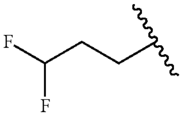, 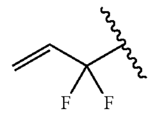,

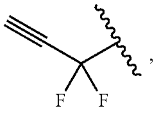, 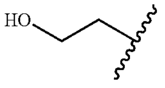, 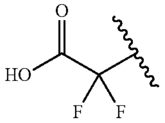,

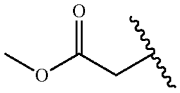, 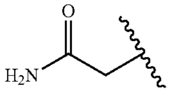,

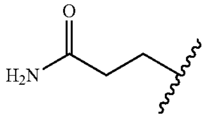, 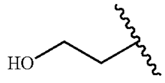,

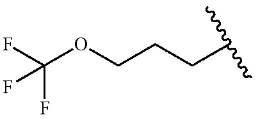, 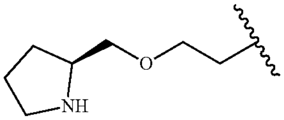,

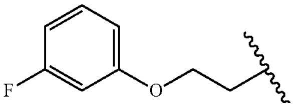, 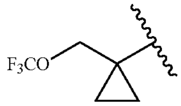,

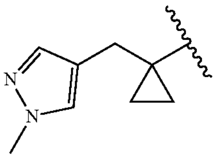, 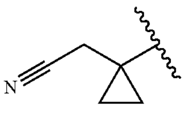,

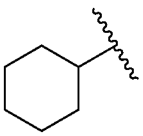, 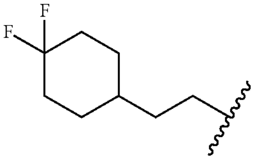,

-continued
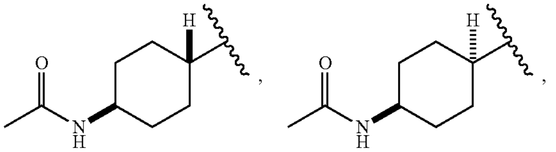
, ,
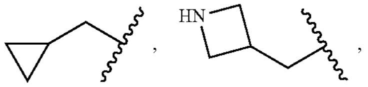
, ,
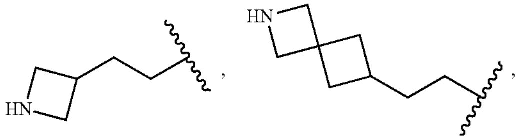
, ,
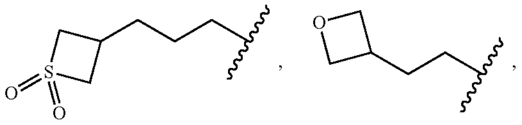
, ,
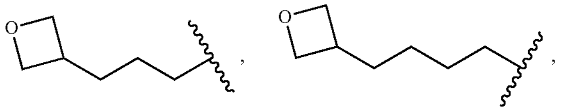
, ,
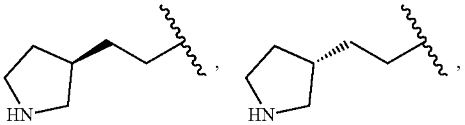
, ,
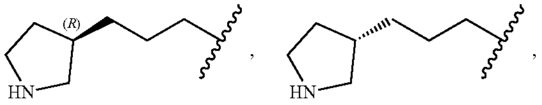
, ,
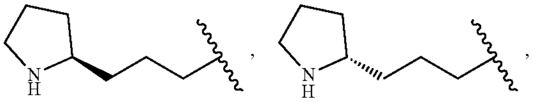
, ,
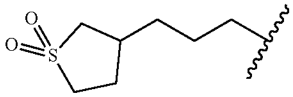
,
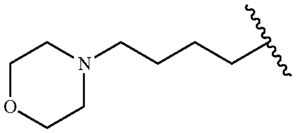
,
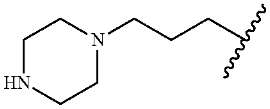
,
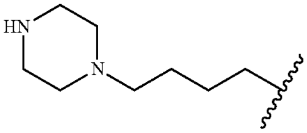
,
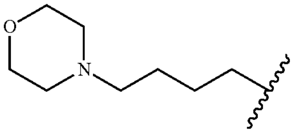
,
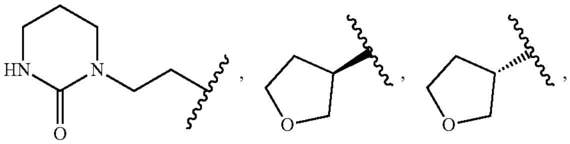
, , ,
-continued
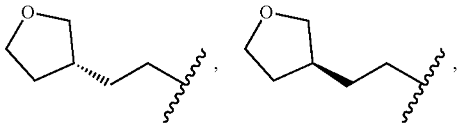
, ,
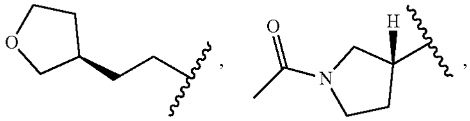
, ,
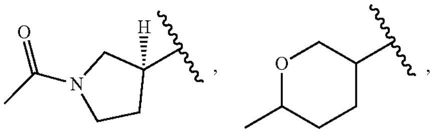
, ,
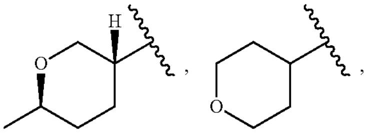
, ,
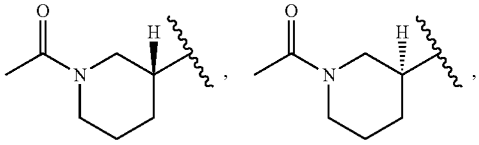
, ,
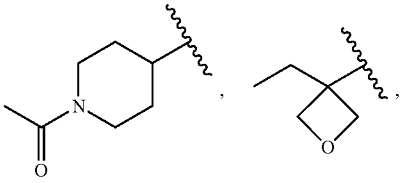
, ,
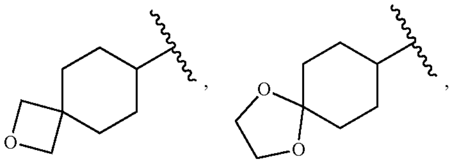
, ,
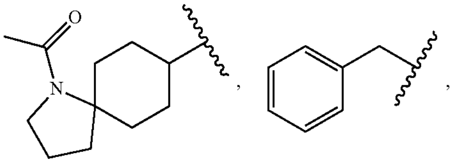
, ,
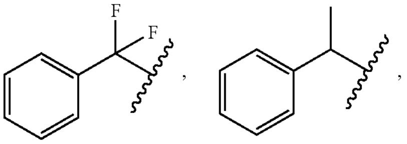
, ,
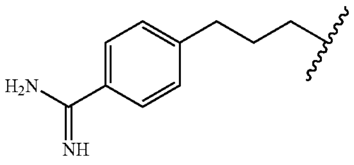
,
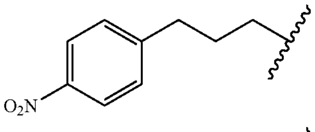
,
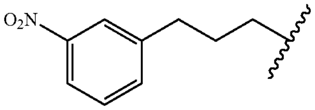
, -continued
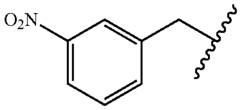
,
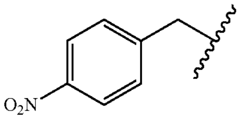
,
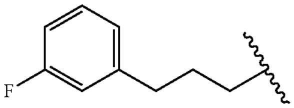
,
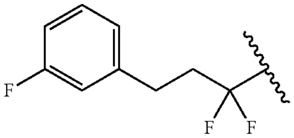
,
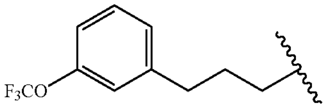
,
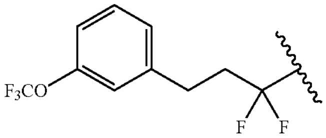
,
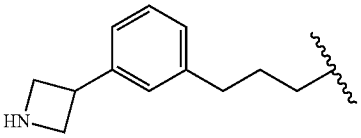
,
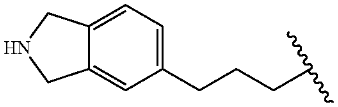
,
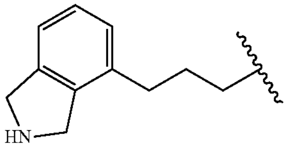
,
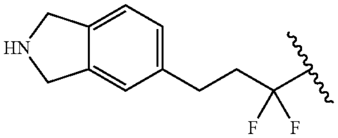
,
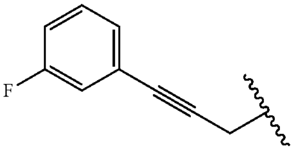
,
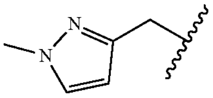
,
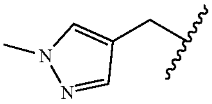
,
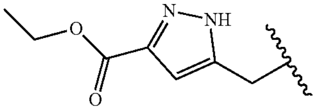
,
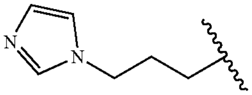
,
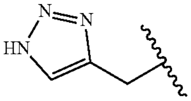
,
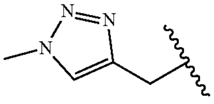
,
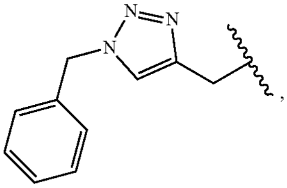
,
-continued
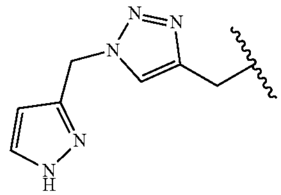
,
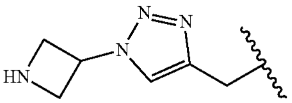
,
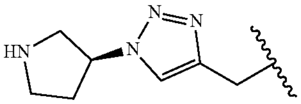
,
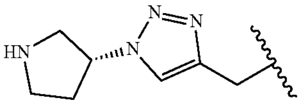
,
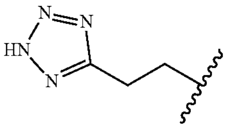
,
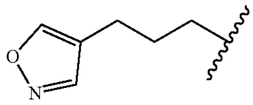
,
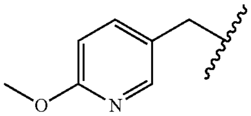
,
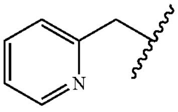
,
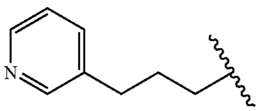
,
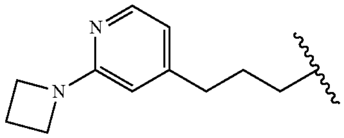
,
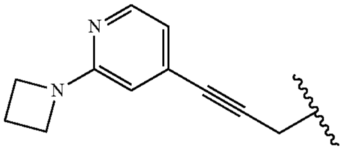
,
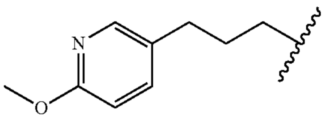
, or
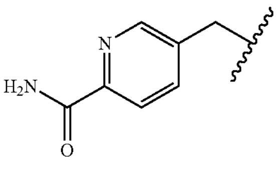
.
In some embodiments, the compound of Formula (I) is of Formula (III-a) to (III-t):

-continued
(III-a)
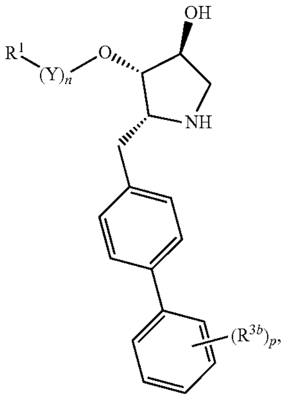
(III-b)
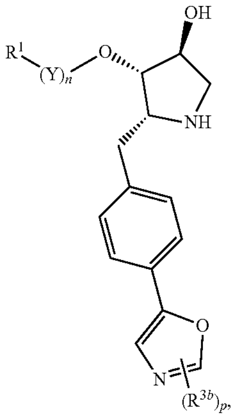
(III-c)
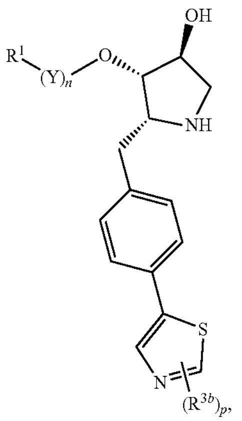
(III-d)
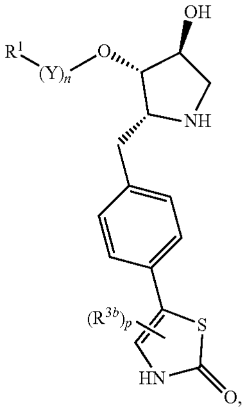
(III-e)
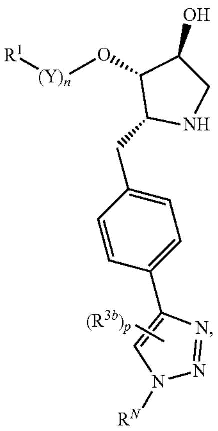
(III-f)
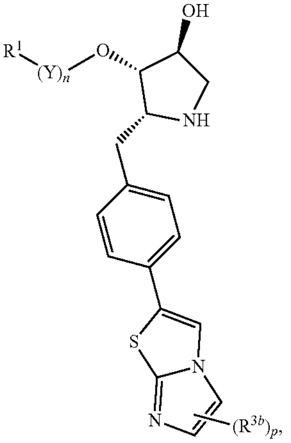
(III-g)
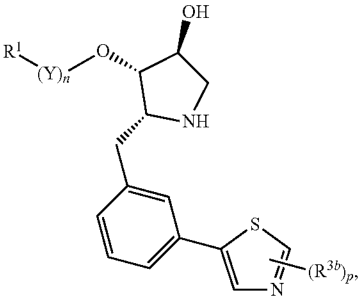
(III-h)
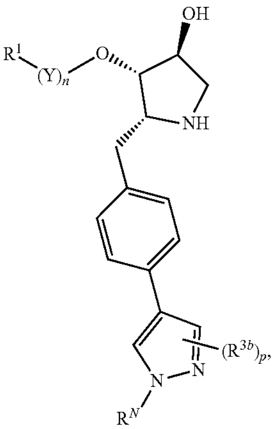

-continued
(III-i)
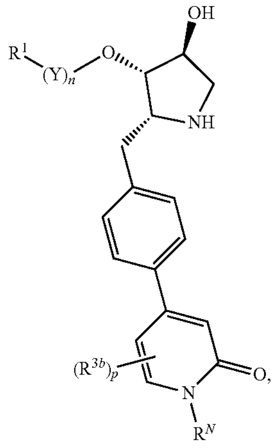
(III-j)
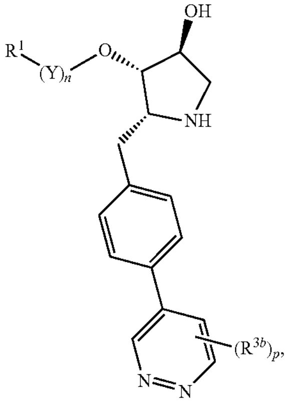
(III-k)
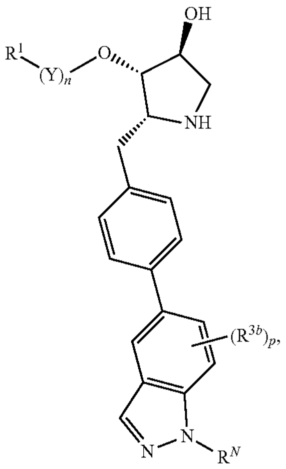
-continued
(III-l)
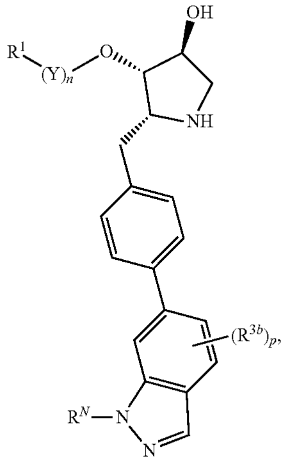
(III-m)
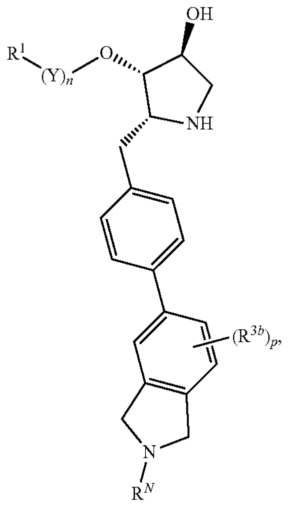
(III-n)
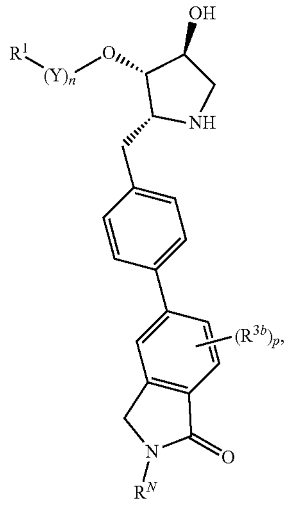

-continued (III-o)

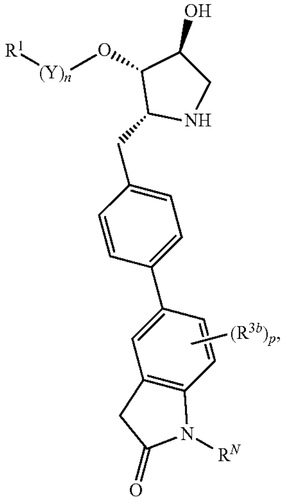

(III-p)

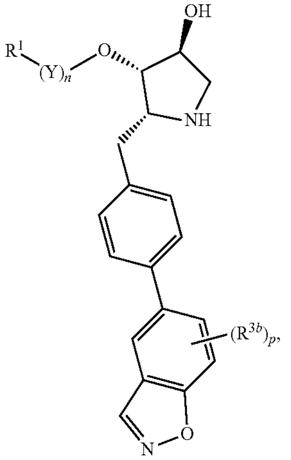

(III-q)

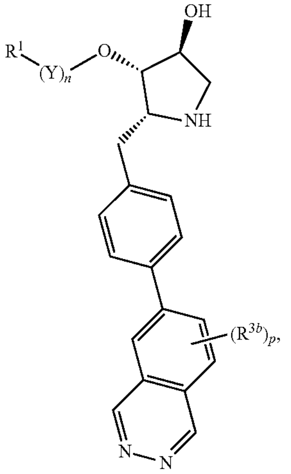

-continued (III-r)

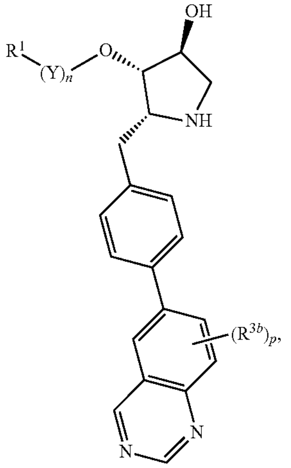

(III-s)

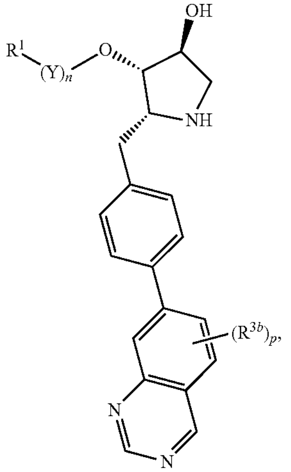

or (III-t)

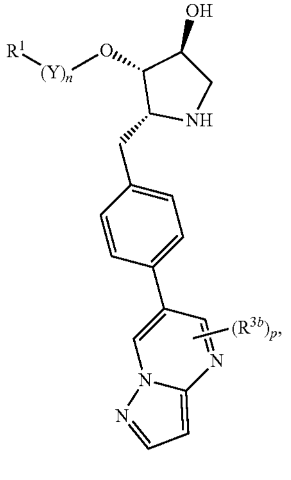

or a pharmaceutically acceptable salt thereof, wherein:

each instance of $R^{3b}$ is independently halogen, optionally substituted alkyl, optionally substituted heterocyclyl, —CN, —$N(R^N)_2$, or —$SF_5$, or two instances of $R^{3b}$ are joined together with their intervening atoms to form an optionally substituted carbocyclic ring or optionally substituted heterocyclic ring;

each instance of $R^N$ is independently hydrogen, optionally substituted alkyl, optionally substituted carbocyclyl, optionally substituted heterocyclyl, optionally substituted aryl, optionally substituted heteroaryl, or a nitrogen protecting group, or two instances of $R^N$ are joined together with their intervening nitrogen atom to form an optionally substituted heterocyclic ring; and p is 0, 1, 2, 3, 4, or 5, as valency permits.

In some embodiments, the compound of Formula (I) is of Formula (III-a), or a pharmaceutically acceptable salt thereof. In some embodiments, the compound of Formula (I) is of Formula (III-b), or a pharmaceutically acceptable salt thereof. In some embodiments, the compound of Formula (I) is of Formula (III-c), or a pharmaceutically acceptable salt thereof. In some embodiments, the compound of Formula (I) is of Formula (III-d), or a pharmaceutically acceptable salt thereof. In some embodiments, the compound of Formula (I) is of Formula (III-e), or a pharmaceutically acceptable salt thereof. In some embodiments, the compound of Formula (I) is of Formula (III-f), or a pharmaceutically acceptable salt thereof. In some embodiments, the compound of Formula (I) is of Formula (III-g), or a pharmaceutically acceptable salt thereof. In some embodiments, the compound of Formula (I) is of Formula (III-h), or a pharmaceutically acceptable salt thereof. In some embodiments, the compound of Formula (I) is of Formula (III-i), or a pharmaceutically acceptable salt thereof. In some embodiments, the compound of Formula (I) is of Formula (III-j), or a pharmaceutically acceptable salt thereof. In some embodiments, the compound of Formula (I) is of Formula (III-k), or a pharmaceutically acceptable salt thereof. In some embodiments, the compound of Formula (I) is of Formula (III-l), or a pharmaceutically acceptable salt thereof. In some embodiments, the compound of Formula (I) is of Formula (III-m), or a pharmaceutically acceptable salt thereof. In some embodiments, the compound of Formula (I) is of Formula (III-n), or a pharmaceutically acceptable salt thereof. In some embodiments, the compound of Formula (I) is of Formula (III-o), or a pharmaceutically acceptable salt thereof. In some embodiments, the compound of Formula (I) is of Formula (III-p), or a pharmaceutically acceptable salt thereof. In some embodiments, the compound of Formula (I) is of Formula (III-q), or a pharmaceutically acceptable salt thereof. In some embodiments, the compound of Formula (I) is of Formula (III-r), or a pharmaceutically acceptable salt thereof. In some embodiments, the compound of Formula (I) is of Formula (III-s), or a pharmaceutically acceptable salt thereof. In some embodiments, the compound of Formula (I) is of Formula (III-t), or a pharmaceutically acceptable salt thereof.

In some embodiments of Formula (III-a) to (III-t), or a pharmaceutically acceptable salt thereof, $R^1$ is $C_{3-6}$ carbocyclyl, 4-6 membered heterocyclyl containing 1 ring N atom or 1 ring O atom, 8-10 membered heterocyclyl containing 1 or 2 ring heteroatoms selected from O and N, phenyl, 5-6 membered heteroaryl containing 1, 2, or 3 ring N atoms, or 8-10 membered heteroaryl containing 1, 2, or 3 ring N atoms; wherein the carbocyclyl, heterocyclyl, phenyl, or heteroaryl is substituted with 0, 1, or 2 instances of $R^{1b}$, as valency permits; wherein each instance of $R^{1b}$ is independently halogen, optionally substituted $C_{1-4}$ alkyl, optionally substituted 4-6 membered heterocyclyl, $—OR^{1c}$, $—N(R^{1c})_2$, —CN, $—NO_2$, $—C(=O)R^{1c}$, $—C(=O)OR^{1c}$, $—C(=O)N(R^{1c})_2$, $—C(=NR^{1c})N(R^{1c})_2$, or $—NR^{1c}C(=O)R^{1c}$, or two instances of $R^{1b}$ are taken together to form =O, as valency permits, or two instances of $R^{1b}$ are joined together with their intervening atoms to form an optionally substituted 5-6 membered heterocyclic ring; and each instance of $R^{1c}$ is independently hydrogen, optionally substituted $C_{1-3}$ alkyl, or optionally substituted 5-6 membered heteroaryl; and each instance of $R^{1c}$ is independently hydrogen, optionally substituted $C_{1-3}$ alkyl, or optionally substituted 5-6 membered heteroaryl.

In some embodiments of Formula (III-a) to (III-t), or a pharmaceutically acceptable salt thereof, $R^1$ is unsubstituted $C_{1-3}$ alkyl or $C_{1-3}$ haloalkyl, and n is 0. In some embodiments of Formula (III-a) to (III-t), or a pharmaceutically acceptable salt thereof, $R^1$ is unsubstituted $C_{1-3}$ alkyl, and n is 0. In some embodiments of Formula (III-a) to (III-t), or a pharmaceutically acceptable salt thereof, $R^1$ is $C_{1-3}$ haloalkyl, and n is 0. In some embodiments of Formula (III-e), (III-h), (III-i), (III-k), (III-l), (III-m), (III-n), or (III-o), or a pharmaceutically acceptable salt thereof, $R^N$ is hydrogen, unsubstituted $C_{1-3}$ alkyl, or $C_{1-3}$ haloalkyl. In some embodiments of Formula (III-e), (III-h), (III-i), (III-k), (III-l), (III-m), (III-n), or (III-o), or a pharmaceutically acceptable salt thereof, $R^N$ is hydrogen. In some embodiments of Formula (III-e), (III-h), (III-i), (III-k), (III-l), (III-m), (III-n), or (III-o), or a pharmaceutically acceptable salt thereof, $R^N$ is unsubstituted $C_{1-3}$ alkyl. In some embodiments of Formula (III-e), (III-h), (III-i), (III-k), (III-l), (III-m), (III-n), or (III-o), or a pharmaceutically acceptable salt thereof, $R^N$ is $C_{1-3}$ haloalkyl.

In some embodiments of Formula (III-e), (III-h), (III-i), (III-k), (III-l), (III-m), (III-n), or (III-o), or a pharmaceutically acceptable salt thereof, $R^1$ is unsubstituted $C_{1-3}$ alkyl or $C_{1-3}$ haloalkyl; n is 0; and $R^N$ is hydrogen, unsubstituted $C_{1-3}$ alkyl, or $C_{1-3}$ haloalkyl. In some embodiments of Formula (III-e), (III-h), (III-i), (III-k), (III-l), (III-m), (III-n), or (III-o), or a pharmaceutically acceptable salt thereof, $R^1$ is unsubstituted $C_{1-3}$ alkyl; n is 0; and $R^N$ is hydrogen, unsubstituted $C_{1-3}$ alkyl, or $C_{1-3}$ haloalkyl. In some embodiments of Formula (III-e), (III-h), (III-i), (III-k), (III-l), (III-m), (III-n), or (III-o), or a pharmaceutically acceptable salt thereof, $R^1$ is $C_{1-3}$ haloalkyl; n is 0; and $R^N$ is hydrogen, unsubstituted $C_{1-3}$ alkyl, or $C_{1-3}$ haloalkyl. In some embodiments of Formula (III-e), (III-h), (III-i), (III-k), (III-l), (III-m), (III-n), or (III-o), or a pharmaceutically acceptable salt thereof, $R^1$ is unsubstituted $C_{1-3}$ alkyl or $C_{1-3}$ haloalkyl; n is 0; and $R^N$ is hydrogen. In some embodiments of Formula (III-e), (III-h), (III-i), (III-k), (III-l), (III-m), (III-n), or (III-o), or a pharmaceutically acceptable salt thereof, $R^1$ is unsubstituted $C_{1-3}$ alkyl or Cis haloalkyl; n is 0; and $R^N$ is unsubstituted $C_{1-3}$ alkyl. In some embodiments of Formula (III-e), (III-h), (III-i), (III-k), (III-l), (III-m), (III-n), or (III-o), or a pharmaceutically acceptable salt thereof, $R^1$ is unsubstituted $C_{1-3}$ alkyl or $C_{1-3}$ haloalkyl; n is 0; and $R^N$ is $C_{1-3}$ haloalkyl.

In some embodiments of Formula (III-a) to (III-t), or a pharmaceutically acceptable salt thereof,

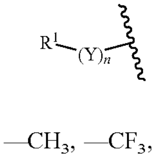

is of formula: —H, $—CH_3$, $—CF_3$, $—CH_2CH_3$,

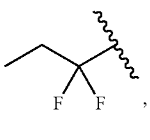,
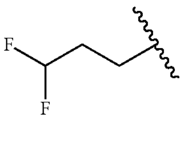,
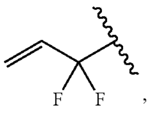,

-continued
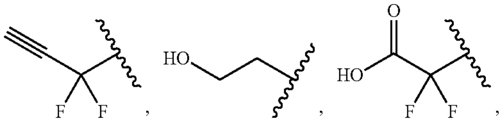
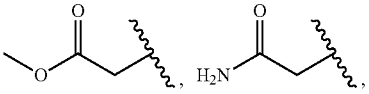
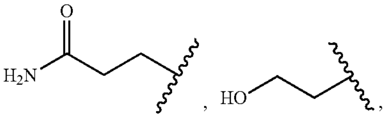
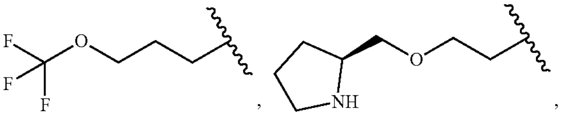
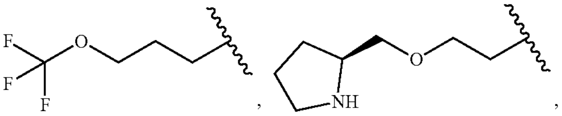
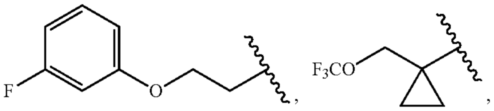
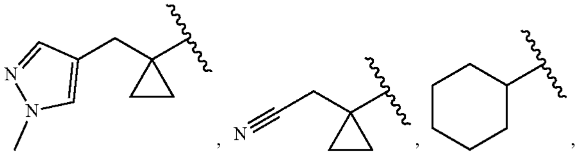
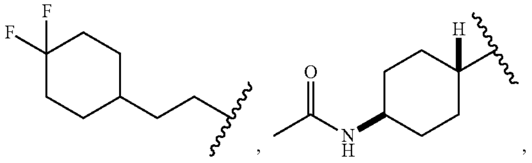
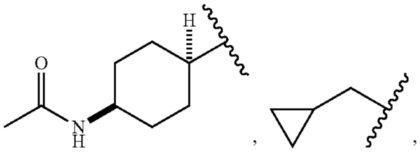
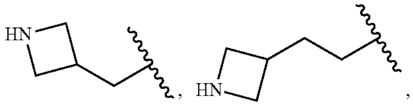
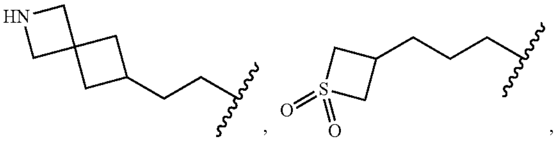
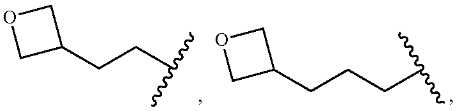
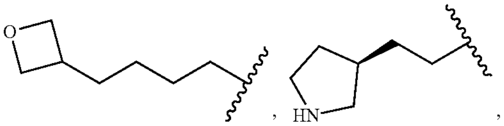
-continued
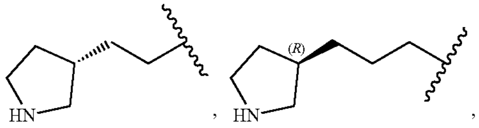
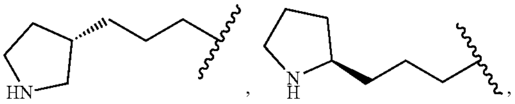
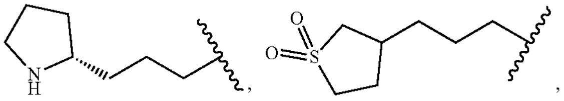
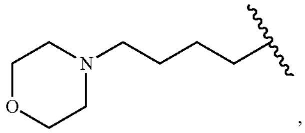
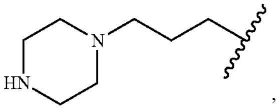
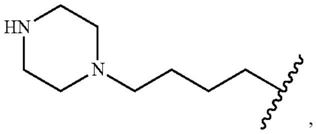
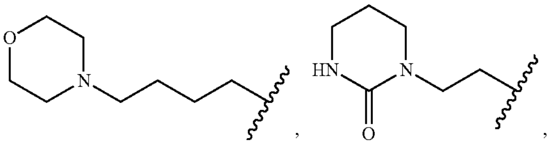
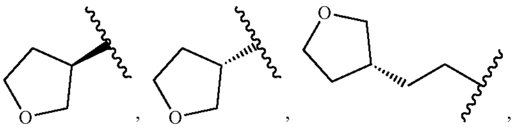
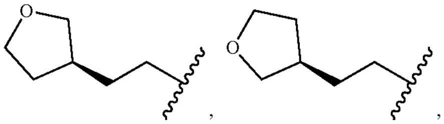
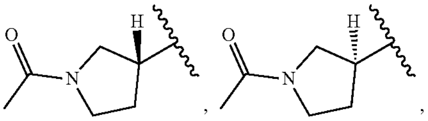
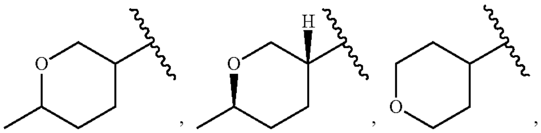
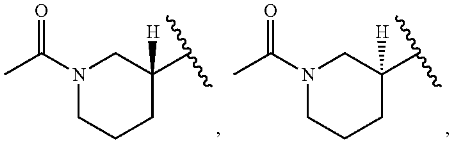
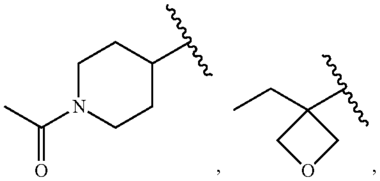

-continued
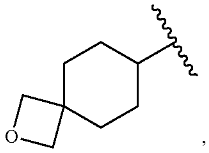 , 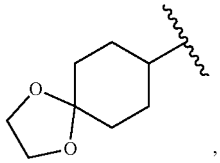 ,
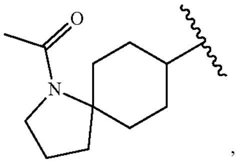 , 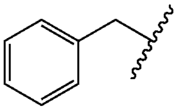 ,
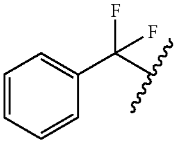 , 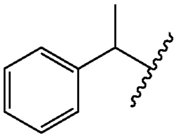 ,
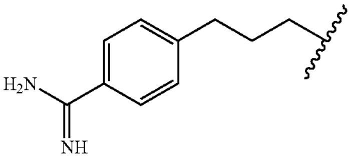 ,
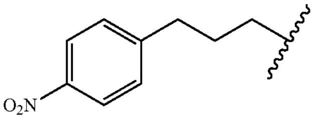 ,
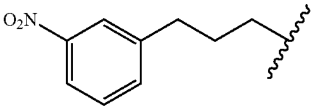 , 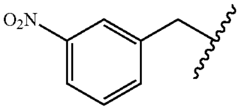 ,
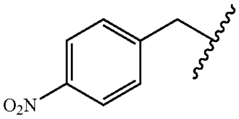 , 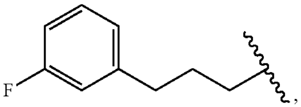 ,
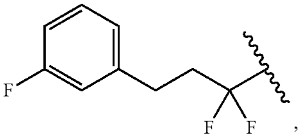 ,
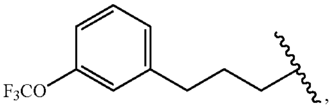 ,
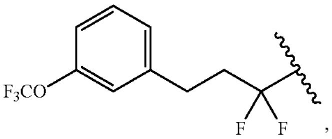 ,
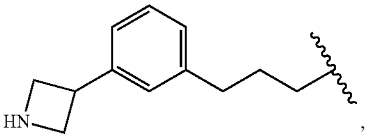 ,
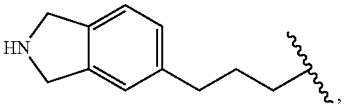 ,
-continued
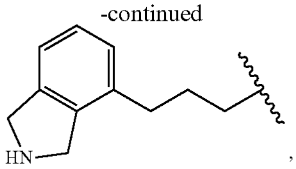 ,
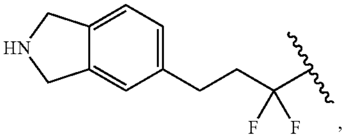 ,
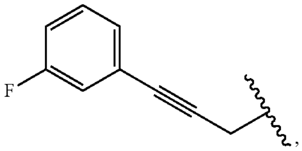 , 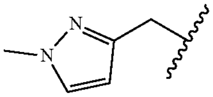 ,
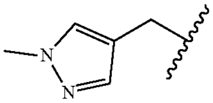 , 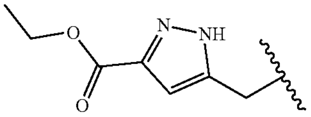 ,
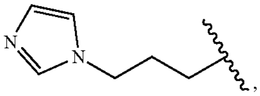 , 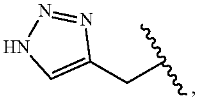 ,
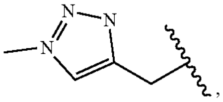 , 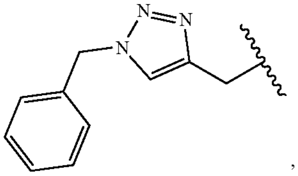 ,
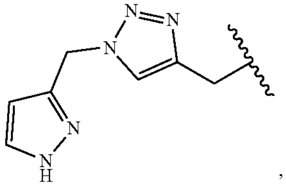 ,
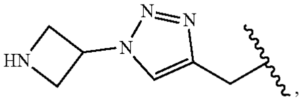 ,
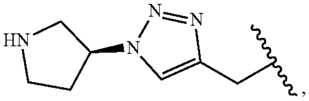 ,
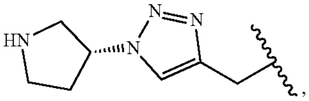 , 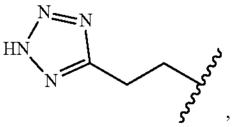 ,
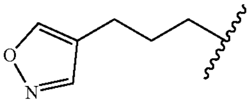 , 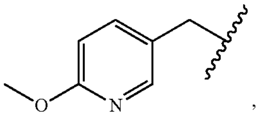 ,
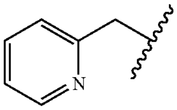 , 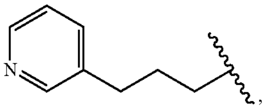 ,
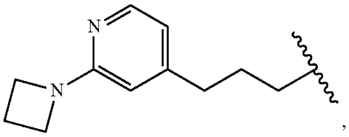 , -continued
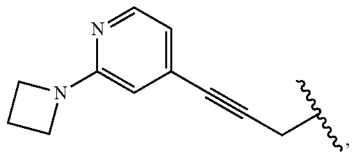
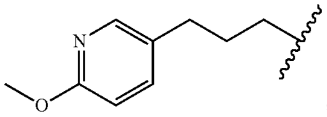
, or
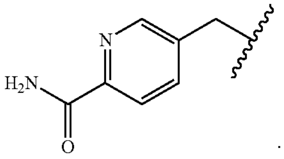
.
In some embodiments of Formula (III-a) to (III-t),
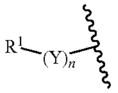
is of formula: $—CH_2CH_3$ or
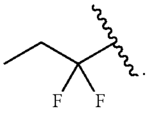
In some embodiments, the compound of Formula (I) is of Formula (IV):
(IV)
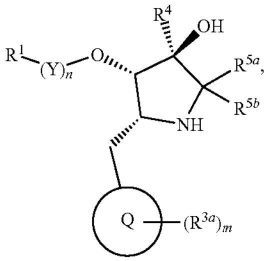
or a pharmaceutically acceptable salt thereof, wherein:
Ring Q is of formula:
(B-1)
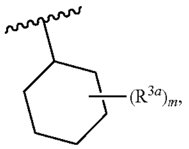
-continued
(C-1)
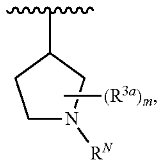
(C-2)
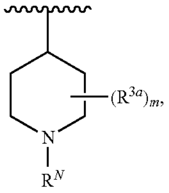
(D-1)
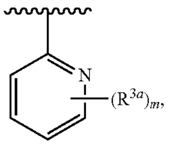
(D-2)
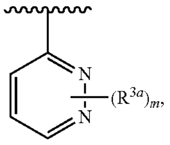
(D-3)
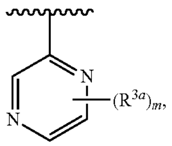
(D-4)
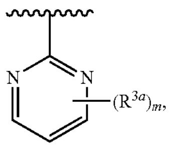
(D-5)
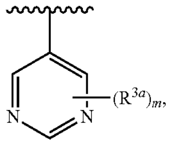
(D-6)
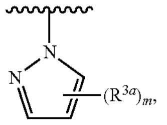
(D-7)
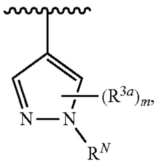
or
(D-8)
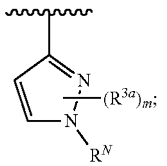

each instance of $R^{3a}$ is independently halogen, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, —CN, —$OR^A$, —SCN, —$SR^A$, —$SSR^A$, —$N_3$, —NO, —$N(R^A)_2$, —$NO_2$, —C(═O)$R^A$, —C(═O)$OR^A$, —C(═O)$SR^A$, —C(═O)$N(R^A)_2$, —C(═$NR^A$)$R^A$, —C(═$NR^A$)$OR^A$, —C(═$NR^A$)$SR^A$, —C(═$NR^A$)$N(R^A)_2$, —S(═O)$R^A$, —S(═O)$OR^A$, —S(═O)$SR^A$, —S(═O)$N(R^A)_2$, —$S(═O)_2R^A$, —$S(═O)_2OR^A$, —$S(═O)_2SR^A$, —$S(═O)_2N(R^A)_2$, —OC(═O)$R^A$, —OC(═O)$OR^A$, —OC(═O)$SR^A$, —OC(═O)$N(R^A)_2$, —OC(═$NR^A$)$R^A$, —OC(═$NR^A$)$OR^A$, —OC(═$NR^A$)$SR^A$, —OC(═$NR^A$)$N(R^A)_2$, —OS(═O)$R^A$, —OS(═O)$OR^A$, —OS(═O)$SR^A$, —OS(═O)$N(R^A)_2$, —$OS(═O)_2R^A$, —$OS(═O)_2OR^A$, $OS(═O)_2SR^A$, —$OS(═O)_2N(R^A)_2$, —$ON(R^A)_2$, —SC(═O)$R^A$, —SC(═O)$OR^A$, —SC(═O)$SR^A$, —SC(═O)$N(R^A)_2$, —SC(═$NR^A$)$R^A$, —SC(═$NR^A$)$OR^A$, —SC(═$NR^A$)$SR^A$, —SC(═$NR^A$)$N(R^A)_2$, —$NR^A$C(═O)$R^A$, —$NR^A$C(═O)$OR^A$, —$NR^A$C(═O)$SR^A$, —$NR^A$C(═O)$N(R^A)_2$, —$NR^A$C(═$NR^A$)$R^A$, —$NR^A$C(═$NR^A$)$OR^A$, —$NR^A$C(═$NR^A$)$SR^A$, —$NR^A$C(═$NR^A$)$N(R^A)_2$, —$NR^A$S(═O)$R^A$, —$NR^A$S(═O)$OR^A$, —$NR^A$S(═O)$SR^A$, —$NR^A$S(═O)$N(R^A)_2$, —$NR^AS(═O)_2R^A$, —$NR^AS(═O)_2OR^A$, —$NR^AS(═O)_2SR^A$, —$NR^AS(═O)_2N(R^A)_2$, —$Si(R^A)_3$, —$Si(R^A)_2OR^A$, —$Si(R^A)(OR^A)_2$, —$Si(OR^A)_3$, —$OSi(R^A)_3$, —$OSi(R^A)_2OR^A$, —$OSi(R^A)(OR^A)_2$, —$OSi(OR^A)_3$, or —$B(OR^A)_2$;

each instance of $R^A$ is independently hydrogen, optionally substituted acyl, optionally substituted alkyl, optionally substituted alkenyl, optionally substituted alkynyl, optionally substituted heteroalkyl, optionally substituted heteroalkenyl, optionally substituted heteroalkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, or a sulfur protecting group when attached to a sulfur atom, or two instances of $R^A$ are joined together with their intervening atom to form an optionally substituted heterocyclic ring or optionally substituted heteroaryl ring;

$R^N$ is hydrogen, optionally substituted alkyl, optionally substituted carbocyclyl, optionally substituted heterocyclyl, optionally substituted aryl, optionally substituted heteroaryl, or a nitrogen protecting group; and m is 0, 1, 2, 3, 4, or 5, as valency permits.

In some embodiments of Formula (IV), or a pharmaceutically acceptable salt thereof, Ring Q is of formula (B-1). In some embodiments of Formula (IV), or a pharmaceutically acceptable salt thereof, Ring Q is of formula (C-1). In some embodiments of Formula (IV), or a pharmaceutically acceptable salt thereof, Ring Q is of formula (C-2). In some embodiments of Formula (IV), or a pharmaceutically acceptable salt thereof, Ring Q is of formula (D-1). In some embodiments of Formula (IV), or a pharmaceutically acceptable salt thereof, Ring Q is of formula (D-2). In some embodiments of Formula (IV), or a pharmaceutically acceptable salt thereof, Ring Q is of formula (D-3). In some embodiments of Formula (IV), or a pharmaceutically acceptable salt thereof, Ring Q is of formula (D-4). In some embodiments of Formula (IV), or a pharmaceutically acceptable salt thereof, Ring Q is of formula (D-5). In some embodiments of Formula (IV), or a pharmaceutically acceptable salt thereof, Ring Q is of formula (D-6). In some embodiments of Formula (IV), or a pharmaceutically acceptable salt thereof, Ring Q is of formula (D-7). In some embodiments of Formula (IV), or a pharmaceutically acceptable salt thereof. Ring Q is of formula (D-8).

In some embodiments, the compound of Formula (I) is of Formula (V):

(V)

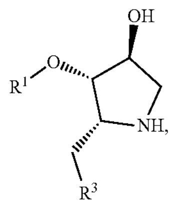

or a pharmaceutically acceptable salt thereof, wherein $R^1$ is optionally substituted alkyl, optionally substituted alkenyl, optionally substituted alkynyl, optionally substituted carbocyclyl, or optionally substituted heterocyclyl.

In some embodiments of Formula (V), or a pharmaceutically acceptable salt thereof, $R^1$ is optionally substituted alkyl. In some embodiments of Formula (V), or a pharmaceutically acceptable salt thereof, $R^1$ is optionally substituted $C_{1-6}$ alkyl. In some embodiments of Formula (V), or a pharmaceutically acceptable salt thereof, $R^1$ is $C_{1-3}$ alkyl substituted with 0, 1, 2, or 3 instances of halogen. In some embodiments of Formula (V), or a pharmaceutically acceptable salt thereof, $R^1$ is $C_{1-3}$ alkyl substituted with 0, 1, 2, or 3 instances of —F. In some embodiments of Formula (V), or a pharmaceutically acceptable salt thereof, $R^1$ is —$CH_3$, —$CH_2CH_3$, —$CF_3$,

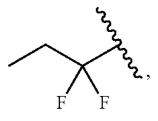, or

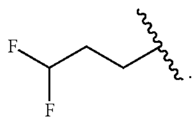.

In some embodiments, the compound of Formula (V) is of Formula (V-a) to (V-e):

(V-a)

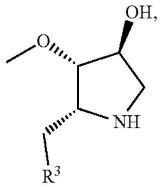

(V-b)

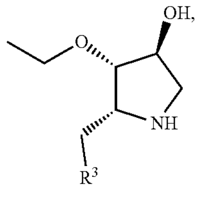

-continued (V-c)

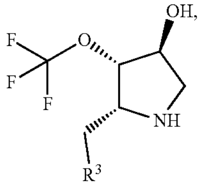

(V-d)

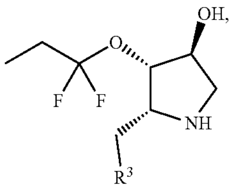

or (V-e)

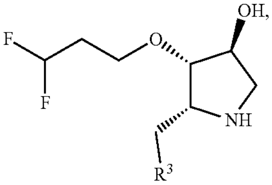

or a pharmaceutically acceptable salt thereof.

In some embodiments of Formula (V), or a subgenus thereof (e.g., Formula (V-a), (V-b), (V-c), (V-d), or (V-e)), or a pharmaceutically acceptable salt thereof, $R^3$ is of formula (A-2), (A-7), (A-10), (A-13), (A-14), (A-16), (A-20), (A-25), (A-26), (A-28), (A-29), (A-31), or (A-32). In some embodiments of Formula (V), or a subgenus thereof, or a pharmaceutically acceptable salt thereof, $R^3$ is of formula (A-2), (A-7), (A-10), (A-13), (A-14), (A-16), (A-20), or (A-25). In some embodiments of Formula (V), or a subgenus thereof, or a pharmaceutically acceptable salt thereof, $R^3$ is of formula (A-2b), (A-2c), (A-2d), (A-7a), (A-7b), (A-7c), (A-10a), (A-10b), (A-10c), (A-13a), (A-13b), (A-13c), (A-14b), (A-16b), (A-20b), (A-20c), (A-20d), (A-25b), (A-25c), (A-26a), (A-28a), (A-29a), (A-31a), or (A-32a). In some embodiments of Formula (V), or a subgenus thereof, or a pharmaceutically acceptable salt thereof, $R^3$ is of formula (A-2b), (A-2c), (A-2d), (A-7a), (A-7b), (A-7c), (A-10a), (A-10b), (A-10c), (A-13a), (A-13b), (A-13c), (A-14b), (A-16b), (A-20b), (A-20c), (A-20d), (A-25b), or (A-25c).

In some embodiments of Formula (V), or a subgenus thereof, or a pharmaceutically acceptable salt thereof, $R^3$ is of formula (A-7a), (A-10a), (A-13a), (A-26a), (A-28a), (A-29a), (A-31a), or (A-32a). In some embodiments of Formula (V), or a subgenus thereof, or a pharmaceutically acceptable salt thereof, $R^3$ is of formula (A-2b), (A-2c), (A-2d), (A-7a), (A-7b), (A-7c), (A-10a), (A-10b), (A-10c), (A-13a), (A-13b), (A-13c), (A-14b), (A-16b), (A-20b), (A-20c), (A-20d), (A-25b), or (A-25c). In some embodiments of Formula (V), or a subgenus thereof, $R^3$ is of formula (A-7a), (A-7b), (A-7c), (A-16a), (A-16b), (A-26a), (A-28a), (A-29a), (A-31a), or (A-32a), wherein $R^N$ is hydrogen or optionally substituted alkyl. In some embodiments of Formula (V), or a subgenus thereof, $R^3$ is of formula (A-7a), (A-7b), (A-7c), (A-16a), (A-16b), (A-26a), (A-28a), (A-29a), (A-31a), or (A-32a), wherein $R^N$ is hydrogen, $C_{1-3}$ alkyl, or $C_{1-3}$ haloalkyl. In some embodiments of Formula (V), or a subgenus thereof, $R^3$ is of formula (A-7a), (A-7b), (A-7c), (A-16a), (A-16b), (A-26a), (A-28a), (A-29a), (A-31a), or (A-32a), wherein $R^N$ is hydrogen, $—CH_3$, or $—CHF_2$.

In some embodiments, the compound of Formula (I) is selected from those in Tables 1-2, and pharmaceutically acceptable salts thereof. In some embodiments, the compound of Formula (I) is selected from pharmaceutically acceptable salts of those in Tables 1-2. In some embodiments, the compound of Formula (I) is selected from those in Tables 1-2.

In some embodiments, the compound of Formula (I) is selected from those in Table 1, and pharmaceutically acceptable salts thereof. In some embodiments, the compound of Formula (I) is selected from pharmaceutically acceptable salts of those in Table 1. In some embodiments, the compound of Formula (I) is selected from those in Table 1.

In some embodiments, the compound of Formula (I) is selected from those in Table 2, and pharmaceutically acceptable salts thereof. In some embodiments, the compound of Formula (I) is selected from pharmaceutically acceptable salts of those in Table 2. In some embodiments, the compound of Formula (I) is selected from those in Table 2.

TABLE 1

| Compounds of Formula (I)<br>Example #<br>Structure and Chemical Name |
|---|
| EXAMPLE 1 |
| 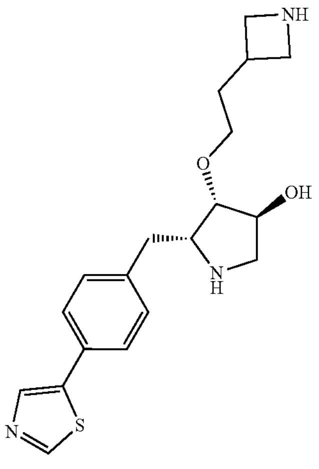 [SMILES: O[C@H]1CN[C@H](Cc2ccc(-c3cncs3)cc2)[C@@H]1OCCC1CNC1] |
| (3S,4S,5R)-4-[2-(azetidin-3-yl)ethoxy]-5-{[4-(1,3-thiazol-5-yl)phenyl]methyl}pyrrolidin-3-ol |

TABLE 1-continued

| Compounds of Formula (I) Example # Structure and Chemical Name |
|---|
| EXAMPLE 2 |
| 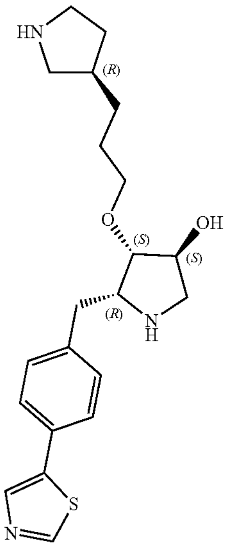 |
| (3S,4S,5R)-4-{3-[(3R)-pyrrolidin-3-yl]propoxy}-5-{[4-(1,3-thiazol-5-yl)phenyl]methyl}pyrrolidin-3-ol |
| EXAMPLE 3 |
| 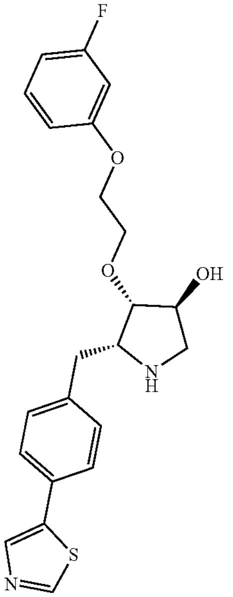 [SMILES: O[C@H]1CN[C@H](Cc2ccc(-c3cncs3)cc2)[C@@H]1OCCOc1cccc(F)c1] |
| (3S,4S,5R)-4-[2-(3-fluorophenoxy)ethoxy]-5-{[4-(1,3-thiazol-5-yl)phenyl]methyl}pyrrolidin-3-ol |

TABLE 1-continued

| Compounds of Formula (I) Example # Structure and Chemical Name |
|---|
| EXAMPLE 4 |
| 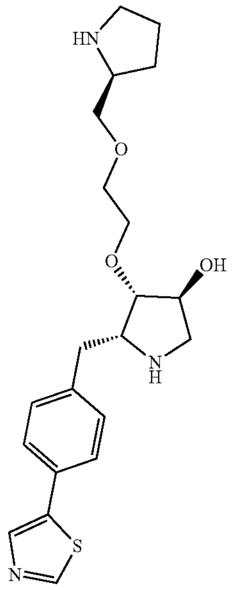 [SMILES: O[C@H]1CN[C@H](Cc2ccc(-c3cncs3)cc2)[C@@H]1OCCOC[C@@H]1CCCN1] |
| (3S,4S,5R)-4-{2-[(2S)-pyrrolidin-2-ylmethoxy]ethoxy}-5-{[4-(1,3-thiazol-5-yl)phenyl]methyl}pyrrolidin-3-ol |
| EXAMPLE 5 |
| 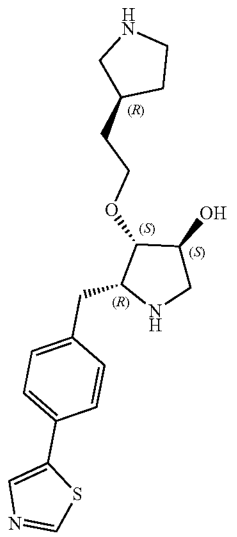 |
| (3S,4S,5R)-4-{2-[(3S)-pyrrolidin-3-yl]ethoxy}-5-{[4-(1,3-thiazol-5-yl)phenyl]methyl}pyrrolidin-3-ol |

TABLE 1-continued

| Compounds of Formula (I) Example # Structure and Chemical Name |
|---|
| EXAMPLE 6 |
| 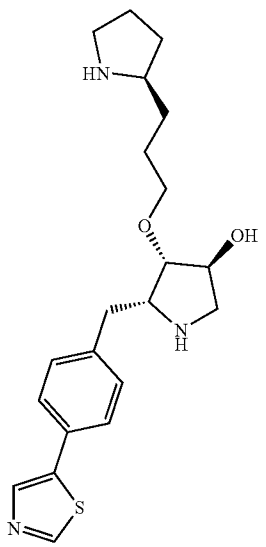 [SMILES: O[C@H]1CN[C@H](Cc2ccc(-c3cncs3)cc2)[C@@H]1OCCC[C@@H]1CCCN1] |
| (3S,4S,5R)-4-{2-[(2S)-pyrrolidin-2-ylmethoxy]ethoxy}-5-{[4-(1,3-thiazol-5-yl)phenyl]methyl}pyrrolidin-3-ol |
| EXAMPLE 7 |
| 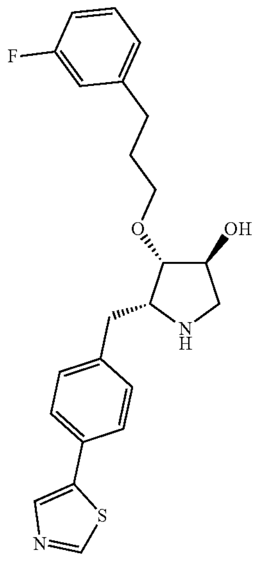 [SMILES: O[C@H]1CN[C@H](Cc2ccc(-c3cncs3)cc2)[C@@H]1OCCCc1cccc(F)c1] |
| (3S,4S,5R)-4-[3-(3-fluorophenyl)propoxy]-5-{[4-(1,3-thiazol-5-yl)phenyl]methyl}pyrrolidin-3-ol |

TABLE 1-continued

| Compounds of Formula (I) Example # Structure and Chemical Name |
|---|
| EXAMPLE 8 |
| 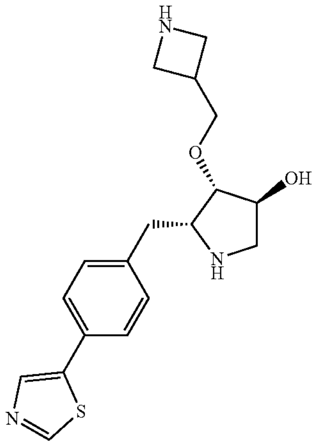 [SMILES: O[C@H]1CN[C@H](Cc2ccc(-c3cncs3)cc2)[C@@H]1OCC1CNC1] |
| (3S,4S,5R)-4-(azetidin-3-ylmethoxy)-5-{[4-(1,3-thiazol-5-yl)phenyl]methyl}pyrrolidin-3-ol |
| EXAMPLE 9 |
| 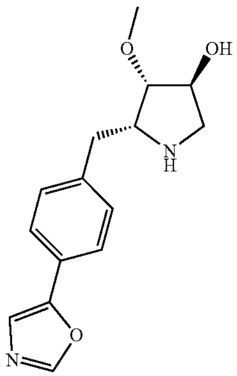 [SMILES: CO[C@@H]1[C@@H](O)CN[C@@H]1Cc1ccc(-c2cnco2)cc1] |
| (3S,4S,5R)-4-methoxy-5-{[4-(1,3-oxazol-5-yl)phenyl]methyl}pyrrolidin-3-ol |

TABLE 1-continued

| Compounds of Formula (I) Example # Structure and Chemical Name |
| --- |
| EXAMPLE 10 |
| 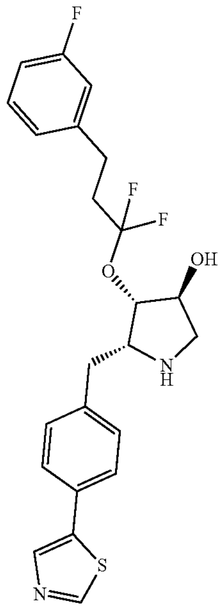 [SMILES: O[C@H]1CN[C@H](Cc2ccc(-c3cncs3)cc2)[C@@H]1OC(F)(F)CCc1cccc(F)c1] |
| (3S,4S,5R)-4-[1,1-difluoro-3-(3-fluorophenyl)propoxy]-5-{[4-(1,3-thiazol-5-yl)phenyl]methyl}pyrrolidin-3-ol |
| EXAMPLE 11 |
| 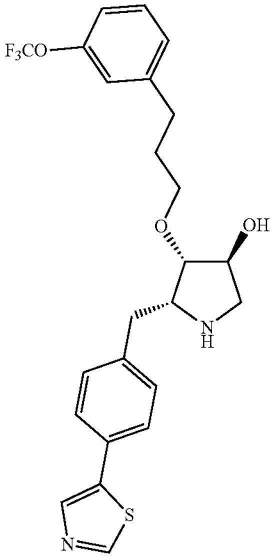 [SMILES: O[C@H]1CN[C@H](Cc2ccc(-c3cncs3)cc2)[C@@H]1OCCCc1cccc(OC(F)(F)F)c1] |
| (3S,4S,5R)-5-{[4-(1,3-thiazol-5-yl)phenylmethyl}-4-{3-[3-(trifluoromethoxy)phenyl]propoxy} pyrrolidin-3-ol |

TABLE 1-continued

| Compounds of Formula (I) Example # Structure and Chemical Name |
| --- |
| EXAMPLE 12 |
| 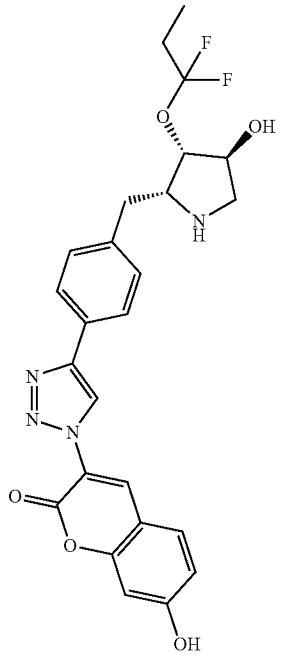 [SMILES: CCC(F)(F)O[C@@H]1[C@@H](O)CN[C@@H]1Cc1ccc(-c2cn(-c3cc4ccc(O)cc4oc3=O)nn2)cc1] |
| 3-[4-(4-{[(2R,3S,4S)-3-(1,1-difluoropropoxy)-4-hydroxypyrrolidin-2-yl]methyl}phenyl)-1,2,3-triazol-1-yl]-7-hydroxychromen-2-one |
| EXAMPLE 13 |
| 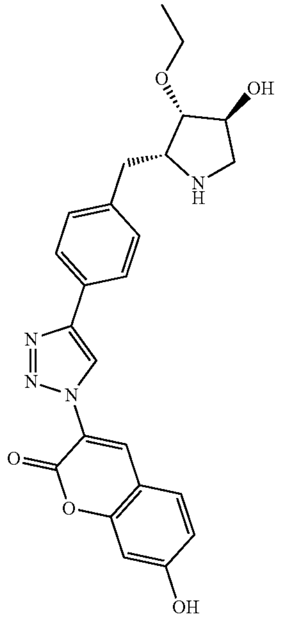 [SMILES: CCO[C@@H]1[C@@H](O)CN[C@@H]1Cc1ccc(-c2cn(-c3cc4ccc(O)cc4oc3=O)nn2)cc1] |
| 3-[4-(4-{[(2R,3S,4S)-3-ethoxy-4-hydroxypyrrolidin-2-yl]methyl}phenyl)-1,2,3-triazol-1-yl]-7-hydroxychromen-2-one |

TABLE 1-continued

Compounds of Formula (I)
Example #
Structure and Chemical Name

EXAMPLE 14

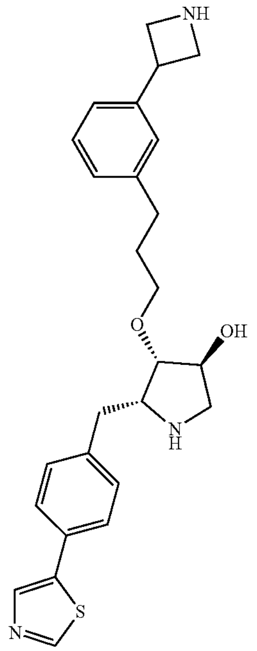 [SMILES: O[C@H]1CN[C@H](Cc2ccc(-c3cncs3)cc2)[C@@H]1OCCCc1cccc(C2CNC2)c1]

(3S,4S,5R)-4-{3-[3-(azetidin-3-yl)phenyl]propoxy}-5-{[4-(1,3-thiazol-5-yl)phenyl]methyl}pyrrolidin-3-ol

EXAMPLE 15

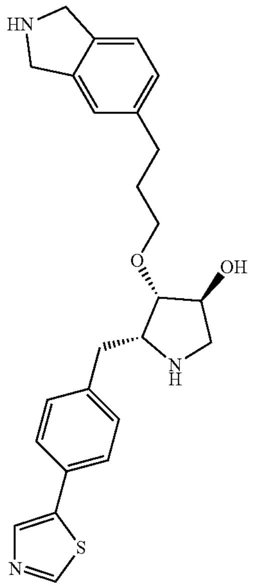 [SMILES: O[C@H]1CN[C@H](Cc2ccc(-c3cncs3)cc2)[C@@H]1OCCCc1ccc2c(c1)CNC2]

(3S,4S,5R)-4-[3-(2,3-dihydro-1H-isoindol-5-yl)propoxy]-5-{[4-(1,3-thiazol-5-yl)phenyl]methyl}pyrrolidin-3-ol TABLE 1-continued Compounds of Formula (I)
Example #
Structure and Chemical Name

EXAMPLE 16

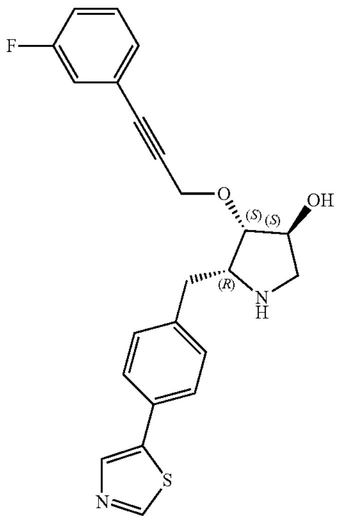

(3S,4S,5R)-4-{[3-(3-fluorophenyl)prop-2-yn-1-yl]oxy}-5-{[4-(1,3-thiazol-5-yl)phenyl]methyl}pyrrolidin-3-ol

EXAMPLE 17

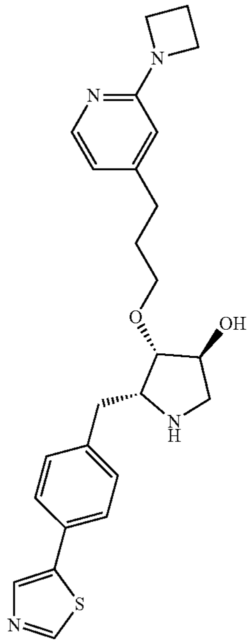 [SMILES: O[C@H]1CN[C@H](Cc2ccc(-c3cncs3)cc2)[C@@H]1OCCCc1ccnc(N2CCC2)c1]

(3S,4S,5R)-4-{3-[2-(azetidin-1-yl)pyridin-4-yl]propoxy}-5-{[4-(1,3-thiazol-5-yl)phenyl]methyl}pyrrolidin-3-ol TABLE 1-continued

| Compounds of Formula (I) Example # Structure and Chemical Name |
|---|
| EXAMPLE 18 |
| 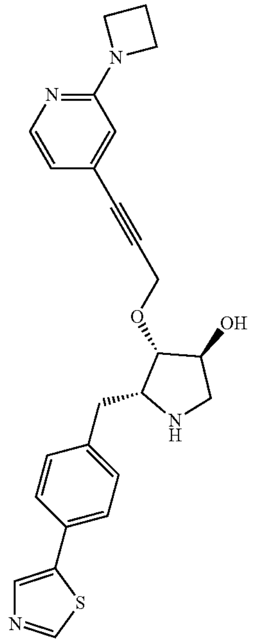 [SMILES: O[C@H]1CN[C@H](Cc2ccc(-c3cncs3)cc2)[C@@H]1OCC#Cc1ccnc(N2CCC2)c1] |
| (3S,4S,5R)-4-({3-[2-(azetidin-1-yl)pyridin-4-yl]prop-2-yn-1-yl}oxy)-5-{[4-(1,3-thiazol-5-yl)phenyl]methyl}pyrrolidin-3-ol |
| EXAMPLE 19 |
| 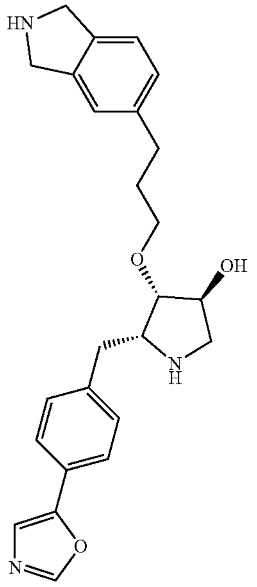 [SMILES: O[C@H]1CN[C@H](Cc2ccc(-c3cnco3)cc2)[C@@H]1OCCCc1ccc2c(c1)CNC2] |
| (3S,4S,5R)-4-[3-(2,3-dihydro-1H-isoindol-5-yl)propoxy]-5-{[4-(1,3-oxazol-5-yl)phenyl]methyl}pyrrolidin-3-ol |

TABLE 1-continued

| Compounds of Formula (I) Example # Structure and Chemical Name |
|---|
| EXAMPLE 20 |
| 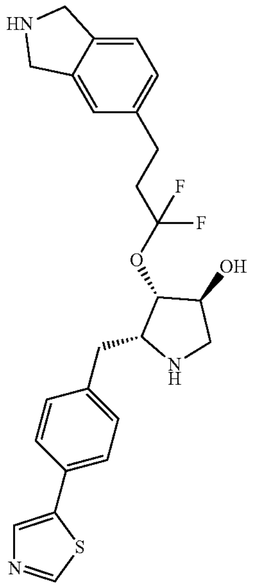 [SMILES: O[C@H]1CN[C@H](Cc2ccc(-c3cncs3)cc2)[C@@H]1OC(F)(F)CCc1ccc2c(c1)CNC2] |
| (3S,4S,5R)-4-[3-(2,3-dihydro-1H-isoindol-5-yl)-1,1-difluoropropoxy]-5-{[4-(1,3-thiazol-5-yl)phenyl]methyl}pyrrolidin-3-ol |
| EXAMPLE 21 |
| 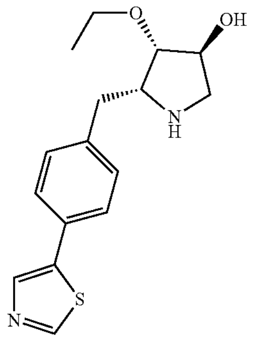 [SMILES: CCO[C@@H]1[C@@H](O)CN[C@@H]1Cc1ccc(-c2cncs2)cc1] |
| (3S,4S,5R)-4-methoxy-5-{[4-(1,3-oxazol-5-yl)phenyl]methyl}pyrrolidin-3-ol |

TABLE 1-continued

| Compounds of Formula (I) Example # Structure and Chemical Name |
| --- |
| EXAMPLE 22 |
| 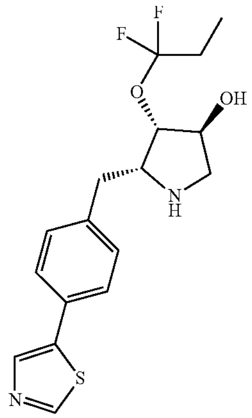 [SMILES: CCC(F)(F)O[C@@H]1[C@@H](O)CN[C@@H]1Cc1ccc(-c2cncs2)cc1] |
| (3S,4S,5R)-4-(1,1-difluoropropoxy)-5-{[4-(1,3-thiazol-5-yl)phenyl]methyl}pyrrolidin-3-ol |
| EXAMPLE 23 |
| 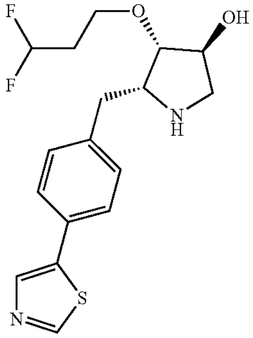 [SMILES: O[C@H]1CN[C@H](Cc2ccc(-c3cncs3)cc2)[C@@H]1OCCC(F)F] |
| (3S,4S,5R)-4-methoxy-5-{[4-(1,3-oxazol-5-yl)phenyl]methyl}pyrrolidin-3-ol |

TABLE 1-continued

| Compounds of Formula (I) Example # Structure and Chemical Name |
| --- |
| EXAMPLE 24 |
| 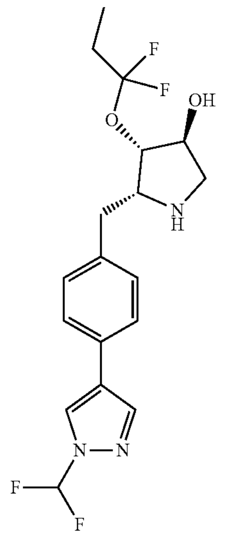 [SMILES: CCC(F)(F)O[C@@H]1[C@@H](O)CN[C@@H]1Cc1ccc(-c2cnn(C(F)F)c2)cc1] |
| (3S,4S,5R)-5-(4-(1-(difluoromethyl)-1H-pyrazol-4-yl)benzyl)-4-(1,1-difluoropropoxy)pyrrolidin-3-ol |
| EXAMPLE 25 |
| 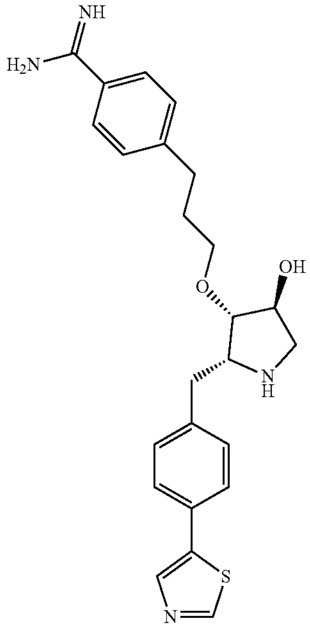 [SMILES: N=C(N)c1ccc(CCCO[C@@H]2[C@@H](O)CN[C@@H]2Cc2ccc(-c3cncs3)cc2)cc1] |
| 4-(3-(((2R,3S,4S)-4-hydroxy-2-(4-(thiazol-5-yl)benzyl)pyrrolidin-3-yl)oxy)propyl)benzimidamide |

TABLE 1-continued

| Compounds of Formula (I) Example # Structure and Chemical Name |
|---|
| EXAMPLE 26 |
| 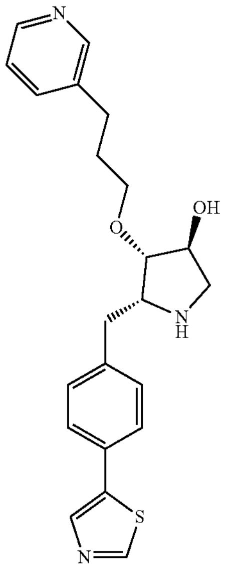 [SMILES: O[C@H]1CN[C@H](Cc2ccc(-c3cncs3)cc2)[C@@H]1OCCCc1cccnc1] |
| (3S,4S,5R)-4-(3-(pyridin-3-yl)propoxy)-5-(4-(thiazol-5-yl)benzyl)pyrrolidin-3-ol |
| EXAMPLE 27 |
| 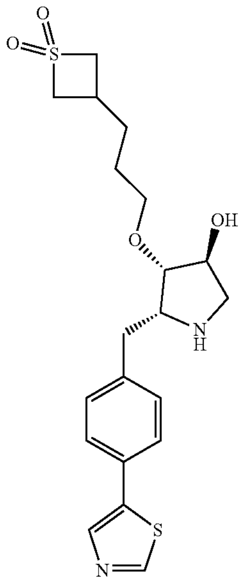 [SMILES: O=S1(=O)CC(CCCO[C@@H]2[C@@H](O)CN[C@@H]2Cc2ccc(-c3cncs3)cc2)C1] |
| 3-(3-(((2R,3S,4S)-4-hydroxy-2-(4-(thiazol-5-yl)benzyl)pyrrolidin-3-yl)oxy)propyl)thietane 1,1-dioxide |

TABLE 1-continued

| Compounds of Formula (I) Example # Structure and Chemical Name |
|---|
| EXAMPLE 28 |
| 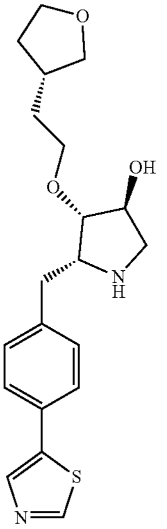 [SMILES: O[C@H]1CN[C@H](Cc2ccc(-c3cncs3)cc2)[C@@H]1OCC[C@@H]1CCOC1] |
| (3S,4S,5R)-4-(2-((S)-tetrahydrofuran-3-yl)ethoxy)-5-(4-(thiazol-5-yl)benzyl)pyrrolidin-3-ol |
| EXAMPLE 29 |
| 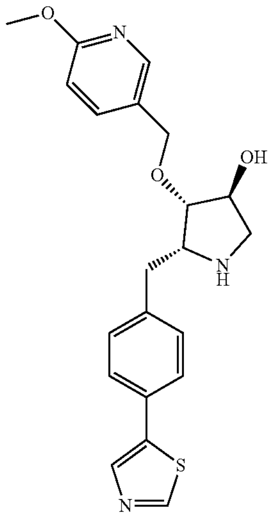 [SMILES: COc1ccc(CO[C@@H]2[C@@H](O)CN[C@@H]2Cc2ccc(-c3cncs3)cc2)cn1] |
| (3S,4S,5R)-4-((6-methoxypyridin-3-yl)methoxy)-5-(4-(thiazol-5-yl)benzyl)pyrrolidin-3-ol |

TABLE 1-continued

| Compounds of Formula (I) Example # Structure and Chemical Name |
|---|
| EXAMPLE 30 |
| 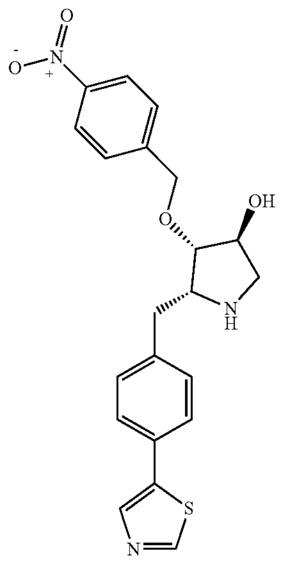 |
| (3S,4S,5R)-4-((4-nitrobenzyl)oxy)-5-(4-(thiazol-5-yl)benzyl)pyrrolidin-3-ol |
| EXAMPLE 31 |
| 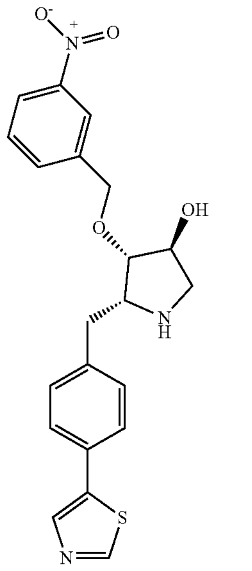 |
| (3S,4S,5R)-4-((3-nitrobenzyl)oxy)-5-(4-(thiazol-5-yl)benzyl)pyrrolidin-3-ol |

TABLE 1-continued

| Compounds of Formula (I) Example # Structure and Chemical Name |
|---|
| EXAMPLE 32 |
| 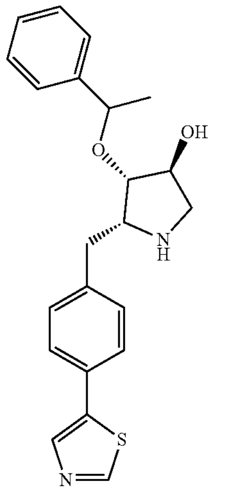 [SMILES: CC(O[C@@H]1[C@@H](O)CN[C@@H]1Cc1ccc(-c2cncs2)cc1)c1ccccc1] |
| (3S,4S,5R)-4-(1-phenylethoxy)-5-(4-(thiazol-5-yl)benzyl)pyrrolidin-3-ol |
| EXAMPLE 33 |
| 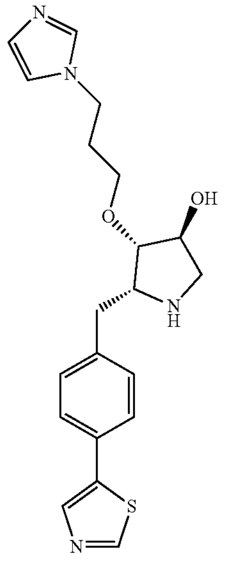 [SMILES: O[C@H]1CN[C@H](Cc2ccc(-c3cncs3)cc2)[C@@H]1OCCCn1ccnc1] |
| (3S,4S,5R)-4-(3-(1H-imidazol-1-yl)propoxy)-5-(4-(thiazol-5-yl)benzyl)pyrrolidin-3-ol |

TABLE 1-continued

| Compounds of Formula (I) Example # Structure and Chemical Name |
|---|
| EXAMPLE 34 |
| 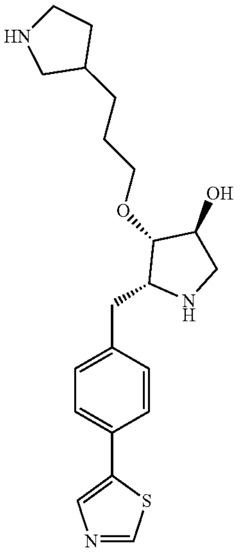 [SMILES: O[C@H]1CN[C@H](Cc2ccc(-c3cncs3)cc2)[C@@H]1OCCCC1CCNC1] |
| (3S,4S,5R)-4-(3-((S)-pyrrolidin-3-yl)propoxy)-5-(4-(thiazol-5-yl)benzyl)pyrrolidin-3-ol |
| EXAMPLE 35 |
| 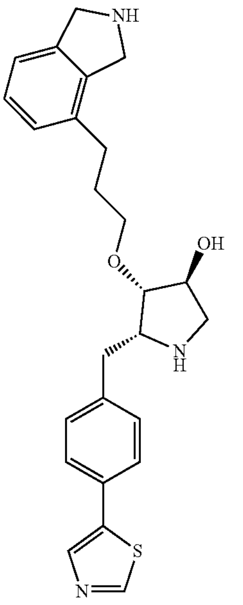 [SMILES: O[C@H]1CN[C@H](Cc2ccc(-c3cncs3)cc2)[C@@H]1OCCCc1cccc2c1CNC2] |
| (3S,4S,5R)-4-(3-(isoindolin-4-yl)propoxy)-5-(4-(thiazol-5-yl)benzyl)pyrrolidin-3-ol |

TABLE 1-continued

| Compounds of Formula (I) Example # Structure and Chemical Name |
|---|
| EXAMPLE 36 |
| 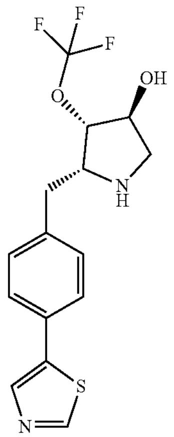 [SMILES: O[C@H]1CN[C@H](Cc2ccc(-c3cncs3)cc2)[C@@H]1OC(F)(F)F] |
| (3S,4S,5R)-5-(4-(thiazol-5-yl)benzyl)-4-(trifluoromethoxy)pyrrolidin-3-ol |
| EXAMPLE 37 |
| 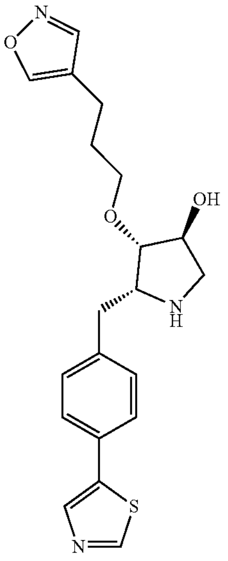 [SMILES: O[C@H]1CN[C@H](Cc2ccc(-c3cncs3)cc2)[C@@H]1OCCCc1cnoc1] |
| (3S,4S,5R)-4-(3-(isoxazol-4-yl)propoxy)-5-(4-(thiazol-5-yl)benzyl)pyrrolidin-3-ol |

TABLE 1-continued

| Compounds of Formula (I) Example # Structure and Chemical Name |
|---|

EXAMPLE 38

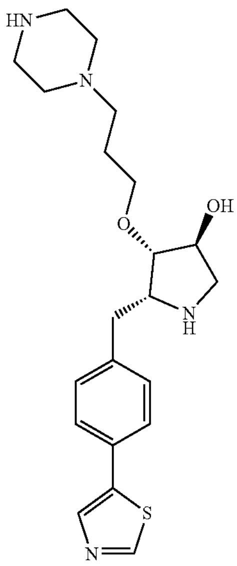 [SMILES: O[C@H]1CN[C@H](Cc2ccc(-c3cncs3)cc2)[C@@H]1OCCCN1CCNCC1]

(3S,4S,5R)-4-(3-(piperazin-1-yl)propoxy)-5-(4-(thiazol-5-yl)benzyl)pyrrolidin-3-ol

EXAMPLE 39

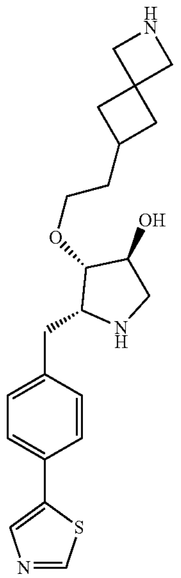 [SMILES: O[C@H]1CN[C@H](Cc2ccc(-c3cncs3)cc2)[C@@H]1OCCC1CC2(CNC2)C1]

(3S,4S,5R)-4-(2-(2-azaspiro[3.3]heptan-6-yl)ethoxy)-5-(4-(thiazol-5-yl)benzyl)pyrrolidin-3-ol TABLE 1-continued

| Compounds of Formula (I) Example # Structure and Chemical Name |
|---|

EXAMPLE 40

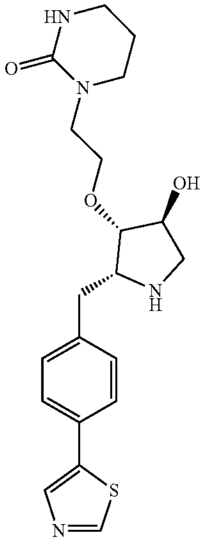 [SMILES: O=C1NCCCN1CCO[C@@H]1[C@@H](O)CN[C@@H]1Cc1ccc(-c2cncs2)cc1]

1-(2-(((2R,3S,4S)-4-hydroxy-2-(4-(thiazol-5-yl)benzyl)pyrrolidin-3-yl)oxy)ethyl)tetrahydropyrimidin-2(1H)-one

EXAMPLE 41

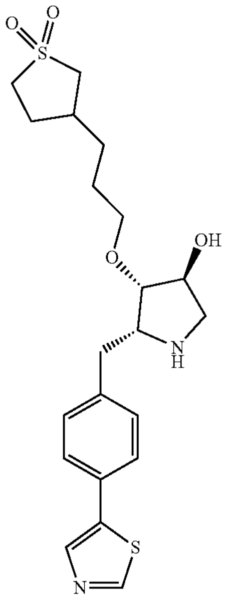 [SMILES: O=S1(=O)CCC(CCCO[C@@H]2[C@@H](O)CN[C@@H]2Cc2ccc(-c3cncs3)cc2)C1]

3-(3-(((2R,3S,4S)-4-hydroxy-2-(4-(thiazol-5-yl)benzyl)pyrrolidin-3-yl)oxy)propyl)tetrahydrothiophene 1,1-dioxide

| Compounds of Formula (I) Example # Structure and Chemical Name |
|---|

EXAMPLE 42

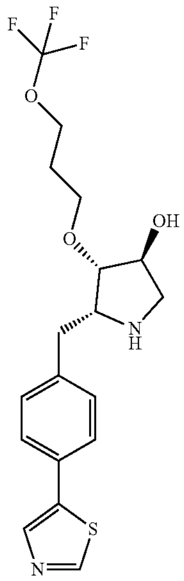 [SMILES: O[C@H]1CN[C@H](Cc2ccc(-c3cncs3)cc2)[C@@H]1OCCCOC(F)(F)F]

(3S,4S,5R)-5-(4-(thiazol-5-yl)benzyl)-4-(3-(trifluoromethoxy)propoxy)pyrrolidin-3-ol

EXAMPLE 43

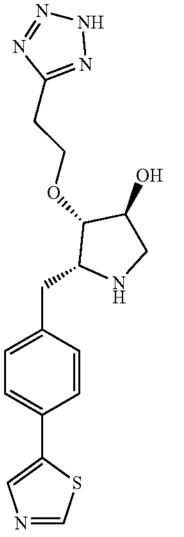 [SMILES: O[C@H]1CN[C@H](Cc2ccc(-c3cncs3)cc2)[C@@H]1OCCc1nn[nH]n1]

(3S,4S,5R)-4-(2-(2H-tetrazol-5-yl)ethoxy)-5-(4-(thiazol-5-yl)benzyl)pyrrolidin-3-ol

| Compounds of Formula (I) Example # Structure and Chemical Name |
|---|

EXAMPLE 44

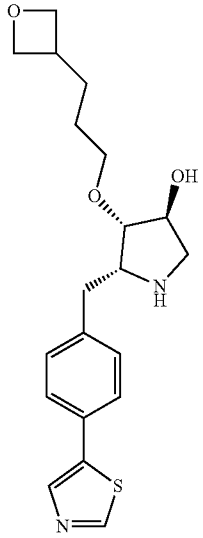 [SMILES: O[C@H]1CN[C@H](Cc2ccc(-c3cncs3)cc2)[C@@H]1OCCCC1COC1]

(3S,4S,5R)-4-(3-(oxetan-3-yl)propoxy)-5-(4-(thiazol-5-yl)benzyl)pyrrolidin-3-ol

EXAMPLE 45

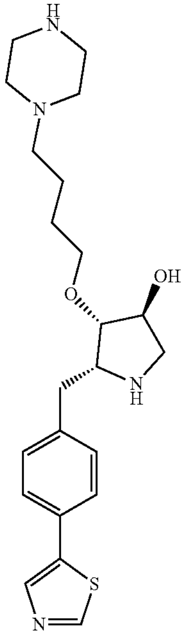 [SMILES: O[C@H]1CN[C@H](Cc2ccc(-c3cncs3)cc2)[C@@H]1OCCCCN1CCNCC1]

(3S,4S,5R)-4-(4-(piperazin-1-yl)butoxy)-5-(4-(thiazol-5-yl)benzyl)pyrrolidin-3-ol TABLE 1-continued

| Compounds of Formula (I) Example # Structure and Chemical Name |
| --- |
| EXAMPLE 46 |
| 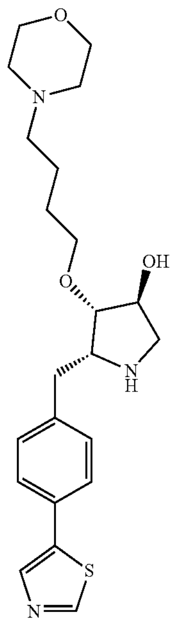 [SMILES: O[C@H]1CN[C@H](Cc2ccc(-c3cncs3)cc2)[C@@H]1OCCCCN1CCOCC1] |
| (3S,4S,5R)-4-(4-morpholinobutoxy)-5-(4-(thiazol-5-yl)benzyl)pyrrolidin-3-ol |
| EXAMPLE 47 |
| 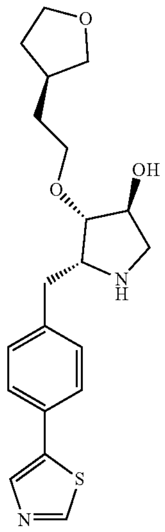 [SMILES: O[C@H]1CN[C@H](Cc2ccc(-c3cncs3)cc2)[C@@H]1OCC[C@H]1CCOC1] |
| (3S,4S,5R)-4-(2-((R)-tetrahydrofuran-3-yl)ethoxy)-5-(4-(thiazol-5-yl)benzyl)pyrrolidin-3-ol |

TABLE 1-continued

| Compounds of Formula (I) Example # Structure and Chemical Name |
| --- |
| EXAMPLE 48 |
| 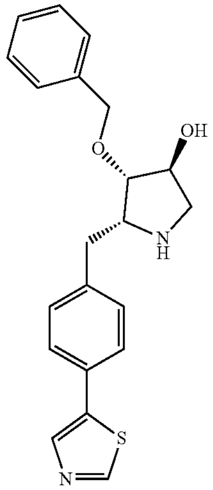 [SMILES: O[C@H]1CN[C@H](Cc2ccc(-c3cncs3)cc2)[C@@H]1OCc1ccccc1] |
| (3S,4S,5R)-4-(benzyloxy)-5-(4-(thiazol-5-yl)benzyl)pyrrolidin-3-ol |
| EXAMPLE 49 |
| 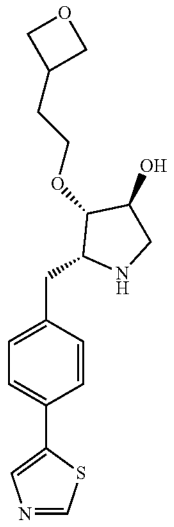 [SMILES: O[C@H]1CN[C@H](Cc2ccc(-c3cncs3)cc2)[C@@H]1OCCC1COC1] |
| (3S,4S,5R)-4-(2-(oxetan-3-yl)ethoxy)-5-(4-(thiazol-5-yl)benzyl)pyrrolidin-3-ol |

TABLE 1-continued

| Compounds of Formula (I) Example # Structure and Chemical Name |
|---|
| EXAMPLE 50 |
| 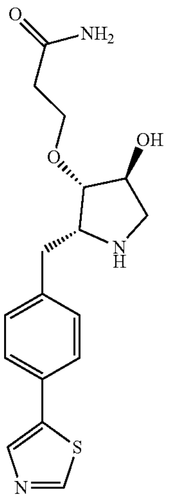 [SMILES: NC(=O)CCO[C@@H]1[C@@H](O)CN[C@@H]1Cc1ccc(-c2cncs2)cc1] |
| 3-(((2R,3S,4S)-4-hydroxy-2-(4-(thiazol-5-yl)benzyl)pyrrolidin-3-yl)oxy)propanamide |
| EXAMPLE 51 |
| 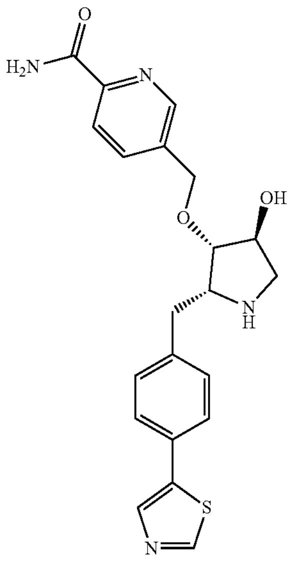 [SMILES: NC(=O)c1ccc(CO[C@@H]2[C@@H](O)CN[C@@H]2Cc2ccc(-c3cncs3)cc2)cn1] |
| 5-((((2R,3S,4S)-4-hydroxy-2-(4-(thiazol-5-yl)benzyl)pyrrolidin-3-yl)oxy)methyl)picolinamide |

TABLE 1-continued

| Compounds of Formula (I) Example # Structure and Chemical Name |
|---|
| EXAMPLE 52 |
| 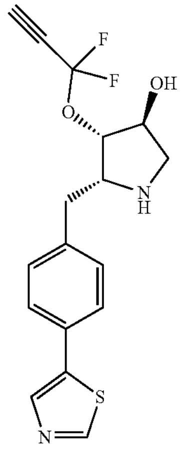 [SMILES: C#CC(F)(F)O[C@@H]1[C@@H](O)CN[C@@H]1Cc1ccc(-c2cncs2)cc1] |
| (3S,4S,5R)-4-((1,1-difluoroprop-2-yn-1-yl)oxy)-5-(4-(thiazol-5-yl)benzyl)pyrrolidin-3-ol |
| EXAMPLE 53 |
| 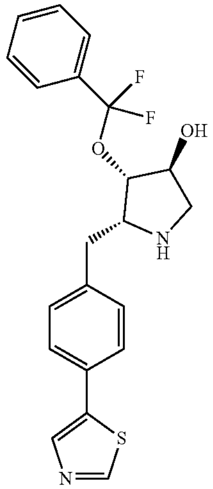 [SMILES: O[C@H]1CN[C@H](Cc2ccc(-c3cncs3)cc2)[C@@H]1OC(F)(F)c1ccccc1] |
| (3S,4S,5R)-4-(difluoro(phenyl)methoxy)-5-(4-(thiazol-5-yl)benzyl)pyrrolidin-3-ol |

TABLE 1-continued

| Compounds of Formula (I) Example # Structure and Chemical Name |
|---|
| EXAMPLE 54 |
| 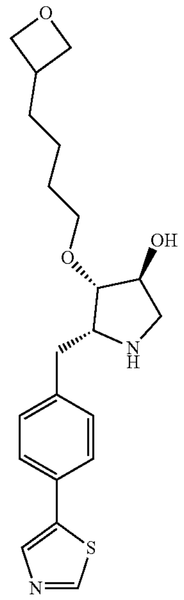 [SMILES: O[C@H]1CN[C@H](Cc2ccc(-c3cncs3)cc2)[C@@H]1OCCCCC1COC1] |
| (3S,4S,5R)-4-(4-(oxetan-3-yl)butoxy)-5-(4-(thiazol-5-yl)benzyl)pyrrolidin-3-ol |
| EXAMPLE 55 |
| 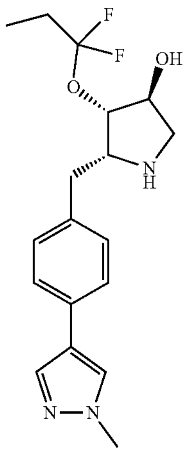 [SMILES: CCC(F)(F)O[C@@H]1[C@@H](O)CN[C@@H]1Cc1ccc(-c2cnn(C)c2)cc1] |
| (3S,4S,5R)-4-(1,1-difluoropropoxy)-5-(4-(1-methyl-1H-pyrazol-4-yl)benzyl)pyrrolidin-3-ol |

TABLE 1-continued

| Compounds of Formula (I) Example # Structure and Chemical Name |
|---|
| EXAMPLE 56 |
| 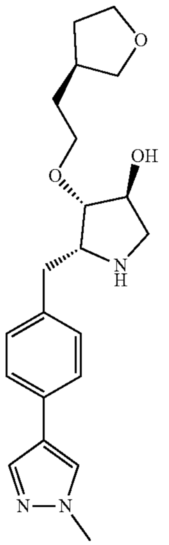 [SMILES: Cn1cc(-c2ccc(C[C@H]3NC[C@H](O)[C@H]3OCC[C@H]3CCOC3)cc2)cn1] |
| (3S,4S,5R)-5-(4-(1-methyl-1H-pyrazol-4-yl)benzyl)-4-(2-((R)-tetrahydrofuran-3-yl)ethoxy)pyrrolidin-3-ol |
| EXAMPLE 57 |
| 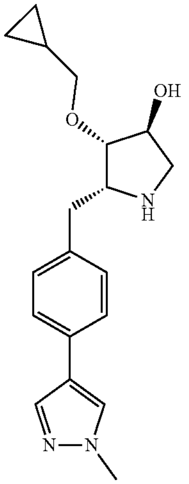 [SMILES: Cn1cc(-c2ccc(C[C@H]3NC[C@H](O)[C@H]3OCC3CC3)cc2)cn1] |
| (3S,4S,5R)-4-(cyclopropylmethoxy)-5-(4-(1-methyl-1H-pyrazol-4-yl)benzyl)pyrrolidin-3-ol |

TABLE 1-continued

| Compounds of Formula (I) Example # Structure and Chemical Name |
| --- |
| EXAMPLE 58 |
| 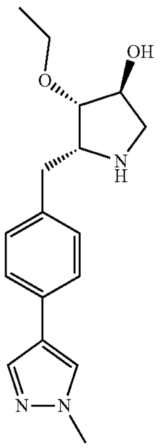 [SMILES: CCO[C@@H]1[C@@H](O)CN[C@@H]1Cc1ccc(-c2cnn(C)c2)cc1] |
| (3S,4S,5R)-4-ethoxy-5-(4-(1-methyl-1H-pyrazol-4-yl)benzyl)pyrrolidin-3-ol |
| EXAMPLE 59 |
| 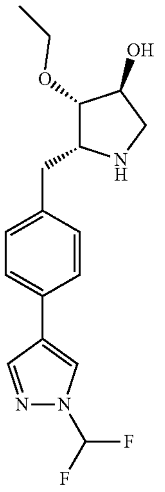 [SMILES: CCO[C@@H]1[C@@H](O)CN[C@@H]1Cc1ccc(-c2cnn(C(F)F)c2)cc1] |
| (3S,4S,5R)-5-(4-(1-(difluoromethyl)-1H-pyrazol-4-yl)benzyl)-4-ethoxypyrrolidin-3-ol |

TABLE 1-continued

| Compounds of Formula (I) Example # Structure and Chemical Name |
| --- |
| EXAMPLE 60 |
| 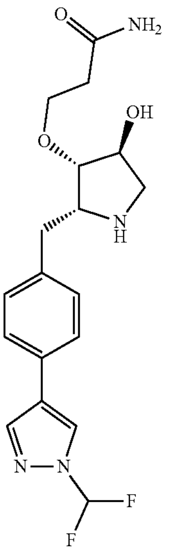 [SMILES: NC(=O)CCO[C@@H]1[C@@H](O)CN[C@@H]1Cc1ccc(-c2cnn(C(F)F)c2)cc1] |
| 3-(((2R,3S,4S)-2-(4-(1-(difluoromethyl)-1H-pyrazol-4-yl)benzyl)-4-hydroxypyrrolidin-3-yl)oxy)propanamide |
| EXAMPLE 61 |
| 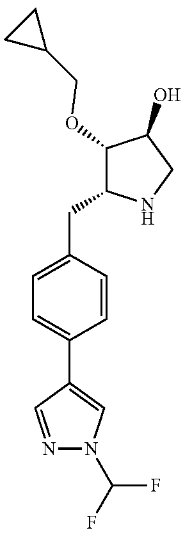 [SMILES: O[C@H]1CN[C@H](Cc2ccc(-c3cnn(C(F)F)c3)cc2)[C@@H]1OCC1CC1] |
| (3S,4S,5R)-4-(cyclopropylmethoxy)-5-(4-(1-(difluoromethyl)-1H-pyrazol-4-yl)benzyl)pyrrolidin-3-ol |

TABLE 1-continued

Compounds of Formula (I)
Example #
Structure and Chemical Name

EXAMPLE 62

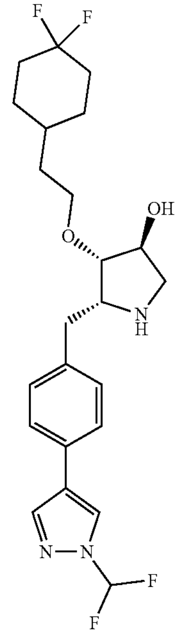 [SMILES: O[C@H]1CN[C@H](Cc2ccc(-c3cnn(C(F)F)c3)cc2)[C@@H]1OCCC1CCC(F)(F)CC1]

(3S,4S,5R)-4-(2-(4,4-difluorocyclohexyl)ethoxy)-5-(4-(1-(difluoromethyl)-1H-pyrazol-4-yl)benzyl)pyrrolidin-3-ol

EXAMPLE 63

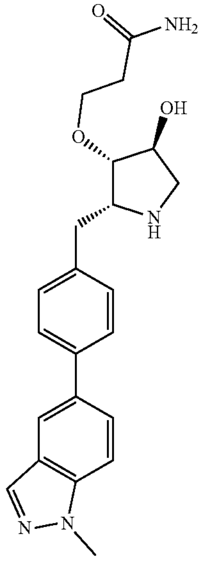 [SMILES: Cn1ncc2cc(-c3ccc(C[C@H]4NC[C@H](O)[C@H]4OCCC(N)=O)cc3)ccc21]

3-(((2R,3S,4S)-4-hydroxy-2-(4-(1-methyl-1H-indazol-5-yl)benzyl)pyrrolidin-3-yl)oxy)propanamide TABLE 1-continued Compounds of Formula (I)
Example #
Structure and Chemical Name

EXAMPLE 64

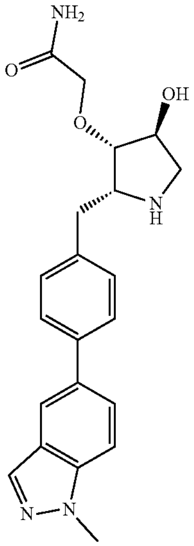 [SMILES: Cn1ncc2cc(-c3ccc(C[C@H]4NC[C@H](O)[C@H]4OCC(N)=O)cc3)ccc21]

2-(((2R,3S,4S)-4-hydroxy-2-(4-(1-methyl-1H-indazol-5-yl)benzyl)pyrrolidin-3-yl)oxy)acetamide

EXAMPLE 65

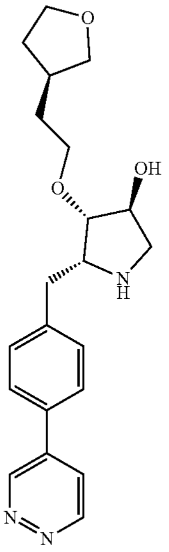 [SMILES: O[C@H]1CN[C@H](Cc2ccc(-c3ccnnc3)cc2)[C@@H]1OCC[C@H]1CCOC1]

(3S,4S,5R)-5-(4-(pyridazin-4-yl)benzyl)-4-(2-((R)-tetrahydrofuran-3-yl)ethoxy)pyrrolidin-3-ol TABLE 1-continued

| Compounds of Formula (I) Example # Structure and Chemical Name |
|---|
| EXAMPLE 66 |
| 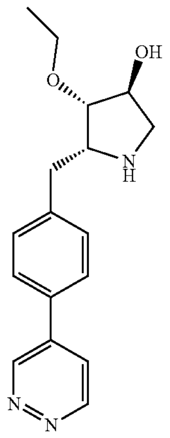 [SMILES: CCO[C@@H]1[C@@H](O)CN[C@@H]1Cc1ccc(-c2ccnnc2)cc1] |
| (3S,4S,5R)-4-ethoxy-5-(4-(pyridazin-4-yl)benzyl)pyrrolidin-3-ol |
| EXAMPLE 67 |
| 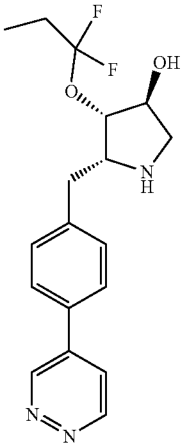 [SMILES: CCC(F)(F)O[C@@H]1[C@@H](O)CN[C@@H]1Cc1ccc(-c2ccnnc2)cc1] |
| (3S,4S,5R)-4-(1,1-difluoropropoxy)-5-(4-(pyridazin-4-yl)benzyl)pyrrolidin-3-ol |

TABLE 1-continued

| Compounds of Formula (I) Example # Structure and Chemical Name |
|---|
| EXAMPLE 68 |
| 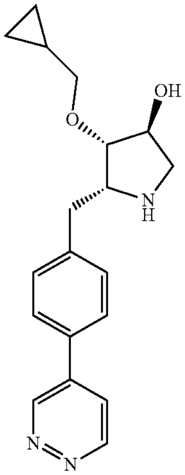 [SMILES: O[C@H]1CN[C@H](Cc2ccc(-c3ccnnc3)cc2)[C@@H]1OCC1CC1] |
| (3S,4S,5R)-4-(cyclopropylmethoxy)-5-(4-(pyridazin-4-yl)benzyl)pyrrolidin-3-ol |
| EXAMPLE 69 |
| 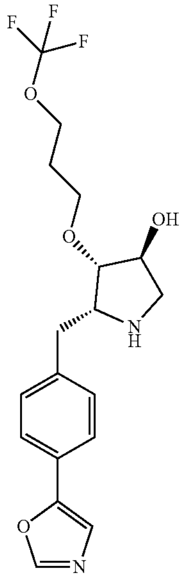 |
| (3S,4S,5R)-5-(4-(oxazol-5-yl)benzyl)-4-(3-(trifluoromethoxy)propoxy)pyrrolidin-3-ol |

TABLE 1-continued

| Compounds of Formula (I) Example # Structure and Chemical Name |
|---|
| EXAMPLE 70 |
| 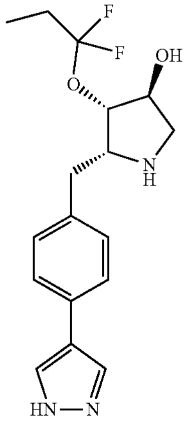 [SMILES: CCC(F)(F)O[C@@H]1[C@@H](O)CN[C@@H]1Cc1ccc(-c2cn[nH]c2)cc1] |
| (3S,4S,5R)-5-(4-(1H-pyrazol-4-yl)benzyl)-4-(1,1-difluoropropoxy)pyrrolidin-3-ol |
| EXAMPLE 71 |
| 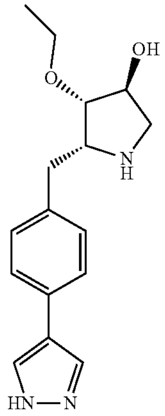 |
| (3S,4S,5R)-5-(4-(1H-pyrazol-4-yl)benzyl)-4-ethoxypyrrolidin-3-ol |

TABLE 1-continued

| Compounds of Formula (I) Example # Structure and Chemical Name |
|---|
| EXAMPLE 72 |
| 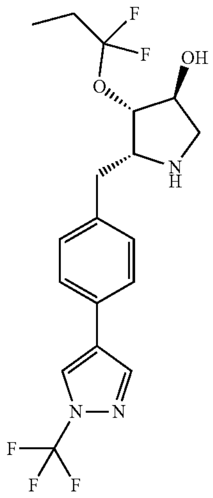 [SMILES: CCC(F)(F)O[C@@H]1[C@@H](O)CN[C@@H]1Cc1ccc(-c2cnn(C(F)(F)F)c2)cc1] |
| (3S,4S,5R)-4-(1,1-difluoropropoxy)-5-(4-(1-(trifluoromethyl)-1H-pyrazol-4-yl)benzyl)pyrrolidin-3-ol |
| EXAMPLE 73 |
| 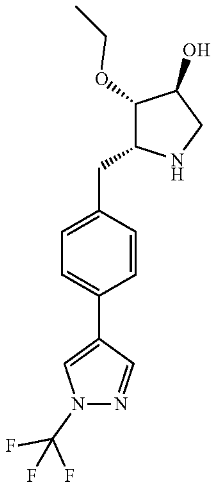 [SMILES: CCO[C@@H]1[C@@H](O)CN[C@@H]1Cc1ccc(-c2cnn(C(F)(F)F)c2)cc1] |
| (3S,4S,5R)-4-ethoxy-5-(4-(1-(trifluoromethyl)-1H-pyrazol-4-yl)benzyl)pyrrolidin-3-ol |

TABLE 1-continued

| Compounds of Formula (I) Example # Structure and Chemical Name |
| --- |
| EXAMPLE 74 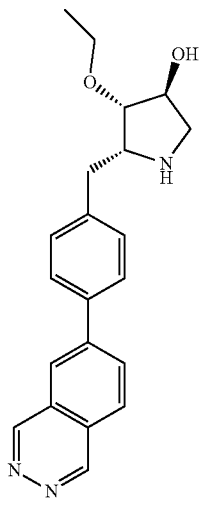 [SMILES: CCO[C@@H]1[C@@H](O)CN[C@@H]1Cc1ccc(-c2ccc3cnncc3c2)cc1] (3S,4S,5R)-4-ethoxy-5-(4-(phthalazin-6-yl)benzyl)pyrrolidin-3-ol |
| EXAMPLE 75 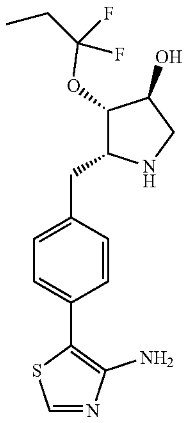 [SMILES: CCC(F)(F)O[C@@H]1[C@@H](O)CN[C@@H]1Cc1ccc(-c2scnc2N)cc1] (3S,4S,5R)-5-(4-(4-aminothiazol-5-yl)benzyl)-4-(1,1-difluoropropoxy)pyrrolidin-3-ol |

TABLE 1-continued

| Compounds of Formula (I) Example # Structure and Chemical Name |
| --- |
| EXAMPLE 76 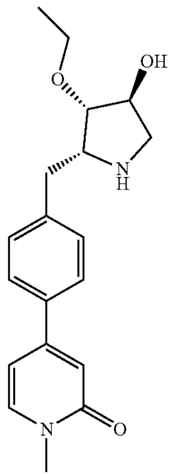 [SMILES: CCO[C@@H]1[C@@H](O)CN[C@@H]1Cc1ccc(-c2ccn(C)c(=O)c2)cc1] 4-(4-(((2R,3S,4S)-3-ethoxy-4-hydroxypyrrolidin-2-yl)methyl)phenyl)-1-methylpyridin-2(1H)-one |
| EXAMPLE 77 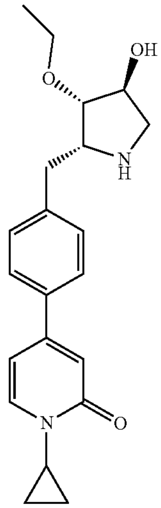 [SMILES: CCO[C@@H]1[C@@H](O)CN[C@@H]1Cc1ccc(-c2ccn(C3CC3)c(=O)c2)cc1] 1-cyclopropyl-4-(4-(((2R,3S,4S)-3-ethoxy-4-hydroxypyrrolidin-2-yl)methyl)phenyl)pyridin-2(1H)-one |

TABLE 1-continued

| Compounds of Formula (I) Example # Structure and Chemical Name |
| --- |
| EXAMPLE 78 |
| 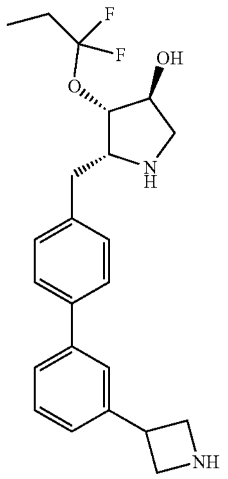 [SMILES: CCC(F)(F)O[C@@H]1[C@@H](O)CN[C@@H]1Cc1ccc(-c2cccc(C3CNC3)c2)cc1] |
| (3S,4S,5R)-5-((3'-(azetidin-3-yl)-[1,1'-biphenyl]-4-yl)methyl)-4-(1,1-difluoropropoxy)pyrrolidin-3-ol |
| EXAMPLE 79 |
| 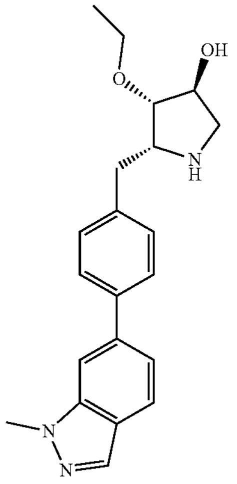 [SMILES: CCO[C@@H]1[C@@H](O)CN[C@@H]1Cc1ccc(-c2ccc3cnn(C)c3c2)cc1] |
| (3S,4S,5R)-4-ethoxy-5-(4-(1-methyl-1H-indazol-6-yl)benzyl)pyrrolidin-3-ol |

TABLE 1-continued

| Compounds of Formula (I) Example # Structure and Chemical Name |
| --- |
| EXAMPLE 80 |
| 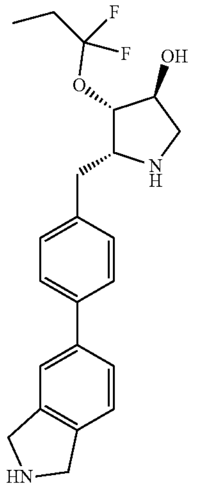 [SMILES: CCC(F)(F)O[C@@H]1[C@@H](O)CN[C@@H]1Cc1ccc(-c2ccc3c(c2)CNC3)cc1] |
| (3S,4S,5R)-4-(1,1-difluoropropoxy)-5-(4-(isoindolin-5-yl)benzyl)pyrrolidin-3-ol |
| EXAMPLE 81 |
| 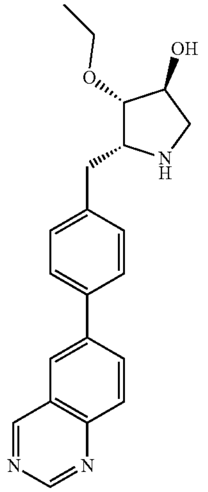 [SMILES: CCO[C@@H]1[C@@H](O)CN[C@@H]1Cc1ccc(-c2ccc3ncncc3c2)cc1] |
| (3S,4S,5R)-4-ethoxy-5-(4-(quinazolin-6-yl)benzyl)pyrrolidin-3-ol |

TABLE 1-continued

| Compounds of Formula (I) Example # Structure and Chemical Name |
|---|
| EXAMPLE 82 |
| 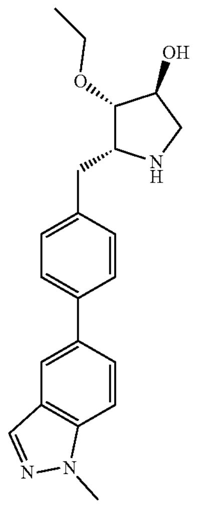 [SMILES: CCO[C@@H]1[C@@H](O)CN[C@@H]1Cc1ccc(-c2ccc3c(cnn3C)c2)cc1] |
| (3S,4S,5R)-4-ethoxy-5-(4-(1-methyl-1H-indazol-5-yl)benzyl)pyrrolidin-3-ol |
| EXAMPLE 83 |
| 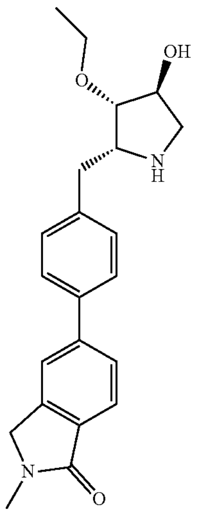 [SMILES: CCO[C@@H]1[C@@H](O)CN[C@@H]1Cc1ccc(-c2ccc3c(c2)CN(C)C3=O)cc1] |
| 5-(4-(((2R,3S,4S)-3-ethoxy-4-hydroxypyrrolidin-2-yl)methyl)phenyl)-2-methylisoindolin-1-one |

TABLE 1-continued

| Compounds of Formula (I) Example # Structure and Chemical Name |
|---|
| EXAMPLE 84 |
| 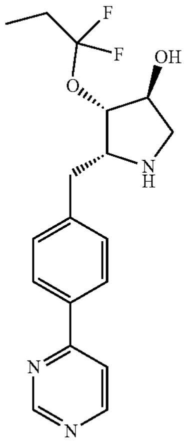 |
| (3S,4S,5R)-4-(1,1-difluoropropoxy)-5-(4-(pyrimidin-4-yl)benzyl)pyrrolidin-3-ol |
| EXAMPLE 85 |
| 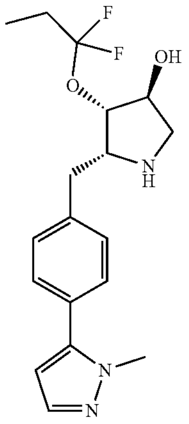 [SMILES: CCC(F)(F)O[C@@H]1[C@@H](O)CN[C@@H]1Cc1ccc(-c2ccnn2C)cc1] |
| (3S,4S,5R)-4-(1,1-difluoropropoxy)-5-(4-(1-methyl-1H-pyrazol-5-yl)benzyl)pyrrolidin-3-ol |

TABLE 1-continued

| Compounds of Formula (I) Example # Structure and Chemical Name |
|---|

EXAMPLE 86

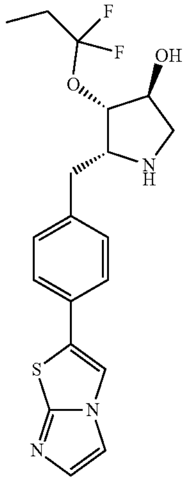 [SMILES: CCC(F)(F)O[C@@H]1[C@@H](O)CN[C@@H]1Cc1ccc(-c2cn3ccnc3s2)cc1]

(3S,4S,5R)-4-(1,1-difluoropropoxy)-5-(4-(imidazo[2,1-b]thiazol-2-yl)benzyl)pyrrolidin-3-ol

EXAMPLE 87

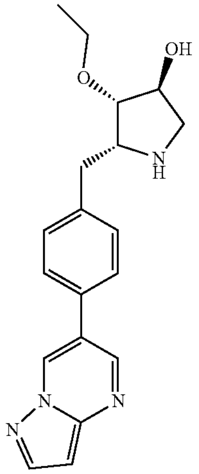 [SMILES: CCO[C@@H]1[C@@H](O)CN[C@@H]1Cc1ccc(-c2cnc3ccnn3c2)cc1]

(3S,4S,5R)-4-ethoxy-5-(4-(pyrazolo[1,5-a]pyrimidin-6-yl)benzyl)pyrrolidin-3-ol

TABLE 1-continued

| Compounds of Formula (I) Example # Structure and Chemical Name |
|---|

EXAMPLE 88

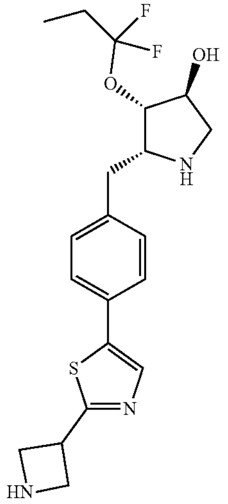 [SMILES: CCC(F)(F)O[C@@H]1[C@@H](O)CN[C@@H]1Cc1ccc(-c2cnc(C3CNC3)s2)cc1]

(3S,4S,5R)-5-(4-(2-(azetidin-3-yl)thiazol-5-yl)benzyl)-4-(1,1-difluoropropoxy)pyrrolidin-3-ol

EXAMPLE 89

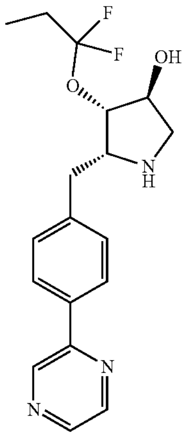 [SMILES: CCC(F)(F)O[C@@H]1[C@@H](O)CN[C@@H]1Cc1ccc(-c2cnccn2)cc1]

(3S,4S,5R)-4-(1,1-difluoropropoxy)-5-(4-(pyrazin-2-yl)benzyl)pyrrolidin-3-ol

TABLE 1-continued

| Compounds of Formula (I) Example # Structure and Chemical Name |
|---|
| EXAMPLE 90 |
| 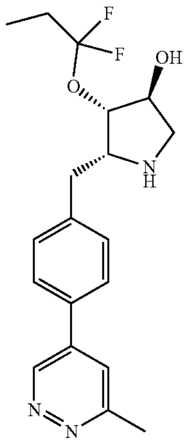 [SMILES: CCC(F)(F)O[C@@H]1[C@@H](O)CN[C@@H]1Cc1ccc(-c2cnnc(C)c2)cc1] |
| (3S,4S,5R)-4-(1,1-difluoropropoxy)-5-(4-(6-methylpyridazin-4-yl)benzyl)pyrrolidin-3-ol |
| EXAMPLE 91 |
| 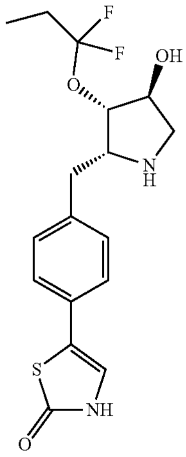 [SMILES: CCC(F)(F)O[C@@H]1[C@@H](O)CN[C@@H]1Cc1ccc(-c2c[nH]c(=O)s2)cc1] |
| 5-(4-(((2R,3S,4S)-3-(1,1-difluoropropoxy)-4-hydroxypyrrolidin-2-yl)methyl)phenyl)thiazol-2(3H)-one |

TABLE 1-continued

| Compounds of Formula (I) Example # Structure and Chemical Name |
|---|
| EXAMPLE 92 |
| 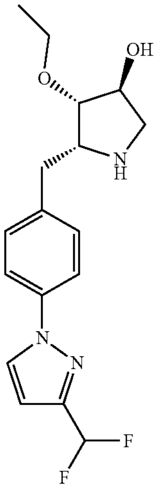 [SMILES: CCO[C@@H]1[C@@H](O)CN[C@@H]1Cc1ccc(-n2ccc(C(F)F)n2)cc1] |
| (3S,4S,5R)-5-(4-(3-(difluoromethyl)-1H-pyrazol-1-yl)benzyl)-4-ethoxypyrrolidin-3-ol |
| EXAMPLE 93 |
| 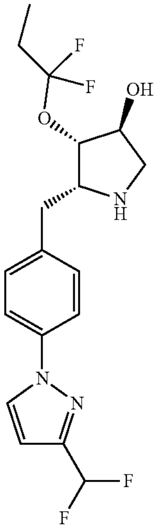 [SMILES: CCC(F)(F)O[C@@H]1[C@@H](O)CN[C@@H]1Cc1ccc(-n2ccc(C(F)F)n2)cc1] |
| (3S,4S,5R)-5-(4-(3-(difluoromethyl)-1H-pyrazol-1-yl)benzyl)-4-(1,1-difluoropropoxy)pyrrolidin-3-ol |

TABLE 1-continued

| Compounds of Formula (I) Example # Structure and Chemical Name |
|---|

EXAMPLE 94

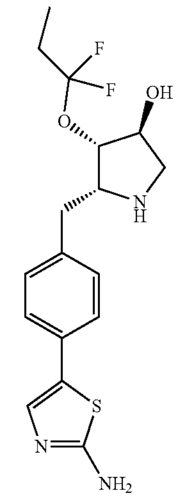 [SMILES: CCC(F)(F)O[C@@H]1[C@@H](O)CN[C@@H]1Cc1ccc(-c2cnc(N)s2)cc1]

(3S,4S,5R)-5-(4-(2-aminothiazol-5-yl)benzyl)-4-(1,1-difluoropropoxy)pyrrolidin-3-ol

EXAMPLE 95

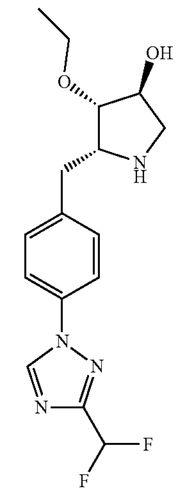 [SMILES: CCO[C@@H]1[C@@H](O)CN[C@@H]1Cc1ccc(-n2cnc(C(F)F)n2)cc1]

(3S,4S,5R)-5-(4-(3-(difluoromethyl)-1H-1,2,4-triazol-1-yl)benzyl)-4-ethoxypyrrolidin-3-ol TABLE 1-continued

| Compounds of Formula (I) Example # Structure and Chemical Name |
|---|

EXAMPLE 96

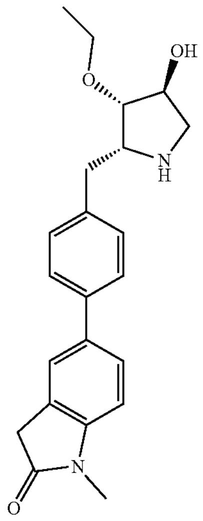 [SMILES: CCO[C@@H]1[C@@H](O)CN[C@@H]1Cc1ccc(-c2ccc3c(c2)CC(=O)N3C)cc1]

5-(4-(((2R,3S,4S)-3-ethoxy-4-hydroxypyrrolidin-2-yl)methyl)phenyl)-1-methylindolin-2-one

EXAMPLE 97

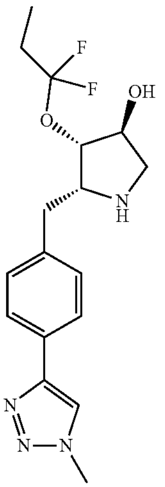 [SMILES: CCC(F)(F)O[C@@H]1[C@@H](O)CN[C@@H]1Cc1ccc(-c2cn(C)nn2)cc1]

(3S,4S,5R)-4-(1,1-difluoropropoxy)-5-(4-(1-methyl-1H-1,2,3-triazol-4-yl)benzyl)pyrrolidin-3-ol TABLE 1-continued

| Compounds of Formula (I) Example # Structure and Chemical Name |
|---|
| EXAMPLE 98 |
| 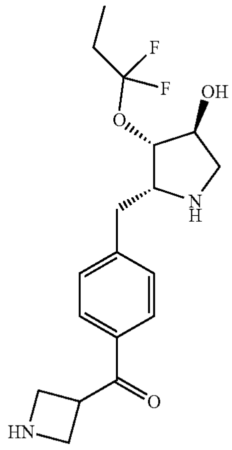 [SMILES: CCC(F)(F)O[C@@H]1[C@@H](O)CN[C@@H]1Cc1ccc(C(=O)C2CNC2)cc1] |
| azetidin-3-yl(4-(((2R,3S,4S)-3-(1,1-difluoropropoxy)-4-hydroxypyrrolidin-2-yl)methyl)phenyl)methanone |
| EXAMPLE 99 |
| 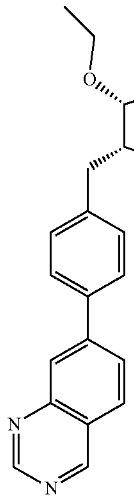 |
| (3S,4S,5R)-4-ethoxy-5-(4-(quinazolin-7-yl)benzyl)pyrrolidin-3-ol |

TABLE 1-continued

| Compounds of Formula (I) Example # Structure and Chemical Name |
|---|
| EXAMPLE 100 |
| 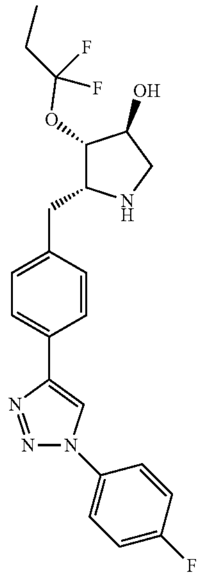 [SMILES: CCC(F)(F)O[C@@H]1[C@@H](O)CN[C@@H]1Cc1ccc(-c2cn(-c3ccc(F)cc3)nn2)cc1] |
| (3S,4S,5R)-4-(1,1-difluoropropoxy)-5-(4-(1-(4-fluorophenyl)-1H-1,2,3-triazol-4-yl)benzyl)pyrrolidin-3-ol |
| EXAMPLE 101 |
| 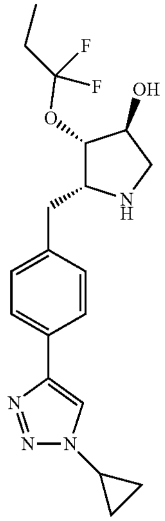 [SMILES: CCC(F)(F)O[C@@H]1[C@@H](O)CN[C@@H]1Cc1ccc(-c2cn(C3CC3)nn2)cc1] |
| (3S,4S,5R)-5-(4-(1-cyclopropyl-1H-1,2,3-triazol-4-yl)benzyl)-4-(1,1-difluoropropoxy)pyrrolidin-3-ol |

TABLE 1-continued

| Compounds of Formula (I) Example # Structure and Chemical Name |
|---|
| EXAMPLE 102 |
| 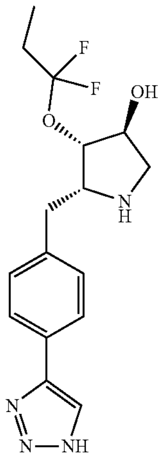 [SMILES: CCC(F)(F)O[C@@H]1[C@@H](O)CN[C@@H]1Cc1ccc(-c2c[nH]nn2)cc1] |
| (3S,4S,5R)-5-(4-(1H-1,2,3-triazol-4-yl)benzyl)-4-(1,1-difluoropropoxy)pyrrolidin-3-ol |
| EXAMPLE 103 |
| 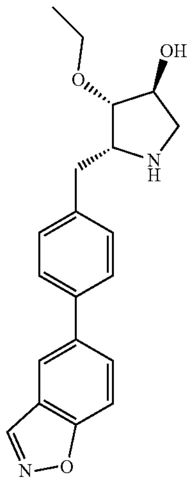 [SMILES: CCO[C@@H]1[C@@H](O)CN[C@@H]1Cc1ccc(-c2ccc3oncc3c2)cc1] |
| (3S,4S,5R)-5-(4-(benzo[d]isoxazol-5-yl)benzyl)-4-ethoxypyrrolidin-3-ol |

TABLE 1-continued

| Compounds of Formula (I) Example # Structure and Chemical Name |
|---|
| EXAMPLE 104 |
| 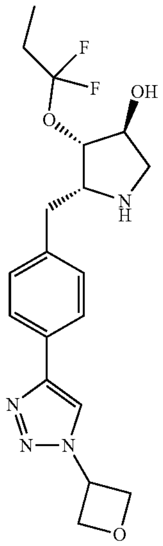 [SMILES: CCC(F)(F)O[C@@H]1[C@@H](O)CN[C@@H]1Cc1ccc(-c2cn(C3COC3)nn2)cc1] |
| (3S,4S,5R)-4-(1,1-difluoropropoxy)-5-(4-(1-(oxetan-3-yl)-1H-1,2,3-triazol-4-yl)benzyl)pyrrolidin-3-ol |
| EXAMPLE 105 |
| 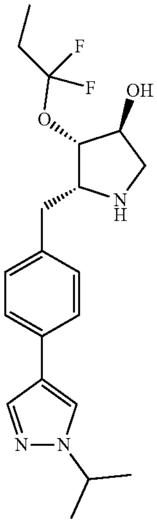 [SMILES: CCC(F)(F)O[C@@H]1[C@@H](O)CN[C@@H]1Cc1ccc(-c2cnn(C(C)C)c2)cc1] |
| (3S,4S,5R)-4-(1,1-difluoropropoxy)-5-(4-(1-isopropyl-1H-pyrazol-4-yl)benzyl)pyrrolidin-3-ol |

TABLE 1-continued

| Compounds of Formula (I) Example # Structure and Chemical Name |
|---|

EXAMPLE 106

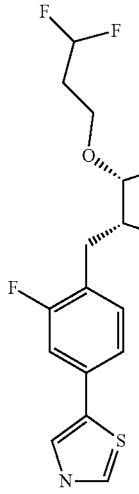

(3S,4S,5R)-4-(3,3-difluoropropoxy)-5-(2-fluoro-4-(thiazol-5-yl)benzyl)pyrrolidin-3-ol

EXAMPLE 107

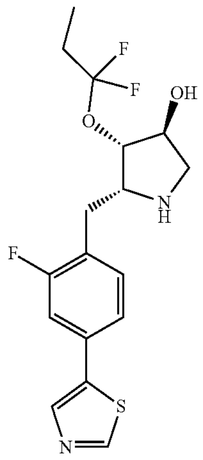 [SMILES: CCC(F)(F)O[C@@H]1[C@@H](O)CN[C@@H]1Cc1ccc(-c2cncs2)cc1F]

(3S,4S,5R)-4-(1,1-difluoropropoxy)-5-(2-fluoro-4-(thiazol-5-yl)benzyl)pyrrolidin-3-ol TABLE 1-continued

| Compounds of Formula (I) Example # Structure and Chemical Name |
|---|

EXAMPLE 108

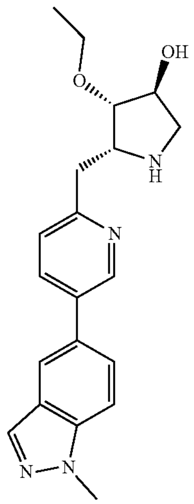

(3S,4S,5R)-4-ethoxy-5-((5-(1-methyl-1H-indazol-5-yl)pyridin-2-yl)methyl)pyrrolidin-3-ol

EXAMPLE 109

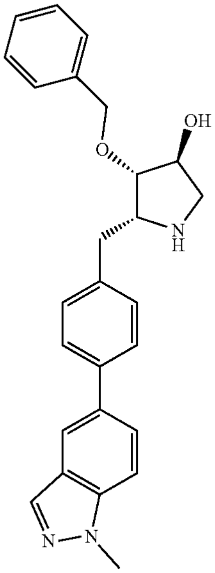 [SMILES: Cn1ncc2cc(-c3ccc(C[C@H]4NC[C@H](O)[C@H]4OCc4ccccc4)cc3)ccc21]

(3S,4S,5R)-5-(4-(1-methyl-1H-indazol-5-yl)benzyl)-4-(pyridin-2-ylmethoxy)pyrrolidin-3-ol TABLE 1-continued

| Compounds of Formula (I) Example # Structure and Chemical Name |
| --- |

EXAMPLE 110

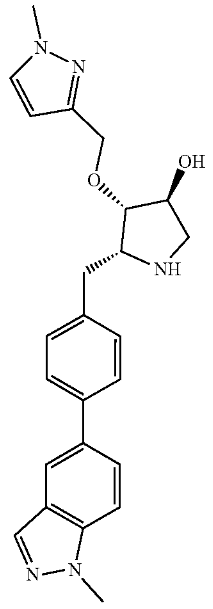 [SMILES: Cn1ccc(CO[C@@H]2[C@@H](O)CN[C@@H]2Cc2ccc(-c3ccc4c(cnn4C)c3)cc2)n1]

(3S,4S,5R)-5-(4-(1-methyl-1H-indazol-5-yl)benzyl)-4-((1-methyl-1H-pyrazol-3-yl)methoxy)pyrrolidin-3-ol

EXAMPLE 111

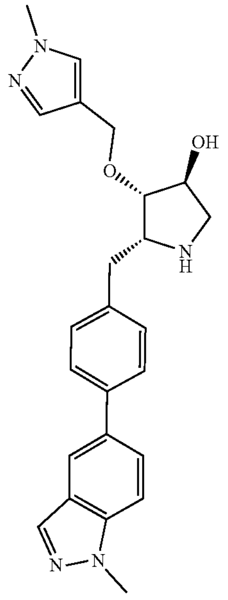 [SMILES: Cn1cc(CO[C@@H]2[C@@H](O)CN[C@@H]2Cc2ccc(-c3ccc4c(cnn4C)c3)cc2)cn1]

(3S,4S,5R)-5-(4-(1-methyl-1H-indazol-5-yl)benzyl)-4-((1-methyl-1H-pyrazol-4-yl)methoxy)pyrrolidin-3-ol TABLE 1-continued

| Compounds of Formula (I) Example # Structure and Chemical Name |
| --- |

EXAMPLE 112

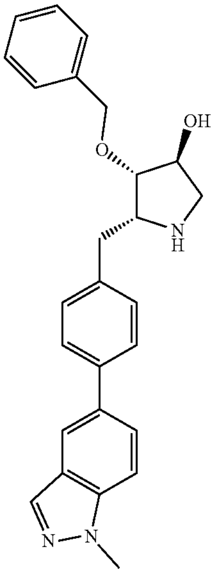 [SMILES: Cn1ncc2cc(-c3ccc(C[C@H]4NC[C@H](O)[C@H]4OCc4ccccc4)cc3)ccc21]

(3S,4S,5R)-4-(benzyloxy)-5-(4-(1-methyl-1H-indazol-5-yl)benzyl)pyrrolidin-3-ol

EXAMPLE 113

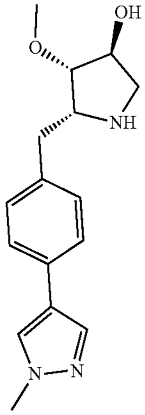 [SMILES: CO[C@@H]1[C@@H](O)CN[C@@H]1Cc1ccc(-c2cnn(C)c2)cc1]

(3S,4S,5R)-4-methoxy-5-(4-(1-methyl-1H-pyrazol-4-yl)benzyl)pyrrolidin-3-ol

TABLE 1-continued

| Compounds of Formula (I) Example # Structure and Chemical Name |
| --- |
| EXAMPLE 114 |
| 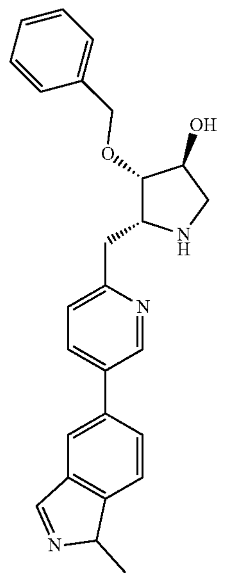 [SMILES: CC1N=Cc2cc(-c3ccc(C[C@H]4NC[C@H](O)[C@H]4OCc4ccccc4)nc3)ccc21] |
| (3S,4S,5R)-4-(benzyloxy)-5-((5-(1-methyl-1H-indazol-5-yl)pyridin-2-yl)methyl)pyrrolidin-3-ol |
| EXAMPLE 115 |
| 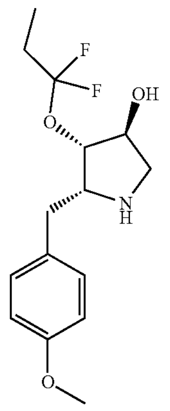 [SMILES: CCC(F)(F)O[C@@H]1[C@@H](O)CN[C@@H]1Cc1ccc(OC)cc1] |
| (3S,4S,5R)-4-(1,1-difluoropropoxy)-5-(4-methoxybenzyl)pyrrolidin-3-ol |

TABLE 1-continued

| Compounds of Formula (I) Example # Structure and Chemical Name |
| --- |
| EXAMPLE 116 |
| 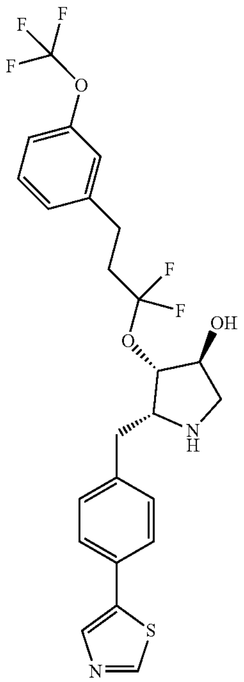 [SMILES: O[C@H]1CN[C@H](Cc2ccc(-c3cncs3)cc2)[C@@H]1OC(F)(F)CCc1cccc(OC(F)(F)F)c1] |
| (3S,4S,5R)-4-(1,1-difluoro-3-(3-(trifluoromethoxy)phenyl)propoxy)-5-(4-(thiazol-5-yl)benzyl)pyrrolidin-3-ol |
| EXAMPLE 117 |
| 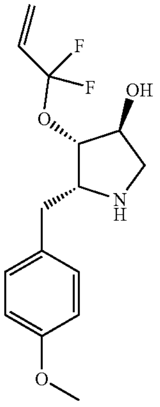 [SMILES: C=CC(F)(F)O[C@@H]1[C@@H](O)CN[C@@H]1Cc1ccc(OC)cc1] |
| (3S,4S,5R)-4-((1,1-difluoroallyl)oxy)-5-(4-methoxybenzyl)pyrrolidin-3-ol |

TABLE 1-continued

| Compounds of Formula (I) Example # Structure and Chemical Name |
|---|
| EXAMPLE 118 |
| 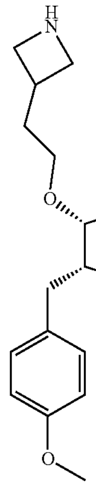 |
| (3S,4S,5R)-4-(2-(azetidin-3-yl)ethoxy)-5-(4-methoxybenzyl)pyrrolidin-3-ol |
| EXAMPLE 119 |
| 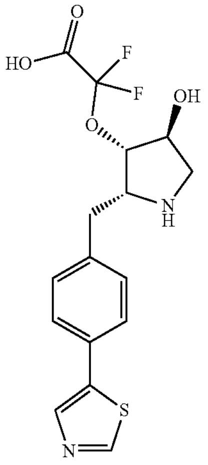 [SMILES: O=C(O)C(F)(F)O[C@@H]1[C@@H](O)CN[C@@H]1Cc1ccc(-c2cncs2)cc1] |
| 2,2-difluoro-2-(((2R,3S,4S)-4-hydroxy-2-(4-(thiazol-5-yl)benzyl)pyrrolidin-3-yl)oxy)acetic acid |

TABLE 1-continued

| Compounds of Formula (I) Example # Structure and Chemical Name |
|---|
| EXAMPLE 120 |
| 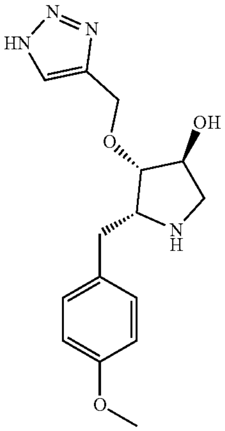 [SMILES: COc1ccc(C[C@H]2NC[C@H](O)[C@H]2OCc2c[nH]nn2)cc1] |
| (3S,4S,5R)-4-((1H-1,2,3-triazol-4-yl)methoxy)-5-(4-methoxybenzyl)pyrrolidin-3-ol |
| EXAMPLE 121 |
| 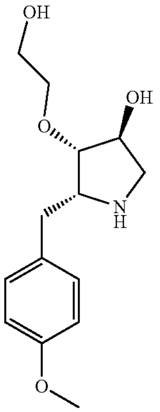 [SMILES: COc1ccc(C[C@H]2NC[C@H](O)[C@H]2OCCO)cc1] |
| (3S,4S,5R)-4-(2-hydroxyethoxy)-5-(4-methoxybenzyl)pyrrolidin-3-ol |

TABLE 1-continued
| Compounds of Formula (I) Example # Structure and Chemical Name |
|---|
| EXAMPLE 122 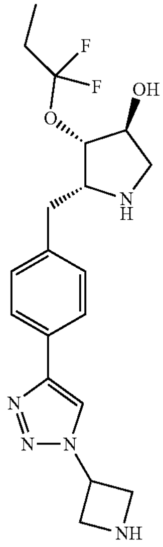 [SMILES: CCC(F)(F)O[C@@H]1[C@@H](O)CN[C@@H]1Cc1ccc(-c2cn(C3CNC3)nn2)cc1] (3S,4S,5R)-5-(4-(1-(azetidin-3-yl)-1H-1,2,3-triazol-4-yl)benzyl)-4-(1,1-difluoropropoxy)pyrrolidin-3-ol — |
TABLE 2
| Additional Compounds of Formula (I) Structure |
|---|
| 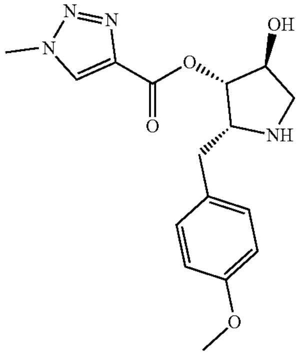 [SMILES: COc1ccc(C[C@H]2NC[C@H](O)[C@H]2OC(=O)c2cn(C)nn2)cc1] |
TABLE 2-continued
| Additional Compounds of Formula (I) Structure |
|---|
| 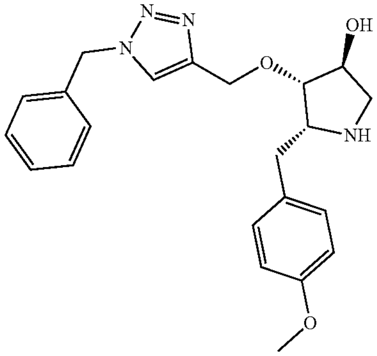 [SMILES: COc1ccc(C[C@H]2NC[C@H](O)[C@H]2OCc2cn(Cc3ccccc3)nn2)cc1] |
| 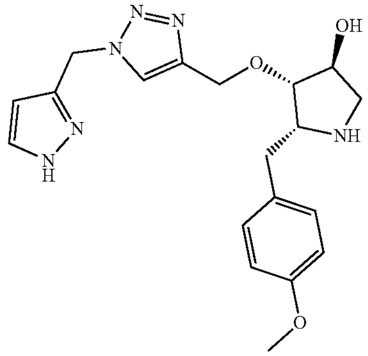 [SMILES: COc1ccc(C[C@H]2NC[C@H](O)[C@H]2OCc2cn(Cc3cc[nH]n3)nn2)cc1] |
| 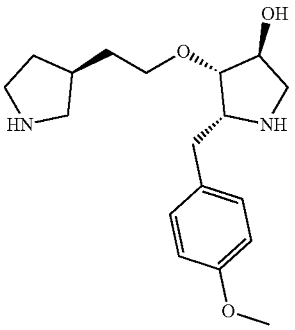 [SMILES: COc1ccc(C[C@H]2NC[C@H](O)[C@H]2OCC[C@@H]2CCNC2)cc1] |
| 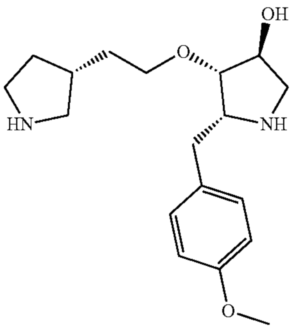 [SMILES: COc1ccc(C[C@H]2NC[C@H](O)[C@H]2OCC[C@H]2CCNC2)cc1] |

TABLE 2-continued

| Additional Compounds of Formula (I) Structure |
| --- |
| 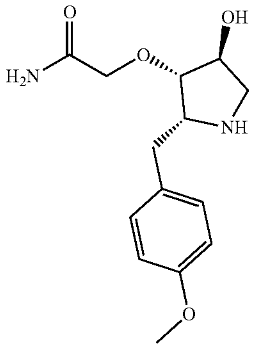 [SMILES: COc1ccc(C[C@H]2NC[C@H](O)[C@H]2OCC(N)=O)cc1] |
| 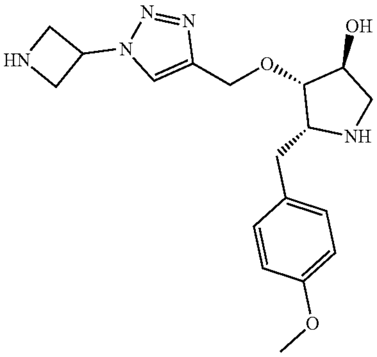 [SMILES: COc1ccc(C[C@H]2NC[C@H](O)[C@H]2OCc2cn(C3CNC3)nn2)cc1] |
| 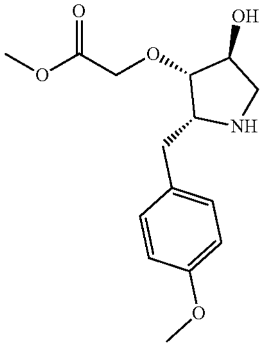 [SMILES: COC(=O)CO[C@@H]1[C@@H](O)CN[C@@H]1Cc1ccc(OC)cc1] |
| 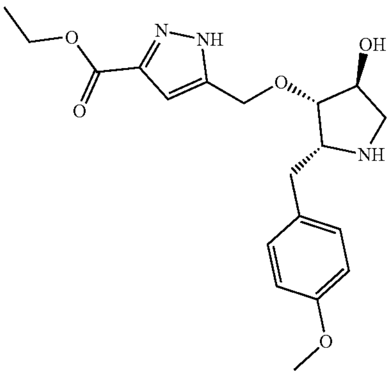 [SMILES: CCOC(=O)c1cc(CO[C@@H]2[C@@H](O)CN[C@@H]2Cc2ccc(OC)cc2)[nH]n1] |

TABLE 2-continued

| Additional Compounds of Formula (I) Structure |
| --- |
| 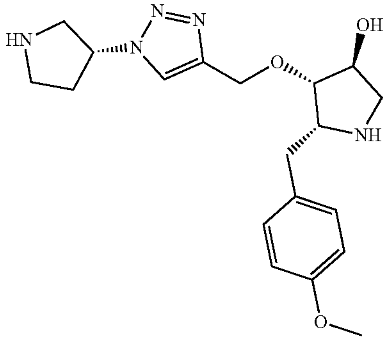 [SMILES: COc1ccc(C[C@H]2NC[C@H](O)[C@H]2OCc2cn([C@@H]3CCNC3)nn2)cc1] |
| 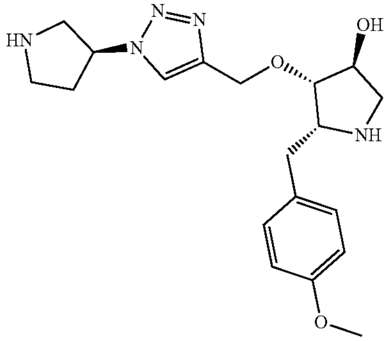 [SMILES: COc1ccc(C[C@H]2NC[C@H](O)[C@H]2OCc2cn([C@H]3CCNC3)nn2)cc1] |

In another aspect, the present disclosure provides a compound selected from those in Tables 1-2, and pharmaceutically acceptable salts, stereoisomers, and tautomers thereof. In another aspect, the present disclosure provides a compound selected from those in Tables 1-2, and pharmaceutically acceptable salts and stereoisomers thereof. In another aspect, the present disclosure provides a compound selected from those in Tables 1-2, and pharmaceutically acceptable salts and tautomers thereof. In another aspect, the present disclosure provides a stereoisomer of a compound selected from those in Tables 1-2, and pharmaceutically acceptable salts thereof. In another aspect, the present disclosure provides a tautomer of a compound selected from those in Tables 1-2, and pharmaceutically acceptable salts thereof.

Pharmaceutical Compositions, Kits, and Administration

The present disclosure provides pharmaceutical compositions comprising a compound provided herein, or a pharmaceutically acceptable salt thereof (e.g., a compound of Formula (I), or a pharmaceutically acceptable salt thereof), and optionally a pharmaceutically acceptable excipient. In some embodiments, the pharmaceutical composition described herein comprises a compound provided herein, or a pharmaceutically acceptable salt thereof, and a pharmaceutically acceptable excipient. In certain embodiments, a compound described herein is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include bringing the compound described herein (i.e., the "active ingredient")

into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable carrier or excipient, and/or any additional ingredients in a pharmaceutical composition described herein will vary, depending upon the identity, size, and/or condition of the subject treated and further depending upon the route by which the composition is to be administered.

Pharmaceutically acceptable carriers/excipients used in the manufacture of provided pharmaceutical compositions include inert diluents, solvents, dispersing and/or granulating agents, surface active agents and/or emulsifiers, disintegrating agents, binding agents, preservatives, buffering agents, lubricating agents, oils, butters, and/or waxes. Excipients such as coloring agents, coating agents, sweetening agents, flavoring agents, and fragrances may also be present in the composition.

The compounds and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for case of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form a single unit dosage form. Thus, in one aspect, provided are kits including a first container comprising a compound or pharmaceutical composition described herein. In certain embodiments, the kits are useful for treating and/or preventing a disease, disorder, or condition in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits provide instructions for treating a disease (e.g., cancer) in a subject in need thereof. In certain embodiments, the kits provide instructions for preventing a disease in a subject in need thereof. A kit described herein may include one or more additional pharmaceutical agents described herein as a separate composition.

Methods of Modulating Protein Synthesis

In another aspect, the present disclosure provides a method of modulating protein synthesis in a subject in need thereof or in a cell, tissue, or biological sample, comprising administering to the subject in need thereof or contacting the cell, tissue, or biological sample with an effective amount of a provided compound (e.g., a compound of the present disclosure, or a pharmaceutically acceptable salt thereof), or a pharmaceutical composition thereof. In another aspect, the present disclosure provides a method of modulating protein synthesis in a subject in need thereof or in a cell, tissue, or biological sample, comprising administering to the subject in need thereof or contacting the cell, tissue, or biological sample with an effective amount of a compound of Formula (I), or a pharmaceutical composition thereof.

In some embodiments, the present disclosure provides a method of modulating protein synthesis in a subject in need thereof, comprising administering to the subject in need thereof an effective amount of a provided compound, or a pharmaceutical composition thereof. In some embodiments, the present disclosure provides a method of modulating protein synthesis in a cell, tissue, or biological sample, comprising contacting the cell, tissue, or biological sample with an effective amount of a provided compound, or a pharmaceutical composition thereof. In some embodiments, the present disclosure provides a provided compound, or a pharmaceutical composition thereof, for use in modulating protein synthesis in a subject in need thereof. In some embodiments, the present disclosure provides a provided compound, or a pharmaceutical composition thereof, for use in the manufacture of a medicament for modulating protein synthesis in a subject in need thereof.

In some embodiments modulating protein synthesis comprises modulating synthesis of a target protein. In some embodiments, modulating protein synthesis comprises decreasing protein synthesis. In some embodiments, the protein synthesis is decreased by at least about 10%, at least about 20%, at least about 30%, at least about 40%, at least about 50%, at least about 60%, at least about 70%, at least about 80%, at least about 90%, at least about 95%, or at least about 98%. In some embodiments, protein synthesis is decreased by not more than about 10%, not more than about 20%, not more than about 30%, not more than about 40%, not more than about 50%, not more than about 60%, not more than about 70%, not more than about 80%, not more than about 90%, not more than about 95%, or not more than about 98%. In some embodiments, protein synthesis is decreased by a range between a percentage described in this paragraph and another percentage described in this paragraph, inclusive.

In another aspect, the present disclosure provides a method of decreasing protein synthesis in a subject in need thereof or in a cell, tissue, or biological sample, comprising administering to the subject in need thereof or contacting the cell, tissue, or biological sample with an effective amount of a provided compound (e.g., a compound of the present disclosure, or a pharmaceutically acceptable salt thereof), or a pharmaceutical composition thereof. In some embodiments, the present disclosure provides a method of decreasing protein synthesis in a subject in need thereof, comprising administering to the subject in need thereof an effective amount of a provided compound, or a pharmaceutical composition thereof. In some embodiments, the present disclosure provides a method of decreasing protein synthesis in a cell, tissue, or biological sample, comprising contacting the cell, tissue, or biological sample with an effective amount of a provided compound, or a pharmaceutical composition thereof. In some embodiments, the present disclosure provides a provided compound, or a pharmaceutical composition thereof, for use in decreasing protein synthesis in a subject in need thereof. In some embodiments, the present disclosure provides a provided compound, or a pharmaceutical composition thereof, for use in the manufacture of a medicament for decreasing protein synthesis in a subject in need thereof.

In some embodiments, decreasing protein synthesis comprises decreasing synthesis of a target protein. In some embodiments, the protein synthesis is decreased by at least about 10%, at least about 20%, at least about 30%, at least about 40%, at least about 50%, at least about 60%, at least about 70%, at least about 80%, at least about 90%, at least about 95%, or at least about 98%. In some embodiments, protein synthesis is decreased by not more than about 10%, not more than about 20%, not more than about 30%, not more than about 40%, not more than about 50%, not more than about 60%, not more than about 70%, not more than about 80%, not more than about 90%, not more than about 95%, or not more than about 98%. In some embodiments, protein synthesis is decreased by a range between a percentage described in this paragraph and another percentage described in this paragraph, inclusive.

In some embodiments, the method is selective for decreasing synthesis of a first protein compared to synthesis of a second protein. In some embodiments, the ratio of the decrease in synthesis of the first protein to the decrease in synthesis of the second protein is about 1.1:1, about 1.2:1, about 1.3:1, about 1.4:1, about 1.5:1, about 1.6:1, about 1.7:1, about 1.8:1, about 1.9:1, about 2:1, about 2.5:1, about 3:1, about 3.5:1, about 4:1, about 4.5:1, about 5:1, about 6:1, about 7:1, about 8:1, about 9:1, about 10:1, about 15:1, about 20:1, about 25:1, about 50:1, about 75:1, about 100:1, about 200:1, about 300:1, about 400:1, about 500:1, about 1.000:1, about 10,000:1, or about 100.000:1. In some embodiments, the ratio of the decrease in synthesis of the first protein to the decrease in synthesis of the second protein is between a ratio described in this paragraph and another ratio described in this paragraph, inclusive.

In some embodiments, the method further comprises decreasing an amount of mRNA, wherein the mRNA is associated with synthesis of the target protein. In some embodiments, the amount of mRNA is decreased by at least about 10%, at least about 20%, at least about 30%, at least about 40%, at least about 50%, at least about 60%, at least about 70%, at least about 80%, at least about 90%, at least about 95%, or at least about 98%. In some embodiments, the amount of mRNA is decreased by not more than 10%, not more than 20%, not more than 30%, not more than 40%, not more than 50%, not more than 60%, not more than 70%, not more than 80%, not more than 90%, not more than 95%, or not more than 98%. In some embodiments, the amount of mRNA is decreased by a range between a percentage described in this paragraph and another percentage described in this paragraph, inclusive.

In some embodiments, the method is in vitro. In some embodiments, the method is in vivo.

In some embodiments, the target protein is B-cell lymphoma 2 (BCL-2), MYC proto-oncogene bHLH transcription factor (MYC), cyclin D1 (CCND1), myeloid cell leukemia 1 (MCL-1), anaplastic lymphoma kinase (ALK), or GTPase KRas G12D mutant (KRAS-G12D). In some embodiments, the target protein is BCL-2. In some embodiments, the target protein is MYC. In some embodiments, the target protein is CCND1. In some embodiments, the target protein is MCL-1. In some embodiments, the target protein is ALK. In some embodiments, the target protein is KRAS-G12D. The target proteins KRAS-G12D, BCL-2, MYC, CCND1, MCL-1, ALK, and KRAS-G12D are exemplary target proteins, and the methods disclosed herein are not limited to these target proteins.

In some embodiments, the cell is a cancer cell. In some embodiments, the cell is a HEK 293T, HPAF-II, KLE, LS411N, MCF7, NCI-H1915, HCC38, HEPG2, KATO-III, MS751, or T47D cell. In some embodiments, the cell is a HEK 293T cell. In some embodiments, the cell is a HPAF-II cell. In some embodiments, the cell is a KLE cell. In some embodiments, the cell is a LS411N cell. In some embodiments, the cell is a MCF7 cell. In some embodiments, the cell is a NCI-H1915 cell. In some embodiments, the cell is a HCC38 cell. In some embodiments, the cell is a HEPG2 cell. In some embodiments, the cell is a KATO-III cell. In some embodiments, the cell is a MS751 cell. In some embodiments, the cell is a T47D cell.

Methods of Treatment and Prevention

In another aspect, the present disclosure provides a method comprising administering to a subject a provided compound (e.g., a compound of the present disclosure, or a pharmaceutically acceptable salt thereof), or a pharmaceutical composition thereof. In another aspect, the present disclosure provides a method comprising administering to a subject a compound of Formula (I), or a pharmaceutical composition thereof.

In another aspect, the present disclosure provides a method of treating or preventing a disease in a subject in need thereof, comprising administering to the subject in need thereof an effective amount of a provided compound (e.g., a compound of the present disclosure, or a pharmaceutically acceptable salt thereof), or a pharmaceutical composition thereof. In some embodiments, the present disclosure provides a method of treating a disease in a subject in need thereof, comprising administering to the subject in need thereof a therapeutically effective amount of a provided compound, or a pharmaceutical composition thereof. In some embodiments, the present disclosure provides a method of preventing a disease in a subject in need thereof, comprising administering to the subject in need thereof a prophylactically effective amount of a provided compound, or a pharmaceutical composition thereof. In another aspect, the present disclosure provides a method of treating or preventing a disease in a subject in need thereof, comprising administering to the subject in need thereof an effective amount of a compound of Formula (I), or a pharmaceutical composition thereof. In another aspect, the present disclosure provides a method of treating a disease in a subject in need thereof, comprising administering to the subject in need thereof a therapeutically effective amount of a compound of Formula (I), or a pharmaceutical composition thereof. In another aspect, the present disclosure provides a method of preventing a disease in a subject in need thereof, comprising administering to the subject in need thereof a prophylactically effective amount of a compound of Formula (I), or a pharmaceutical composition thereof.

In some embodiments, the present disclosure provides a provided compound, or a pharmaceutical composition thereof, for use in treating or preventing a disease in a subject in need thereof. In some embodiments, the present disclosure provides a provided compound, or a pharmaceutical composition thereof, for use in treating a disease in a subject in need thereof. In some embodiments, the present disclosure provides a provided compound, or a pharmaceutical composition thereof, for use in preventing a disease in a subject in need thereof.

In some embodiments, the present disclosure provides a provided compound, or a pharmaceutical composition thereof, for use in the manufacture of a medicament for treating or preventing a disease in a subject in need thereof. In some embodiments, the present disclosure provides a provided compound, or a pharmaceutical composition thereof, for use in the manufacture of a medicament for treating a disease in a subject in need thereof. In some embodiments, the present disclosure provides a provided compound, or a pharmaceutical composition thereof, for use in the manufacture of a medicament for preventing a disease in a subject in need thereof.

In some embodiments, the disease is a proliferative disease (e.g., cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma)), neurological disease (e.g., cerebellar ataxia, neurodegenerative disease (e.g., Alzheimer's disease, Parkinson's disease, amyotrophic lateral sclerosis, tauopathy (including frontotemporal dementia), Huntington's disease, Friedreich's ataxia)), or immune disorder (e.g., psoriasis, lupus, rheumatoid arthritis).

In some embodiments, the disease is a proliferative disease (e.g., cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma)). In some embodiments, the proliferative disease is cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma). In some embodiments, the cancer is prostate cancer (e.g., prostate adenocarcinoma), pancreatic cancer (e.g., pancreatic andenocarcinoma, intraductal papillary mucinous neoplasm (IPMN), Islet cell tumors), lung cancer (e.g., bronchogenic carcinoma, small cell lung cancer (SCLC), non-small cell lung cancer (NSCLC), adenocarcinoma of the lung), breast cancer (e.g., adenocarcinoma of the breast, papillary carcinoma of the breast, mammary cancer, medullary carcinoma of the breast, triple-negative breast cancer (TNBC)), colorectal cancer (e.g., colon cancer, rectal cancer, colorectal adenocarcinoma), endometrial cancer (e.g., uterine cancer, uterine sarcoma), ovarian cancer (e.g., cystadenocarcinoma, ovarian embryonal carcinoma, ovarian adenocarcinoma), cervical cancer (e.g., cervical adenocarcinoma), esophageal cancer (e.g., adenocarcinoma of the esophagus, Barrett's adenocarcinoma), bladder cancer, biliary cancer (e.g., cholangiocarcinoma), hematopoietic cancer (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/ leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), or neuroblastoma.

In some embodiments, the cancer is prostate cancer (e.g., prostate adenocarcinoma). In some embodiments, the cancer is prostate adenocarcinoma. In some embodiments, the cancer is pancreatic cancer (e.g., pancreatic andenocarcinoma, intraductal papillary mucinous neoplasm (IPMN), Islet cell tumors). In some embodiments, the cancer is pancreatic andenocarcinoma. In some embodiments, the cancer is intraductal papillary mucinous neoplasm (IPMN). In some embodiments, the cancer is Islet cell tumors. In some embodiments, the cancer is lung cancer (e.g., bronchogenic carcinoma, small cell lung cancer (SCLC), non-small cell lung cancer (NSCLC), adenocarcinoma of the lung). In some embodiments, the cancer is bronchogenic carcinoma. In some embodiments, the cancer is small cell lung cancer (SCLC). In some embodiments, the cancer is non-small cell lung cancer (NSCLC). In some embodiments, the cancer is adenocarcinoma of the lung. In some embodiments, the cancer is breast cancer (e.g., adenocarcinoma of the breast, papillary carcinoma of the breast, mammary cancer, medullary carcinoma of the breast, triple-negative breast cancer (TNBC)). In some embodiments, the cancer is adenocarcinoma of the breast. In some embodiments, the cancer is papillary carcinoma of the breast. In some embodiments, the cancer is mammary cancer. In some embodiments, the cancer is medullary carcinoma of the breast. In some embodiments, the cancer is triple-negative breast cancer (TNBC). In some embodiments, the cancer is colorectal cancer (e.g., colon cancer, rectal cancer, colorectal adenocarcinoma). In some embodiments, the cancer is colon cancer. In some embodiments, the cancer is rectal cancer. In some embodiments, the cancer is colorectal adenocarcinoma. In some embodiments, the cancer is endometrial cancer (e.g., uterine cancer, uterine sarcoma). In some embodiments, the cancer is uterine cancer. In some embodiments, the cancer is uterine sarcoma. In some embodiments, the cancer is ovarian cancer (e.g., cystadenocarcinoma, ovarian embryonal carcinoma, ovarian adenocarcinoma). In some embodiments, the cancer is cystadenocarcinoma. In some embodiments, the cancer is ovarian embryonal carcinoma. In some embodiments, the cancer is ovarian adenocarcinoma. In some embodiments, the cancer is cervical cancer (e.g., cervical adenocarcinoma). In some embodiments, the cancer is cervical adenocarcinoma. In some embodiments, the cancer is esophageal cancer (e.g., adenocarcinoma of the esophagus, Barrett's adenocarcinoma). In some embodiments, the cancer is adenocarcinoma of the esophagus. In some embodiments, the cancer is Barrett's adenocarcinoma. In some embodiments, the cancer is bladder cancer. In some embodiments, the cancer is biliary cancer (e.g., cholangiocarcinoma). In some embodiments, the cancer is cholangiocarcinoma. In some embodiments, the cancer is hematopoietic cancer (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)). In some embodiments, the cancer is leukemia (e.g., acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)). In some embodiments, the cancer is acute lymphocytic leukemia (ALL) (e.g., B-cell ALL, T-cell ALL). In some embodiments, the cancer is B-cell ALL. In some embodiments, the cancer is T-cell ALL. In some embodiments, the cancer is acute myelocytic leukemia (AML) (e.g., B-cell AML, T-cell AML). In some embodiments, the cancer is B-cell AML. In some embodiments, the cancer is T-cell AML. In some embodiments, the cancer is chronic myelocytic leukemia (CML) (e.g., B-cell CML, T-cell CML). In some embodiments, the cancer is B-cell CML. In some embodiments, the cancer is T-cell CML. In some embodiments, the cancer is chronic lymphocytic leukemia (CLL) (e.g., B-cell CLL, T-cell CLL). In some embodiments, the cancer is B-cell CLL. In some embodiments, the cancer is T-cell CLL. In some embodiments, the cancer is lymphoma (e.g., Hodgkin lymphoma (HL) (e.g., B-cell HL, T-cell HL); non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma. Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma); T-cell NHL (e.g., precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma)). In some embodiments, the cancer is Hodgkin lymphoma (HL) (e.g., B-cell HL, T-cell HL). In some embodiments, the cancer is B-cell HL. In some embodiments, the cancer is T-cell HL. In some embodiments, the cancer is non-Hodgkin lymphoma (NHL) (e.g., B-cell NHL such as diffuse large cell lymphoma (DLCL)

(e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma). In some embodiments, the cancer is diffuse large cell lymphoma (DLCL) (e.g., diffuse large B-cell lymphoma). In some embodiments, the cancer is diffuse large B-cell lymphoma. In some embodiments, the cancer is follicular lymphoma. In some embodiments, the cancer is chronic lymphocytic leukemia/small lymphocytic lymphoma (CLL/SLL). In some embodiments, the cancer is mantle cell lymphoma (MCL). In some embodiments, the cancer is marginal zone B-cell lymphomas (e.g., mucosa-associated lymphoid tissue (MALT) lymphomas, nodal marginal zone B-cell lymphoma, splenic marginal zone B-cell lymphoma). In some embodiments, the cancer is mucosa-associated lymphoid tissue (MALT) lymphomas. In some embodiments, the cancer is nodal marginal zone B-cell lymphoma. In some embodiments, the cancer is splenic marginal zone B-cell lymphoma. In some embodiments, the cancer is primary mediastinal B-cell lymphoma. In some embodiments, the cancer is Burkitt lymphoma. In some embodiments, the cancer is lymphoplasmacytic lymphoma (i.e., Waldenström's macroglobulinemia). In some embodiments, the cancer is Waldenström's macroglobulinemia. In some embodiments, the cancer is hairy cell leukemia (HCL). In some embodiments, the cancer is immunoblastic large cell lymphoma. In some embodiments, the cancer is precursor B-lymphoblastic lymphoma. In some embodiments, the cancer is primary central nervous system (CNS) lymphoma. In some embodiments, the cancer is T-cell NHL (e.g., precursor T-lymphoblastic lymphoma/leukemia, peripheral T-cell lymphoma (PTCL) (e.g., cutaneous T-cell lymphoma (CTCL) (e.g., mycosis fungoides. Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma)). In some embodiments, the cancer is precursor T-lymphoblastic lymphoma/leukemia. In some embodiments, the cancer is peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma). In some embodiments, the cancer is cutaneous T-cell lymphoma (CTCL) (e.g., mycosis fungoides. Sezary syndrome). In some embodiments, the cancer is mycosis fungoides. In some embodiments, the cancer is Sezary syndrome. In some embodiments, the cancer is angioimmunoblastic T-cell lymphoma. In some embodiments, the cancer is extranodal natural killer T-cell lymphoma. In some embodiments, the cancer is enteropathy type T-cell lymphoma. In some embodiments, the cancer is subcutaneous panniculitis-like T-cell lymphoma. In some embodiments, the cancer is anaplastic large cell lymphoma. In some embodiments, the cancer is a mixture of one or more leukemia/lymphoma as described above. In some embodiments, the cancer is multiple myeloma (MM). In some embodiments, the cancer is neuroblastoma.

In some embodiments, the disease is a neurological disease (e.g., cerebellar ataxia, neurodegenerative disease (e.g., Alzheimer's disease, Parkinson's disease, amyotrophic lateral sclerosis, tauopathy (including frontotemporal dementia), Huntington's disease, Friedreich's ataxia)). In some embodiments, the neurological disease is cerebellar ataxia. In some embodiments, the neurological disease is a neurodegenerative disease (e.g., Alzheimer's disease, Parkinson's disease, amyotrophic lateral sclerosis, tauopathy (including frontotemporal dementia), Huntington's disease, Friedreich's ataxia). In some embodiments, the neurodegenerative disease is Alzheimer's disease. In some embodiments, the neurodegenerative disease is Parkinson's disease. In some embodiments, the neurodegenerative disease is amyotrophic lateral sclerosis. In some embodiments, the neurodegenerative disease is tauopathy (e.g., frontotemporal dementia). In some embodiments, the neurodegenerative disease is frontotemporal dementia. In some embodiments, the neurodegenerative disease is Huntington's disease. In some embodiments, the neurodegenerative disease is Friedreich's ataxia.

In some embodiments, the disease is an immune disorder (e.g., psoriasis, lupus, rheumatoid arthritis). In some embodiments, the immune disorder is psoriasis. In some embodiments, the immune disorder is lupus. In some embodiments, the immune disorder is rheumatoid arthritis.

In some embodiments, the disease is associated with BCL-2, MYC, CCND1, MCL-1, ALK, or KRAS-G12D. In some embodiments, the disease is associated with MYC, ALK, or KRAS-G12D. In some embodiments, the disease associated with BCL-2, MYC, CCND1, MCL-1, ALK, or KRAS-G12D is a proliferative disease (e.g., cancer (e.g., prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, neuroblastoma)), neurological disease (e.g., cerebellar ataxia, neurodegenerative disease (e.g., Alzheimer's disease, Parkinson's disease, amyotrophic lateral sclerosis, tauopathy (including frontotemporal dementia), Huntington's disease, Friedreich's ataxia)), or immune disorder (e.g., psoriasis, lupus, rheumatoid arthritis).

In certain embodiments, the disease or disorder is cancer. In some embodiments, the cancer is breast cancer, lung cancer, prostate cancer, bladder cancer, liver cancer, colorectal cancer, endometrial cancer, ovarian cancer, pancreatic cancer, esophagus cancer, gastric cancer, esophageal cancer, uterine cancer, skin cancer, leukemia, or lymphoma.

In some embodiments, the disease or disorder is Breast cancer, NSCLC, Prostate cancer, Bladder cancer, Colorectal cancer, Endometrial cancer, Melanoma, Ovarian cancer, Pancreatic cancer, Hepatocellular cancer, Esophagus cancer, Gastric cancer, Diffuse Large B-cell lymphoma, Uterine sarcoma, or Acute myeloid leukemia.

In certain embodiments, the disease or disorder is Acral Lentiginous Melanoma, Acute Lymphoblastic Leukemia, Acute Myeloid Leukemia, Adenocarcinoma of the Gastroesophageal Junction, AL Amyloidosis, ALK-Positive Anaplastic Large Cell Lymphoma, ALK-Positive Large B-Cell Lymphoma, Anal Carcinoma, Anaplastic Large Cell Lymphoma, Astrocytoma, B-Cell Acute Lymphoblastic Leukemia, B-Cell Lymphoma, B-Cell Non-Hodgkin Lymphoma, Biliary Tract Carcinoma, Bladder Carcinoma, Bladder Papillary Urothelial Neoplasm, Brain Glioblastoma, Breast Angiosarcoma, Breast Carcinoma, Bronchogenic Carcinoma, Burkitt Lymphoma, Carcinoma, Central Nervous System Neoplasm, Cholangiocarcinoma, Chondrosarcoma, Chronic Lymphocytic Leukemia, Chronic Lymphocytic Leukemia/Small Lymphocytic Lymphoma, Chronic Myeloid Leukemia, Colon Carcinoma, Colorectal Adenocarcinoma, Colorectal Carcinoma, Dedifferentiated Chondrosarcoma, Desmoid-Type Fibromatosis, Desmoplastic/Nodular Medulloblastoma, Diffuse Large B-Cell Lymphoma, Diffuse Large B-Cell Lymphoma Activated B-Cell Type, Double-Hit Lymphoma, EBV-Positive Diffuse Large B-Cell Lymphoma, Endometrial Serous Adenocarcinoma, Erdheim-Chester Disease, Esophageal Adenocarcinoma, Esophageal Adenosquamous Carcinoma, Esophageal Carcinoma, Esophageal Squamous Cell Carcinoma, Ewing Sarcoma, Follicular Lymphoma, Ganglioneuroblastoma, Gastric Adenocarcinoma, Gastric Adenosquamous Carcinoma, Gastric Carcinoma, Gastric Squamous Cell Carcinoma, Germinal Center B-Cell-Like Diffuse Large B-Cell Lymphoma, Glioblastoma, Hairy Cell Leukemia, Head and Neck Carcinoma, Head and Neck Squamous Cell Carcinoma, Hematopoictic and Lymphoid Malignancy, Hepatocellular Carcinoma, High Grade B-Cell Lymphoma, High Grade B-Cell Lymphoma with MYC and BCL2 and/or BCL6 Rearrangements, High Grade Ovarian Serous Adenocarcinoma, Histiocytic and Dendritic Cell Neoplasm, Hodgkin Lymphoma, Hypopharyngeal Squamous Cell Carcinoma, Inflammatory Myofibroblastic Tumor, Intracranial Primitive Neuroectodermal Neoplasm, Intrahepatic Cholangiocarcinoma, Intraocular Lymphoma, Invasive Breast Carcinoma, Juvenile Myelomonocytic Leukemia, Langerhans Cell Histiocytosis, Large Cell/Anaplastic Medulloblastoma, Laryngeal Squamous Cell Carcinoma, Leukemia, Low Grade Glioma, Lung Adenocarcinoma, Lung Carcinoma, Lymphoma, Lymphoplasmacytic Lymphoma, Malignant Breast Neoplasm, Malignant Central Nervous System Neoplasm, Malignant Colon Neoplasm, Malignant Colorectal Neoplasm, Malignant Endometrial Neoplasm, Malignant Gastric Neoplasm, Malignant Glioma, Malignant Lung Neoplasm, Malignant Ovarian Epithelial Tumor, Malignant Ovarian Neoplasm, Malignant Pancreatic Neoplasm, Malignant Pleural Mesothelioma, Malignant Prostate Neoplasm, Malignant Solid Tumor, Malignant Thyroid Gland Neoplasm, Mantle Cell Lymphoma, Marginal Zone Lymphoma, Mature B-Cell Lymphoma/Leukemia, Mature B-Cell Non-Hodgkin Lymphoma, Mature T-Cell and NK-Cell Lymphoma/Leukemia, Medulloblastoma, Medulloblastoma with Extensive Nodularity, Melanoma, Merkel Cell Carcinoma, Multiple Myeloma, Myelodysplastic/Myeloproliferative Neoplasm, Myeloid Neoplasm, Nasopharyngeal Carcinoma, Neuroblastoma, Non-Hodgkin Lymphoma, Non-Small Cell Lung Carcinoma, Non-Squamous Non-Small Cell Lung Carcinoma, Oral Cavity Carcinoma, Oropharyngeal Squamous Cell Carcinoma, Osteosarcoma, Ovarian Carcinoma, Pancreatic Adenocarcinoma, Pancreatic Carcinoma, Pancreatic Ductal Adenocarcinoma, Penile Carcinoma, Peripheral T-Cell Lymphoma, Primary Central Nervous System Lymphoma, Primary Cutaneous Anaplastic Large Cell Lymphoma, Primary Malignant Liver Neoplasm, Prostate Carcinoma, Rosai-Dorfman Disease, Sarcoma, Small Cell Lung Carcinoma, Small Intestinal Carcinoma, Small Intestinal Lymphoma, Small Lymphocytic Leukemia, Small Lymphocytic Lymphoma, Soft Tissue Sarcoma, Squamous Cell Lung Carcinoma, Synovial Sarcoma, Systemic Anaplastic Large Cell Lymphoma, Thyroid Gland Follicular Carcinoma, Thyroid Gland Medullary Carcinoma, Thyroid Gland Undifferentiated (Anaplastic) Carcinoma, Transformed Non-Hodgkin Lymphoma, Triple-Hit Lymphoma, Urothelial Carcinoma, Vaginal Carcinoma, or Vulvar Carcinoma.

In some embodiments, the disease or disorder is associated with KRAS-G12D. In some embodiments, the disease or disorder is mediated by KRAS-G12D. In some embodiments, the disease or disorder is Juvenile Myelomonocytic Leukemia, Non-Small Cell Lung Carcinoma, Pancreatic Adenocarcinoma, Malignant Ovarian Neoplasm, Colorectal Carcinoma, Malignant Endometrial Neoplasm, Cholangiocarcinoma, Malignant Solid Tumor, Malignant Ovarian Epithelial Tumor, Esophageal Adenocarcinoma, Biliary Tract Carcinoma, Carcinoma, Colorectal Adenocarcinoma, Malignant Gastric Neoplasm, Malignant Colon Neoplasm, Neuroblastoma, Malignant Colorectal Neoplasm, Pancreatic Carcinoma, Intrahepatic Cholangiocarcinoma, Melanoma, Malignant Lung Neoplasm, Myelodysplastic/Myeloproliferative Neoplasm, Pancreatic Ductal Adenocarcinoma, Thyroid Gland Follicular Carcinoma, Malignant Pancreatic Neoplasm, or Lung Adenocarcinoma.

In some embodiments, the disease or disorder is associated with ALK. In some embodiments, the disease or disorder is mediated by ALK. In certain embodiments, the disease or disorder is Small Intestinal Carcinoma, Non-Small Cell Lung Carcinoma, Colon Carcinoma, Soft Tissue Sarcoma, Small Cell Lung Carcinoma, Astrocytoma, Rosai-Dorfman Discase, Colorectal Carcinoma, Malignant Thyroid Gland Neoplasm, Cholangiocarcinoma, Non-Squamous Non-Small Cell Lung Carcinoma, Glioblastoma, Malignant Solid Tumor, Acute Myeloid Leukemia, Leukemia, Erdheim-Chester Disease, Malignant Glioma, Hepatocellular Carcinoma, ALK-Positive Large B-Cell Lymphoma, B-Cell Non-Hodgkin Lymphoma, Thyroid Gland Medullary Carcinoma, EBV-Positive Diffuse Large B-Cell Lymphoma, Colorectal Adenocarcinoma, Systemic Anaplastic Large Cell Lymphoma, Thyroid Gland Undifferentiated (Anaplastic) Carcinoma, Malignant Colon Neoplasm, Hematopoietic and Lymphoid Malignancy, ALK-Positive Anaplastic Large Cell Lymphoma, Diffuse Large B-Cell Lymphoma, Malignant Pleural Mesothelioma, Squamous Cell Lung Carcinoma, Non-Hodgkin Lymphoma, Neuroblastoma, Ganglioneuroblastoma, Malignant Central Nervous System Neoplasm, Primary Cutaneous Anaplastic Large Cell Lymphoma, Malignant Colorectal Neoplasm, Low Grade Glioma, Gastric Carcinoma, Multiple Myeloma, Inflammatory Myofibroblastic Tumor, Pancreatic Carcinoma, Melanoma, Malignant Breast Neoplasm, Malignant Lung Neoplasm, Anaplastic Large Cell Lymphoma, Histiocytic and Dendritic Cell Neoplasm, Central Nervous System Neoplasm, Mature T-Cell and NK-Cell Lymphoma/Leukemia, Esophageal Carcinoma, Pancreatic Ductal Adenocarcinoma, Adenocarcinoma of the Gastroesophageal Junction, Langerhans Cell Histiocytosis, Lymphoma, Mature B-Cell Lymphoma/Leukemia, or Lung Adenocarcinoma.

In certain embodiments, the disease or disorder is associated with CCND-1. In certain embodiments, the disease or disorder is mediated by CCND-1. In some embodiments, the disease or disorder is Non-Small Cell Lung Carcinoma, Malignant Ovarian Neoplasm, Soft Tissue Sarcoma, Malignant Prostate Neoplasm, Oropharyngeal Squamous Cell Carcinoma, Nasopharyngeal Carcinoma, Mature B-Cell Lymphoma/Leukemia, Lung Carcinoma, Oral Cavity Carcinoma, Primary Central Nervous System Lymphoma, Laryngeal Squamous Cell Carcinoma, Malignant Solid Tumor, Osteosarcoma, Bronchogenic Carcinoma, AL Amyloidosis, Bladder Carcinoma, Malignant Glioma, B-Cell Non-Hodgkin Lymphoma, Hypopharyngeal Squamous Cell Carcinoma, Mantle Cell Lymphoma, Squamous Cell Lung Carcinoma, Non-Hodgkin Lymphoma, Malignant Colorectal Neoplasm, Multiple Myeloma, Melanoma, Malignant Breast Neoplasm, Acral Lentiginous Melanoma, Breast Carcinoma, Dedifferentiated Chondrosarcoma, Anaplastic Large Cell Lymphoma, Head and Neck Squamous Cell Carcinoma, Histiocytic and Dendritic Cell Neoplasm, Bladder Papillary Urothelial Neoplasm, Primary Malignant Liver Neoplasm, Chondrosarcoma, Lymphoma, Malignant Pancreatic Neoplasm, or Urothelial Carcinoma.

In some embodiments, the disease or disorder is associated with CCNE1. In some embodiments, the disease or disorder is mediated by CCNE1. In certain embodiments, the disease or disorder is Vaginal Carcinoma, High Grade Ovarian Serous Adenocarcinoma, Malignant Ovarian Neoplasm, Soft Tissue Sarcoma, Gastric Adenocarcinoma, Vulvar Carcinoma, Malignant Solid Tumor, Osteosarcoma, Hepatocellular Carcinoma, Penile Carcinoma, Anal Carcinoma, Synovial Sarcoma, Non-Hodgkin Lymphoma, Multiple Myeloma, Malignant Breast Neoplasm, Malignant Lung Neoplasm, Breast Carcinoma, Histiocytic and Dendritic Cell Neoplasm, Malignant Pancreatic Neoplasm, or Malignant Ovarian Epithelial Tumor.

In certain embodiments, the disease or disorder is BCL-2. In some embodiments, the disease or disorder is mediated by BCL-2. In some embodiments, the disease or disorder is Non-Small Cell Lung Carcinoma, Burkitt Lymphoma, Small Cell Lung Carcinoma, Acute Lymphoblastic Leukemia, Follicular Lymphoma, Malignant Endometrial Neoplasm, Invasive Breast Carcinoma, Glioblastoma, Malignant Solid Tumor, Acute Myeloid Leukemia, Chronic Lymphocytic Leukemia, B-Cell Non-Hodgkin Lymphoma, Diffuse Large B-Cell Lymphoma Activated B-Cell Type, EBV-Positive Diffuse Large B-Cell Lymphoma, High Grade B-Cell Lymphoma, High Grade B-Cell Lymphoma with MYC and BCL2 and/or BCL6 Rearrangements, Triple-Hit Lymphoma, Chronic Myeloid Leukemia, Transformed Non-Hodgkin Lymphoma, Double-Hit Lymphoma, B-Cell Acute Lymphoblastic Leukemia, Hematopoietic and Lymphoid Malignancy, Diffuse Large B-Cell Lymphoma, Non-Hodgkin Lymphoma, Multiple Myeloma, B-Cell Lymphoma, Hodgkin Lymphoma, Diffuse Large B-Cell Lymphoma, Breast Carcinoma, Head and Neck Squamous Cell Carcinoma, Germinal Center B-Cell-Like Diffuse Large B-Cell Lymphoma, Lymphoma, or Mature B-Cell Lymphoma/Leukemia.

In some embodiments, the disease or disorder is associated with MCL-1. In some embodiments, the disease or disorder is mediated by MCL-1. In some embodiments, the disease or disorder is Melanoma, Malignant Breast Neoplasm, Lymphoma, Non-Small Cell Lung Carcinoma, Malignant Ovarian Neoplasm, Breast Carcinoma, Acute Lymphoblastic Leukemia, Head and Neck Squamous Cell Carcinoma, Hepatocellular Carcinoma, Malignant Prostate Neoplasm, Malignant Thyroid Gland Neoplasm, Pancreatic Ductal Adenocarcinoma, Malignant Colorectal Neoplasm, Malignant Solid Tumor, or Multiple Myeloma.

In some embodiments, the disease or disorder is associated with MYC. In certain embodiments, the disease or disorder is mediated by MYC. In some embodiments, the disease or disorder is Vaginal Carcinoma, Pancreatic Adenocarcinoma, Soft Tissue Sarcoma, Marginal Zone Lymphoma, Small Cell Lung Carcinoma, Follicular Lymphoma, Medulloblastoma, B-Cell Non-Hodgkin Lymphoma, Ewing Sarcoma, Small Lymphocytic Leukemia, Peripheral T-Cell Lymphoma, Transformed Non-Hodgkin Lymphoma, Double-Hit Lymphoma, Intraocular Lymphoma, Neuroblastoma, Merkel Cell Carcinoma, Head and Neck Squamous Cell Carcinoma, Myeloid Neoplasm, Adenocarcinoma of the Gastroesophageal Junction, Hodgkin Lymphoma, Mature B-Cell Non-Hodgkin Lymphoma, High Grade Ovarian Serous Adenocarcinoma, Gastric Squamous Cell Carcinoma, Acute Lymphoblastic Leukemia, Vulvar Carcinoma, Malignant Prostate Neoplasm, Glioblastoma, Esophageal Adenocarcinoma, Small Intestinal Lymphoma, Breast Angiosarcoma, Esophageal Squamous Cell Carcinoma, Diffuse Large B-Cell Lymphoma Activated B-Cell Type, EBV-Positive Diffuse Large B-Cell Lymphoma, High Grade B-Cell Lymphoma, High Grade B-Cell Lymphoma with MYC and BCL2 and/or BCL6 Rearrangements, Triple-Hit Lymphoma, Diffuse Large B-Cell Lymphoma, Chronic Lymphocytic Leukemia/Small Lymphocytic Lymphoma, B-Cell Lymphoma, Pancreatic Carcinoma, Endometrial Serous Adenocarcinoma, Pancreatic Ductal Adenocarcinoma, Lymphoma, Burkitt Lymphoma, Malignant Solid Tumor, Acute Myeloid Leukemia, Osteosarcoma, Ovarian Carcinoma, Leukemia, Bladder Carcinoma, Chronic Lymphocytic Leukemia, Penile Carcinoma, Anal Carcinoma, Sarcoma, Hematopoietic and Lymphoid Malignancy, Small Lymphocytic Lymphoma, Non-Hodgkin Lymphoma, Malignant Esophageal Neoplasm, Multiple Myeloma, Melanoma, Diffuse Large B-Cell Lymphoma, Malignant Breast Neoplasm, Breast Carcinoma, Germinal Center B-Cell-Like Diffuse Large B-Cell Lymphoma, Esophageal Adenosquamous Carcinoma, Non-Small Cell Lung Carcinoma, Malignant Ovarian Neoplasm, Prostate Carcinoma, Gastric Adenocarcinoma, Colorectal Carcinoma, Hairy Cell Leukemia, Gastric Adenosquamous Carcinoma, Brain Glioblastoma, Head and Neck Carcinoma, Esophageal Adenoid Cystic Carcinoma, Mantle Cell Lymphoma, Malignant Colorectal Neoplasm, Lymphoplasmacytic Lymphoma, Malignant Lung Neoplasm, or Mature B-Cell Lymphoma/Leukemia.

In some embodiments, the disease or disorder is associated with beta-catenin. In certain embodiments, the disease or disorder is mediated by beta-catenin. In some embodiments, the disease or disorder is Desmoplastic/Nodular Medulloblastoma, Non-Small Cell Lung Carcinoma, Colon Carcinoma, Gastric Adenocarcinoma, Colorectal Carcinoma, Medulloblastoma, Malignant Endometrial Neoplasm, Malignant Solid Tumor, Acute Myeloid Leukemia, Hepatocellular Carcinoma, Desmoid-Type Fibromatosis, Large Cell/Anaplastic Medulloblastoma, Colorectal Adenocarcinoma, Malignant Colon Neoplasm, Medulloblastoma with Extensive Nodularity, Malignant Colorectal Neoplasm, Intracranial Primitive Neuroectodermal Neoplasm, Malignant Lung Neoplasm, Primary Malignant Liver Neoplasm, or Pancreatic Ductal Adenocarcinoma.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting in their scope.

TABLE 2

| Abbreviations | |
|---|---|
| Abbreviation | Name |
| Ac | Acetyl |
| $B_2(OH)_4$ | Tetrahydroxydiboron |
| Boc | tert-butoxycarbonyl |
| Bn | Benzyl |
| dba | Dibenzylideneacetone |
| DIPEA, DIEA | N,N-diisopropylethylamine |

TABLE 2-continued

| Abbreviations | |
|---|---|
| Abbreviation | Name |
| DCM, $CH_2Cl_2$ | Dichloromethane |
| DMF | Dimethylformamide |
| DMSO | Dimethyl sulfoxide |
| dppf | Bis(diphenylphosphino)ferrocene |
| Et | ethyl |
| EtOAc, EA | Ethyl acetate |
| EtOH | Ethanol |
| Me | Methyl |
| MeCN, ACN | Acetonitrile |
| MeOH | Methanol |
| MTBE | Methyl t-butyl ether |
| n-BuLi | n-Butyllithium |
| Pd/C | Palladium on carbon |
| $Pd_2(dba)_3$ | Tris(dibenzylideneacetone)dipalladium |
| $Pd(dppf)Cl_2$ | [1,1'-Bis(diphenylphosphino)ferrocene]dichloro-palladium(II) |
| $Pd(PPh_3)_4$ | Tetrakis(triphenylphosphine)palladium(0) |
| PE | Petroleum ether |
| Ph | Phenyl |
| $PPh_3$ | Triphenylphosphine |
| $P(o\text{-}tol)_3$ | Tri(o-tolyl)phosphine |
| TEA | Triethylamine |
| TFA | Trifluoroacetic acid |
| THF | Tetrahydrofuran |
| Ts | Tosyl or p-toluenesulfonyl |
| TsCl | p-toluenesulfonyl chloride |
| $CDCl_3$ | Chloroform-d |
| DAST | Diethylaminosulfur trifluoride |
| DMA | Dimethylacetamide |
| Dtbpy | 4,4'-Di-tert-butyl-2,2'-dipyridyl |
| KHMDS | Potassium bis(trimethylsilyl)amide |
| MEM | 2-Methoxyethoxymethyl |
| MeOD | methanol-$d_4$ |
| $Pd(OAc)_2$ | Palladium (II) acetate |
| SEM | 2-(Trimethylsilyl)ethoxymethyl |
| TEA, $ET_3N$ | Triethylamine |
| TMAA | Trimethylamine alane |

Preparation of Synthetic Intermediates

Scheme 1

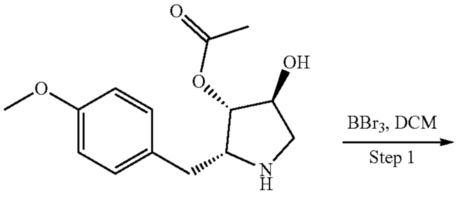

anisomycin

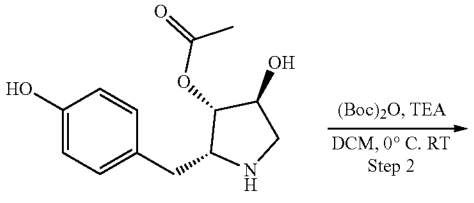

1-1

-continued

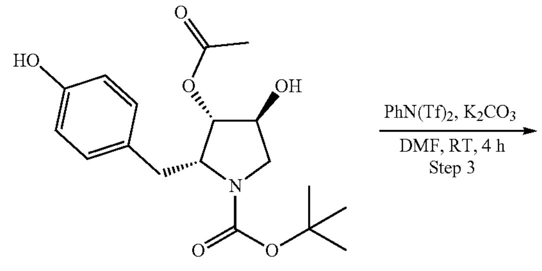

1-2

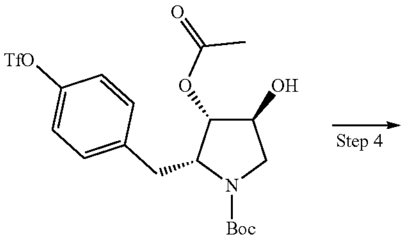

Int-3

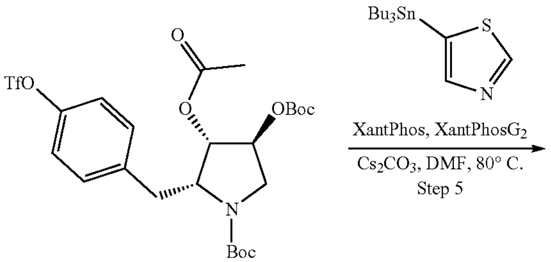

Int-5

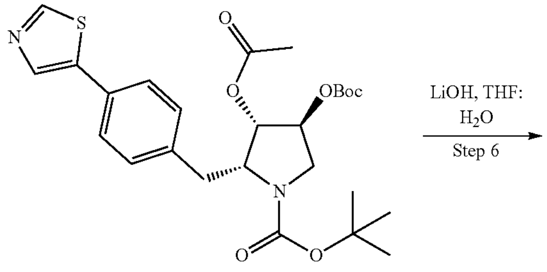

1-3

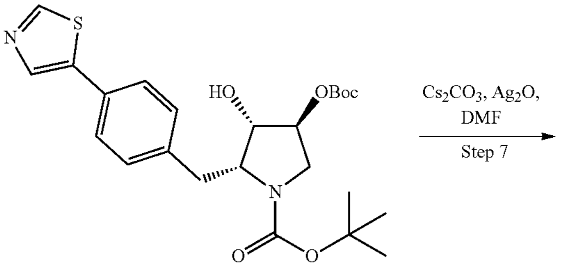

Int-12

-continued

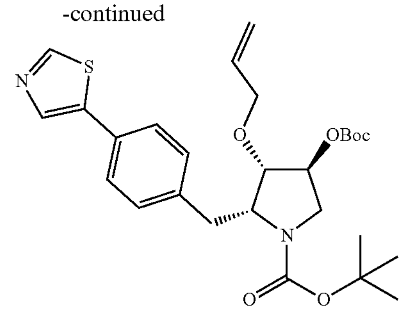

Int-14

Tert-butyl (2R,3S,4S)-4-[(tert-butoxycarbonyl)oxy]-3-(prop-2-en-1-yloxy)-2-{[4-(1,3-thiazol-5-yl)phenyl]methyl}pyrrolidine-1-carboxylate (Int-14) (Scheme 1)

Step 1: (2R,3S,4S)-4-hydroxy-2-[(4-hydroxyphenyl)methyl]pyrrolidin-3-yl acetate (1-1). Boron tribromide (16.8 mL, 3 equiv) at −78° C. was added to a stirred solution of anisomycin (1.5 g, 5.65 mmol, 1 equiv) in dichloromethane (8 mL). The reaction mixture was stirred at −78° C. for 2 h and warmed to room temperature. The mixture was stirred for 1 h at room temperature and quenched by saturated $NaHCO_3$ solution. The DCM was removed, and the solution was lyophilized to obtain 1-1 (1.8 g, 85.41%) as a crude. MS: m/z: Calc'd for $C_{13}H_{17}NO_4$ $[M+H]^+$ 252; found 252.

Step 2: tert-butyl (2R,3S,4S)-3-(acetyloxy)-4-hydroxy-2-[(4-hydroxyphenyl)methyl]pyrrolidine-1-carboxylate (1-2). Di-tert-butyl dicarbonate (1.88 g, 8.59 mmol, 1.2 equiv) was added to a stirred solution of 1-1 (1.8 g, 7.16 mmol, 1 equiv) and triethylamine (2.54 g, 25.07 mmol, 3.5 equiv) in DCM (30 mL) at 0° C. The mixture was stirred at room temperature for 3 h. After completion of the reaction monitored by LCMS, the reaction mixture was filtrated. The filtrate was concentrated. The residue was purified by a reversed-phase column to obtain 1-2 (1.7 g, 67.54%) as a white solid. MS: m/z: Calc'd for $C_{18}H_{25}NO_6$ $[M-H]^-$ 350; found 350.

Step 3: tert-butyl (2R,3S,4S)-3-(acetyloxy)-4-hydroxy-2-{[4-(trifluoromethanesulfonyloxy)phenyl]methyl} pyrrolidine-1-carboxylate (Int-3), 1,1,1-trifluoro-N-phenyl-N-trifluoromethanesulfonylmethanesulfonamide (2.25 g, 6.28 mmol, 1.3 equiv) was added to a stirred solution of 1-2 (1.7 g, 4.83 mmol,) and potassium carbonate (2.01 g, 14.51 mmol, 3 equiv) in DMF (16 mL) at 0° C. The reaction mixture was stirred at room temperature for 2 h. After completion of the reaction monitored by LCMS, the reaction mixture was filtrated. The filtrate was injected into a reversed-phase column and purified to obtain Int-3 (1.5 g, 64.13%) as a white solid. MS: m/z: Calc'd for Step 4: tert-butyl (2R,3S,4S)-3-(acetyloxy)-4-[(tert-butoxycarbonyl)oxy]-2-{[4-(trifluoromethanesulfonyloxy)phenyl]methyl}pyrrolidine-1-carboxylate (Int-5). Di-tert-butyl dicarbonate (4514.3 mg, 20.68 mmol, 10 equiv) was added to a stirred mixture of Int-3 (1000 mg, 2.06 mmol, 1 equiv) and DMAP (505.4 mg, 4.13 mmol, 2 equiv) in Py (10 mL) at room temperature. The resulting mixture was stirred at room temperature overnight. The resulting mixture was concentrated under reduced pressure. The residue was dissolved in MeCN (5 mL). The residue was purified by reversed-phase flash chromatography to afford Int-5 (1000 mg, 82.8% yield, 95% purity) as a yellow solid. MS: m/z: Calc'd for $C_{24}H_{32}F_3NO_{10}S$ $[M+22]^+$ 606; found 606.

Step 5: tert-butyl (2R,3S,4S)-3-(acetyloxy)-4-[(tert-butoxycarbonyl)oxy]-2-{[4-(1,3-thiazol-5-yl)phenyl]methyl} pyrrolidine-1-carboxylate (1-3). XantPhos (158.6 mg, 0.27 mmol, 0.4 equiv) and XantPhos Pd G2 (121.8 mg, 0.13 mmol, 0.2 equiv) was added to a stirred mixture of Int-5 (400 mg, 0.685 mmol, 1.00 equiv) and CuCl (135.7 mg, 1.37 mmol, 2 equiv) in DMF (10 mL) at room temperature under nitrogen atmosphere. The resulting mixture was stirred at 80° C. overnight under nitrogen atmosphere. The residue was purified by reversed-phase flash chromatography to afford 1-3 (300 mg, 84.3% yield, 90% purity) as a white solid. MS: m/z: Calc'd for C26H34N2O7S [M+H]+ 519, found 519.

Step 6: tert-butyl (2R,3S,4S)-4-[(tert-butoxycarbonyl)oxy]-3-hydroxy-2-{[4-(1,3-thiazol-5-yl)phenyl]methyl} pyrrolidine-1-carboxylate (Int-12). LiOH (41.5 mg, 1.73 mmol, 3 equiv) was added to a stirred mixture of 1-3 (300 mg, 0.57 mmol, 1 equiv) in THF (7.5 mL) and Water (2.5 mL) at room temperature. The resulting mixture was stirred at room temperature for 2 h. The reaction mixture was neutralized to pH 7 with conc. HCl, quenched with water, and extracted with EA. The extracts were washed with brine, dried over anhydrous sodium sulfate, filtered, and concentrated. This resulted in Int-12 (250 mg, 90.6% yield, 90% purity) as a white oil. MS: m/z: Calc'd for $C_{24}H_{22}N_2O_6S$ [M+H]+ 477. found 477.

Step 7: tert-butyl (2R,3S,4S)-4-[(tert-butoxycarbonyl)oxy]-3-(prop-2-en-1-yloxy)-2-{[4-(1,3-thiazol-5-yl)phenyl]methyl}pyrrolidine-1-carboxylate (Int-14). $Cs_2CO_3$ (410.2 mg, 1.26 mmol, 3 eq.) and $Ag_2O$ (291.74 mg, 1.26 mmol, 3 equiv) were added to a stirred solution of Int-12 (200 mg, 0.42 mmol, 1 eq.) and allyl bromide (152.3 mg, 1.26 mmol, 3 eq.) in DMF (6 mL). The mixture was stirred at room temperature for overnight. LCMS showed the mixture was completed. The mixture was diluted with water and extracted with EA, the combined organic layers were washed with brine and dried over anhydrous sodium sulfate. After filtration, the filtrate was concentrated under reduced pressure. The resulting residue was purified by reversed-phase column to obtain Int-14 (150 mg, 69.2% yield, 90% purity) as a yellow oil. MS: m/z: Calc'd for $C_{27}H_{36}N_2O_6S$ $[M+H]^+$ 517; Found, 517.

Scheme 2

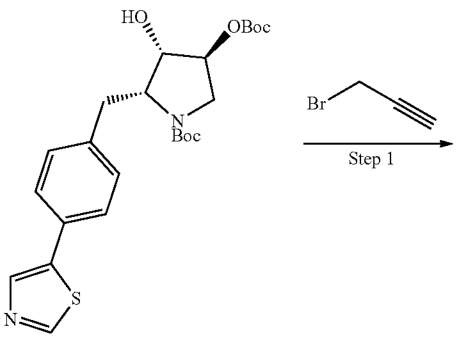

Int-12

-continued

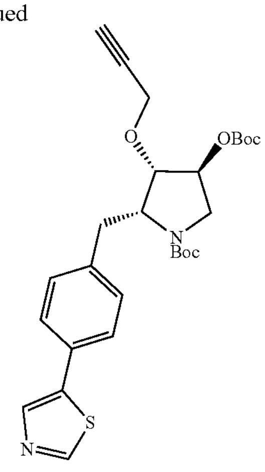

Int-15

Tert-butyl (2R,3S,4S)-4-[(tert-butoxycarbonyl)oxy]-3-(prop-2-yn-1-yloxy)-2-{[4-(1,3-thiazol-5-yl)phenyl]methyl}pyrrolidine-1-carboxylate (Int-15) (Scheme 2)

Step 1: tert-butyl (2R,3S,4S)-4-[(tert-butoxycarbonyl)oxy]-3-(prop-2-yn-1-yloxy)-2-{[4-(1,3-thiazol-5-yl)phenyl]methyl}pyrrolidine-1-carboxylate (Int-15). CsOH·$H_2O$ (211.4 mg, 1.26 mmol, 3 eq.) and KI (104.5 mg, 0.63 mmol, 1.5 eq.) was added to a stirred solution of Int-12 (200 mg, 0.42 mmol, 1 eq.) and propargyl bromide (149.8 mg, 1.26 mmol, 3 eq.) in DMF (6 mL). The mixture was stirred at room temperature for 2 h. LCMS showed the mixture was completed. The mixture was diluted with water and extracted with EtOAc, the combined organic layers were washed with brine and dried over anhydrous sodium sulfate. After filtration, the filtrate was concentrated under reduced pressure. The resulting residue was purified by reversed-phase column to obtain Int-15 (160 mg, 74.1% yield, 90% purity) as a yellow oil. MS: m/z: Calc'd for $C_{27}H_{34}N_2O_6S$ $[M+H]^+$ 515; Found, 515.

Scheme 3

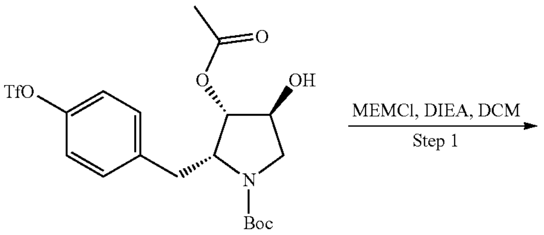

Int-3

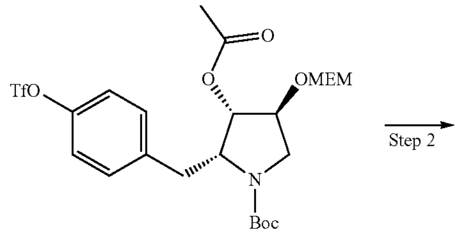

3-1

-continued

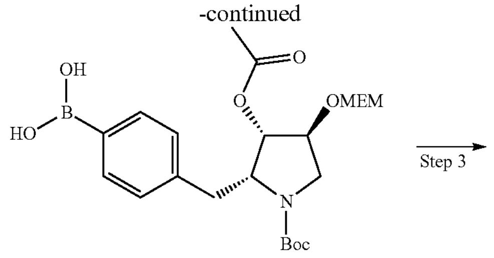

3-2

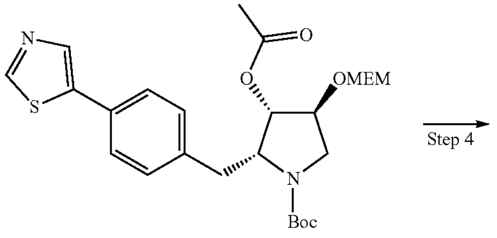

3-3

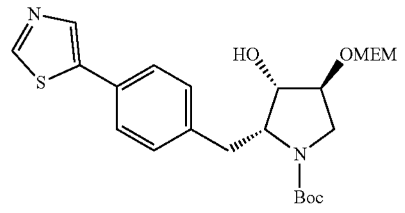

Int-16

Tert-butyl (2R,3S,4S)-3-hydroxy-4-[(2-methoxyethoxy)methoxy]-2-{[4-(1,3-thiazol-5-yl)phenyl]methyl}pyrrolidine-1-carboxylate (Int-16) (Scheme 3)

Step 1: tert-butyl (2R,3S,4S)-3-(acetyloxy)-4-[(2-methoxyethoxy)methoxy]-2-{[4-(trifluoromethanesulfonyloxy)phenyl]methyl}pyrrolidine-1-carboxylate (3-1). To a stirred mixture of Int-3 (500 mg, 1.04 mmol, 1 equiv) and DIEA (534.8 mg, 4.16 mmol, 4 equiv) in DCM (10 mL) was added 1-(chloromethoxy)-2-methoxyethane (386.6 mg, 3.12 mmol, 3 equiv) at 0° C. The resulting mixture was stirred at room temperature for overnight. The reaction mixture was quenched with water and extracted with EA. The extracts were washed with brine, dried over anhydrous sodium sulfate, filtered and concentrated. The residue was purified by reversed-phase flash chromatography to afford 3-1 (500 mg, 84.9% yield, 90% purity) as a yellow oil. MS: m/z: Calc'd for $C_{23}H_{32}F_3NO_{10}S$ $[M+H-56]^+$ 516; found 516.

Step 2: 4-{[(2R,3S,4S)-3-(acetyloxy)-1-(tert-butoxycarbonyl)-4-[(2-methoxyethoxy)methoxy]pyrrolidin-2-yl]methyl}phenylboronic acid (3-2). Under a nitrogen atmosphere, to a stirred mixture of 3-1 (500 mg, 0.85 mmol, 1 equiv), $B_2(OH)_4$ (156.8 mg, 1.70 mmol, 2 equiv) and DIEA (339.0 mg, 2.65 mmol, 3 equiv) in EtOH (10 mL) were added PPh; (45.89 mg, 0.175 mmol, 0.2 equiv) and [3-(diphenylphosphanyl)propyl]diphenylphosphane dihydrochloride nickel (47.4 mg, 0.08 mmol, 0.1 equiv) at room temperature. The resulting mixture was stirred at 80° C. for overnight. The reaction mixture was quenched with water and extracted with EA. The extracts were washed with brine, dried over anhydrous sodium sulfate, filtered and concentrated. The residue was purified by reversed-phase flash chromatography to afford 3-2 (300 mg, 73.3% yield, 90% purity) as a yellow oil. MS: m/z: Calc'd for $C_{22}H_{34}BNO_9$ $[M+H]^+$ 468; found 468.

Step 3: tert-butyl (2R,3S,4S)-3-(acetyloxy)-4-[(2-methoxyethoxy)methoxy]-2-{[4-(1,3-thiazol-5-yl)phenyl]methyl}pyrrolidine-1-carboxylate (3-3). To a stirred mixture of 5-bromo-1,3-thiazole (210.9 mg, 1.28 mmol, 2 equiv) and 3-2 (300 mg, 0.64 mmol, 1.00 equiv) in Dioxane (10 mL) and $H_2O$ (1 mL) was added $Pd(dppf)Cl_2$ (93.5 mg, 0.18 mmol, 0.2 equiv) and $Na_2CO_3$ (204.2 mg, 1.96 mmol, 3 equiv) at room temperature under nitrogen atmosphere. The resulting mixture was stirred at 80° C. for overnight under nitrogen atmosphere. The reaction mixture was quenched with water and extracted with EA. The extracts were washed with brine, dried over anhydrous sodium sulfate, filtered and concentrated. The residue was purified by reversed-phase flash chromatography to afford 3-3 (300 mg, 92.4% yield, 90% purity) as a yellow solid. MS: m/z: Calc'd for $C_{25}H_{34}N_2O_7S$ $[M+H]^+$ 507; found 507.

Step 4: tert-butyl (2R,3S,4S)-3-(acetyloxy)-4-[(2-methoxyethoxy)methoxy]-2-{[4-(1,3-thiazol-5-yl)phenyl]methyl}pyrrolidine-1-carboxylate (Int-16). To a stirred mixture of 3-3 (200 mg, 0.35 mmol, 1 equiv) in THF (5 mL) and $H_2O$ (1 mL) was added LiOH (14.18 mg, 0.59 mmol, 1.5 equiv) at 0° C. The resulting mixture was stirred at room temperature for 3 h. The reaction mixture was diluted with water and extracted with EA. The extracts were washed with brine, dried over anhydrous sodium sulfate, filtered and concentrated. The residue was purified by reversed-phase flash chromatography to afford Int-16 as a yellow oil. MS: m/z: Calc'd for $C_{23}H_3N_2O_6S$ $[M+H]^+$ 465; found 465.

Scheme 4

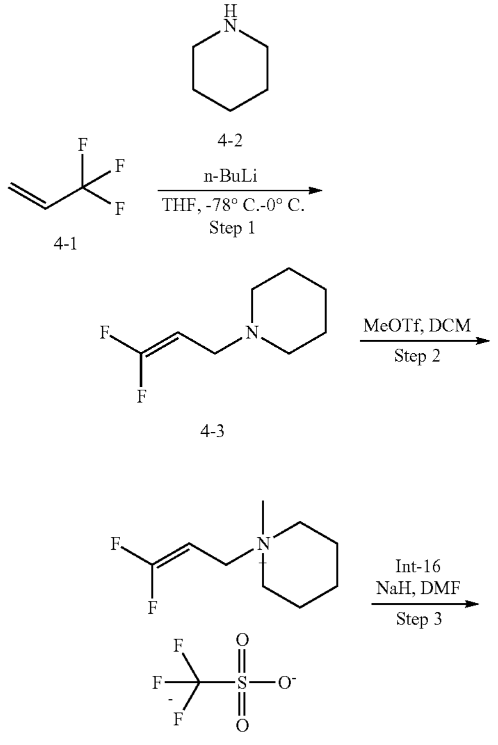

-continued

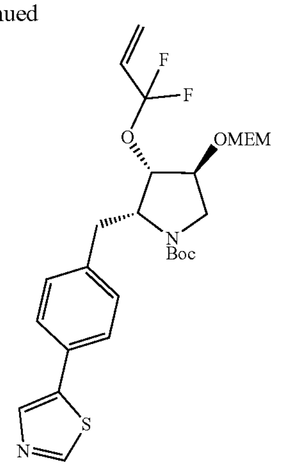

Int-17

Tert-butyl (2R,3S,4S)-3-[(1,1-difluoroprop-2-en-1-yl)oxy]-4-[(2-methoxyethoxy)methoxy]-2-{[4-(1,3-thiazol-5-yl)phenyl]methyl}pyrrolidine-1-carboxylate (Int-17) (Scheme 4)

Step 1: 1-(3,3-difluoroprop-2-en-1-yl) piperidine (4-3). To a stirred solution of piperidine (1000 mg, 11.74 mmol, 1 eq) in THF (20 mL) was added n-BuLi (7 mL, 17.62 mmol, 1.5 eq) dropwise at −78° C. under nitrogen atmosphere. Then the mixture was stirred at −78° C. for 1 h, 3,3,3-trifluoro-1-propene (2256 mg, 23.49 mmol, 2 eq) was added the mixture slowly and warmed to 0° C. The mixture was stirred at 0° C. for 1 h. TLC showed the mixture was completed. The mixture was quenched with saturated aqueous $NH_4Cl$ and extracted with DCM. The combined organic layers were washed with brine and dried over anhydrous sodium sulfate. After filtration, the filtrate was concentrated under reduced pressure at ice bath temperature to obtain 4-3 crude as a yellow oil. No MS signal observed on LCMS.

Step 2: 1-(3,3-difluoroprop-2-en-1-yl)-1-methylpiperidin-1-ium triflate (4-4). To a stirred solution of 4-3 (1000 mg, 6.2 mmol, 1 eq) in DCM (15 mL) was added methyl trifluoromethanesulfonate (1068.9 mg, 6.51 mmol, 1.05 eq) dropwise at 0° C. and the mixture was stirred at room temperature for overnight. LCMS showed the reaction was completed. The mixture was concentrated to obtain 4-4 (1800 mg) crude as a yellow oil which was used directly in the next step without further purification. MS: m/z: Calc'd for $C_{10}H_{16}F_5NO_3S$ $[M+H]^+$ 176; Found, 176.

Step 3: tert-butyl (2R,3S,4S)-3-[(1,1-difluoroprop-2-en-1-yl)oxy]-4-[(2-methoxyethoxy)methoxy]-2-{[4-(1,3-thiazol-5-yl)phenyl]methyl}pyrrolidine-1-carboxylate (Int-17). To a stirred solution of Int-16 (700 mg, 1.5 mmol, 1 eq) in DMF (10 mL) was added NaH (180.8 mg, 4.52 mmol, 3 eq, 60%) slowly at 0° C. and the mixture was stirred at 0° C. for 0.5 h. Then a solution of 4-4 (1960.5 mg, 6.02 mmol, 4 eq) in DMF was added the mixture dropwise and the mixture was stirred at room temperature for 2 h. LCMS showed the reaction was completed. The reaction was quenched with water and extracted with EA. The combined organic layers were washed with brine and dried over anhydrous sodium sulfate. After filtration, the filtrate was concentrated under reduced pressure. The resulting residue was purified by reversed-phase column to obtain Int-17 (650 mg, 79.8% yield, 90% purity) as a yellow oil. MS: m/z: Calc'd for $C_{26}H_{34}F_2N_2O_6S$ $[M+H]^+$ 541; Found, 541.

Scheme 5A

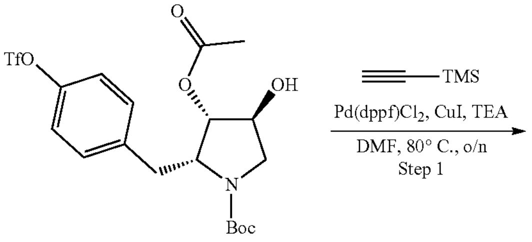

Int-3

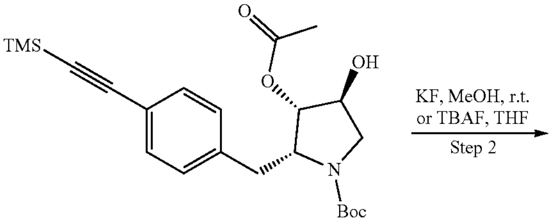

5-1

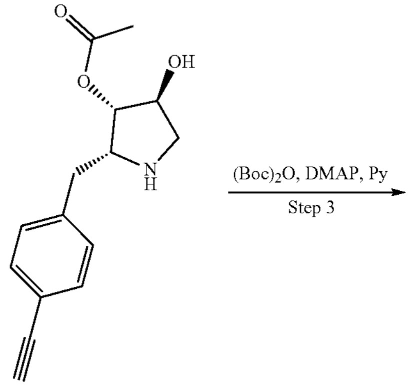

Int-4

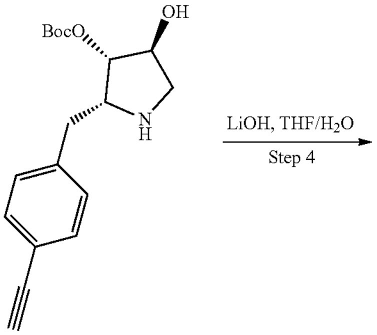

5-2

-continued

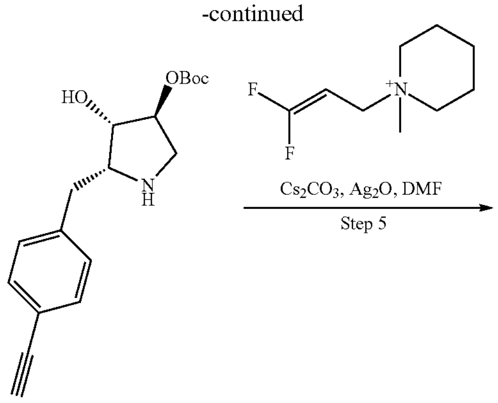

5-3

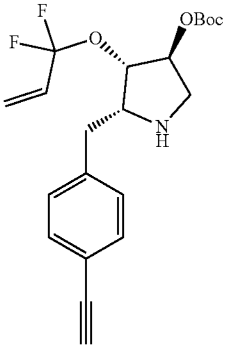

Int-18

Tert-butyl (2R,3S,4S)-4-[(tert-butoxycarbonyl)oxy]-3-[(1,1-difluoroprop-2-en-1-yl)oxy]-2-[(4-ethynylphenyl)methyl]pyrrolidine-1-carboxylate (Int-18) (Scheme 5A)

Step 1: tert-butyl (2R,3S,4S)-3-(acetyloxy)-4-hydroxy-2-({4-[2-(trimethylsilyl) ethynyl]phenyl}methyl)pyrrolidine-1-carboxylate (5-1). To a stirred solution of Int-3 (200 mg, 0.42 mmol, 1 equiv) and trimethylsilylacetylene (121.9 mg, 1.24 mmol, 3 equiv) in DMF (10 mL) was added TEA (167.4 mg, 1.65 mmol, 4 equiv), CuI (7.9 mg, 0.04 mmol, 0.1 equiv) and $Pd(dppf)Cl_2 \cdot CH_2Cl_2$ (50.6 mg, 0.06 mmol, 0.15 equiv) in portions at room. The reaction was placed under vacuum, sonicated and backfilled with nitrogen. The solution was stirred at 80° C. for 12 h. Desired product could be detected by LCMS. Water was used to quench the reaction, extracted with EA, concentrated, the residue was purified by Prep-TLC (PE/EA 2:1) to afford 5-1 (160 mg, 89.6%) as a yellow oil. MS: m/z: Calc'd for $C_{23}H_{33}NO_5Si$ $[M-100]^+$ 332; found 332.

Step 2: tert-butyl (2R,3S,4S)-3-(acetyloxy)-2-[(4-ethynylphenyl)methyl]-4-hydroxypyrrolidine-1-carboxylate (Int-4). A solution of 5-1 (170 mg, 0.39 mmol, 1 equiv) and Triethylamine trihydrofluoride (190.5 mg, 1.18 mmol, 3.0 equiv) in THF (5 mL) was stirred at 60° C. for 12 h. Desired product could be detected by LCMS. Concentrated, the residue was purified by Prep-TLC (PE/EA 3:1) to afford Int-4 (135 mg, 95.36%) as a light yellow solid. MS: m/z: Calc'd for $C_{20}H_{25}NO_5$ $[M-56]^+$ 304; found 304.

Step 3: (2R,3S,4S)-3-(acetyloxy)-4-[(tert-butoxycarbonyl)oxy]-2-[(4-ethynylphenyl)methyl]pyrrolidine-1-carboxylate (5-2). To a stirred solution of Int-4 (500 mg, 1.39 mmol, 1 eq.) and DMAP (254.9 mg, 2.09 mmol, 1.5 eq.) in Pyridine (10 mL) was added $Boc_2O$ (1.5 g, 6.95 mmol, 5 eq.) at room temperature. The resulting mixture was stirred at room temperature for 12 h. After completion of reaction monitored by LCMS. The residue was purified by flash. This resulted in 5-2 (625 mg, 97.8%) as a light yellow oil. MS: m/z: Calc'd for $C_{25}H_{33}NO_7$ $[M+H+22+41]^+$ 523, found 523.

Step 4: tert-butyl (2R,3S,4S)-4-[(tert-butoxycarbonyl)oxy]-2-[(4-ethynylphenyl)methyl]-3-hydroxypyrrolidine-1-carboxylate (5-3). To a stirred solution of 5-2 (600 mg, 1.30 mmol, 1 eq.) in THF (9 mL) and $H_2O$ (3 mL) was added LiOH (93.8 mg, 3.91 mmol, 3 eq.) at room temperature. The resulting mixture was stirred at room temperature for overnight. The resulting mixture was extracted with EtOAc (2×100 mL). The combined organic layers were washed with brine (2×50 mL), dried over anhydrous $Na_2SO_4$. After filtration, the filtrate was concentrated under reduced pressure to afford 5-3 (560 mg, 102.7% yield, 80% purity) as a brown yellow solid which was used directly in the next step without further purification. MS: m/z: Calc'd for $C_{23}H_{31}NO_6$ $[M+H-56-56]^+$ 306; Found, 306.

Step 5: tert-butyl (2R,3S,4S)-4-[(tert-butoxycarbonyl)oxy]-3-[(1,1-difluoroprop-2-en-1-yl)oxy]-2-[(4-ethynylphenyl)methyl]pyrrolidine-1-carboxylate (Int-18). To a stirred solution of 5-3 (100 mg, 0.24 mmol, 1 eq.) and 4-4 (155.8 mg, 0.48 mmol, 2 eq.) in DMF (3 mL) were added $CS_2CO_3$ (234.1 mg, 0.72 mmol, 3 eq.) and $Ag_2O$ (166.5 mg, 0.72 mmol, 3 eq.) at room temperature. The resulting mixture was stirred at room temperature for overnight, and quenched with water, the resulting mixture was extracted with EtOAc (2×100 mL). The combined organic layers were washed with brine (2×50 mL), dried over anhydrous $Na_2SO_4$. After filtration, the filtrate was concentrated under reduced pressure. The crude product was purified by reverse phase flash (with the following conditions, MeCN/0.5% TFA in $H_2O$) to afford Int-18 (75 mg, 63.4% yield, 90% purity) as a light yellow solid. MS: m/z: Calc'd for $C_{26}H_{33}F_2NO_6$ $[M+H-56-56]^+$ 382; Found, 382.

Scheme 5B

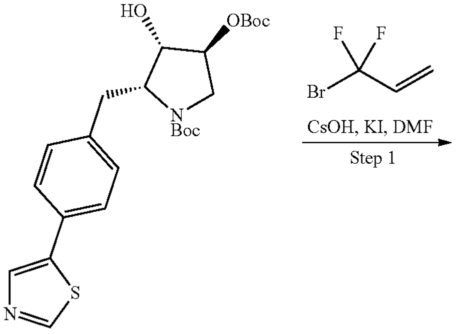

Int-12

-continued

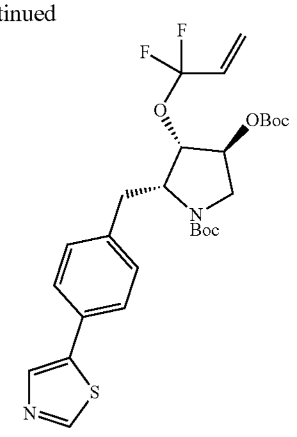

Int-19

Tert-butyl (2R,3S,4S)-4-[(tert-butoxycarbonyl)oxy]-3-[(1,1-difluoroprop-2-en-1-yl)oxy]-2-{[4-(1,3-thiazol-5-yl)phenyl]methyl}pyrrolidine-1-carboxylate (Int-19) (Scheme 5B)

Step 1: tert-butyl (2R,3S,4S)-4-[(tert-butoxycarbonyl)oxy]-3-[(1,1-difluoroprop-2-en-1-yl)oxy]-2-{[4-(1,3-thiazol-5-yl)phenyl]methyl}pyrrolidine-1-carboxylate (Int-19). To a stirred solution of Int-12 (250 mg, 0.52 mmol, 1 eq.) and 3-bromo-3,3-difluoroprop-1-ene (164.6 mg, 1.05 mmol, 2 eq.) in DMF (5 mL) were added $CsOH \cdot H_2O$ (264.2 mg, 1.57 mmol, 3 eq.) and KI (174.1 mg, 1.05 mmol, 2 eq.) at 0° C. The resulting mixture was stirred at room temperature for overnight. The reaction mixture was quenched with water and extracted with EA. The extracts were washed with brine, dried over anhydrous sodium sulfate, filtered and concentrated. The crude product was purified by reverse phase flash with (with the following conditions, MeCN/0.5% TFA in $H_2O$) to afford Int-19 (35 mg, 12.0% yield, 95% purity) as a light yellow solid. MS: m/z: Calc'd for $C_{27}H_{34}F_2N_2O_6S$ $[M+H]^+$ 553; Found, 553.

Synthesis of Compounds of the Present Disclosure

O-alkylation reaction with NaH for synthesis of ether; General Procedure I. To a stirred solution of Int-16 (0.17 mmol, 1 eq.) in DMF (3 mL) was added NaH (0.86 mmol, 5 eq.) at 0° C. and stirred for 30 min. The corresponding halide (2 eq.) was added at 0° C. The resulting mixture was stirred at room temperature for 12 h. After completion, the reaction was poured into ice water and extracted with EtOAc (2×100 mL). The combined organic layers were washed with brine (2×50 mL), dried over anhydrous $Na_2SO_4$. After filtration, the filtrate was concentrated under reduced pressure. The residue was purified by silica gel column chromatography.

O-alkylation reaction with $Cs_2CO_3$, $Ag_2O$ for synthesis of ether; General Procedure II. To a stirred solution of Int-16 (0.10 mmol, 1 equiv) and corresponding halide (2 eq.) in DMF (3 mL) were added $Ag_2O$ (0.21 mmol, 2 equiv) and $Cs_2CO_3$ (0.31 mmol, 3 equiv) at 0° C. The mixture was stirred at r.t. for overnight. After completion, the solid was filtered out. The filtrate was purified by reversed phase column chromatography.

Boc Deprotection; General Procedure III. The corresponding Boc-protected amine (1 equiv) was dissolved in anhydrous $CH_2Cl_2$ (5 mL/mmol), and TFA (5 mL/mmol) was added. The mixture was stirred at r.t. for 2 h. After removal of the volatiles, the oily residue was treated with toluene to azeotropically remove the TFA residue. The residue was purified by prep-HPLC.

Conversion of alcohol to iodides; General Procedure IV. To a solution of corresponding alcohol (1.65 mmol, 1 equiv) in DCM (10 mL) was added Iodine (1.90 mmol, 1.15 equiv), $PPh_3$ (1.90 mmol, 1.15 equiv) and Imidazole (2.48 mmol, 1.5 equiv) at 0° C. The mixture was stirred at r.t. for 3 h. LCMS showed the reaction was completed. The resulting mixture was added brine and extracted with DCM. The organic layers were dried over sodium sulfate, concentrated. The residue was purified by column chromatography with ethyl acetate/petroleum.

Heck Coupling with $Pd_2(dba)_3$, tris(2-methylphenyl) phosphate, TEA; General Procedure V. To a solution of Int-14 (0.19 mmol, 1 eq.) and corresponding boric acid (3 eq.) in DMF (5 mL) were added CsF (2 eq.). $Pd_2(dba)_3$ (0.2 eq.). P(o-tol)$_3$ (0.4 eq.) and $Et_3N$ (3 eq.) at room temperature. The solution was heated at 80° C. under a nitrogen atmosphere for 16 h. Upon completion, the mixture was cooled to r.t., filtered and concentrated in vacuo. The residue was purified by reversed-phase flash chromatography.

Reduction reaction with Pd/C, hydrogen; General Procedure VI. To a solution of corresponding alkene or alkyne analogues (0.155 mmol, 1 equiv) in 3 mL MeOH was added Pd/C (10%, 150 mg) in a pressure tank. The mixture was hydrogenated at room temperature under 30 atm of hydrogen pressure for overnight, filtered through a Celite pad and concentrated under reduced pressure to afford product which was used directly in the next step without further purification.

Sonogashira Coupling with $Pd(PPh_3)_4$, CuI, TEA; General Procedure VII. To a stirred solution of Int-15 (0.19 mmol, 1 eq.) and corresponding halide (0.39 mmol, 2 eq.) in $Et_3N$ (5 mL) were added $Pd(PPh_3)_4$ (0.04 mmol, 0.2 eq.) and CuI (0.04 mmol, 0.2 eq.). The resulting mixture was subsequently degassed by bubbling nitrogen through the solution for 5 minutes and then stirred at 100° C. for overnight. Upon completion, the mixture was cooled to r.t., filtered and concentrated in vacuo. The residue was purified by reversed-phase flash chromatography.

Boc and MEM Deprotection; General Procedure VIII. TFA (2.0 mL) was added dropwise to a stirred solution of the substrate containing N-Boc and MEM protecting groups in DCM (4.0 mL). The resulting mixture was stirred at rt for 12 h. The reaction mixture was concentrated, and the resulting residue was purified by Prep-HPLC to afford the 3-hydroxypyrrolidine derivative.

Example 1: (3S,4S,5R)-4-[2-(azetidin-3-yl)ethoxy]-5-{[4-(1,3-thiazol-5-yl)phenyl]methyl}pyrrolidin-3-ol

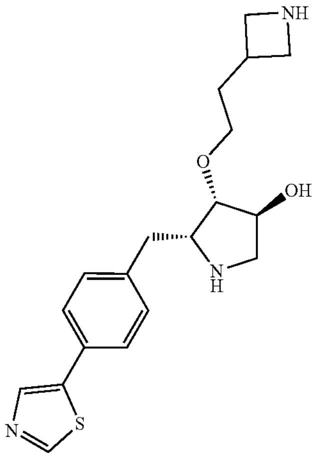 [SMILES: O[C@H]1CN[C@H](Cc2ccc(-c3cncs3)cc2)[C@@H]1OCCC1CNC1]

Step 1-2: (3S,4S,5R)-4-[2-(azetidin-3-yl)ethoxy]-5-{[4-(1,3-thiazol-5-yl)phenyl]methyl}pyrrolidin-3-ol. The title compound was prepared in 10.2% overall yield as a light yellow semi-solid according to General Procedure I using tert-butyl 3-(2-bromoethyl) azetidine-1-carboxylate in STEP 1; Boc Deprotection; General Procedure III in STEP 2. MS obsd. (ESI$^+$): 360 $[M+H]^+$. $^1H$ NMR (400 MHz, Methanol-$d_4$) δ 9.00 (s, 1H), 8.20 (s, 1H), 7.75-7.68 (m, 2H), 7.45 (d, J=8.1 Hz, 2H), 4.49 (d, J=4.1 Hz, 1H), 4.19 (t, J=9.7 Hz, 2H), 4.10-4.07 (m, 1H), 3.96-3.87 (m, 2H), 3.80-3.68 (m, 2H), 3.58 (dd, J=12.6, 4.2 Hz, 1H), 3.54-3.46 (m, 1H), 3.30-3.18 (m, 2H), 3.16-3.04 (m, 2H), 2.09-1.97 (m, 2H), 1.31 (s, 2H).

Example 2: (3S,4S,5R)-4-{3-[(3R)-pyrrolidin-3-yl]propoxy}-5-{[4-(1,3-thiazol-5-yl)phenyl]methyl}pyrrolidin-3-ol Scheme 6

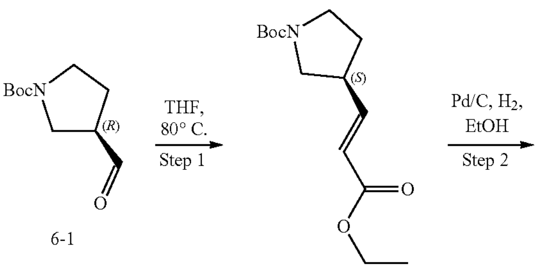

6-1

6-2

-continued

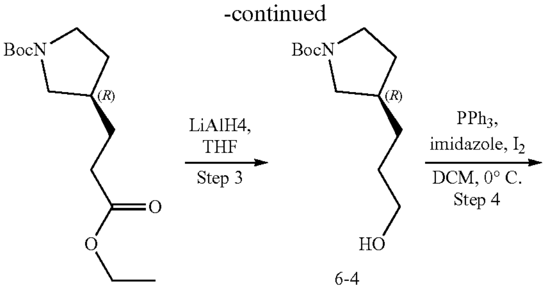

6-4

6-3

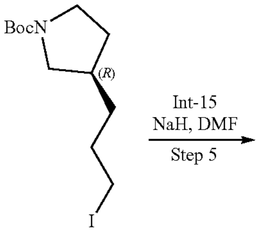

6-5

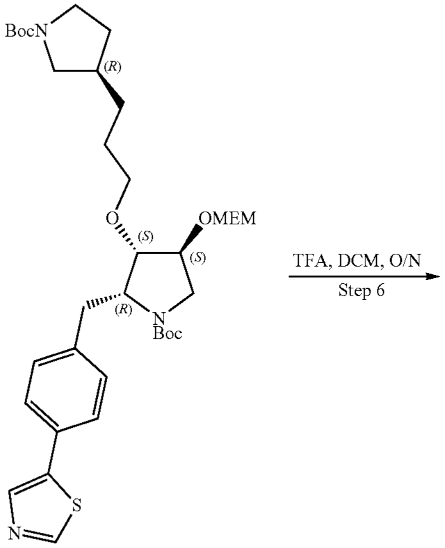

6-6

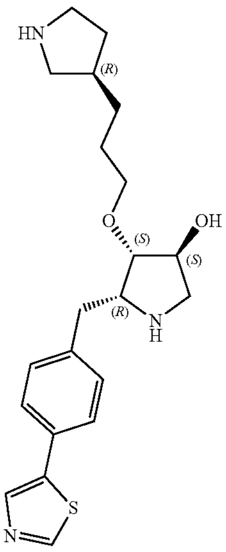

Step 1: tert-butyl (3S)-3-(3-ethoxy-3-oxoprop-1-en-1-yl) pyrrolidine-1-carboxylate (6-2). To a solution of tert-butyl (3R)-3-formylpyrrolidine-1-carboxylate (500 mg, 2.50 mmol, 1 equiv) in THF (10 mL) was added ethyl 2-(triphenyl-λ5-phosphanylidene)acetate (961.6 mg, 2.76 mmol, 1.1 equiv) at room temperature. The mixture was stirred at 80° C. for o/n. The LCMS showed the reaction was completed. The reaction was cooled to r.t. and added water. Extracted with EA and washed with brine, the organic layer was dried over sodium sulfate, concentrated. The residue was purified by silica gel chromatography column to obtain 6-2 (590 mg, 87.2% yield, 95.8% purity) as a colorless oil. MS obsd. ($ESI^+$): 214 $[M+H]^+$.

Step 2: tert-butyl (3R)-3-(3-ethoxy-3-oxopropyl)pyrrolidine-1-carboxylate (6-3). To a solution of 6-2 (590 mg, 2.19 mmol, 1 equiv) in EtOH (5 mL) was added Pd/C (120 mg) under $N_2$. The mixture was stirred at r.t. for 2 h under hydrogen gas. LCMS showed the reaction was completed. The solid was filtered out and washed with EtOH. The filtrate was concentrated under vacuum. 6-3 (550 mg, 92.5% yield, 86% purity) was thus obtained and used directly in the next step without further purification. MS obsd. ($ESI^+$): 216 $[M+H]^+$.

Step 3: tert-butyl (3R)-3-(3-hydroxypropyl)pyrrolidine-1-carboxylate (6-4). To a solution of 6-3 (550 mg, 2.02 mmol, 1 equiv) in THF (10 mL) was added Lithium aluminum hydride (2.5 M in THF) (1 mL, 1.2 equiv) at 0° C. The mixture was stirred at 0° C. for 2 h. Upon completion, the reaction was quenched by Sodium sulfate decahydrate. The solid was filtered and washed with THF. The filtrate was concentrated under vacuum. 6-4 (380 mg, 81.7% yield) was obtain as a light-yellow oil. MS obsd. ($ESI^+$): 174 $[M+H]^+$.

Steps 4-6: (3S,4S,5R)-4-{3-[(3R)-pyrrolidin-3-yl] propoxy}-5-{[4-(1,3-thiazol-5-yl)phenyl] methyl}pyrrolidin-3-ol. The title compound was prepared in 49.7% overall yield as a light yellow semi-solid according to Conversion of alcohol to iodides; General Procedure IV using tert-butyl (2S)-2-[(2-hydroxyethoxy)methyl]pyrrolidine-1-carboxylate (6-4) in STEP 4; O-Alkylation reaction with NaH for synthesis of ether; General Procedure I using tert-butyl (2S)-2-[(2-iodoethoxy)methyl]pyrrolidine-1-carboxylate (6-5) in STEP 5; Boc Deprotection; General Procedure III in STEP 6. MS obsd. ($ESI^+$): 388 $[M+H]^+$. $^1H$ NMR (400 MHz, Methanol-$d_4$) δ 9.00 (s, 1H), 8.19 (s, 1H), 7.71 (d, J=8.1 Hz, 2H), 7.44 (d, J=8.1 Hz, 2H), 4.50 (d, J=4.3 Hz, 1H), 4.09 (d, J=7.8, 3.2 Hz, 1H), 3.79-3.68 (m, 2H), 3.65-3.56 (m, 1H), 3.55-3.45 (m, 2H), 3.4-3.37 (m, 1H), 3.27 (dd, J=14.3, 7.4 Hz, 2H), 3.19 (d, J=12.5 Hz, 1H), 3.12 (dd, J=14.0, 8.0 Hz, 1H), 2.86 (dd, J=11.5, 9.2 Hz, 1H), 2.43-2.18 (m, 2H), 1.82-1.51 (m, 5H).

Example 3: (3S,4S,5R)-4-[2-(3-fluorophenoxy) ethoxy]-5-{[4-(1,3-thiazol-5-yl)phenyl] methyl}pyrrolidin-3-ol

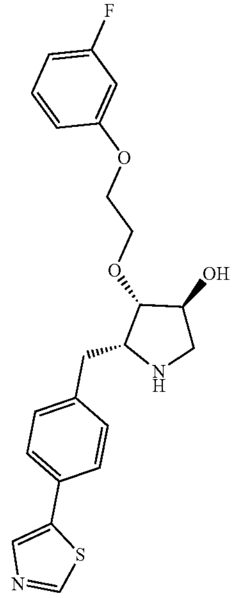 [SMILES: O[C@H]1CN[C@H](Cc2ccc(-c3cncs3)cc2)[C@@H]1OCCOc1cccc(F)c1]

Step 1-2: (3S,4S,5R)-4-[2-(3-fluorophenoxy)ethoxy]-5-{[4-(1,3-thiazol-5-yl)phenyl]methyl}pyrrolidin-3-ol. The title compound was prepared in 16.7% overall yield as a yellow oil according to O-Alkylation reaction with $Cs_2CO_3$, $Ag_2O$ for synthesis of ether; General Procedure II using 1-(2-bromoethoxy)-3-fluorobenzene in STEP 1; Boc Deprotection, General Procedure III in STEP 2. MS obsd. ($ESI^+$): 415 $[M+H]^+$. $^1H$ NMR (400 MHz, Methanol-$d_4$) δ 8.99 (s, 1H), 8.16 (s, 1H), 7.66-7.59 (m, 2H), 7.45 (d, J=8.0 Hz, 2H), 7.36-7.26 (m, 1H), 6.80 (dd, J=8.4, 2.4 Hz, 1H), 6.77-6.67 (m, 2H), 4.57 (d, J=4.3 Hz, 1H), 4.20 (t, J=4.2 Hz, 2H), 4.13-3.99 (m, 2H), 3.97-3.89 (m, 1H), 3.88 (d, J=3.3 Hz, 1H), 3.64 (dd, J=12.5, 4.4 Hz, 1H), 3.31-3.18 (m, 2H), 3.11 (dd, J=13.7, 7.4 Hz, 1H).

Example 4: (3S,4S,5R)-4-{2-[(2S)-pyrrolidin-2-ylmethoxy]ethoxy}-5-{[4-(1,3-thiazol-5-yl)phenyl] methyl}pyrrolidin-3-ol Scheme 7

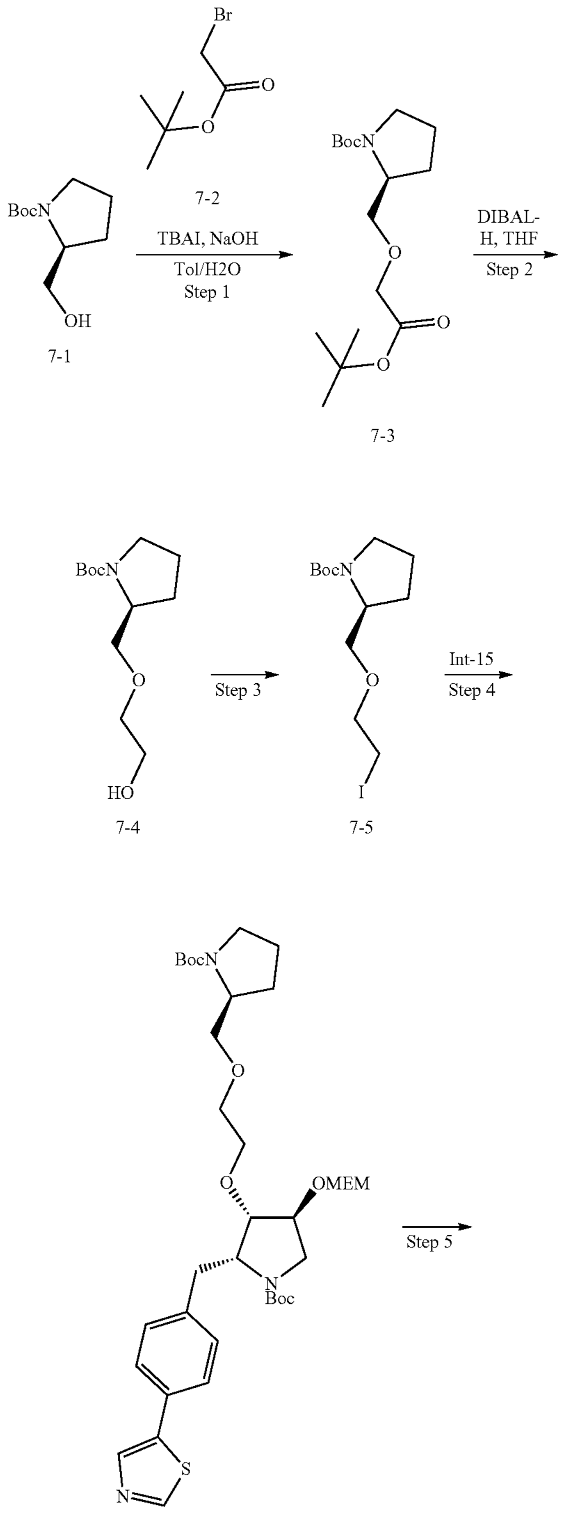

7-1, 7-2, 7-3, 7-4, 7-5, 7-6

-continued

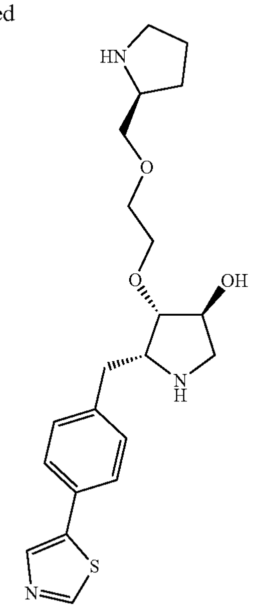

Step 1: tert-butyl (2S)-2-{[2-(tert-butoxy)-2-oxoethoxy]methyl}pyrrolidine-1-carboxylate (7-3). To a solution of tert-butyl (2S)-2-(hydroxymethyl)pyrrolidine-1-carboxylate (7-2) (1.0 g, 4.96 mmol, 1 equiv) and tert-butyl 2-bromoacetate (1.94 g, 9.93 mmol, 2 equiv) in toluene (24 mL) was added a solution of NaOH (3.58 g, 89.44 mmol, 18 equiv) in $H_2O$ (12 mL) and tetrabutylammonium iodide (0.92 g, 2.485 mmol, 0.5 equiv) at 0° C. The mixture was stirred at r.t. for o/n. The LCMS showed the reaction was successful. The resulting mixture was added brine and extracted with EA. The organic layers were dried over sodium sulfate, concentrated. The residue was applied onto a silica gel column and eluted with ethyl acetate/petroleum ether (1:3) to obtain 7-3 (1.2 g, 76.5% yield, 100% purity) as a light-yellow oil. MS obsd. ($ESI^+$): 316 $[M+H]^+$.

Step 2: tert-butyl (2S)-2-[(2-hydroxyethoxy)methyl]pyrrolidine-1-carboxylate (7-4). To a solution of 7-3 (1.2 g, 3.80 mmol, 1 equiv) in THF (15 mL) was added diisobutylaluminium hydride (25% in toluene) (11.6 mL, 3 equiv) at 0° C. and stirred for 20 min. Then the mixture was stirred at r.t. for 2 h. It was subsequently cooled in an ice-bath and quenched slowly with an aqueous solution of Rochelle's salt (60 mL). MTBE (90 mL) was added, and the resulting mixture was stirred vigorously at room temperature for 1 hour. This mixture was then transferred to a separatory funnel and the layers were separated. The aqueous layer was extracted with MTBE (2×100 mL). The combined organic layers were washed with brine (25 mL), dried over sodium sulfate, filtered and concentrated under reduced pressure. The residue was purified by silica gel chromatography eluting with a gradient from 0% to 70% ethyl acetate in heptane to afford the product as a light-yellow oil, 7-4 (640 mg, 68.5% yield, 100% purity). MS obsd. ($ESI^+$): 246 $[M+H]^+$.

Steps 3-5: (3S,4S,5R)-4-{2-[(2S)-pyrrolidin-2-ylmethoxy]ethoxy}-5-{[4-(1,3-thiazol-5-yl)phenyl]methyl}pyrrolidin-3-ol The title compound was prepared in 67.2% overall yield as a light yellow semi-solid according to Conversion of alcohol to iodides; General Procedure IV using 7-4 in STEP 3; O-Alkylation reaction with NaH for synthesis of ether; General Procedure I using tert-butyl (2S)-2-[(2-iodoethoxy)methyl]pyrrolidine-1-carboxylate (7-5) in STEP 4; Boc Deprotection; General Procedure III in STEP 5. MS obsd. ($ESI^+$): 404 $[M+H]^+$. $^1H$ NMR (400 MHz, Methanol-$d_4$) δ 9.00 (s, 1H), 8.20 (s, 1H), 7.75-7.68 (m, 2H), 7.50-7.43 (m, 2H), 4.55-4.49 (m, 1H), 4.09 (d, J=7.7, 3.2 Hz, 1H), 3.92-3.71 (m, 7H), 3.69-3.58 (m, 2H), 3.37-3.08 (m, 5H), 2.23-1.96 (m, 3H), 1.87-1.72 (m, 1H).

Example 5: (3S,4S,5R)-4-{2-[(3S)-pyrrolidin-3-yl]ethoxy}-5-{[4-(1,3-thiazol-5-yl)phenyl]methyl}pyrrolidin-3-ol

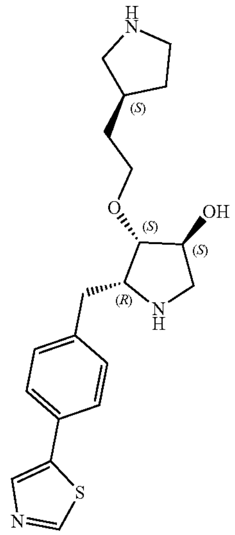

Step 1-2: (3S,4S,5R)-4-{2-[(3S)-pyrrolidin-3-yl]ethoxy}-5-{[4-(1,3-thiazol-5-yl)phenyl]methyl}pyrrolidin-3-ol. The title compound was prepared in 29.5% overall yield as a light yellow semi-solid according to Conversion of alcohol to iodides; General Procedure IV using tert-butyl (3S)-3-(2-hydroxyethyl)pyrrolidine-1-carboxylate in STEP 1; O-Alkylation reaction with NaH for synthesis of ether; General Procedure I using tert-butyl (3S)-3-(2-iodoethyl)pyrrolidine-1-carboxylate in STEP 2; Boc Deprotection; General Procedure III in STEP 3. MS obsd. ($ESI^+$): 374 $[M+H]^+$. $^1H$ NMR (400 MHz, Methanol-$d_4$) δ 9.00 (s, 1H), 8.20 (s, 1H), 7.75-7.67 (m, 2H), 7.48-7.42 (m, 2H), 4.52 (d, J=4.2 Hz, 1H), 4.11 (d, J=8.0, 3.4 Hz, 1H), 3.82-3.73 (m, 2H), 3.65-3.48 (m, 3H), 3.47-3.37 (m, 1H), 3.30-3.19 (m, 1H), 3.20 (d, J=12.5 Hz, 1H), 3.12 (dd, J=14.0, 8.3 Hz, 1H), 2.97-2.87 (m, 1H), 2.53-2.40 (m, 1H), 2.32-2.19 (m, 1H), 1.95-1.77 (m, 2H), 1.76-1.65 (m, 1H).

Example 6: (3S,4S,5R)-4-{2-[(2S)-pyrrolidin-2-ylmethoxy]ethoxy}-5-{[4-(1,3-thiazol-5-yl)phenyl]methyl}pyrrolidin-3-ol Scheme 8

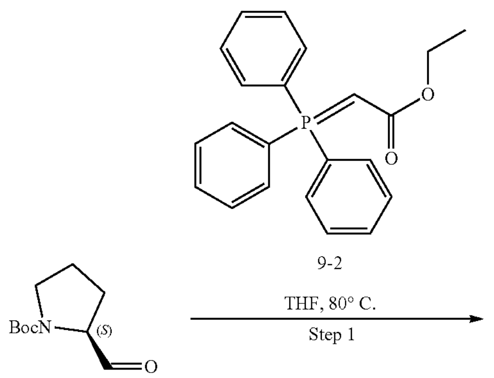

9-2

8-1

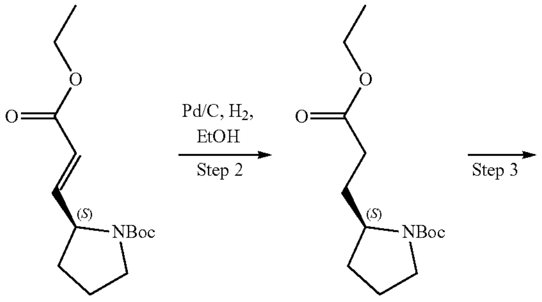

8-3

8-4

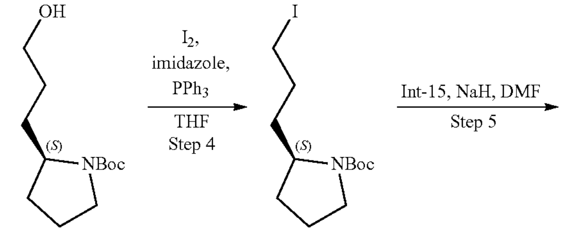

8-5

8-6

-continued

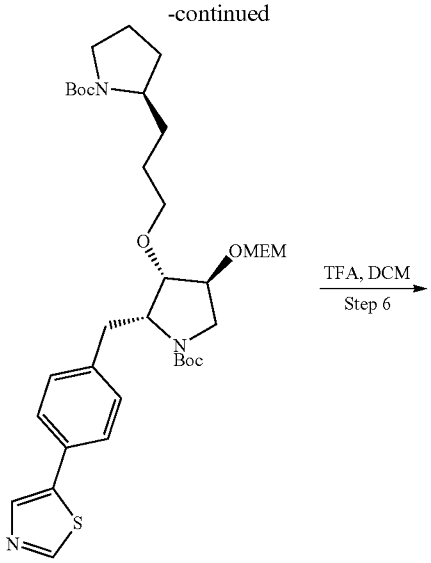

8-6

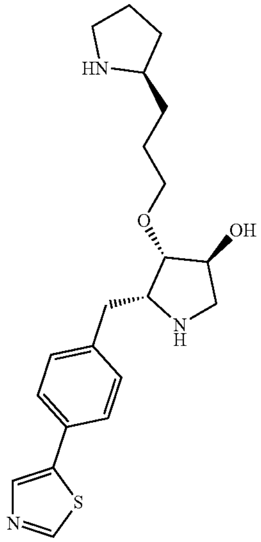

Step 1: tert-butyl (2S)-2-(3-ethoxy-3-oxoprop-1-en-1-yl)pyrrolidine-1-carboxylate (8-3). To a stirred solution of tert-butyl (2S)-2-formylpyrrolidine-1-carboxylate (1 g, 5.01 mmol, 1 eq.) in THF (10 mL) were added ethyl 2-(triphenyl-λ 5-phosphanylidene)acetate (1.7 g, 5.01 mmol, 1 eq.) at room temperature. The resulting mixture was stirred at 80° C. for overnight. The resulting mixture was extracted with EtOAc (2×100 mL). The combined organic layers were washed with brine (2×50 mL), dried over anhydrous $Na_2SO_4$. After filtration, the filtrate was concentrated under reduced pressure. The residue was purified by silica gel column chromatography, eluted with PE/EA (3:1) to afford 8-3 (1.3 g, 96.1% yield, 90% purity) as a light yellow oil. MS obsd. ($ESI^+$): 170 $[M+H]^+$.

Step 2: tert-butyl (2S)-2-(3-ethoxy-3-oxopropyl)pyrrolidine-1-carboxylate (8-4). To a stirred solution of 8-3 (1.3 g, 4.82 mmol, 1 eq.) in EtOH (15 mL) was added Pd/C (1.0 g, 9.65 mmol, 2 eq.) at room temperature under $N_2$, the mixture was then subjected to a hydrogen atmosphere for 2 hours. The resulting mixture was filtered, the filter cake was washed with EtOH (15 mL) (2×50 mL). The filtrate was concentrated under reduced pressure to afford 8-4 (1.3 g) as a light yellow solid. MS obsd. ($ESI^+$): 272 $[M+H]^+$.

Step 3: tert-butyl (2S)-2-(3-hydroxypropyl)pyrrolidine-1-carboxylate (8-5). To a stirred solution of 8-4 (600 mg, 2.21 mmol, 1 eq.) in THF (10 mL) was added $LiAlH_4$ (100.6 mg, 2.65 mmol, 1.2 eq.) at room temperature. The resulting mixture was stirred at room temperature for 2 h. The reaction was quenched by the addition of Sodium sulfate decahydrate at 0° C. The reaction mixture was filtered and concentrated. The residue was purified by silica gel column chromatography, eluted with PE/EA (3:1) to afford 8-5 (300 mg, 59.1% yield, 90% purity) as a light yellow solid. MS obsd. ($ESI^+$): 174 $[M+H]^+$.

Steps 4-6: (3S,4S,5R)-4-{2-[(2S)-pyrrolidin-2-yl-methoxy]ethoxy}-5-{[4-(1,3-thiazol-5-yl)phenyl]methyl}pyrrolidin-3-ol The title compound was prepared in 31.8% overall yield as an off-white semi-solid according to Conversion of alcohol to iodides; General Procedure IV using 8-5 in STEP 4; O-Alkylation reaction with NaH for synthesis of ether; General Procedure I using tert-butyl (2S)-2-(3-iodopropyl) pyrrolidine-1-carboxylate (8-6) in STEP 5; Boc Deprotection; General Procedure III in STEP 6. MS obsd. ($ESI^+$): 388 $[M+H]^+$. $^1H$ NMR (400 MHz, Methanol-$d_4$) δ 9.00 (s, 1H), 8.20 (s, 1H), 7.74-7.68 (m, 2H), 7.45 (d, J=8.0 Hz, 2H), 4.90 (s, 1H), 4.51 (d, J=4.3 Hz, 1H), 4.10 (td, J=7.7, 3.2 Hz, 1H), 3.82-3.79 (m, 1H), 3.76-3.71 (m, 1H), 3.58-3.56 (m, 3H), 3.27 (dd, J=14.0, 7.1 Hz, 1H), 3.20-3.13 (m, 3H), 2.27-2.24 (m, 1H), 2.17-1.99 (m, 2H), 1.89-1.63 (m, 5H).

Example 7: (3S,4S,5R)-4-[3-(3-fluorophenyl)propoxy]-5-{[4-(1,3-thiazol-5-yl)phenyl]methyl}pyrrolidin-3-ol

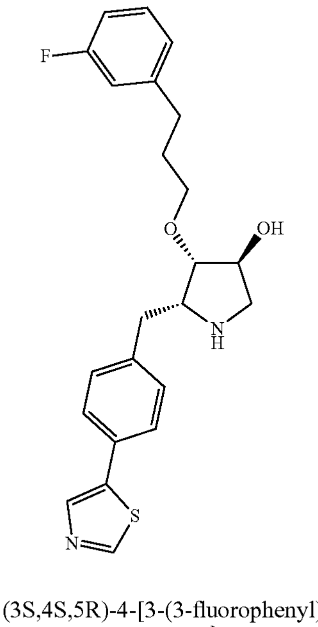

Step 1-3: (3S,4S,5R)-4-[3-(3-fluorophenyl)propoxy]-5-{[4-(1,3-thiazol-5-yl)phenyl]methyl}pyrrolidin-3-ol. The title compound was prepared in 16.0% overall yield as a light yellow semi-solid according to Conversion of alcohol to iodides; General Procedure IV using 3-(3-fluorophenyl) propan-1-ol in STEP 1; O-Alkylation reaction with NaH for synthesis of ether; General Procedure I using 1-fluoro-3-(3-iodopropyl)benzene in STEP 2; Boc Deprotection; General Procedure III in STEP 3. MS obsd. ($ESI^+$): 413 $[M+H]^+$. $^1H$ NMR (400 MHz, Methanol-$d_4$) δ 8.99 (s, 1H), 8.18 (s, 1H), 7.69 (d, J=7.9 Hz, 2H), 7.43 (d, J=7.9 Hz, 2H), 7.35-7.27 (m, 1H), 7.05 (d, J=7.7 Hz, 1H), 7.02-6.90 (m, 2H), 4.46 (d, J=4.3 Hz, 1H), 4.13-4.05 (m, 1H), 3.78-3.68 (m, 2H), 3.61 (dd, J=12.6, 4.4 Hz, 1H), 3.52 (d, J=3.2 Hz, 1H), 3.30-3.25 (m, 1H), 3.19 (d, J=12.6 Hz, 1H), 3.15-3.10 (m, 1H), 2.84-2.73 (m, 2H), 2.05-1.94 (m, 2H).

Example 8: (3S,4S,5R)-4-(azetidin-3-ylmethoxy)-5-{[4-(1,3-thiazol-5-yl)phenyl]methyl}pyrrolidin-3-ol

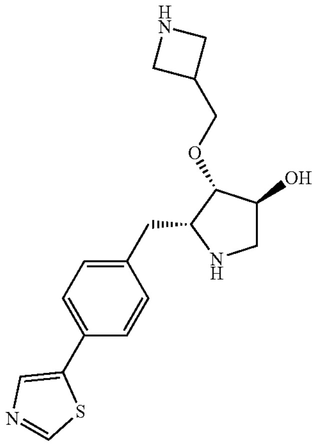 [SMILES: O[C@H]1CN[C@H](Cc2ccc(-c3cncs3)cc2)[C@@H]1OCC1CNC1]

Step 1-2: (3S,4S,5R)-4-(azetidin-3-ylmethoxy)-5-{[4-(1,3-thiazol-5-yl)phenyl]methyl}pyrrolidin-3-ol The title compound was prepared in 17.5% overall yield as an 1 off-white semi-solid according to O-Alkylation reaction with NaH for synthesis of ether; General Procedure I using tert-butyl 3-(bromomethyl) azetidine-1-carboxylate in STEP 1; Boc Deprotection; General Procedure III in STEP 2. MS obsd. ($ESI^+$): 346 $[M+H]^+$. $^1H$ NMR (400 MHz, Methanol-$d_4$) δ 9.00 (s, 1H), 8.20 (s, 1H), 7.87-7.58 (m, 2H), 7.58-7.29 (m, 2H), 4.56 (d, J=4.4 Hz, 1H), 4.29-4.17 (m, 2H), 4.17-4.09 (m, 2H), 4.01 (dd, J=10.8, 6.6 Hz, 1H), 3.93-3.83 (m, 2H), 3.76-3.64 (m, 2H), 3.34 (s, OH), 3.30 (d, J=6.6 Hz, 1H), 3.27-3.11 (m, 3H).

Example 9: (3S,4S,5R)-4-methoxy-5-{[4-(1,3-oxazol-5-yl)phenyl]methyl}pyrrolidin-3-ol Scheme 9

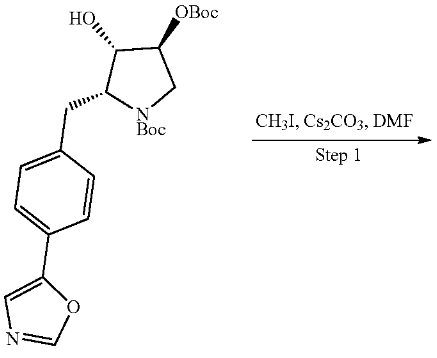

Int-9

-continued

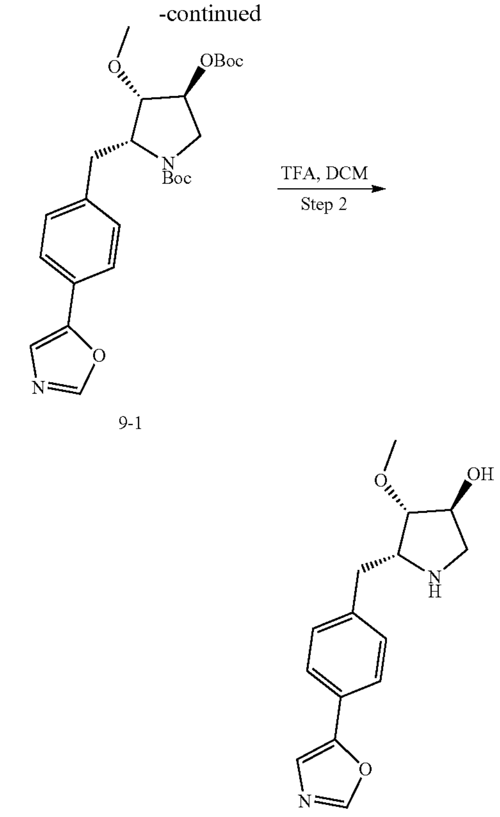

9-1

Step 1: tert-butyl (2R,3S,4S)-4-[(tert-butoxycarbonyl)oxy]-3-methoxy-2-{[4-(1,3-oxazol-5-yl)phenyl]methyl}pyrrolidine-1-carboxylate (9-1). To a stirred solution of Int-9 (100 mg, 0.21 mmol, 1 eq.) and $Cs_2CO_3$ (212.2 mg, 0.65 mmol, 3 eq.) in DMF (3 mL) were added $CH_3I$ (154.1 mg, 1.08 mmol, 5 eq.) at 0° C. The resulting mixture was stirred at room temperature for overnight. The reaction mixture was quenched with water and extracted with EA. The combined organic layers were washed with brine (2×50 mL), dried over anhydrous $Na_2SO_4$. After filtration, the filtrate was concentrated under reduced pressure. The residue was purified by Prep-TLC (PE/EA 3:1) to afford 9-1 (15 mg, 14.5% yield, 95% purity) as a light yellow solid. MS obsd. ($ESI^+$): 475 $[M+H]^+$.

Step 2: (3S,4S,5R)-4-methoxy-5-{[4-(1,3-oxazol-5-yl)phenyl]methyl}pyrrolidin-3-ol The title compound was prepared in 31.8% yield as a yellow solid according to Boc Deprotection; General Procedure III in STEP 2. MS obsd. ($ESI^+$): 275 $[M+H]^+$. $^1H$ NMR (400 MHz, Methanol-$d_4$) δ 8.27 (s, 1H), 7.77 (d, J=7.9 Hz, 2H), 7.54 (s, 1H), 7.45 (d, J=7.9 Hz, 2H), 4.52 (d, J=4.4 Hz, 1H), 4.07-4.01 (m, 1H), 3.64-3.54 (m, 2H), 3.50 (s, 3H), 3.25 (dd, J=13.9, 7.6 Hz, 1H), 3.17 (d, J=12.8 Hz, 1H), 3.08 (dd, J=13.9, 8.0 Hz, 1H).

Example 10: (3S,4S,5R)-4-[1,1-difluoro-3-(3-fluorophenyl)propoxy]-5-{[4-(1,3-thiazol-5-yl)phenyl]methyl}pyrrolidin-3-ol

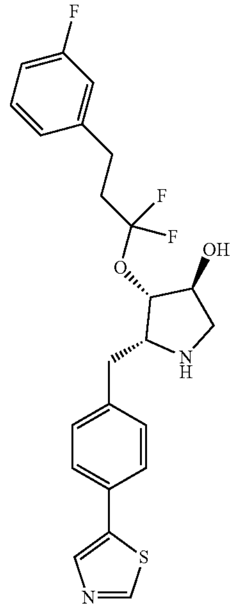 [SMILES: O[C@H]1CN[C@H](Cc2ccc(-c3cncs3)cc2)[C@@H]1OC(F)(F)CCc1cccc(F)c1]

Step 1-3: (3S,4S,5R)-4-[1,1-difluoro-3-(3-fluorophenyl)propoxy]-5-{[4-(1,3-thiazol-5-yl)phenyl]methyl}pyrrolidin-3-ol The title compound was prepared in 22.1% overall yield as a white solid according to Heck Coupling with $Pd_2(dba)_3$, tris(2-methylphenyl)phosphate, TEA; General Procedure V using Int-19 instead of Int-14, 3-fluorophenylboronic acid in STEP 1; Reduction reaction with Pd/C, hydrogen; General Procedure VI in STEP 2; Boc Deprotection; General Procedure III in STEP 3. MS obsd. ($ESI^+$): 449 $[M+H]^+$. $^1H$ NMR (400 MHz, Methanol-$d_4$) δ 8.99 (s, 1H), 8.19 (s, 1H), 7.75-7.68 (m, 2H), 7.50-7.44 (m, 2H), 7.36-7.29 (m, 1H), 7.11 (d, J=7.7 Hz, 1H), 7.05 (dt, J=10.0, 2.1 Hz, 1H), 7.01-6.91 (m, 1H), 4.79 (d, J=3.3 Hz, 1H), 4.52 (d, J=3.9 Hz, 1H), 4.33-4.24 (m, 1H), 3.61 (dd, J=12.8, 4.2 Hz, 1H), 3.32-3.20 (m, 2H), 3.06 (dd, J=14.6, 9.6 Hz, 1H), 2.95 (dd, J=10.2, 6.3 Hz, 2H), 2.54-2.40 (m, 2H).

Example 11: (3S,4S,5R)-5-{[4-(1,3-thiazol-5-yl)phenyl]methyl}-4-{3-[3-(trifluoromethoxy)phenyl]propoxy}pyrrolidin-3-ol

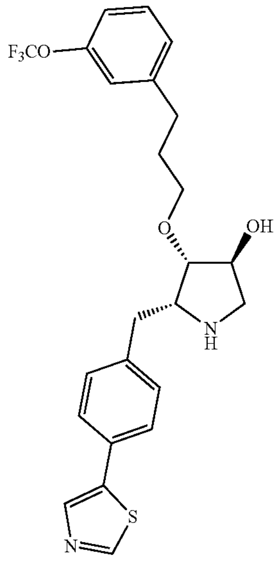 [SMILES: O[C@H]1CN[C@H](Cc2ccc(-c3cncs3)cc2)[C@@H]1OCCCc1cccc(OC(F)(F)F)c1]

Step 1-3: (3S,4S,5R)-5-{[4-(1,3-thiazol-5-yl)phenyl]methyl}-4-{3-[3-(trifluoromethoxy)phenyl]propoxy}pyrrolidin-3-ol The title compound was prepared in 10.0% overall yield as a white solid according to Heck Coupling with $Pd_2(dba)_3$, tris(2-methylphenyl)phosphate, TEA; General Procedure V using 1-bromo-3-(trifluoromethoxy)benzene in STEP 1; Reduction reaction with Pd/C, hydrogen; General Procedure VI in STEP 2; Boc Deprotection; General Procedure III in STEP 3. MS obsd. ($ESI^+$): 479 $[M+H]^+$. $^1H$ NMR (400 MHz, Methanol-$d_4$) δ 9.00 (s, 1H), 8.19 (s, 1H), 7.72-7.66 (m, 2H), 7.47-7.37 (m, 3H), 7.25 (d, J=7.6 Hz, 1H), 7.18-7.10 (m, 2H), 4.47 (d, J=4.3 Hz, 1H), 4.14-4.05 (m, 1H), 3.78-3.68 (m, 2H), 3.66-3.58 (m, 1H), 3.58-3.49 (m, 1H), 3.31-3.23 (m, 1H), 3.23-3.08 (m, 2H), 2.90-2.74 (m, 2H), 2.07-1.95 (m, 2H).

Example 12: 3-[4-(4-{[(2R,3S,4S)-3-(1,1-difluoropropoxy)-4-hydroxypyrrolidin-2-yl]methyl}phenyl)-1,2,3-triazol-1-yl]-7-hydroxychromen-2-one Scheme 10

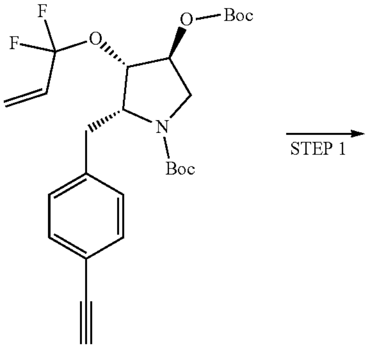

Int-18

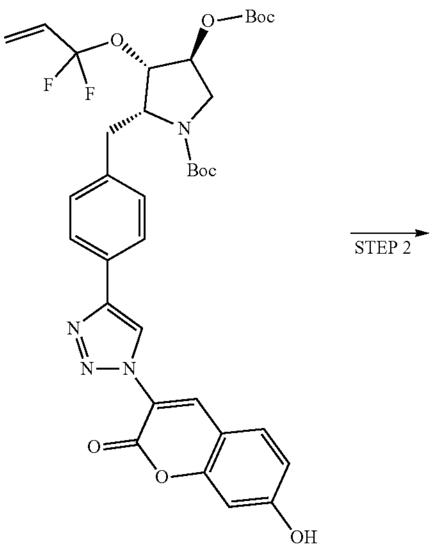

10-2

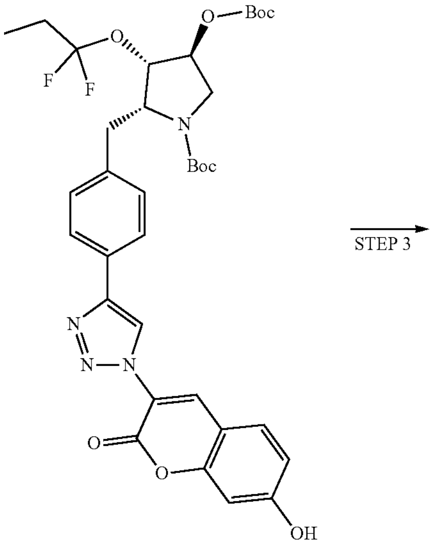

10-3

-continued

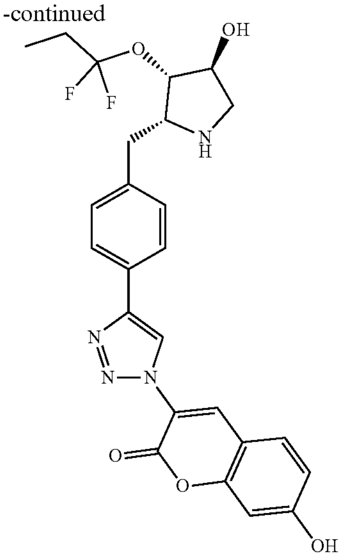

Step 1: tert-butyl (2R,3S,4S)-4-[(tert-butoxycarbonyl)oxy]-3-[(1,1-difluoroprop-2-en-1-yl)oxy]-2-({4-[1-(7-hydroxy-2-oxochromen-3-yl)-1,2,3-triazol-4-yl]phenyl}methyl)pyrrolidine-1-carboxylate (10-2). To a stirred solution of Int-18 (70 mg, 0.14 mmol, 1 eq.) and 3-azido-7-hydroxychromen-2-one (57.6 mg, 0.28 mmol, 2 eq.) in methanol (3 mL) were added $CuSO_4 \cdot 5H_2O$ (35.4 mg, 0.14 mmol, 1 eq.) and L-sodium ascorbate (56.1 mg, 0.28 mmol, 2 eq.) at 0° C. The resulting mixture was stirred at room temperature for overnight. The resulting mixture was filtered, the filter cake was washed with methanol (2×20 mL). The filtrate was concentrated under reduced pressure. The crude product was purified by reverse phase flash (with the following conditions MeCN/0.5% TFA in $H_2O$) to afford 11-2 (55 mg, 55.6% yield, 90% purity) as a light yellow solid. MS: m/z: Calc'd for $C_{35}H_{38}F_2N_4O_9$ $[M+H]^+$ 697; Found, 697.

Steps 2-3: 3-[4-(4-{[(2R,3S,4S)-3-(1,1-difluoropropoxy)-4-hydroxypyrrolidin-2-yl]methyl}phenyl)-1,2,3-triazol-1-yl]-7-hydroxychromen-2-one. The title compound was prepared in 31.8% overall yield as an off-white semi-solid according to Reduction reaction with Pd/C, hydrogen; General Procedure VI using $PtO_2$, toluene instead of Pd/C, MeOH; 10-2 in STEP 2; Boc Deprotection; General Procedure III in STEP 3. MS: m/z Calc'd for $C_{25}H_{24}F_2N_4O_5$ $[M+H]^+$ 499, found 499. $^1$H NMR (400 MHz, Methanol-$d_4$) δ 8.92 (s, 1H), 8.59 (s, 1H), 7.97 (d, J=8.3 Hz, 2H), 7.70 (d, J=8.7 Hz, 1H), 7.50 (d, J=8.1 Hz, 2H), 6.94 (dd, J=8.5, 2.3 Hz, 1H), 6.87 (d, J=2.3 Hz, 1H), 4.78 (s, 1H), 4.52 (d, J=4.2 Hz, 1H), 4.29 (dd, J=9.2, 4.7 Hz, 1H), 3.62 (dd, J=12.7, 4.3 Hz, 1H), 3.28-3.19 (m, 1H), 3.17-3.11 (m, 1H), 3.06 (dd, J=14.7, 9.6 Hz, 1H), 2.16 (td, J=11.3, 7.6 Hz, 2H), 1.16 (t, J=7.5 Hz, 3H).

Example 13: 3-[4-(4-{[(2R,3S,4S)-3-ethoxy-4-hydroxypyrrolidin-2-yl]methyl}phenyl)-1,2,3-triazol-1-yl]-7-hydroxychromen-2-one Scheme 11

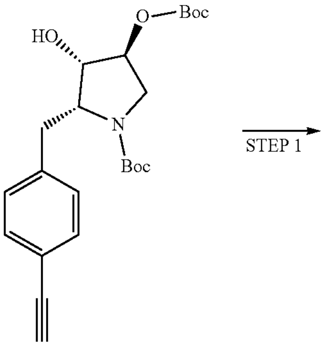

5-3

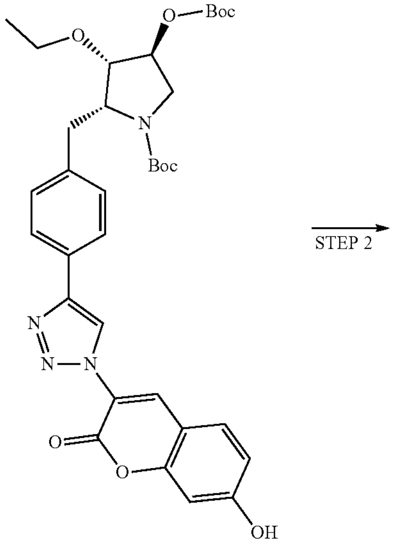

11-2

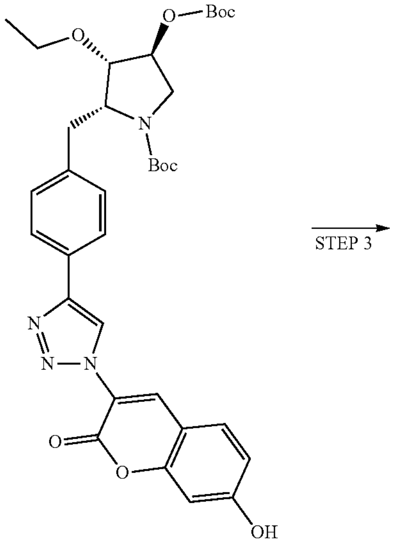

11-3

-continued

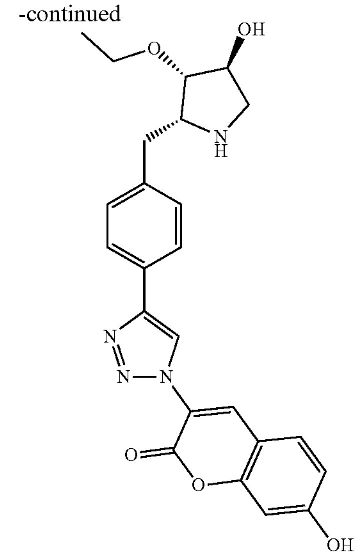

Step 1: tert-butyl (2R,3S,4S)-4-[(tert-butoxycarbonyl)oxy]-3-ethoxy-2-[(4-ethynylphenyl)methyl]pyrrolidine-1-carboxylate (11-2). To a stirred solution of Int-18 (100 mg, 0.240 mmol, 1 equiv) and ethyl iodide (74.7 mg, 0.48 mmol, 2 eq.) in acetone (3 mL) were added $CS_2CO_3$ (234.1 mg, 0.72 mmol, 3 eq.) at room temperature. The resulting mixture was stirred at 80° C. for overnight. The resulting mixture was extracted with EtOAc (2×100 mL). The combined organic layers were washed with brine (2×50 mL), dried over anhydrous $Na_2SO_4$. After filtration, the filtrate was concentrated under reduced pressure. The crude product was purified by reverse phase flash (with the following conditions, MeCN/0.5% TFA in $H_2O$) to afford 12-1 (75 mg, 70.2% yield) as a light yellow solid. MS: m/z: Calc'd for $C_{25}H_{35}NO_6$ $[M+H-56-56]^+$ 334; Found, 334.

Step 2: tert-butyl (2R,3S,4S)-4-[(tert-butoxycarbonyl)oxy]-3-ethoxy-2-({4-[1-(7-hydroxy-2-oxochromen-3-yl)-1,2,3-triazol-4-yl]phenyl}methyl)pyrrolidine-1-carboxylate (12-3). To a stirred solution of 12-2 (70 mg, 0.15 mmol, 1 eq.) and 3-azido-7-hydroxychromen-2-one (63.8 mg, 0.31 mmol, 2 eq.) in methanol (3 mL) were added $CuSO_4 \cdot 5H_2O$ (39.2 mg, 0.15 mmol, 1 eq.) and sodium (2S)-2-[(1S)-1,2-dihydroxyethyl]-4-hydroxy-5-oxooxolan-3-olate (62.2 mg, 0.31 mmol, 2 eq.) at 0° C. The resulting mixture was stirred at room temperature for overnight. The resulting mixture was filtered, the filter cake was washed with methanol (2×20 mL). The filtrate was concentrated under reduced pressure. The crude product was purified by reverse phase flash (with the following conditions, MeCN/0.5% TFA in $H_2O$) to afford 12-2 (75 mg, 73.5% yield, 90% purity) as a yellow solid. MS: m/z: Calc'd for $C_{34}H_{40}N_4O_9$ $[M+H]^+$ 649; Found, 649.

Step 3: 3-[4-(4-{[(2R,3S,4S)-3-ethoxy-4-hydroxypyrrolidin-2-yl]methyl}phenyl)-1,2,3-triazol-1-yl]-7-hydroxychromen-2-one. The title compound was prepared in 31.8% yield as a light yellow semi-solid according to Boc Deprotection; General Procedure III. MS: m/z Calc'd for $C_{24}H_{24}N_4O_5$ $[M+H]^+$ 449; Found, 449. $^1H$ NMR (400 MHz, Methanol-$d_4$) δ 8.91 (s, 1H), 8.58 (s, 1H), 7.99-7.91 (m, 2H), 7.70 (d, J=8.6 Hz, 1H), 7.48 (d, J=8.3 Hz, 2H), 6.94 (dd, J=8.6, 2.3 Hz, 1H), 6.87 (d, J=2.3 Hz, 1H), 4.79 (s, 1H), 4.69 (d, J=4.4 Hz, 1H), 4.07 (td, J=7.7, 3.0 Hz, 1H), 3.85-3.72 (m, 2H), 3.69-3.51 (m, 1H), 3.27 (d, J=7.6 Hz, 1H), 3.18 (s, 1H), 3.15-3.07 (m, 1H), 1.31 (t, J=7.0 Hz, 3H).

Example 14: (3S,4S,5R)-4-{3-[3-(azetidin-3-yl)phenyl]propoxy}-5-{[4-(1,3-thiazol-5-yl)phenyl]methyl}pyrrolidin-3-ol

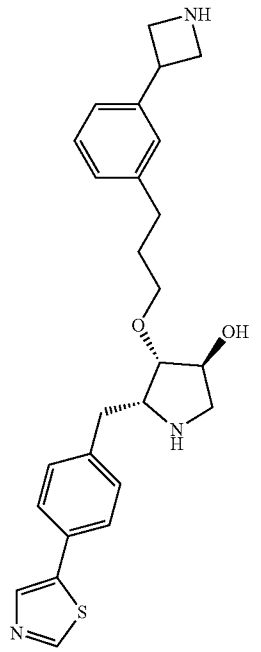 [SMILES: O[C@H]1CN[C@H](Cc2ccc(-c3cncs3)cc2)[C@@H]1OCCCc1cccc(C2CNC2)c1]

Step 1-3: (3S,4S,5R)-4-{3-[3-(azetidin-3-yl)phenyl]propoxy}-5-{[4-(1,3-thiazol-5-yl)phenyl]methyl}pyrr- olidin-3-ol. The title compound was prepared in 17.1% overall yield as an off-white solid according to Sonogashira Coupling with $Pd(PPh_3)_4$, CuI, TEA; General Procedure VII using tert-butyl 3-(3-bromophenyl) azetidine-1-carboxylate in STEP 1; Reduction reaction with Pd/C, hydrogen; General Procedure VI using tert-butyl (2R,3S,4S)-3-[(3-{3-[1-(tert-butoxycarbonyl) azetidin-3-yl]phenyl}prop-2-yn-1-yl)oxy]-4-[(tert-butoxycarbonyl)oxy]-2-{[4-(1,3-thiazol-5-yl)phenyl]methyl}pyrrolidine-1-carboxylate in STEP 2; Boc Deprotection; General Procedure III in STEP 3. MS: m/z Calc'd for $C_{26}H_{31}N_3O_2S$ $[M+H]^+$ 450; Found, 450. $^1H$ NMR (400 MHz, Methanol-$d_4$) δ 9.00 (s, 1H), 8.20 (s, 1H), 7.75-7.67 (m, 2H), 7.48-7.42 (m, 2H), 4.52 (d, J=4.2 Hz, 1H), 4.11 (d, J=8.0, 3.4 Hz, 1H), 3.82-3.73 (m, 2H), 3.65-3.48 (m, 3H), 3.47-3.37 (m, 1H), 3.30-3.19 (m, 1H), 3.20 (d, J=12.5 Hz, 1H), 3.12 (dd, J=14.0, 8.3 Hz, 1H), 2.97-2.87 (m, 1H), 2.53-2.40 (m, 1H), 2.32-2.19 (m, 1H), 1.95-1.77 (m, 2H), 1.76-1.65 (m, 1H).

Example 15: (3S,4S,5R)-4-[3-(2,3-dihydro-1H-isoindol-5-yl)propoxy]-5-{[4-(1,3-thiazol-5-yl)phenyl]methyl}pyrrolidin-3-ol

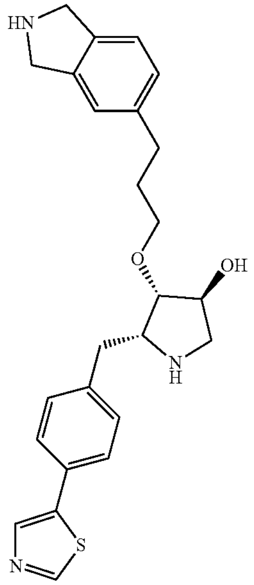

Step 1-3: (3S,4S,5R)-4-[3-(2,3-dihydro-1H-isoindol-5-yl)propoxy]-5-{[4-(1,3-thiazol-5-yl)phenyl]methyl}pyrrolidin-3-ol. The title compound was prepared in 29.3% overall yield as an off-white solid according to Sonogashira Coupling with $Pd(PPh_3)_4$, CuI, TEA; General Procedure VII using tert-butyl 5-bromo-1,3-dihydroisoindole-2-carboxylate in STEP 1; Reduction reaction with Pd/C, hydrogen; General Procedure VI using tert-butyl 5-(3-{[(2R,3S,4S)-1-(tert-butoxycarbonyl)-4-[(tert-butoxycarbonyl)oxy]-2-{[4-(1,3-thiazol-5-yl)phenyl]methyl}pyrrolidin-3-yl]oxy}prop-1-yn-1-yl)-1,3-dihydroisoindole-2-carboxylate in STEP 2; Boc Deprotection; General Procedure III in STEP 3. MS: m/z Calc'd for $C_{25}H_{29}N_3O_2S$ $[M+H]^+$ 436; Found, 436. $^1H$ NMR (400 MHz, Methanol-$d_4$) δ 9.00 (s, 1H), 8.18 (s, 1H), 7.69 (d, J=7.8 Hz, 2H), 7.44-7.25 (m, 5H), 4.60 (s, 4H), 4.48 (d, J=4.3 Hz, 1H), 4.15-4.05 (m, 1H), 3.74 (dd, J=9.8, 3.4 Hz, 2H), 3.62 (dd, J=12.5, 4.4 Hz, 1H), 3.58-3.48 (m, 1H), 3.32-3.24 (m, 1H), 3.24-3.09 (m, 2H), 2.80 (dd, J=9.1, 6.4 Hz, 2H), 2.04-1.92 (m, 2H).

Example 16: (3S,4S,5R)-4-{[3-(3-fluorophenyl)prop-2-yn-1-yl]oxy}-5-{[4-(1,3-thiazol-5-yl)phenyl]methyl}pyrrolidin-3-ol

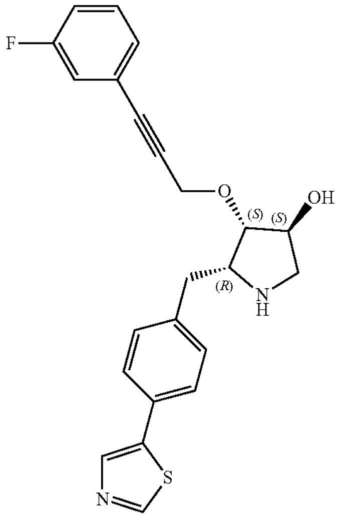

Step 1-2: (3S,4S,5R)-4-{[3-(3-fluorophenyl) prop-2-yn-1-yl]oxy}-5-{[4-(1,3-thiazol-5-yl)phenyl]methyl}pyrrolidin-3-ol. The title compound was prepared in 29.8% overall yield as a white solid according to General Procedure VII using 1-fluoro-3-iodobenzene in STEP 1; Boc Deprotection; General Procedure III in STEP 2. MS: m/z Calc'd for $C_{23}H_{21}FN_2O_2S$ $[M+H-56]^+$ 409; Found, 409. $^1H$ NMR (400 MHz, Methanol-$d_4$) δ 8.98 (s, 1H), 8.08 (s, 1H), 7.62-7.56 (m, 2H), 7.51-7.44 (m, 2H), 7.37-7.27 (m, 1H), 7.23-7.16 (m, 1H), 7.15-7.05 (m, 2H), 4.70-4.61 (m, 3H), 4.16 (s, 1H), 4.08 (d, J=3.3 Hz, 1H), 3.66 (dd, J=12.6, 4.5 Hz, 1H), 3.33-3.21 (m, 2H), 3.15 (dd, J=13.6, 7.0 Hz, 1H).

Example 17: (3S,4S,5R)-4-{3-[2-(azetidin-1-yl)pyridin-4-yl]propoxy}-5-{[4-(1,3-thiazol-5-yl)phenyl]methyl}pyrrolidin-3-ol

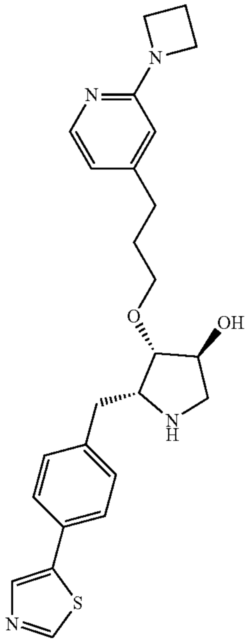 [SMILES: O[C@H]1CN[C@H](Cc2ccc(-c3cncs3)cc2)[C@@H]1OCCCc1ccnc(N2CCC2)c1]

Step 1-3: (3S,4S,5R)-4-{3-[2-(azetidin-1-yl)pyridin-4-yl]propoxy}-5-{[4-(1,3-thiazol-5-yl)phenyl]methyl}pyrrolidin-3-ol. The title compound was prepared in 10.1% overall yield as a yellow solid according to Heck Coupling with $Pd_2(dba)_3$, tris(2-methylphenyl)phosphate, TEA; General Procedure V using 2-(azetidin-1-yl)-4-bromopyridine in STEP 1; Reduction reaction with Pd/C, hydrogen; General Procedure VI using tert-butyl (2R,3S,4S)-3-{[(2E)-3-[2-(azetidin-1-yl)pyridin-4-yl]prop-2-en-1-yl]oxy}-4-[(tert-butoxycarbonyl)oxy]-2-{[4-(1,3-thiazol-5-yl)phenyl]methyl}pyrrolidine-1-carboxylate in STEP 2; Boc Deprotection; General Procedure III in STEP 3. MS: m/z Calc'd for $C_{25}H_{30}N_{402}S$ $[M+H]^+$ 451, found 451. $^1H$ NMR (400 MHz, Methanol-$d_4$) δ 8.96 (s, 1H), 8.15 (d, J=0.7 Hz, 1H), 7.90 (d, J=5.4 Hz, 1H), 7.63-7.55 (m, 2H), 7.38-7.32 (m, 2H), 6.56 (dd, J=5.5, 1.5 Hz, 1H), 6.24 (s, 1H), 4.27-4.21 (m, 1H), 4.05-3.96 (m, 4H), 3.68-3.58 (m, 1H), 3.54-3.47 (m, 1H), 3.46-3.34 (m, 3H), 3.02 (dd, J=13.4, 8.7 Hz, 1H), 2.91 (dd, J=13.4, 6.5 Hz, 1H), 2.78-2.62 (m, 3H), 2.44-2.32 (m, 2H), 2.02-1.89 (m, 2H), 1.31 (s, 1H).

Example 18: (3S,4S,5R)-4-({3-[2-(azetidin-1-yl)pyridin-4-yl]prop-2-yn-1-yl}oxy)-5-{[4-(1,3-thiazol-5-yl)phenyl]methyl}pyrrolidin-3-ol Scheme 12

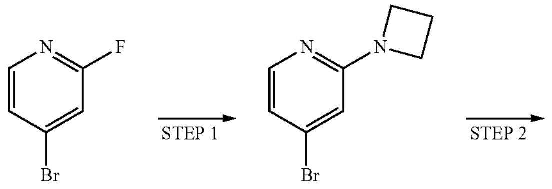

12-1 12-2

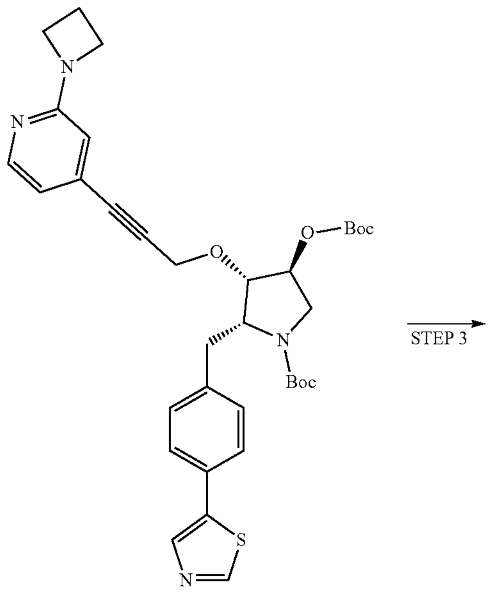

12-3

-continued

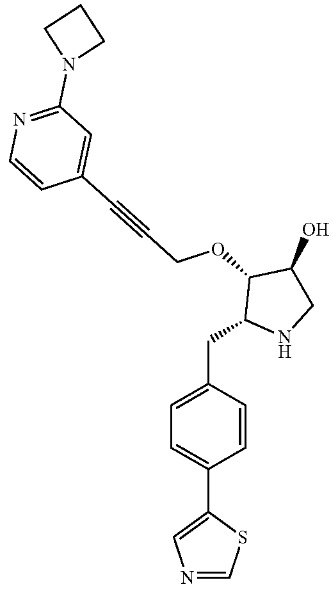

Step 1: 2-(azetidin-1-yl)-4-bromopyridine (12-2). To a stirred mixture of azetidine (1.62 g, 28.41 mmol, 1 equiv) and 4-bromo-2-fluoropyridine (5 g, 28.41 mmol, 1.00 equiv) in DMF (20 mL) was added $Cs_2CO_3$ (27.7 g, 85.23 mmol, 3 equiv) at room temperature. The resulting mixture was stirred at 60° C. for overnight under nitrogen atmosphere. The reaction mixture was quenched with water and extracted with EA. The extracts were washed with brine, dried over anhydrous sodium sulfate, filtered and concentrated. The residue was purified by silica gel column chromatography to afford 13-2 (4 g, 66.0% yield, 95% purity) as a white solid.

Steps 2-3: (3S,4S,5R)-4-({3-[2-(azetidin-1-yl)pyridin-4-yl]prop-2-yn-1-yl}oxy)-5-{[4-(1,3-thiazol-5-yl)phenyl]methyl}pyrrolidin-3-ol. The title compound was prepared in 39.3% overall yield as a yellow solid according to Sonogashira Coupling with $Pd(PPh_3)_4$, CuI, TEA; General Procedure VII using 13-2 in STEP 2; Boc Deprotection; General Procedure III in STEP 3. MS: m/z Calc'd for $C_{25}H_{26}N_{402}S$ $[M+H]^+$ 447, found 447. $^1H$ NMR (400 MHz, Methanol-$d_4$) δ 9.01 (s, 1H), 8.11 (s, 1H), 7.72 (dd, J=6.5, 0.8 Hz, 1H), 7.64-7.57 (m, 2H), 7.49-7.42 (m, 2H), 6.64 (dd, J=6.5, 1.5 Hz, 1H), 6.62-6.59 (m, 1H), 4.70 (d, J=16.9 Hz, 1H), 4.63-4.55 (m, 2H), 4.29-4.18 (m, 5H), 4.06 (d, J=3.5 Hz, 1H), 3.65 (dd, J=12.6, 4.4 Hz, 1H), 3.27 (d, J=12.4 Hz, 1H), 3.24-3.13 (m, 2H), 2.61-2.48 (m, 2H).

Example 19: (3S,4S,5R)-4-[3-(2,3-dihydro-1H-isoindol-5-yl)propoxy]-5-{[4-(1,3-oxazol-5-yl)phenyl]methyl}pyrrolidin-3-ol

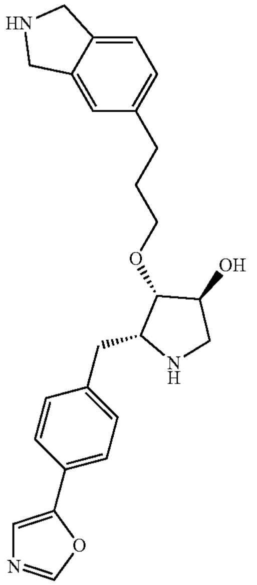 [SMILES: O[C@H]1CN[C@H](Cc2ccc(-c3cnco3)cc2)[C@@H]1OCCCc1ccc2c(c1)CNC2]

Step 1-3: (3S,4S,5R)-4-[3-(2,3-dihydro-1H-isoindol-5-yl)propoxy]-5-{[4-(1,3-oxazol-5-yl)phenyl]methyl}pyrrolidin-3-ol. The title compound was prepared in 17.8% overall yield as a light yellow solid according to Heck Coupling with $Pd_2(dba)_3$, tris(2-methylphenyl)phosphate, TEA; General Procedure V using tert-butyl 5-bromo-1,3-dihydroisoindole-2-carboxylate in STEP 1; Reduction reaction with Pd/C, hydrogen; General Procedure VI using tert-butyl 5-[(1E)-3-{[(2R,3S,4S)-1-(tert-butoxycarbonyl)-4-[(tert-butoxycarbonyl)oxy]-2-{[4-(1,3-oxazol-5-yl)phenyl]methyl}pyrrolidin-3-yl]oxy}prop-1-en-1-yl]-1,3-dihydroisoindole-2-carboxylate in STEP 2; Boc Deprotection; General Procedure III in STEP 3. MS: m/z Calc'd for $C_{25}H_{29}N_3O_3$ $[M+H]^+$ 420, found 420. $^1H$ NMR (400 MHz, Methanol-$d_4$) δ 8.28 (s, 1H), 7.80-7.73 (m, 2H), 7.54 (s, 1H), 7.49-7.43 (m, 2H), 7.37 (d, J=7.8 Hz, 1H), 7.33-7.25 (m, 2H), 4.60 (s, 4H), 4.48 (d, J=4.3 Hz, 1H), 4.15-4.05 (m, 1H), 3.74 (d, J=9.4 Hz, 2H), 3.61 (dd, J=12.5, 4.4 Hz, 1H), 3.53-3.50 (m, 1H), 3.30-3.06 (m, 3H), 2.85-2.76 (m, 2H), 1.98-1.96 (m, 2H).

Example 20: (3S,4S,5R)-4-[3-(2,3-dihydro-1H-isoindol-5-yl)-1,1-difluoropropoxy]-5-{[4-(1,3-thiazol-5-yl)phenyl]methyl}pyrrolidin-3-ol Scheme 13

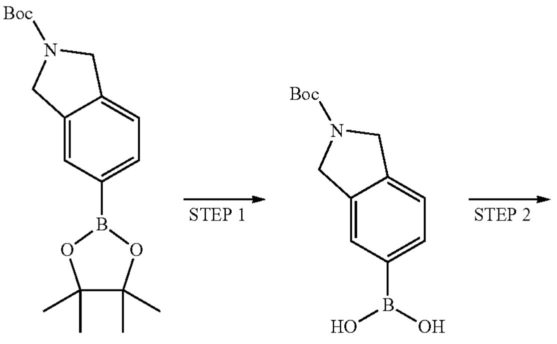

13-1 13-2

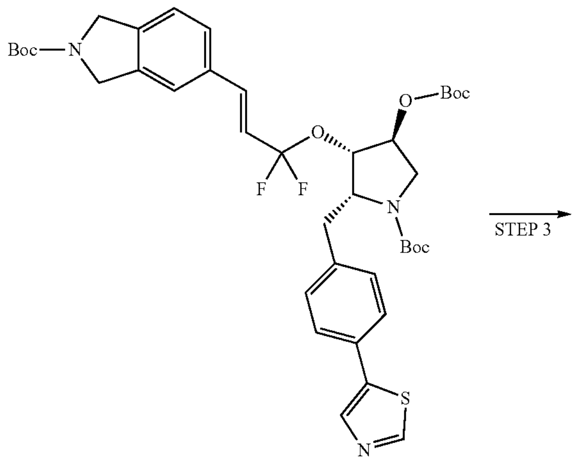

13-3

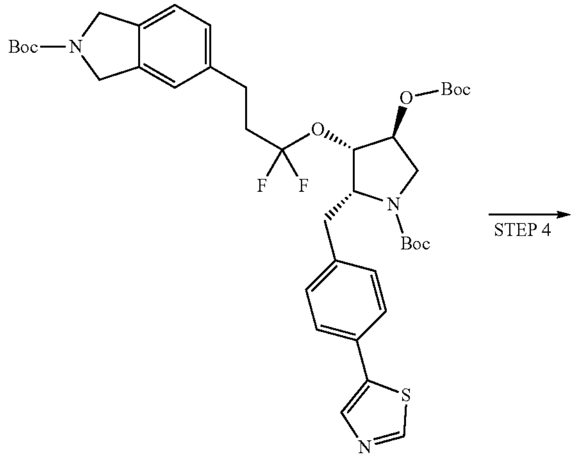

13-4

-continued

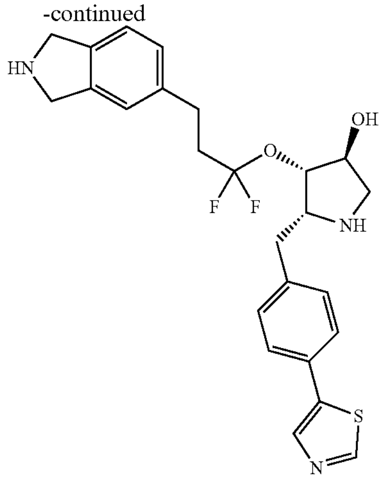

Step 1: 2-(tert-butoxycarbonyl)-1,3-dihydroisoindol-5-ylboronic acid (13-2). To a solution of tert-butyl 5-(4,4,5,5-tetramethyl-1,3,2-dioxaborolan-2-yl)-1,3-dihydroisoindole-2-carboxylate (13-1, 500 mg, 1.44 mmol, 1 equiv) in THF (20 mL) and Water (4 mL) were added $NaIO_4$ (929.2 mg, 4.34 mmol, 3 equiv). After stirring for 0.5 h at room temperature under a nitrogen atmosphere, to the above mixture was added HCl (0.97 mL, 2.89 mmol, 2 equiv) dropwise at room temperature. The resulting mixture was stirred for additional 1.5 h. Upon completion, the resulting mixture was diluted with water (30 mL), and extracted with EtOAc (2x30 mL). The combined organic layers were washed with brine (2x20 mL), dried over anhydrous $Na_2SO_4$. After filtration, the filtrate was concentrated under reduced pressure. The residue was purified by reversed-phase flash chromatography to afford 13-2 (330 mg, 86.61% yield, 97% purity) as a light yellow solid. MS: m/z: Calc'd for $C_{13}H_{18}BNO_4$ $[M-56]^+$ 208, found 208.

Step 2: tert-butyl 5-[(1E)-3-{[(2R,3S,4S)-1-(tert-butoxycarbonyl)-4-[(tert-butoxycarbonyl)oxy]-2-{[4-(1,3-thiazol-5-yl)phenyl]methyl}pyrrolidin-3-yl]oxy}-3,3-difluoroprop-1-en-1-yl]-1,3-dihydroisoindole-2-carboxylate (13-3). To a solution of Int-19 (100 mg, 0.18 mmol, 1 equiv) and 13-2 (71.4 mg, 0.27 mmol, 1.5 equiv) in N,N-dimethylacetamide (3 mL) was added $Pd(OAc)_2$ (8.1 mg, 0.036 mmol, 0.2 equiv) under nitrogen atmosphere in a 50 mL round-bottom flask. The mixture was oxygenated at room temperature for overnight under oxygen atmosphere using an oxygen balloon, filtered through a Celite pad and concentrated under reduced pressure. The residue was purified by reversed-phase flash chromatography to afford 13-3 (50 mg, 35.89% yield, 100% purity) as a light yellow solid. MS: m/z: Calc'd for $C_{40}H_{49}F_2N_3O_8S$ $[M+H]^+$ 770, found 770.

Step 3 & 4: (3S,4S,5R)-4-[3-(2,3-dihydro-1H-isoindol-5-yl)-1,1-difluoropropoxy]-5-{[4-(1,3-thiazol-5-yl)phenyl]methyl}pyrrolidin-3-ol The title compound was prepared in 21.5% overall yield as a white solid according to Reduction reaction with Pd/C, hydrogen; General Procedure VI using tert-butyl 5-[(1E)-3-{[(2R,3S,4S)-1-(tert-butoxycarbonyl)-4-[(tert-butoxycarbonyl)oxy]-2-{[4-(1,3-thiazol-5-yl)phenyl]methyl}pyrrolidin-3-yl]oxy}-3,3-difluoroprop-1-en-1-yl]-1,3-dihydroisoindole-2-carboxylate in STEP 3; Boc Deprotection; General Procedure III in STEP 4. MS: m/z Calc'd for $C_{25}H_{27}F_2N_3O_2S$ $[M+H]^+$ 472, found 472. $^1H$ NMR (400 MHz, Methanol-$d_4$) δ 9.00 (s, 1H), 8.20 (s, 1H), 7.82-7.63 (m, 2H), 7.48 (d, J=8.1 Hz, 2H), 7.37 (p, J=7.8 Hz, 3H), 4.79 (d, J=3.3 Hz, 1H), 4.62 (d, J=4.5 Hz, 4H), 4.54-4.49 (m, 1H), 4.28 (dt, J=9.1, 4.8 Hz, 1H), 3.66 (dd, J=12.7, 4.4 Hz, 1H), 3.30-3.21 (m, 2H), 3.10 (dd, J=14.6, 9.5 Hz, 1H), 2.98 (dd, J=10.6, 6.2 Hz, 2H), 2.55-2.38 (m, 2H).

Example 21: (3S,4S,5R)-4-methoxy-5-{[4-(1,3-oxazol-5-yl)phenyl]methyl}pyrrolidin-3-ol Scheme 14

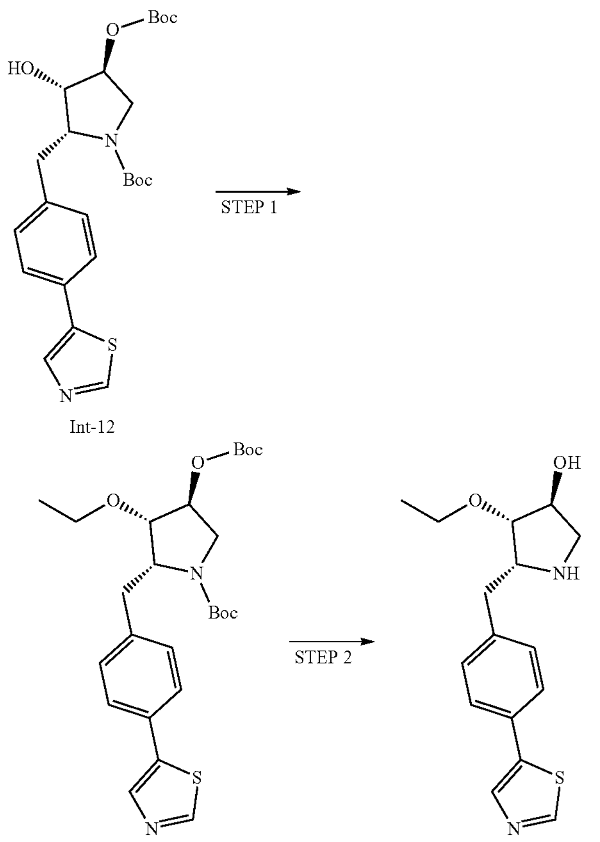

Int-12

14-2

Step 1: tert-butyl (2R,3S,4S)-4-[(tert-butoxycarbonyl)oxy]-3-ethoxy-2-{[4-(1,3-thiazol-5-yl)phenyl]methyl}pyrrolidine-1-carboxylate (14-2). To a stirred solution of Int-12 (80 mg, 0.16 mmol, 1 eq.) and $Cs_2CO_3$ (164.0 mg, 0.50 mmol, 3 eq.) in acetone (3 mL) were added ethyl iodide (52.3 mg, 0.33 mmol, 2 eq.) at 0° C. The resulting mixture was stirred at room temperature for overnight. The resulting mixture was concentrated under reduced pressure. The crude product was purified by reversed phase flash to afford 15-2 (65 mg, 76.7% yield, 90% purity) as a white solid. MS: m/z: Calc'd for $C_{26}H_{36}N_2O_6S$ $[M+H]^+$ 505, found 505.

Step 2: (3S,4S,5R)-4-methoxy-5-{[4-(1,3-oxazol-5-yl)phenyl]methyl}pyrrolidin-3-ol The title compound was prepared in 29.4% yield as a white solid according to Boc Deprotection; General Procedure III in STEP 2. MS: m/z Calc'd for $C_{20}H_{25}N_3O_4$ $[M+H]^+$ 372, found 372. $^1H$ NMR (400 MHz, Methanol-$d_4$) δ 8.99 (d, J=0.8 Hz, 1H), 8.19 (d, J=0.8 Hz, 1H), 7.74-7.71 (m, 1H), 7.70-7.67 (m, 1H), 7.48-7.45 (m, 1H), 7.44-7.41 (m, 1H), 4.49 (d, J=4.4 Hz, 1H), 4.06 (dd, J=7.8, 3.2 Hz, 1H), 3.84-3.73 (m, 1H), 3.73 (d, J=3.3 Hz, 1H), 3.65-3.50 (m, 2H), 3.27 (dd, J=13.9, 7.6 Hz, 1H), 3.17 (d, J=12.5 Hz, 1H), 3.10 (dd, J=13.8, 8.0 Hz, 1H), 1.29 (d, J=7.0 Hz, 3H).

Example 22: (3S,4S,5R)-4-(1,1-difluoropropoxy)-5-{[4-(1,3-thiazol-5-yl)phenyl]methyl}pyrrolidin-3-ol

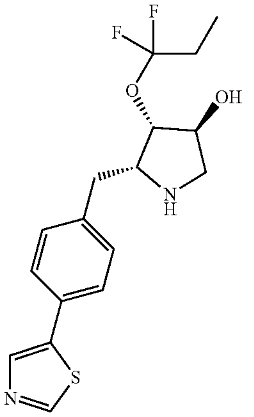 [SMILES: CCC(F)(F)O[C@@H]1[C@@H](O)CN[C@@H]1Cc1ccc(-c2cncs2)cc1]

Step 1-2: (3S,4S,5R)-4-(1,1-difluoropropoxy)-5-{[4-(1,3-thiazol-5-yl)phenyl]methyl}pyrrolidin-3-ol The title compound was prepared in 13.5% overall yield as a white solid according to Reduction reaction with Pd/C, hydrogen; General Procedure VI using Int-19 in STEP 1; Boc Deprotection; General Procedure III in STEP 2. MS: m/z Calc'd for $C_{17}H_{20}F_2N_2O_2S$ $[M+H]^+$ 355; Found, 355. $^1H$ NMR (400 MHz, Methanol-$d_4$) δ 8.99 (s, 1H), 8.20 (s, 1H), 7.76-7.68 (m, 2H), 7.46 (d, J=8.2 Hz, 2H), 4.76 (d, J=3.3 Hz, 1H), 4.51 (d, J=4.2 Hz, 1H), 4.27 (dd, J=9.3, 4.8 Hz, 1H), 3.62 (dd, J=12.7, 4.3 Hz, 1H), 3.23 (d, J=12.8 Hz, 2H), 3.04 (dd, J=14.6, 9.6 Hz, 1H), 2.15-2.13 (m, 2H), 1.15 (t, J=7.5 Hz, 3H).

Example 23: (3S,4S,5R)-4-methoxy-5-{[4-(1,3-oxazol-5-yl)phenyl]methyl}pyrrolidin-3-ol Scheme 15

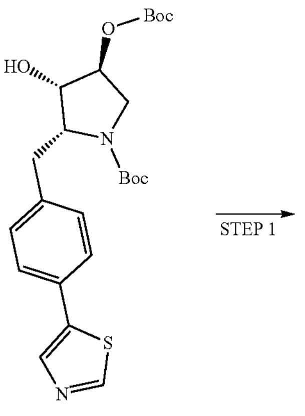

Int-12

-continued

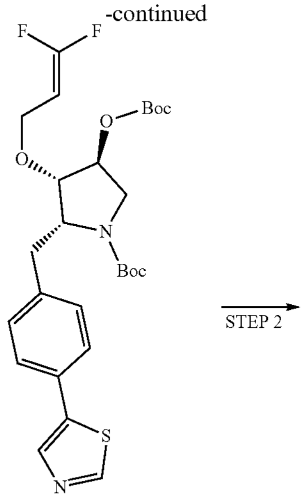

15-2

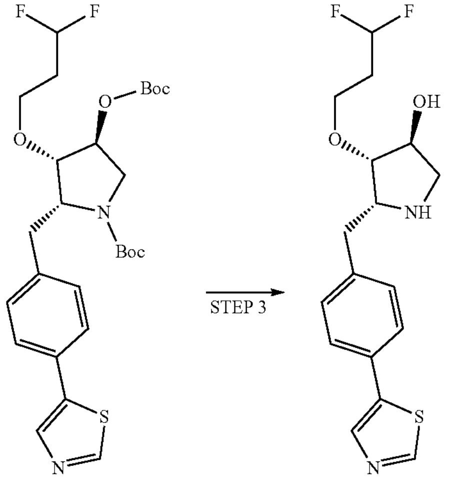

15-3

Step 1: tert-butyl (2R,3S,4S)-4-[(tert-butoxycarbonyl)oxy]-3-[(3,3-difluoroprop-2-en-1-yl)oxy]-2-{[4-(1,3-thiazol-5-yl)phenyl]methyl}pyrrolidine-1-carboxylate (15-2). To a stirred solution of Int-12 (250 mg, 0.52 mmol, 1 eq.) and 3-bromo-3,3-difluoroprop-1-ene (164.6 mg, 1.05 mmol, 2 eq.) in DMF (5 mL) were added CsOH·$H_2O$ (264.2 mg, 1.57 mmol, 3 eq.) and KI (174.1 mg, 1.05 mmol, 2 eq.) at 0° C. The resulting mixture was stirred at room temperature for overnight. The crude product was purified by reverse phase flash to afford 15-2 (38 mg, 13.11% yield, 90% purity) as a light yellow solid together with a regio isomer tert-butyl (2R,3S,4S)-4-((tert-butoxycarbonyl)oxy)-3-((1,1-difluoroallyl)oxy)-2-(4-(thiazol-5-yl)benzyl)pyrrolidine-1-carboxylate (35 mg, 12.0% yield, 90% purity) as a light yellow solid. MS: m/z: Calc'd for $C_{27}H_{34}F_2N_2O_6S$ $[M+H]^+$ 553; Found, 553.

Step 2-3: (3S,4S,5R)-4-methoxy-5-{[4-(1,3-oxazol-5-yl)phenyl]methyl}pyrrolidin-3-ol. The title compound was prepared in 31.1% overall yield as a yellow solid according to Reduction reaction with Pd/C, hydrogen; General Procedure VI using 15-2 in STEP 2; Boc Deprotection; General Procedure III in STEP 3. MS: m/z Calc'd for $C_{17}H_{20}F_2N_2O_2S$ $[M+H]^+$ 355; Found, 355. $^1H$ NMR (400 MHz, Methanol-$d_4$) δ 8.99 (s, 1H), 8.20 (s, 1H), 7.75-7.68 (m, 2H), 7.48-7.41 (m, 2H), 6.10 (t, J=4.6 Hz, 1H), 4.51 (d, J=4.4 Hz, 1H), 4.10

(dd, J=7.7, 3.2 Hz, 1H), 3.93-3.83 (m, 1H), 3.83-3.75 (m, 1H), 3.69 (dd, J=9.7, 5.7 Hz, 1H), 3.60 (dd, J=12.5, 4.4 Hz, 1H), 3.27 (dd, J=14.0, 7.4 Hz, 1H), 3.20 (d, J=12.5 Hz, 1H), 3.10 (dd, J=14.0, 8.2 Hz, 1H), 2.92 (s, 1H), 2.29-2.13 (m, 2H).
Example 24: (3S,4S,5R)-5-(4-(1-(difluoromethyl)-1H-pyrazol-4-yl)benzyl)-4-(1,1-difluoropropoxy)pyrrolidin-3-ol
Scheme 16
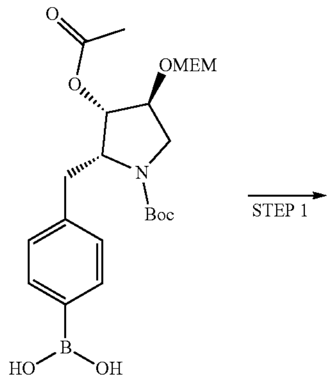
3-2
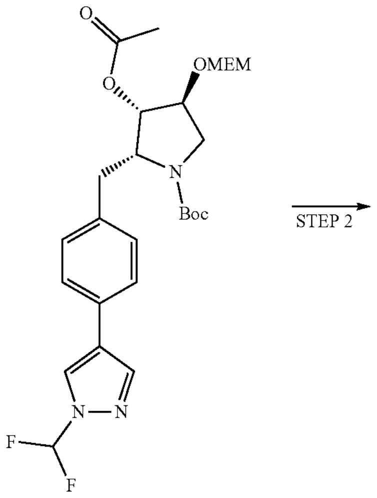
16-2
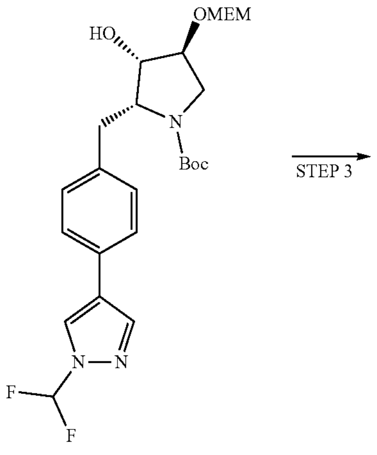
16-3
-continued
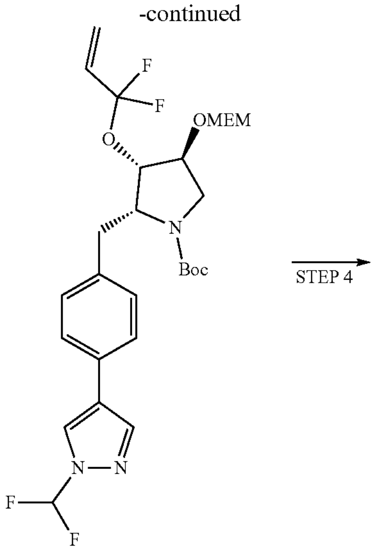
16-4
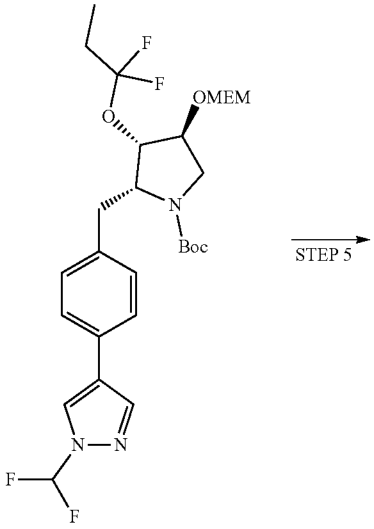
16-5
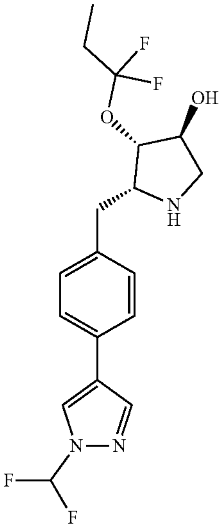
Step 1: tert-butyl (2R,3S,4S)-3-acetoxy-2-(4-(1-(difluoromethyl)-1H-pyrazol-4-yl)benzyl)-4-((2-methoxyethoxy)

methoxy)pyrrolidine-1-carboxylate (16-2). A mixture of 1-(difluoromethyl)-4-iodo-1H-pyrazole (1.25 g), (4-(((2R, 3S,4S)-3-acetoxy-1-(tert-butoxycarbonyl)-4-((2-methoxy-ethoxy)methoxy)pyrrolidin-2-yl)methyl)phenyl) boronic acid (2.0 g), and $Na_2CO_3$ (1.36 g) was suspended in Dioxane (20 mL) and $H_2O$ (2.0 mL) under $N_2$ before Pd(dppf)$Cl_2$ (626 mg) was added. The mixture was heated to 80° C. overnight before cooling to rt. Water was added, the biphasic mixture was extracted with EtOAc, and the organic extracts were combined. The organic extract was washed with brine, dried over $Na_2SO_4$, filtered and concentrated. The residue was purified by reversed-phase flash chromatography to afford the title compound as a yellow oil (1.3 g). MS obsd. ($ESI^+$): 484.2 $[(M+H-56)]^+$.

Step 2: tert-butyl (2R,3S,4S)-2-(4-(1-(difluoromethyl)-1H-pyrazol-4-yl)benzyl)-3-hydroxy-4-((2-methoxyethoxy) methoxy)pyrrolidine-1-carboxylate (16-3). Lithium hydroxide (160 mg) was added to a mixture of tert-butyl (2R,3S, 4S)-3-acetoxy-2-(4-(1-(difluoromethyl)-1H-pyrazol-4-yl) benzyl)-4-((2-methoxyethoxy)methoxy)pyrrolidine-1-carboxylate (1.3 g) in THF (15.0 mL) and $H_2O$ (5.0 mL) at 0° C. The resulting mixture was stirred at rt for 1 h, diluted with water, and extracted with EtOAc. The organic extracts were washed with brine, dried over $Na_2SO_4$, filtered and concentrated. The residue was purified by reversed-phase flash chromatography to afford the title compound as a yellow oil (900 mg). MS obsd. ($ESI^+$): 398.2 $[(M+H-100)]^+$.

Step 3: tert-butyl (2R,3S,4S)-3-((1,1-difluoroallyl)oxy)-2-(4-(1-(difluoromethyl)-1H-pyrazol-4-yl)benzyl)-4-((2-methoxyethoxy)methoxy)pyrrolidine-1-carboxylate (16-4). Sodium hydride (123 mg) was slowly added to a solution of tert-butyl (2R,3S,4S)-2-(4-(1-(difluoromethyl)-1H-pyrazol-4-yl)benzyl)-3-hydroxy-4-((2-methoxyethoxy)methoxy) pyrrolidine-1-carboxylate (900 mg) in DMF (20.0 mL) at 0° C. After 30 min, a solution of 1-(3,3-difluoroprop-2-en-1-yl)-1-methylpiperidin-1-ium triflate (2.35 g) in DMF (1 mL) was added in a dropwise manner. The ice bath was removed, and the mixture was stirred at rt for 12 h, concentrated, and purified by preparative TLC to afford the title compound as a yellow oil (800 mg). MS obsd. ($ESI^+$): 518.2 $[(M+H-56)]^+$.

Step 4: tert-butyl (2R,3S,4S)-2-(4-(1-(difluoromethyl)-1H-pyrazol-4-yl)benzyl)-3-(1,1-difluoropropoxy)-4-((2-methoxyethoxy)methoxy)pyrrolidine-1-carboxylate (16-5). Under a nitrogen atmosphere, Pd/C (160 mg) was slowly added to a solution of Tert-butyl (2R,3S,4S)-3-((1,1-difluoroallyl)oxy)-2-(4-(1-(difluoromethyl)-1H-pyrazol-4-yl)benzyl)-4-((2-methoxyethoxy)methoxy) pyrrolidine-1-carboxylate (800 mg) was dissolved in MeOH (15.0 mL) and the solution was placed under $N_2$ before Pd/C (160 mg) was slowly added. The reaction vessel was fitted with a $H_2$ balloon and after 2 h the reaction mixture was filtered through Celite, and the solids were washed with EtOAc. The filtrate was collected and concentrated under reduced pressure to afford the title compound as a yellow oil. (750 mg). MS obsd. ($ESI^+$): 576.3 $[(M+H)]^+$.

Step 5: (3S,4S,5R)-5-(4-(1-(difluoromethyl)-1H-pyrazol-4-yl)benzyl)-4-(1,1-difluoropropoxy)pyrrolidin-3-ol. Trifluoroacetic acid (5.0 mL) was added dropwise to a stirred solution of tert-butyl (2R,3S,4S)-2-(4-(1-(difluoromethyl)-1H-pyrazol-4-yl)benzyl)-3-(1,1-difluoropropoxy)-4-((2-methoxyethoxy)methoxy)pyrrolidine-1-carboxylate (750 mg) in DCM (5.0 mL). The resulting mixture was stirred at rt for 12 h, concentrated, and the resulting residue was purified by Prep-HPLC to afford the title compound as a white solid (203.6 mg). $^1H$ NMR (400 MHz, Methanol-$d_4$) δ 8.39 (s, 1H), 8.08 (s, 1H), 7.66-7.49 (m, 3H), 7.34 (d, J=8.2 Hz, 2H), 4.42 (s, 1H), 4.32 (d, J=5.4 Hz, 1H), 3.60 (s, 1H), 3.42-3.36 (m, 1H), 2.97 (dd, J=13.9, 6.5 Hz, 1H), 2.82 (dd, J=13.9, 7.8 Hz, 1H), 2.74 (d, J=12.2 Hz, 1H), 2.13-2.02 (m, 2H), 1.12 (t, J=7.5 Hz, 3H), 1° F. NMR (400 MHz, Methanol-$d_4$) δ −75.4 to −74.0 (m), −95.9 (s); MS obsd. ($ESI^+$): 388.2 $[(M+H)]^+$.

Example 25: 4-(3-(((2R,3S,4S)-4-hydroxy-2-(4-(thiazol-5-yl)benzyl)pyrrolidin-3-yl)oxy)propyl) benzimidamide Scheme 17

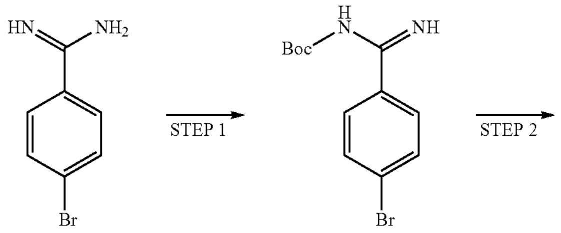

17-1 17-2

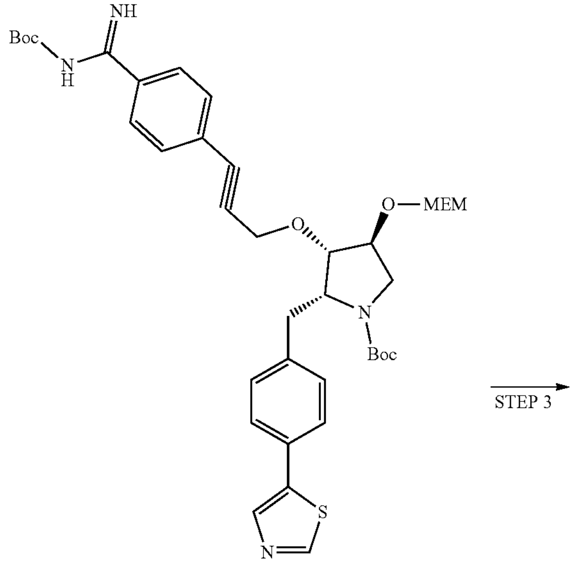

17-3

-continued

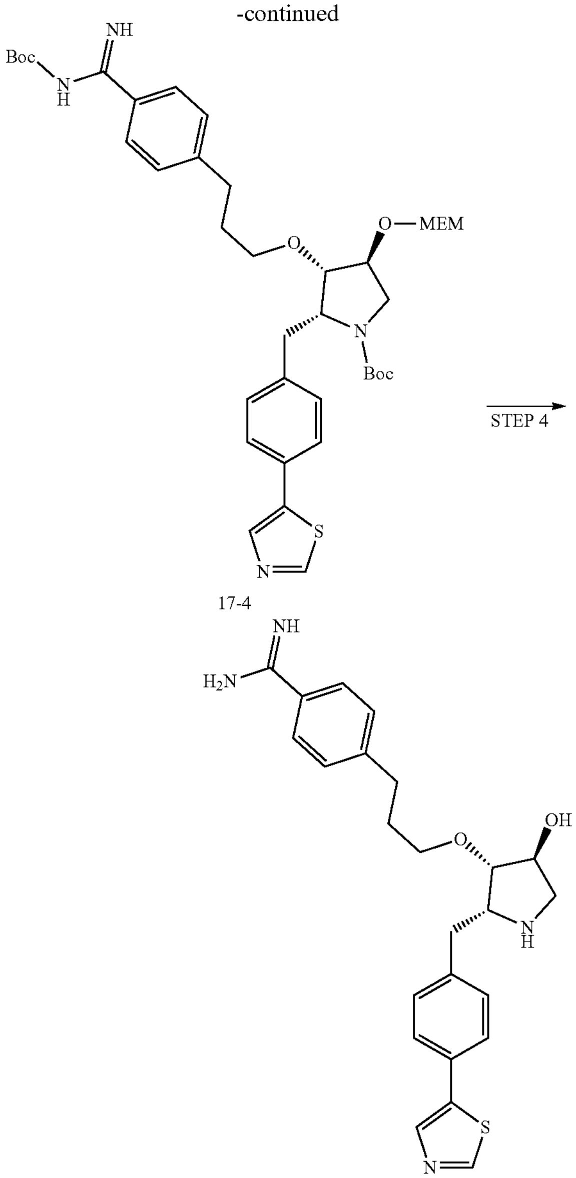

17-4

Step 1: ((4-bromophenyl) (imino)methyl) carbamate (17-2). To a stirred solution of 4-bromobenzimidamide (500 mg) and $Et_3N$ (762 mg) in DCM (20 mL) was added $Boc_2O$ (1.1 g) at 0° C. The resulting mixture was stirred at room temperature overnight, concentrated, and the residue was purified by silica gel column chromatography to afford the title compound as a light-yellow oil (740 mg). MS obsd. ($ESI^+$): 299.1 $[(M+H)]^+$.

Step 2: tert-butyl (2R,3S,4S)-3-((3-(4-(N-(tert-butoxycarbonyl) carbamimidoyl)phenyl) prop-2-yn-1-yl)oxy)-4-((2-methoxyethoxy)methoxy)-2-(4-(thiazol-5-yl)benzyl)pyrrolidine-1-carboxylate (17-3). To a stirred solution of tert-butyl (2R,3S,4S)-3-hydroxy-4-((2-methoxyethoxy)methoxy)-2-(4-(thiazol-5-yl)benzyl)pyrrolidine-1-carboxylate (100 mg) and tert-butyl N-(4-bromobenzenecarboximidoyl) carbamate (119 mg) in $Et_3N$ (5 mL) were added $Pd(PPh_3)_4$ (275 mg) and CuI (4 mg) at room temperature. The resulting mixture was stirred at 80° C. for overnight under nitrogen atmosphere. The reaction was diluted with water, and extracted with EtOAc. The organic extracts were washed with brine, dried over $Na_2SO_4$, filtered and concentrated. The residue was purified by reversed-phase flash chromatography to afford the title compound as a light yellow oil (300 mg). MS obsd. ($ESI^+$): 720.8 $[(M+H)]^+$.

Step 3: tert-butyl (2R,3S,4S)-3-(3-(4-(N-(tert-butoxycarbonyl) carbamimidoyl)phenyl)propoxy)-4-((2-methoxyethoxy)methoxy)-2-(4-(thiazol-5-yl)benzyl)pyrrolidine-1-carboxylate (17-4). Under a nitrogen atmosphere, Pd/C (30 mg) was slowly added to a solution of tert-butyl (2R,3S,4S)-3-((3-(4-(N-(tert-butoxycarbonyl) carbamimidoyl)phenyl) prop-2-yn-1-yl)oxy)-4-((2-methoxyethoxy)methoxy)-2-(4-(thiazol-5-yl)benzyl)pyrrolidine-1-carboxylate (140 mg) dissolved in methanol (8 mL) under $N_2$. The reaction vessel was fitted with a $H_2$ balloon and after 12 h the reaction mixture was filtered through Celite, and the solids were washed with EtOAc. The filtrate was collected and concentrated under reduced pressure to afford the title compound as a yellow oil (70 mg). MS obsd. ($ESI^+$): 724.9 $[(M+H)]^+$.

Step 4: 4-(3-(((2R,3S,4S)-4-hydroxy-2-(4-(thiazol-5-yl)benzyl)pyrrolidin-3-yl)oxy)propyl)benzimidamide. The title compound was prepared in_overall yield as a while solid according to General Procedure III using 17-4 in dioxane. MS obsd. ($ESI^+$): 436.5 $[(M+H)]^+$. $^1H$ NMR (400 MHz, MeOD) δ 9.00 (s, 1H), 8.18 (s, 1H), 7.78 (d, J=8.3 Hz, 2H), 7.69 (d, J=8.2 Hz, 2H), 7.51 (d, J=8.2 Hz, 2H), 7.44 (d, J=8.1 Hz, 2H), 4.50 (d, J=4.2 Hz, 1H), 4.14-4.09 (m, 1H), 3.79-3.73 (m, 2H), 3.60-3.52 (m, 2H), 3.22-3.11 (m, 3H), 2.93-2.86 (m, 2H), 2.04 (dd, J=14.1, 6.9 Hz, 2H).

Example 26: (3S,4S,5R)-4-(3-(pyridin-3-yl)propoxy)-5-(4-(thiazol-5-yl)benzyl)pyrrolidin-3-ol Scheme 18

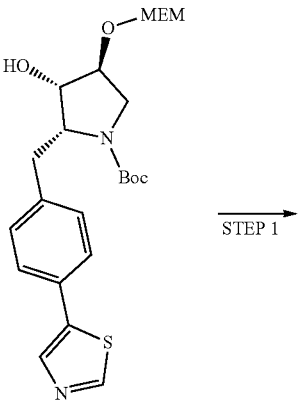

Int-16

-continued

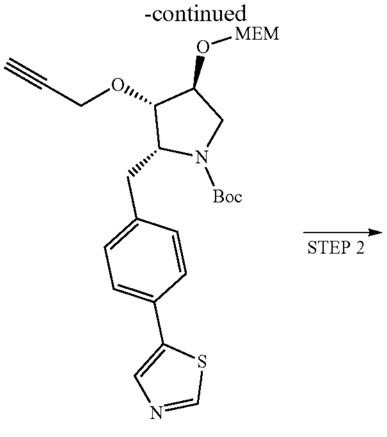

18-1

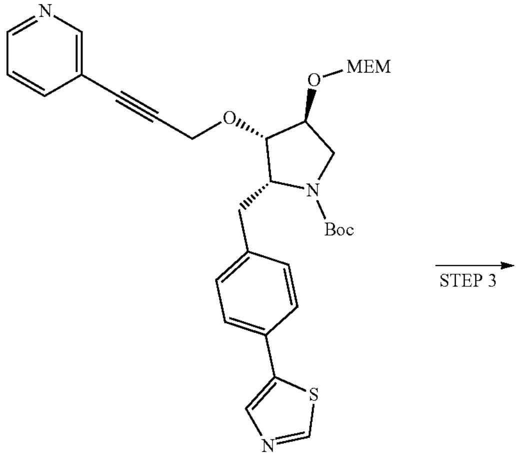

18-2

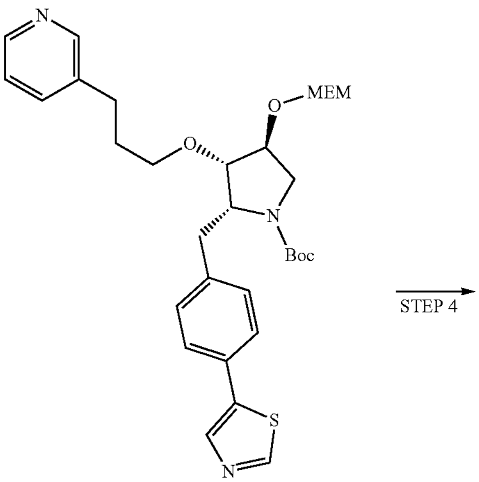

18-3

-continued

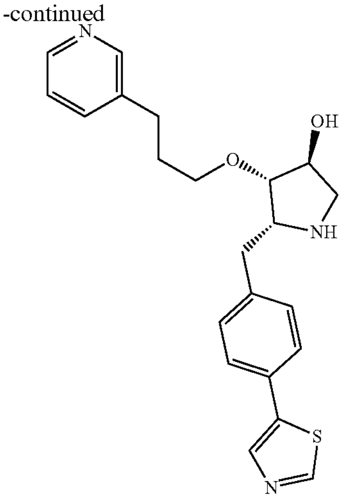

Step 1: tert-butyl (2R,3S,4S)-4-((2-methoxyethoxy)methoxy)-3-(prop-2-yn-1-yloxy)-2-(4-(thiazol-5-yl)benzyl)pyrrolidine-1-carboxylate (18-1). CsOH (484 mg) and KI (357 mg) were added to a stirred solution of tert-butyl (2R,3S,4S)-3-hydroxy-4-((2-methoxyethoxy)methoxy)-2-(4-(thiazol-5-yl)benzyl)pyrrolidine-1-carboxylate (500 mg) and propargyl bromide (384 mg) in DMF (10 mL) at 0° C. The resulting mixture was stirred at room temperature for 2 h before it was diluted with water and extracted with EtOAc. The organic extracts were washed with brine, dried over $Na_2SO_4$, filtered and concentrated. The residue was purified by preparative TLC to afford the title compound as a light-yellow oil (512 mg). MS obsd. ($ESI^+$): 502.6 $[(M+H)]^+$.

Step 2: tert-butyl (2R,3S,4S)-4-((2-methoxyethoxy)methoxy)-3-((3-(pyridin-3-yl) prop-2-yn-1-yl)oxy)-2-(4-(thiazol-5-yl)benzyl)pyrrolidine-1-carboxylate (18-2). $Pd(PPh_3)+$ (275 mg) and CuI (4 mg) were added to a stirred solution of tert-butyl (2R,3S,4S)-4-((2-methoxyethoxy)methoxy)-3-(prop-2-yn-1-yloxy)-2-(4-(thiazol-5-yl)benzyl)pyrrolidine-1-carboxylate (100 mg) and 3-bromopyridine (63 mg) in $Et_3N$ (5 mL) at room temperature. The resulting mixture was stirred at 80° C. for 2 h under nitrogen atmosphere before it was diluted with water and extracted with EtOAc. The organic extracts were washed with brine, dried over $Na_2SO_4$, filtered and concentrated. The residue was purified by preparative TLC to afford the title compound as a light-yellow oil (95 mg). MS obsd. ($ESI^+$): 579.7 $[(M+H)]^+$.

Step 3: tert-butyl (2R,3S,4S)-4-((2-methoxyethoxy)methoxy)-3-(3-(pyridin-3-yl)propoxy)-2-(4-(thiazol-5-yl)benzyl)pyrrolidine-1-carboxylate (18-3). Under a nitrogen atmosphere. Pd/C (36 mg) was slowly added to a solution of tert-butyl (2R,3S,4S)-4-((2-methoxyethoxy)methoxy)-3-((3-(pyridin-3-yl) prop-2-yn-1-yl)oxy)-2-(4-(thiazol-5-yl)benzyl)pyrrolidine-1-carboxylate (90 mg) in methanol (5 mL). The reaction vessel was fitted with a $H_2$ balloon and after 12 h the reaction mixture was filtered through celite, and the solids were washed with EtOAc. The filtrate was collected and concentrated under reduced pressure to afford the title compound as a yellow oil (90 mg). MS obsd. ($ESI^+$): 583.7 $[(M+H)]^+$.

Step 4: (3S,4S,5R)-4-(3-(pyridin-3-yl)propoxy)-5-(4-(thiazol-5-yl)benzyl)pyrrolidin-3-ol. To a stirred solution of tert-butyl (2R,3S,4S)-4-((2-methoxyethoxy)methoxy)-3-(3-(pyridin-3-yl)propoxy)-2-(4-(thiazol-5-yl)benzyl)pyrrolidine-1-carboxylate (90 mg) in DCM (2 mL) was added trifluoroacetic acid (2 mL) at 0° C. The resulting mixture was stirred at room temperature for 12 h. concentrated and the residue was purified by Prep-HPLC to afford the title compound as a yellow solid (14.5 mg). MS obsd. ($ESI^+$): 395.5 $[(M+H)]^+$. $^1H$ NMR (400 MHz, MeOD) δ 8.96 (s, 1H), 8.44 (s, 1H), 8.39 (d, J=4.9 Hz, 1H), 8.15 (s, 1H), 7.74 (d, J=7.8 Hz, 1H), 7.61 (d, J=8.1 Hz, 2H), 7.38 (t, J=8.5 Hz, 3H), 4.24 (d, J=4.8 Hz, 1H), 3.68-3.60 (m, 1H), 3.53 (d, J=7.2 Hz, 1H), 3.46-3.37 (m, 3H), 3.03 (dd, J=13.5, 8.5 Hz, 1H), 2.92 (dd, J=13.4, 6.6 Hz, 1H), 2.81 (t, J=7.6 Hz, 2H), 2.75 (d, J=10.5 Hz, 1H), 2.03-1.92 (m, 2H).

Example 27: 3-(3-(((2R,3S,4S)-4-hydroxy-2-(4-(thiazol-5-yl)benzyl)pyrrolidin-3-yl)oxy)propyl) thietane 1,1-dioxide Scheme 19

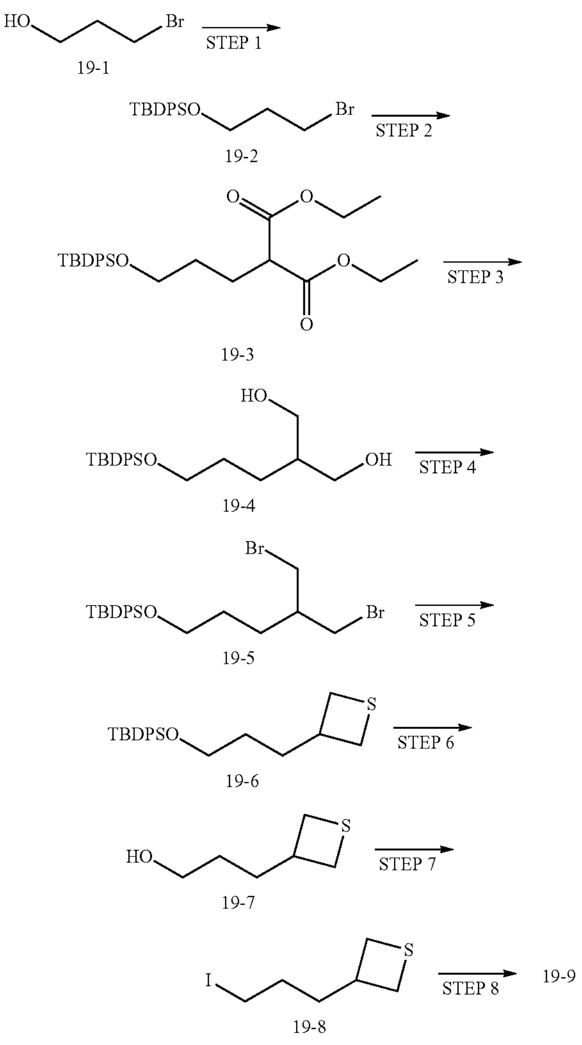

-continued

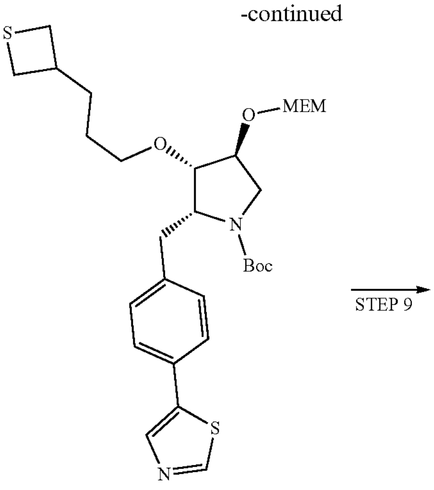

19-9

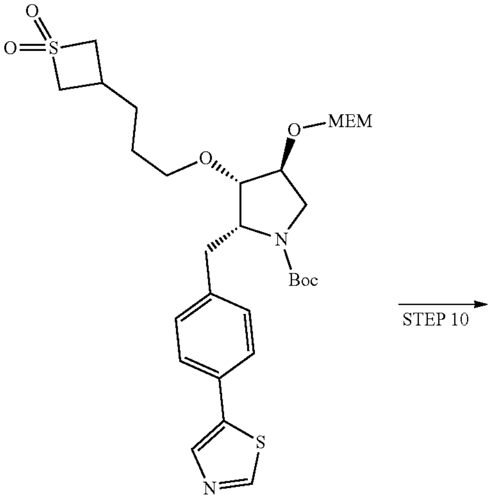

19-10

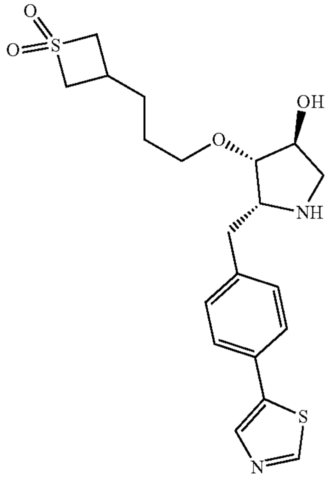

Step 1: (3-bromopropoxy)(tert-butyl)diphenylsilane (19-2). Imidazole (7347 mg) and tert-butylchlorodiphenylsilane (14.8 g) were added to a stirred solution of 3-bromopropan-1-ol (5 g) in DCM (100 mL) at 0° C. The resulting mixture was stirred at room temperature overnight. The reaction was diluted with water and extracted with DCM. The organic extracts were washed with brine, dried over $Na_2SO_4$, filtered and concentrated. The residue was purified by silica gel column chromatography to afford the title compound as a colorless oil (13.1 g). $^1$H NMR (400 MHz, $CDCl_3$) δ 7.76-7.66 (m, 4H), 7.52-7.37 (m, 6H), 3.81 (t, J=5.7 Hz, 2H), 3.61 (t, J=6.6 Hz, 2H), 2.17-2.05 (m, 2H), 1.08 (s, 9H).

Step 2: diethyl 2-(3-((tert-butyldiphenylsilyl)oxy)propyl) malonate (19-3). NaH (953 mg) was added to a stirred solution of diethyl malonate (3.2 g) in THF (100 mL) 0° C. for 30 min followed by the addition of (3-bromopropoxy)(tert-butyl)diphenylsilane (5 g) at 0° C. The resulting mixture was stirred at room temperature for 4 h. The reaction mixture was quenched with water and extracted with EtOAc. The extracts were washed with brine, dried over anhydrous sodium sulfate, filtered and concentrated. The residue was purified by silica gel column chromatography to afford the title compound as a light-yellow oil (2.6 g). MS obsd. ($ESI^+$): 457.2 $[(M+H)]^+$.

Step 3: 2-(3-((tert-butyldiphenylsilyl)oxy)propyl) propane-1,3-diol (19-4). Lithium aluminum hydriden (922 mg) was added to a stirred solution of diethyl 2-(3-((tert-butyldiphenylsilyl)oxy)propyl)malonate (3.7 g) in THF (100 mL) at 0° C. The resulting mixture was stirred at 0° C. for 2 h. The reaction mixture was quenched with water and extracted with EA. The extracts were washed with brine, dried over anhydrous sodium sulfate, filtered and concentrated. The residue was purified by silica gel column chromatography to afford the title compound as a light-yellow oil (2.3 g). $^1$H NMR (400 MHz, DMSO) δ 7.67-7.58 (m, 4H), 7.52-7.39 (m, 6H), 4.28 (t, J=5.2 Hz, 2H), 3.63 (t, J=6.5 Hz, 2H), 3.40-3.33 (m, 4H), 1.61-1.52 (m, 1H), 1.48-1.37 (m, 1H), 1.34-1.22 (m, 3H), 1.00 (s, 9H). Step 4: ((5-bromo-4-(bromomethyl)pentyl)oxy)(tert-butyl)diphenylsilane (19-5). $PPh_3$ (4.9 g) was added to a stirred solution of tetrabromomethane (6.1 g) in THF (100 mL) 0° C. for 5 min followed by the addition of 2-(3-((tert-butyldiphenylsilyl)oxy)propyl) propane-1,3-diol (2.3 g) at 0° C. The resulting mixture was stirred at room temperature for 2 h before it was diluted with water and extracted with EtOAc. The organic extracts were washed with brine, dried over $Na_2SO_4$, filtered and concentrated. The residue was purified by silica gel column chromatography to afford the title compound as a light-yellow oil (1.0 g). $^1$H NMR (400 MHz, DMSO) δ 7.67-7.60 (m, 4H), 7.53-7.41 (m, 6H), 3.70-3.61 (m, 4H), 3.55 (dd, J=10.3, 6.0 Hz, 2H), 2.06-1.98 (m, 1H), 1.62-1.47 (m, 4H), 1.00 (s, 9H).

Step 5: tert-butyldiphenyl(3-(thietan-3-yl)propoxy)silane (19-6). (Sodiosulfanyl) sodium (469 mg) was added to a stirred solution of ((5-bromo-4-(bromomethyl)pentyl)oxy)(tert-butyl)diphenylsilane (1.0 g) in MeCN (30 mL) and $H_2O$ (4 mL) at room temperature. The resulting mixture was stirred at 50° C. overnight. The next day it was diluted with water and extracted with EtOAc. The organic extracts were washed with brine, dried over $Na_2SO_4$, filtered and concentrated. The residue was purified by silica gel column chromatography to afford the title compound as a light-yellow oil (700 mg). $^1$H NMR (400 MHz, CDCl3) δ 7.73-7.62 (m, 4H), 7.50-7.36 (m, 6H), 4.21-4.10 (m, 2H), 3.76-3.64 (m, 2H), 3.24 (dd, J=11.0, 6.6 Hz, 1H), 2.79 (dd, J=11.0, 6.9 Hz, 1H), 2.02-1.91 (m, 1H), 1.66-1.55 (m, 3H), 1.29 (t, J=7.1 Hz, 1H), 1.08 (d, J=1.2 Hz, 9H).

Step 6: 3-(thietan-3-yl) propan-1-ol (19-7). Pyridine hydrofluoride (1 mL) was added to a stirred solution of tert-butyldiphenyl(3-(thietan-3-yl)propoxy)silane (700 mg) in THF (15 mL) at 0° C. The resulting mixture was stirred at 0° C. for 2 h. before it was concentrated and the residue was purified by silica gel column chromatography to afford the title compound as a light yellow oil (150 mg). $^1$H NMR (400 MHz, $CDCl_3$) δ 3.65 (t, J=6.5 Hz, 2H), 3.36-6.26 (m, 1H), 3.19 (t, J=8.4 Hz, 2H), 3.05 (dd, J=9.0, 7.5 Hz, 2H), 1.70-1.60 (m, 2H), 1.54-1.44 (m, 2H).

Step 7: 3-(3-iodopropyl)thietane (19-8). Iodine (96 mg) was added to a stirred solution of imidazole (28 mg) and $PPh_3$ (99 mg) in DCM (3 mL) at 0° C. for 3 min under nitrogen atmosphere followed by the addition of 3-(thietan-3-yl) propan-1-ol (50 mg) at 0° C. The resulting mixture was stirred at room temperature for 4 h under nitrogen atmosphere before it was diluted with water and extracted with EtOAc. The organic extracts were washed with brine, dried over $Na_2SO_4$, filtered, and concentrated. The residue was purified by preparative TLC to afford the title compound 3-(3-iodopropyl)thietane as a light yellow oil (40 mg). $^1$H NMR (400 MHz, $CDCl_3$) δ 3.38-3.24 (m, 1H), 3.24-3.14 (m, 4H), 3.05 (dd, J=9.0, 7.6 Hz, 2H), 1.81-1.62 (m, 4H).

Step 8: tert-butyl (2R,3S,4S)-4-((2-methoxyethoxy)methoxy)-2-(4-(thiazol-5-yl)benzyl)-3-(3-(thietan-3-yl)propoxy)pyrrolidine-1-carboxylate (19-9). $CsOH \cdot H_2O$ (108 mg) and KI (107 mg) were added to a stirred solution of tert-butyl (2R,3S,4S)-3-hydroxy-4-((2-methoxyethoxy)methoxy)-2-(4-(thiazol-5-yl)benzyl)pyrrolidine-1-carboxylate (111 mg) in DMF (10 mL) at 0° C. The resulting mixture was stirred at room temperature overnight. The next day the reaction was diluted with water, and extracted with EtOAc. The organic extracts were washed with brine, dried over $Na_2SO_4$, filtered, and concentrated. The residue was purified by preparative TLC to afford the title compound as a light-yellow oil (50 mg). MS obsd. ($ESI^+$): 578.8 $[(M+H)]^+$.

Step 9: tert-butyl (2R,3S,4S)-3-(3-(1,1-dioxidothietan-3-yl)propoxy)-4-((2-methoxyethoxy)methoxy)-2-(4-(thiazol-5-yl)benzyl)pyrrolidine-1-carboxylate (19-10), m-CPBA (33 mg) was added to a stirred solution of tert-butyl (2R,3S,4S)-4-((2-methoxyethoxy)methoxy)-2-(4-(thiazol-5-yl)benzyl)-3-(3-(thietan-3-yl)propoxy)pyrrolidine-1-carboxylate (45 mg) in DCM (5 mL) at 0° C. The resulting mixture was stirred at room temperature for 2 h. The reaction mixture was quenched with saturated $Na_2S_2O_3$ aqueous solution and extracted with EA. The extracts were washed with brine, dried over anhydrous sodium sulfate, filtered, and concentrated. The residue was purified by preparative TLC to afford the title compound as a light-yellow oil (43 mg). MS obsd. ($ESI^+$): 610.8 $[(M+H)]^+$.

Step 10: 3-(3-(((2R,3S,4S)-4-hydroxy-2-(4-(thiazol-5-yl)benzyl)pyrrolidin-3-yl)oxy)propyl)thietane 1,1-dioxide. TFA (1 mL) was added to a stirred solution of tert-butyl (2R,3S,4S)-3-(3-(1,1-dioxidothietan-3-yl)propoxy)-4-((2-methoxyethoxy)methoxy)-2-(4-(thiazol-5-yl)benzyl)pyrrolidine-1-carboxylate (40 mg) in DCM (2 mL) at 0° C. The resulting mixture was stirred at room temperature overnight. The next day the reaction was concentrated, and the residue was purified by Prep-HPLC to afford the title compound as a white solid (11.9 mg). MS obsd. ($ESI^+$): 422.6 $[(M+H)]^+$. $^1$H NMR (400 MHz, MeOD) δ 8.96 (s, 1H), 8.17 (s, 1H), 7.68-7.60 (m, 2H), 7.44-7.34 (m, 2H), 4.32-4.18 (m, 3H), 3.87-3.77 (m, 2H), 3.69-3.63 (m, 1H), 3.60-3.51 (m, 1H), 3.48-3.37 (m, 3H), 3.04 (dd, J=13.6, 8.4 Hz, 1H), 2.92 (dd, J=13.5, 6.7 Hz, 1H), 2.81-2.74 (m, 1H), 2.63-2.50 (m, 1H), 1.81-1.76 (m, 2H), 1.71-1.56 (m, 2H).

Example 28: (3S,4S,5R)-4-(2-((S)-tetrahydrofuran-3-yl)ethoxy)-5-(4-(thiazol-5-yl)benzyl)pyrrolidin-3-ol Scheme 20

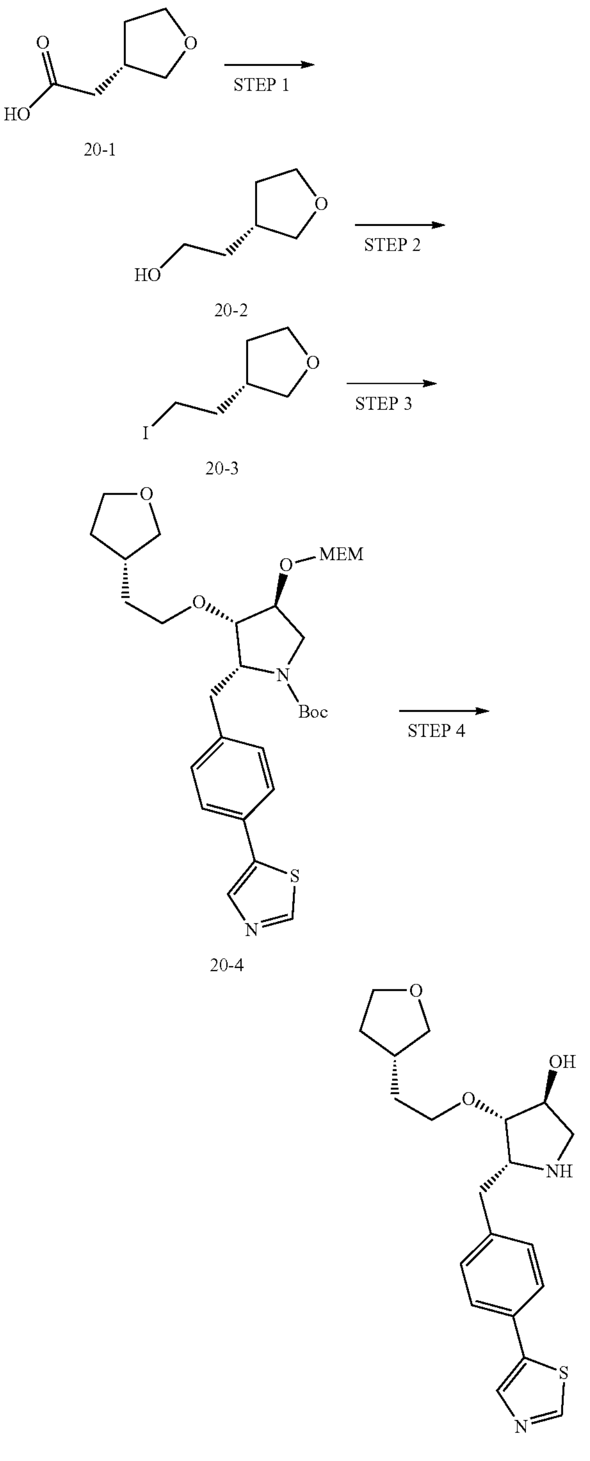

20-1, 20-2, 20-3, 20-4

Step 1: (R)-2-(tetrahydrofuran-3-yl) ethan-1-ol (20-2). Borane-tetrahydrofuran complex (2 mL) was added to a stirred solution of(S)-2-(tetrahydrofuran-3-yl)acetic acid (250 mg) in THF (4 mL) at 0° C. The resulting mixture was stirred at 60° C. overnight. The reaction mixture was quenched with MeOH at 0° C., concentrated, and the crude product was used in the next step directly without further purification. MS obsd. ($ESI^+$): 116.1 $[(M+H)]^+$.

Step 2: (S)-3-(2-iodoethyl)tetrahydrofuran (20-3). Imidazole (404 mg), $PPh_3$ (1.1 g) and Iodine (1.0 g) were added to a stirred solution of (R)-2-(tetrahydrofuran-3-yl) ethan-1-ol (230 mg) in DCM (23 mL) at 0° C. The resulting mixture was stirred at room temperature overnight. The next day the reaction was diluted with water and extracted with EtOAc. The organic extracts were washed with brine, dried over $Na_2SO_4$, filtered, and concentrated. The residue was purified by silica gel column chromatography to afford the title compound as a light-yellow oil (200 mg). MS obsd. ($ESI^+$): 226.0 $[(M+H)]^+$.

Step 3-4: (3S,4S,5R)-4-(2-((S)-tetrahydrofuran-3-yl) ethoxy)-5-(4-(thiazol-5-yl)benzyl)pyrrolidin-3-ol. The title compound was prepared in 37% overall yield as an off-white solid according to General Procedure I using Int-16 (100 mg) and(S)-3-(2-iodoethyl)tetrahydrofuran (97 mg) in THF in STEP 3, and General Procedure VIII in STEP 4. $^1H$ NMR (400 MHz, MeOD) δ 8.96 (s, 1H), 8.16 (s, 1H), 7.69-7.60 (m, 2H), 7.38 (d, J=8.0 Hz, 2H), 4.30 (d, J=5.0 Hz, 1H), 3.62-3.54 (m, 1H), 3.98-3.84 (m, 2H), 3.70-3.63 (m, 1H), 3.71-3.63 (m, 1H), 3.49-3.37 (m, 4H), 3.05 (t, J=11.0 Hz, 1H), 2.94 (dd, J=13.7, 6.6 Hz, 1H), 2.80 (d, J=12.3 Hz, 1H), 2.41-2.31 (m, 1H), 2.17-2.06 (m, 1H), 1.78-1.69 (m, 2H), 1.66-1.55 (m, 1H). MS obsd. ($ESI^+$): 375.2 $[(M+H)]^+$

Example 29: (3S,4S,5R)-4-((6-methoxypyridin-3-yl)methoxy)-5-(4-(thiazol-5-yl)benzyl)pyrrolidin-3-ol Scheme 21

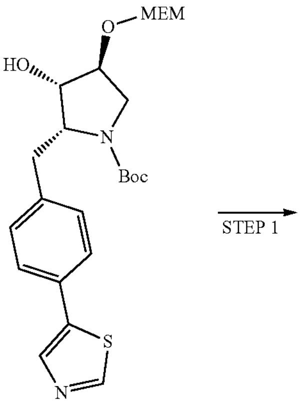

Int-16

-continued

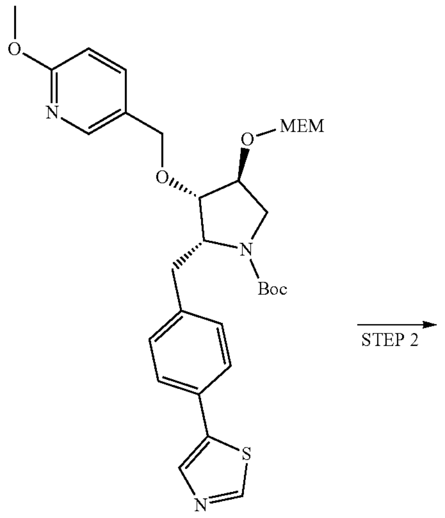

21-2

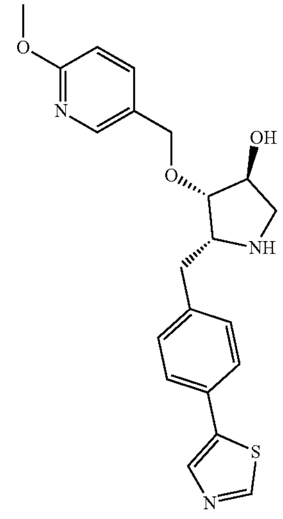

Step 1-2: (3S,4S,5R)-4-((6-methoxypyridin-3-yl) methoxy)-5-(4-(thiazol-5-yl)benzyl)pyrrolidin-3-ol. The title compound was prepared in 57% overall yield as a white solid according to General Procedure I using Int-16 (60 mg) and 5-(bromomethyl)-2-methoxypyridine (73 mg) in DMF in STEP 1, and General Procedure VIII in STEP 2. $^{1}H$ NMR (400 MHz, MeOD) δ 8.96 (s, 1H), 8.19-8.11 (m, 2H), 7.71 (dd, J=8.5, 2.4 Hz, 1H), 7.60-7.54 (m, 2H), 7.33-7.26 (m, 2H), 6.81 (dd, J=8.5, 0.7 Hz, 1H), 4.65 (d, J=11.5 Hz, 1H), 4.44-4.37 (m, 2H), 3.92 (s, 3H), 3.58 (d, J=4.5 Hz, 2H), 3.51-3.42 (m, 1H), 3.04-2.89 (m, 2H), 2.81 (d, J=10.5 Hz, 1H). MS obsd. ($ESI^+$): 397.4 $[(M+H)]^+$.

Example 30: (3S,4S,5R)-4-((4-nitrobenzyl)oxy)-5-(4-(thiazol-5-yl)benzyl)pyrrolidin-3-ol Scheme 22

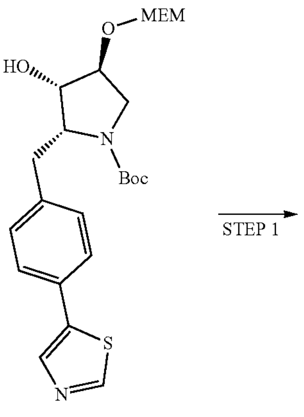

Int-16

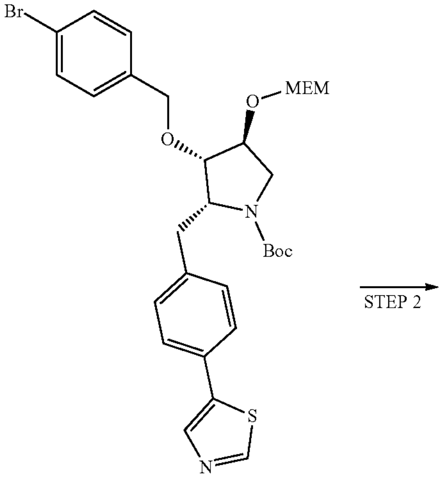

22-2

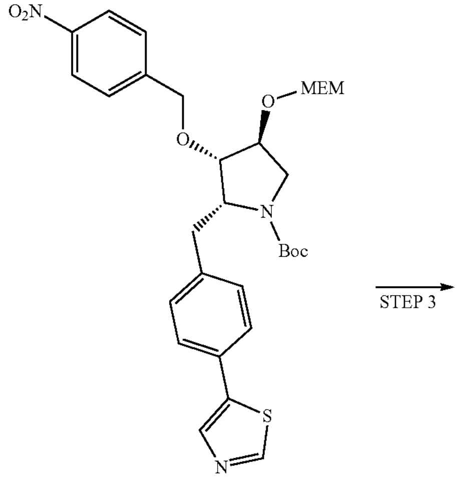

22-3

-continued

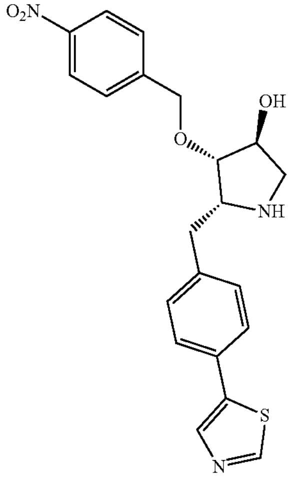 [SMILES: O=[N+]([O-])c1ccc(CO[C@@H]2[C@@H](O)CN[C@@H]2Cc2ccc(-c3cncs3)cc2)cc1]

Step 1: tert-butyl (2R,3S,4S)-3-((4-bromobenzyl)oxy)-4-((2-methoxyethoxy)methoxy)-2-(4-(thiazol-5-yl)benzyl) pyrrolidine-1-carboxylate (22-2). NaH (15 mg) was added to a stirred solution of tert-butyl (2R,3S,4S)-3-hydroxy-4-((2-methoxyethoxy)methoxy)-2-(4-(thiazol-5-yl)benzyl)pyrrolidine-1-carboxylate (100 mg) in DMF (5 mL) at 0° C. The reaction was stirred for 30 min, followed by the addition of 1-bromo-4-(bromomethyl)benzene (107 mg) at 0° C. The resulting mixture was stirred at room temperature for 2 h. diluted with water and extracted with EtOAc. The organic extracts were washed with brine, dried over $Na_2SO_4$, filtered, and concentrated. The residue was purified by preparative TLC to afford the title compound as a light-yellow oil (120 mg). MS obsd. ($ESI^+$): 633.6 $[(M+H)]^+$.

Step 2: tert-butyl (2R,3S,4S)-4-((2-methoxyethoxy) methoxy)-3-((4-nitrobenzyl)oxy)-2-(4-(thiazol-5-yl)benzyl) pyrrolidine-1-carboxylate (22-3). Tert-butyl (2R,3S,4S)-3-((4-bromobenzyl)oxy)-4-((2-methoxyethoxy)methoxy)-2-(4-(thiazol-5-yl)benzyl)pyrrolidine-1-carboxylate (127 mg) and 8-[2-(2-methoxyethoxy)ethyl]-2,5,11,14-tetraoxa-8-azapentadecane (3 mg) were added to a stirred solution of $Pd_2(dba)_3$ (2 mg), t-BuBrettPhos (116 mg) and NaNO3 (27 mg) in t-BuOH (10 mL) at room temperature. The resulting mixture was stirred at 80° C. for 12 h before it was diluted with water and extracted with EtOAc. The organic extracts were washed with brine, dried over $Na_2SO_4$, filtered, and concentrated. The residue was purified by reversed-phase flash chromatography to afford the title compound as a light brown oil (50 mg). MS obsd. ($ESI^+$): 599.7 $[(M+H)]^+$.

Step 3: (3S,4S,5R)-4-((4-nitrobenzyl)oxy)-5-(4-(thiazol-5-yl)benzyl)pyrrolidin-3-ol. The title compound was prepared in 48% overall yield as a white solid according to General Procedure VIII in STEP 3. $^1H$ NMR (400 MHz, MeOD) δ 8.95 (s, 1H), 8.24 (d, J=8.6 Hz, 2H), 8.14 (s, 1H), 7.64 (d, J=8.4 Hz, 2H), 7.58 (d, J=8.1 Hz, 2H), 7.32 (d, J=8.0 Hz, 2H), 4.81 (s, 1H), 4.58 (d, J=13.1 Hz, 1H), 4.38 (dd, J=6.0, 2.5 Hz, 1H), 3.62-3.52 (m, 2H), 3.46 (dd, J=12.3, 5.8 Hz, 1H), 3.07 (dd, J=13.5, 8.3 Hz, 1H), 2.97 (dd, J=13.5, 6.5 Hz, 1H), 2.77 (dd, J=12.3, 2.6 Hz, 1H). MS obsd. ($ESI^+$): 411.5 $[(M+H)]^+$.

Example 31: (3S,4S,5R)-4-((3-nitrobenzyl)oxy)-5-(4-(thiazol-5-yl)benzyl)pyrrolidin-3-ol Scheme 23

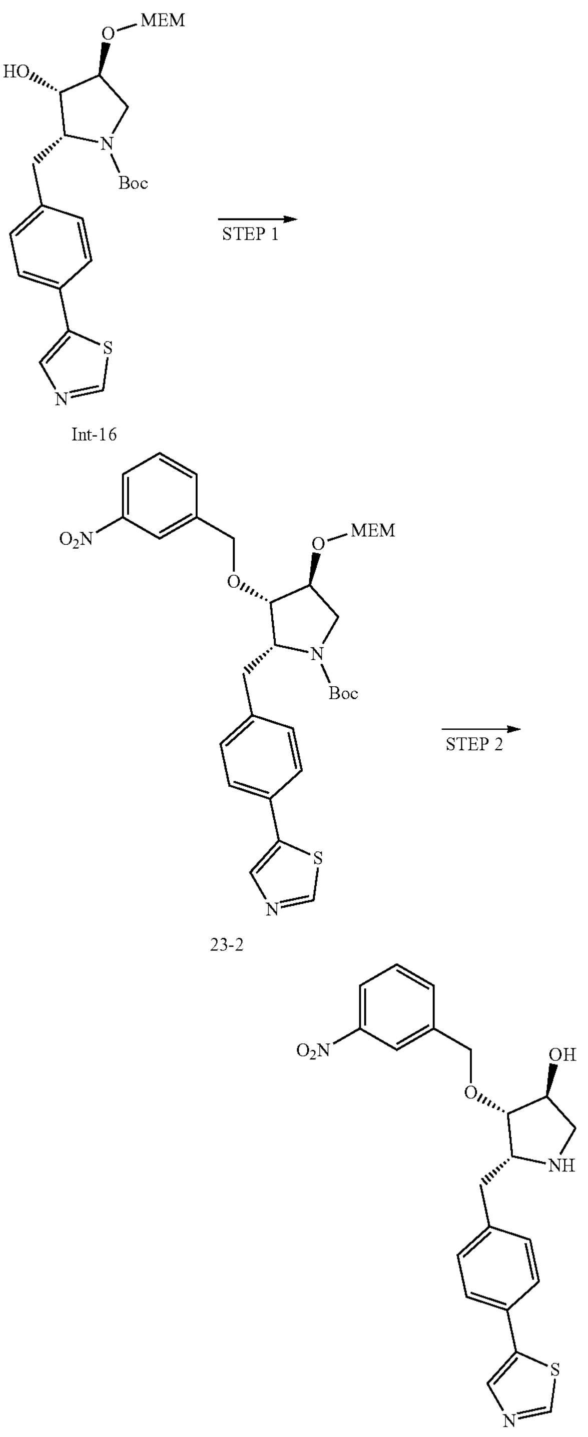

Int-16

23-2

Step 1 and 2: (3S,4S,5R)-4-((3-nitrobenzyl)oxy)-5-(4-(thiazol-5-yl)benzyl)pyrrolidin-3-ol. The title compound was prepared in 54% overall yield as a white solid according to General Procedure I using Int-16 (60 mg) and 1-(bromomethyl)-3-nitrobenzene (55 mg) in DMF in STEP 1, and General Procedure VIII in STEP 2. $^1H$ NMR (400 MHz, MeOD) δ 8.95 (d, J=0.7 Hz, 1H), 8.29 (t, J=2.0 Hz, 1H), 8.21-8.16 (m, 1H), 8.15-8.13 (m, 1H), 7.82-7.78 (m, 1H), 7.62 (t, J=7.9 Hz, 1H), 7.59-7.55 (m, 2H), 7.34-7.29 (m, 2H), 4.82 (d, J=12.4 Hz, 1H), 4.56 (d, J=12.4 Hz, 1H), 4.42-4.37 (m, 1H), 3.63-3.60 (m, 1H), 3.59-3.53 (m, 1H), 3.46 (dd, J=12.2, 5.8 Hz, 1H), 3.05 (dd, J=13.6, 8.5 Hz, 1H), 2.96 (dd, J=13.6, 6.6 Hz, 1H), 2.76 (dd, J=12.2, 2.6 Hz, 1H). MS obsd. ($ESI^+$): 411.5 $[(M+H)]^+$.

Example 32: (3S,4S,5R)-4-(1-phenylethoxy)-5-(4-(thiazol-5-yl)benzyl)pyrrolidin-3-ol Scheme 24

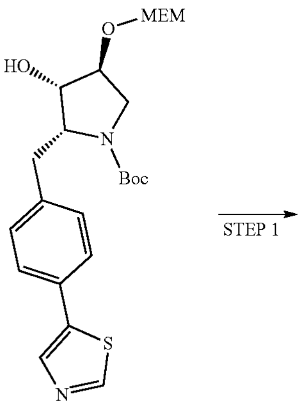

Int-16

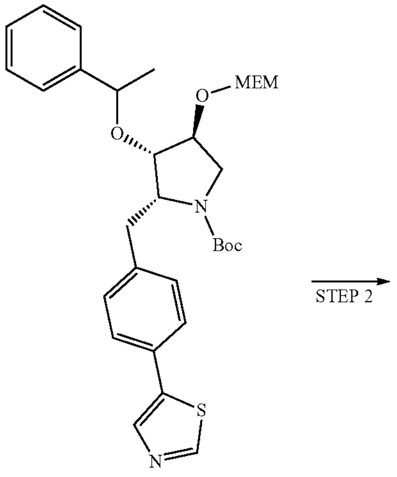

24-2

-continued

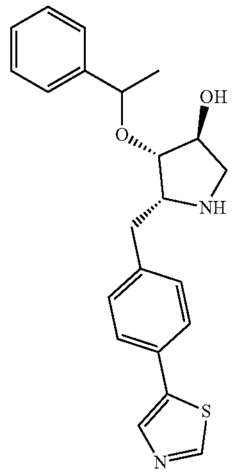

Step 1-2: (3S,4S,5R)-4-(1-phenylethoxy)-5-(4-(thiazol-5-yl)benzyl)pyrrolidin-3-ol. The title compound was prepared in 26% overall yield as a white solid according to General Procedure I using Int-16 (100 mg) and (1-bromoethyl) benzene (47 mg) in DMF in STEP 1, and General Procedure VIII in STEP 2. $^1H$ NMR (400 MHz, MeOD) δ 8.96 (d, J=5.5 Hz, 1H), 8.15 (d, J=21.4 Hz, 1H), 7.69-7.12 (m, 9H), 4.58 (m, 1H), 2.66 (m, 1H), 1.45 (m, 3H), 4.17 (m, 1H), 3.68-3.51 (m, 1H), 3.51-3.36 (m, 1H), 3.30-2.87 (m, 3H). MS obsd. ($ESI^+$): 381.2 $[(M+H)]^+$.

Example 33: (3S,4S,5R)-4-(3-(1H-imidazol-1-yl)propoxy)-5-(4-(thiazol-5-yl)benzyl)pyrrolidin-3-ol Scheme 25

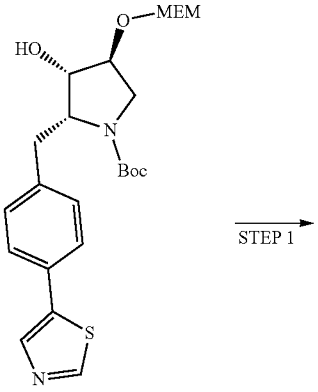

Int-16

-continued

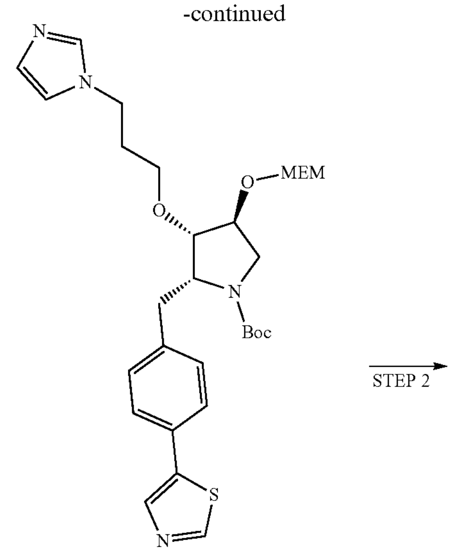

25-2

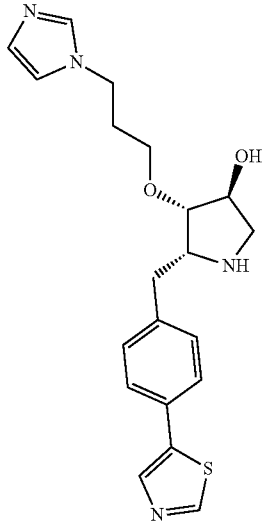

Step 1-2: (3S,4S,5R)-4-(3-(1H-imidazol-1-yl)propoxy)-5-(4-(thiazol-5-yl)benzyl)pyrrolidin-3-ol. The title compound was prepared in 15.1% overall yield as a white solid according to General Procedure I using Int-16 (100 mg) and 1-(3-bromopropyl)-1H-imidazole (196 mg) in DMF in STEP 1, and General Procedure VIII in STEP 2. $^{1}H$ NMR (400 MHz, MeOD) δ 9.01 (d, J=10.1 Hz, 2H), 8.19 (s, 1H), 7.74-7.67 (m, 3H), 7.62 (d, J=1.8 Hz, 1H), 7.46 (d, J=7.9 Hz, 2H), 4.50 (d, J=4.4 Hz, 1H), 4.43 (m, 2H), 4.12 (m, 1H), 3.84-3.73 (m, 2H), 3.62 (m, 2H), 3.29-3.10 (m, 3H), 2.36-2.18 (m, 2H). MS obsd. ($ESI^+$): 385.2 $[(M+H)]^+$.

Example 34: (3S,4S,5R)-4-(3-((S)-pyrrolidin-3-yl)propoxy)-5-(4-(thiazol-5-yl)benzyl)pyrrolidin-3-ol Scheme 26

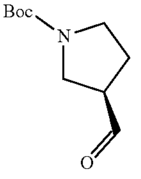

26-1

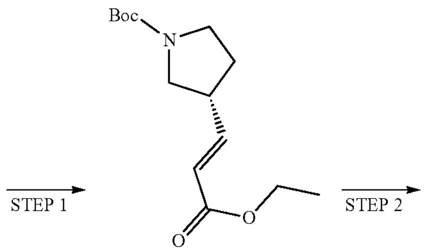

26-2

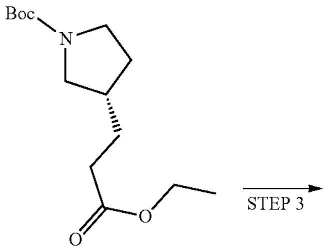

26-3

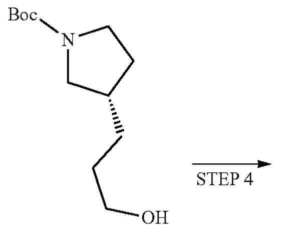

26-4

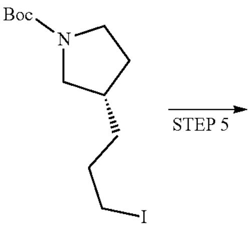

26-5

-continued

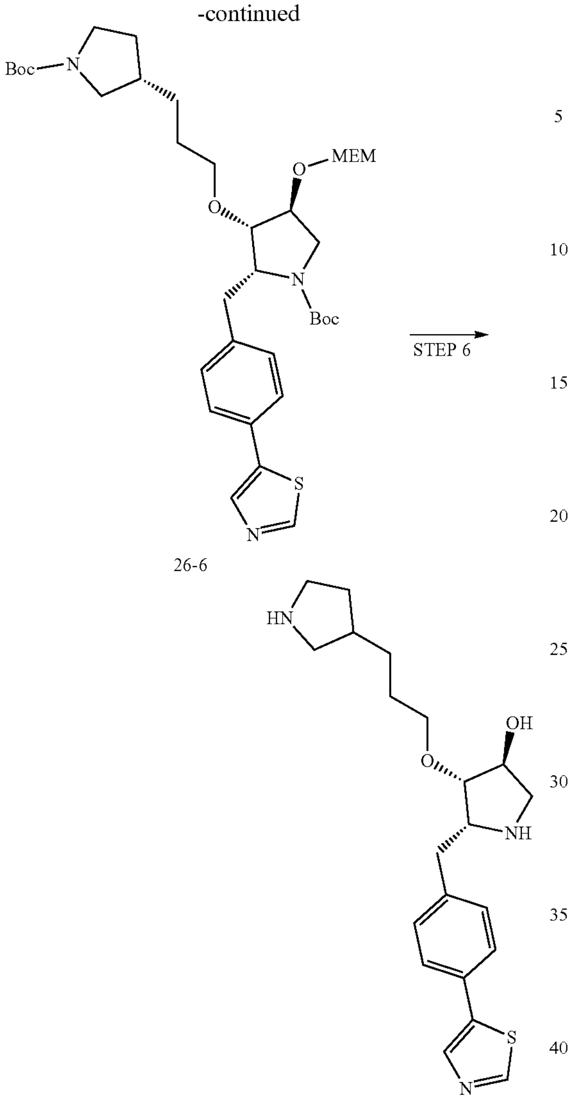

26-6

Step 1: tert-butyl (R,E)-3-(3-ethoxy-3-oxoprop-1-en-1-yl)pyrrolidine-1-carboxylate (26-2). Ethyl 2-(triphenyl-lambda5-phosphanylidene)acetate (874 mg) was added to a stirred solution of tert-butyl (R)-3-formylpyrrolidine-1-carboxylate (500 mg) in THF (10 mL) at room temperature. The resulting mixture was stirred at 80° C. overnight. The next day the reaction was diluted with water, and extracted with EtOAc. The organic extracts were washed with brine, dried over $Na_2SO_4$, filtered, and concentrated. The residue was purified by reversed-phase flash chromatography to afford the title compound as a light-yellow oil (660 mg). MS obsd. ($ESI^+$): 270.2 $[(M+H)]^+$.

Step 2: tert-butyl(S)-3-(3-ethoxy-3-oxopropyl)pyrrolidine-1-carboxylate (26-3). Under a nitrogen atmosphere, Pd/C (260 mg) was slowly added to a solution of tert-butyl (R,E)-3-(3-ethoxy-3-oxoprop-1-en-1-yl)pyrrolidine-1-carboxylate (660 mg) dissolved in EtOH (20 mL) under $N_2$. The reaction vessel was fitted with a $H_2$ balloon and after 12 h the reaction mixture was filtered through Celite, and the solids were washed with EtOAc. The filtrate was collected and concentrated under reduced pressure to afford the title compound as a yellow oil (630 mg). MS obsd. ($ESI^+$): 272.2 $[(M+H)]^+$ Step 3: tert-butyl(S)-3-(3-hydroxypropyl)pyrrolidine-1-carboxylate (26-4). $LiAlH_4$ (2.3 mL) was added to a stirred solution of tert-butyl(S)-3-(3-ethoxy-3-oxopropyl)pyrrolidine-1-carboxylate (620 mg) in THF (10 mL) at 0° C. The resulting mixture was stirred for 2 h before it was quenched with $Na_2SO_4 \cdot 10H_2O$. The resulting mixture was filtered and washed with EtOAc. The filtrate was concentrated under reduced pressure to afford the title compound as a yellow oil (200 mg). MS obsd. ($ESI^+$): 230.2 $[(M+H)]^+$.

Step 4: tert-butyl(S)-3-(3-iodopropyl)pyrrolidine-1-carboxylate (26-5). $PPh_3$ (651 mg) and Iodine (420 mg) were added to a stirred solution of tert-butyl(S)-3-(3-hydroxypropyl)pyrrolidine-1-carboxylate (190 mg) and Imidazole (112 mg) in THF (0.5 mL) at 0° C. The resulting mixture was stirred at room temperature for 2 h. The reaction was quenched with water at room temperature, diluted with water, and extracted with EtOAc. The organic extracts were washed with brine, dried over $Na_2SO_4$, filtered and concentrated. The residue was purified by reversed-phase flash chromatography to afford the title compound as a yellow oil (200 mg). MS obsd. ($ESI^+$): 340.1 $[(M+H)]^+$.

Step 5-6: (3S,4S,5R)-4-(3-(pyrrolidin-3-yl)propoxy)-5-(4-(thiazol-5-yl)benzyl)pyrrolidin-3-ol The title compound was prepared in 48.0% overall yield as a white solid according to General Procedure I using Int-16 (100 mg) and tert-butyl(S)-3-(3-iodopropyl)pyrrolidine-1-carboxylate (65 mg) in DMF in STEP 5, and General Procedure VIII in STEP 6. $^1$H NMR (400 MHz, MeOD) δ 9.00 (s, 1H), 8.19 (s, 1H), 7.71 (d, J=8.1 Hz, 2H), 7.44 (m, 2H), 4.50 (d, J=4.2 Hz, 1H), 4.09-406 (m, 1H), 3.77 (d, J=3.2 Hz, 2H), 3.75-3.56 (m, 2H), 3.54-3.37 (m, 2H), 3.32-3.21 (m, 2H), 3.22-3.08 (m, 2H), 2.86 (t, J=10.3 Hz, 1H), 2.41-2.19 (m, 2H), 1.81-1.50 (m, 5H). MS obsd. ($ESI^+$): 388.2 $[(M+H)]^+$.

Example 35: (3S,4S,5R)-4-(3-(isoindolin-4-yl)propoxy)-5-(4-(thiazol-5-yl)benzyl)pyrrolidin-3-ol Scheme 27

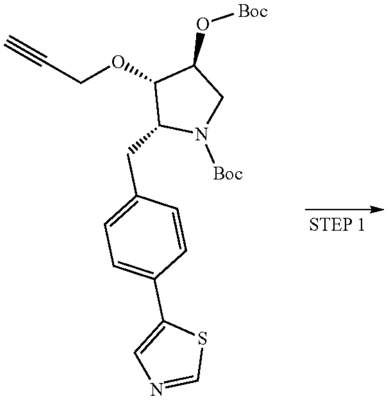

Int-15

-continued

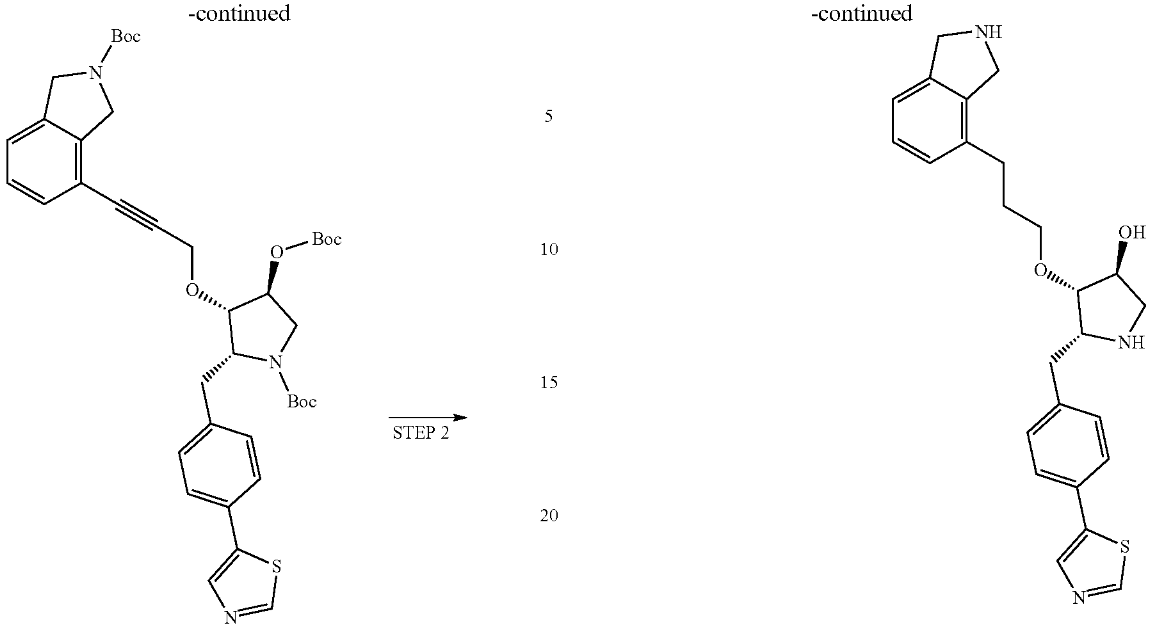

27-2

-continued

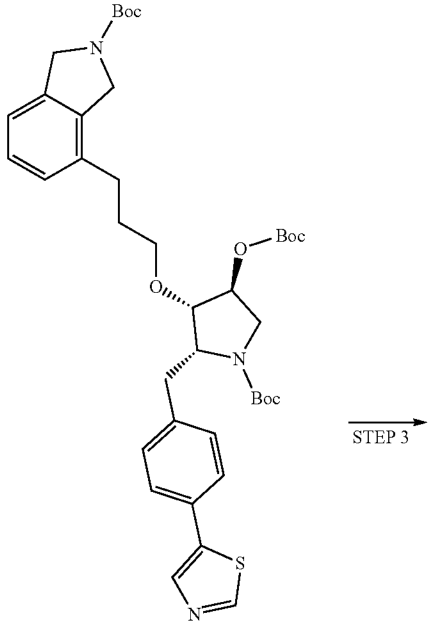

27-3

Step 1-3: (3S,4S,5R)-4-(3-(isoindolin-4-yl)propoxy)-5-(4-(thiazol-5-yl)benzyl)pyrrolidin-3-ol. The title compound was prepared in 35.2% overall yield as a yellow solid according to General Procedure VII using Int-15 (200 mg) and tert-butyl 4-bromoisoindoline-2-carboxylate (231 mg) in STEP 1, and General Procedure VI using tert-butyl 4-(3-(((2R,3S,4S)-1-(tert-butoxycarbonyl)-4-((tert-butoxycarbonyl)oxy)-2-(4-(thiazol-5-yl)benzyl)pyrrolidin-3-yl)oxy) prop-1-yn-1-yl) isoindoline-2-carboxylate in STEP 2, and General Procedure VIII in STEP 3. $^1$H NMR (400 MHz, Methanol-$d_4$) δ 8.99 (d, J=0.7 Hz, 1H), 8.18 (d, J=0.7 Hz, 1H), 7.72-7.65 (m, 2H), 7.44 (d, J=8.0 Hz, 2H), 7.42-7.34 (m, 1H), 7.28 (dd, J=15.1, 7.6 Hz, 2H), 4.69-4.60 (m, 4H), 4.50 (d, J=4.2 Hz, 1H), 4.16-4.05 (m, 1H), 3.82-3.72 (m, 2H), 3.60 (dd, J=4.4, 2.3 Hz, 1H), 3.58-3.49 (m, 1H), 3.31-3.25 (m, 1H), 3.20 (dd, J=12.6, 2.7 Hz, 1H), 3.17-3.10 (m, 1H), 2.77 (dd, J=9.1, 6.5 Hz, 2H), 2.04-1.92 (m, 2H). MS obsd. (ESI$^+$): 436.2 [(M+H)]$^+$.

Example 36: (3S,4S,5R)-5-(4-(thiazol-5-yl)benzyl)-4-(trifluoromethoxy)pyrrolidin-3-ol Scheme 28

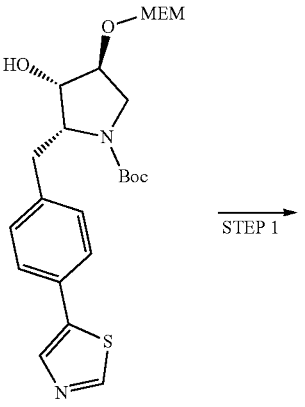

Int-16

-continued

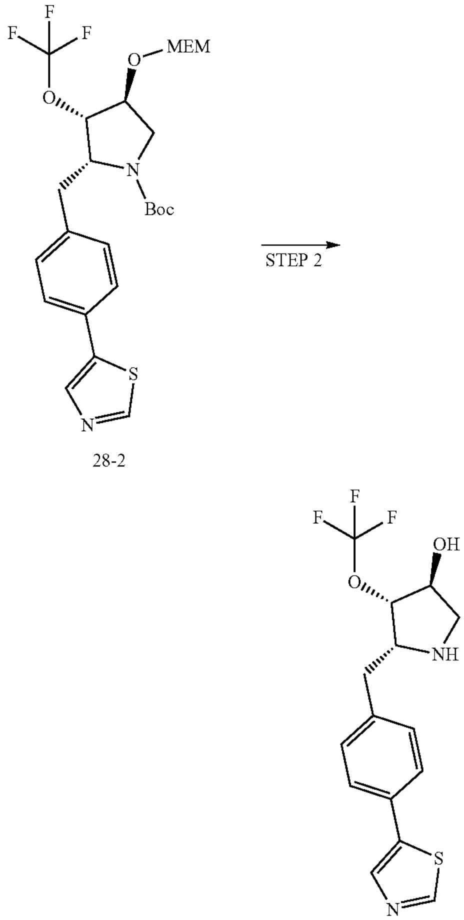

28-2

Step 1: tert-butyl (2R,3S,4S)-4-((2-methoxyethoxy)methoxy)-2-(4-(thiazol-5-yl)benzyl)-3-(trifluoromethoxy)pyrrolidine-1-carboxylat (28-2). KF (37 mg), 2-fluoropyridine (47 mg), and trimethyl(trifluoromethyl)silane (60 mg) were added to a stirred solution of tert-butyl (2R,3S,4S)-3-hydroxy-4-((2-methoxyethoxy)methoxy)-2-(4-(thiazol-5-yl)benzyl)pyrrolidine-1-carboxylate (100 mg), argentio trifluoromethanesulfonate (108 mg), and 4-(chloromethyl)-1-fluoro-1,4-diazabicyclo[2.2.2]octane-1,4-diium; bis(tetrafluoroboranuide) (112 mg) in ethyl acetate (10 mL) at 0° C. The resulting mixture was stirred at room temperature overnight under nitrogen atmosphere. The next day it was diluted with water, and extracted with EtOAc. The organic extracts were washed with brine, dried over $Na_2SO_4$, filtered and concentrated. The residue was purified by reversed-phase flash chromatography to afford the title compound as a yellow oil (15 mg). MS obsd. ($ESI^+$): 533.2 $[(M+H)]^+$.

Step 2: (3S,4S,5R)-5-(4-(thiazol-5-yl)benzyl)-4-(trifluoromethoxy)pyrrolidin-3-ol. The title compound was prepared in 13.2% overall yield as a brown solid according to General Procedure VIII in STEP 2. $^1H$ NMR (400 MHz, MeOD) δ 9.00 (s, 1H), 8.21 (s, 1H), 7.76-7.69 (m, 2H), 7.48 (d, J=8.0 Hz, 2H), 4.87-4.81 (m, 1H), 4.61 (d, J=4.3 Hz, 1H), 4.40-4.31 (m, 1H), 3.68 (dd, J=12.9, 4.3 Hz, 1H), 3.32-3.25 (m, 2H), 3.11 (dd, J=14.6, 9.8 Hz, 1H). MS obsd. ($ESI^+$): 345.1 $[(M+H)]^+$.

Example 37: (3S,4S,5R)-4-(3-(isoxazol-4-yl)propoxy)-5-(4-(thiazol-5-yl)benzyl)pyrrolidin-3-ol Scheme 29

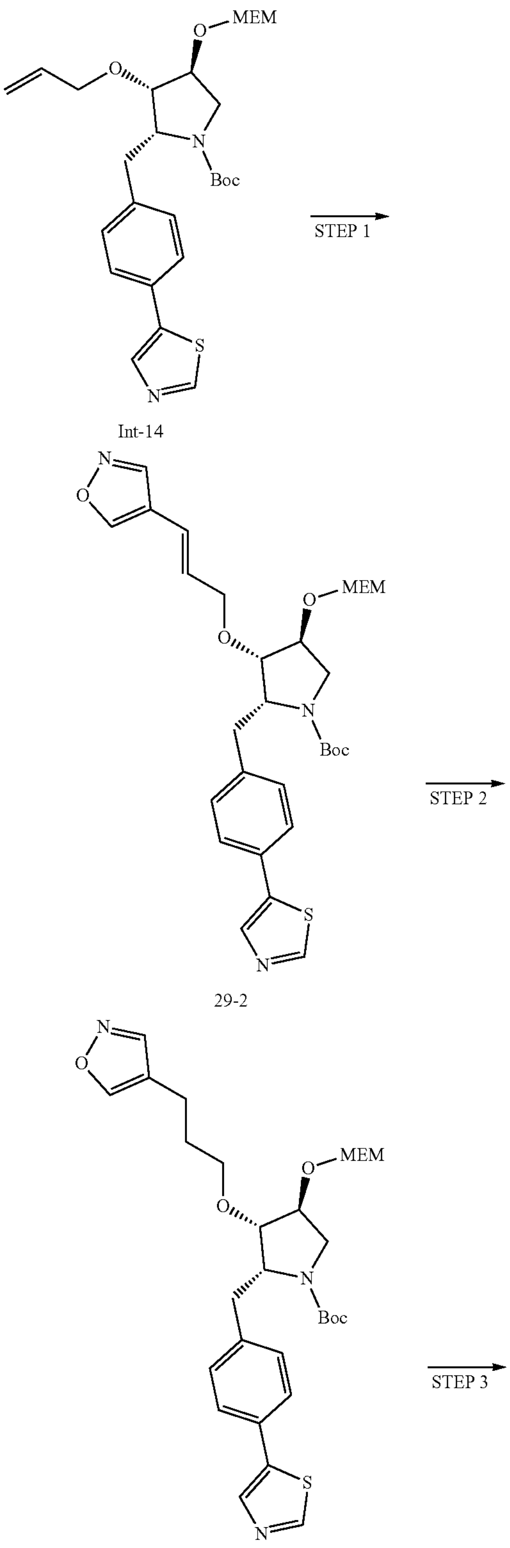

Int-14

29-2

29-3

-continued

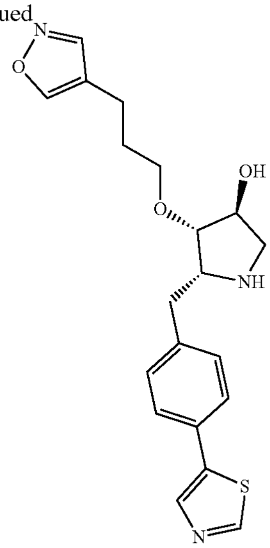

Step 1: tert-butyl (2R,3S,4S)-3-(((E)-3-(isoxazol-4-yl) allyl)oxy)-4-((2-methoxyethoxy)methoxy)-2-(4-(thiazol-5-yl)benzyl)pyrrolidine-1-carboxylate (29-2). $Pd(OAc)_2$ (7 mg) was added to a stirred solution of 1,2-oxazol-4-ylboronic acid (54 mg) and tert-butyl (2R,3S,4S)-4-[(2-methoxyethoxy)methoxy]-3-(prop-2-en-1-yloxy)-2-{[4-(1,3-thiazol-5-yl)phenyl]methyl}pyrrolidine-1-carboxylate (80 mg) in N,N-dimethylacetamide (5 mL) at room temperature. The resulting mixture was stirred at room temperature overnight under oxygen atmosphere before it was diluted with water and extracted with EtOAc. The organic extracts were washed with brine, dried over $Na_2SO_4$, filtered and concentrated. The residue was purified by reversed-phase flash chromatography to afford the title compound as a yellow solid (80 mg). MS obsd. ($ESI^+$): 572.2 $[(M+H)]^+$.

Step 2-3: (3S,4S,5R)-4-(3-(isoxazol-4-yl)propoxy)-5-(4-(thiazol-5-yl)benzyl)pyrrolidin-3-ol. The title compound was prepared in 30.5% overall yield as a white solid according to Reduction reaction with Pd/C, hydrogen; General Procedure VI in STEP 2; Boc Deprotection; General Procedure VIII in STEP 3. $^1H$ NMR (400 MHz, MeOD) δ 8.95 (d, J=0.7 Hz, 1H), 8.48 (s, 1H), 8.36 (s, 1H), 8.15 (d, J=0.7 Hz, 1H), 7.67-7.57 (m, 2H), 7.43-7.32 (m, 2H), 4.25-4.18 (m, 1H), 3.69-3.57 (m, 1H), 3.52-3.42 (m, 1H), 3.42-3.35 (m, 3H), 3.00 (dd, J=13.4, 8.7 Hz, 1H), 2.89 (dd, J=13.4, 6.4 Hz, 1H), 2.70 (dd, J=12.3, 2.6 Hz, 1H), 2.66-2.60 (m, 2H), 2.00-1.83 (m, 2H). MS obsd. ($ESI^+$): 386.1 $[(M+H)]^+$.

Example 38 (3S,4S,5R)-4-(3-(piperazin-1-yl)propoxy)-5-(4-(thiazol-5-yl)benzyl)pyrrolidin-3-ol Scheme 30

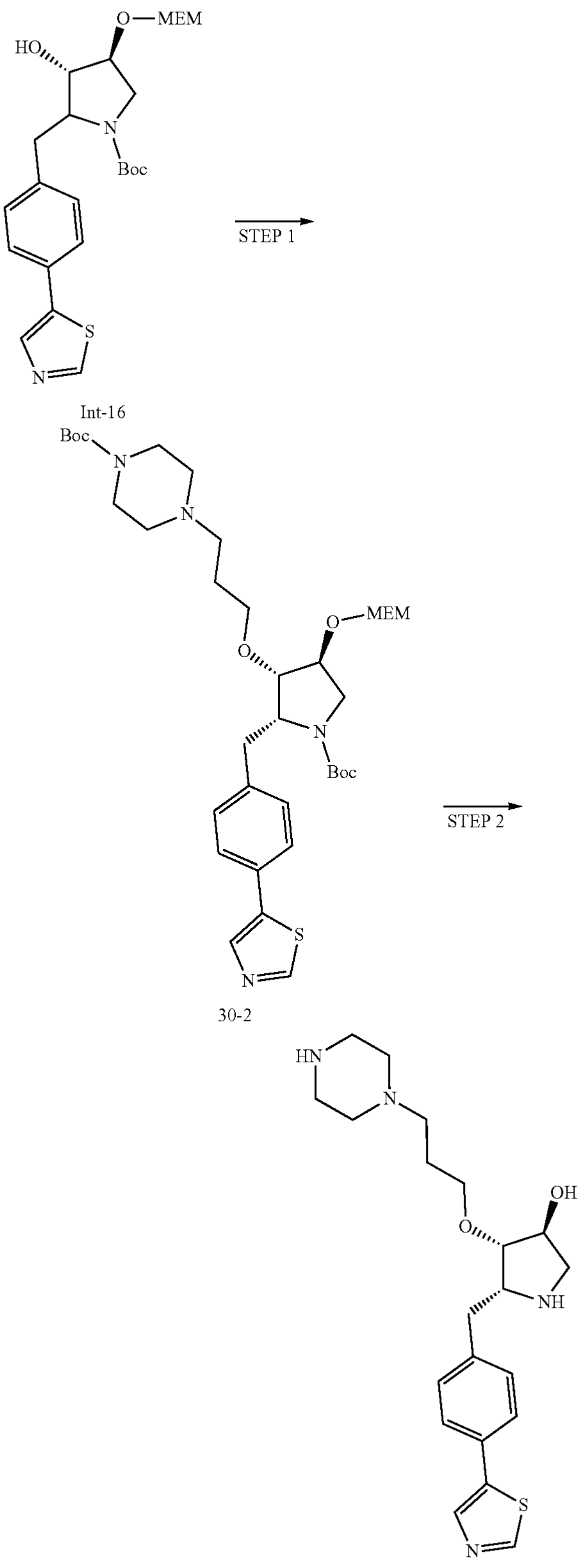

Int-16

30-2

Step 1-2: (3S,4S,5R)-4-(3-(piperazin-1-yl)propoxy)-5-(4-(thiazol-5-yl)benzyl)pyrrolidin-3-ol. The title compound was prepared in 40.1% overall yield as an off-white solid according to General Procedure I using Int-16 (80 mg) and tert-butyl 4-(3-bromopropyl) piperazine-1-carboxylate (106 mg) in DMF in STEP 1, and General Procedure VIII in STEP 2. $^1$H NMR (400 MHz, MeOD) δ 9.00 (s, 1H), 8.19 (s, 1H), 7.71 (dd, J=12.0, 5.6 Hz, 2H), 7.45 (d, J=8.2 Hz, 2H), 4.51 (d, J=4.8 Hz, 1H), 4.10 (s, 1H), 3.80 (s, 3H), 3.73-3.50 (m, 9H), 3.37 (s, 1H), 3.31-3.23 (m, 2H), 3.17 (dd, J=18.3, 10.7 Hz, 2H), 2.09 (d, J=31.8 Hz, 2H). MS obsd. (ESI$^+$): 403.2 [(M+H)]$^+$.

Example 39: (3S,4S,5R)-4-(2-(2-azaspiro[3.3]heptan-6-yl)ethoxy)-5-(4-(thiazol-5-yl)benzyl)pyrrolidin-3-ol Scheme 31

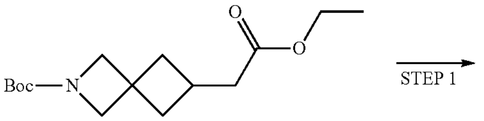

31-1

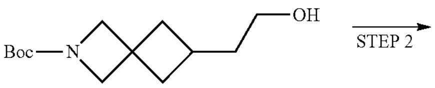

31-2

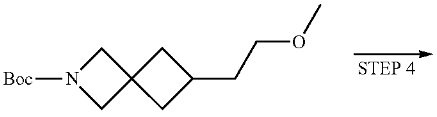

31-3

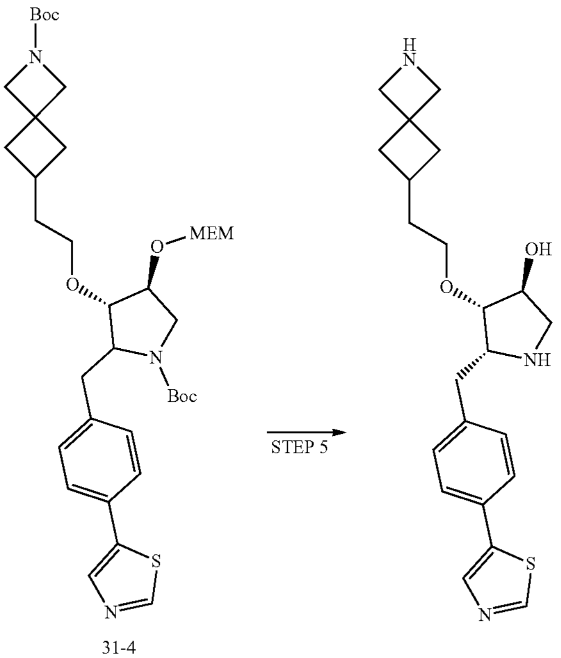

31-4

Step 1: tert-butyl 6-(2-hydroxyethyl)-2-azaspiro[3.3]heptane-2-carboxylate (31-2). Diisobutylaluminium hydride (4.7 mL) was added to a stirred solution of tert-butyl 6-(2-ethoxy-2-oxoethyl)-2-azaspiro[3.3]heptane-2-carboxylate (450 mg) in THF (5 mL) at 0° C. The resulting mixture was stirred at room temperature overnight. The reaction mixture was quenched by water and extracted with DCM. The residue was purified by silica gel column chromatography to afford the title compound as a light-yellow oil (250 mg). MS obsd. (ESI$^+$): 242.2 [(M+H)]$^+$.

Step 2: tert-butyl 6-(2-((methylsulfonyl)oxy)ethyl)-2-azaspiro[3.3]heptane-2-carboxylate (31-3). $Et_3N$ (63 mg) and chlorotrimethylsilane (45 mg) were added to a stirred solution of tert-butyl 6-(2-hydroxyethyl)-2-azaspiro[3.3]heptane-2-carboxylate (50 mg) in DCM (2 mL) at 0° C. The resulting mixture was stirred overnight before it was diluted with water and extracted with DCM. The organic extracts were washed with brine, dried over $Na_2SO_4$, filtered, and concentrated. The residue was purified by silica gel column chromatography to afford the title compound as a light-yellow oil (40 mg). MS obsd. (ESI$^+$): 320.1 [(M+H)]$^+$.

Step 3-4: (3S,4S,5R)-4-(2-(2-azaspiro[3.3]heptan-6-yl)ethoxy)-5-(4-(thiazol-5-yl)benzyl)pyrrolidin-3-ol. The title compound was prepared in 30.1% overall yield as a light-yellow solid according to General Procedure I using Int-16 (80 mg) and tert-butyl 6-[2-(methanesulfonyloxy)ethyl]-2-azaspiro[3.3]heptane-2-carboxylate (55 mg) in DMF in STEP 1, and General Procedure VIII in STEP 2. $^1$H NMR (400 MHz, MeOD) δ 9.00 (s, 1H), 8.19 (s, 1H), 7.74-7.67 (m, 2H), 7.47-7.40 (m, 2H), 4.46 (d, J=4.2 Hz, 1H), 4.13 (s, 2H), 4.10-4.03 (m, 1H), 4.00 (s, 2H), 3.74-3.69 (m, 1H), 3.69-3.53 (m, 2H), 3.46-3.37 (m, 1H), 3.29-3.01 (m, 3H), 2.50-2.41 (m, 2H), 2.39-2.26 (m, 1H), 2.07-1.94 (m, 2H), 1.74 (q, J=6.7 Hz, 2H). MS obsd. (ESI$^+$): 400.1 [(M+H)]$^+$.

Example 40: 1-(2-(((2R,3S,4S)-4-hydroxy-2-(4-(thiazol-5-yl)benzyl)pyrrolidin-3-yl)oxy)ethyl)tetrahydropyrimidin-2(1H)-one Scheme 32

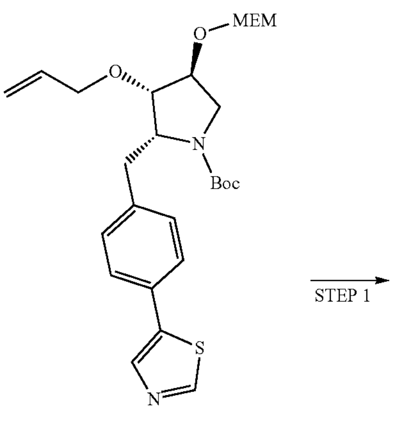

Int-14

-continued
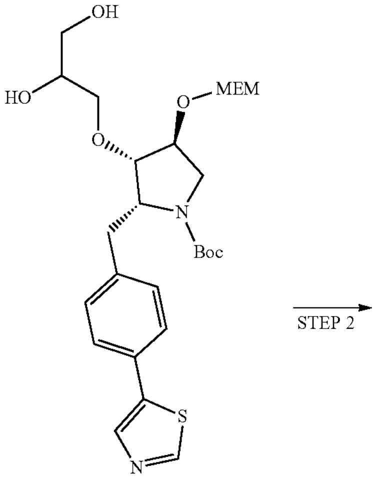
32-2
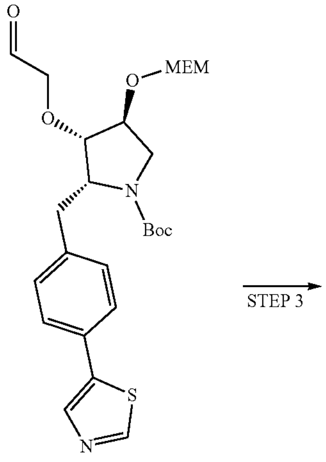
32-3
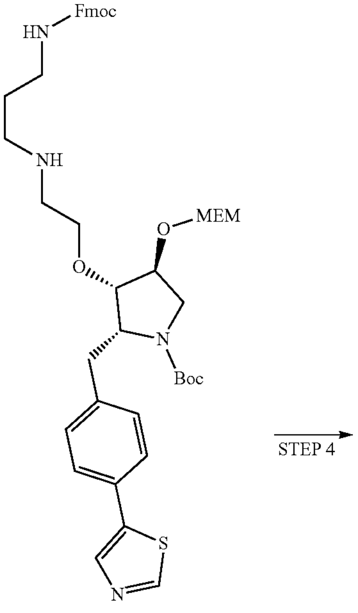
32-4
-continued
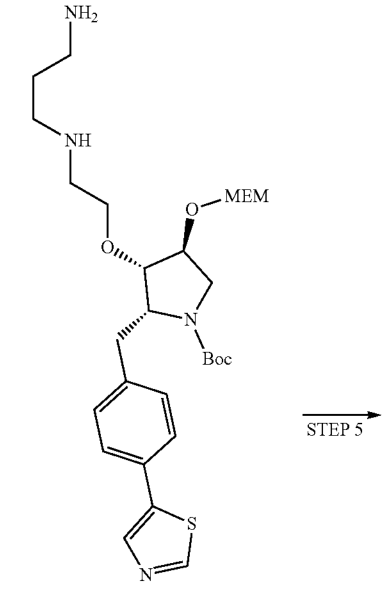
32-5
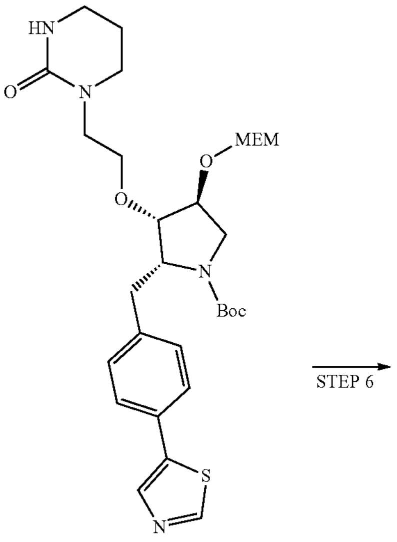
32-6

-continued

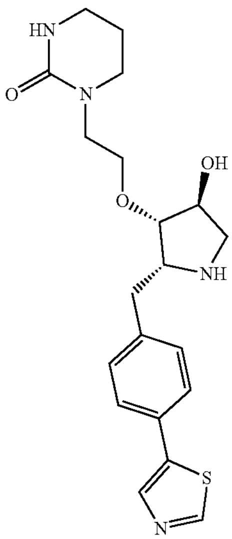

Step 1: tert-butyl (2R,3S,4S)-3-(2,3-dihydroxypropoxy)-4-[(2-methoxyethoxy)methoxy]-2-{[4-(1,3-thiazol-5-yl)phenyl]methyl}pyrrolidine-1-carboxylate (32-2). 4-methylmorpholin-4-ium-4-olate (125 mg) and 2-hydroxypropane-1,2,3-tricarboxylic acid (205 mg) were added to a stirred solution of tert-butyl (2R,3S,4S)-4-[(2-methoxyethoxy)methoxy]-3-(prop-2-en-1-yloxy)-2-{[4-(1,3-thiazol-5-yl)phenyl]methyl}pyrrolidine-1-carboxylate (270 mg) and Potassium osmate(VI) dihydrate (98 mg) in t-BuOH (4 mL) and $H_2O$ (2 mL) at 0° C. The resulting mixture was stirred at room temperature for 2 h before it was diluted with water and extracted with DCM. The organic extracts were washed with brine, dried over $Na_2SO_4$, filtered, and concentrated. The residue was purified by silica gel column chromatography to afford the title compound as a light-yellow oil (250 mg). MS obsd. ($ESI^+$): 539.2 $[(M+H)]^+$.

Step 2: tert-butyl (2R,3S,4S)-4-((2-methoxyethoxy)methoxy)-3-(2-oxoethoxy)-2-(4-(thiazol-5-yl)benzyl)pyrrolidine-1-carboxylate (32-3). $NaIO_4$ (298 mg) was added to a stirred solution of tert-butyl (2R,3S,4S)-3-(2,3-dihydroxypropoxy)-4-[(2-methoxyethoxy)methoxy]-2-{[4-(1,3-thiazol-5-yl)phenyl]methyl}pyrrolidine-1-carboxylate (250 mg) in t-BuOH (4 mL) and $H_2O$ (2 mL) at 0° C. The resulting mixture was stirred at room temperature for overnight before it was diluted with water and extracted with DCM. The organic extracts were washed with brine, dried over $Na_2SO_4$, filtered, and concentrated. The residue was purified by reversed-phase flash chromatography to afford the title compound as a light-yellow oil (150 mg). MS obsd. ($ESI^+$): 507.1 $[(M+H)]^+$.

Step 3: tert-butyl (2R,3S,4S)-3-(2-((3-((((9H-fluoren-9-yl)methoxy) carbonyl)amino)propyl)amino)ethoxy)-4-((2-methoxyethoxy)methoxy)-2-(4-(thiazol-5-yl)benzyl)pyrrolidine-1-carboxylate (32-4). HOAc (35 mg) and Sodium cyanoborohydride (25 mg) were added to a stirred solution of tert-butyl (2R,3S,4S)-4-((2-methoxyethoxy)methoxy)-3-(2-oxoethoxy)-2-(4-(thiazol-5-yl)benzyl)pyrrolidine-1-carboxylate (100 mg) and 9H-fluoren-9-ylmethyl N-(3-aminopropyl) carbamate (87 mg) in methanol (5 mL) at 0° C. The resulting mixture was stirred at room temperature for 2 h before it was diluted with water and extracted with DCM. The organic extracts were washed with brine, dried over $Na_2SO_4$, filtered and concentrated. The residue was purified by reversed-phase flash chromatography to afford the title compound as a light-yellow oil (120 mg). MS obsd. ($ESI^+$): 787.2 $[(M+H)]^+$.

Step 4: tert-butyl (2R,3S,4S)-3-(2-((3-aminopropyl)amino)ethoxy)-4-((2-methoxyethoxy)methoxy)-2-(4-(thiazol-5-yl)benzyl)pyrrolidine-1-carboxylate (32-5). Piperidine (1 mL) was added to a stirred solution of tert-butyl (2R,3S,4S)-3-(2-((3-((((9H-fluoren-9-yl)methoxy) carbonyl)amino)propyl)amino)ethoxy)-4-((2-methoxyethoxy)methoxy)-2-(4-(thiazol-5-yl)benzyl)pyrrolidine-1-carboxylate (50 mg) in anhydrous DMF (3 mL) at 0° C. The resulting mixture was stirred at room temperature for 2 h before it was diluted with water and extracted with DCM. The organic extracts were washed with brine, dried over $Na_2SO_4$, filtered and concentrated. The residue was purified by reversed-phase flash chromatography to afford the title compound as a light-yellow oil (50 mg). MS obsd. ($ESI^+$): 565.2 $[(M+H)]^+$.

Step 5: tert-butyl (2R,3S,4S)-4-((2-methoxyethoxy)methoxy)-3-(2-(2-oxotetrahydropyrimidin-1(2H)-yl)ethoxy)-2-(4-(thiazol-5-yl)benzyl)pyrrolidine-1-carboxylate (32-6). CDI (86 mg) and $Et_3N$ (53 mg) were added to a stirred solution of tert-butyl (2R,3S,4S)-3-(2-((3-aminopropyl)amino)ethoxy)-4-((2-methoxyethoxy)methoxy)-2-(4-(thiazol-5-yl)benzyl)pyrrolidine-1-carboxylate (100 mg) in THF (3 mL) at 0° C. The resulting mixture was stirred at 60° C. overnight. The resulting mixture was purified by reversed-phase flash chromatography to afford the title compound as a light-yellow oil (60 mg). MS obsd. ($ESI^+$): 591.2 $[(M+H)]^+$.

Step 6: 1-(2-(((2R,3S,4S)-4-hydroxy-2-(4-(thiazol-5-yl)benzyl)pyrrolidin-3-yl)oxy)ethyl)tetrahydropyrimidin-2(1H)-one. The title compound was prepared in 10.1% overall yield as a white solid according to General Procedure VIII in STEP 6. $^1H$ NMR (400 MHz, MeOD) δ 8.96 (s, 1H), 8.17 (s, 1H), 7.68-7.62 (m, 2H), 7.39 (d, J=8.0 Hz, 2H), 4.31 (d, J=5.1 Hz, 1H), 3.75 (s, 1H), 3.62-3.50 (m, 4H), 3.50-3.40 (m, 4H), 3.28 (t, J=5.9 Hz, 2H), 3.08 (dd, J=13.2, 8.7 Hz, 1H), 2.94 (dd, J=13.5, 6.8 Hz, 1H), 2.82 (d, J=12.3 Hz, 1H), 2.02-1.86 (m, 2H). MS obsd. ($ESI^+$): 417.1 $[(M+H)]^+$.

Example 41: 3-(3-(((2R,3S,4S)-4-hydroxy-2-(4-(thiazol-5-yl)benzyl)pyrrolidin-3-yl)oxy)propyl)tetrahydrothiophene 1,1-dioxide Scheme 33

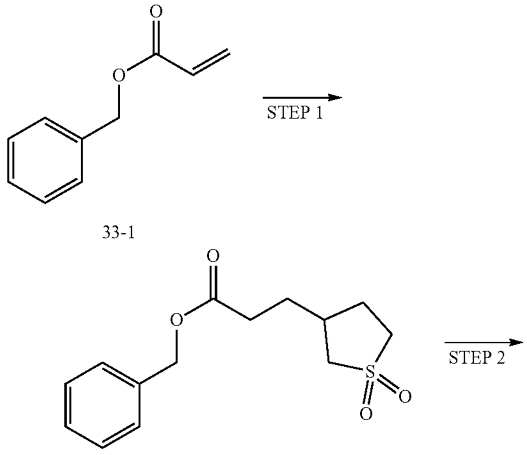

33-1

33-2

-continued

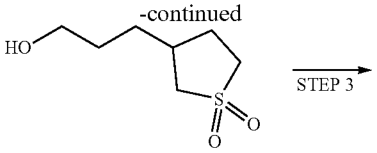

33-3

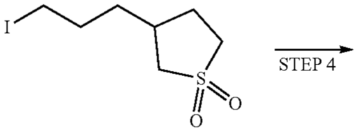

33-4

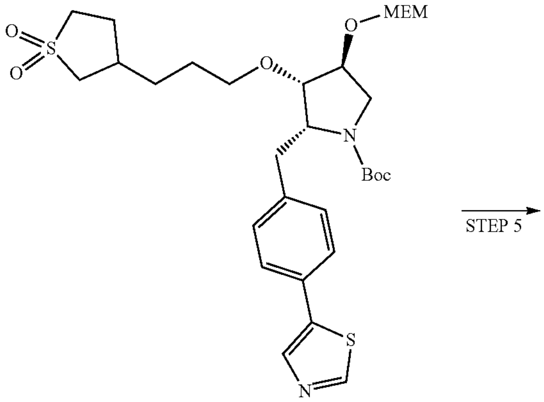

33-5

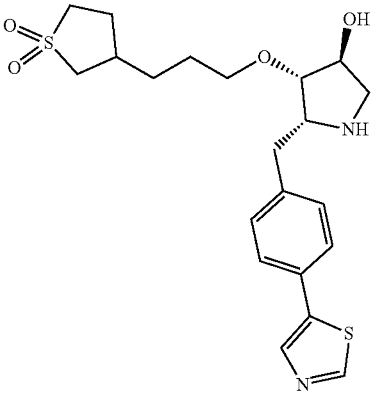

Step 1: benzyl 3-(1,1-dioxidotetrahydrothiophen-3-yl) propanoate (33-2). $FeCl_3$ (500 mg) was added to a solution of benzyl prop-2-enoate (1 g) and 1lambda6-thiolane-1,1-dione (3.7 g) in MeCN (15 mL). The vial was sealed and then placed on a stir plate 2-3 inches away from a 390 nm Kessil lamp. Ambient temperature was maintained with the use of a fan above the set-up. After 36 hours, the reaction mixture was concentrated in vacuo and purified using silica gel flash column chromatography, using ethyl acetate/hexanes as the eluent. The residue was purified by reversed-phase flash chromatography to afford the title compound as a yellow oil (800 mg). MS obsd. ($ESI^+$): 283.1 $[(M+H)]^+$.

Step 2: 3-(3-hydroxypropyl)tetrahydrothiophene 1,1-dioxide (33-3). Lithium aluminum hydride (134 mg) was added to a stirred solution of benzyl 3-(1,1-dioxo-1lambda6-thiolan-3-yl) propanoate (400 mg) in THF (8 mL) at 0° C.

The resulting mixture was stirred at for 2 h before it was quenched by the addition of $Na_2SO_4{\cdot}10H_2O$ in THF (20 mL) at 0° C., filtered, and washed with THF. The filtrate was concentrated under reduced pressure. The resulting mixture was used in the next step directly without further purification. MS obsd. ($ESI^+$): 179.1 $[(M+H)]^+$.

Step 3: 3-(3-iodopropyl)tetrahydrothiophene 1,1-dioxide (33-4). 2H-imidazole (125 mg), Iodine (259 mg) and 3-(3-hydroxypropyl)tetrahydrothiophene 1,1-dioxide (140 mg) were added to a stirred solution of $PPh_3$ (268 mg) in DCM (5 mL) at 0° C. The resulting mixture was stirred at room temperature overnight before it was diluted with water and extracted with DCM. The organic extracts were washed with brine, dried over $Na_2SO_4$, filtered, and concentrated. The residue was purified by reversed-phase flash chromatography to afford the title compound as a yellow oil (120 mg). MS obsd. ($ESI^+$): 289.0 $[(M+H)]^+$.

Step 4-5:3-(3-(((2R,3S,4S)-4-hydroxy-2-(4-(thiazol-5-yl) benzyl)pyrrolidin-3-yl)oxy)propyl)tetrahydrothiophene 1,1-dioxide. The title compound was prepared in 15.5% overall yield as a white solid according to General Procedure I using Int-16 (100 mg) and 3-(3-iodopropyl)tetrahydrothiophene 1,1-dioxide (124 mg) in DMF in STEP 1, and General Procedure VIII in STEP 2. $^1H$ NMR (400 MHz, Methanol-$d_4$) δ 8.96 (s, 1H), 8.17 (s, 1H), 7.66-7.61 (m, 2H), 7.42-7.38 (m 2H), 4.42 (d, J=4.0 Hz, 1H), 3.66-3.55 (m, 2H), 3.45-3.42 (m, 4H), 3.24-3.18 (m, 2H), 3.12-3.02 (m, 2H), 2.96-2.91 (m, 1H), 2.79-2.70 (m, 2H), 2.47 (s, 1H), 1.39 (s, 1H), 1.87-1.81 (m, 1H), 1.66-1.64 (s, 3H). MS obsd. ($ESI^+$): 437.1 $[(M+H)]^+$.

Example 42: (3S,4S,5R)-5-(4-(thiazol-5-yl)benzyl)-4-(3-(trifluoromethoxy)propoxy)pyrrolidin-3-ol Scheme 34

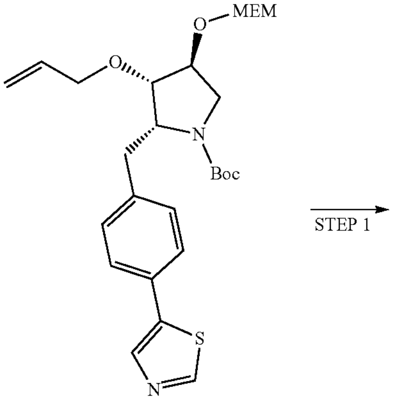

Int-14

-continued

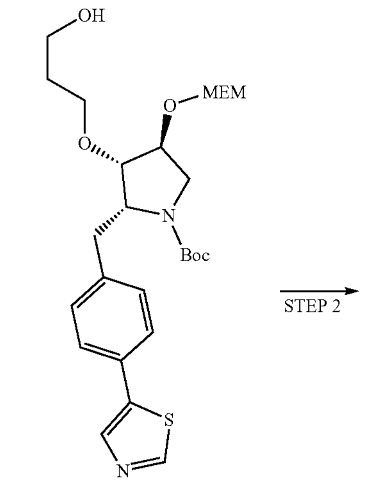

34-2

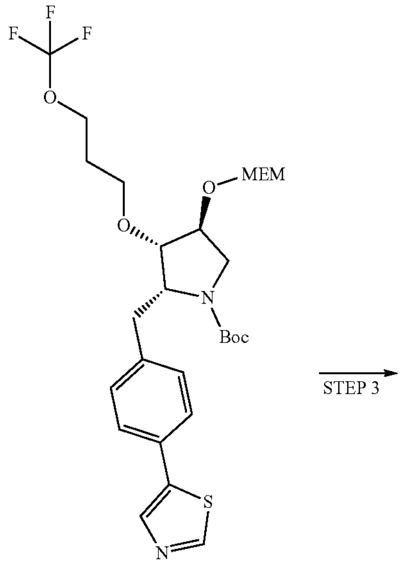

34-3

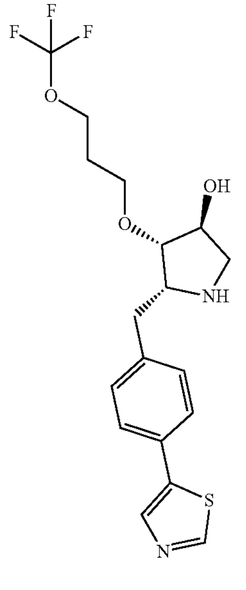

Step 1: tert-butyl (2R,3S,4S)-3-(3-hydroxypropoxy)-4-((2-methoxyethoxy)methoxy)-2-(4-(thiazol-5-yl)benzyl)pyrrolidine-1-carboxylate (34-2). Borane-tetrahydrofuran complex (153 mg) was added to a stirred solution of tert-butyl (2R,3S,4S)-3-(allyloxy)-4-((2-methoxyethoxy)methoxy)-2-(4-(thiazol-5-yl)benzyl)pyrrolidine-1-carboxylate (300 mg) in THF (10 mL) at 0° C., followed by the addition of NaOH (71 mg) and $H_2O_2$ (22 mg). The reaction mixture was diluted with water and extracted with DCM. The organic extracts were washed with brine, dried over $Na_2SO_4$, filtered and concentrated. The residue was purified by reversed-phase flash chromatography to afford the title compound as a yellow oil (250 mg). MS obsd. ($ESI^+$): 523.2 $[(M+H)]^+$.

Step 2: tert-butyl (2R,3S,4S)-4-((2-methoxyethoxy)methoxy)-2-(4-(thiazol-5-yl)benzyl)-3-(3-(trifluoromethoxy)propoxy)pyrrolidine-1-carboxylate (34-3). KF (83 mg), 2-fluoropyridine (92 mg) and trimethyl(trifluoromethyl)silane (136 mg) were added to a stirred solution of tert-butyl (2R,3S,4S)-3-(3-hydroxypropoxy)-4-((2-methoxyethoxy)methoxy)-2-(4-(thiazol-5-yl)benzyl)pyrrolidine-1-carboxylate (250 mg) silver trifluoromethanesulfonate (245 mg) and 4-(chloromethyl)-1-fluoro-1,4-diazabicyclo[2.2.2]octane-1,4-diium; bis (tetrafluoroboranuide) (254 mg) in ethyl acetate (10 mL) at room temperature. The resulting mixture was stirred overnight at room temperature under nitrogen atmosphere. The next day it was diluted with water and extracted with DCM. The organic extracts were washed with brine, dried over $Na_2SO_4$, filtered and concentrated. The residue was purified by reversed-phase flash chromatography to afford the title compound as a yellow solid (30 mg). MS obsd. ($ESI^+$): 591.2 $[(M+H)]^+$.

Step 3: (3S,4S,5R)-5-(4-(thiazol-5-yl)benzyl)-4-(3-(trifluoromethoxy)propoxy)pyrrolidin-3-ol. The title compound was prepared in 20.6% overall yield as an off-white solid according to General Procedure VIII in STEP 3.1H NMR (400 MHz, MeOD) δ 9.69 (s, 1H), 8.55 (s, 1H), 7.78 (d, J=7.9 Hz, 2H), 7.51 (d, J=7.9 Hz, 2H), 4.50 (d, J=4.4 Hz, 1H), 4.28-4.15 (m, 2H), 4.15-4.06 (m, 1H), 3.77 (d, J=3.3 Hz, 2H), 3.67-3.55 (m, 2H), 3.33 (s, 1H), 3.29-3.11 (m, 2H), 2.12-2.00 (m, 2H). MS obsd. ($ESI^+$): 403.1 $[(M+H)]^+$.

Example 43: (3S,4S,5R)-4-(2-(2H-tetrazol-5-yl)ethoxy)-5-(4-(thiazol-5-yl)benzyl)pyrrolidin-3-ol Scheme 35

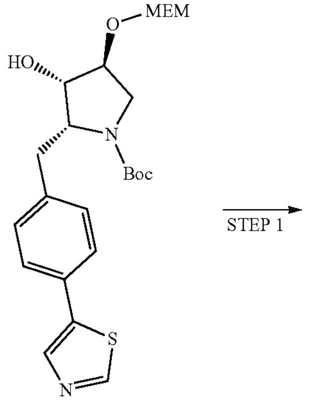

Int-16

-continued

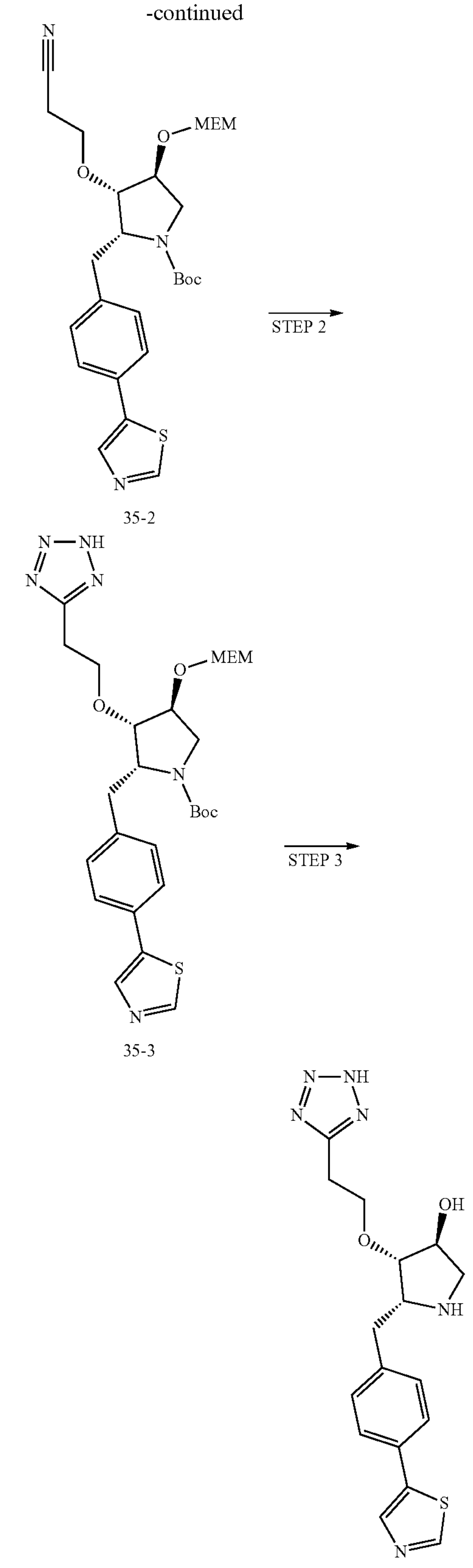

35-2

35-3

Step 1: tert-butyl (2R,3S,4S)-3-(2-cyanoethoxy)-4-((2-methoxyethoxy)methoxy)-2-(4-(thiazol-5-yl)benzyl)pyrrolidine-1-carboxylate (35-2). $Cs_2CO_3$ (210 mg) was added to a stirred solution of acrylonitrile (22 mg) and tert-butyl (2R,3S,4S)-3-hydroxy-4-((2-methoxyethoxy)methoxy)-2-(4-(thiazol-5-yl)benzyl)pyrrolidine-1-carboxylate (100 mg) in MeCN (5 mL) at room temperature. The resulting mixture was diluted with water and extracted with EtOAc. The organic extracts were washed with brine, dried over $Na_2SO_4$, filtered, and concentrated. The residue was purified by reversed-phase flash chromatography to afford the title compound as a yellow oil (55 mg). MS obsd. ($ESI^+$): 518.2 $[(M+H)]^+$.

Step 2: tert-butyl (2R,3S,4S)-3-(2-(2H-tetrazol-5-yl)ethoxy)-4-((2-methoxyethoxy)methoxy)-2-(4-(thiazol-5-yl)benzyl)pyrrolidine-1-carboxylate (35-3). Azidotrimethylsilane (36 mg) was added to a stirred solution of dibutyltin oxide (26 mg) and tert-butyl (2R,3S,4S)-3-(2-cyanoethoxy)-4-((2-methoxyethoxy)methoxy)-2-(4-(thiazol-5-yl)benzyl)pyrrolidine-1-carboxylate (55 mg) in toluene (10 mL) at room temperature. The resulting mixture was stirred at 110° C. overnight. The resulting mixture was diluted with water and extracted with EtOAc. The organic extracts were washed with brine, dried over $Na_2SO_4$, filtered, and concentrated. The residue was purified by reversed-phase flash chromatography to afford the title compound as a yellow solid (50 mg). MS obsd. ($ESI^+$): 561.2 $[(M+H)]^+$.

Step 3: (3S,4S,5R)-4-(2-(2H-tetrazol-5-yl)ethoxy)-5-(4-(thiazol-5-yl)benzyl)pyrrolidin-3-ol. The title compound was prepared in 25.6% overall yield as a white solid according to General Procedure VIII in STEP 3. $^1H$ NMR (400 MHz, MeOD) δ 8.99 (s, 1H), 8.19 (s, 1H), 7.71-7.64 (m, 2H), 7.32-7.26 (m, 2H), 4.50 (d, J=4.3 Hz, 1H), 4.18-4.09 (m, 1H), 4.09-4.00 (m, 1H), 3.95-3.85 (m, 1H), 3.77 (d, J=3.2 Hz, 1H), 3.49 (dd, J=12.6, 4.4 Hz, 1H), 3.32 (s, 2H), 3.16 (d, J=12.5 Hz, 1H), 3.07 (d, J=7.6 Hz, 1H), 2.97 (dd, J=14.0, 8.0 Hz, 1H). MS obsd. ($ESI^+$): 373.1 $[(M+H)]^+$.

Example 44: (3S,4S,5R)-4-(3-(oxetan-3-yl)propoxy)-5-(4-(thiazol-5-yl)benzyl)pyrrolidin-3-ol Scheme 36

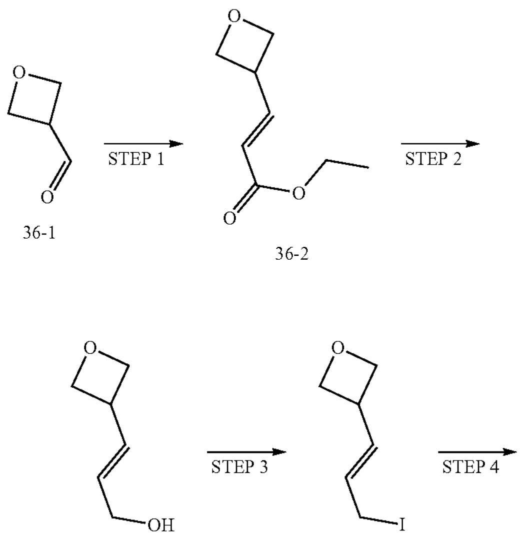

36-1

36-2

36-3

36-4

-continued

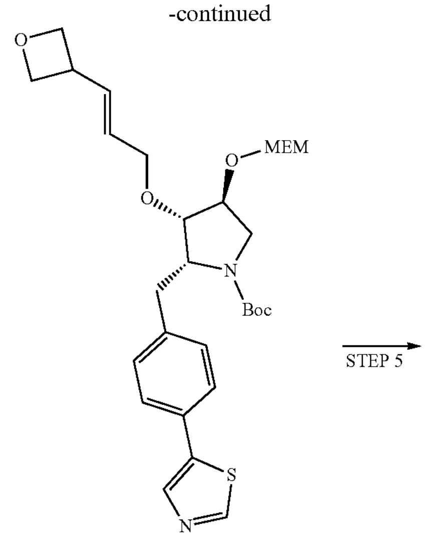

36-5

-continued

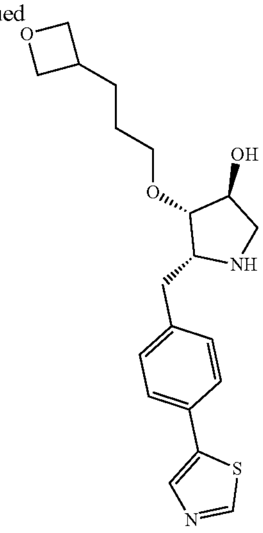

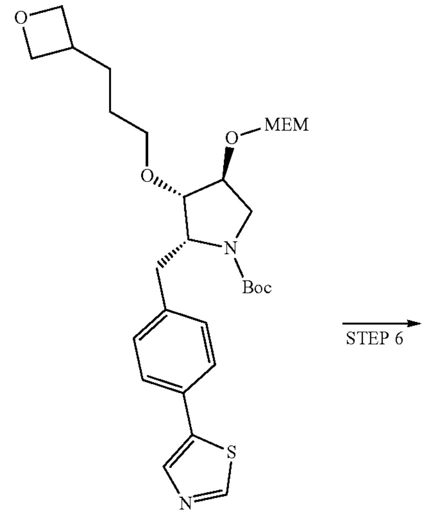

36-6

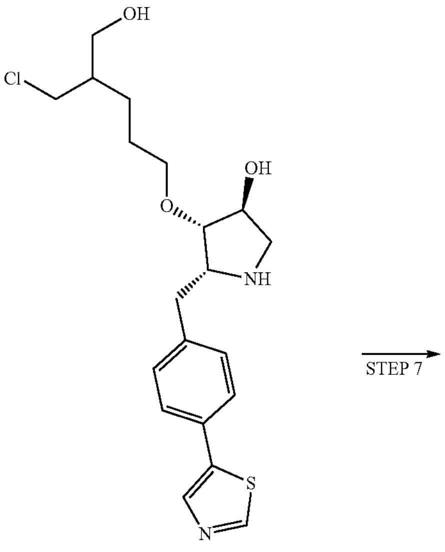

36-7

Step 1: ethyl (E)-3-(oxetan-3-yl) acrylate (36-2). added DBU (2.12 g) and LiCl (689 mg) were added to a stirred solution of triethyl phosphonoacetate (5.2 g) in MeCN (20 mL) at 0° C. for 30 min, followed by the addition of oxetane-3-carbaldehyde (1 g) at 0° C. The resulting mixture was stirred at room temperature overnight, before it was diluted with water and extracted with EtOAc. The organic extracts were washed with brine, dried over $Na_2SO_4$, filtered and concentrated. The residue was purified by silica gel column chromatography to afford the title compound as a light-yellow oil (1.3 g). $^1$H NMR (400 MHz, $CDCl_3$) δ 7.22 (dd, J=15.6, 8.4 Hz, 1H), 5.88 (dd, J=15.6, 1.1 Hz, 1H), 4.90 (dd, J=8.1, 6.1 Hz, 2H), 4.64 (t, J=6.3 Hz, 2H), 4.27-4.19 (m, 2H), 3.93-3.81 (m, 1H), 1.32 (t, J=7.1 Hz, 3H).

Step 2: (E)-3-(oxetan-3-yl) prop-2-en-1-ol (36-3). Diisobutylaluminum hydride (2.2 g) was added to a stirred solution of ethyl (2E)-3-(oxetan-3-yl) prop-2-enoate (800 mg) in DCM (80 mL) was added and then stirred at −78° C. for 2 h. The resulting mixture was diluted with water and extracted with EtOAc. The organic extracts were washed with brine, dried over $Na_2SO_4$, filtered, and concentrated. The residue was purified by reversed-phase flash chromatography to afford the title compound as a light-yellow oil (186 mg). $^1$H NMR (400 MHz, $CDCl_3$) δ 6.09-5.99 (m, 1H), 5.76-5.56 (m, 1H), 4.86 (dd, J=8.1, 6.0 Hz, 2H), 4.58 (t, J=6.4 Hz, 2H), 4.17 (dd, J=5.6, 1.5 Hz, 2H), 3.75-3.72 (m, 1H).

Step 3: (E)-3-(3-iodoprop-1-en-1-yl) oxetane (36-4). Imidazole (322 mg), $PPh_3$ (827 mg) and Iodine (800 mg) were added to a stirred solution of (2E)-3-(oxetan-3-yl) prop-2-en-1-ol (180 mg) in DCM (18 mL) at 0° C. The resulting mixture was diluted with water and extracted with EtOAc. The organic extracts were washed with brine, dried over $Na_2SO_4$, filtered and concentrated. The residue was purified by reversed-phase flash chromatography to afford the title compound as a light-yellow oil (80 mg). MS obsd. ($ESI^+$): 225.0 $[(M+H)]^+$.

Step 4-5: tert-butyl (2R,3S,4S)-4-((2-methoxyethoxy) methoxy)-3-(3-(oxetan-3-yl)propoxy)-2-(4-(thiazol-5-yl) benzyl)pyrrolidine-1-carboxylate (36-6). The title compound was prepared in 80.1% overall yield as a light yellow solid according to General Procedure I using Int-16 (80 mg) and (E)-3-(oxetan-3-yl) prop-2-en-1-ol (77 mg) in DMF in STEP 4, and General Procedure VI in STEP 5. MS obsd. ($ESI^+$): 562.7 $[(M+H)]^+$.

Step 6: (3S,4S,5R)-4-((5-chloro-4-(hydroxymethyl)pentyl)oxy)-5-(4-(thiazol-5-yl)benzyl)pyrrolidin-3-ol (36-7). HCl (0.5 mL) was added to a stirred solution of tert-butyl (2R,3S,4S)-4-((2-methoxyethoxy)methoxy)-3-(3-(oxetan-3-yl)propoxy)-2-(4-(thiazol-5-yl)benzyl)pyrrolidine-1-carboxylate (100 mg) in THF (5 mL) at 0° C. The resulting mixture was stirred at room temperature for 2 h. The crude product was used in the next step directly without further purification. MS obsd. ($ESI^+$): 411.1 $[(M+H)]^+$.

Step 7: (3S,4S,5R)-4-(3-(oxetan-3-yl)propoxy)-5-(4-(thiazol-5-yl)benzyl)pyrrolidin-3-ol. KOH (16 mg) was added to a stirred solution of (3S,4S,5R)-4-((5-chloro-4-(hydroxymethyl)pentyl)oxy)-5-(4-(thiazol-5-yl)benzyl)pyrrolidin-3-ol (60 mg) in THF (5 mL) at room temperature. The resulting mixture was diluted with water and extracted with EtOAc. The organic extracts were washed with brine, dried over $Na_2SO_4$, filtered, and concentrated. The residue was purified by silica gel column chromatography to afford the title compound as a white solid (29.8 mg). $^1H$ NMR (400 MHz, MeOD) δ 8.96 (s, 1H), 8.17 (s, 1H), 7.64 (d, J=8.0 Hz, 2H), 7.39 (dd, J=8.3, 2.1 Hz, 2H), 5.07 (s, 1H), 4.84-4.79 (m, 1H), 4.43-4.37 (m, 1H), 4.31 (d, J=5.2 Hz, 1H), 4.04 (d, J=10.5 Hz, 1H), 3.70-3.58 (m, 2H), 3.52-3.39 (m, 3H), 3.12-3.03 (m, 1H), 3.00-2.92 (m, 1H), 2.83 (dd, J=12.6, 2.7 Hz, 1H), 2.22 (t, J=7.8 Hz, 1H), 1.87-1.48 (m, 4H). MS obsd. ($ESI^+$): 374.5 $[(M+H)]^+$.

Example 45: (3S,4S,5R)-4-(4-(piperazin-1-yl)butoxy)-5-(4-(thiazol-5-yl)benzyl)pyrrolidin-3-ol Scheme 37

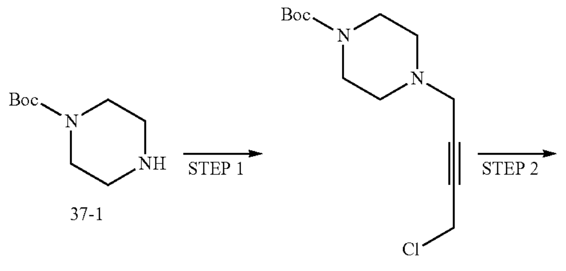

37-1

37-2

-continued

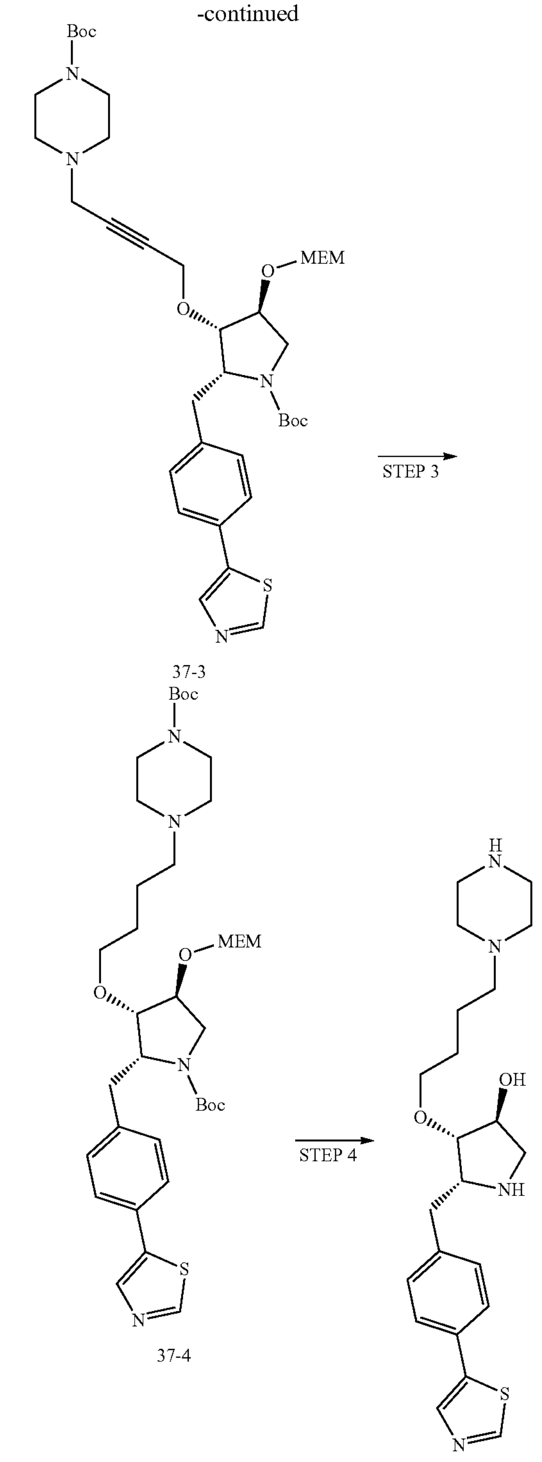

37-3

37-4

Step 1: tert-butyl 4-(4-chlorobut-2-yn-1-yl) piperazine-1-carboxylate (37-2). 1,4-dichlorobut-2-yne (660 mg) and $K_2CO_3$ (1113 mg) were added to a stirred solution of tert-butyl piperazine-1-carboxylate (500 mg) in ACN (10 mL) at 0° C. The resulting mixture was stirred at room temperature overnight before it was diluted with water and extracted with EtOAc. The organic extracts were washed with brine, dried over $Na_2SO_4$, filtered, and concentrated. The residue was purified by silica gel column chromatography to afford the title compound as a yellow oil (500 mg). MS obsd. ($ESI^+$): 273.2 $[(M+H)]^+$.

Step 2-4: (3S,4S,5R)-4-(4-(piperazin-1-yl) butoxy)-5-(4-(thiazol-5-yl)benzyl)pyrrolidin-3-ol. The title compound was prepared in 45.1% overall yield as a yellow oil according to General Procedure I using Int-16 (80 mg) and tert-butyl 4-(4-chlorobut-2-yn-1-yl) piperazine-1-carboxylate (94 mg) in DMF in STEP 2, and General Procedure VI in STEP 3, and General Procedure VIII in STEP 4. $^{1}H$ NMR (400 MHz, Methanol-$d_4$) δ 9.00 (s, 1H), 8.20 (s, 1H), 7.71 (d, J=8.0 Hz, 2H), 7.45 (d, J=8.0 Hz, 2H), 4.51 (d, J=4.2 Hz, 1H), 4.13-4.05 (m, 1H), 3.81-3.71 (m, 2H), 3.66-3.50 (m, 6H), 3.42 (s, 4H), 3.27 (dd, J=14.3, 7.4 Hz, 1H), 3.19 (d, J=12.5 Hz, 1H), 3.16-3.06 (m, 3H), 1.94-1.82 (m, 2H), 1.75 (s, 2H). MS obsd. ($ESI^+$): 417.2 $[(M+H)]^+$.

Example 46: (3S,4S,5R)-4-(4-morpholinobutoxy)-5-(4-(thiazol-5-yl)benzyl)pyrrolidin-3-ol Scheme 38

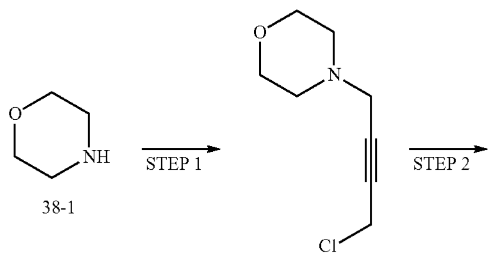

38-1

38-2

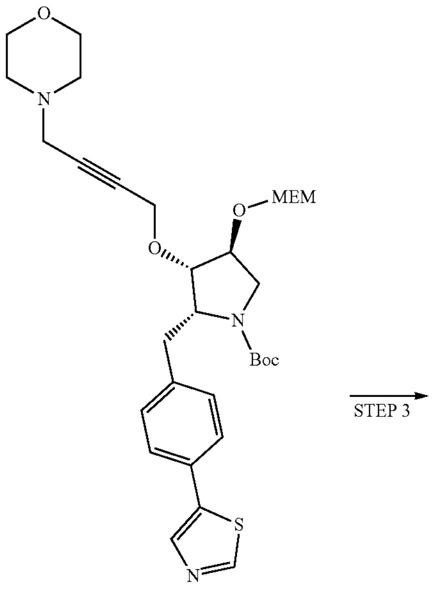

38-3

-continued

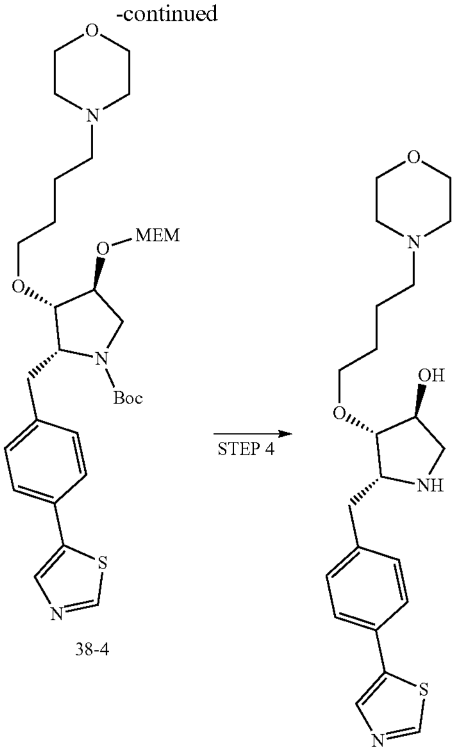

38-4

Step 1: 4-(4-chlorobut-2-yn-1-yl) morpholine (73-1). 1,4-dichlorobut-2-yne (1411 mg) and $K_2CO_3$ (2379 mg) were added to a stirred solution of morpholine (500 mg) in Toluene (10 mL) at 0° C. The resulting mixture was stirred at 50° C. for 4 h before it was diluted with water and extracted with EtOAc. The organic extracts were washed with brine, dried over $Na_2SO_4$, filtered, and concentrated. The residue was purified by silica gel column chromatography to afford the title compound as a light-yellow oil (480 mg). MS obsd. ($ESI^+$): 174.1 $[(M+H)]^+$.

Step 2-4: (3S,4S,5R)-4-(4-morpholinobutoxy)-5-(4-(thiazol-5-yl)benzyl)pyrrolidin-3-ol. The title compound was prepared in 39.6% overall yield as a white semi-solid according to General Procedure I using Int-16 (80 mg) and 4-(4-chlorobut-2-yn-1-yl) morpholine (60 mg) in DMF in STEP 2, and General Procedure VI in STEP 3, and General Procedure VIII in STEP 4. $^{1}H$ NMR (400 MHz, Methanol-$d_4$) δ 8.89 (s, 1H), 8.10 (s, 1H), 7.57 (d, J=8.1 Hz, 2H), 7.32 (d, J=8.0 Hz, 2H), 4.31-4.15 (m, 1H), 3.77-3.64 (m, 5H), 3.61-3.51 (m, 1H), 3.44-3.33 (m, 3H), 3.12-3.05 (m, 1H), 2.98-2.90 (m, 1H), 2.88-2.76 (m, 1H), 2.54-2.49 (m, 4H), 2.46-2.39 (m, 2H), 1.65-1.51 (m, 4H). MS obsd. ($ESI^+$): 418.2 $[(M+H)]^+$.

Example 47: (3S,4S,5R)-4-(2-((R)-tetrahydrofuran-3-yl)ethoxy)-5-(4-(thiazol-5-yl)benzyl)pyrrolidin-3-ol Scheme 39

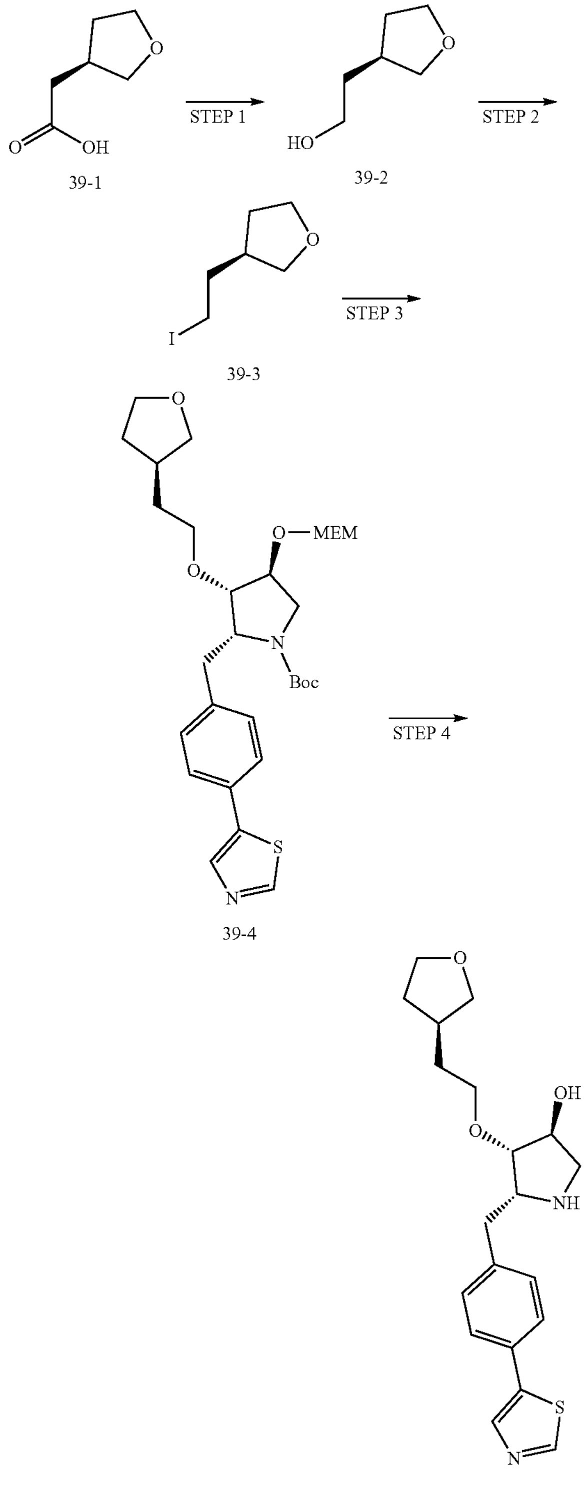

39-1 39-2 39-3 39-4

Step 1: (S)-2-(tetrahydrofuran-3-yl) ethan-1-ol (39-2). Borane-tetrahydrofuran complex (3 mL) was added to a stirred solution of (R)-2-(tetrahydrofuran-3-yl)acetic acid (250 mg) in THF (3 mL) at 0° C. The resulting mixture was stirred at room temperature overnight before it was diluted with water and extracted with EtOAc. The organic extracts were washed with brine, dried over $Na_2SO_4$, filtered, and concentrated. The residue was purified by silica gel column chromatography to afford the title compound as a light-yellow oil (220 mg). MS obsd. ($ESI^+$): 117.1 $[(M+H)]^+$.

Step 2: (R)-3-(2-iodoethyl)tetrahydrofuran (39-3). $PPh_3$ (768 mg) and Iodine (1114 mg) were added to a stirred solution of(S)-2-(tetrahydrofuran-3-yl) ethan-1-ol (170 mg) and Imidazole (299 mg) in DCM (5 mL) at ° C. The resulting mixture was stirred at room temperature for 2 h before it was diluted with water and extracted with EtOAc. The organic extracts were washed with brine, dried over $Na_2SO_4$, filtered, and concentrated. The residue was purified by silica gel column chromatography to afford the title compound as a light-yellow oil (200 mg). MS obsd. ($ESI^+$): 227.0 $[(M+H)]^+$.

Step 3 and 4: (3S,4S,5R)-4-(2-((R)-tetrahydrofuran-3-yl) ethoxy)-5-(4-(thiazol-5-yl)benzyl)pyrrolidin-3-ol. The title compound was prepared in 25.1% overall yield as a yellow solid according to General Procedure I using Int-16 (70 mg) and (R)-3-(2-iodoethyl)tetrahydrofuran (68 mg) in DMF in STEP 1, and General Procedure VIII in STEP 2. $^1H$ NMR (400 MHz, MeOD) δ 8.96 (s, 1H), 8.16 (s, 1H), 7.64 (d, J=8.0 Hz, 2H), 7.38 (d, J=8.0 Hz, 2H), 4.29 (d, J=5.3 Hz, 1H), 3.98-3.91 (m, 1H), 3.89-3.83 (m, 1H), 3.81-3.77 (m, 1H), 3.72-3.63 (m, 1H), 3.55 (d, J=9.5 Hz, 1H), 3.44 (dd, J=11.8, 4.3 Hz, 1H), 3.43-3.36 (m, 3H), 3.05 (dd, J=13.6, 8.4 Hz, 1H), 2.93 (dd, J=13.6, 6.8 Hz, 1H), 2.78 (dd, J=12.3, 2.2 Hz, 1H), 2.37 (d, J=7.4 Hz, 1H), 2.10 (dd, J=12.2, 7.5 Hz, 1H), 1.72 (d, J=6.7 Hz, 2H), 1.61-1.59 (m, 1H). MS obsd. ($ESI^+$): 375.2 $[(M+H)]^+$.

Example 48: (3S,4S,5R)-4-(benzyloxy)-5-(4-(thiazol-5-yl)benzyl)pyrrolidin-3-ol

Scheme 40

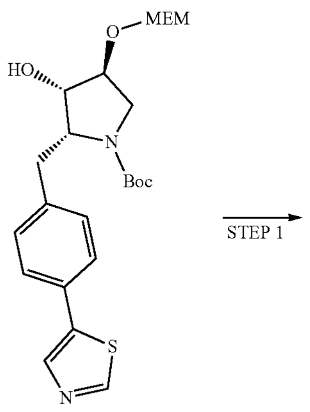

Int-16

-continued

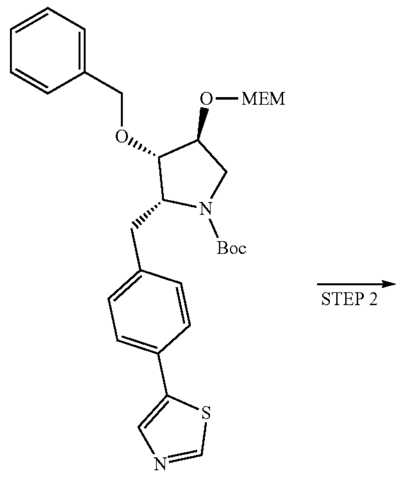

40-2

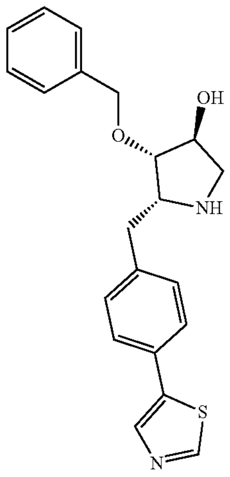

Step 1 and 2: (3S,4S,5R)-4-(benzyloxy)-5-(4-(thiazol-5-yl)benzyl)pyrrolidin-3-ol. The title compound was prepared in 35.6% overall yield as a yellow solid according to General Procedure I using Int-16 (70 mg) and (bromomethyl)benzene (51 mg) in DMF in STEP 1, and General Procedure VIII in STEP 2. $^1$H NMR (400 MHz, MeOD) δ 8.95 (d, J=0.7 Hz, 1H), 8.15 (d, J=0.7 Hz, 1H), 7.62-7.54 (m, 2H), 7.44-7.28 (m, 7H), 4.70 (d, J=11.6 Hz, 1H), 4.46 (d, J=11.5 Hz, 1H), 4.41-4.34 (m, 1H), 3.58 (d, J=3.6 Hz, 1H), 3.55-3.49 (m, 1H), 3.45-3.40 (m, 1H), 3.04 (dd, J=13.4, 8.4 Hz, 1H), 2.92 (dd, J=13.4, 6.5 Hz, 1H), 2.75 (dd, J=12.4, 2.4 Hz, 1H). MS obsd. ($ESI^+$): 367.1 $[(M+H)]^+$.

Example 49: (3S,4S,5R)-4-(2-(oxetan-3-yl)ethoxy)-5-(4-(thiazol-5-yl)benzyl)pyrrolidin-3-ol Scheme 41

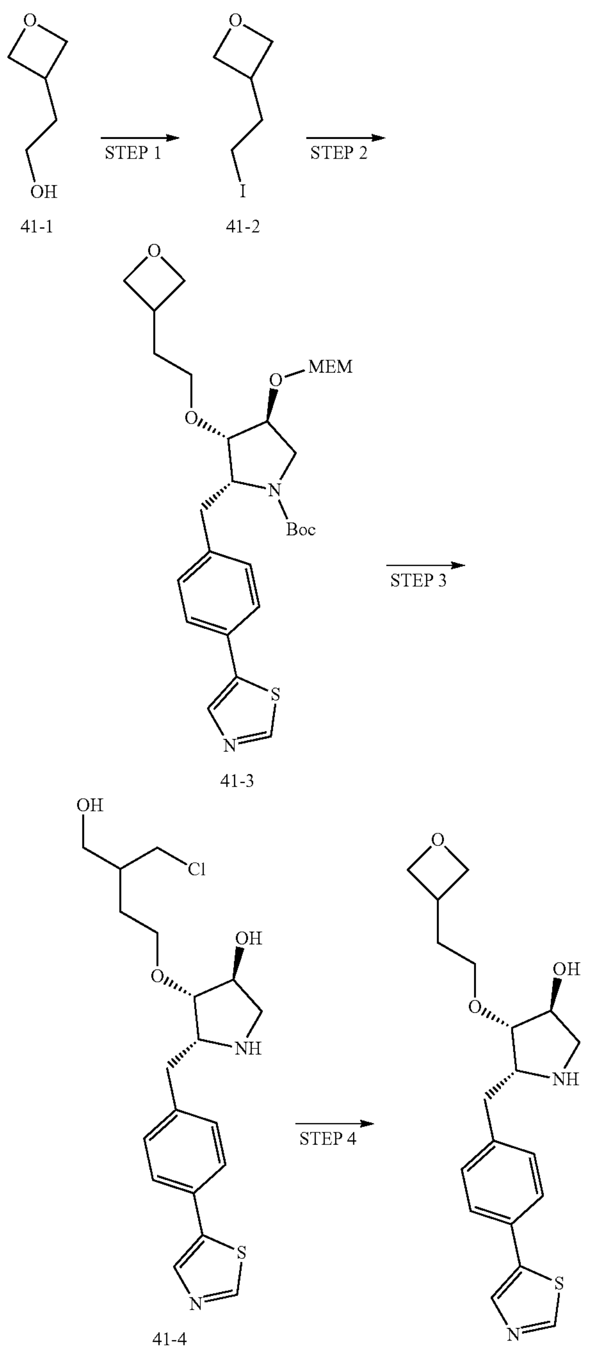

41-1

41-2

41-3

41-4

Step 1: 3-(2-iodoethyl) oxetane (41-2). PPh; (770 mg) and Iodine (994 mg) were added to a stirred solution of 2-(oxetan-3-yl) ethan-1-ol (200 mg) and Imidazole (400 mg) in THF (5 mL) at 0° C. The resulting mixture was stirred at room temperature for 2 h before it was diluted with water and extracted with EtOAc. The organic extracts were washed with brine, dried over $Na_2SO_4$, filtered, and concentrated. The residue was purified by silica gel column chromatography to afford the title compound as a light-yellow oil (160 mg). MS obsd. ($ESI^+$): 213.0 $[(M+H)]^+$.

Step 2: tert-butyl (2R,3S,4S)-4-((2-methoxyethoxy)methoxy)-3-(2-(oxetan-3-yl)ethoxy)-2-(4-(thiazol-5-yl)benzyl)pyrrolidine-1-carboxylate (41-3). The title compound was prepared in 50.6% overall yield as a light-yellow oil according to General Procedure I using Int-16 (100 mg) and 3-(2-iodoethyl) oxetane (91 mg) in DMF in STEP 2. MS obsd. ($ESI^+$): 549.3 $[(M+H)]^+$.

Step 3: (3S,4S,5R)-4-(4-chloro-3-(hydroxymethyl)butoxy)-5-(4-(thiazol-5-yl)benzyl)pyrrolidin-3-ol (41-4). HCl in 1,4-dioxane (1 mL) was added to a stirred solution of tert-butyl (2R,3S,4S)-4-((2-methoxyethoxy)methoxy)-3-(2-(oxetan-3-yl)ethoxy)-2-(4-(thiazol-5-yl)benzyl)pyrrolidine-1-carboxylate (30 mg) in Dioxane (1 mL) at 0° C. The resulting mixture was stirred at room temperature for 2 h before it was concentrated under reduced pressure to afford the title compound as a light-yellow oil (30 mg). MS obsd. ($ESI^+$): 397.1 $[(M+H)]^+$.

Step 4: (3S,4S,5R)-4-(2-(oxetan-3-yl)ethoxy)-5-(4-(thiazol-5-yl)benzyl)pyrrolidin-3-ol. KOH (85 mg) was added to a stirred solution of (3S,4S,5R)-4-(4-chloro-3-(hydroxymethyl) butoxy)-5-(4-(thiazol-5-yl)benzyl)pyrrolidin-3-ol (30 mg) in methanol (3 mL) at room temperature. The resulting mixture was stirred at 60° C. for overnight before it was diluted with water and extracted with EtOAc. The organic extracts were washed with brine, dried over $Na_2SO_4$, filtered, and concentrated. The residue was purified by Prep-HPLC to afford the title compound as a white solid. $^1H$ NMR (400 MHz, MeOD) δ 8.96 (s, 1H), 8.16 (s, 1H), 7.67-7.54 (m, 2H), 7.41-7.33 (m, 2H), 4.50 (t, J=6.2 Hz, 1H), 4.27 (s, 1H), 3.89-3.80 (m, 1H), 3.77-3.65 (m, 1H), 3.59 (s, 3H), 3.24-3.16 (m, 1H), 2.93 (dd, J=31.4, 12.6 Hz, 2H), 2.72 (s, 1H), 2.07-1.90 (m, 2H), 1.67 (d, J=6.3 Hz, 1H), 1.31-1.29 (m, 2H). MS obsd. ($ESI^+$): 361.2 $[(M+H)]^+$.

Example 50: 3-(((2R,3S,4S)-4-hydroxy-2-(4-(thiazol-5-yl)benzyl)pyrrolidin-3-yl)oxy)propanamide Scheme 42

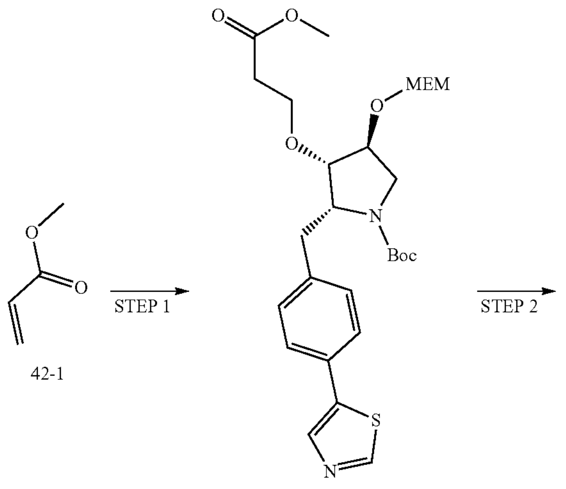

42-1

42-2

-continued

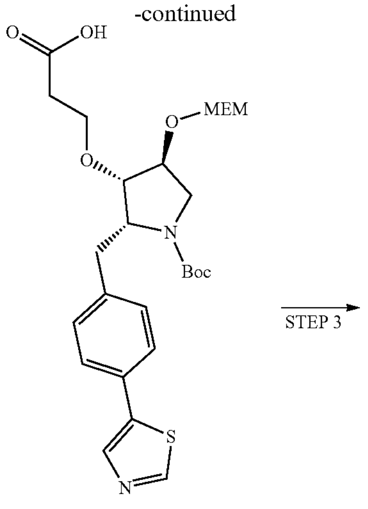

42-3

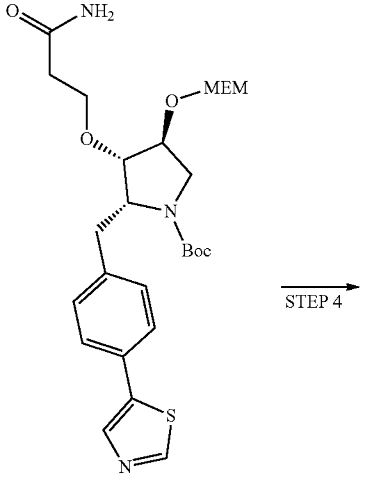

42-4

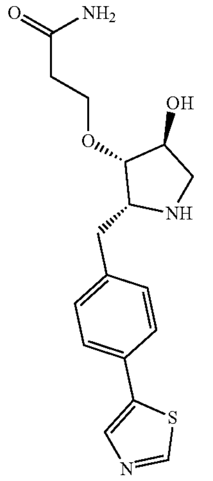

Step 1: tert-butyl (2R,3S,4S)-3-(3-methoxy-3-oxopropoxy)-4-((2-methoxyethoxy)methoxy)-2-(4-(thiazol-5-yl)benzyl)pyrrolidine-1-carboxylate (42-2). Methyl acrylate (55 mg) and $Cs_2CO_3$ (210 mg) were added to a stirred solution of tert-butyl (2R,3S,4S)-3-hydroxy-4-((2-methoxyethoxy)methoxy)-2-(4-(thiazol-5-yl)benzyl)pyrrolidine-1-carboxylate (100 mg) in ACN (5 mL) at room temperature. The resulting mixture was stirred at 60° C. overnight before it was diluted with water and extracted with EA. The organic extracts were washed with brine, dried over $Na_2SO_4$, filtered, and concentrated. The residue was purified by reversed-phase flash chromatography to afford the title compound as a light-yellow oil (60 mg). MS obsd. ($ESI^+$): 551.2 $[(M+H)]^+$.

Step 2: 3-(((2R,3S,4S)-1-(tert-butoxycarbonyl)-4-((2-methoxyethoxy)methoxy)-2-(4-(thiazol-5-yl)benzyl)pyrrolidin-3-yl)oxy) propanoic acid (42-3). LiOH (8 mg) was added to a stirred solution of tert-butyl (2R,3S,4S)-3-(3-methoxy-3-oxopropoxy)-4-((2-methoxyethoxy)methoxy)-2-(4-(thiazol-5-yl)benzyl)pyrrolidine-1-carboxylate (60 mg) in THF (3 mL) and $H_2O$ (1 mL) at 0° C. The resulting mixture was stirred at room temperature for 1 h before it was diluted with water and extracted with EtOAc. The organic extracts were washed with brine, dried over $Na_2SO_4$, filtered, and concentrated. The residue was purified by reversed-phase flash chromatography to afford the title compound as a light-yellow oil (60 mg). MS obsd. ($ESI^+$): 537.2 $[(M+H)]^+$.

Step 3: tert-butyl (2R,3S,4S)-3-(3-amino-3-oxopropoxy)-4-((2-methoxyethoxy)methoxy)-2-(4-(thiazol-5-yl)benzyl) pyrrolidine-1-carboxylate (42-4). HATU (106 mg), DIEA (36 mg) and $NH_4Cl$ (25 mg) were added to a stirred solution of 3-(((2R,3S,4S)-1-(tert-butoxycarbonyl)-4-((2-methoxyethoxy)methoxy)-2-(4-(thiazol-5-yl)benzyl)pyrrolidin-3-yl) oxy) propanoic acid (50 mg) in DMF (5 mL) at 0° C. The resulting mixture was stirred at room temperature overnight before it was diluted with water and extracted with EtOAc. The organic extracts were washed with brine, dried over $Na_2SO_4$, filtered, and concentrated. The residue was purified by reversed-phase flash chromatography to afford the title compound as a light-yellow oil (47 mg). MS obsd. ($ESI^+$): 536.2 $[(M+H)]^+$.

Step 4: 3-(((2R,3S,4S)-4-hydroxy-2-(4-(thiazol-5-yl)benzyl)pyrrolidin-3-yl)oxy)propanamide.

The title compound was prepared in 15.6% overall yield as a white solid according to General Procedure VIII in STEP 4. $^1H$ NMR (400 MHz, MeOD) δ 8.95 (s, 1H), 8.15 (s, 1H), 7.65-7.59 (m, 2H), 7.41-7.35 (m, 2H), 4.29 (dd, J=6.0, 2.3 Hz, 1H), 3.92-3.82 (m, 1H), 3.64 (dd, J=9.3, 6.6 Hz, 1H), 3.49-3.45 (m, 1H), 3.41-3.34 (m, 2H), 3.02 (dd, J=13.3, 8.6 Hz, 1H), 2.88 (dd, J=13.3, 6.3 Hz, 1H), 2.72 (dd, J=12.3, 2.3 Hz, 1H), 2.59-2.43 (m, 2H). MS obsd. ($ESI^+$): 348.1 $[(M+H)]^+$.

Example 51: 5-((((2R,3S,4S)-4-hydroxy-2-(4-(thiazol-5-yl)benzyl)pyrrolidin-3-yl)oxy)methyl)picolinamide Scheme 43

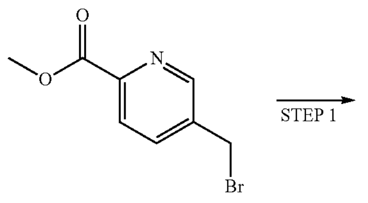

43-1

-continued

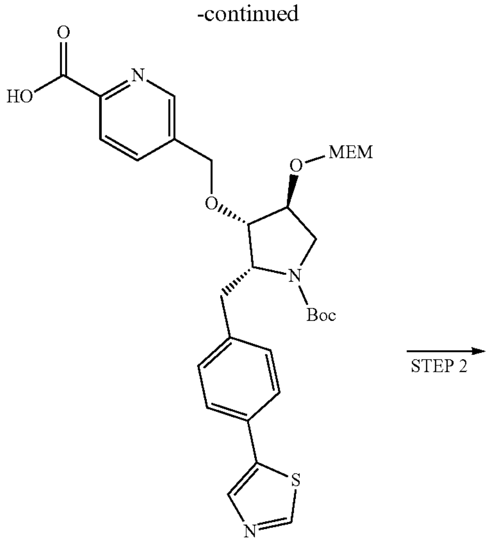

43-2

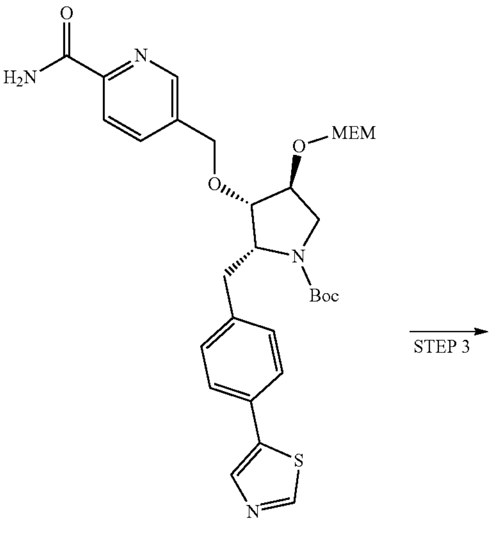

43-3

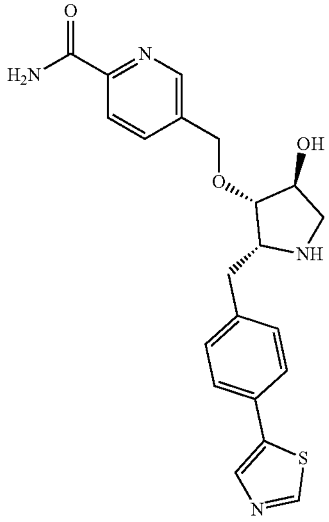

Step 1: 5-((((2R,3S,4S)-1-(tert-butoxycarbonyl)-4-((2-methoxyethoxy)methoxy)-2-(4-(thiazol-5-yl)benzyl)pyrrolidin-3-yl)oxy)methyl) picolinic acid (43-2). CsOH (64 mg)

and KI (71 mg) were added to a stirred solution of tert-butyl (2R,3S,4S)-3-hydroxy-4-((2-methoxyethoxy)methoxy)-2-(4-(thiazol-5-yl)benzyl)pyrrolidine-1-carboxylate (100 mg) and methyl 5-(bromomethyl) picolinate (99 mg) in DMF (5 mL) at room temperature. The resulting mixture was stirred at 60° C. overnight. The crude product was purified by reversed-phase flash chromatography to afford the title compound as a light-yellow oil (60 mg). MS obsd. ($ESI^+$): 600.2 $[(M+H)]^+$.

Step 2: tert-butyl (2R,3S,4S)-3-((6-carbamoylpyridin-3-yl)methoxy)-4-((2-methoxyethoxy)methoxy)-2-(4-(thiazol-5-yl)benzyl)pyrrolidine-1-carboxylate (43-3). HATU (109 mg), DIEA (25 mg) and ammonium chloride (10 mg) were added to a stirred solution of 5-((((2R,3S,4S)-1-(tert-butoxycarbonyl)-4-((2-methoxyethoxy)methoxy)-2-(4-(thiazol-5-yl)benzyl)pyrrolidin-3-yl)oxy)methyl) picolinic acid (57 mg) in DMF (3 mL) at 0° C. The resulting mixture was stirred at room temperature overnight before it was diluted with water and extracted with EtOAc. The organic extracts were washed with brine, dried over $Na_2SO_4$, filtered, and concentrated. The residue was purified by reversed-phase flash chromatography to afford the title compound as a light-yellow oil (55 mg). MS obsd. ($ESI^+$): 599.2 $[(M+H)]^+$.

Step 3: 5-((((2R,3S,4S)-4-hydroxy-2-(4-(thiazol-5-yl)benzyl)pyrrolidin-3-yl)oxy)methyl)picolinamide. The title compound was prepared in 35.6% overall yield as a white solid according to General Procedure VIII in STEP 3. $^1H$ NMR (400 MHz, MeOD) δ 8.98 (s, 1H), 8.70 (s, 1H), 8.56 (s, 1H), 8.20-8.11 (m, 1H), 8.05-7.98 (m, 1H), 7.65 (d, J=7.9 Hz, 2H), 7.36 (d, J=8.0 Hz, 2H), 4.67 (d, J=12.3 Hz, 1H), 4.62-4.55 (m, 2H), 4.00 (d, J=3.6 Hz, 1H), 3.87 (s, 1H), 3.62 (dd, J=12.6, 4.9 Hz, 1H), 3.21 (dd, J=13.9, 7.8 Hz, 1H), 3.16-3.04 (m, 2H). MS obsd. ($ESI^+$): 411.1 $[(M+H)]^+$.

Example 52: (3S,4S,5R)-4-((1,1-difluoroprop-2-yn-1-yl)oxy)-5-(4-(thiazol-5-yl)benzyl)pyrrolidin-3-ol Scheme 44

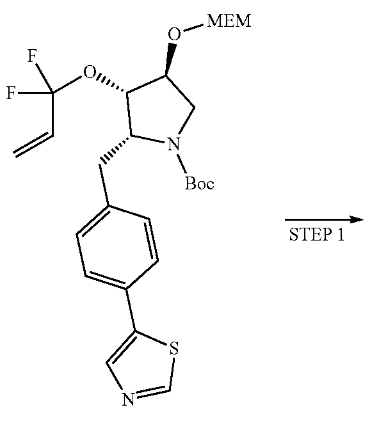

Int-19

-continued

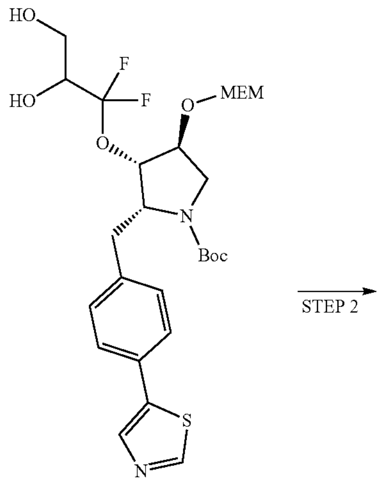

44-2

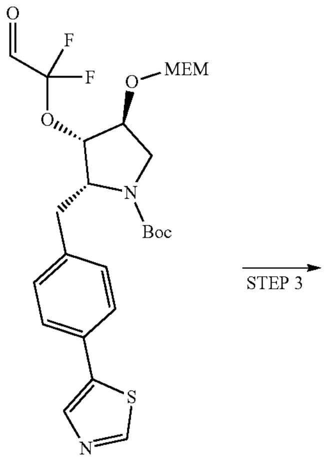

44-3

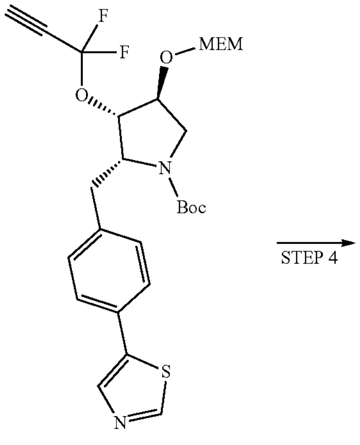

. . .

-continued 44-4

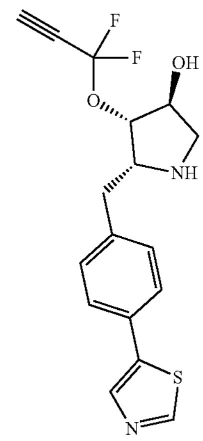

Step 1: tert-butyl (2R,3S,4S)-3-(1,1-difluoro-2,3-dihydroxypropoxy)-4-((2-methoxyethoxy)methoxy)-2-(4-(thiazol-5-yl)benzyl)pyrrolidine-1-carboxylate (44-2). Citric acid (462 mg), 4-methylmorpholin-4-ium-4-olate (281 mg) and Potassium osmate(VI) dihydrate (44 mg) were added to a stirred solution of tert-butyl (2R,3S,4S)-3-((1,1-difluoroallyl)oxy)-4-((2-methoxyethoxy)methoxy)-2-(4-(thiazol-5-yl)benzyl)pyrrolidine-1-carboxylate (650 mg) in t-BuOH (8 mL) and $H_2O$ (8 mL) at 0° C. and the mixture was stirred at room temperature overnight. The resulting mixture was diluted with water and extracted with EA. The organic extracts were washed with brine, dried over $Na_2SO_4$, filtered, and concentrated. The residue was purified by reversed-phase flash chromatography to afford the title compound as a yellow solid (580 mg). MS obsd. ($ESI^+$): 575.2 $[(M+H)]^+$.

Step 2: tert-butyl (2R,3S,4S)-3-(1,1-difluoro-2-oxoethoxy)-4-((2-methoxyethoxy)methoxy)-2-(4-(thiazol-5-yl)benzyl)pyrrolidine-1-carboxylate (44-3). $NaIO_4$ (647 mg) was added to a stirred solution of tert-butyl (2R,3S,4S)-3-(1,1-difluoro-2,3-dihydroxypropoxy)-4-((2-methoxyethoxy)methoxy)-2-(4-(thiazol-5-yl)benzyl)pyrrolidine-1-carboxylate (580 mg) in t-BuOH (5 mL) and $H_2O$ (3 mL) at 0° C. and the mixture was stirred at room temperature overnight. The resulting mixture was diluted with water, and extracted with EtOAc. The organic extracts were washed with brine, dried over $Na_2SO_4$, filtered, and concentrated. The residue was purified by reversed-phase flash chromatography to afford the title compound as a yellow oil (500 mg). MS obsd. ($ESI^+$): 543.2 $[(M+H)]^+$. Step 3: tert-butyl (2R,3S,4S)-3-((1,1-difluoroprop-2-yn-1-yl)oxy)-4-((2-methoxyethoxy)methoxy)-2-(4-(thiazol-5-yl)benzyl)pyrrolidine-1-carboxylate (44-4). $K_2CO_3$ (46 mg) and (1-diazo-2-oxo-propyl)-phosphonic acid dimethyl ester (42 mg) were added to a stirred solution of tert-butyl (2R,3S,4S)-3-(1,1-difluoro-2-oxoethoxy)-4-((2-methoxyethoxy)methoxy)-2-(4-(thiazol-5-yl)benzyl)pyrrolidine-1-carboxylate (60 mg) in methanol (5 mL) at 0° C. The resulting mixture was diluted with water and extracted with EtOAc. The organic extracts were washed with brine, dried over $Na_2SO_4$, filtered, and concentrated. The residue was purified by reversed-phase flash chromatography to afford the title compound as a yellow solid (35 mg). MS obsd. ($ESI^+$): 539.2 $[(M+H)]^+$.

Step 4: (3S,4S,5R)-4-((1,1-difluoroprop-2-yn-1-yl)oxy)-5-(4-(thiazol-5-yl)benzyl)pyrrolidin-3-ol. The title compound was prepared in 15.6% overall yield as a yellow semi-solid according to General Procedure VIII in STEP 3. $^1H$ NMR (400 MHz, Methanol-$d_4$) δ 8.99 (s, 1H), 8.20 (s, 1H), 7.75-7.69 (m, 2H), 7.51-7.44 (m, 2H), 4.81 (d, J=3.3 Hz, 1H), 4.58 (d, J=4.3 Hz, 1H), 4.37-4.28 (m, 1H), 4.01-3.95 (m, 1H), 3.67 (dd, J=12.8, 4.3 Hz, 1H), 3.33-3.23 (m, 2H), 3.11 (dd, J=14.5, 9.5 Hz, 1H). MS obsd. ($ESI^+$): 351.1 $[(M+H)]^+$.

Example 53: (3S,4S,5R)-4-(difluoro (phenyl) methoxy)-5-(4-(thiazol-5-yl)benzyl)pyrrolidin-3-ol Scheme 45

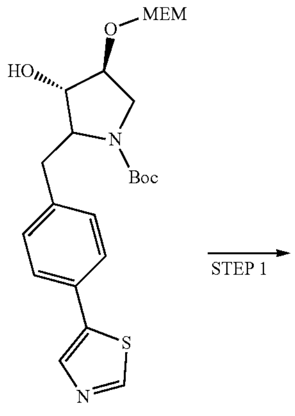

Int-16

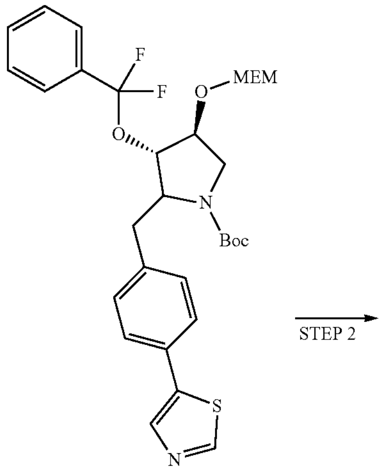

45-2

-continued

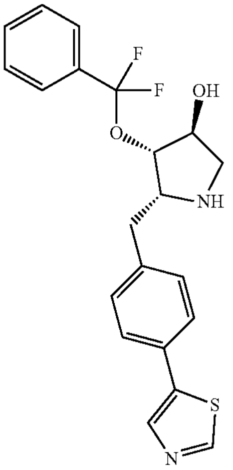

Step 1 and 2: (3S,4S,5R)-4-(difluoro (phenyl)methoxy)-5-(4-(thiazol-5-yl)benzyl)pyrrolidin-3-ol. The title compound was prepared in 5.6% overall yield as a yellow solid according to General Procedure I using Int-16 (200 mg) and (bromodifluoromethyl)benzene (267 mg) in DMF in STEP 1, and General Procedure VIII in STEP 2. $^1$H NMR (400 MHz, MeOD) δ 8.95 (d, J=0.6 Hz, 1H), 8.15 (d, J=0.7 Hz, 1H), 7.74-7.65 (m, 2H), 7.65-7.56 (m, 2H), 7.60-7.46 (m, 3H), 7.42-7.25 (m, 2H), 4.62 (d, J=3.6 Hz, 1H), 4.49-4.43 (m, 1H), 3.67 (dd, J=7.9, 3.6 Hz, 1H), 3.43 (dd, J=12.3, 5.7 Hz, 1H), 3.05 (dd, J=14.0, 6.4 Hz, 1H), 2.90 (dd, J=13.9, 7.9 Hz, 1H), 2.77 (dd, J=12.2, 2.3 Hz, 1H). MS obsd. (ESI$^+$): 403.2 [(M+H)]$^+$.

Example 54: (3S,4S,5R)-4-(4-(oxetan-3-yl) butoxy)-5-(4-(thiazol-5-yl)benzyl)pyrrolidin-3-ol Scheme 46

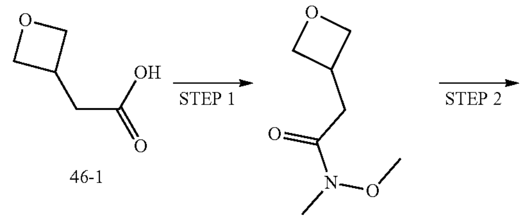

46-1 46-2

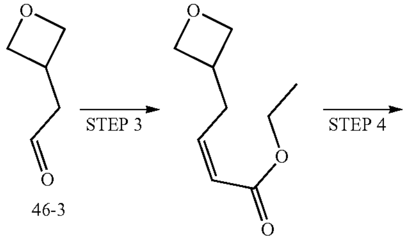

46-3 46-4

-continued

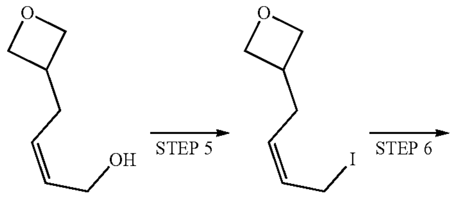

46-5 46-6

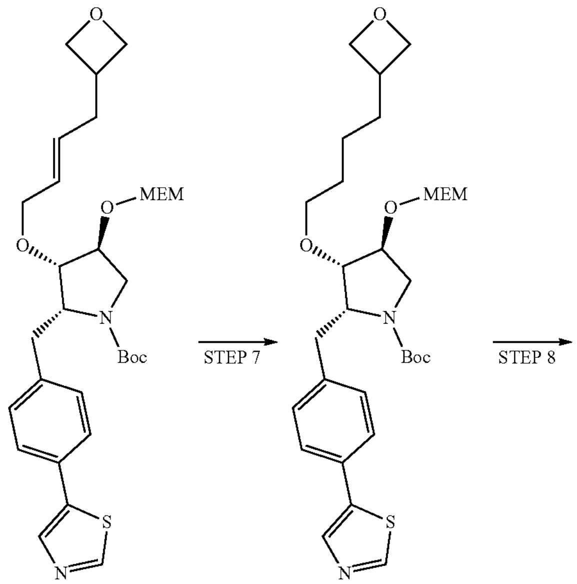

46-7 46-8

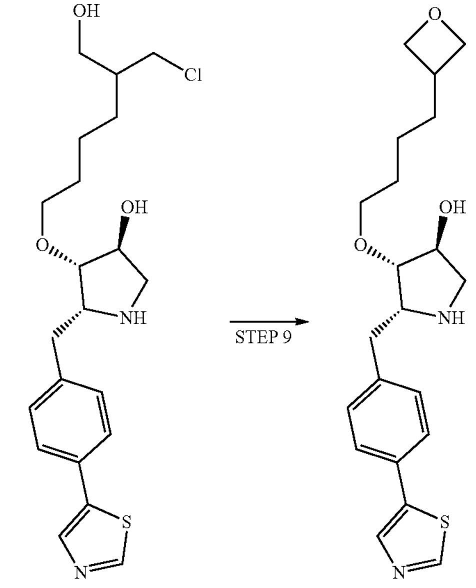

46-9

Step 1: N-methoxy-N-methyl-2-(oxetan-3-yl)acetamide (46-2). CDI (2.8 g), N,O-dimethylhydroxylamine hydrochloride (1.7 g) and $Et_3N$ (1.7 g) were added to a stirred solution of oxetan-3-ylacetic acid (2 g) in DCM (40 mL) at 0° C. The resulting mixture was stirred at room temperature for overnight. diluted with water, and extracted with EA. The organic extracts were washed with brine, dried over $Na_2SO_4$, filtered and concentrated. The residue was purified by reversed-phase flash chromatography to afford the title compound as a yellow oil (2.0 g). MS obsd. ($ESI^+$): 160.1 $[(M+H)]^+$.

Step 2: 2-(oxetan-3-yl) acetaldehyde (46-3). Lithium aluminum hydride (500 mg) was added to a stirred solution of N-methoxy-N-methyl-2-(oxetan-3-yl)acetamide (2.0 g) in THF (20 mL) at 0° C. The resulting mixture was stirred at room temperature for 2 h. The reaction was quenched with $Na_2SO_4 \cdot 10H_2O$ at 0° C. before it was filtered, washed with DCM, and concentrated under reduced pressure to afford 2-(oxetan-3-yl) acetaldehyde as a yellow oil (700 mg). MS obsd. ($ESI^+$): 101.1 $[(M+H)]^+$.

Step 3: ethyl (E)-4-(oxetan-3-yl) but-2-enoate (46-4). DBU (1.3 g) and LiCl (415 mg) were added to a stirred solution of triethyl phosphonoacetate (3.1 g) in MeCN (10 mL) at 0° C. The resulting mixture was stirred for 2 h. followed by the addition of 2-(oxetan-3-yl) acetaldehyde (700 mg) at 0° C. The reaction was stirred at room temperature overnight before it was diluted with water, and extracted with EtOAc. The organic extracts were washed with brine, dried over $Na_2SO_4$, filtered, and concentrated. The residue was purified by reversed-phase flash chromatography to afford the title compound as a yellow oil (700 mg). MS obsd. ($ESI^+$): 171.1 $[(M+H)]^+$.

Step 4: (E)-4-(oxetan-3-yl) but-2-en-1-ol (46-5). Diisobutylaluminum hydride (1002 mg) was added to a stirred solution of ethyl (2E)-4-(oxetan-3-yl) but-2-enoate (300 mg) in DCM (10 mL) at −78° C. The resulting mixture was stirred at −78° C. for 2 h before it was diluted with water and extracted with EtOAc. The organic extracts were washed with brine, dried over $Na_2SO_4$, filtered, and concentrated. The residue was purified by silica gel column chromatography to afford the title compound as a yellow oil (200 mg). MS obsd. ($ESI^+$): 129.1 $[(M+H)]^+$.

Step 5: tert-butyldiphenyl(3-(thietan-3-yl)propoxy)silane (46-6). (2E)-4-(oxetan-3-yl) but-2-en-1-ol (150 mg) was added to a stirred solution of Imidazole (87 mg), $PPh_3$ (307 mg) and Iodine (297 mg) in DCM (6 mL) was added at 0° C. The resulting mixture was stirred at room temperature for 4 h before it was diluted with water and extracted with EtOAc. The organic extracts were washed with brine, dried over $Na_2SO_4$, filtered, and concentrated. The residue was purified by silica gel column chromatography to afford the title compound as a light-yellow oil (98 mg). MS obsd. ($ESI^+$): 238.1 $[(M+H)]^+$.

Step 6 and 7: tert-butyl (2R,3S,4S)-4-((2-methoxyethoxy) methoxy)-3-(4-(oxetan-3-yl) butoxy)-2-(4-(thiazol-5-yl) benzyl)pyrrolidine-1-carboxylate (46-8). The title compound was prepared in 59.6% overall yield as a white semi-solid according to General Procedure I using Int-16 (100 mg) and (E)-3-(4-iodobut-2-en-1-yl) oxetane (256 mg) in DMF in STEP 6, and General Procedure VI in STEP 7. MS obsd. ($ESI^+$): 576.7 $[(M+H)]^+$.

Step 8: (3S,4S,5R)-4-((6-chloro-5-(hydroxymethyl) hexyl)oxy)-5-(4-(thiazol-5-yl)benzyl)pyrrolidin-3-ol (46-9). HCl (0.2 mL) was added to a stirred solution of tert-butyl (2R,3S,4S)-4-((2-methoxyethoxy)methoxy)-3-(4-(oxetan-3-yl) butoxy)-2-(4-(thiazol-5-yl)benzyl)pyrrolidine-1-carboxylate (60 mg) in THF (2 mL) at 0° C. The resulting mixture was stirred at room temperature for 2 h. The crude product was used in the next step directly without further purification. MS obsd. ($ESI^+$): 425.0 $[(M+H)]^+$.

Step 9: (3S,4S,5R)-4-(4-(oxetan-3-yl) butoxy)-5-(4-(thiazol-5-yl)benzyl)pyrrolidin-3-ol. KOH (59 mg) was added to a stirred solution of (3S,4S,5R)-4-((6-chloro-5-(hydroxymethyl) hexyl)oxy)-5-(4-(thiazol-5-yl)benzyl)pyrrolidin-3-ol (45 mg) in i-PrOH (9 mL) at room temperature. The resulting mixture was stirred at 80° C. for overnight. The residue was purified by Prep-HPLC to afford the title compound as a light-yellow solid (27 mg). $^1$H NMR (400 MHz, MeOD) δ 8.96 (s, 1H), 8.17 (d, J=0.7 Hz, 1H), 7.68-7.59 (m, 2H), 7.44-7.35 (m, 2H), 4.82 (dd, J=7.8, 5.8 Hz, 2H), 4.40 (t, J=6.1 Hz, 2H), 4.28 (t, J=3.6 Hz, 1H), 3.68-3.53 (m, 2H), 3.48-3.37 (m, 3H), 3.10-2.99 (m, 2H), 2.97-2.89 (m, 1H), 2.83-2.75 (m, 1H), 1.78-1.70 (m, 2H), 1.67-1.58 (m, 2H), 1.42-1.33 (m, 2H). MS obsd. ($ESI^+$): 388.5 $[(M+H)]^+$.

Example 55: (3S,4S,5R)-4-(1,1-difluoropropoxy)-5-(4-(1-methyl-1H-pyrazol-4-yl)benzyl)pyrrolidin-3-ol Scheme 47

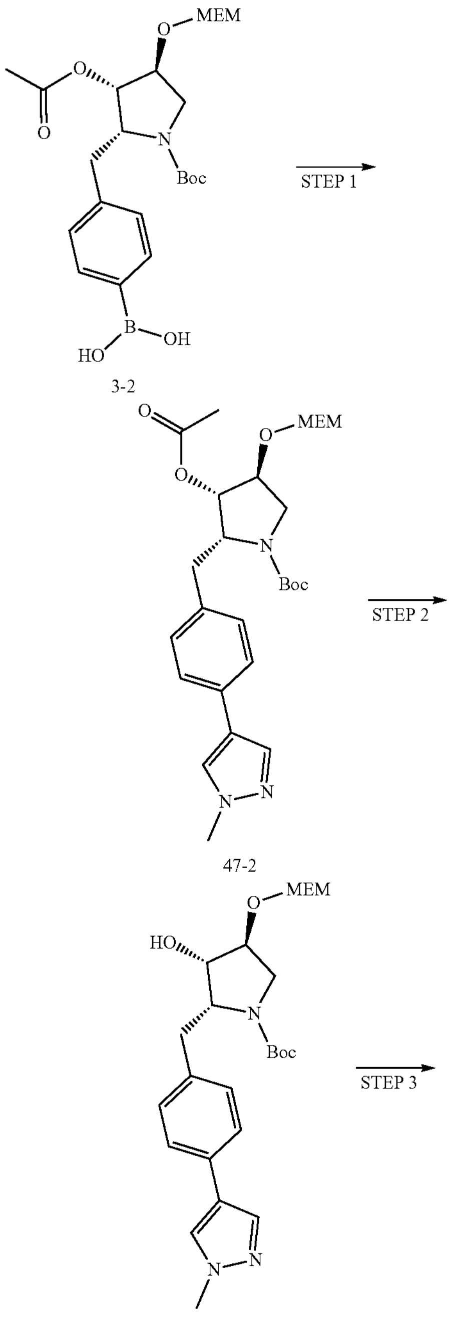

3-2

47-2

47-3

-continued

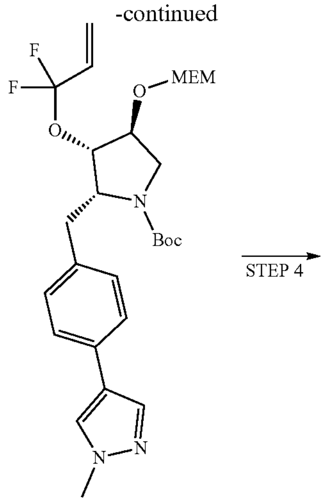

47-4

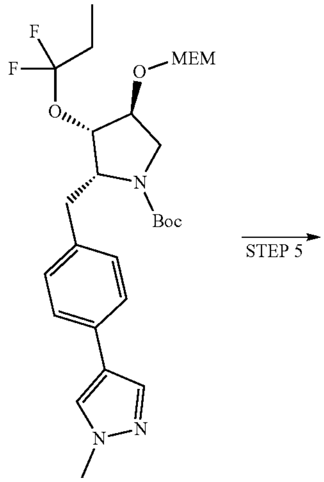

47-5

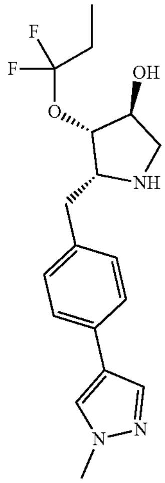

Step 1: tert-butyl (2R,3S,4S)-3-acetoxy-4-((2-methoxyethoxy)methoxy)-2-(4-(1-methyl-1H-pyrazol-4-yl)benzyl)pyrrolidine-1-carboxylate (47-2). A mixture of tert-butyl (2R,3S,4S)-3-(acetyloxy)-1-(tert-butoxycarbonyl)-4-[(2-methoxyethoxy)methoxy]pyrrolidine-2-yl]methyl}phe- nyl-boronic acid (500 mg), 4-bromo-1-methyl-1H-pyrazole (207 mg), and $Na_2CO_3$ (340 mg), and $Pd(dppf)Cl_2$ was suspended in 1,4-dioxane (10 mL) and $H_2O$ (1 mL) at rt and heated to 80° C. for 12 h. After cooling to room temperature, water was added, and the mixture was extracted with EtOAc. The organic extracts were washed with brine, dried over $Na_2SO_4$, filtered and concentrated. The residue was purified by silica gel column chromatography to afford the title compound as a yellow solid. MS obsd. ($ESI^+$): 502.2 $[(M+H)]^+$.

Step 2: tert-butyl (2R,3S,4S)-3-hydroxy-4-((2-methoxyethoxy)methoxy)-2-(4-(1-methyl-1H-pyrazol-4-yl)benzyl)pyrrolidine-1-carboxylate (47-3). Lithium hydroxide (17 mg) was added to a solution of tert-butyl (2R,3S,4S)-3-acetoxy-4-((2-methoxyethoxy)methoxy)-2-(4-(1-methyl-1H-pyrazol-4-yl)benzyl)pyrrolidine-1-carboxylate (120 mg) in THF (3.0 mL) and $H_2O$ (1.0 mL) at 0° C. The resulting mixture was stirred at rt for 1 h and concentrated. The residue was purified by reversed-phase flash chromatography to afford the title compound as a yellow oil (70 mg). MS obsd. ($ESI^+$): 460.2 $[(M+H)]^+$.

Step 3-5: (3S,4S,5R)-4-(1,1-difluoropropoxy)-5-(4-(1-methyl-1H-pyrazol-4-yl)benzyl)pyrrolidin-3-ol. The title compound was prepared in 30.6% overall yield as a white solid according to General Procedure I using tert-butyl (2R,3S,4S)-3-hydroxy-4-((2-methoxyethoxy)methoxy)-2-(4-(1-methyl-1H-pyrazol-4-yl)benzyl)pyrrolidine-1-carboxylate (75 mg) and 1-(2,2-difluoroethenyl)-1-methylpiperidin-1-ium triflate (101 mg) in DMF in STEP 3, and General Procedure VI in STEP 3 and General Procedure VIII in STEP 3. $^1H$ NMR (400 MHz, MeOD) δ 7.97 (s, 1H), 7.82 (s, 1H), 7.63-7.55 (m, 2H), 7.37 (d, J=8.1 Hz, 2H), 4.74 (d, J=3.3 Hz, 1H), 4.51 (d, J=4.3 Hz, 1H), 4.28-4.19 (m, 1H), 3.94 (s, 3H), 3.65-3.57 (m, 1H), 3.26-3.17 (m, 2H), 3.05-2.94 (m, 1H), 2.23-2.07 (m, 2H), 1.19-1.11 (m, 3H). MS obsd. ($ESI^+$): 352.2 $[(M+H)]^+$.

Example 56: (3R,4S,5R)-5-(4-(1-methyl-1H-pyrazol-4-yl)benzyl)-4-(2-((R)-tetrahydrofuran-3-yl)ethoxy)pyrrolidin-3-ol Scheme 83

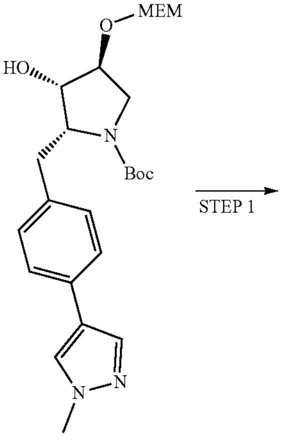

47-3

-continued

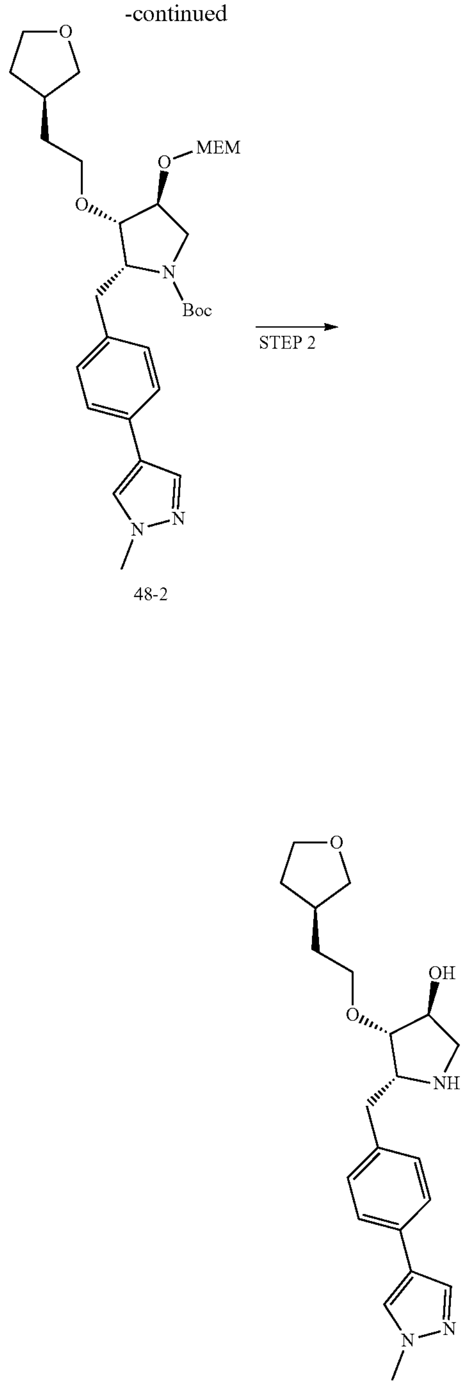

48-2

Step 1-2: (3R,4S,5R)-5-(4-(1-methyl-1H-pyrazol-4-yl) benzyl)-4-(2-((R)-tetrahydrofuran-3-yl)ethoxy)pyrrolidin-3-ol. The title compound was prepared in 35.6% overall yield as a yellow solid according to General Procedure I using 47-3 (40 mg) and (3R)-3-(2-iodoethyl)oxolane (39 mg) in DMF in STEP 1, and General Procedure VIII in STEP 2. $^{1}$H NMR (400 MHz, MeOD) δ 7.95 (s, 1H), 7.80 (s, 1H), 7.56-7.49 (m, 2H), 7.29 (d, J=8.1 Hz, 2H), 4.33 (d, J=5.1 Hz, 1H), 3.94 (s, 4H), 3.90-3.83 (m, 1H), 3.80-3.73 (m, 1H), 3.73-3.63 (m, 2H), 3.51 (s, 1H), 3.49-3.37 (m, 3H), 3.10-3.00 (m, 1H), 2.98-2.84 (m, 2H), 2.43-2.30 (m, 1H), 2.17-2.05 (m, 1H), 1.78-1.68 (m, 2H), 1.68-1.54 (m, 1H). MS obsd. (ESI$^{+}$): 372.2 [(M+H)]$^{+}$.

Example 57: (3S,4S,5R)-4-(cyclopropylmethoxy)-5-(4-(1-methyl-1H-pyrazol-4-yl)benzyl)pyrrolidin-3-ol Scheme 49

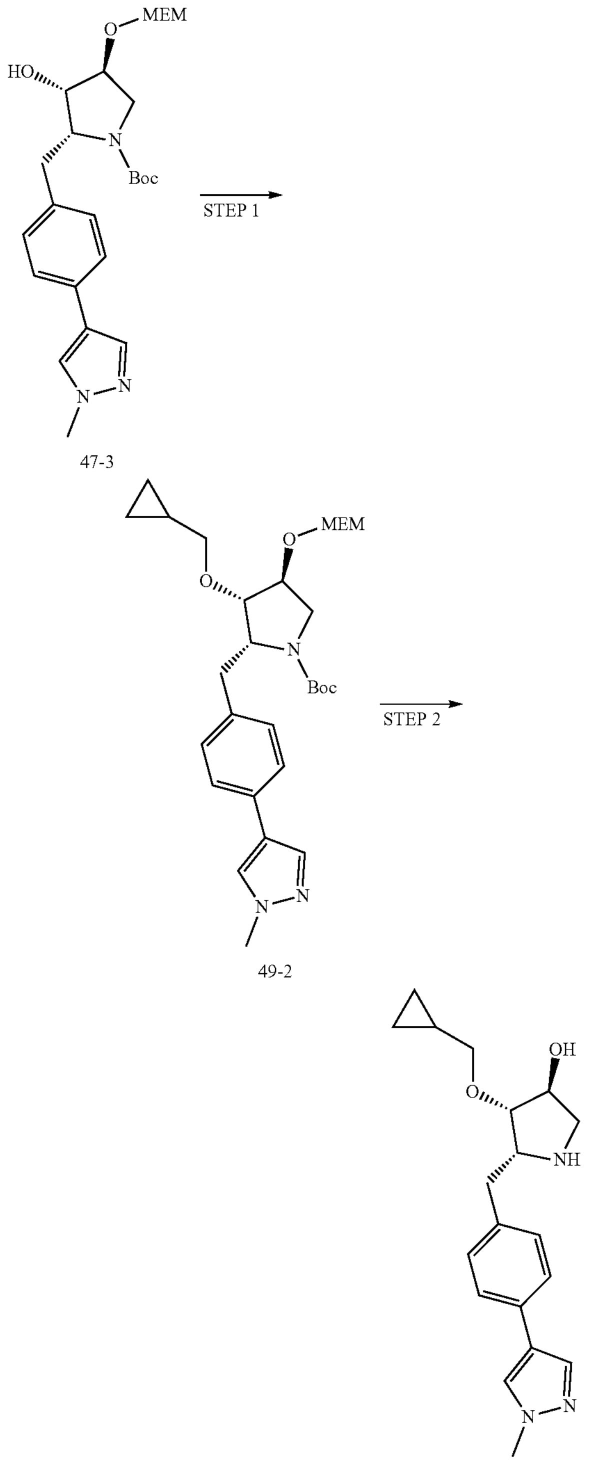

47-3

49-2

Step 1 and 2: (3S,4S,5R)-4-(cyclopropylmethoxy)-5-(4-(1-methyl-1H-pyrazol-4-yl)benzyl)pyrrolidin-3-ol. The title compound was prepared in 37.6% overall yield as a white solid according to General Procedure I using 47-3 (100 mg)

and (bromomethyl)cyclopropane (60 mg) in DMF in STEP 1, and General Procedure VIII in STEP 2. $^{1}$H NMR (400 MHz, MeOD) δ 7.93 (d, J=0.8 Hz, 1H), 7.79 (d, J=0.9 Hz, 1H), 7.53-7.46 (m, 2H), 7.33-7.26 (m, 2H), 4.29-4.23 (m, 1H), 3.93 (s, 3H), 3.51-3.37 (m, 4H), 3.30-3.21 (m, 1H), 3.06-2.96 (m, 1H), 2.92-2.83 (m, 1H), 2.77-2.69 (m, 1H), 1.17-1.03 (m, 1H), 0.63-0.49 (m, 2H), 0.33-0.19 (m, 2H). MS obsd. (ESI$^{+}$): 328.2 [(M+H)]$^{+}$.

Example 58: (3S,4S,5R)-4-ethoxy-5-(4-(1-methyl-1H-pyrazol-4-yl)benzyl)pyrrolidin-3-ol Scheme 50

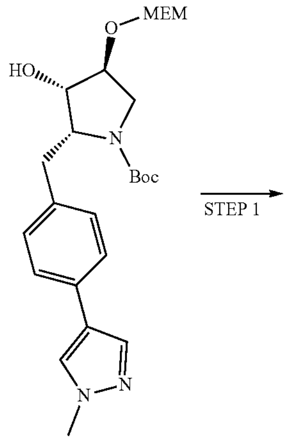

47-3

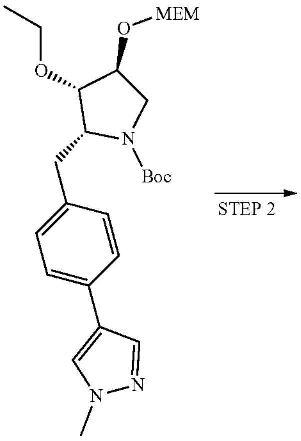

50-2

-continued

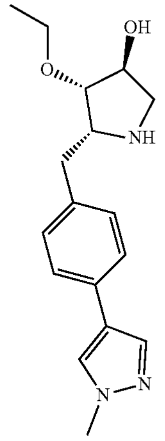

Step 1-2: (3S,4S,5R)-4-ethoxy-5-(4-(1-methyl-1H-pyrazol-4-yl)benzyl)pyrrolidin-3-ol. The title compound was prepared in 66.6% overall yield as a white solid according to General Procedure I using 47-3 (200 mg) and ethyl iodide (202 mg) in DMF in STEP 1, and General Procedure VIII in STEP 2. $^{1}$H NMR (400 MHz, MeOD) δ 7.90 (d, J=1.8 Hz, 1H), 7.77 (d, J=1.9 Hz, 1H), 7.50-7.43 (m, 2H), 7.25 (dd, J=8.2, 2.0 Hz, 2H), 4.23 (d, J=5.5 Hz, 1H), 3.90 (d, J=1.9 Hz, 3H), 3.73-3.59 (m, 1H), 3.50-3.33 (m, 4H), 3.01-2.91 (m, 1H), 2.84 (dd, J=13.7, 6.6 Hz, 1H), 2.71 (dd, J=12.3, 2.5 Hz, 1H), 1.33-1.09 (m, 3H). MS obsd. (ESI$^{+}$): 302.1 [(M+H)]$^{+}$.

Example 59: (3S,4S,5R)-5-(4-(1-(difluoromethyl)-1H-pyrazol-4-yl)benzyl)-4-ethoxypyrrolidin-3-ol Scheme 51

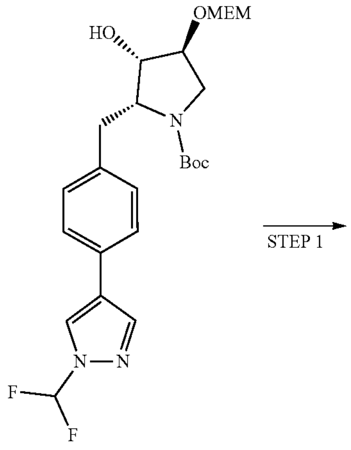

16-3

-continued

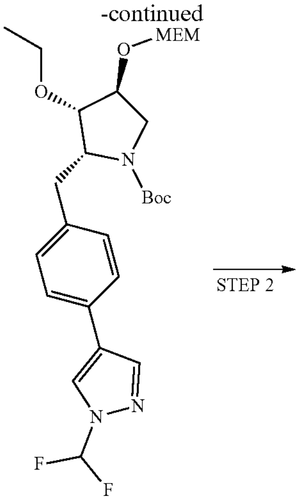

51-2

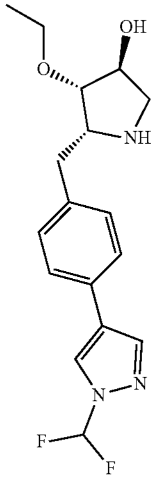

Step 1-2: (3S,4S,5R)-5-(4-(1-(difluoromethyl)-1H-pyrazol-4-yl)benzyl)-4-ethoxypyrrolidin-3-ol. The title compound was prepared in 24.8% overall yield as a white solid according to General Procedure I using 16-3 (95 mg) and ethyl iodide (90 mg) in DMF in STEP 1, and General Procedure VIII in STEP 2. $^1H$ NMR (400 MHz, DMSO) δ 8.56 (d, J=4.0 Hz, 1H), 8.19 (s, 1H), 7.90-7.47 (m, 3H), 7.26 (d, J=7.5 Hz, 2H), 4.08 (d, J=5.4 Hz, 1H), 3.74-3.48 (m, 1H), 3.48-3.16 (m, 4H), 2.89-2.67 (m, 2H), 2.56 (d, J=12.4 Hz, 1H), 1.21-1.02 (m, 3H); MS obsd. ($ESI^+$): 338.2 $[(M+H)]^+$.

Example 60: 3-(((2R,3S,4S)-2-(4-(1-(difluoromethyl)-1H-pyrazol-4-yl)benzyl)-4-hydroxypyrrolidin-3-yl)oxy)propanamide Scheme 52

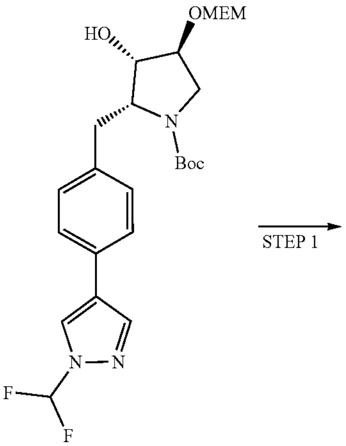

16-3

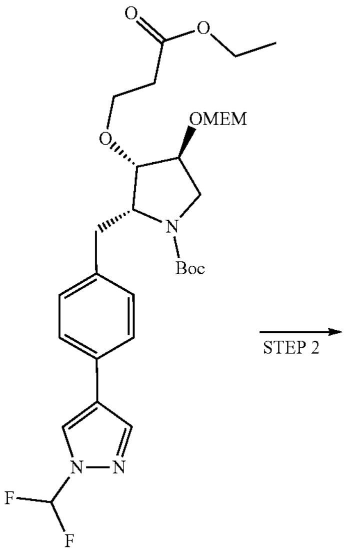

52-2

-continued

-continued

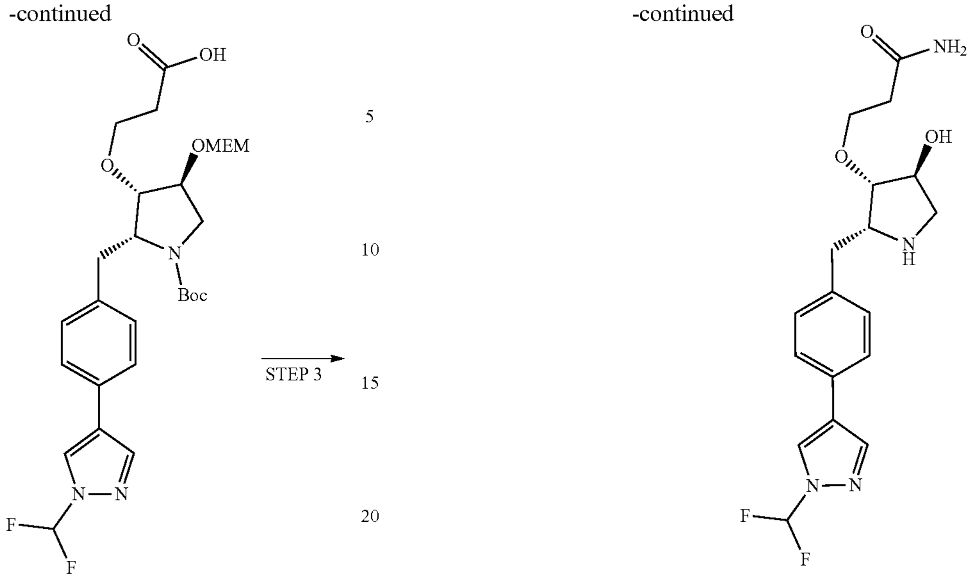

52-3

Step 1: tert-butyl (2R,3S,4S)-2-(4-(1-(difluoromethyl)-1H-pyrazol-4-yl)benzyl)-3-(3-ethoxy-3-oxopropoxy)-4-((2-methoxyethoxy)methoxy)pyrrolidine-1-carboxylate (52-2). $Cs_2CO_3$ (196 mg) was added to a stirred solution of tert-butyl (2R,3S,4S)-2-(4-(1-(difluoromethyl)-1H-pyrazol-4-yl)benzyl)-3-hydroxy-4-((2-methoxyethoxy)methoxy)pyrrolidine-1-carboxylate (100 mg) and methyl acrylate (34 mg) in MeCN (10 mL) at room temperature. The resulting mixture was stirred at 60° C. overnight before it was diluted with water and extracted with EtOAc. The organic extracts were washed with brine, dried over $Na_2SO_4$, filtered, and concentrated. The residue was purified by reversed-phase flash chromatography to afford the title compound as a yellow oil (40 mg). MS obsd. ($ESI^+$): 598.3 $[(M+H)]^+$.

Step 2: 3-(((2R,3S,4S)-1-(tert-butoxycarbonyl)-2-(4-(1-(difluoromethyl)-1H-pyrazol-4-yl)benzyl)-4-((2-methoxyethoxy)methoxy)pyrrolidin-3-yl)oxy) propanoic acid (52-3). LiOH (5 mg) was added to a stirred solution of tert-butyl tert-butyl (2R,3S,4S)-2-(4-(1-(difluoromethyl)-1H-pyrazol-4-yl)benzyl)-3-(3-ethoxy-3-oxopropoxy)-4-((2-methoxyethoxy)methoxy)pyrrolidine-1-carboxylate (40 mg) in THF (3 mL) and $H_2O$ (1 mL) at 0° C. The resulting mixture was stirred at room temperature overnight before water was added and the mixture was extracted with EtOAc. The organic extracts were washed with brine, diluted with water, and extracted with EtOAc. The organic extracts were washed with brine, dried over $Na_2SO_4$, filtered, and concentrated. The residue was purified by reversed-phase flash chromatography to afford the title compound as a yellow oil (35 mg). MS obsd. ($ESI^+$): 570.3 $[(M+H)]^+$.

Step 3: tert-butyl (2R,3S,4S)-3-(3-amino-3-oxopropoxy)-2-(4-(1-(difluoromethyl)-1H-pyrazol-4-yl)benzyl)-4-((2-methoxyethoxy)methoxy)pyrrolidine-1-carboxylate (52-4). HATU (35 mg), DIEA (23 mg) and $NH_4Cl$ (10 mg) was added to a stirred solution of 3-(((2R,3S,4S)-1-(tert-butoxycarbonyl)-2-(4-(1-(difluoromethyl)-1H-pyrazol-4-yl)benzyl)-4-((2-methoxyethoxy)methoxy)pyrrolidin-3-yl)oxy) propanoic acid (35 mg) in DMF (5 mL) at 0° C. The resulting mixture was stirred at room temperature overnight before it was diluted with water and extracted with EtOAc. The organic extracts were washed with brine, dried over $Na_2SO_4$, filtered, and concentrated. The residue was purified

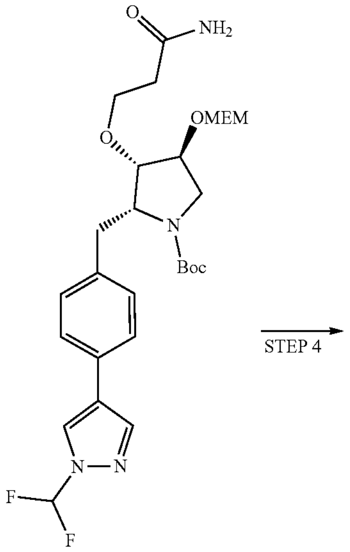

52-3 by reversed-phase flash chromatography to afford the title compound as a yellow solid (15 mg). MS obsd. ($ESI^+$): 569.3 $[(M+H)]^+$ Step 4: 3-(((2R,3S,4S)-2-(4-(1-(difluoromethyl)-1H-pyrazol-4-yl)benzyl)-4-hydroxypyrrolidin-3-yl)oxy)propanamide. The title compound was prepared in 6.9% overall yield as an off-white according to General Procedure VIII in STEP 4. $^1H$ NMR (400 MHz, MeOD) δ 8.43 (s, 1H), 8.10 (s, 1H), 7.71-7.50 (m, 2H), 7.52-7.34 (m, 3H), 4.53 (d, J=4.3 Hz, 1H), 4.07-3.92 (m, 2H), 3.83-3.72 (m, 2H), 3.58 (dd, J=12.5, 4.4 Hz, 1H), 3.28-3.19 (m, 1H), 3.15 (dd, J=12.5, 6.0 Hz, 1H), 3.05 (dd, J=13.9, 8.0 Hz, 1H), 2.65-2.48 (m, 2H). MS obsd. ($ESI^+$): 381.2 $[(M+H)]^+$.

Example 61: (3S,4S,5R)-4-(cyclopropylmethoxy)-5-(4-(1-(difluoromethyl)-1H-pyrazol-4-yl)benzyl)pyrrolidin-3-ol Scheme 53

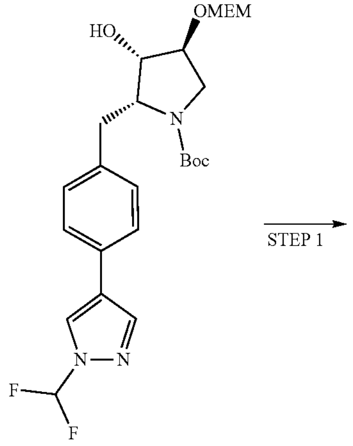

16-3

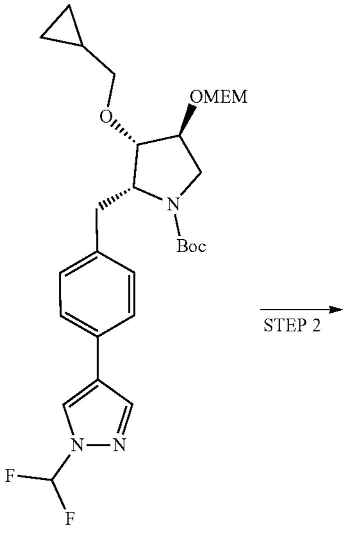

53-2

-continued

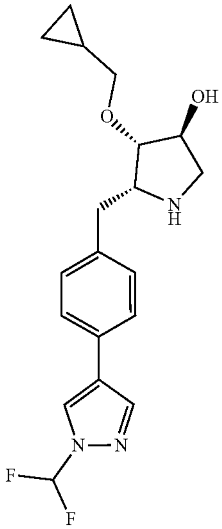

Step 1-2: (3S,4S,5R)-4-(cyclopropylmethoxy)-5-(4-(1-(difluoromethyl)-1H-pyrazol-4-yl)benzyl)pyrrolidin-3-ol. The title compound was prepared in 28.8% overall yield as a light yellow semi-solid according to General Procedure I using 16-3 (60 mg) and (bromomethyl)cyclopropane (33 mg) in DMF in STEP 1, and General Procedure VIII in STEP 2. $^1H$ NMR (400 MHz, DMSO) δ 8.73 (s, 1H), 8.29 (s, 1H), 8.05-7.63 (m, 3H), 7.38 (d, J=7.9 Hz, 2H), 5.73-5.53 (m, 1H), 4.43-4.32 (m, 1H), 3.91-3.80 (m, 1H), 3.66 (d, J=3.4 Hz, 1H), 3.50-3.38 (m, 2H), 3.30-3.24 (m, 1H), 3.12 (dd, J=13.8, 7.6 Hz, 1H), 3.05-2.90 (m, 2H), 1.16-1.02 (m, 1H), 0.61-0.48 (m, 2H), 0.26 (d, J=4.9 Hz, 2H). MS obsd. ($ESI^+$): 364.2 $[(M+H)]^+$.

Example 62: (3S,4S,5R)-4-(2-(4,4-difluorocyclohexyl)ethoxy)-5-(4-(1-(difluoromethyl)-1H-pyrazol-4-yl)benzyl)pyrrolidin-3-ol Scheme 54

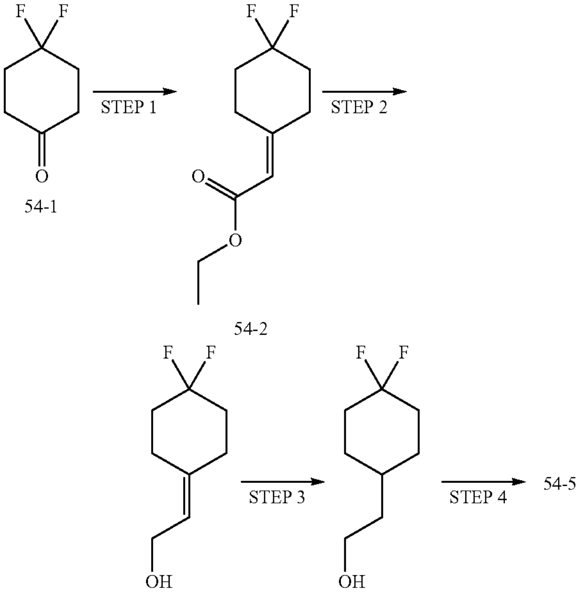

54-1 54-2 54-3 54-5

-continued

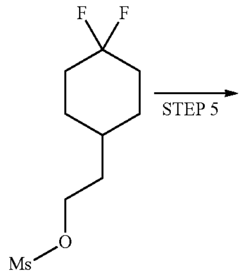

54-5

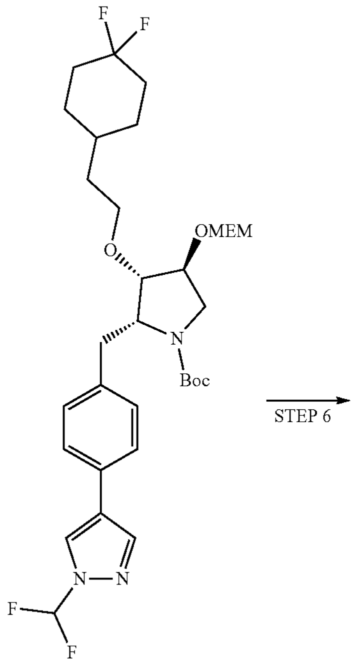

54-6

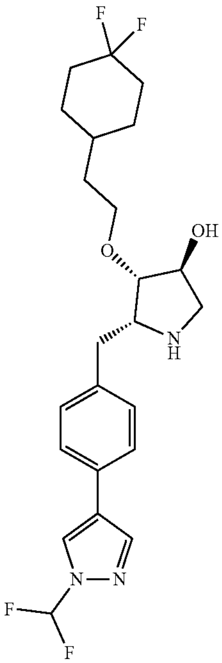 [SMILES: O[C@H]1CN[C@H](Cc2ccc(-c3cnn(C(F)F)c3)cc2)[C@@H]1OCCC1CCC(F)(F)CC1]

Step 1: ethyl 2-(4,4-difluorocyclohexylidene)acetate (54-2). To a stirred solution of ethyl 2-(diethoxyphosphoryl) acetate (1003 mg) in MeCN (12 mL) was added DBU (408 mg) and LiCl (132 mg) at 0° C. for 30 min. Followed by the addition of 4,4-difluorocyclohexan-1-one (300 mg) at 0° C. The resulting mixture was stirred at room temperature for 12 h. Diluted with water, and extracted with EA. The organic extracts were washed with brine, dried over $Na_2SO_4$, filtered and concentrated. The residue was purified by silica gel column chromatography to afford the title compound as a light-yellow oil (400 mg). $^1H$ NMR (400 MHz, $CDCl_3$) δ 5.80-5.69 (m, 1H), 4.25-4.12 (m, 2H), 3.13-3.02 (m, 2H), 2.48-2.35 (m, 2H), 2.17-1.97 (m, 4H), 1.31 (t, J=7.1 Hz, 3H).

Step 2: 2-(4,4-difluorocyclohexylidene) ethan-1-ol (54-3). Diisobutylaluminum hydride (835 mg) was added to a stirred solution of ethyl 2-(4,4-difluorocyclohexylidene)acetate (400 mg) in DCM (15 mL) at −78° C. The resulting mixture was stirred at room temperature for 2 h before it was diluted with water and extracted with EtOAc. The organic extracts were washed with brine, dried over $Na_2SO_4$, filtered, and concentrated. The residue was purified by silica gel column chromatography to afford the title compound as a colorless oil (300 mg). MS obsd. ($ESI^+$): 163.1 $[(M+H)]^+$.

Step 3: 2-(4,4-difluorocyclohexyl) ethan-1-ol (54-4). The title compound was prepared in 95.6% overall yield as a colorless oil according to General Procedure VI in STEP 3. MS obsd. ($ESI^+$): 165.1 $[(M+H)]^+$.

Step 4: 2-(4,4-difluorocyclohexyl)ethyl methanesulfonate (54-5). Methanesulfonyl methanesulfonate (515 mg) and TEA (599 mg) were added to a stirred solution of 2-(4,4-difluorocyclohexyl) ethan-1-ol (324 mg) in DCM (10 mL) at 0° C. The resulting mixture was stirred at room temperature for 1 h before it was diluted with water, and extracted with EtOAc. The organic extracts were washed with brine, dried over $Na_2SO_4$, filtered, and concentrated. The crude product was used in the next step directly without further purification.

Step 5 and 6: (3S,4S,5R)-4-(2-(4,4-difluorocyclohexyl) ethoxy)-5-(4-(1-(difluoromethyl)-1H-pyrazol-4-yl)benzyl) pyrrolidin-3-ol. The title compound was prepared in 13.8% overall yield as a white solid according to General Procedure I using 54-5 (35 mg) and 2-(4,4-difluorocyclohexyl)ethyl methanesulfonate (34 mg) in DMF in STEP 1, and General Procedure VIII in STEP 2. $^1H$ NMR (400 MHz, MeOD) δ 8.40 (d, J=0.9 Hz, 1H), 8.09 (s, 1H), 7.69-7.49 (m, 3H), 7.41-7.29 (m, 2H), 4.29 (d, J=5.3 Hz, 1H), 3.75-3.68 (m, 1H), 3.57 (s, 1H), 3.48-3.39 (m, 3H), 3.03 (dd, J=13.5, 8.5 Hz, 1H), 2.91 (dd, J=13.6, 6.6 Hz, 1H), 2.79 (d, J=11.5 Hz, 1H), 2.03 (d, J=7.3 Hz, 2H), 1.87-1.65 (m, 4H), 1.59 (s, 3H), 1.31 (s, 1H), 1.28 (s, 1H). MS obsd. ($ESI^+$): 456.2 $[(M+H)]^+$.

Example 63: 3-(((2R,3S,4S)-4-hydroxy-2-(4-(1-methyl-1H-indazol-5-yl)benzyl)pyrrolidin-3-yl)oxy) propanamide Scheme 55

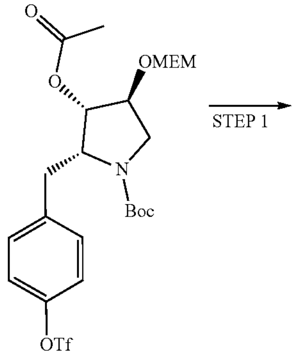

3-1

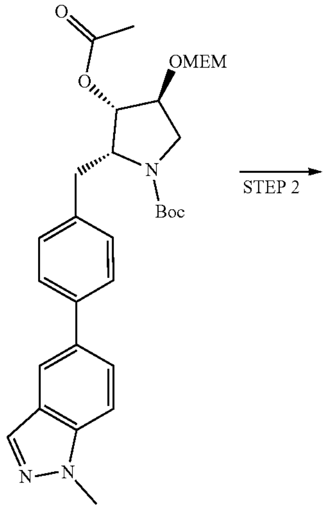

55-2

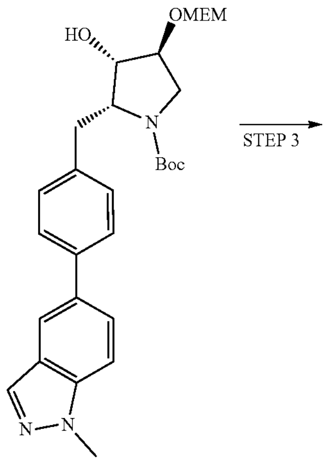

55-3

-continued

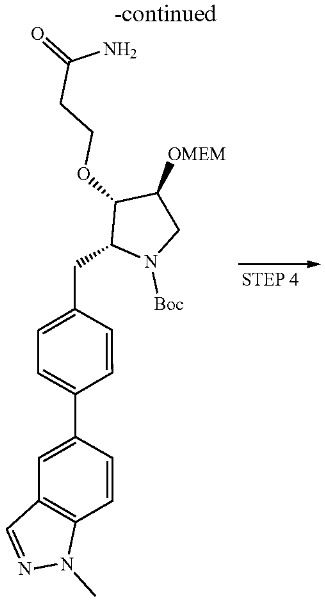

55-4

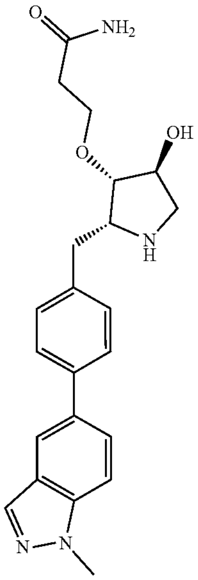

Step 1: tert-butyl (2R,3S,4S)-3-acetoxy-4-((2-methoxyethoxy)methoxy)-2-(4-(1-methyl-1H-indazol-5-yl)benzyl) pyrrolidine-1-carboxylate (55-2). XPhos (33 mg), XPhos Pd G3 (59 mg) and $NaHCO_3$ (88 mg) were added to a stirred solution of tert-butyl (2R,3S,4S)-3-acetoxy-4-((2-methoxyethoxy)methoxy)-2-(4-(((trifluoromethyl) sulfonyl)oxy) benzyl)pyrrolidine-1-carboxylate (200 mg) and 1-methyl-5-(4,4,5,5-tetramethyl-1,3,2-dioxaborolan-2-yl)-1H-indazole (135 mg) in DMF (5 mL) at room temperature. The resulting mixture was stirred at 80° C. for 12 h before it was diluted with water and extracted with EtOAc. The organic extracts were washed with brine, dried over $Na_2SO_4$, filtered, and concentrated. The residue was purified by silica gel column chromatography to afford the title compound as a light-yellow oil (190 mg). MS obsd. ($ESI^+$): 554.3 $[(M+H)]^+$.

Step 2: tert-butyl (2R,3S,4S)-3-hydroxy-4-((2-methoxyethoxy)methoxy)-2-(4-(1-methyl-1H-indazol-5-yl)benzyl) pyrrolidine-1-carboxylate (55-3). LiOH (27 mg) was added to a stirred solution of tert-butyl (2R,3S,4S)-3-acetoxy-4-

((2-methoxyethoxy)methoxy)-2-(4-(1-methyl-1H-indazol-5-yl)benzyl)pyrrolidine-1-carboxylate (213 mg) in THF (9 mL) and $H_2O$ (3 mL) at 0° C. The resulting mixture was stirred at room temperature for 2 h before it was diluted with water and extracted with EtOAc. The organic extracts were washed with brine, dried over $Na_2SO_4$, filtered, and concentrated. The residue was purified by reversed-phase column chromatography to afford the title compound as a light-yellow oil (194 mg). MS obsd. ($ESI^+$): 512.3 $[(M+H)]^+$.

Step 3: tert-butyl (2R,3S,4S)-3-(3-amino-3-oxopropoxy)-4-((2-methoxyethoxy)methoxy)-2-(4-(1-methyl-1H-indazol-5-yl)benzyl)pyrrolidine-1-carboxylate (55-4). $Cs_2CO_3$ (382 mg) was added to a stirred solution of tert-butyl (2R,3S,4S)-3-hydroxy-4-((2-methoxyethoxy)methoxy)-2-(4-(1-methyl-1H-indazol-5-yl)benzyl)pyrrolidine-1-carboxylate (200 mg) and acrylamide (55 mg) in MeCN (10 mL) at room temperature. The resulting mixture was stirred at 80° C. overnight before it was diluted with water and extracted with EtOAc. The organic extracts were washed with brine, dried over $Na_2SO_4$, filtered, and concentrated. The residue was purified by reversed-phase column chromatography to afford the title compound as a yellow solid (15 mg). MS obsd. ($ESI^+$): 583.3 $[(M+H)]^+$.

Step 4: 3-(((2R,3S,4S)-4-hydroxy-2-(4-(1-methyl-1H-indazol-5-yl)benzyl)pyrrolidin-3-yl)oxy)propanamide. The title compound was prepared in 13.6% overall yield as a white solid according to General Procedure VIII in STEP 2. $^1H$ NMR (400 MHz, MeOD) δ 8.06 (d, J=0.9 Hz, 1H), 7.98 (dd, J=1.7, 0.8 Hz, 1H), 7.74 (dd, J=8.8, 1.7 Hz, 1H), 7.67-7.59 (m, 3H), 7.42-7.35 (m, 2H), 4.34-4.27 (m, 1H), 4.11 (s, 3H), 3.94-3.84 (m, 1H), 3.72-3.62 (m, 1H), 3.51-3.34 (m, 3H), 3.04 (dd, J=13.2, 8.5 Hz, 1H), 2.90 (dd, J=13.3, 6.3 Hz, 1H), 2.73 (dd, J=12.3, 2.3 Hz, 1H), 2.61-2.45 (m, 2H). MS obsd. ($ESI^+$): 395.2 $[(M+H)]^+$.

Example 64: 2-(((2R,3S,4S)-4-hydroxy-2-(4-(1-methyl-1H-indazol-5-yl)benzyl)pyrrolidin-3-yl)oxy)acetamide Scheme 56

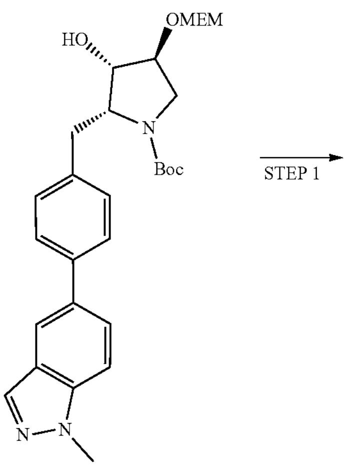

55-3

-continued

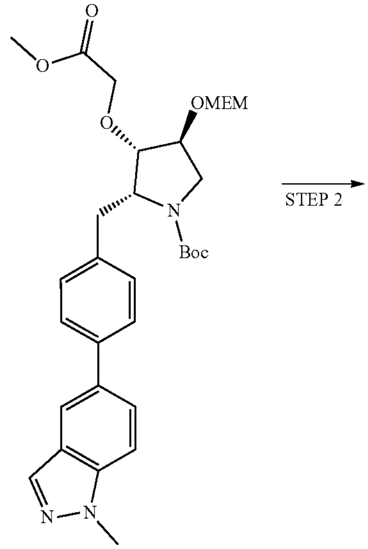

56-2

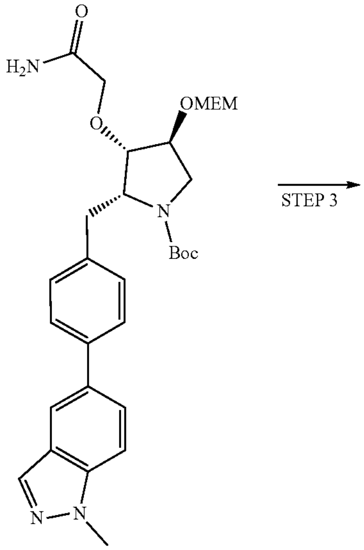

56-3

-continued

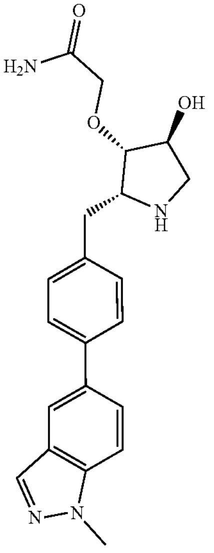

Step 1: tert-butyl (2R,3S,4S)-3-(2-methoxy-2-oxoethoxy)-4-((2-methoxyethoxy)methoxy)-2-(4-(1-methyl-1H-indazol-5-yl)benzyl)pyrrolidine-1-carboxylate (56-2). CsOH·$H_2O$ (98 mg) and KI (97 mg) were added to a stirred solution of tert-butyl (2R,3S,4S)-3-hydroxy-4-((2-methoxyethoxy)methoxy)-2-(4-(1-methyl-1H-indazol-5-yl)benzyl)pyrrolidine-1-carboxylate (100 mg) and methyl 2-bromoacetate (45 mg) in DMF (3 mL) at 0° C. The resulting mixture was stirred at room temperature for 16 h before it was diluted with water and extracted with EtOAc. The organic extracts were washed with brine, dried over $Na_2SO_4$, filtered, and concentrated. The residue was purified by reversed-phase column chromatography to afford the title compound as a light-yellow oil (55 mg). MS obsd. ($ESI^+$): 584.3 $[(M+H)]^+$.

Step 2: tert-butyl (2R,3S,4S)-3-(2-amino-2-oxoethoxy)-4-((2-methoxyethoxy)methoxy)-2-(4-(1-methyl-1H-indazol-5-yl)benzyl)pyrrolidine-1-carboxylate (56-3). $NH_3$·$H_2O$ (16 mg) were added to a stirred solution of tert-butyl (2R,3S,4S)-3-(2-methoxy-2-oxoethoxy)-4-((2-methoxyethoxy)methoxy)-2-(4-(1-methyl-1H-indazol-5-yl)benzyl)pyrrolidine-1-carboxylate (55 mg) in MeOH (3 mL) at 0° C. The resulting mixture was stirred at room temperature for 12 h before it was diluted with water and extracted with EtOAc. The organic extracts were washed with brine, dried over $Na_2SO_4$, filtered, and concentrated. The residue was purified by reversed-phase column chromatography to afford the title compound as a light-yellow oil (40 mg). MS obsd. ($ESI^+$): 569.3 $[(M+H)]^+$.

Step 3: 2-(((2R,3S,4S)-4-hydroxy-2-(4-(1-methyl-1H-indazol-5-yl)benzyl)pyrrolidin-3-yl)oxy)acetamide. The title compound was prepared in 33.7% overall yield as a white solid according to General Procedure VIII in STEP 3. $^1H$ NMR (400 MHz, MeOD) δ 8.03 (d, J=1.1 Hz, 1H), 7.95 (t, J=1.6 Hz, 1H), 7.71 (dq, J=8.8, 1.6 Hz, 1H), 7.65-7.56 (m, 3H), 7.35 (d, J=8.0 Hz, 2H), 4.26 (dd, J=6.2, 2.6 Hz, 1H), 4.15-4.01 (m, 4H), 3.90 (d, J=15.2 Hz, 1H), 3.56-3.40 (m, 3H), 3.10-2.90 (m, 2H), 2.75 (dd, J=12.2, 2.5 Hz, 1H). MS obsd. ($ESI^+$): 381.2 $[(M+H)]^+$.

Example 65: (3S,4S,5R)-5-(4-(pyridazin-4-yl)benzyl)-4-(2-((R)-tetrahydrofuran-3-yl)ethoxy)pyrrolidin-3-ol Scheme 57

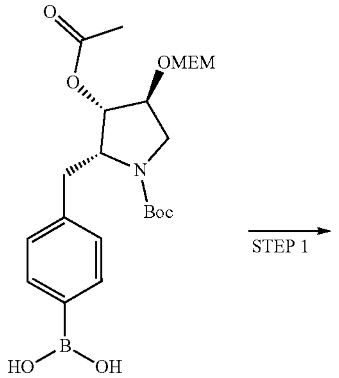

3-2

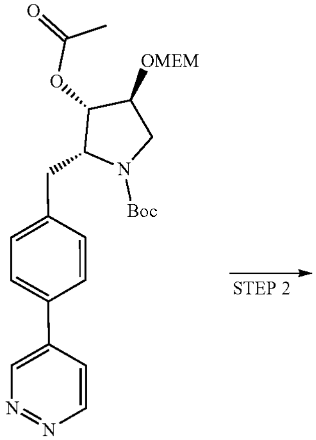

57-2

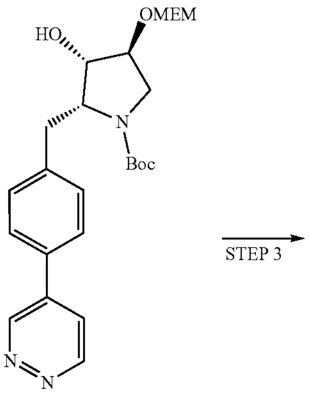

57-3

-continued

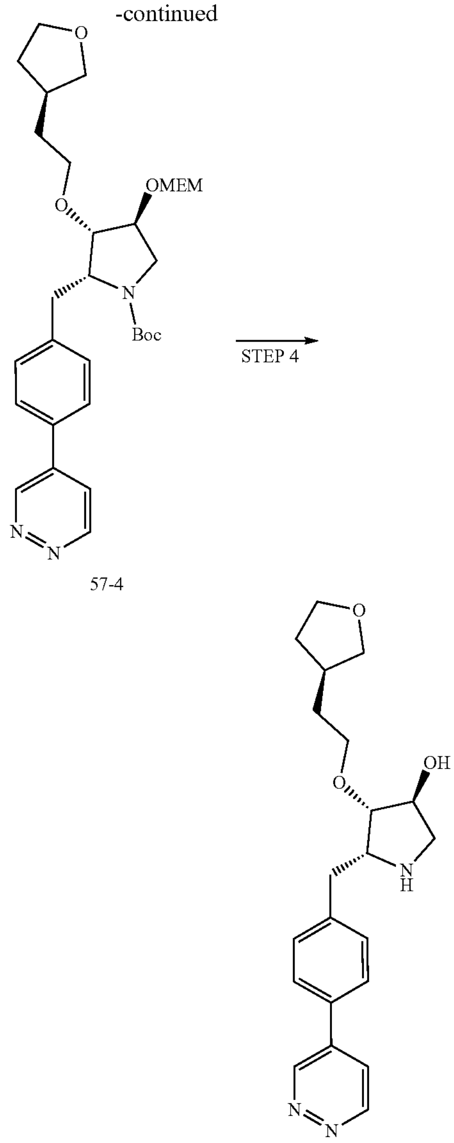

57-4

Step 1: tert-butyl (2R,3S,4S)-3-(acetyloxy)-4-[(2-methoxyethoxy)methoxy]-2-{[4-(pyridazin-4-yl)phenyl]methyl}pyrrolidine-1-carboxylate (57-2)

A mixture of tert-butyl (2R,3S,4S)-3-(acetyloxy)-1-(tert-butoxycarbonyl)-4-[(2-methoxyethoxy)methoxy]pyrrolidine-2-yl]methyl}phenylboronic acid (150 mg), 4-bromopyridazine (102 mg), and $Na_2CO_3$ (102 mg), and $Pd(dppf)Cl_2$ was suspended in 1,4-dioxane (3.0 mL) and $H_2O$ (0.3 mL) at rt and heated to 80° C. for 12 h. After cooling to room temperature, water was added, and the mixture was extracted with EtOAc. The organic extracts were washed with brine, dried over $Na_2SO_4$, filtered, and concentrated. The residue was purified by silica gel column chromatography to afford the title compound as a yellow solid (120 mg). MS obsd. ($ESI^+$): 502.2 $[(M+H)]^+$.

Step 2: tert-butyl (2R,3S,4S)-3-hydroxy-4-((2-methoxyethoxy)methoxy)-2-(4-(pyridazin-4-yl)benzyl)pyrrolidine-1-carboxylate (57-3). Lithium hydroxide (17 mg) was added to a solution of tert-butyl (2R,3S,4S)-3-(acetyloxy)-4-[(2-methoxyethoxy)methoxy]-2-{[4-(pyridazin-4-yl)phenyl]methyl}pyrrolidine-1-carboxylate (120 mg) in THF (3.0 mL) and $H_2O$ (1.0 mL) at 0° C. . . . The resulting mixture was stirred at rt for 1 h and concentrated. The residue was purified by reversed-phase flash chromatography to afford the title compound as a yellow oil (70 mg). MS obsd. ($ESI^+$): 460.2 $[(M+H)]^+$.

Step 3-4: (3S,4S,5R)-5-(4-(pyridazin-4-yl)benzyl)-4-(2-((R)-tetrahydrofuran-3-yl)ethoxy)pyrrolidin-3-ol. The title compound was prepared in 32.5% overall yield as an off-white solid according to General Procedure I using 57-3 (70 mg) and (R)-3-(2-iodoethyl)tetrahydrofuran (69 mg) in DMF in STEP 1, and General Procedure VIII in STEP 2. $^1H$ NMR (400 MHz, MeOD) δ 9.56 (dd, J=2.5, 1.2 Hz, 1H), 9.21 (dd, J=5.5, 1.2 Hz, 1H), 8.02 (dd, J=5.5, 2.5 Hz, 1H), 7.89-7.81 (m, 2H), 7.51 (d, J=8.2 Hz, 2H), 4.30-4.24 (m, 1H), 3.97-3.94 (m, 1H), 3.92-3.87 (m, 1H), 3.85-3.83 (m, 1H), 3.81-3.63 (m, 1H), 3.54 (dd, J=8.4, 6.7 Hz, 1H), 3.46-3.35 (m, 4H), 3.09 (dd, J=13.5, 8.4 Hz, 1H), 2.96 (dd, J=13.5, 6.7 Hz, 1H), 2.74 (dd, J=12.2, 2.4 Hz, 1H), 2.36 (dd, J=14.8, 7.4 Hz, 1H), 2.11 (dd, J=12.1, 4.6 Hz, 1H), 1.73 (d, J=6.6 Hz, 2H), 1.61 (dd, J=12.3, 7.9 Hz, 1H). MS obsd. ($ESI^+$): 370.2 $[(M+H)]^+$.

Example 66: (3S,4S,5R)-4-ethoxy-5-(4-(pyridazin-4-yl)benzyl)pyrrolidin-3-ol

Scheme 58

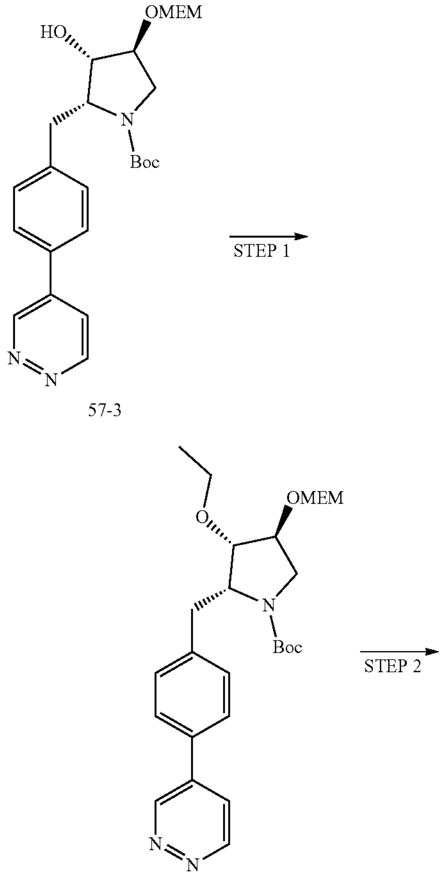

57-3

58-2

-continued

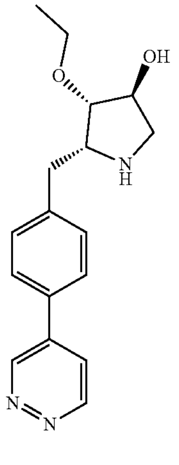

Step 1 and 2: (3S,4S,5R)-4-ethoxy-5-(4-(pyridazin-4-yl)benzyl)pyrrolidin-3-ol. The title compound was prepared in 45.9% overall yield as a yellow semi-solid according to General Procedure I using 57-3 (65 mg) and iodoethane (44 mg) in DMF in STEP 1, and General Procedure VIII in STEP 2. $^1$H NMR (400 MHz, MeOD) δ 9.57 (dd, J=2.6, 1.2 Hz, 1H), 9.21 (dd, J=5.5, 1.2 Hz, 1H), 8.02 (dd, J=5.5, 2.5 Hz, 1H), 7.88-7.80 (m, 2H), 7.55-7.48 (m, 2H), 4.26 (dd, J=5.7, 2.5 Hz, 1H), 3.70 (dd, J=9.3, 7.0 Hz, 1H), 3.53-3.42 (m, 1H), 3.45-3.36 (m, 3H), 3.08 (dd, J=13.3, 8.6 Hz, 1H), 2.95 (dd, J=13.3, 6.5 Hz, 1H), 2.72 (dd, J=12.3, 2.4 Hz, 1H), 1.26 (t, J=7.0 Hz, 3H). MS obsd. (ESI$^+$): 300.2 [(M+H)]$^+$.

Example 67: (3S,4S,5R)-4-(1,1-difluoropropoxy)-5-(4-(pyridazin-4-yl)benzyl)pyrrolidin-3-ol Scheme 59

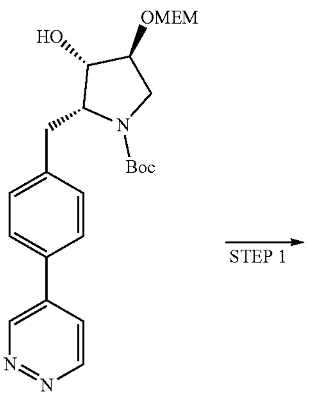

57-3

-continued

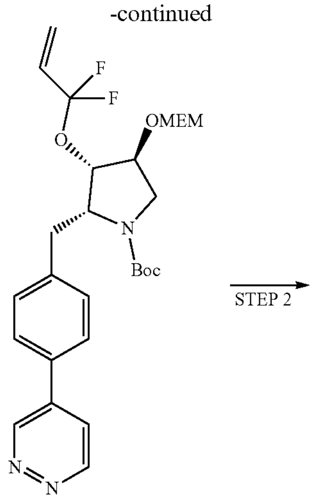

59-2

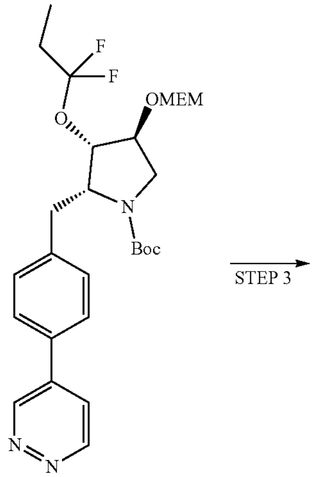

59-3

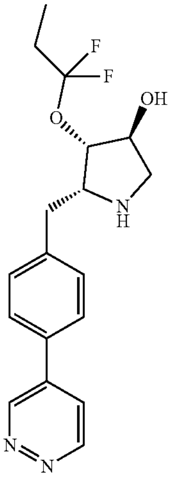 [SMILES: CCC(F)(F)O[C@@H]1[C@@H](O)CN[C@@H]1Cc1ccc(-c2ccnnc2)cc1]

Step 1-3: (3S,4S,5R)-4-(1,1-difluoropropoxy)-5-(4-(pyridazin-4-yl)benzyl)pyrrolidin-3-ol. The title compound was prepared in 55.9% overall yield as a white solid according to General Procedure I using 35-2 (560 mg) and 1-(3,3-difluoroprop-2-en-1-yl)-1-methylpiperidin-1-ium triflate (991 mg) in DMF in STEP 1, and General Procedure VI in STEP 2, and General Procedure VIII in STEP 3. $^1$H NMR (400 MHz, MeOD) δ 9.56 (dd, J=2.5, 1.2 Hz, 1H), 9.20 (dd, J=5.5, 1.2 Hz, 1H), 8.02 (dd, J=5.5, 2.5 Hz, 1H), 7.84 (d, J=7.9 Hz, 2H), 7.52 (d, J=7.9 Hz, 2H), 4.43 (d, J=3.6 Hz, 1H), 4.32 (d, J=5.4 Hz, 1H), 3.65 (s, 1H), 3.38 (dd, J=12.3, 5.6 Hz, 1H), 3.04 (dd, J=14.0, 6.3 Hz, 1H), 2.90 (dd, J=14.0, 7.9 Hz, 1H), 2.79-2.71 (m, 1H), 2.16-2.00 (m, 2H), 1.12 (t, J=7.5 Hz, 3H). MS obsd. ($ESI^+$): 350.2 $[(M+H)]^+$.

Example 68: (3S,4S,5R)-4-(cyclopropylmethoxy)-5-(4-(pyridazin-4-yl)benzyl)pyrrolidin-3-ol Scheme 60

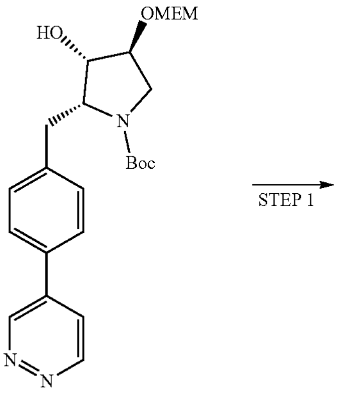

57-3

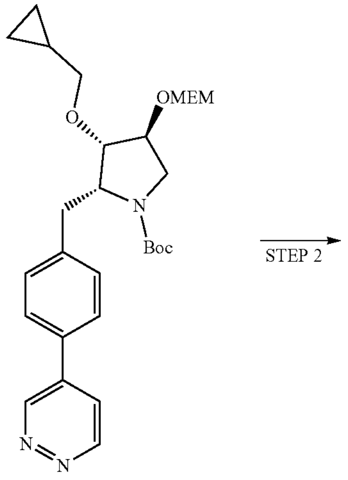

60-2

-continued

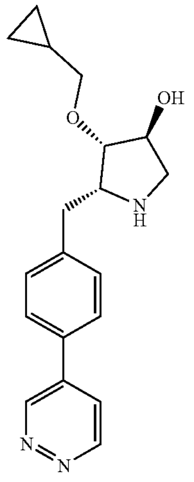

Step 1-2: (3S,4S,5R)-4-(cyclopropylmethoxy)-5-(4-(pyridazin-4-yl)benzyl)pyrrolidin-3-ol. The title compound was prepared in 58.7% overall yield as a white solid according to General Procedure I using 57-3 (105 mg) and (bromomethyl)cyclopropane (55 mg) in DMF in STEP 1, and General Procedure VIII in STEP 2. $^1H$ NMR (400 MHz, MeOD) δ 9.57 (dd, J=2.6, 1.2 Hz, 1H), 9.21 (dd, J=5.5, 1.2 Hz, 1H), 8.03 (dd, J=5.5, 2.5 Hz, 1H), 7.89-7.78 (m, 2H), 7.55 (d, J=8.2 Hz, 2H), 4.31 (d, J=5.4 Hz, 1H), 3.60 (s, 1H), 3.52-3.41 (m, 3H), 3.28 (s, 1H), 3.15 (dd, J=13.2, 8.7 Hz, 1H), 3.00 (dd, J=13.4, 6.5 Hz, 1H), 2.81 (d, J=12.1 Hz, 1H), 1.17-1.06 (m, 1H), 0.58 (d, J=8.4 Hz, 2H), 0.27 (t, J=5.5 Hz, 2H). MS obsd. ($ESI^+$): 326.2 $[(M+H)]^+$.

Example 69: (3S,4S,5R)-5-(4-(oxazol-5-yl)benzyl)-4-(3 (trifluoromethoxy)propoxy)pyrrolidin-3-ol Scheme 61

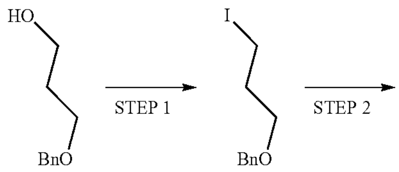

61-1 61-2

-continued

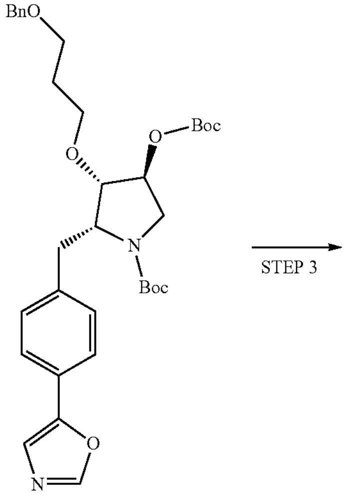

61-3

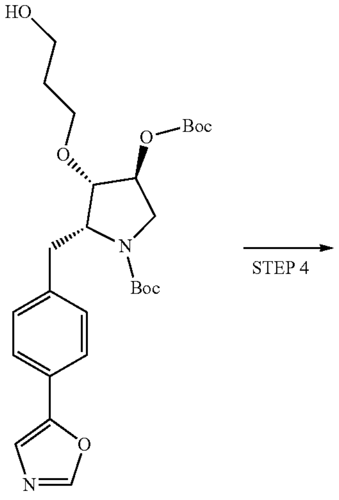

61-4

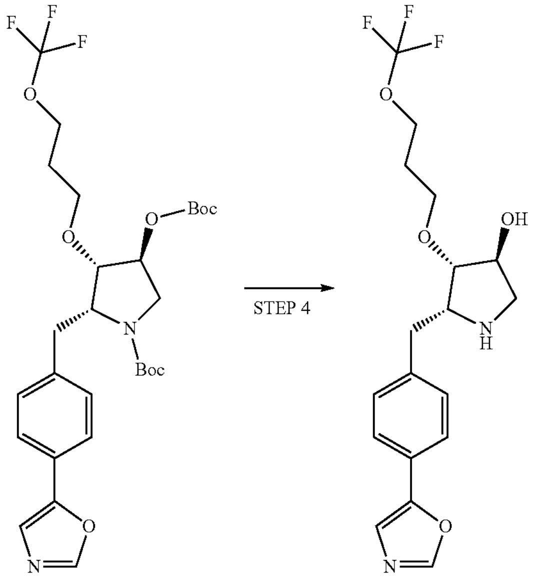

61-5

Step 1: ((3-iodopropoxy)methyl)benzene (61-2). $PPh_3$ (5.4 g), Imidazole (1.8 g) and Iodine (5.3 g) were added to a stirred solution of 3-(benzyloxy) propan-1-ol (3.0 g) in MeCN (10 mL) at 0° C. The resulting mixture was stirred at room temperature for overnight before it was diluted with water and extracted with EtOAc. The organic extracts were washed with brine, dried over $Na_2SO_4$, filtered, and concentrated. The residue was purified by reversed-phase flash chromatography to afford the title compound as a yellow oil (4.5 g). MS obsd. ($ESI^+$): 277.0 $[(M+H)]^+$.

Step 2-3: tert-butyl (2R,3S,4S)-4-((tert-butoxycarbonyl) oxy)-3-(3-hydroxypropoxy)-2-(4-(oxazol-5-yl)benzyl)pyrrolidine-1-carboxylate (61-3). The title compound was prepared in 81.7% overall yield as a yellow oil according to General Procedure I using Int-9 (300 mg) and ((3-iodopropoxy)methyl)benzene (359 mg) in DMF in STEP 2, and General Procedure VI in STEP 3. MS obsd. ($ESI^+$): 519.3 $[(M+H)]^+$.

Step 4: tert-butyl (2R,3S,4S)-4-((tert-butoxycarbonyl) oxy)-2-(4-(oxazol-5-yl)benzyl)-3-(3-(trifluoromethoxy) propoxy)pyrrolidine-1-carboxylate (61-4). KF (33 mg), 2-fluoropyridine (37 mg) and trimethyl(trifluoromethyl)silane (54 mg) were added to a stirred solution of tert-butyl (2R,3S,4S)-4-((tert-butoxycarbonyl)oxy)-3-(3-hydroxypropoxy)-2-(4-(oxazol-5-yl)benzyl)pyrrolidine-1-carboxylate (100 mg), argentio trifluoromethanesulfonate (99 mg) and 4-(chloromethyl)-1-fluoro-1,4-diazabicyclo[2.2.2]octane-1,4-diium; bis(tetrafluoroboranuide) (102 mg) in ethyl acetate (10 mL) at room temperature. The resulting mixture was stirred at room temperature overnight under nitrogen atmosphere before it was diluted with water and extracted with EtOAc. The organic extracts were washed with brine, dried over $Na_2SO_4$, filtered, and concentrated. The residue was purified by reversed-phase flash chromatography to afford the title compound as a yellow oil (50 mg). MS obsd. ($ESI^+$): 587.3 $[(M+H)]^+$.

Step 5: (3S,4S,5R)-5-(4-(oxazol-5-yl)benzyl)-4-(3 (trifluoromethoxy)propoxy)pyrrolidin-3-ol. The title compound was prepared in 28.7% yield as a yellow oil according to General Procedure VIII in STEP 5. $^1H$ NMR (400 MHz, Methanol-$d_4$) δ 8.28 (s, 1H), 7.78 (d, J=8.0 Hz, 2H), 7.55 (s, 1H), 7.46 (d, J=8.0 Hz, 2H), 4.50 (d, J=4.3 Hz, 1H), 4.22 (dd, J=6.1, 1.9 Hz, 1H), 4.15-4.05 (m, 1H), 3.88-3.70 (m, 2H), 3.68-3.54 (m, 2H), 3.33-3.32 (m, 1H), 3.32-3.16 (m, 2H), 3.11 (dd, J=14.0, 8.2 Hz, 1H), 2.11-2.03 (m, 2H). MS obsd. ($ESI^+$): 387.1 $[(M+H)]^+$.

Example 70: (3S,4S,5R)-5-(4-(1H-pyrazol-4-yl) benzyl)-4-(1,1-difluoropropoxy)pyrrolidin-3-ol Scheme 62

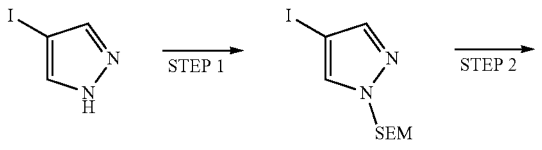

-continued

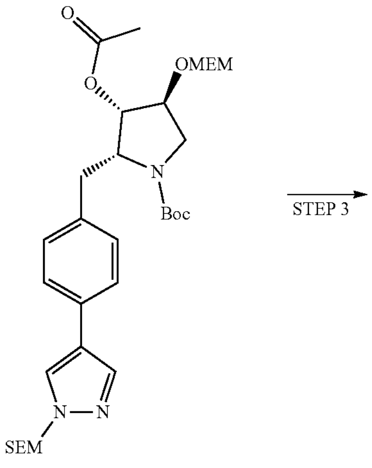

62-3

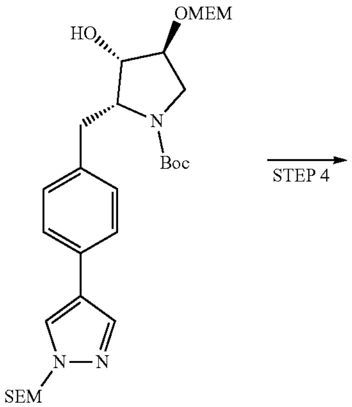

62-4

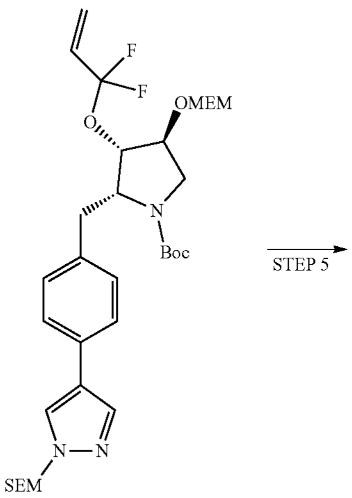

62-5

-continued

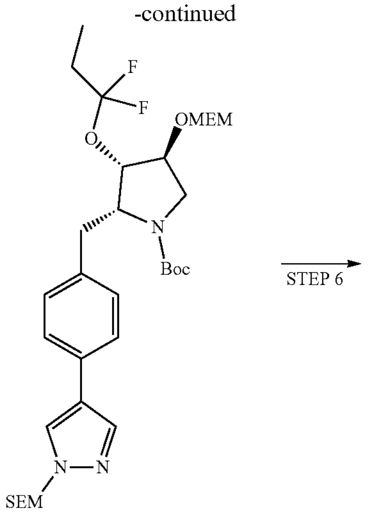

62-6

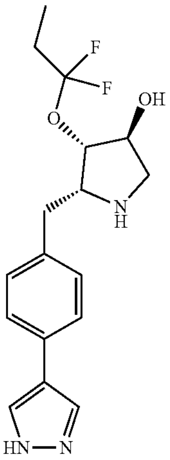

Step 1: 4-iodo-1-((2-(trimethylsilyl)ethoxy)methyl)-1H-pyrazole (62-2). NaH (155 mg) was slowly added to a solution of 4-iodopyrazole (500 mg) in DMF (4 mL) t 0° C. and the mixture was stirred at 0° C. for 0.5 h. Then a solution of [2-(chloromethoxy)ethyl]trimethylsilane (473 mg) in DMF (1 mL) was added dropwise. The resulting mixture was stirred at room temperature for 1 h, diluted with water, and extracted with EtOAc. The organic extracts were washed with brine, dried over $Na_2SO_4$, filtered, and concentrated. The residue was purified by reversed-phase flash chromatography to afford the title compound as a light-yellow oil (800 mg). MS obsd. ($ESI^+$): 325.0 $[(M+H)]^+$.

Step 2: tert-butyl (2R,3S,4S)-3-acetoxy-4-((2-methoxyethoxy)methoxy)-2-(4-(1-((2-(trimethylsilyl)ethoxy)methyl)-1H-pyrazol-4-yl)benzyl)pyrrolidine-1-carboxylate (62-3). Under a nitrogen atmosphere, XPhos Pd $G_3$ (72 mg), XPhos (82 mg) and $K_2CO_3$ (237 mg) were added to a stirred solution of 3-2 (400 mg) and 4-iodo-1-((2-(trimethylsilyl)ethoxy)methyl)-1H-pyrazole (555 mg) in 1,4-Dioxane (10 mL) and $H_2O$ (1 mL) at room temperature. The resulting mixture was stirred at 100° C. for 16 h before it was diluted with water and extracted with EtOAc. The organic extracts were washed with brine, dried over $Na_2SO_4$, filtered, and concentrated. The residue was purified by reversed-phase flash chromatography to afford the title compound as a light-yellow oil (150 mg). MS obsd. ($ESI^+$): 620.3 $[(M+H)]^+$.

Step 3: tert-butyl (2R,3S,4S)-3-hydroxy-4-((2-methoxyethoxy)methoxy)-2-(4-(1-((2-(trimethylsilyl)ethoxy)methyl)-1H-pyrazol-4-yl)benzyl)pyrrolidine-1-carboxylate (62-3). LiOH (17 mg) was added to a stirred solution of tert-butyl (2R,3S,4S)-3-acetoxy-4-((2-methoxyethoxy)methoxy)-2-(4-(1-((2-(trimethylsilyl)ethoxy)methyl)-1H-pyrazol-4-yl)benzyl)pyrrolidine-1-carboxylate (150 mg) in THF (5 mL) and $H_2O$ (1 mL). The resulting mixture was stirred at room temperature for 16 h, diluted with water, and extracted with EtOAc. The organic extracts were washed with brine, dried over $Na_2SO_4$, filtered, and concentrated. The residue was purified by reversed-phase flash chromatography to afford the title compound as a light-yellow oil (130 mg). MS obsd. ($ESI^+$): 578.3 $[(M+H)]^+$.

Step 4-6: (3S,4S,5R)-5-(4-(1H-pyrazol-4-yl)benzyl)-4-(1,1-difluoropropoxy)pyrrolidin-3-ol. The title compound was prepared in 48.1% overall yield as a white solid according to General Procedure I using tert-butyl (2R,3S,4S)-3-hydroxy-4-((2-methoxyethoxy)methoxy)-2-(4-(1-((2-(trimethylsilyl)ethoxy)methyl)-1H-pyrazol-4-yl)benzyl)pyrrolidine-1-carboxylate (62-4) (80 mg) and 1-(3,3-difluoroprop-2-en-1-yl)-1-methylpiperidin-1-ium triflate (90 mg) in DMF in STEP 4, and General Procedure VI in step 5, and General Procedure VIII in STEP 6. $^1$H NMR (400 MHz, MeOD) δ 7.91 (s, 2H), 7.54-7.47 (m, 2H), 7.30-7.23 (m, 2H), 4.39 (d, J=3.6 Hz, 1H), 4.33-4.26 (m, 1H), 3.62-3.51 (m, 1H), 3.34 (dd, J=12.2, 5.6 Hz, 1H), 2.92 (dd, J=13.9, 6.4 Hz, 1H), 2.78 (dd, J=13.9, 7.8 Hz, 1H), 2.70 (dd, J=12.2, 2.2 Hz, 1H), 2.13-1.97 (m, 2H), 1.10 (t, J=7.5 Hz, 3H). MS obsd. ($ESI^+$): 338.2 $[(M+H)]^+$.

Example 71: (3S,4S,5R)-5-(4-(1H-pyrazol-4-yl)benzyl)-4-ethoxypyrrolidin-3-ol

Scheme 63

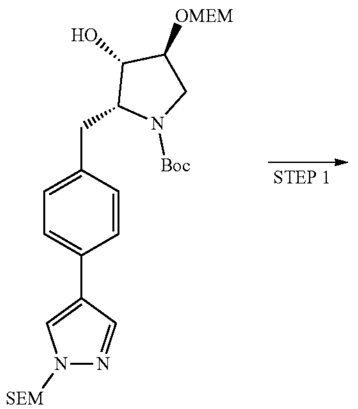

62-4

-continued

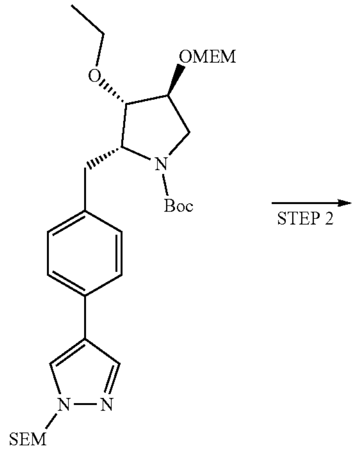

63-2

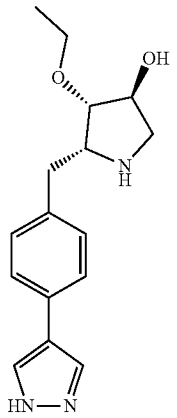

Step 1-2: (3S,4S,5R)-5-(4-(1H-pyrazol-4-yl)benzyl)-4-ethoxypyrrolidin-3-ol. The title compound was prepared in 24.3% overall yield as a white solid according to General Procedure I using 62-4 (60 mg) and ethyl iodide (32 mg) in DMF in STEP 1, and General Procedure VIII in STEP 2. $^1$H NMR (400 MHz, MeOD) δ 7.94 (s, 2H), 7.58-7.50 (m, 2H), 7.33-7.25 (m, 2H), 4.28-4.25 (m, 1H), 3.74-3.65 (m, 1H), 3.56-3.48 (m, 1H), 3.49-3.37 (m, 3H), 3.01 (dd, J=13.3, 8.7 Hz, 1H), 2.89 (dd, J=13.4, 6.5 Hz, 1H), 2.78 (dd, J=12.3, 2.1 Hz, 1H), 1.26 (t, J=7.0 Hz, 3H). MS obsd. ($ESI^+$): 288.2 $[(M+H)]^+$.

Example 72: (3S,4S,5R)-4-(1,1-difluoropropoxy)-5-(4-(1-(trifluoromethyl)-1H-pyrazol-4-yl)benzyl)pyrrolidin-3-ol
Scheme 64
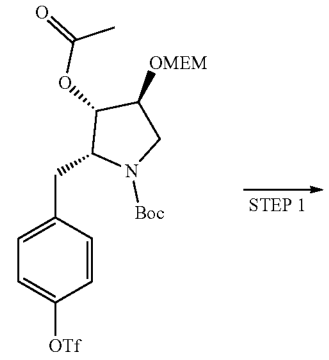
3-1
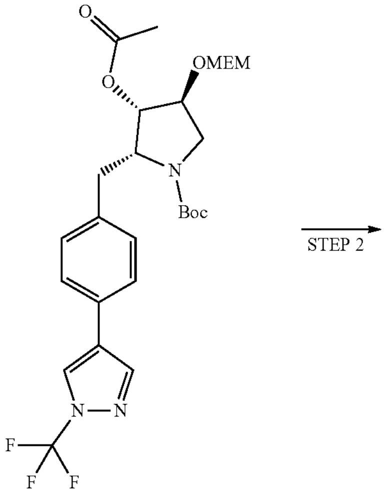
54-2
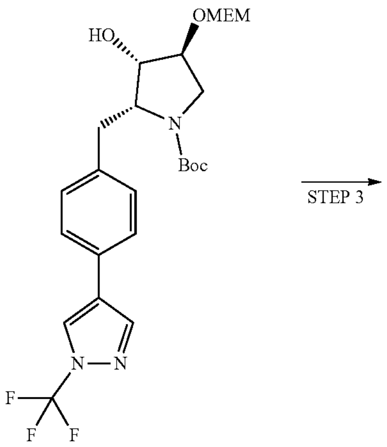
64-3
-continued
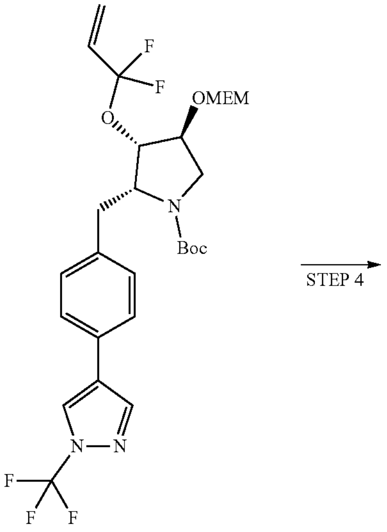
64-4
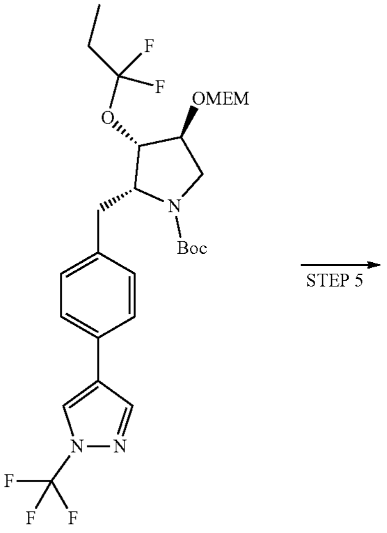
54-5
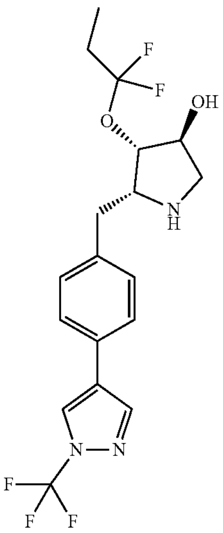

Step 1: tert-butyl (2R,3S,4S)-3-acetoxy-4-((2-methoxyethoxy)methoxy)-2-(4-(1-(trifluoromethyl)-1H-pyrazol-4-yl)benzyl)pyrrolidine-1-carboxylate (64-2). XPhos (42 mg), XPhos Pd $G_3$ (148 mg) were added to a stirred solution of tert-butyl (2R,3S,4S)-3-(acetyloxy)-4-[(2-methoxyethoxy)methoxy]-2-{[4-(trifluoromethanesulfonyloxy)phenyl]methyl}pyrrolidine-1-carboxylate (500 mg), 4-(4,4,5,5-tetramethyl-1,3,2-dioxaborolan-2-yl)-1-(trifluoromethyl)pyrazole (344 mg), and $NaHCO_3$ (221 mg) in DMF (10 mL) room temperature. The resulting mixture was stirred at 80° C. for 16 h, before it was diluted with water and extracted with EtOAc. The organic extracts were washed with brine, dried over $Na_2SO_4$, filtered and concentrated. The residue was purified by reversed-phase flash chromatography to afford the title compound as a yellow oil (540 mg). MS obsd. ($ESI^+$): 558.2 $[(M+H)]^+$.

Step 2: tert-butyl (2R,3S,4S)-3-hydroxy-4-((2-methoxyethoxy)methoxy)-2-(4-(1-(trifluoromethyl)-1H-pyrazol-4-yl)benzyl)pyrrolidine-1-carboxylate (64-3). LiOH (70 mg) was added to a stirred solution of tert-butyl (2R,3S,4S)-3-acetoxy-4-((2-methoxyethoxy)methoxy)-2-(4-(1-(trifluoromethyl)-1H-pyrazol-4-yl)benzyl)pyrrolidine-1-carboxylate (540 mg) in THF (5 mL) and $H_2O$ (1 mL). The resulting mixture was stirred at room temperature for 6 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (410 mg). MS obsd. ($ESI^+$): 516.2 $[(M+H)]^+$.

Step 3-5: (3S,4S,5R)-4-(1,1-difluoropropoxy)-5-(4-(1-(trifluoromethyl)-1H-pyrazol-4-yl)benzyl)pyrrolidin-3-ol. The title compound was prepared in 49.1% overall yield as a white solid according to General Procedure I using tert-butyl (2R,3S,4S)-3-hydroxy-4-((2-methoxyethoxy)methoxy)-2-(4-(1-(trifluoromethyl)-1H-pyrazol-4-yl)benzyl)pyrrolidine-1-carboxylate (118-2) (250 mg) and 1-(3,3-difluoroprop-2-en-1-yl)-1-methylpiperidin-1-ium triflate (2.4 g)) in DMF in STEP 3, and General Procedure VI in step 4, and General Procedure VIII in STEP 5. $^1H$ NMR (400 MHz, MeOD) δ 8.55 (s, 1H), 8.21 (s, 1H), 7.65-7.58 (m, 2H), 7.35 (d, J=7.9 Hz, 2H), 4.42 (d, J=3.5 Hz, 1H), 4.32 (d, J=5.4 Hz, 1H), 3.66-3.57 (m, 1H), 3.38 (dd, J=12.3, 5.6 Hz, 1H), 2.98 (dd, J=14.0, 6.4 Hz, 1H), 2.84 (dd, J=14.0, 7.8 Hz, 1H), 2.75 (dd, J=12.2, 2.1 Hz, 1H), 2.16-2.00 (m, 2H), 1.17-1.08 (m, 3H); MS obsd. ($ESI^+$): 406.1 $[(M+H)]^+$.

Example 73: (3S,4S,5R)-4-ethoxy-5-(4-(1-(trifluoromethyl)-1H-pyrazol-4-yl)benzyl)pyrrolidin-3-ol Scheme 65

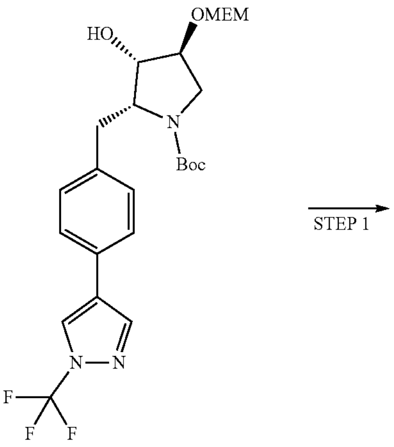

64-3

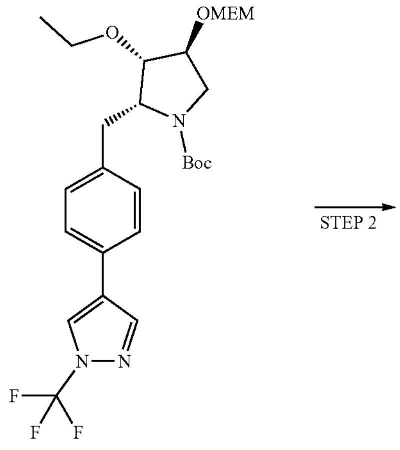

65-2

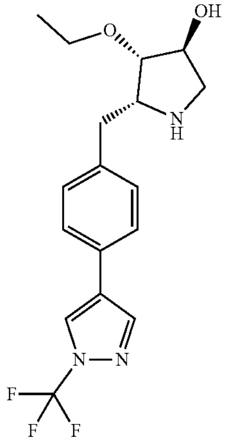

Step 1 and 2: (3S,4S,5R)-4-ethoxy-5-(4-(1-(trifluoromethyl)-1H-pyrazol-4-yl)benzyl)pyrrolidin-3-ol. The title compound was prepared in 27.3% overall yield as a white solid according to General Procedure I using 64-3 (200 mg) and ethyl iodide (121 mg) in DMF in STEP 1, and General Procedure VIII in STEP 2. $^1H$ NMR (400 MHz, MeOD) δ 8.54 (s, 1H), 8.21 (s, 1H), 7.64-7.57 (m, 2H), 7.34 (d, J=7.8

Hz, 2H), 4.28-4.21 (m, 1H), 3.75-3.63 (m, 1H), 3.48-3.35 (m, 4H), 3.05-2.83 (m, 2H), 2.74-2.66 (m, 1H), 1.33-1.21 (m, 3H). MS obsd. ($ESI^+$): 356.2 $[(M+H)]^+$.

Example 74: (3S,4S,5R)-4-ethoxy-5-(4-(phthalazin-6-yl)benzyl)pyrrolidin-3-ol

Scheme 66

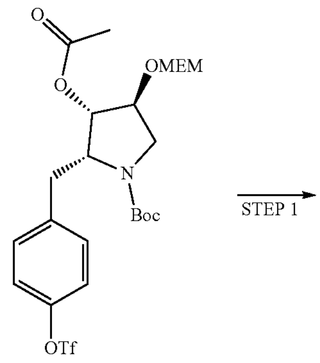

3-1

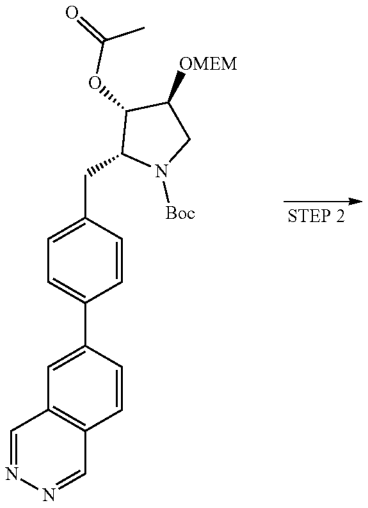

66-2

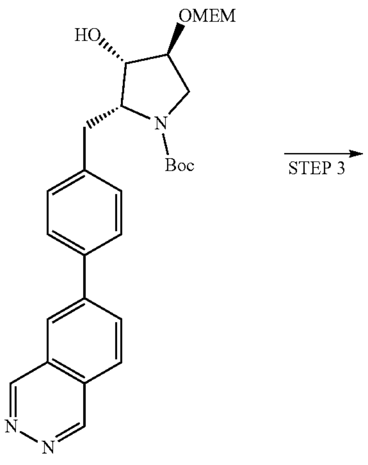

66-3

-continued

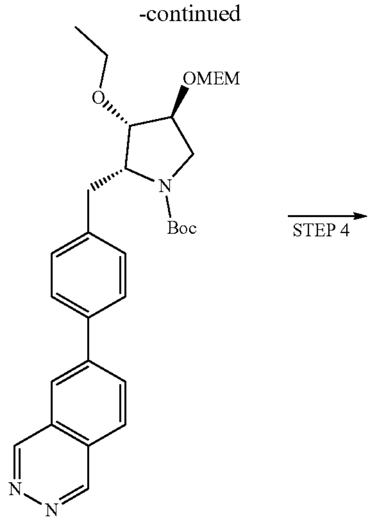

66-4

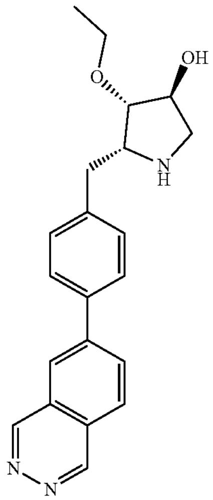

Step 1: tert-butyl (2R,3S,4S)-3-acetoxy-4-((2-methoxyethoxy)methoxy)-2-(4-(phthalazin-6-yl)benzyl)pyrrolidine-1-carboxylate (66-2). $Pd(PPh_3)_2Cl_2$ (30 mg) and $Na_2CO_3$ (136 mg) were added to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (200 mg) and 6-bromophthalazine (178 mg) in 1,4-dioxane (10 mL) and $H_2O$ (2 mL) at room temperature. The resulting mixture was stirred at 80° C. for overnight under nitrogen atmosphere before it was diluted with water and extracted with EtOAc. The organic extracts were washed with brine, dried over $Na_2SO_4$, filtered, and concentrated. The residue was purified by reversed-phase flash chromatography to afford the title compound as a white solid (190 mg). MS obsd. ($ESI^+$): 552.3 $[(M+H)]^+$.

Step 2: tert-butyl (2R,3S,4S)-3-hydroxy-4-((2-methoxyethoxy)methoxy)-2-(4-(phthalazin-6-yl)benzyl)pyrrolidine-1-carboxylate (66-3). LiOH (11 mg) was added to a stirred solution of tert-butyl (2R,3S,4S)-3-acetoxy-4-((2-methoxyethoxy)methoxy)-2-(4-(phthalazin-6-yl)benzyl)pyrrolidine-1-carboxylate (180 mg) in THF (9 mL) and $H_2O$ (3 mL) at 0° C. The resulting mixture was stirred at room temperature overnight, before it was diluted with water and extracted with EtOAc. The organic extracts were washed with brine, dried over $Na_2SO_4$, filtered, and concentrated. The residue was purified by reversed-phase flash chromatography to afford the title compound as a white solid (150 mg). (ESI$^+$): 510.3 $[(M+H)]^+$.

Step 3 and 4: (3S,4S,5R)-4-ethoxy-5-(4-(phthalazin-6-yl) benzyl)pyrrolidin-3-ol. The title compound was prepared in 37.3% overall yield as a white solid according to General Procedure I using 66-3 (150 mg) and ethyl iodide (50 mg) in DMF in STEP 3, and General Procedure VIII in STEP 4. $^1$H NMR (400 MHz, MeOD) δ 9.67 (d, J=2.8 Hz, 1H), 9.65-9.59 (m, 1H), 8.45-8.34 (m, 2H), 8.25 (dd, J=8.6, 3.9 Hz, 1H), 7.87-7.79 (m, 2H), 7.53-7.46 (m, 2H), 4.28 (dd, J=5.8, 2.2 Hz, 1H), 3.78-3.66 (m, 1H), 3.57-3.49 (m, 1H), 3.49-3.40 (m, 3H), 3.15-3.04 (m, 1H), 2.96 (dd, J=13.5, 6.5 Hz, 1H), 2.75 (dd, J=12.4, 2.3 Hz, 1H), 1.33-1.23 (m, 3H). MS obsd. (ESI$^+$): 350.2 $[(M+H)]^+$.

Example 75: (3S,4S,5R)-5-(4-(4-aminothiazol-5-yl) benzyl)-4-(1,1-difluoropropoxy)pyrrolidin-3-ol Scheme 67

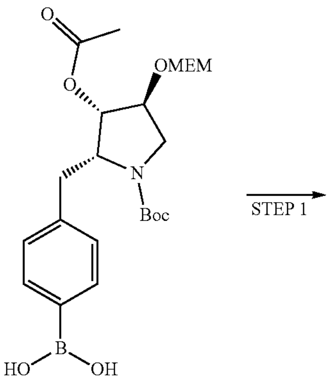

3-2

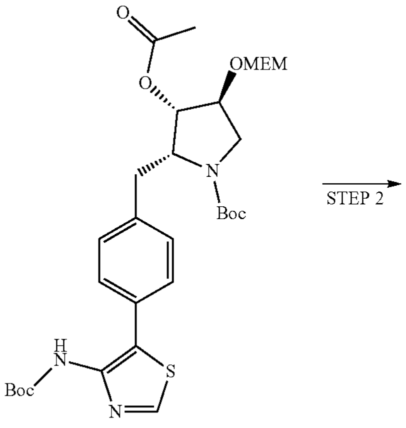

67-2

-continued

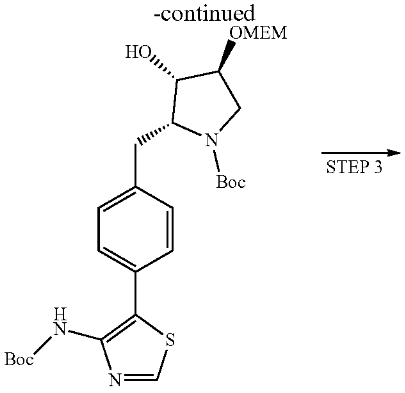

67-3

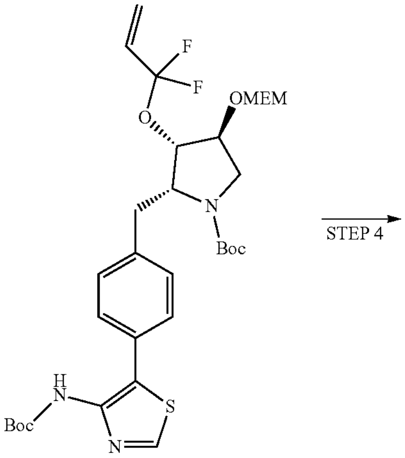

67-4

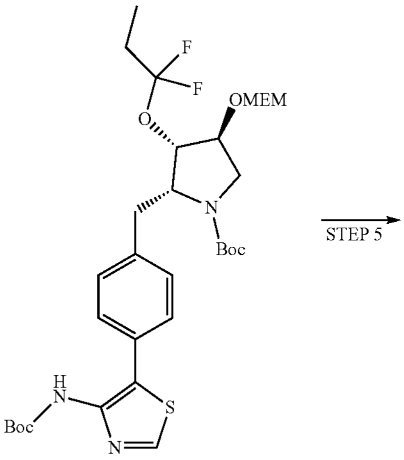

67-5

-continued

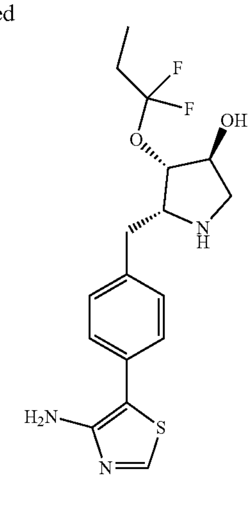

Step 1: tert-butyl (2R,3S,4S)-3-acetoxy-2-(4-(4-((tert-butoxycarbonyl)amino)thiazol-5-yl)benzyl)-4-((2-methoxyethoxy)methoxy)pyrrolidine-1-carboxylate (67-2). Pd(dppf)$Cl_2$ (52 mg) was added to a stirred solution of tert-butyl N-(5-bromo-1,3-thiazol-4-yl) carbamate (99 mg), (4-(((2R,3S,4S)-3-acetoxy-1-(tert-butoxycarbonyl)-4-((2-methoxyethoxy)methoxy)pyrrolidin-2-yl)methyl)phenyl) boronic acid (200 mg) and $Na_2CO_3$ (113 mg) in Dioxane (8 mL) and $H_2O$ (1.5 mL) at room temperature. The resulting mixture was stirred at 80° C. for overnight before it was diluted with water and extracted with EtOAc. The organic extracts were washed with brine, dried over $Na_2SO_4$, filtered, and concentrated. The residue was purified by reversed-phase column chromatography to afford the title compound as a yellow oil (180 mg). MS obsd. ($ESI^+$): 622.3 $[(M+H)]^+$.

Step 2: tert-butyl (2R,3S,4S)-2-(4-(4-((tert-butoxycarbonyl)amino)thiazol-5-yl)benzyl)-3-hydroxy-4-((2-methoxyethoxy)methoxy)pyrrolidine-1-carboxylate (67-3). LiOH (9 mg) was added to a stirred solution of tert-butyl (2R,3S,4S)-3-acetoxy-2-(4-(4-((tert-butoxycarbonyl)amino)thiazol-5-yl)benzyl)-4-((2-methoxyethoxy)methoxy)pyrrolidine-1-carboxylate (80 mg) in THF (9 mL) and $H_2O$ (3 mL) at 0° C. The resulting mixture was stirred at room temperature for overnight, before it was diluted with water and extracted with EtOAc. The organic extracts were washed with brine, dried over $Na_2SO_4$, filtered, and concentrated. The residue was purified by reversed-phase flash chromatography to afford the title compound as a yellow oil (80 mg). MS obsd. ($ESI^+$): 580.3 $[(M+H)]^+$.

Step 3 and 4 and 5: (3S,4S,5R)-5-(4-(4-aminothiazol-5-yl)benzyl)-4-(1,1-difluoropropoxy)pyrrolidin-3-ol. The title compound was prepared in 23.2% overall yield as a light yellow semi-solid according to General Procedure I using tert-butyl (2R,3S,4S)-2-(4-(4-((tert-butoxycarbonyl)amino)thiazol-5-yl)benzyl)-3-hydroxy-4-((2-methoxyethoxy)methoxy)pyrrolidine-1-carboxylate (123-2) (60 mg) and 1-(3,3-difluoroprop-2-en-1-yl)-1-methylpiperidin-1-ium triflate (67 mg) in DMF in STEP 3, and General Procedure VI in step 4, and General Procedure VIII in STEP 5. $^1H$ NMR (400 MHz, MeOD) δ 8.63 (s, 1H), 7.51-7.46 (m, 2H), 7.40-7.34 (m, 2H), 4.42 (d, J=3.6 Hz, 1H), 4.35-4.29 (m, 1H), 3.61-3.51 (m, 1H), 3.38 (d, J=5.6 Hz, 1H), 2.97 (dd, J=13.9, 6.1 Hz, 1H), 2.82 (dd, J=14.0, 8.0 Hz, 1H), 2.72 (dd, J=12.2, 2.3 Hz, 1H), 2.13-2.01 (m, 2H), 1.12 (t, J=7.5 Hz, 3H). MS obsd. ($ESI^+$): 370.1 $[(M+H)]^+$.

Example 76: 4-(4-(((2R,3S,4S)-3-ethoxy-4-hydroxypyrrolidin-2-yl)methyl)phenyl)-1-methylpyridin-2(1H)-one Scheme 68

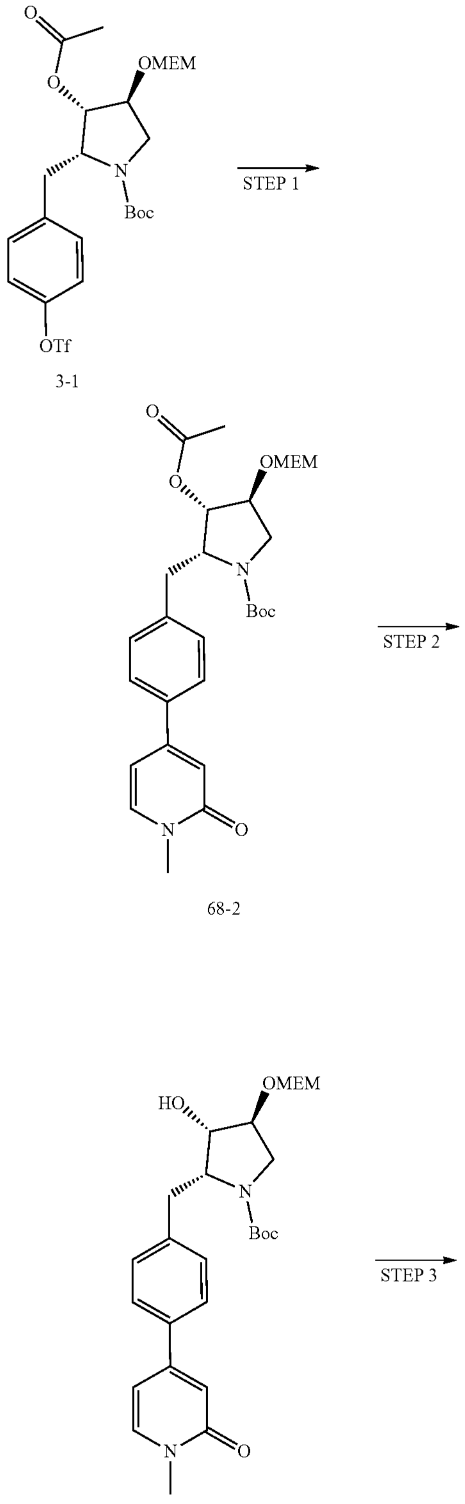

3-1

68-2

68-3

-continued

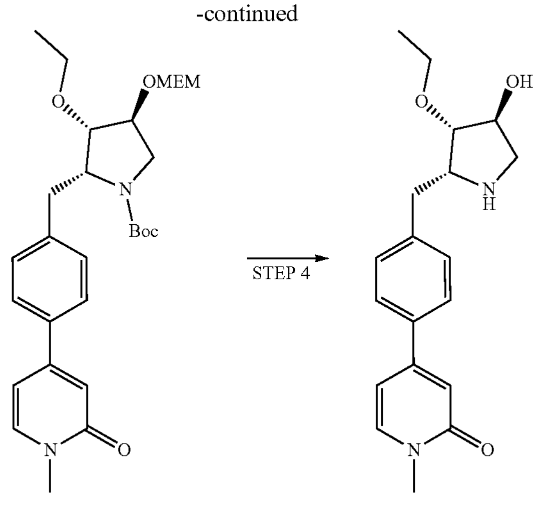

68-4

Example 77: 1-cyclopropyl-4-(4-(((2R,3S,4S)-3-ethoxy-4-hydroxypyrrolidin-2-yl)methyl)phenyl)pyridin-2(1H)-one Scheme 69

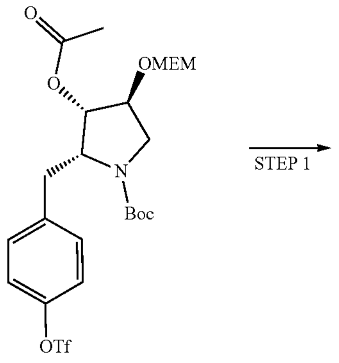

3-1

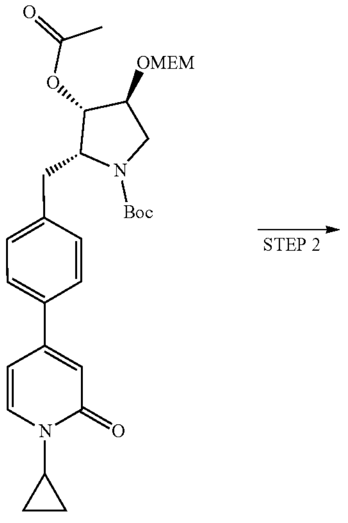

69-2

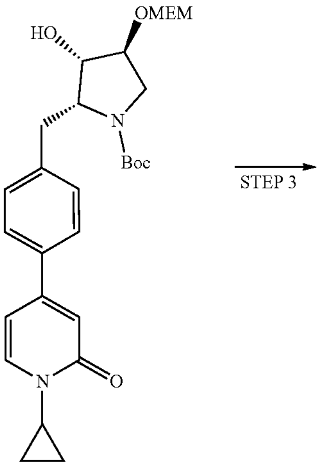

69-3

Step 1: tert-butyl (2R,3S,4S)-3-acetoxy-4-((2-methoxyethoxy)methoxy)-2-(4-(1-methyl-2-oxo-1,2-dihydropyridin-4-yl)benzyl)pyrrolidine-1-carboxylate (68-2). XPhos (13 mg) and XPhos Pd $G_3$ (44 mg) were added to a stirred solution of 1-methyl-4-(4,4,5,5-tetramethyl-1,3,2-dioxaborolan-2-yl)pyridin-2-one (93 mg), tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (150 mg) and $NaHCO_3$ (66 mg) in DMF (5 mL) at room temperature. The resulting mixture was stirred at 80° C. for overnight before it was diluted with water and extracted with EtOAc. The organic extracts were washed with brine, dried over $Na_2SO_4$, filtered, and concentrated. The residue was purified by reversed-phase column chromatography to afford the title compound as a yellow oil (130 mg). MS obsd. ($ESI^+$): 531.3 $[(M+H)]^+$.

Step 2: tert-butyl (2R,3S,4S)-3-hydroxy-4-((2-methoxyethoxy)methoxy)-2-(4-(1-methyl-2-oxo-1,2-dihydropyridin-4-yl)benzyl)pyrrolidine-1-carboxylate (68-3). LiOH (17 mg) at 0° C. was added to a stirred solution of tert-butyl (2R,3S,4S)-3-acetoxy-2-(4-(4-((tert-butoxycarbonyl)amino)thiazol-5-yl)benzyl)-4-((2-methoxyethoxy)methoxy)pyrrolidine-1-carboxylate (125 mg) in THF (6 mL) and $H_2O$ (2 mL). The resulting mixture was stirred at room temperature for 2 h before it was diluted with water and extracted with EtOAc. The organic extracts were washed with brine, dried over $Na_2SO_4$, filtered, and concentrated. The residue was purified by reversed-phase flash chromatography to afford the title compound as a yellow oil (100 mg). MS obsd. ($ESI^+$): 489.3 $[(M+H)]^+$.

Step 3 and 4:4-(4-(((2R,3S,4S)-3-ethoxy-4-hydroxypyrrolidin-2-yl)methyl)phenyl)-1-methylpyridin-2(1H)-one. The title compound was prepared in 36.3% overall yield as a yellow semi-solid according to General Procedure I using 68-3 (80 mg) and ethyl iodide (58 mg) in DMF in STEP 3, and General Procedure VIII in STEP 4. $^1H$ NMR (400 MHz, MeOD) δ 7.72 (d, J=7.0 Hz, 1H), 7.69-7.62 (m, 2H), 7.47-7.37 (m, 2H), 6.80 (d, J=2.0 Hz, 1H), 6.78-6.71 (m, 1H), 4.31-4.25 (m, 1H), 3.70 (dq, J=9.3, 7.0 Hz, 1H), 3.62 (s, 3H), 3.49-3.37 (m, 3H), 3.13-3.03 (m, 1H), 2.99-2.90 (m, 2H), 2.81-2.73 (m, 1H), 1.30-1.20 (m, 3H); MS obsd. ($ESI^+$): 329.2 $[(M+H)]^+$.

-continued

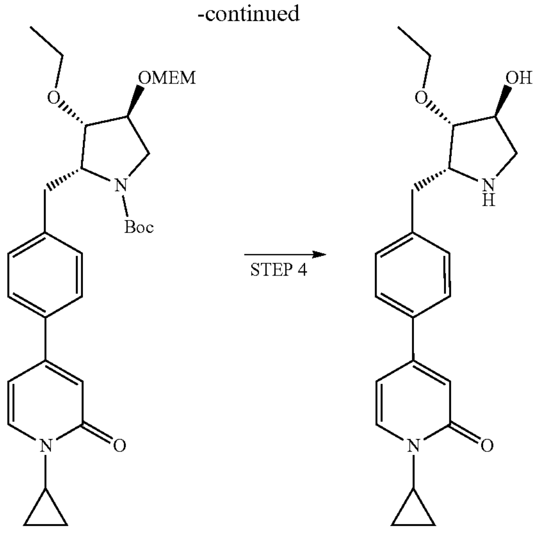

69-4

Step 1: tert-butyl (2R,3S,4S)-3-acetoxy-2-(4-(1-cyclopropyl-2-oxo-1,2-dihydropyridin-4-yl)benzyl)-4-((2-methoxyethoxy)methoxy)pyrrolidine-1-carboxylate (69-2). Under a nitrogen atmosphere, to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (150 mg), 4-bromo-1-cyclopropylpyridin-2-one (103 mg) and $NaHCO_3$ (81 mg) in DMF (3 mL) were added XPhos Pd $G_3$ (27 mg) and XPhos (31 mg) at room temperature. The resulting mixture was stirred at 80° C. for 2 h. diluted with water, and extracted with EA. The organic extracts were washed with brine, dried over $Na_2SO_4$, filtered and concentrated. The residue was purified by reversed-phase flash chromatography to afford the title compound as a light-yellow oil (120 mg). MS obsd. ($ESI^+$): 557.3 $[(M+H)]^+$.

Step 2: tert-butyl (2R,3S,4S)-2-(4-(1-cyclopropyl-2-oxo-1,2-dihydropyridin-4-yl)benzyl)-3-hydroxy-4-((2-methoxyethoxy)methoxy)pyrrolidine-1-carboxylate (69-3). To a stirred solution of tert-butyl (2R,3S,4S)-3-acetoxy-2-(4-(1-cyclopropyl-2-oxo-1,2-dihydropyridin-4-yl)benzyl)-4-((2-methoxyethoxy)methoxy)pyrrolidine-1-carboxylate (120 mg) in THF (5 mL) and $H_2O$ (1 mL) was added LiOH (9 mg) at 0° C. The resulting mixture was stirred at room temperature for 16 h. diluted with water, and extracted with EA. The organic extracts were washed with brine, dried over $Na_2SO_4$, filtered and concentrated. The residue was purified by reversed-phase flash chromatography to afford the title compound as a light-yellow oil (65 mg). MS obsd. ($ESI^+$): 515.2 $[(M+H)]^+$.

Step 3-4:1-cyclopropyl-4-(4-(((2R,3S,4S)-3-ethoxy-4-hydroxypyrrolidin-2-yl)methyl)phenyl)pyridin-2(1H)-one. The title compound was prepared in 30.3% overall yield as a white solid according to General Procedure I using 69-3 (65 mg) and ethyl iodide (30 mg) in DMF in STEP 3, and General Procedure VIII in STEP 4. $^1H$ NMR (400 MHz, MeOD) δ 7.71-7.61 (m, 3H), 7.46-7.39 (m, 2H), 6.78 (d, J=2.1 Hz, 1H), 6.72 (dd, J=7.2, 2.1 Hz, 1H), 4.27-4.25 (m, 1H), 3.74-3.59 (m, 1H), 3.59-3.45 (m, 1H), 3.48-3.34 (m, 4H), 3.07 (dd, J=13.3, 8.6 Hz, 1H), 2.93 (dd, J=13.3, 6.6 Hz, 1H), 2.75 (dd, J=12.3, 2.2 Hz, 1H), 1.25 (t, J=7.0 Hz, 3H), 1.22-1.08 (m, 2H), 1.01-0.92 (m, 2H). MS obsd. ($ESI^+$): 355.3 $[(M+H)]^+$.

Example 78: (3S,4S,5R)-5-((3'-(azetidin-3-yl)-[1,1'-biphenyl]-4-yl)methyl)-4-(1,1-difluoropropoxy)pyrrolidin-3-ol Scheme 70

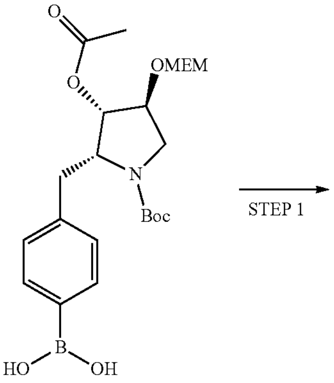

3-2

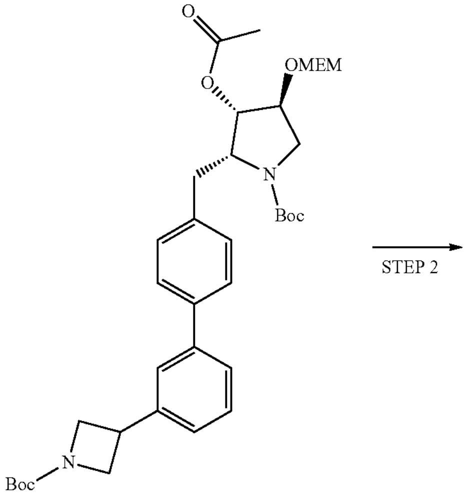

70-2

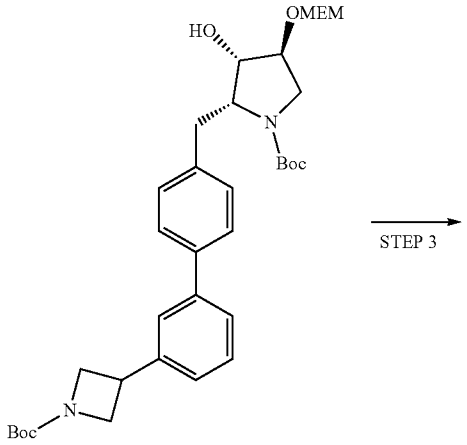

70-3

-continued

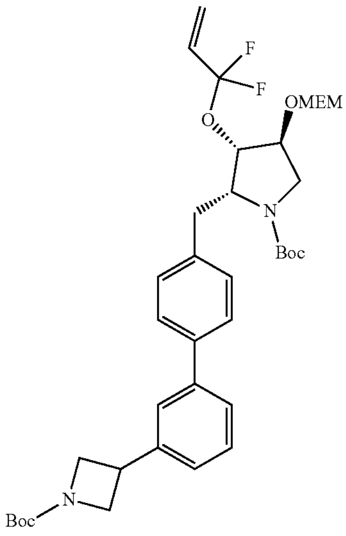

70-4

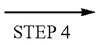

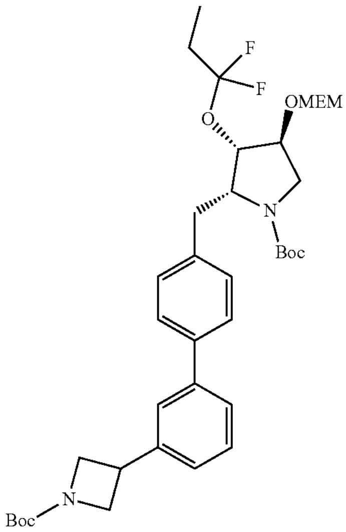

70-5

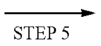

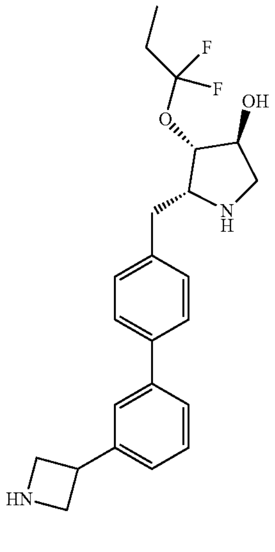

Step 1: tert-butyl (2R,3S,4S)-3-acetoxy-2-((3'-(1-(tert-butoxycarbonyl) azetidin-3-yl)-[1,1'-biphenyl]-4-yl)methyl)-4-((2-methoxyethoxy)methoxy)pyrrolidine-1-carboxylate (70-2). Under a nitrogen atmosphere, $Pd(dppf)Cl_2$ (62 mg) was added to a stirred solution of tert-butyl 3-(3-bromophenyl) azetidine-1-carboxylate (267 mg), (4-(((2R,3S,4S)-3-acetoxy-1-(tert-butoxycarbonyl)-4-((2-methoxyethoxy)methoxy)pyrrolidin-2-yl)methyl)phenyl) boronic acid (200 mg) and $Na_2CO_3$ (136 mg) in Dioxane (10 mL) and $H_2O$ (1 mL) at room temperature. The resulting mixture was stirred at 80° C. overnight, before it was diluted with water and extracted with EtOAc. The organic extracts were washed with brine, dried over $Na_2SO_4$, filtered, and concentrated. The residue was purified by reversed-phase flash chromatography to afford the title compound as a yellow solid (250 mg). MS obsd. ($ESI^+$): 655.4 $[(M+H)]^+$.

Step 2: tert-butyl (2R,3S,4S)-2-((3'-(1-(tert-butoxycarbonyl) azetidin-3-yl)-[1,1'-biphenyl]-4-yl)methyl)-3-hydroxy-4-((2-methoxyethoxy)methoxy)pyrrolidine-1-carboxylate (70-3). LiOH (27 mg) was added to a stirred solution of tert-butyl (2R,3S,4S)-3-acetoxy-2-((3'-(1-(tert-butoxycarbonyl) azetidin-3-yl)-[1,1'-biphenyl]-4-yl)methyl)-4-((2-methoxyethoxy)methoxy)pyrrolidine-1-carboxylate (250 mg) in THF (9 mL) and $H_2O$ (3 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (220 mg). MS obsd. ($ESI^+$): 613.3 $[(M+H)]^+$.

Step 3-5: (3S,4S,5R)-5-((3'-(azetidin-3-yl)-[1,1'-biphenyl]-4-yl)methyl)-4-(1,1-difluoropropoxy)pyrrolidin-3-ol. The title compound was prepared in 53.2% overall yield as a yellow solid according to General Procedure I using tert-butyl (2R,3S,4S)-2-((3'-(1-(tert-butoxycarbonyl) azetidin-3-yl)-[1,1'-biphenyl]-4-yl)methyl)-3-hydroxy-4-((2-methoxyethoxy)methoxy)pyrrolidine-1-carboxylate (126-2) (200 mg) and 1-(3,3-difluoroprop-2-en-1-yl)-1-methylpiperidin-1-ium triflate (212 mg) in DMF in STEP 3, and General Procedure VI in step 4, and General Procedure VIII in STEP 5. $^1H$ NMR (400 MHz, MeOD) δ 7.74-7.68 (m, 2H), 7.68-7.64 (m, 1H), 7.64-7.57 (m, 1H), 7.56-7.46 (m, 3H), 7.45-7.38 (m, 1H), 4.74 (d, J=3.4 Hz, 1H), 4.52 (dd, J=4.1, 1.4 Hz, 1H), 4.48-4.40 (m, 2H), 4.39-4.22 (m, 4H), 3.64 (dd, J=12.7, 4.3 Hz, 1H), 3.31-3.18 (m, 2H), 3.08 (dd, J=14.5, 9.1 Hz, 1H), 2.25-2.07 (m, 2H), 1.21-1.11 (m, 3H). MS obsd. ($ESI^+$): 403.2 $[(M+H)]^+$.

Example 79: (3S,4S,5R)-4-ethoxy-5-(4-(1-methyl-1H-indazol-6-yl)benzyl)pyrrolidin-3-ol Scheme 71

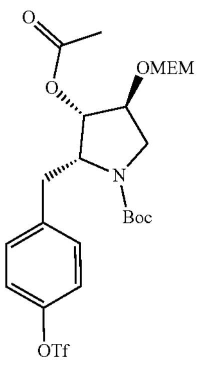

3-1

-continued

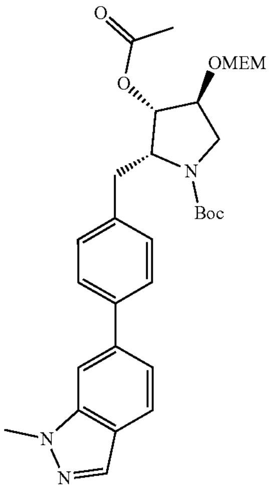

71-2

STEP 2

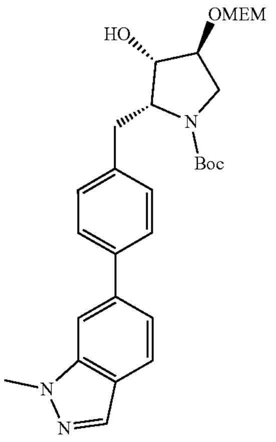

71-3

STEP 3

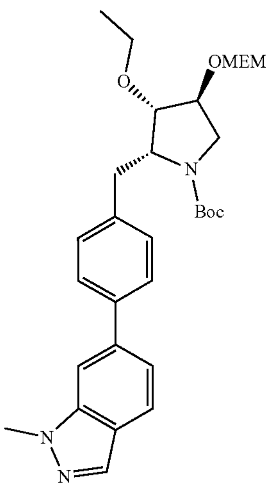

71-4

STEP 4

-continued

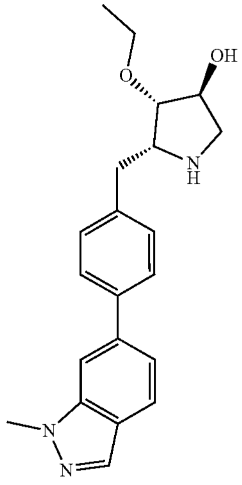

Step 1: tert-butyl (2R,3S,4S)-3-acetoxy-4-((2-methoxyethoxy)methoxy)-2-(4-(1-methyl-1H-indazol-6-yl)benzyl) pyrrolidine-1-carboxylate (71-2). Under a nitrogen atmosphere, XPhos (8 mg) and XPhos Pd $G_3$ (30 mg) were added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (100 mg), 1-methyl-6-(4,4,5,5-tetramethyl-1,3,2-dioxaborolan-2-yl)-1H-indazole (90 mg) and $NaHCO_3$ (44 mg) in DMF (5 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (80 mg). MS obsd. ($ESI^+$): 554.3 $[(M+H)]^+$.

Step 2: tert-butyl (2R,3S,4S)-3-hydroxy-4-((2-methoxyethoxy)methoxy)-2-(4-(1-methyl-1H-indazol-6-yl)benzyl) pyrrolidine-1-carboxylate (71-3). LiOH (10 mg) was added to a stirred solution of tert-butyl (2R,3S,4S)-3-acetoxy-4-((2-methoxyethoxy)methoxy)-2-(4-(1-methyl-1H-indazol-6-yl)benzyl)pyrrolidine-1-carboxylate (75 mg) in THF (3 mL) and $H_2O$ (1 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (60 mg). MS obsd. ($ESI^+$): 512.3 $[(M+H)]^+$.

Step 3-4: (3S,4S,5R)-4-ethoxy-5-(4-(1-methyl-1H-indazol-6-yl)benzyl)pyrrolidin-3-ol. The title compound was prepared in 36.3% overall yield as a yellow semi-solid according to General Procedure I using 71-3 (80 mg) and ethyl iodide (58 mg) in DMF in STEP 3, and General Procedure VIII in STEP 4. $^1H$ NMR (400 MHz, MeOD) δ 8.03 (d, J=1.0 Hz, 1H), 7.86-7.74 (m, 4H), 7.51-7.44 (m, 3H), 4.50 (d, J=4.4 Hz, 1H), 4.13 (s, 3H), 4.11-4.06 (m, 1H), 3.86-3.78 (m, 1H), 3.78-3.73 (m, 1H), 3.67-3.52 (m, 2H), 3.32-3.25 (m, 1H), 3.23-3.08 (m, 2H), 1.36-1.28 (m, 3H). MS obsd. ($ESI^+$): 352.2 $[(M+H)]^+$.

Example 80: (3S,4S,5R)-4-(1,1-difluoropropoxy)-5-(4-(isoindolin-5-yl)benzyl)pyrrolidin-3-ol
Scheme 72
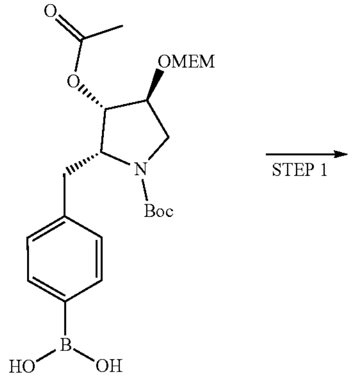
3-2
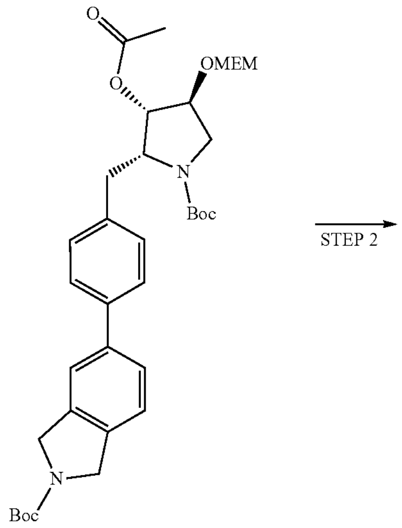
72-2
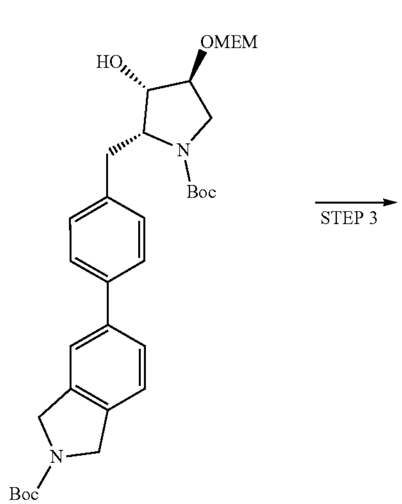
72-3
-continued
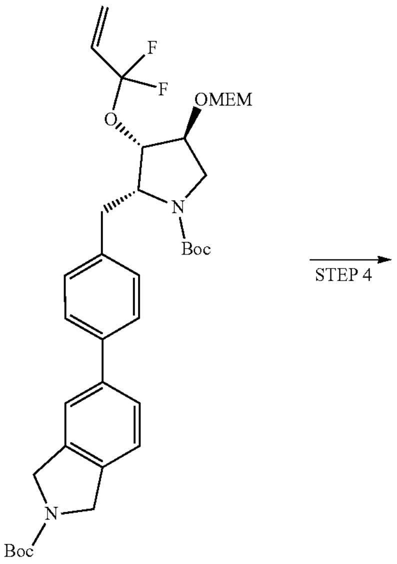
72-4
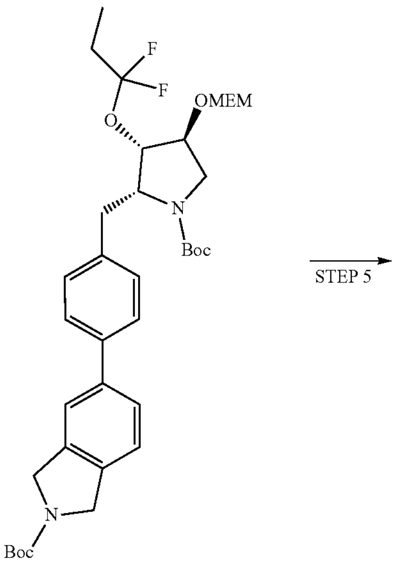
72-5

-continued

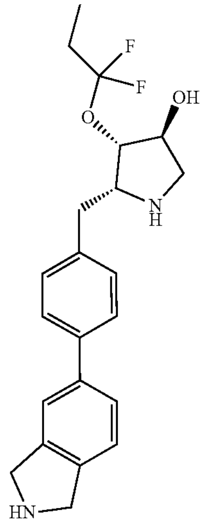

Step 1: tert-butyl 5-(4-(((2R,3S,4S)-3-acetoxy-1-(tert-butoxycarbonyl)-4-((2-methoxyethoxy)methoxy)pyrrolidin-2-yl)methyl)phenyl) isoindoline-2-carboxylate (72-2). Under a nitrogen atmosphere, $Pd(dppf)Cl_2$ (46.9 mg) were added to a stirred solution of tert-butyl 5-bromo-1,3-dihydroisoindole-2-carboxylate (191 mg), (4-(((2R,3S,4S)-3-acetoxy-1-(tert-butoxycarbonyl)-4-((2-methoxyethoxy)methoxy)pyrrolidin-2-yl)methyl)phenyl) boronic acid (200 mg) and $Na_2CO_3$ (113 mg) in 1,4-Dioxane (10 mL) and $H_2O$ (1.0 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (198 mg). MS obsd. ($ESI^+$): 641.3 $[(M+H)]^+$.

Step 2: tert-butyl 5-(4-(((2R,3S,4S)-1-(tert-butoxycarbonyl)-3-hydroxy-4-((2-methoxyethoxy)methoxy)pyrrolidin-2-yl)methyl)phenyl) isoindoline-2-carboxylate (72-3). LiOH (20 mg) was added to a stirred solution of tert-butyl 5-(4-(((2R,3S,4S)-3-acetoxy-1-(tert-butoxycarbonyl)-4-((2-methoxyethoxy)methoxy)pyrrolidin-2-yl)methyl)phenyl) isoindoline-2-carboxylate (180 mg) in THF (5 mL) and $H_2O$ (1 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (144 mg). MS obsd. ($ESI^+$): 599.3 $[(M+H)]^+$.

Step 3-5: (3S,4S,5R)-4-(1,1-difluoropropoxy)-5-(4-(isoindolin-5-yl)benzyl)pyrrolidin-3-ol. The title compound was prepared in 43.2% overall yield as a white solid according to General Procedure I using 72-3 (140 mg) and 1-(3,3-difluoroprop-2-en-1-yl)-1-methylpiperidin-1-ium triflate (152 mg) in DMF in STEP 3, and General Procedure VI in step 4, and General Procedure VIII in STEP 5. $^1H$ NMR (400 MHz, MeOD) δ 7.73-7.65 (m, 4H), 7.50 (dd, J=15.8, 8.1 Hz, 3H), 4.77-4.73 (m, 1H), 4.69 (d, J=7.7 Hz, 4H), 4.51 (d, J=4.2 Hz, 1H), 4.30-4.24 (m, 1H), 3.63 (dd, J=12.7, 4.3 Hz, 1H), 3.30-3.20 (m, 2H), 3.08 (dd, J=14.5, 9.2 Hz, 1H), 2.21-2.04 (m, 2H), 1.15 (t, J=7.5 Hz, 3H). MS obsd. ($ESI^+$): 389.2 $[(M+H)]^+$.

Example 81: (3S,4S,5R)-4-ethoxy-5-(4-(quinazolin-6-yl)benzyl)pyrrolidin-3-ol

Scheme 73

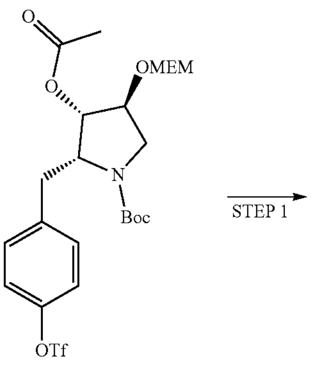

3-1

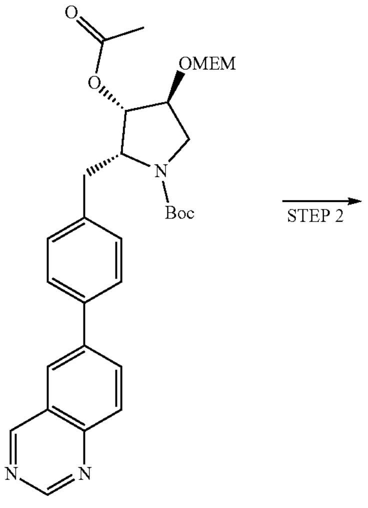

73-2

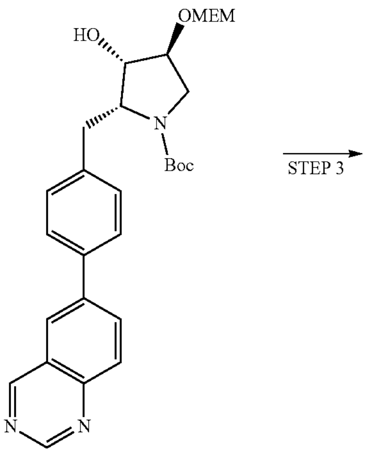

73-3

-continued

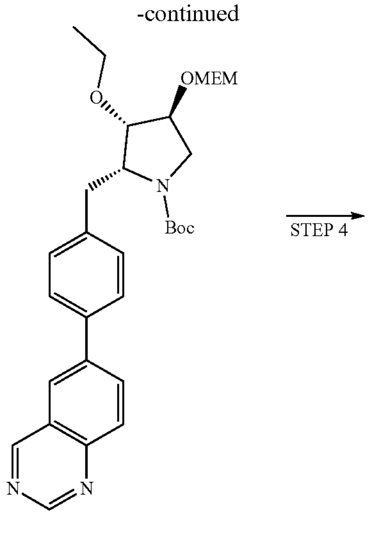

73-4

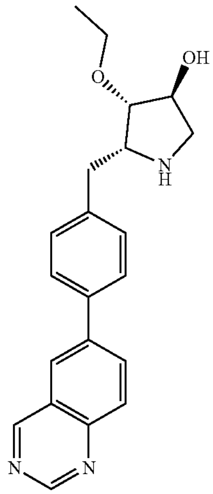

Step 1: tert-butyl (2R,3S,4S)-3-acetoxy-4-((2-methoxyethoxy)methoxy)-2-(4-(quinazolin-6-yl)benzyl)pyrrolidine-1-carboxylate (73-2). Under a nitrogen atmosphere, XPhos Pd $G_3$ (22 mg) and XPhos (25 mg) were added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (150 mg), 6-(4,4,5,5-tetramethyl-1,3,2-dioxaborolan-2-yl) quinazoline (101 mg) and $NaHCO_3$ (66 mg) in DMF (3 mL) at room temperature. The resulting mixture was stirred at 80° C. for 3 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil (130 mg). MS obsd. ($ESI^+$): 552.3 $[(M+H)]^+$.

Step 2: tert-butyl (2R,3S,4S)-3-hydroxy-4-((2-methoxyethoxy)methoxy)-2-(4-(quinazolin-6-yl)benzyl)pyrrolidine-1-carboxylate (73-3). LiOH (17 mg) was added to a stirred solution of tert-butyl (2R,3S,4S)-3-acetoxy-4-((2-methoxyethoxy)methoxy)-2-(4-(quinazolin-6-yl)benzyl)pyrrolidine-1-carboxylate (130 mg) in THF (5 mL) and $H_2O$ (1 mL) at 0° C. The resulting mixture was stirred at room temperature for 6 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil (100 mg). MS obsd. ($ESI^+$): 510.3 $[(M+H)]^+$.

Step 3-4: (3S,4S,5R)-4-ethoxy-5-(4-(quinazolin-6-yl)benzyl)pyrrolidin-3-ol. The title compound was prepared in 21.6% overall yield as a white solid according to General Procedure I using 73-3 (100 mg) and ethyl iodide (61 mg) in DMF in STEP 3, and General Procedure VIII in STEP 4. $^1H$ NMR (400 MHz, MeOD) δ 9.61 (s, 1H), 9.25 (s, 1H), 8.42-8.33 (m, 2H), 8.16-8.09 (m, 1H), 7.83-7.70 (m, 2H), 7.47 (d, J=8.1 Hz, 2H), 4.28 (dd, J=6.2, 2.4 Hz, 1H), 3.77-3.65 (m, 1H), 3.56-3.46 (m, 1H), 3.48-3.34 (m, 3H), 3.08 (dd, J=13.2, 8.7 Hz, 1H), 2.95 (dd, J=13.3, 6.4 Hz, 1H), 2.75 (dd, J=12.3, 2.3 Hz, 1H), 1.27 (t, J=7.0 Hz, 3H). MS obsd. ($ESI^+$): 350.2 $[(M+H)]^+$.

Example 82: (3S,4S,5R)-4-ethoxy-5-(4-(1-methyl-1H-indazol-5-yl)benzyl)pyrrolidin-3-ol Scheme 74

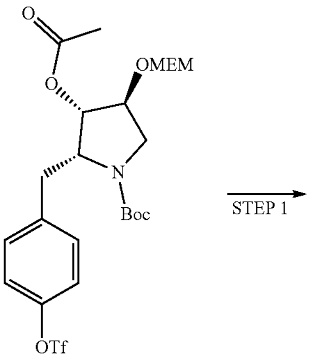

3-1

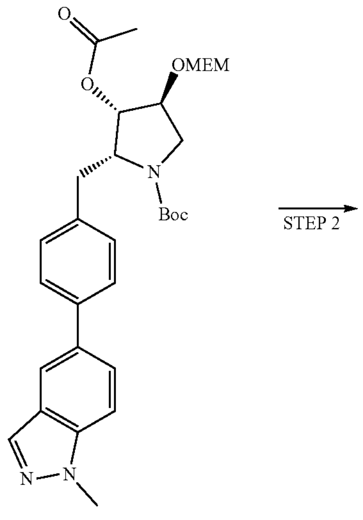

74-2

-continued

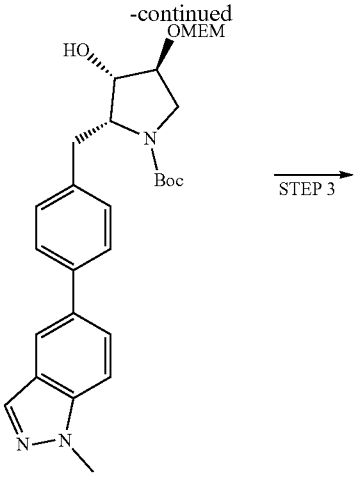

74-3

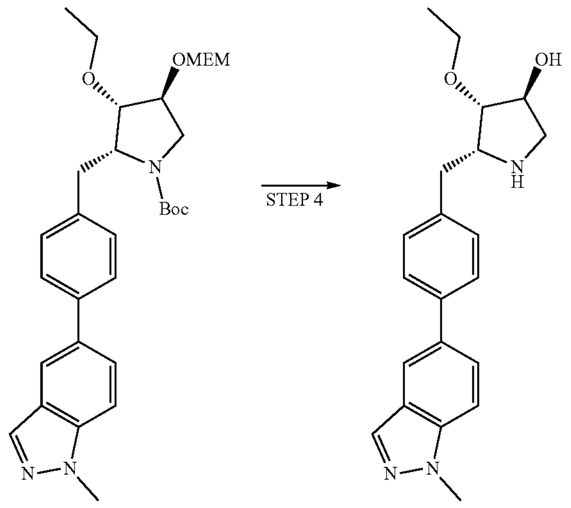

74-4

Step 1: tert-butyl (2R,3S,4S)-3-acetoxy-4-((2-methoxyethoxy)methoxy)-2-(4-(1-methyl-1H-indazol-5-yl)benzyl) pyrrolidine-1-carboxylate (74-2). Under a nitrogen atmosphere, $NaHCO_3$ (88 mg), XPhos (33 mg) and XPhos Pd $G_3$ (30 mg) were added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (200 mg) and 1-methyl-5-(4,4,5,5-tetramethyl-1,3,2-dioxaborolan-2-yl) indazole (135 mg) in DMF (5 mL) at room temperature. The resulting mixture was stirred at 80° C. for 2 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (150 mg). MS obsd. ($ESI^+$): 554.3 $[(M+H)]^+$.

Step 2: tert-butyl (2R,3S,4S)-3-hydroxy-4-((2-methoxyethoxy)methoxy)-2-(4-(1-methyl-1H-indazol-5-yl)benzyl) pyrrolidine-1-carboxylate (74-3). LiOH (19 mg) was added to a stirred solution of tert-butyl (2R,3S,4S)-3-acetoxy-4-((2-methoxyethoxy)methoxy)-2-(4-(1-methyl-1H-indazol-5-yl)benzyl)pyrrolidine-1-carboxylate (150 mg) in THF (5 mL) and $H_2O$ (1 mL) at 0° C. The resulting mixture was stirred at room temperature for 12 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (120 mg). MS obsd. ($ESI^+$): 512.3 $[(M+H)]^+$.

Step 3-4: (3S,4S,5R)-4-ethoxy-5-(4-(1-methyl-1H-indazol-5-yl)benzyl)pyrrolidin-3-ol. The title compound was prepared in 61.6% overall yield as a white solid according to General Procedure I using 74-3 (150 mg) and ethyl iodide (55 mg) in DMF in STEP 3, and General Procedure VIII in STEP 4. $^1H$ NMR (400 MHz, MeOD) δ 8.16-7.93 (m, 2H), 7.80-7.58 (m, 4H), 7.43-7.35 (m, 2H), 4.30-4.28 (m, 1H), 4.11 (s, 3H), 3.77-3.67 (m, 1H), 3.61-3.52 (m, 1H), 3.52-3.40 (m, 3H), 3.07 (dd, J=13.3, 8.6 Hz, 1H), 2.94 (dd, J=13.3, 6.6 Hz, 1H), 2.79 (dd, J=12.3, 2.2 Hz, 1H), 1.27 (t, J=7.0 Hz, 3H). MS obsd. ($ESI^+$): 352.2 $[(M+H)]^+$.

Example 83: 5-(4-(((2R,3S,4S)-3-ethoxy-4-hydroxypyrrolidin-2-yl)methyl)phenyl)-2-methylisoindolin-1-one Scheme 75

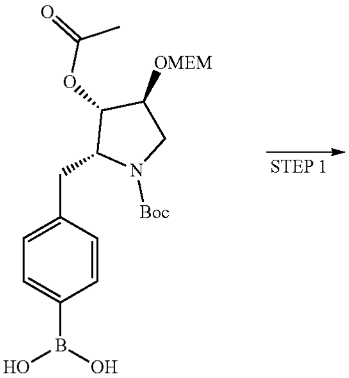

3-1

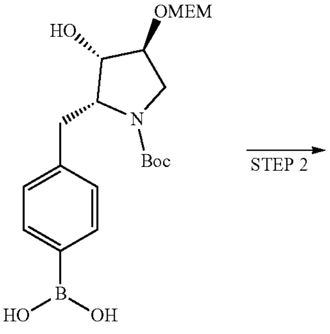

75-2

-continued

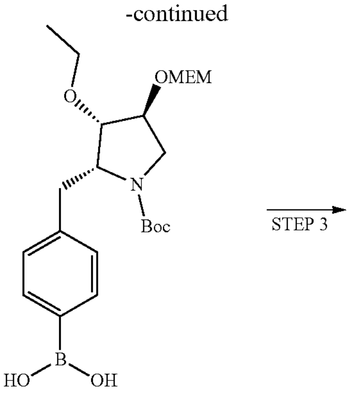

75-3

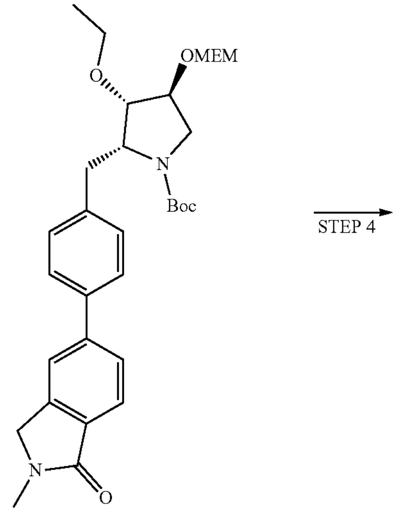

75-4

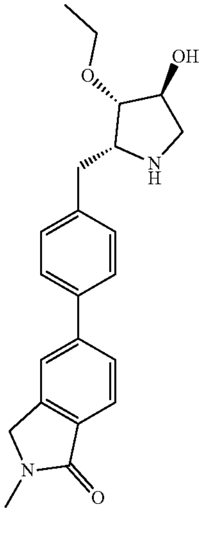 [SMILES: CCO[C@@H]1[C@@H](O)CN[C@@H]1Cc1ccc(-c2ccc3c(c2)CN(C)C3=O)cc1]

Step 1: (4-(((2R,3S,4S)-1-(tert-butoxycarbonyl)-3-hydroxy-4-((2-methoxyethoxy)methoxy)pyrrolidin-2-yl) methyl)phenyl) boronic acid (75-2). LiOH (23 mg) was added to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (150 mg) in THF (3 mL) and $H_2O$ (1 mL) at 0° C. The resulting mixture was stirred at room temperature for 1 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (110 mg). MS obsd. ($ESI^+$): 426.2 $[(M+H)]^+$.

Step 2: (4-(((2R,3S,4S)-1-(tert-butoxycarbonyl)-3-ethoxy-4-((2-methoxyethoxy)methoxy)pyrrolidin-2-yl) methyl)phenyl) boronic acid (75-3). The title compound was prepared in 42.1% yield as a light-yellow oil according to General Procedure I using 75-2 (110 mg) and ethyl iodide (81 mg) in DMF. MS obsd. ($ESI^+$): 454.3 $[(M+H)]^+$.

Step 3: tert-butyl (2R,3S,4S)-3-ethoxy-4-((2-methoxyethoxy)methoxy)-2-(4-(2-methyl-1-oxoisoindolin-5-yl)benzyl)pyrrolidine-1-carboxylate (75-4). Under a nitrogen atmosphere, XPhos (4 mg) and XPhos Pd $G_3$ (15 mg) were added to a stirred solution of (4-(((2R,3S,4S)-1-(tert-butoxycarbonyl)-3-hydroxy-4-((2-methoxyethoxy)methoxy)pyrrolidin-2-yl)methyl)phenyl) boronic acid (40 mg), 5-bromo-2-methylisoindolin-1-one (32 mg) and $NaHCO_3$ (22 mg) in 1,4-dioxane (5 mL) and $H_2O$ (0.5 mL) at room temperature. The resulting mixture was stirred at 80° C. for 1 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil (15 mg). MS obsd. ($ESI^+$): 555.3 $[(M+H)]^+$.

Step 4: 5-(4-(((2R,3S,4S)-3-ethoxy-4-hydroxypyrrolidin-2-yl)methyl)phenyl)-2-methylisoindolin-1-one. The title compound was prepared in 22.1% yield as a white solid according to General Procedure VIII using 75-4 (15 mg) and 4N HCl-1,4-dioxane (1 mL) in 1,4-dioxane. $^1H$ NMR (400 MHz, MeOD) δ 7.86-7.81 (m, 2H), 7.81-7.73 (m, 1H), 7.71-7.62 (m, 2H), 7.46-7.36 (m, 2H), 4.58 (s, 2H), 4.28 (d, J=5.8 Hz, 1H), 3.77-3.65 (m, 1H), 3.53 (s, 1H), 3.49-3.38 (m, 3H), 3.24 (s, 3H), 3.12-3.02 (m, 1H), 2.99-2.89 (m, 1H), 2.76 (d, J=12.2 Hz, 1H), 1.33-1.22 (m, 3H). MS obsd. ($ESI^+$): 367.2 $[(M+H)]^+$.

Example 84: (3S,4S,5R)-4-(1,1-difluoropropoxy)-5-(4-(pyrimidin-4-yl)benzyl)pyrrolidin-3-ol Scheme 76

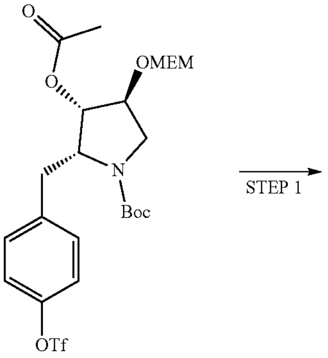

3-2

-continued

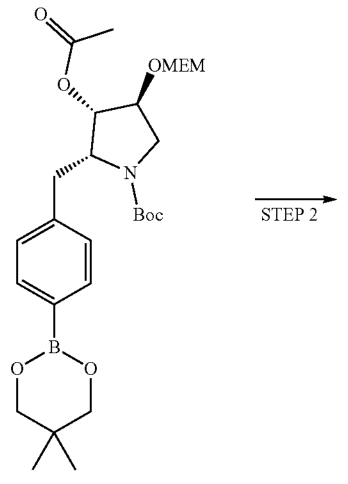

76-2

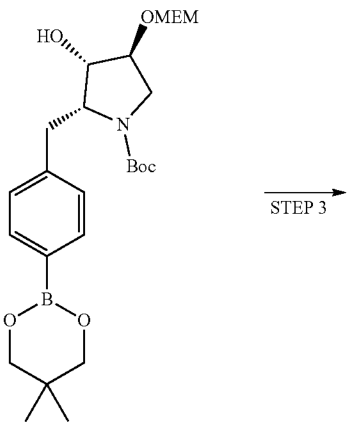

76-3

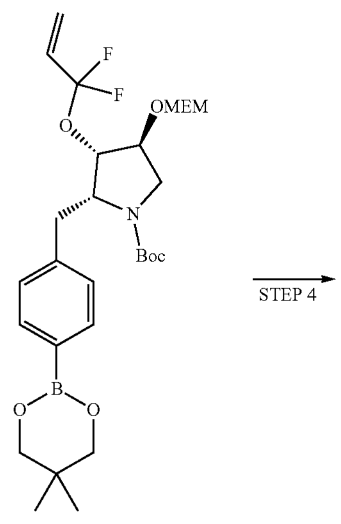

76-4

-continued

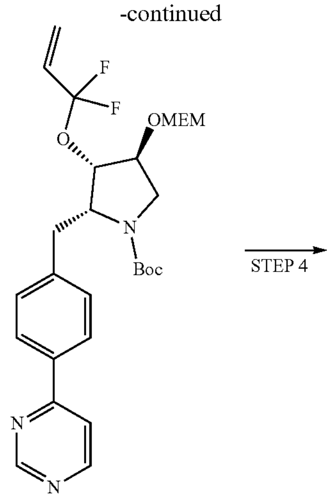

76-5

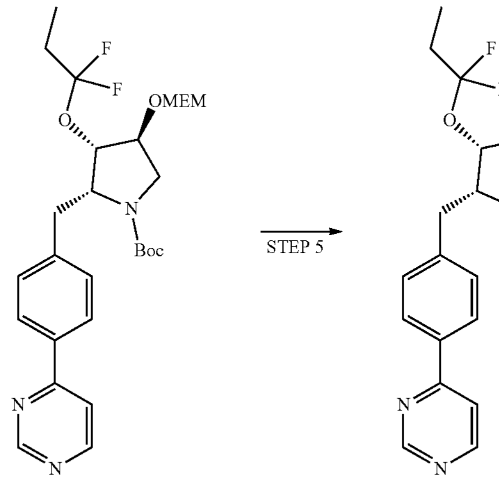

76-6

Step 1: tert-butyl (2R,3S,4S)-3-acetoxy-2-(4-(5,5-dimethyl-1,3,2-dioxaborinan-2-yl)benzyl)-4-((2-methoxyethoxy)methoxy)pyrrolidine-1-carboxylate (76-2). Under a nitrogen atmosphere, Pd(dppf)$Cl_2$ (51 mg) was added to a stirred solution of 2-(5,5-dimethyl-1,3,2-dioxaborinan-2-yl)-5,5-dimethyl-1,3,2-dioxaborinane (94 mg), tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (200 mg), and KOAc (103 mg) in 1,4-dioxane (20 mL) at room temperature. The resulting mixture was stirred at 90° C. for 1 h, then diluted with water and extracted with EtOAc. The organic extracts were washed with brine, dried over $Na_2SO_4$, filtered and concentrated. The residue was purified by reversed-phase flash chromatography to afford the title compound as a light-yellow oil (144 mg). MS obsd. ($ESI^+$): 536.3 $[(M+H)]^+$.

Step 2: tert-butyl (2R,3S,4S)-2-(4-(5,5-dimethyl-1,3,2-dioxaborinan-2-yl)benzyl)-3-hydroxy-4-((2-methoxyethoxy) methoxy)pyrrolidine-1-carboxylate (76-3). LiOH (18 mg) was added to a stirred solution of tert-butyl (2R,3S,4S)-3-acetoxy-2-(4-(5,5-dimethyl-1,3,2-dioxaborinan-2-yl)benzyl)-4-((2-methoxyethoxy)methoxy)pyrrolidine-1-carboxylate (135 mg) in THF (5 mL) and $H_2O$ (1 mL) at 0° C. The resulting mixture was stirred at room temperature for 2 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (98 mg). MS obsd. ($ESI^+$): 494.3 $[(M+H)]^+$.

Step 3: tert-butyl (2R,3S,4S)-3-((1,1-difluoroallyl)oxy)-2-(4-(5,5-dimethyl-1,3,2-dioxaborinan-2-yl)benzyl)-4-((2-methoxyethoxy)methoxy)pyrrolidine-1-carboxylate (76-4). The title compound was prepared in 78.6% yield as a light-yellow oil according to General Procedure I using 76-3 (93 mg) and 1-(3,3-difluoroallyl)-1-methylpiperidin-1-ium trifluoromethanesulfonate (122 mg) in DMF. MS obsd. ($ESI^+$): 570.3 $[(M+H)]^+$.

Step 4: tert-butyl (2R,3S,4S)-3-((1,1-difluoroallyl)oxy)-4-((2-methoxyethoxy)methoxy)-2-(4-(pyrimidin-4-yl)benzyl)pyrrolidine-1-carboxylate (76-5). Under a nitrogen atmosphere, $Pd(dppf)Cl_2$ (12 mg) was added to a stirred solution of 4-chloropyrimidine hydrogen chloride (34 mg), tert-butyl (2R,3S,4S)-3-((1,1-difluoroallyl)oxy)-2-(4-(5,5-dimethyl-1,3,2-dioxaborinan-2-yl)benzyl)-4-((2-methoxyethoxy)methoxy)pyrrolidine-1-carboxylate (65 mg), and $Na_2CO_3$ (30 mg) in 1,4-dioxane (10 mL) and $H_2O$ (1.0 mL) at room temperature. The resulting mixture was stirred at 90° C. for 1 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (31 mg). MS obsd. ($ESI^+$): 536.2 $[(M+H)]^+$.

Step 5-6: (3S,4S,5R)-4-(1,1-difluoropropoxy)-5-(4-(pyrimidin-4-yl)benzyl)pyrrolidin-3-ol. The title compound was prepared in 57.3% overall yield as a white solid according to General Procedure VI using 76-5 (31 mg) and Pd/C (6 mg) in ethyl acetate (5 mL) in STEP 5, and General Procedure VIII in STEP 6. $^1H$ NMR (400 MHz, MeOD) δ 9.18 (d, J=1.4 Hz, 1H), 8.78 (d, J=5.5 Hz, 1H), 8.19-8.11 (m, 2H), 8.00 (dd, J=5.5, 1.4 Hz, 1H), 7.53-7.44 (m, 2H), 4.42 (d, J=3.6 Hz, 1H), 4.37-4.29 (m, 1H), 3.67-3.58 (m, 1H), 3.40-3.34 (m, 1H), 3.03 (dd, J=13.9, 6.3 Hz, 1H), 2.95-2.88 (m, 1H), 2.73 (dd, J=12.2, 2.2 Hz, 1H), 2.15-2.00 (m, 2H), 1.13 (t, J=7.5 Hz, 3H). MS obsd. ($ESI^+$): 350.2 $[(M+H)]^+$.

Example 85: (3S,4S,5R)-4-(1,1-difluoropropoxy)-5-(4-(1-methyl-1H-pyrazol-5-yl)benzyl)pyrrolidin-3-ol Scheme 77

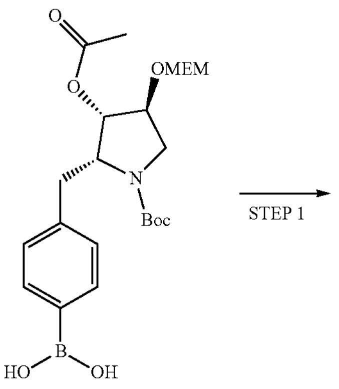

3-2

-continued

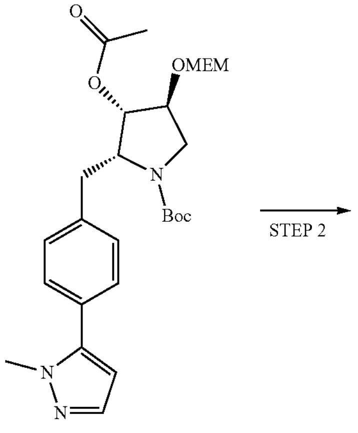

77-2

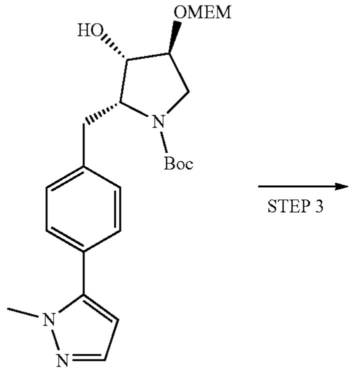

77-3

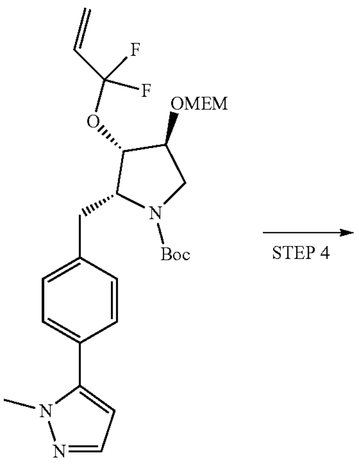

77-4

-continued

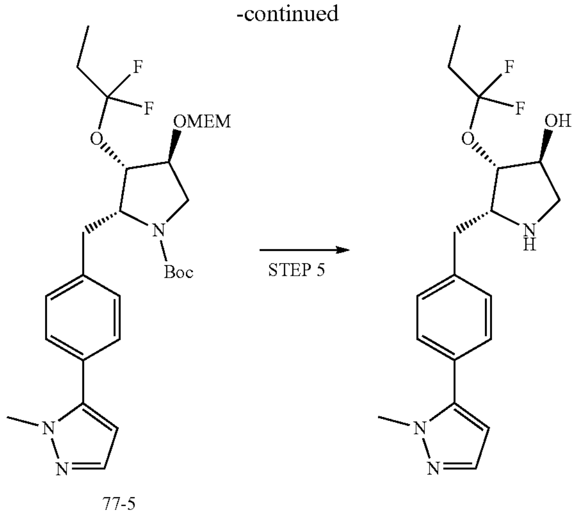

77-5

Step 1: tert-butyl (2R,3S,4S)-3-acetoxy-4-((2-methoxyethoxy)methoxy)-2-(4-(1-methyl-1H-pyrazol-5-yl)benzyl) pyrrolidine-1-carboxylate (77-2). Under a nitrogen atmosphere, Pd(dppf)$Cl_2$ (46 mg) and $Na_2CO_3$ (102 mg) were added to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (150 mg) and 5-iodo-1-methylpyrazole (80 mg) in 1,4-dioxane (3 mL) and $H_2O$ (0.6 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil. MS obsd. ($ESI^+$): 504.3 $[(M+H)]^+$.

Step 2: tert-butyl (2R,3S,4S)-3-hydroxy-4-((2-methoxyethoxy)methoxy)-2-(4-(1-methyl-1H-pyrazol-5-yl)benzyl) pyrrolidine-1-carboxylate (77-3). LiOH (18 mg) was added to a stirred solution of tert-butyl (2R,3S,4S)-3-acetoxy-4-((2-methoxyethoxy)methoxy)-2-(4-(1-methyl-1H-pyrazol-5-yl)benzyl)pyrrolidine-1-carboxylate (130 mg) in THF (3 mL) and $H_2O$ (0.6 mL) at room temperature. The resulting mixture was stirred at room temperature for 1 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil. MS obsd. ($ESI^+$): 462.3 $[(M+H)]^+$.

Step 3-5: (3S,4S,5R)-4-(1,1-difluoropropoxy)-5-(4-(1-methyl-1H-pyrazol-5-yl)benzyl)pyrrolidin-3-ol. The title compound was prepared in 33.2% overall yield as a yellow semi-solid according to General Procedure I using (77-3) (100 mg) and 1-(3,3-difluoroprop-2-en-1-yl)-1-methylpiperidin-1-ium triflate (84 mg) in DMF in STEP 3, and General Procedure VI in step 4, and General Procedure VIII in STEP 5. $^1H$ NMR (400 MHz, MeOD) δ 7.50 (d, J=2.0 Hz, 1H), 7.43 (s, 4H), 6.36 (d, J=2.0 Hz, 1H), 4.43 (d, J=3.6 Hz, 1H), 4.36-4.29 (m, 1H), 3.88 (s, 3H), 3.61 (m, 1H), 3.41-3.35 (m, 1H), 3.01 (m, 1H), 2.87 (m, 1H), 2.73 (m, 1H), 2.16-2.00 (m, 2H), 1.12 (t, J=7.5 Hz, 3H). MS obsd. ($ESI^+$): 352.2 $[(M+H)]^+$.

Example 86: (3S,4S,5R)-4-(1,1-difluoropropoxy)-5-(4-(imidazo[2,1-b]thiazol-2-yl)benzyl)pyrrolidin-3-ol Scheme 78

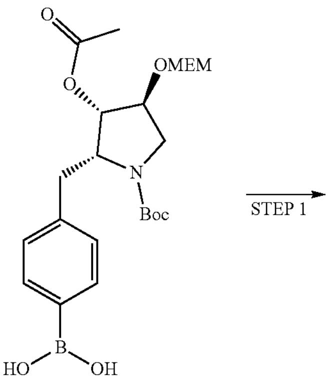

3-2

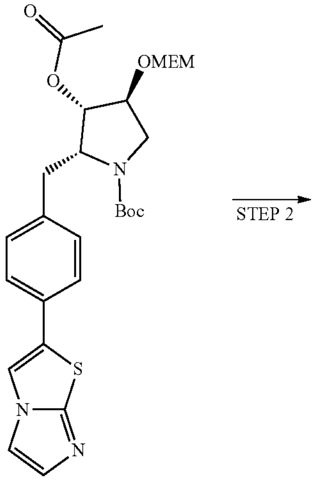

78-2

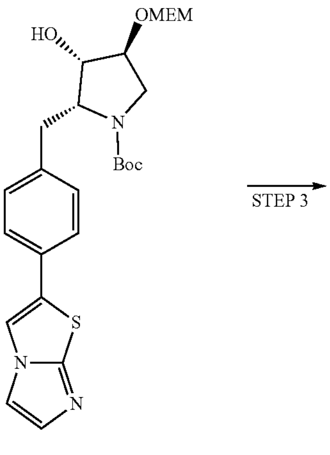

78-3

-continued

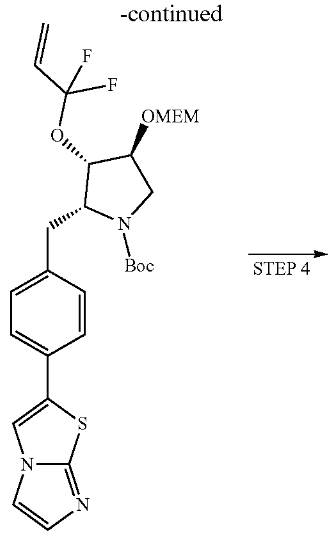

78-4

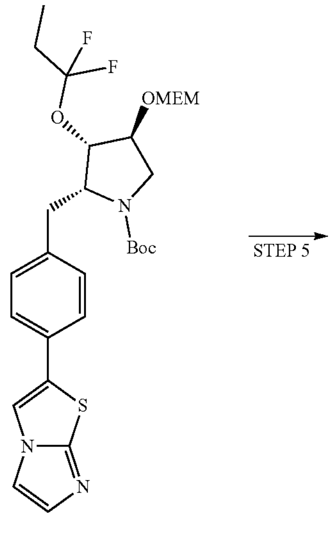

78-5

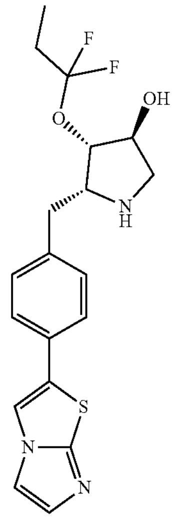

Step 1: tert-butyl (2R,3S,4S)-3-acetoxy-2-(4-(imidazo[2,1-b]thiazol-2-yl)benzyl)-4-((2-methoxyethoxy)methoxy) pyrrolidine-1-carboxylate (78-2). Under a nitrogen atmosphere, $Pd(dppf)Cl_2$ (35 mg) was added to a stirred solution of 2-bromoimidazo[2,1-b]thiazole, (4-(((2R,3S,4S)-3-acetoxy-1-(tert-butoxycarbonyl)-4-((2-methoxyethoxy) methoxy)pyrrolidin-2-yl)methyl)phenyl) boronic acid and $Na_2CO_3$ (136 mg) in 1,4-dioxane (5 mL) and $H_2O$ (1 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow solid (120 mg). MS obsd. ($ESI^+$): 546.2 $[(M+H)]^+$.

Step 2: tert-butyl (2R,3S,4S)-3-hydroxy-2-(4-(imidazo[2,1-b]thiazol-2-yl)benzyl)-4-((2-methoxyethoxy)methoxy) pyrrolidine-1-carboxylate (78-3). LiOH (24 mg) was added to a stirred solution of tert-butyl (2R,3S,4S)-3-acetoxy-2-(4-(imidazo[2,1-b]thiazol-2-yl)benzyl)-4-((2-methoxyethoxy)methoxy)pyrrolidine-1-carboxylate (120 mg) in THF (5 mL) and $H_2O$ (1 mL) at room temperature. The resulting mixture was stirred at room temperature for 1 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil. MS obsd. ($ESI^+$): 504.2 $[(M+H)]^+$.

Step 3-5: (3S,4S,5R)-4-(1,1-difluoropropoxy)-5-(4-(imidazo[2,1-b]thiazol-2-yl)benzyl)pyrrolidin-3-ol. The title compound was prepared in 28.2% overall yield as an orange oil according to General Procedure I using (78-3) (90 mg) and 1-(3,3-difluoroprop-2-en-1-yl)-1-methylpiperidin-1-ium triflate (116 mg) in DMF in STEP 3, and General Procedure VI in step 4, and General Procedure VIII in STEP 5. $^1H$ NMR (400 MHz, MeOD) δ 8.42 (s, 1H), 7.98 (s, 1H), 7.83-7.62 (m, 3H), 7.53 (d, J=8.0 Hz, 2H), 4.73 (d, J=3.2 Hz, 1H), 4.51 (d, J=4.0 Hz, 1H), 4.33-4.21 (m, 1H), 3.64 (dd, J=12.7, 4.3 Hz, 1H), 3.32-3.21 (m, 2H), 3.11 (dd, J=14.6, 9.1 Hz, 1H), 2.25-2.06 (m, 2H), 1.15 (t, J=7.6 Hz, 3H). MS obsd. ($ESI^+$): 394.1 $[(M+H)]^+$.

Example 87: (3S,4S,5R)-4-ethoxy-5-(4-(pyrazolo[1,5-a]pyrimidin-6-yl)benzyl)pyrrolidin-3-ol Scheme 79

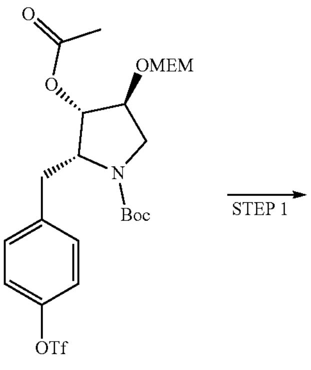

3-1

-continued

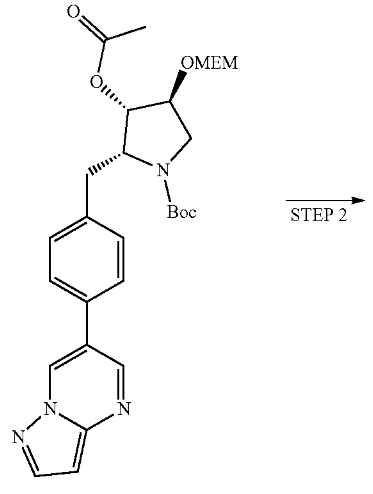

79-2

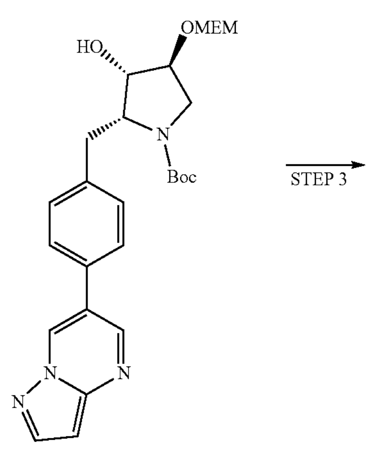

79-3

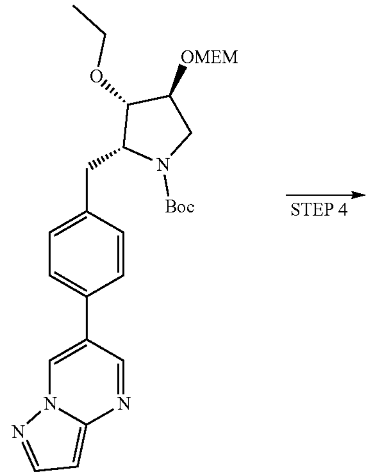

79-4

-continued

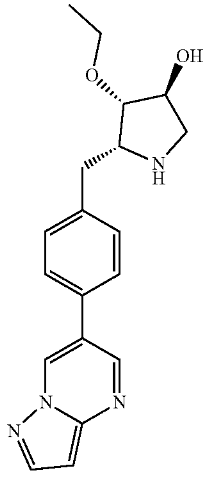

Step 1: tert-butyl (2R,3S,4S)-3-acetoxy-4-((2-methoxyethoxy)methoxy)-2-(4-(pyrazolo[1,5-a]pyrimidin-6-yl)benzyl)pyrrolidine-1-carboxylate (79-2). Under a nitrogen atmosphere. XPhos Pd $G_3$ (30 mg) and XPhos (33 mg) were added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (200 mg), 6-(4,4,5,5-tetramethyl-1,3,2-dioxaborolan-2-yl) pyrazolo[1,5-a]pyrimidine (129 mg) and $NaHCO_3$ (88 mg,) in DMF (3 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (180 mg). MS obsd. ($ESI^+$): 541.3 $[(M+H)]^+$.

Step 2: tert-butyl (2R,3S,4S)-3-hydroxy-4-((2-methoxyethoxy)methoxy)-2-(4-(pyrazolo[1,5-a]pyrimidin-6-yl)benzyl)pyrrolidine-1-carboxylate (79-3). LiOH (24 mg) was added to a stirred solution of tert-butyl (2R,3S,4S)-3-(acetyloxy)-4-[(2-methoxyethoxy)methoxy]-2-[(4-{pyrazolo[1,5-a]pyrimidin-6-yl}phenyl)methyl]pyrrolidine-1-carboxylate (180 mg) in THF (5 mL) and $H_2O$ (1 mL) at 0° C. The resulting mixture was stirred at room temperature for 10 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (120 mg). MS obsd. ($ESI^+$): 499.2 $[(M+H)]^+$.

Step 3-4: (3S,4S,5R)-4-ethoxy-5-(4-(pyrazolo[1,5-a]pyrimidin-6-yl)benzyl)pyrrolidin-3-ol. The title compound was prepared in 57.4% overall yield as a white solid according to General Procedure I using 79-3 (120 mg) and ethyl iodide (56 mg) in DMF in STEP 3, and General Procedure VIII in STEP 2. $^1H$ NMR (400 MHz, MeOD) δ 9.19-9.14 (m, 1H), 8.90-8.85 (m, 1H), 8.21 (d, J=2.4 Hz, 1H), 7.72 (d, J=7.7 Hz, 2H), 7.48 (d, J=8.0 Hz, 2H), 6.78-6.73 (m, 1H), 4.30 (d, J=5.4 Hz, 1H), 3.78-3.66 (m, 1H), 3.57 (s, 1H), 3.44 (q, J=5.2 Hz, 3H), 3.10 (dd, J=13.4, 8.6 Hz, 1H), 2.97 (dd, J=13.3, 6.6 Hz, 1H), 2.79 (d, J=12.2 Hz, 1H), 1.27 (t, J=7.0 Hz, 3H). MS obsd. ($ESI^+$): 339.2 $[(M+H)]^+$.

Example 88: (3S,4S,5R)-5-(4-(2-(azetidin-3-yl)thiazol-5-yl)benzyl)-4-(1,1-difluoropropoxy)pyrrolidin-3-ol
Scheme 80
80-1
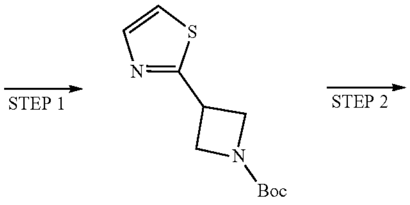
80-2
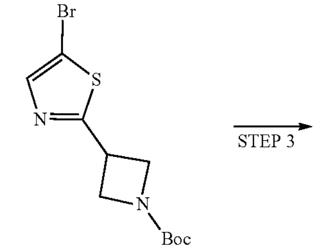
80-2
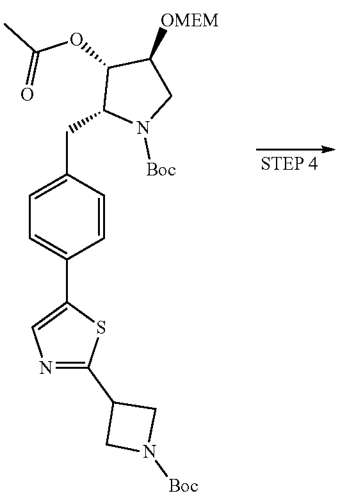
80-4
-continued
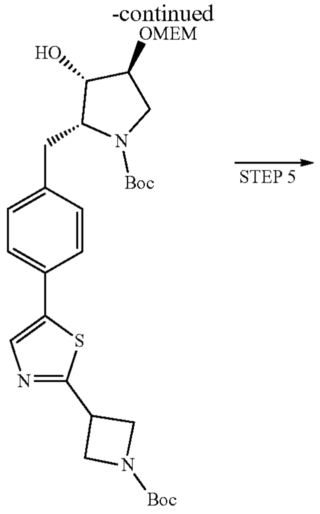
80-5
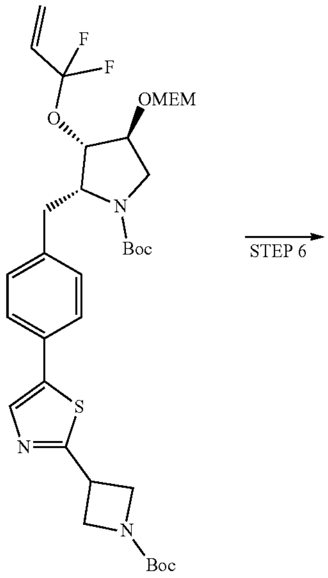
80-6

-continued

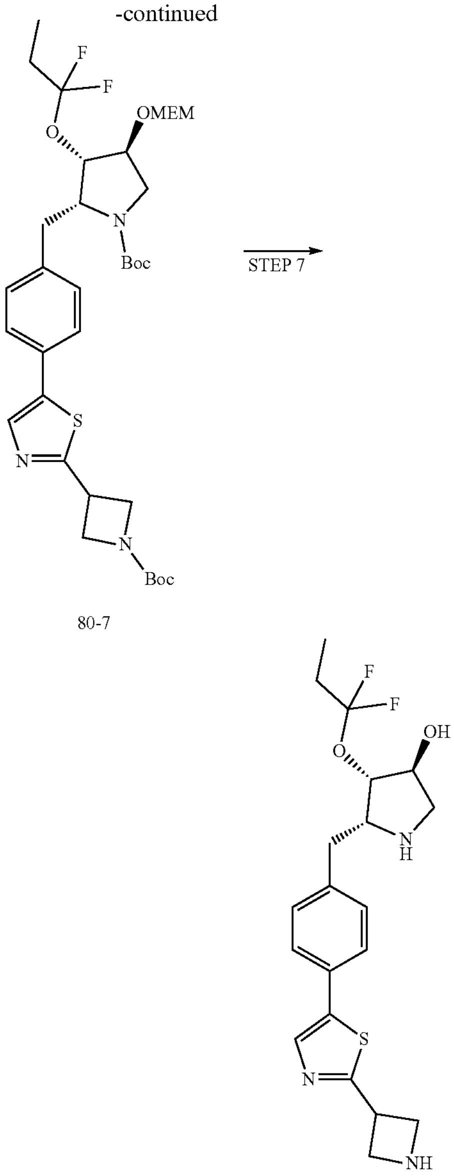

80-7

Step 1: tert-butyl 3-(thiazol-2-yl) azetidine-1-carboxylate (80-2). $K_2S_2O_8$ (3.1 g) and DIEA (3.0 g) was added to a stirred solution of thiazole (500 mg) and tert-butyl 3-iodo-azetidine-1-carboxylate (3.3 g) in DMSO (4.5 mL) and $H_2O$ (1.5 mL) at room temperature. The resulting mixture was stirred at 70° C. overnight, then diluted with water and extracted with EtOAc. The organic extracts were washed with brine, dried over $Na_2SO_4$, filtered, and concentrated. The residue was purified by silica gel column chromatography to afford the title compound as a yellow oil (200 mg). MS obsd. ($ESI^+$): 241.1 $[(M+H)]^+$.

Step 2: tert-butyl 3-(5-bromothiazol-2-yl) azetidine-1-carboxylate (80-3). NBS (168 mg) was added to a stirred solution of tert-butyl 3-(thiazol-2-yl) azetidine-1-carboxylate (190 mg) in DMF (5 mL) at 0° C. The resulting mixture was stirred at room temperature overnight, diluted with water, and extracted with EtOAc. The organic extracts were washed with brine, dried over $Na_2SO_4$, filtered, and concentrated. The residue was purified by silica gel column chromatography to afford the title compound as a yellow oil (160 mg). MS obsd. ($ESI^+$): 319.0 $[(M+H)]^+$.

Step 3: tert-butyl (2R,3S,4S)-3-acetoxy-2-(4-(2-(1-(tert-butoxycarbonyl) azetidin-3-yl)thiazol-5-yl)benzyl)-4-((2-methoxyethoxy)methoxy)pyrrolidine-1-carboxylate (80-4). $K_3PO_4$ (259 mg) and $Pd(PPh_3)_4$ (94 mg) was added to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (190 mg) in dioxane (2 mL) and $H_2O$ (0.4 mL) at room temperature. The resulting mixture was stirred at 60° C. overnight, then was diluted with water and extracted with EtOAc. The organic extracts were washed with brine, dried over $Na_2SO_4$, filtered, and concentrated. The residue was purified by reversed-phase flash chromatography to afford the title compound (200 mg) as a yellow oil (160 mg). MS obsd. ($ESI^+$): 662.3 $[(M+H)]^+$.

Step 4: tert-butyl (2R,3S,4S)-2-(4-(2-(1-(tert-butoxycarbonyl) azetidin-3-yl)thiazol-5-yl)benzyl)-3-hydroxy-4-((2-methoxyethoxy)methoxy)pyrrolidine-1-carboxylate (80-5). LiOH (21 mg) was added to a stirred solution of tert-butyl (2R,3S,4S)-3-acetoxy-2-(4-(2-(1-(tert-butoxycarbonyl) azetidin-3-yl)thiazol-5-yl)benzyl)-4-((2-methoxyethoxy) methoxy)pyrrolidine-1-carboxylate (195 mg) in THF (2 mL) and $H_2O$ (0.5 mL) at 0° C. . . . The resulting mixture was stirred at room temperature for 2 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil (86 mg). MS obsd. ($ESI^+$): 620.3 $[(M+H)]^+$.

Step 5-7: (3S,4S,5R)-5-(4-(2-(azetidin-3-yl)thiazol-5-yl) benzyl)-4-(1,1-difluoropropoxy)pyrrolidin-3-ol. The title compound was prepared in 23.5% overall yield as a yellow semi-solid according to General Procedure I using tert-butyl (2R,3S,4S)-2-(4-(2-(1-(tert-butoxycarbonyl)azetidin-3-yl) thiazol-5-yl)benzyl)-3-hydroxy-4-((2-methoxyethoxy) methoxy)pyrrolidine-1-carboxylate (86 mg) and 1-(2,2-difluoroethenyl)-1-methylpiperidin-1-ium triflate (196 mg) in DMF in STEP 5, and General Procedure VI using tert-butyl (2R,3S,4S)-2-(4-(2-(1-(tert-butoxycarbonyl) azetidin-3-yl) thiazol-5-yl)benzyl)-3-((1,1-difluoroallyl)oxy)-4-((2-methoxyethoxy)methoxy)pyrrolidine-1-carboxylate in MeOH in STEP 6 and General Procedure VIII in STEP 7. $^1H$ NMR (400 MHz, MeOD) δ 8.15 (s, 1H), 7.69 (d, J=8.1 Hz, 2H), 7.46 (d, J=8.0 Hz, 2H), 4.73 (m, 1H), 4.63-4.40 (m, 6H), 4.26 (m, 1H), 3.63 (m, 1H), 3.30-3.20 (m, 2H), 3.07 (m, 1H), 2.15 (m, 2H), 1.15 (m, 3H). MS obsd. ($ESI^+$): 410.2 $[(M+H)]^+$.

Example 89: (3S,4S,5R)-4-(1,1-difluoropropoxy)-5-(4-(pyrazin-2-yl)benzyl)pyrrolidin-3-ol Scheme 81

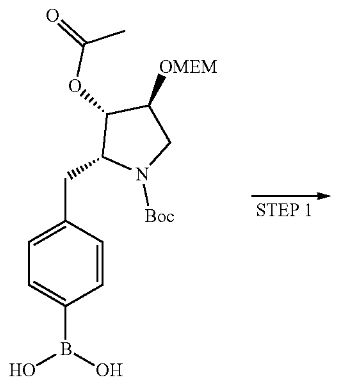

3-2

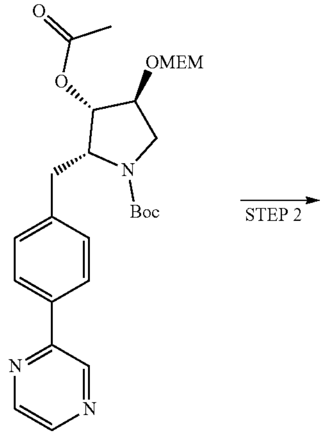

82-2

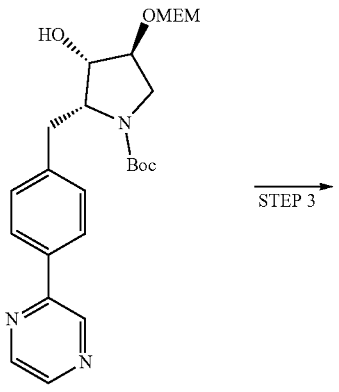

82-3

-continued

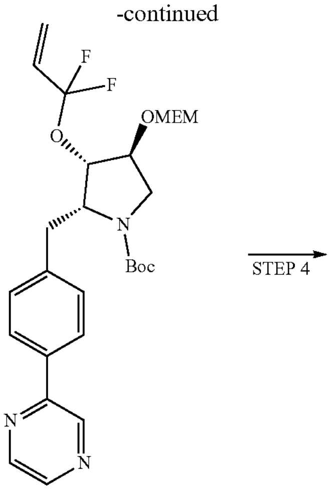

82-4

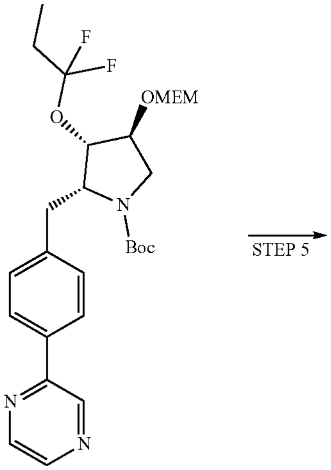

82-5

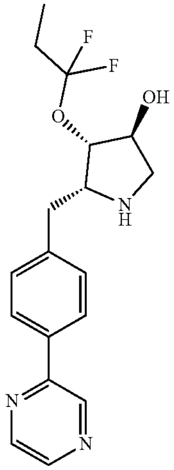

Step 1: tert-butyl (2R,3S,4S)-3-acetoxy-4-((2-methoxyethoxy)methoxy)-2-(4-(pyrazin-2-yl)benzyl)pyrrolidine-1-carboxylate (82-2). Under a nitrogen atmosphere, Pd(dppf)$Cl_2$ (52 mg) was added to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (150 mg), 2-iodopyrazine and $Na_2CO_3$ (102 mg) in Dioxane (5 mL) and $H_2O$ (0.5 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (100 mg). MS obsd. ($ESI^+$): 502.2 $[(M+H)]^+$.

Step 2: tert-butyl (2R,3S,4S)-3-hydroxy-4-((2-methoxyethoxy)methoxy)-2-(4-(pyrazin-2-yl)benzyl)pyrrolidine-1-carboxylate (82-3). LiOH (14 mg) was added to a stirred solution of tert-butyl (2R,3S,4S)-3-acetoxy-4-((2-methoxyethoxy)methoxy)-2-(4-(pyrazin-2-yl)benzyl)pyrrolidine-1-carboxylate (100 mg) in THF (5 mL) and $H_2O$ (1 mL) at 0° C. The resulting mixture was stirred at room temperature for 5 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (70 mg). MS obsd. ($ESI^+$): 460.2 $[(M+H)]^+$.

Step 3-5: (3S,4S,5R)-4-(1,1-difluoropropoxy)-5-(4-(pyrazin-2-yl)benzyl)pyrrolidin-3-ol. The title compound was prepared in 43.5% overall yield as a white solid according to General Procedure I using 82-3 (65 mg) and 1-(3,3-difluoroprop-2-en-1-yl)-1-methylpiperidin-1-ium triflate (88 mg) in DMF in STEP 3, and General Procedure VI using tert-butyl (2R,3S,4S)-3-((1,1-difluoroallyl)oxy)-4-((2-methoxyethoxy)methoxy)-2-(4-(pyrazin-2-yl)benzyl)pyrrolidine-1-carboxylate in MeOH in STEP 4 and General Procedure VIII in STEP 5. $^1H$ NMR (400 MHz, MeOD) δ 9.14 (d, J=1.6 Hz, 1H), 8.73-8.68 (m, 1H), 8.57 (d, J=2.5 Hz, 1H), 8.18-8.11 (m, 2H), 7.59-7.53 (m, 2H), 4.78 (d, J=3.2 Hz, 1H), 4.55-4.50 (m, 1H), 4.35-4.26 (m, 1H), 3.68-3.59 (m, 1H), 3.31-3.20 (m, 2H), 3.15-3.05 (m, 1H), 2.24-2.08 (m, 2H), 1.20-1.12 (m, 3H). MS obsd. ($ESI^+$): 350.2 $[(M+H)]^+$.

Example 90: (3S,4S,5R)-4-(1,1-difluoropropoxy)-5-(4-(6-methylpyridazin-4-yl)benzyl)pyrrolidin-3-ol Scheme 82

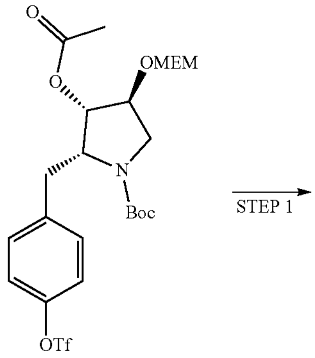

3-1

-continued

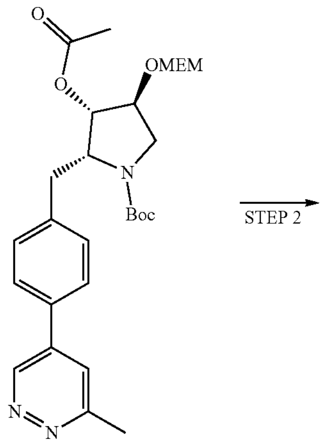

82-2

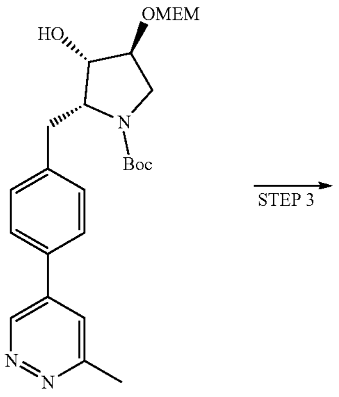

82-3

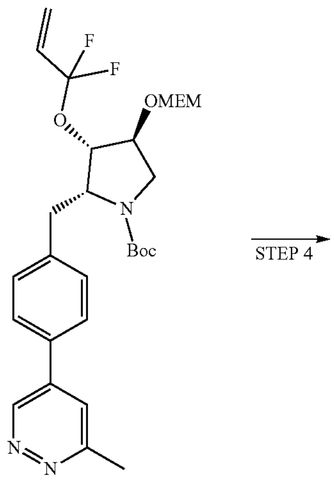

82-4

-continued

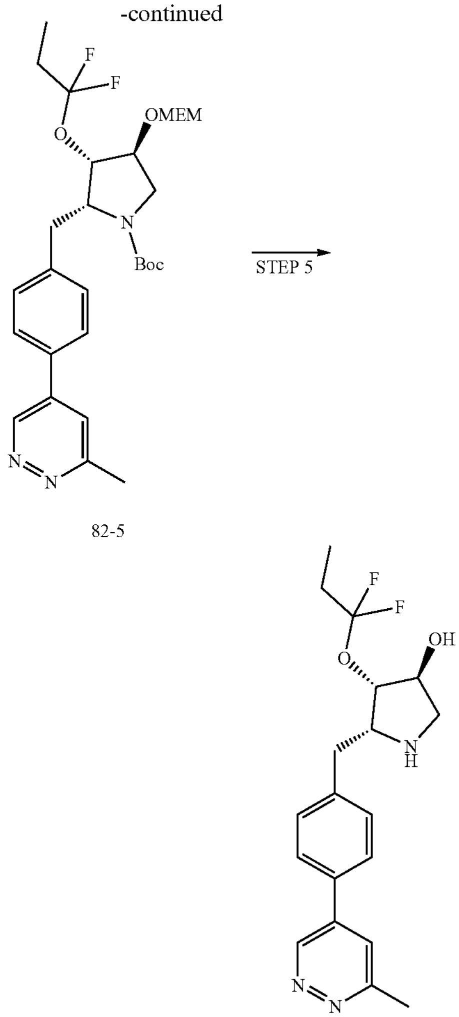

82-5

Step 1: tert-butyl (2R,3S,4S)-3-acetoxy-4-((2-methoxyethoxy)methoxy)-2-(4-(6-methylpyridazin-4-yl)benzyl)pyrrolidine-1-carboxylate (82-2). Under a nitrogen atmosphere, XPhos Pd $G_3$ (59 mg) and XPhos (16 mg) were added to a stirred solution of 3-methyl-5-(4,4,5,5-tetramethyl-1,3,2-dioxaborolan-2-yl)pyridazine (124 mg), tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (200 mg), and $NaHCO_3$ (88 mg) in DMF (5 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a white solid (120 mg). MS obsd. ($ESI^+$): 516.3 $[(M+H)]^+$ Step 2: tert-butyl (2R,3S,4S)-3-hydroxy-4-((2-methoxyethoxy)methoxy)-2-(4-(6-methylpyridazin-4-yl)benzyl)pyrrolidine-1-carboxylate (82-3). LiOH (53 mg) was added to a stirred solution of tert-butyl (2R,3S,4S)-3-acetoxy-4-((2-methoxyethoxy)methoxy)-2-(4-(6-methylpyridazin-4-yl) benzyl)pyrrolidine-1-carboxylate (115 mg) in THF (5 mL) and $H_2O$ (1 mL) at 0° C. The resulting mixture was stirred at room temperature for 2 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (100 mg). MS obsd. ($ESI^+$): 474.3 $[(M+H)]^+$.

Step 3-5: (3S,4S,5R)-4-(1,1-difluoropropoxy)-5-(4-(6-methylpyridazin-4-yl)benzyl)pyrrolidin-3-ol. The title compound was prepared in 23.9% overall yield as a white solid according to General Procedure I using 82-3 (100 mg) and 1-(3,3-difluoroprop-2-en-1-yl)-1-methylpiperidin-1-ium triflate (120 mg) in DMF in STEP 3, and General Procedure VI using tert-butyl (2R,3S,4S)-3-((1,1-difluoroallyl)oxy)-4-((2-methoxyethoxy)methoxy)-2-(4-(6-methylpyridazin-4-yl) benzyl)pyrrolidine-1-carboxylate in MeOH in STEP 4 and General Procedure VIII in STEP 5. $^1H$ NMR (400 MHz, MeOD) δ 9.37 (d, J=2.2 Hz, 1H), 7.92 (d, J=2.3 Hz, 1H), 7.86-7.78 (m, 2H), 7.54-7.47 (m, 2H), 4.42 (d, J=3.6 Hz, 1H), 4.35-4.29 (m, 1H), 3.61-3.58 (m, 1H), 3.42-3.34 (m, 1H), 3.03 (dd, J=14.0, 6.4 Hz, 1H), 2.89 (dd, J=13.9, 7.8 Hz, 1H), 2.78-2.70 (m, 3H), 2.70-2.67 (m, 1H), 2.15-2.05 (m, 2H), 1.13 (t, J=7.5 Hz, 3H). MS obsd. ($ESI^+$): 364.2 $[(M+H)]^+$.

Example 91: 5-(4-(((2R,3S,4S)-3-(1,1-difluoropropoxy)-4-hydroxypyrrolidin-2-yl)methyl)phenyl)thiazol-2(3H)-one Scheme 83

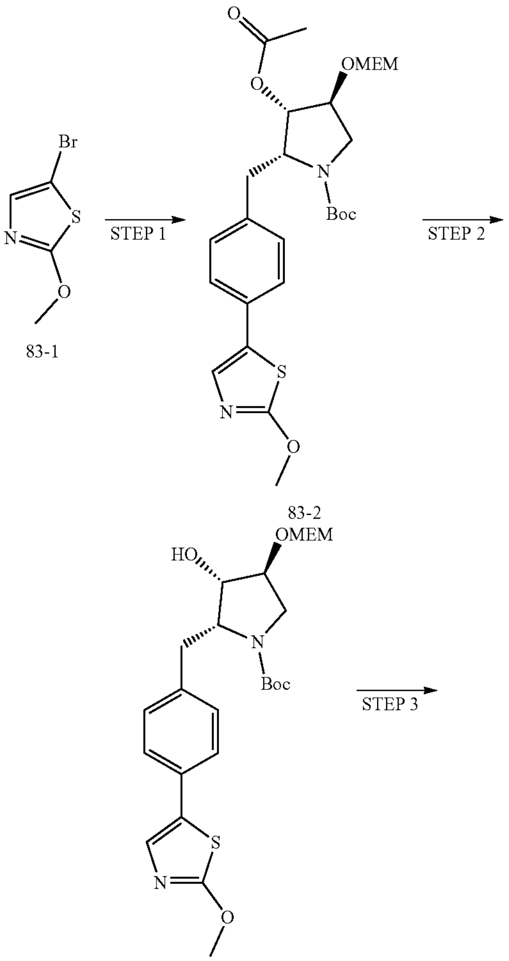

83-1

83-2

83-3

-continued

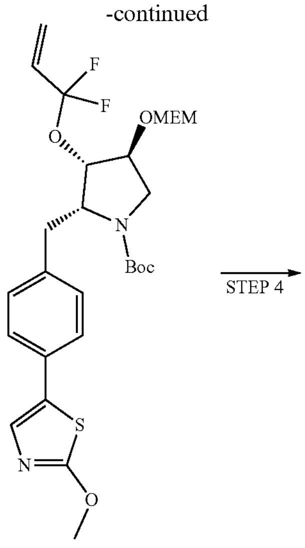

83-4

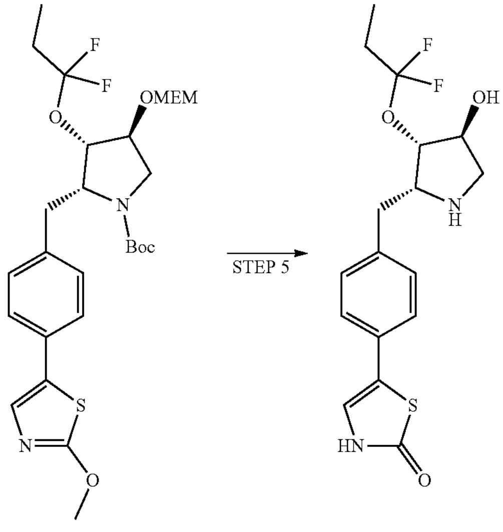

83-5

Step 1: tert-butyl (2R,3S,4S)-3-acetoxy-4-((2-methoxyethoxy)methoxy)-2-(4-(2-methoxythiazol-5-yl)benzyl)pyrrolidine-1-carboxylate (82-2). Under a nitrogen atmosphere, $Pd(dppf)Cl_2$ (46 mg) was added to a stirred solution of 5-bromo-2-methoxythiazole (124 mg), (4-(((2R,3S,4S)-3-acetoxy-1-(tert-butoxycarbonyl)-4-((2-methoxyethoxy)methoxy)pyrrolidin-2-yl)methyl)phenyl) boronic acid (200 mg) and $Na_2CO_3$ (113 mg) in 1,4-dioxane (10 mL) and $H_2O$ (1.0 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (109 mg). MS obsd. (ESI$^+$): 537.2 $[(M+H)]^+$.

Step 2: tert-butyl (2R,3S,4S)-3-hydroxy-4-((2-methoxyethoxy)methoxy)-2-(4-(2-methoxythiazol-5-yl)benzyl)pyrrolidine-1-carboxylate (82-3). LiOH (13 mg) was added to a stirred solution of tert-butyl (2R,3S,4S)-3-acetoxy-4-((2-methoxyethoxy)methoxy)-2-(4-(2-methoxythiazol-5-yl)benzyl)pyrrolidine-1-carboxylate (100 mg) in THF (5 mL) and $H_2O$ (1 mL) was at 0° C. The resulting mixture was stirred at room temperature for 2 h, then was diluted with water and extracted with EtOAc. The organic extracts were washed with brine, dried over $Na_2SO_4$, filtered, and concentrated. The residue was purified by reversed-phase flash chromatography to afford the title compound as a light-yellow oil (90 mg). MS obsd. (ESI$^+$): 495.2 $[(M+H)]^+$.

Step 3-4: tert-butyl (2R,3S,4S)-3-(1,1-difluoropropoxy)-4-((2-methoxyethoxy)methoxy)-2-(4-(2-methoxythiazol-5-yl)benzyl)pyrrolidine-1-carboxylate (83-5). The title compound was prepared in 85.9% overall yield as a light yellow oil according to General Procedure I using 83-3 (90 mg) and 1-(3,3-difluoroprop-2-en-1-yl)-1-methylpiperidin-1-ium triflate (151 mg) in DMF in STEP 3, and General Procedure VI using tert-butyl (2R,3S,4S)-3-((1,1-difluoroallyl)oxy)-4-((2-methoxyethoxy)methoxy)-2-(4-(2-methoxythiazol-5-yl)benzyl)pyrrolidine-1-carboxylate in MeOH in STEP 4. MS obsd. (ESI$^+$): 573.2 $[(M+H)]^+$.

Step 5: 5-(4-(((2R,3S,4S)-3-(1,1-difluoropropoxy)-4-hydroxypyrrolidin-2-yl)methyl)phenyl)thiazol-2(3H)-one. $PBr_3$ (56 mg) was added to a stirred solution of tert-butyl (2R,3S,4S)-3-(1,1-difluoropropoxy)-4-((2-methoxyethoxy)methoxy)-2-(4-(2-methoxythiazol-5-yl)benzyl)pyrrolidine-1-carboxylate (60 mg) and pyridine (8 mg) in Chloroform (5 mL) at 0° C. The resulting mixture was stirred at room temperature for 1 h, then diluted with water and extracted with EtOAc. The organic extracts were washed with brine, dried over $Na_2SO_4$, filtered, and concentrated. The residue was purified by Prep-HPLC to afford the title compound as a white solid. $^1H$ NMR (400 MHz, DMSO) δ 7.41-7.30 (m, 3H), 7.24 (d, J=7.9 Hz, 2H), 5.09 (d, J=4.4 Hz, 1H), 4.28-4.21 (m, 1H), 4.07 (s, 1H), 3.16 (dd, J=11.7, 5.7 Hz, 2H), 2.74 (dd, J=13.9, 5.5 Hz, 1H), 2.61 (dd, J=13.8, 8.2 Hz, 1H), 2.10-1.96 (m, 2H), 1.24 (s, 1H), 1.01 (t, J=7.5 Hz, 3H). MS obsd. (ESI$^+$): 371.1 $[(M+H)]^+$.

Example 92: (3S,4S,5R)-5-(4-(3-(difluoromethyl)-1H-pyrazol-1-yl)benzyl)-4-ethoxypyrrolidin-3-ol Scheme 84

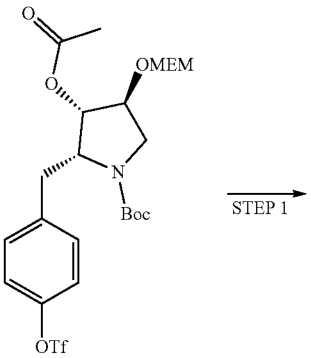

3-1

-continued

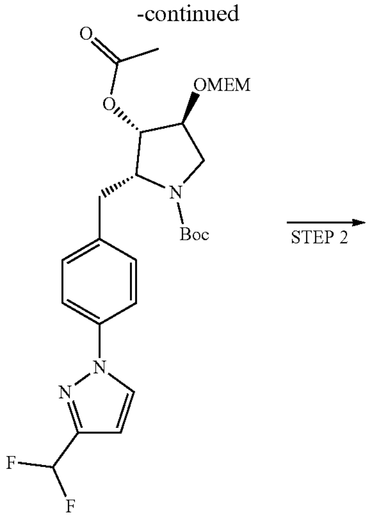

84-2

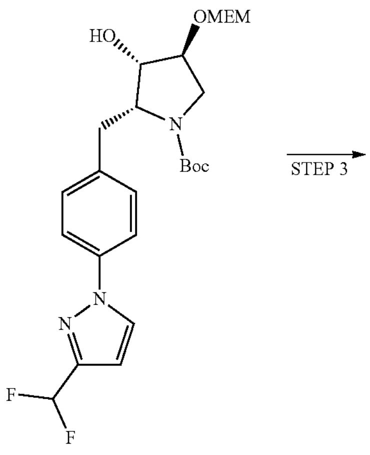

84-3

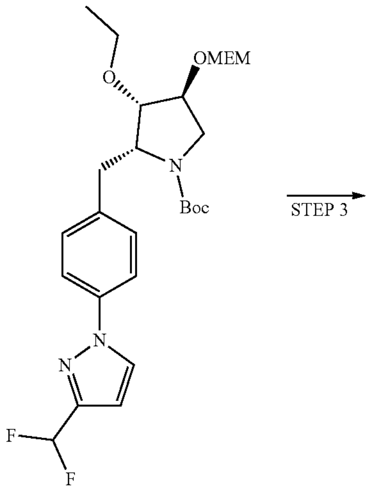

84-4

-continued

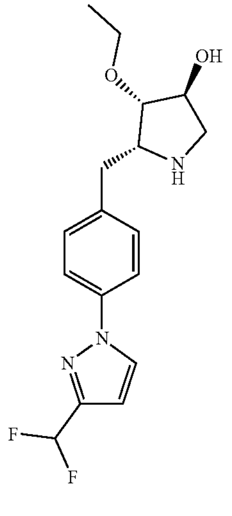

Step 1: tert-butyl (2R,3S,4S)-3-acetoxy-2-(4-(3-(difluoromethyl)-1H-pyrazol-1-yl)benzyl)-4-((2-methoxyethoxy)methoxy)pyrrolidine-1-carboxylate (84-2). Under a nitrogen atmosphere, $Pd_2(dba)_3$ (64 mg) and t-BuBrettPhos (68 mg) were added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (400 mg), 3-(difluoromethyl)-1H-pyrazole (124 mg), and $K_3PO_4$ (223 mg) in 1,4-Dioxane (10 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (150 mg). MS obsd. ($ESI^+$): 540.2 $[(M+H)]^+$.

Step 2: tert-butyl (2R,3S,4S)-2-(4-(3-(difluoromethyl)-1H-pyrazol-1-yl)benzyl)-3-hydroxy-4-((2-methoxyethoxy)methoxy)pyrrolidine-1-carboxylate (84-3). LiOH (60 mg) was added to a stirred solution of tert-butyl (2R,3S,4S)-3-acetoxy-2-(4-(3-(difluoromethyl)-1H-pyrazol-1-yl)benzyl)-4-((2-methoxyethoxy)methoxy)pyrrolidine-1-carboxylate (145 mg) in THF (10 mL) and $H_2O$ (2 mL) at 0° C. The resulting mixture was stirred at room temperature for 2 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (120 mg). MS obsd. ($ESI^+$): 498.2 $[(M+H)]^+$.

Step 3-4: (3S,4S,5R)-5-(4-(3-(difluoromethyl)-1H-pyrazol-1-yl)benzyl)-4-ethoxypyrrolidin-3-ol. The title compound was prepared in 27.8% overall yield as a light-yellow solid according to General Procedure I using 84-3 (55 mg) and ethyl iodide (35 mg) in DMF in STEP 1, and General Procedure VIII in STEP 2. $^1H$ NMR (400 MHz, MeOD) δ 8.28 (d, J=2.6 Hz, 1H), 7.78-7.70 (m, 2H), 7.47-7.40 (m, 2H), 6.89-6.66 (m, 2H), 4.29-4.23 (m, 1H), 3.76-3.64 (m, 1H), 3.52-3.35 (m, 4H), 3.04 (dd, J=13.3, 8.6 Hz, 1H), 2.92 (dd, J=13.3, 6.5 Hz, 1H), 2.72 (dd, J=12.3, 2.4 Hz, 1H), 1.33-1.21 (m, 3H); MS obsd. ($ESI^+$): 338.2 $[(M+H)]^+$.

Example 93: (3S,4S,5R)-5-(4-(3-(difluoromethyl)-1H-pyrazol-1-yl)benzyl)-4-(1,1-difluoropropoxy)pyrrolidin-3-ol Scheme 85

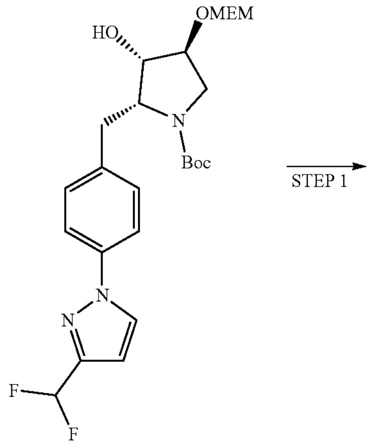

84-3

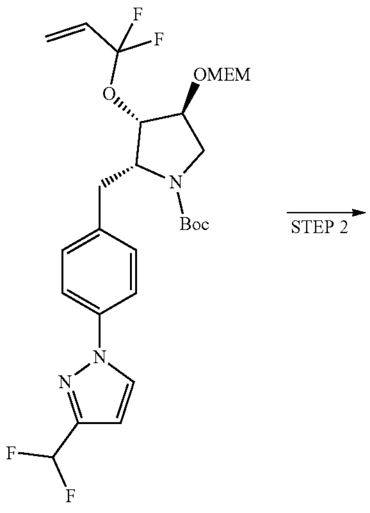

85-2

-continued

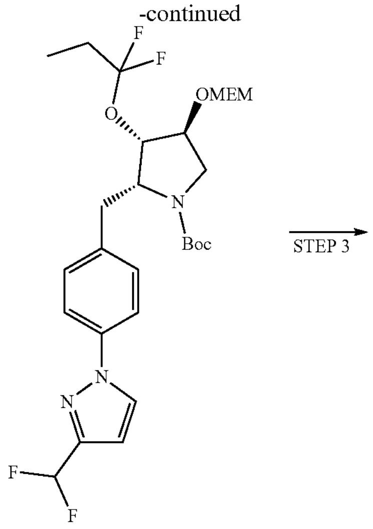

85-3

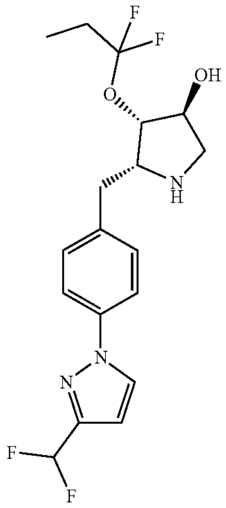

Step 1-3: (3S,4S,5R)-5-(4-(3-(difluoromethyl)-1H-pyrazol-1-yl)benzyl)-4-(1,1-difluoropropoxy)pyrrolidin-3-ol. The title compound was prepared in 35.9% overall yield as a white semi-solid according to General Procedure I using 84-3 (55 mg) and 1-(3,3-difluoroprop-2-en-1-yl)-1-methylpiperidin-1-ium triflate (72 mg) in DMF in STEP 1, and General Procedure VI using tert-butyl (2R,3S,4S)-3-((1,1-difluoroallyl)oxy)-2-(4-(3-(difluoromethyl)-1H-pyrazol-1-yl)benzyl)-4-((2-methoxyethoxy)methoxy)pyrrolidine-1-carboxylate in MeOH in STEP 2, and General Procedure VIII in STEP 3. $^1$H NMR (400 MHz, MeOD) δ 8.28 (d, J=2.5 Hz, 1H), 7.78-7.70 (m, 2H), 7.48-7.40 (m, 2H), 6.90-6.69 (m, 2H), 4.43 (d, J=3.6 Hz, 1H), 4.32 (d, J=5.1 Hz, 1H), 3.67-3.58 (m, 1H), 3.38 (dd, J=12.1, 5.7 Hz, 1H), 3.01 (dd, J=14.0, 6.3 Hz, 1H), 2.87 (dd, J=14.0, 7.9 Hz, 1H), 2.74 (dd, J=12.2, 2.2 Hz, 1H), 2.16-2.00 (m, 2H), 1.17-1.08 (m, 3H). MS obsd. (ESI$^+$): 388.2 [(M+H)]$^+$.

Example 94: (3S,4S,5R)-5-(4-(2-aminothiazol-5-yl)benzyl)-4-(1,1-difluoropropoxy)pyrrolidin-3-ol
Scheme 86
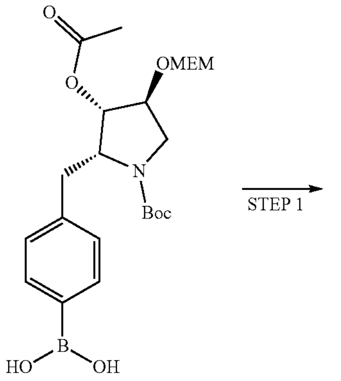
3-2
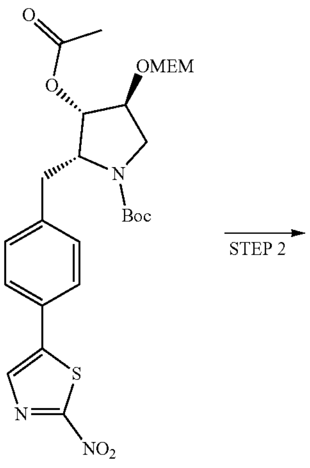
86-2
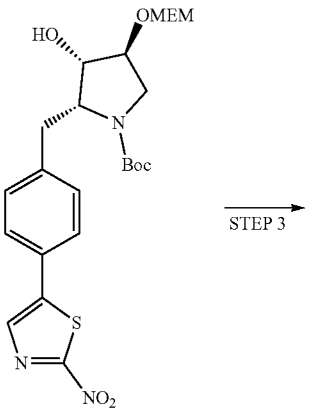
86-3
-continued
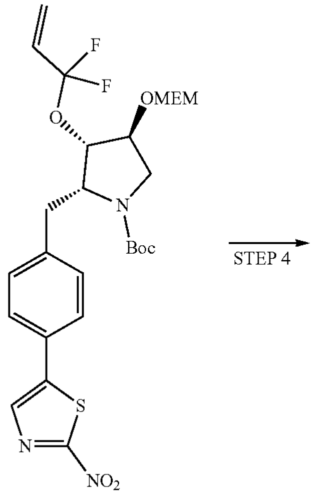
86-4
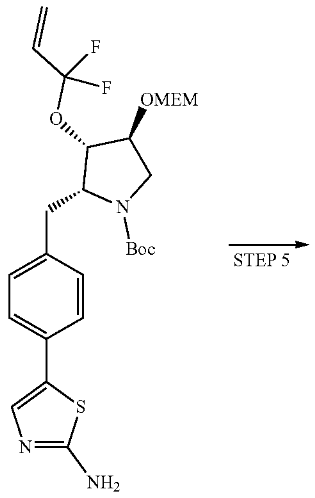
86-5
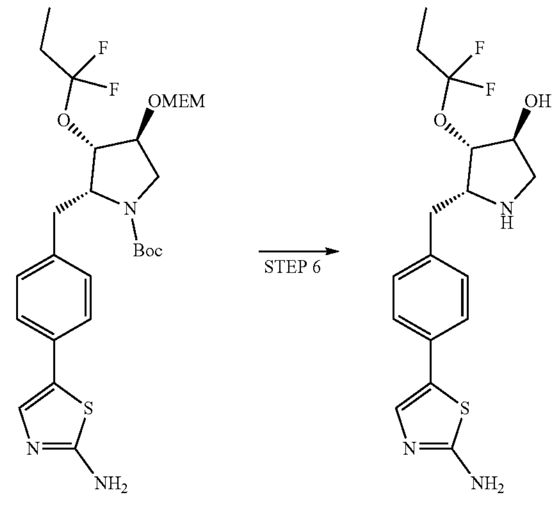
86-6
Step 1: tert-butyl (2R,3S,4S)-3-acetoxy-4-((2-methoxyethoxy)methoxy)-2-(4-(2-nitrothiazol-5-yl)benzyl)pyrrolidine-1-carboxylate (86-2). Under a nitrogen atmosphere, Pd(dppf)$Cl_2$ (70 mg) was added to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (200 mg), 5-bromo-2-nitro-1,3-thiazole (134 mg) and $Na_2CO_3$ (136 mg) in 1,4-dioxane (5 mL) and $H_2O$ (0.5 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (70 mg). MS obsd. ($ESI^+$): 552.2 $[(M+H)]^+$.

Step 2: tert-butyl (2R,3S,4S)-3-hydroxy-4-((2-methoxyethoxy)methoxy)-2-(4-(2-nitrothiazol-5-yl)benzyl)pyrrolidine-1-carboxylate (86-3). LiOH (15 mg) was added to a stirred solution of tert-butyl (2R,3S,4S)-3-acetoxy-4-((2-methoxyethoxy)methoxy)-2-(4-(2-nitrothiazol-5-yl)benzyl) pyrrolidine-1-carboxylate (145 mg) in THF (5 mL) and $H_2O$ (1 mL) at 0° C. The resulting mixture was stirred at room temperature for 12 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (55 mg). MS obsd. ($ESI^+$): 510.2 $[(M+H)]^+$.

Step 3: tert-butyl (2R,3S,4S)-3-((1,1-difluoroallyl)oxy)-4-((2-methoxyethoxy)methoxy)-2-(4-(2-nitrothiazol-5-yl) benzyl)pyrrolidine-1-carboxylate (86-4). The title compound was prepared in 70.6% yield as a light-yellow oil according to General Procedure I using 86-3 (55 mg) and 1-(3,3-difluoroallyl)-1-methylpiperidin-1-ium trifluoromethanesulfonate (67 mg) in DMF. MS obsd. ($ESI^+$): 586.2 $[(M+H)]^+$.

Step 4: tert-butyl (2R,3S,4S)-2-(4-(2-aminothiazol-5-yl) benzyl)-3-((1,1-difluoroallyl)oxy)-4-((2-methoxyethoxy) methoxy)pyrrolidine-1-carboxylate (86-5). Fe (11 mg) and ammonium chloride (7 mg) were added to a stirred solution of tert-butyl (2R,3S,4S)-3-((1,1-difluoroallyl)oxy)-4-((2-methoxyethoxy)methoxy)-2-(4-(2-nitrothiazol-5-yl)benzyl) pyrrolidine-1-carboxylate (30 mg) in EtOH (1 mL) and $H_2O$ (0.2 mL) at room temperature. The resulting mixture was stirred at 80° C. for 12 h. The resulting mixture was filtered and washed with EtOH. The filtrate was concentrated under reduced pressure to afford the title compound as a yellow oil. (25 mg). MS obsd. ($ESI^+$): 556.2 $[(M+H)]^+$.

Step 5-6: (3S,4S,5R)-5-(4-(2-aminothiazol-5-yl)benzyl)-4-(1,1-difluoropropoxy)pyrrolidin-3-ol. The title compound was prepared in 35.9% overall yield as a white solid according to General Procedure VI using 86-5 (25 mg) and $Pd(OH)_2$ (72 mg) in THF in STEP 5, and General Procedure VIII in STEP 6. $^1H$ NMR (400 MHz, MeOD) δ 7.41-7.34 (m, 2H), 7.30-7.21 (m, 3H), 4.40 (d, J=3.5 Hz, 1H), 4.31 (d, J=5.6 Hz, 1H), 3.55 (s, 1H), 3.37 (d, J=5.6 Hz, 1H), 2.93 (dd, J=13.9, 6.4 Hz, 2H), 2.79 (dd, J=13.9, 7.9 Hz, 1H), 2.71 (dd, J=12.2, 2.2 Hz, 1H), 2.11-2.03 (m, 2H), 1.16-1.08 (m, 3H); MS obsd. ($ESI^+$): 370.1 $[(M+H)]^+$.

Example 95: (3S,4S,5R)-5-(4-(3-(difluoromethyl)-1H-1,2,4-triazol-1-yl)benzyl)-4-ethoxypyrrolidin-3-ol Scheme 87

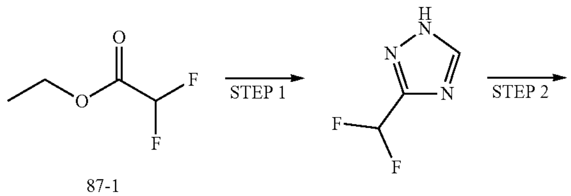

87-1

87-2

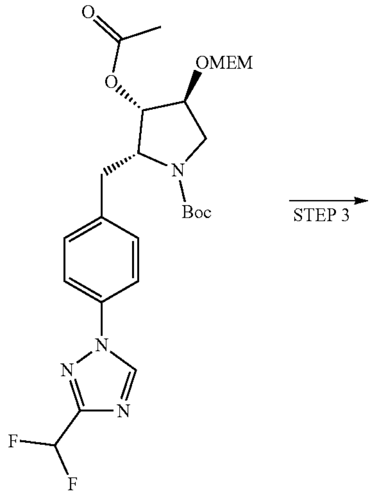

87-3

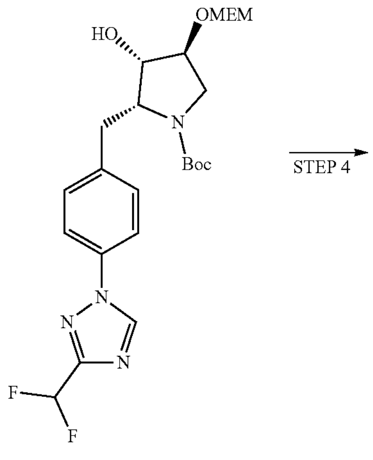

87-4

-continued

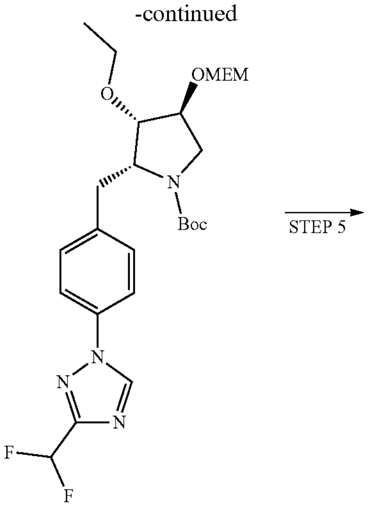

87-5

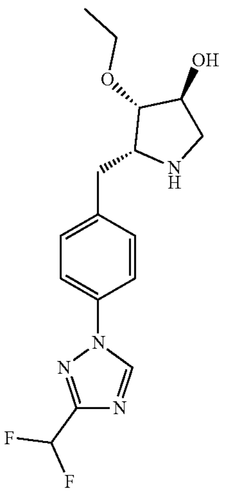

Step 1: 3-(difluoromethyl)-1H-1,2,4-triazole (87-2). $N_2H_4 \cdot H_2O$ (1.86 mL) was added to a stirred solution of ethyl 2,2-difluoroacetate (4.24 mL) in EtOH (50 mL) at 0° C. The resulting mixture was stirred at room temperature overnight, then iminoformamide acetate (4.61 g) in EtOH was added. The resulting mixture was stirred at 90° C. for 5 before it was concentrated. The residue was purified by reversed-phase flash chromatography to afford the title compound as a white solid. MS obsd. ($ESI^+$): 120.0 $[(M+H)]^+$.

Step 2: tert-butyl (2R,3S,4S)-3-acetoxy-2-(4-(3-(difluoromethyl)-1H-1,2,4-triazol-1-yl)benzyl)-4-((2-methoxyethoxy)methoxy)pyrrolidine-1-carboxylate (87-3). Under a nitrogen atmosphere, copper(I) sulfide (11 mg) and N,N,N',N'-Tetramethylethylenediamine (51 mg) were added to a stirred solution of tert-butyl (2R,3S,4S)-3-acetoxy-4-((2-methoxyethoxy)methoxy)-2-(4-(((trifluoromethyl) sulfonyl) oxy)benzyl)pyrrolidine-1-carboxylate (100 mg) and 3-(difluoromethyl)-1H-1,2,4-triazole (63 mg) in MeOH (5 mL) room temperature. The resulting mixture was stirred at 60° C. for 12 h, then it was filtered and the filter cake was washed with EtOH. The filtrate was concentrated under reduced pressure to afford the title compounds a yellow oil (80 mg). MS obsd. ($ESI^+$): 541.2 $[(M+H)]^+$.

Step 3: tert-butyl (2R,3S,4S)-2-(4-(3-(difluoromethyl)-1H-1,2,4-triazol-1-yl)benzyl)-3-hydroxy-4-((2-methoxyethoxy)methoxy)pyrrolidine-1-carboxylate (87-4). LiOH (15 mg) was added to a stirred solution of tert-butyl (2R,3S,4S)-3-acetoxy-2-(4-(3-(difluoromethyl)-1H-1,2,4-triazol-1-yl)benzyl)-4-((2-methoxyethoxy)methoxy)pyrrolidine-1-carboxylate (75 mg) in THF (3 mL) and $H_2O$ (1 mL) at 0° C. The resulting mixture was stirred at room temperature for 12 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (60 mg). MS obsd. ($ESI^+$): 499.2 $[(M+H)]^+$.

Step 4-5: (3S,4S,5R)-5-(4-(3-(difluoromethyl)-1H-1,2,4-triazol-1-yl)benzyl)-4-ethoxypyrrolidin-3-ol. The title compound was prepared in 37.6% overall yield as a light yellow solid according to General Procedure I using 87-4 (60 mg) and ethyl iodide (38 mg) in DMF in STEP 1, and General Procedure VIII in STEP 2. $^1H$ NMR (400 MHz, MeOD) δ 9.16 (s, 1H), 7.83-7.69 (m, 2H), 7.56-7.46 (m, 2H), 6.94 (s, 1H), 4.29-4.22 (m, 1H), 3.76-3.64 (m, 1H), 3.49-3.44 (m, 1H), 3.43-3.40 (m, 1H), 3.40-3.36 (m, 2H), 3.11-3.01 (m, 1H), 2.98-2.89 (m, 1H), 2.77-2.67 (m, 1H), 1.29-1.16 (m, 3H); MS obsd. ($ESI^+$): 339.2 $[(M+H)]^+$.

Example 96: 5-(4-(((2R,3S,4S)-3-ethoxy-4-hydroxypyrrolidin-2-yl)methyl)phenyl)-1-methylindolin-2-one Scheme 88

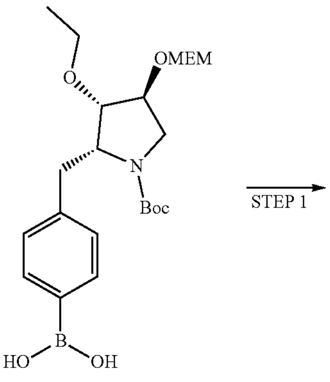

75-3

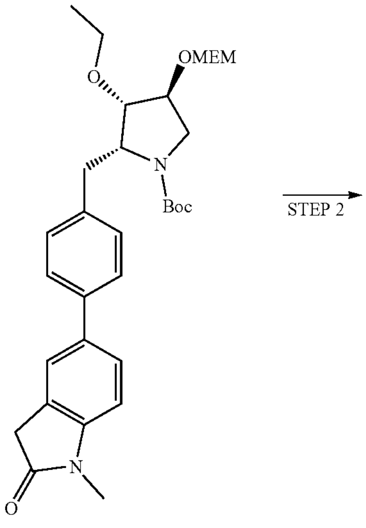

88-2

-continued

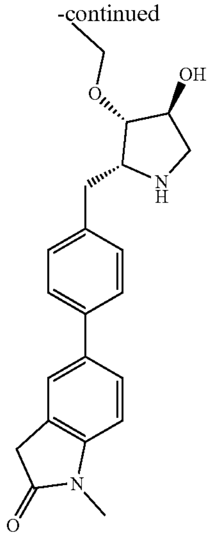

Step 1: tert-butyl (2R,3S,4S)-3-ethoxy-4-((2-methoxyethoxy)methoxy)-2-(4-(1-methyl-2-oxoindolin-5-yl)benzyl)pyrrolidine-1-carboxylate (88-2). Under a nitrogen atmosphere. $Na_2CO_3$ (70 mg) and $Pd(dppf)Cl_2$ (16 mg) were added to a stirred solution of (4-(((2R,3S,4S)-1-(tert-butoxycarbonyl)-3-ethoxy-4-((2-methoxyethoxy)methoxy)pyrrolidin-2-yl)methyl)phenyl) boronic acid (100 mg) and 5-bromo-1-methyl-3H-indol-2-one (99 mg) in Dioxane (5 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow solid. MS obsd. (ESI$^+$): 555.3 [(M+H)]$^+$.

Step 2: 5-(4-(((2R,3S,4S)-3-ethoxy-4-hydroxypyrrolidin-2-yl)methyl)phenyl)-1-methylindolin-2-one. The title compound was prepared in 66.6% yield as a white solid according to General Procedure VIII in DMF. $^1$H NMR (400 MHz, DMSO) δ 7.60-7.50 (m, 4H), 7.29 (d, J=8.1 Hz, 2H), 7.08-7.02 (m, 1H), 4.77 (t, J=3.6 Hz, 1H), 4.03 (s, 1H), 3.61 (s, 3H), 3.40-3.34 (m, 1H), 3.31-3.13 (m, 5H), 2.81 (dd, J=13.3, 7.3 Hz, 1H), 2.66 (dd, J=13.2, 7.0 Hz, 1H), 2.47 (dd, J=11.5, 2.8 Hz, 1H), 1.20-1.10 (m, 3H). MS obsd. (ESI$^+$): 367.2 [(M+H)]$^+$.

Example 97: (3S,4S,5R)-4-(1,1-difluoropropoxy)-5-(4-(1-methyl-1H-1,2,3-triazol-4-yl)benzyl)pyrrolidin-3-ol Scheme 89

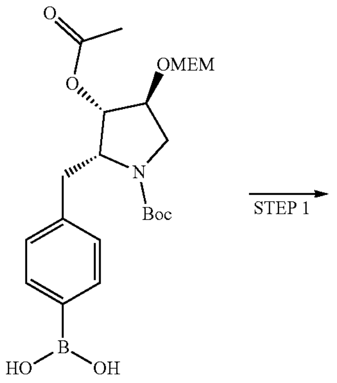

3-2

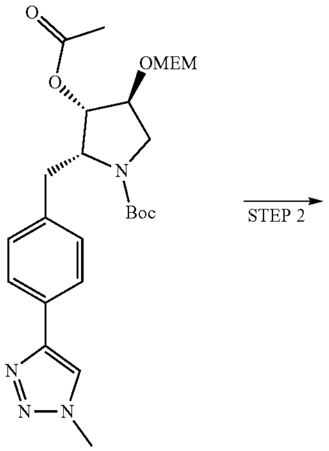

89-2

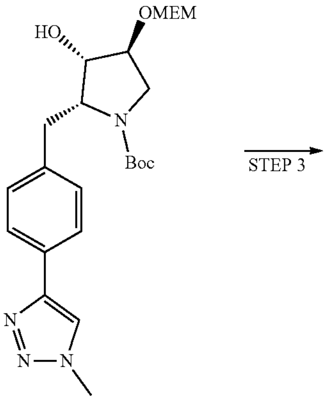

89-3

-continued

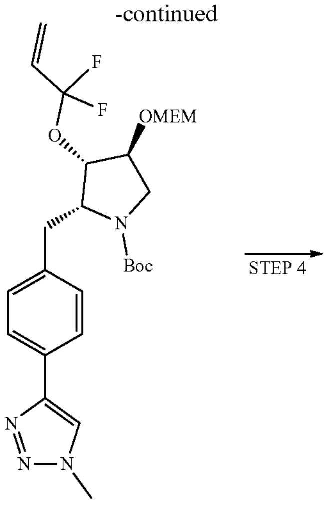

89-4

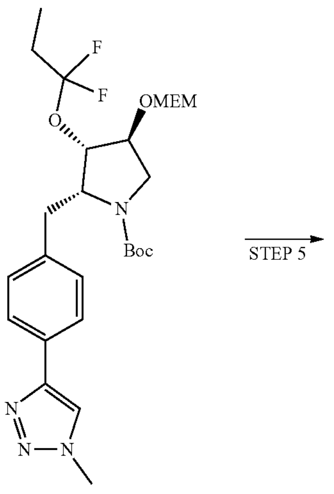

89-5

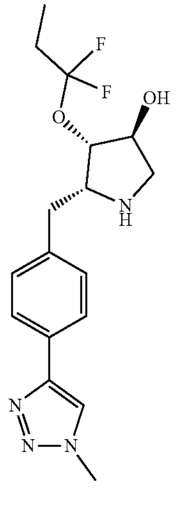

Step 1: tert-butyl (2R,3S,4S)-3-acetoxy-4-((2-methoxyethoxy)methoxy)-2-(4-(1-methyl-1H-1,2,3-triazol-4-yl)benzyl)pyrrolidine-1-carboxylate (89-2). Under a nitrogen atmosphere, Pd(dppf)$Cl_2$ (46 mg) and $Na_2CO_3$ (113 mg) were added to a stirred solution of 4-bromo-1-methyl-1,2,3-triazole (103 mg) and (4-(((2R,3S,4S)-3-acetoxy-1-(tert-butoxycarbonyl)-4-((2-methoxyethoxy)methoxy)pyrrolidin-2-yl)methyl)phenyl) boronic acid (200 mg) in 1,4-dioxane (10 mL) and $H_2O$ (1 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a white solid (200 mg). MS obsd. ($ESI^+$): 505.3 $[(M+H)]^+$.

Step 2: tert-butyl (2R,3S,4S)-3-hydroxy-4-((2-methoxyethoxy)methoxy)-2-(4-(1-methyl-1H-1,2,3-triazol-4-yl)benzyl)pyrrolidine-1-carboxylate (89-3). LiOH (17 mg) was added to a stirred solution of tert-butyl (2R,3S,4S)-3-acetoxy-4-((2-methoxyethoxy)methoxy)-2-(4-(1-methyl-1H-1,2,3-triazol-4-yl)benzyl)pyrrolidine-1-carboxylate (120 mg) in THF (10 mL) and $H_2O$ (2 mL) at 0° C. The resulting mixture was stirred at room temperature for 12 h, then diluted with water and extracted with EtOAc. The organic extracts were washed with brine, dried over $Na_2SO_4$, filtered, and concentrated. The residue was purified by reversed-phase flash chromatography to afford the title compound as a white solid (100 mg). MS obsd. ($ESI^+$): 463.2 $[(M+H)]^+$.

Step 3-5: (3S,4S,5R)-4-(1,1-difluoropropoxy)-5-(4-(1-methyl-1H-1,2,3-triazol-4-yl)benzyl)pyrrolidin-3-ol. The title compound was prepared in 45.1% overall yield as a white solid according to General Procedure I using 89-3 (64 mg) and 1-(3,3-difluoroprop-2-en-1-yl)-1-methylpiperidin-1-ium triflate (90 mg) in DMF in STEP 3, and General Procedure VI using tert-butyl (2R,3S,4S)-3-((1,1-difluoroallyl)oxy)-4-((2-methoxyethoxy)methoxy)-2-(4-(1-methyl-1H-1,2,3-triazol-4-yl)benzyl)pyrrolidine-1-carboxylate in MeOH in STEP 4, and General Procedure VIII in STEP 5. $^1H$ NMR (400 MHz, MeOD) δ 8.25 (s, 1H), 7.80-7.73 (m, 2H), 7.40-7.34 (m, 2H), 4.41 (d, J=3.6 Hz, 1H), 4.34-4.28 (m, 1H), 4.16 (s, 3H), 3.63-3.54 (m, 1H), 3.41-3.33 (m, 1H), 2.97 (dd, J=13.9, 6.4 Hz, 1H), 2.84 (dd, J=14.0, 7.8 Hz, 1H), 2.76-2.65 (m, 1H), 2.15-1.99 (m, 2H), 1.17-1.08 (m, 3H). MS obsd. ($ESI^+$): 353.2 $[(M+H)]^+$.

Example 98: azetidin-3-yl(4-(((2R,3S,4S)-3-(1,1-difluoropropoxy)-4-hydroxypyrrolidin-2-yl)methyl)phenyl)methanone Scheme 90

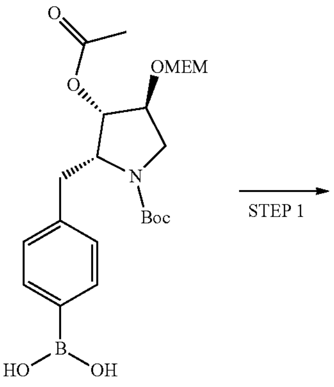

3-2

-continued

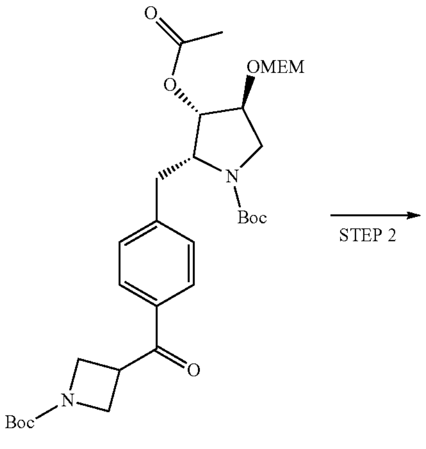

90-2

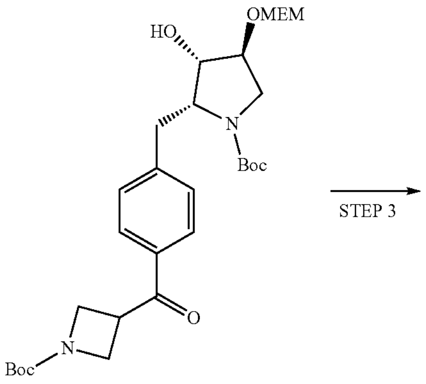

90-3

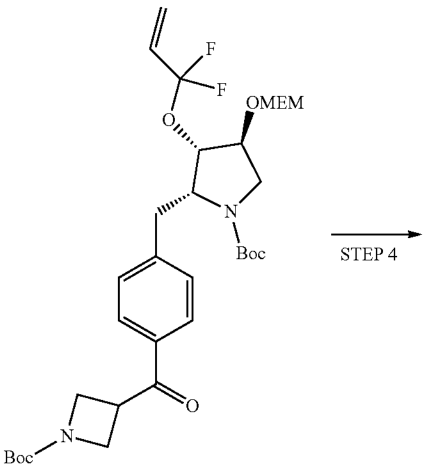

90-4

-continued

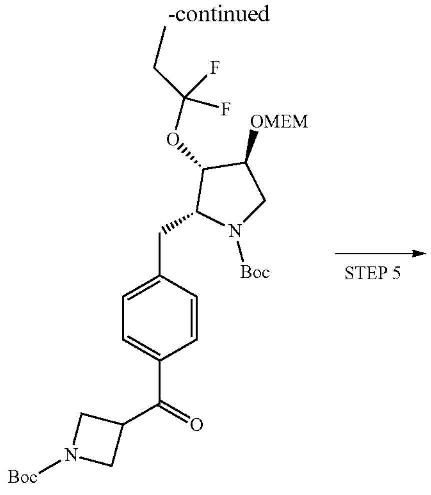

90-5

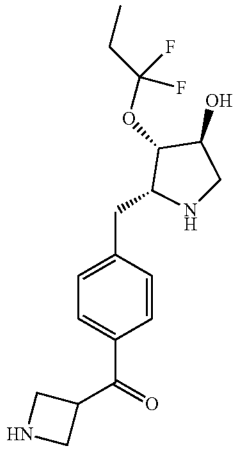

Step 1: tert-butyl (2R,3S,4S)-3-acetoxy-2-(4-(1-(tert-butoxycarbonyl) azetidine-3-carbonyl)benzyl)-4-((2-methoxyethoxy)methoxy)pyrrolidine-1-carboxylate (90-2). Under a nitrogen atmosphere. $(DPPE)_2NiCl_2$ (90 mg), Zinc chloride (117 mg) and $H_2O$ (16 mg) were added to a stirred solution of (4-(((2R,3S,4S)-3-acetoxy-1-(tert-butoxycarbonyl)-4-((2-methoxyethoxy)methoxy)pyrrolidin-2-yl)methyl)phenyl) boronic acid (468 mg) in 1,4-dioxane (13 mL) at room temperature. The resulting mixture was stirred at 100° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow solid (160 mg). MS obsd. ($ESI^+$): 607.3 $[(M+H)]^+$.

Step 2: tert-butyl (2R,3S,4S)-2-(4-(1-(tert-butoxycarbonyl) azetidine-3-carbonyl)benzyl)-3-hydroxy-4-((2-methoxyethoxy)methoxy)pyrrolidine-1-carboxylate (90-3). LiOH (63 mg) was added to a stirred solution of tert-butyl (2R,3S,4S)-3-acetoxy-2-(4-(1-(tert-butoxycarbonyl) azetidine-3-carbonyl)benzyl)-4-((2-methoxyethoxy)methoxy) pyrrolidine-1-carboxylate (160 mg) in THF (6 mL) and $H_2O$ (2 mL) at 0° C. The resulting mixture was stirred at room temperature for 12 h, then diluted with water and extracted with EtOAc. The organic extracts were washed with brine, dried over $Na_2SO_4$, filtered, and concentrated. The residue was purified by reversed-phase flash chromatography to afford the title compound as a white solid (140 mg). MS obsd. ($ESI^+$): 565.3 $[(M+H)]^+$.

Step 3-5: azetidin-3-yl(4-(((2R,3S,4S)-3-(1,1-difluoropropoxy)-4-hydroxypyrrolidin-2-yl)methyl)phenyl)methanone. The title compound was prepared in 25.1% overall yield as a light-yellow semi-solid according to General Procedure I using 90-3 (50 mg) and 1-(3,3-difluoroprop-2-en-1-yl)-1-methylpiperidin-1-ium triflate (86 mg) in DMF in STEP 3, and General Procedure VI using tert-butyl (2R,3S,4S)-2-(4-(1-(tert-butoxycarbonyl) azetidine-3-carbonyl) benzyl)-3-((1,1-difluoroallyl)oxy)-4-((2-methoxyethoxy) methoxy)pyrrolidine-1-carboxylate in MeOH in STEP 4, and General Procedure VIII in STEP 5. $^1$H NMR (400 MHz, MeOD) δ 8.00-7.93 (m, 2H), 7.58 (d, J=7.9 Hz, 2H), 4.82-4.62 (m, 2H), 4.51 (d, J=4.2 Hz, 1H), 4.43 (t, J=10.0 Hz, 2H), 4.38-4.24 (m, 3H), 3.64 (dd, J=12.7, 4.4 Hz, 1H), 3.45-3.16 (dd, J=14.5, 8.8 Hz, 3H), 2.22-2.06 (m, 2H), 1.18-1.09 (m, 3H). MS obsd. (ESI$^+$): 355.2 [(M+H)]$^+$.

Example 99 (3S,4S,5R)-4-ethoxy-5-(4-(quinazolin-7-yl)benzyl)pyrrolidin-3-ol

Scheme 91

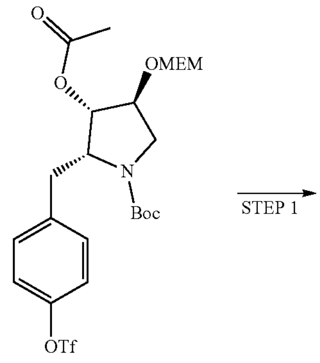

3-1

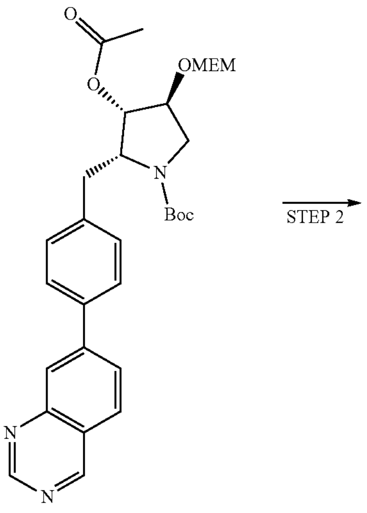

91-2

-continued

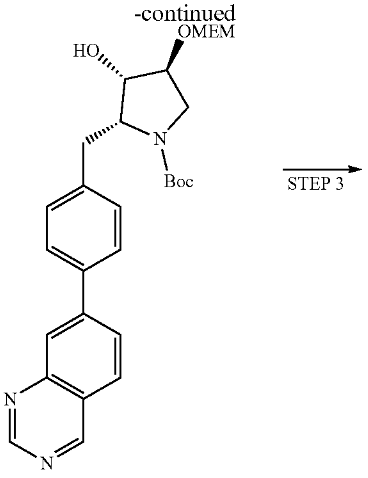

91-3

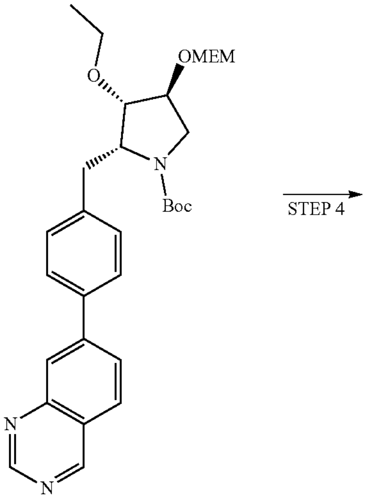

91-4

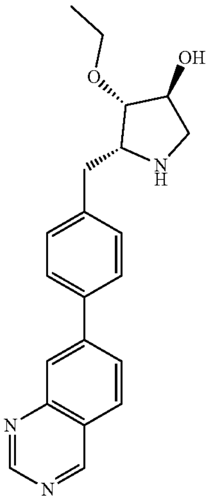

Step 1: tert-butyl (2R,3S,4S)-3-acetoxy-4-((2-methoxyethoxy)methoxy)-2-(4-(quinazolin-7-yl)benzyl)pyrrolidine-1-carboxylate (91-2). Under a nitrogen atmosphere, XPhos (16 mg), XPhos Pd $G_3$ (29 mg) and $NaHCO_3$ (88 mg) was added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (200 mg) and 7-(4,4,5,5-tetramethyl-1,3,2-dioxaborolan-2-yl)quinazoline (107 mg) in DMF (10 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow solid (190 mg). MS obsd. ($ESI^+$): 552.3 $[(M+H)]^+$.

Step 2: tert-butyl (2R,3S,4S)-3-hydroxy-4-((2-methoxyethoxy)methoxy)-2-(4-(quinazolin-7-yl)benzyl)pyrrolidine-1-carboxylate (91-3). LiOH (15 mg) was added to a stirred solution of tert-butyl (2R,3S,4S)-3-acetoxy-4-((2-methoxyethoxy)methoxy)-2-(4-(quinazolin-7-yl)benzyl)pyrrolidine-1-carboxylate (100 mg) in THF (9 mL) and $H_2O$ (3 mL) at 0° C. The resulting mixture was stirred at room temperature overnight, then it was diluted with water and extracted with EtOAc. The organic extracts were washed with brine, dried over $Na_2SO_4$, filtered, and concentrated. The residue was purified by reversed-phase flash chromatography to afford the title compound as a yellow solid (80 mg). MS obsd. ($ESI^+$): 510.3 $[(M+H)]^+$.

Step 3-4: (3S,4S,5R)-4-ethoxy-5-(4-(quinazolin-7-yl)benzyl)pyrrolidin-3-ol. The title compound was prepared in 47.6% overall yield as a white solid according to General Procedure I using 91-3 (80 mg) and ethyl iodide (48 mg) in DMF in STEP 3, and General Procedure VIII in STEP 4. $^1H$ NMR (400 MHz, MeOD) δ 9.56 (s, 1H), 9.27 (s, 1H), 8.27-8.18 (m, 2H), 8.12 (dd, J=8.5, 1.7 Hz, 1H), 7.85-7.72 (m, 2H), 7.50 (d, J=7.9 Hz, 2H), 4.29 (dd, J=6.0, 2.3 Hz, 1H), 3.78-3.66 (m, 1H), 3.59-3.51 (m, 1H), 3.51-3.39 (m, 3H), 3.10 (dd, J=13.3, 8.6 Hz, 1H), 2.97 (dd, J=13.3, 6.6 Hz, 1H), 2.76 (dd, J=12.3, 2.3 Hz, 1H), 1.33-1.18 (m, 3H). MS obsd. ($ESI^+$): 350.2 $[(M+H)]^+$.

Example 100: (3S,4S,5R)-4-(1,1-difluoropropoxy)-5-(4-(1-(4-fluorophenyl)-1H-1,2,3-triazol-4-yl)benzyl)pyrrolidin-3-ol Scheme 92

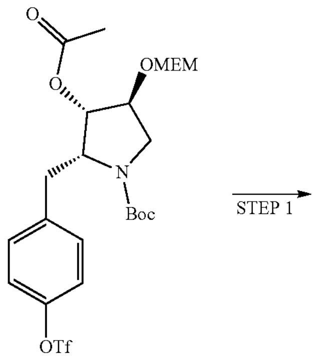

3-1

-continued

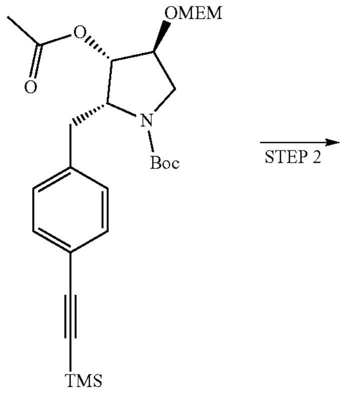

92-2

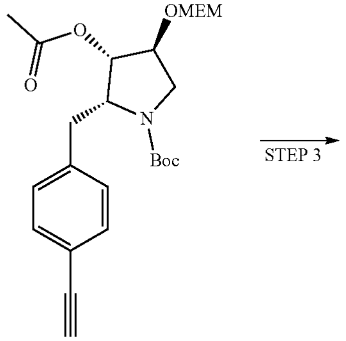

92-3

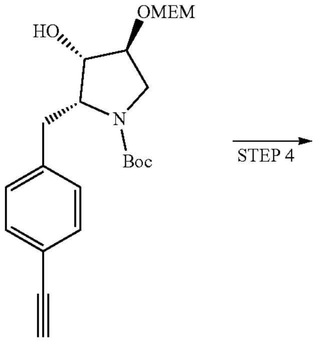

92-4

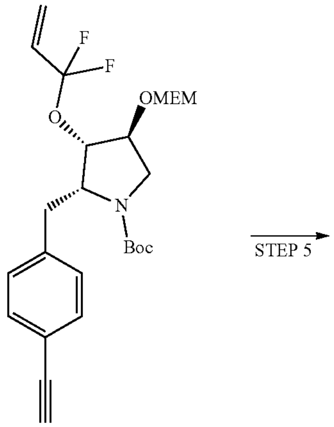

92-5

-continued

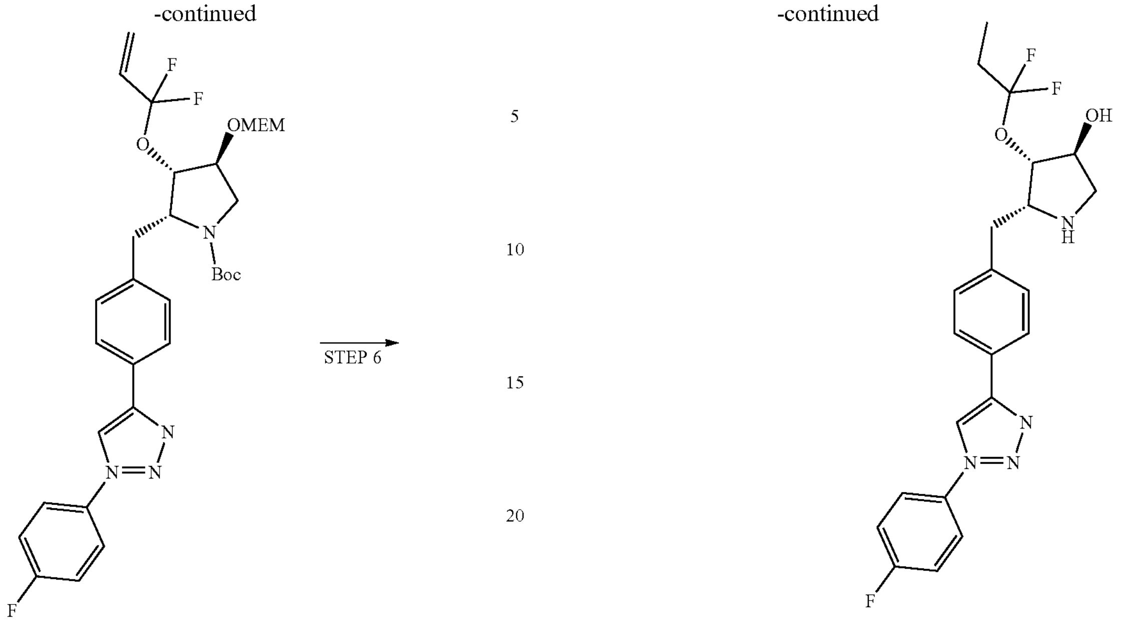

92-6

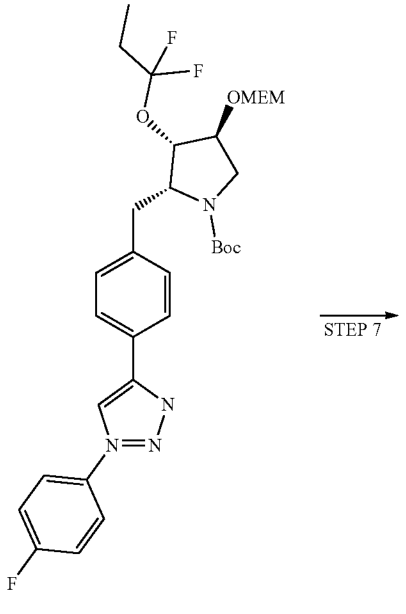

92-7

Step 1: tert-butyl (2R,3S,4S)-3-acetoxy-4-((2-methoxyethoxy)methoxy)-2-(4-((trimethylsilyl) ethynyl)benzyl)pyrrolidine-1-carboxylate (92-2). Under a nitrogen atmosphere, Pd(dppf)$Cl_2$ (0.2 g), CuI (0.03 g) and TEA (0.7 g) were added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (1 g) and trimethylsilylacetylene (0.34 g) in DMF (10 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (800 mg). MS obsd. ($ESI^+$): 520.3 $[(M+H)]^+$.

Step 2: tert-butyl (2R,3S,4S)-3-acetoxy-2-(4-ethynylbenzyl)-4-((2-methoxyethoxy)methoxy)pyrrolidine-1-carboxylate (92-3). Et3N·3HF (744 mg) was added to a stirred solution of tert-butyl (2R,3S,4S)-3-acetoxy-4-((2-methoxyethoxy)methoxy)-2-(4-((trimethylsilyl) ethynyl)benzyl)pyrrolidine-1-carboxylate (800 mg) in THF (20 mL) at room temperature. The resulting mixture was stirred at 60° C. overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (680 mg). MS obsd. ($ESI^+$): 448.2 $[(M+H)]^+$.

Step 3: tert-butyl (2R,3S,4S)-2-(4-ethynylbenzyl)-3-hydroxy-4-((2-methoxyethoxy)methoxy)pyrrolidine-1-carboxylate (92-4). LiOH (72 mg) was added to a stirred solution of tert-butyl (2R,3S,4S)-3-acetoxy-2-(4-ethynylbenzyl)-4-((2-methoxyethoxy)methoxy)pyrrolidine-1-carboxylate (450 mg) in THF (2 mL) and $H_2O$ (2 mL) at 0° C. The resulting mixture was stirred at room temperature for 4 h. then it was diluted with water, and extracted with EtOAc. The organic extracts were washed with brine, dried over $Na_2SO_4$, filtered, and concentrated. The residue was purified by reversed-phase flash chromatography to afford the title compound as a yellow oil (350 mg). MS obsd. ($ESI^+$): 406.2 $[(M+H)]^+$.

Step 4: tert-butyl (2R,3S,4S)-3-((1,1-difluoroallyl)oxy)-2-(4-ethynylbenzyl)-4-((2-methoxyethoxy)methoxy)pyrrolidine-1-carboxylate (92-5). $Cs_2CO_3$ (361 mg) and $Ag_2O$ (257 mg) were added to a stirred solution of tert-butyl (2R,3S,4S)-2-(4-ethynylbenzyl)-3-hydroxy-4-((2-methoxyethoxy)methoxy)pyrrolidine-1-carboxylate (150 mg) and 1-(3,3-difluoroprop-2-en-1-yl)-1-methylpiperidin-1-ium triflate in DMF (2 mL) at 0° C. The resulting mixture was stirred at room temperature overnight, then it was diluted with water and extracted with EtOAc. The organic extracts were washed with brine, dried over $Na_2SO_4$, filtered, and concentrated. The residue was purified by reversed-phase flash chromatography to afford the title compound as a yellow oil (50 mg).

MS obsd. ($ESI^+$): 482.2 $[(M+H)]^+$.

Step 5: tert-butyl (2R,3S,4S)-3-((1,1-difluoroallyl)oxy)-2-(4-(1-(4-fluorophenyl)-1H-1,2,3-triazol-4-yl)benzyl)-4-((2-methoxyethoxy)methoxy)pyrrolidine-1-carboxylate (92-6). $CuSO_4 \cdot 5H_2O$ (25 mg) and sodium (2S)-2-[(1S)-1,2-dihydroxyethyl]-4-hydroxy-5-oxooxolan-3-olate (41 mg) were added to a stirred solution of tert-butyl (2R,3S,4S)-3-((1,1-difluoroallyl)oxy)-2-(4-ethynylbenzyl)-4-((2-methoxyethoxy)methoxy)pyrrolidine-1-carboxylate (50 mg) and 1-azido-4-fluorobenzene (28 mg) in MeOH (5 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (49 mg).

MS obsd. ($ESI^+$): 619.3 $[(M+H)]^+$.

Step 6-7: (3S,4S,5R)-4-(1,1-difluoropropoxy)-5-(4-(1-(4-fluorophenyl)-1H-1,2,3-triazol-4-yl)benzyl)pyrrolidin-3-ol. The title compound was prepared in 57.6% overall yield as a white solid according to General Procedure VI using 92-6 (44 mg) in MeOH in STEP 6, and General Procedure VIII in STEP 7. $^1H$ NMR (400 MHz, MeOD) δ 8.92 (s, 1H), 8.54 (s, 1H), 8.01-7.92 (m, 3H), 7.49 (m, 2H), 7.39 (m, 2H), 4.68 (m, 1H), 4.47 (m, 1H), 4.12 (s, 1H), 3.56 (m, 1H), 3.24-3.19 (m, 1H), 3.11 (m, 1H), 3.06-2.99 (m, 1H), 2.15 (m, 2H), 1.15 (t, J=7.5 Hz, 3H). MS obsd. ($ESI^+$): 433.2 $[(M+H)]^+$.

Example 101: (3S,4S,5R)-5-(4-(1-cyclopropyl-1H-1,2,3-triazol-4-yl)benzyl)-4-(1,1-difluoropropoxy)pyrrolidin-3-ol Scheme 93

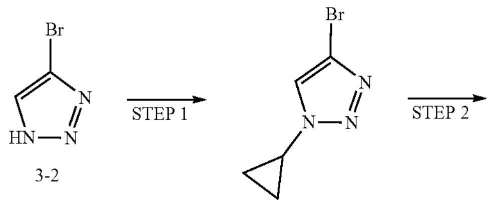

3-2

93-2

-continued

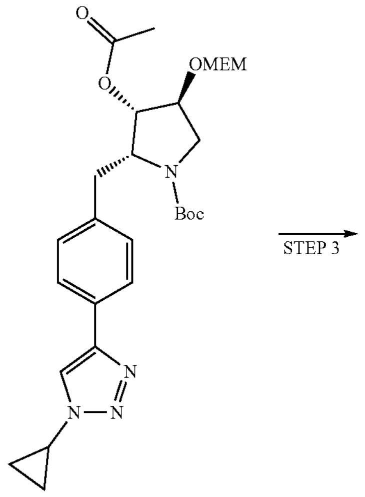

93-3

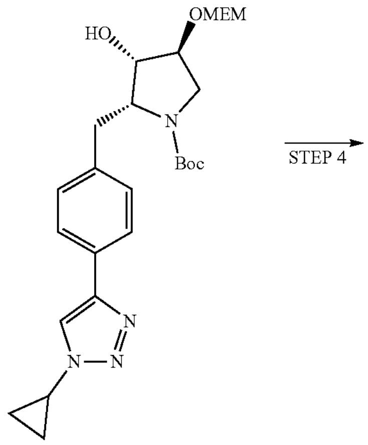

93-4

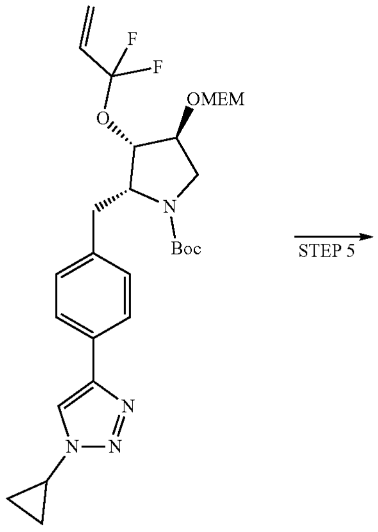

93-5

-continued

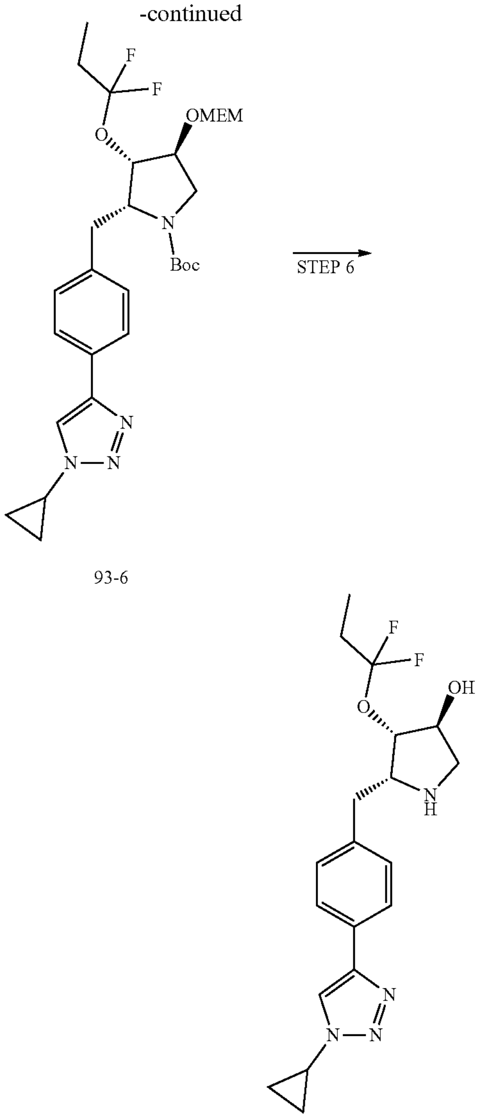

93-6

Step 1: 4-bromo-1-cyclopropyl-1H-1,2,3-triazole (93-2). $Cu(OAc)_2$ (3.1 g), 2-(2-pyridyl)pyridine (1.8 g) and $K_2CO_3$ (3.2 g) were added to a stirred solution of cyclopropylboronic acid (1 g) and 4-bromo-1H-1,2,3-triazole (2.6 g) in 1,2-dichloroethane (40 mL) at room temperature. The resulting mixture was stirred at 50° C. overnight, under nitrogen atmosphere. The reaction mixture was filtered through a pad of celite and the filtrate was concentrated to yield a residue which was purified by preparative TLC to afford the title compound as a light-yellow solid (60 mg). MS obsd. ($ESI^+$): 188.0 $[(M+H)]^+$.

Step 2: tert-butyl (2R,3S,4S)-3-acetoxy-2-(4-(1-cyclopropyl-1H-1,2,3-triazol-4-yl)benzyl)-4-((2-methoxyethoxy)methoxy)pyrrolidine-1-carboxylate (93-3). Under a nitrogen atmosphere, $Pd(dppf)Cl_2$ (23.5 mg) was added to a stirred solution of 4-bromo-1-cyclopropyl-1H-1,2,3-triazole (60 mg), (4-(((2R,3S,4S)-3-acetoxy-1-(tert-butoxycarbonyl)-4-((2-methoxyethoxy)methoxy)pyrrolidin-2-yl)methyl)phenyl) boronic acid (100 mg), and $Na_2CO_3$ (56 mg) in 1,4-dioxane (5 mL) and $H_2O$ (0.5 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by reversed-phase flash chromatography as a light-yellow oil (52 mg). MS obsd. ($ESI^+$): 531.3 $[(M+H)]^+$.

Step 3: tert-butyl (2R,3S,4S)-2-(4-(1-cyclopropyl-1H-1,2,3-triazol-4-yl)benzyl)-3-hydroxy-4-((2-methoxyethoxy)methoxy)pyrrolidine-1-carboxylate (93-4). LiOH (7 mg) was added to a stirred solution of tert-butyl (2R,3S,4S)-3-acetoxy-2-(4-(1-cyclopropyl-1H-1,2,3-triazol-4-yl)benzyl)-4-((2-methoxyethoxy)methoxy)pyrrolidine-1-carboxylate (52 mg) in THF (5 mL) and $H_2O$ (1 mL) at 0° C. The resulting mixture was stirred at room temperature for 4 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil (52 mg). MS obsd. ($ESI^+$): 489.3 $[(M+H)]^+$.

Step 4-6: (3S,4S,5R)-5-(4-(1-cyclopropyl-1H-1,2,3-triazol-4-yl)benzyl)-4-(1,1-difluoropropoxy)pyrrolidin-3-ol. The title compound was prepared in 25.1% overall yield as a white solid according to General Procedure I using 93-4 (45 mg) and 1-(3,3-difluoroprop-2-en-1-yl)-1-methylpiperidin-1-ium triflate (60 mg) in DMF in STEP 4, and General Procedure VI using tert-butyl (2R,3S,4S)-2-(4-(1-cyclopropyl-1H-1,2,3-triazol-4-yl)benzyl)-3-((1,1-difluoroallyl)oxy)-4-((2-methoxyethoxy)methoxy)pyrrolidine-1-carboxylate in MeOH in STEP 5, and General Procedure VIII in STEP 6. $^1H$ NMR (400 MHz, MeOD) δ 8.39 (s, 1H), 7.86 (d, J=8.2 Hz, 2H), 7.46 (d, J=8.1 Hz, 2H), 4.76 (s, 1H), 4.51 (d, J=4.3 Hz, 1H), 4.31-4.20 (m, 1H), 4.03-3.95 (m, 1H), 3.62 (dd, J=12.7, 4.4 Hz, 1H), 3.24 (t, J=12.3 Hz, 2H), 3.04 (dd, J=14.6, 9.7 Hz, 1H), 2.21-2.09 (m, 2H), 1.31 (t, J=4.7 Hz, 2H), 1.28-1.21 (m, 2H), 1.15 (t, J=7.5 Hz, 3H). MS obsd. ($ESI^+$): 379.2 $[(M+H)]^+$.

Example 102: (3S,4S,5R)-5-(4-(1H-1,2,3-triazol-4-yl)benzyl)-4-(1,1-difluoropropoxy)pyrrolidin-3-ol Scheme 94

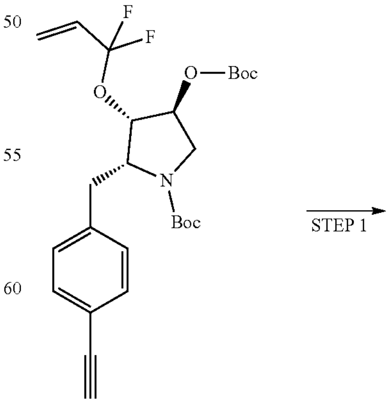

Int-18

-continued

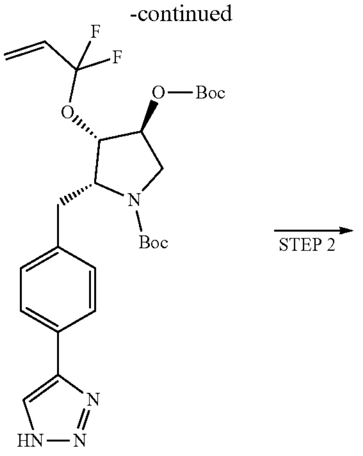

94-2

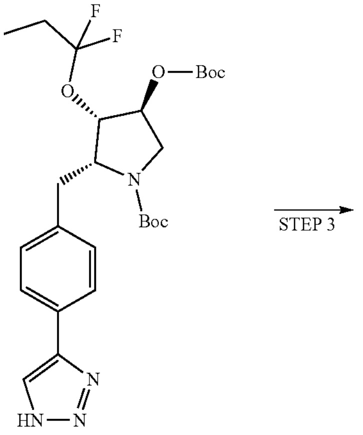

94-3

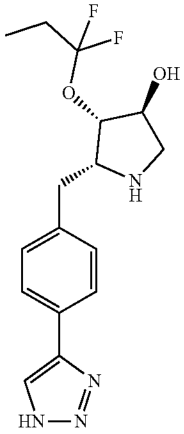

Step 1: tert-butyl (2R,3S,4S)-2-(4-(1H-1,2,3-triazol-4-yl)benzyl)-4-((tert-butoxycarbonyl)oxy)-3-((1,1-difluoroallyl)oxy)pyrrolidine-1-carboxylate (94-2). $CuSO_4 \cdot 5H_2O$ (50 mg) and sodium (2S)-2-[(1S)-1,2-dihydroxyethyl]-4-hydroxy-5-oxooxolan-3-olate (80 mg) were added to a stirred solution of tert-butyl (2R,3S,4S)-4-((tert-butoxycarbonyl)oxy)-3-((1,1-difluoroallyl)oxy)-2-(4-ethynylbenzyl)pyrrolidine-1-carboxylate (100 mg) and azidotrimethylsilane (35 mg) in methanol (5 mL) at 0° C. The resulting mixture was stirred at room temperature for 12 h, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (48 mg). MS obsd. ($ESI^+$): 537.2 $[(M+H)]^+$.

Step 2-3: (3S,4S,5R)-5-(4-(1H-1,2,3-triazol-4-yl)benzyl)-4-(1,1-difluoropropoxy)pyrrolidin-3-ol. The title compound was prepared in 37.6% overall yield as an off-white solid according to General Procedure VI using 94-2 (45 mg) in MeOH in STEP 2, and General Procedure VIII in STEP 3. $^1H$ NMR (400 MHz, MeOD) δ 8.17 (s, 1H), 7.89 (d, J=8.0 Hz, 2H), 7.54-7.43 (m, 2H), 4.80-4.73 (m, 1H), 4.52 (d, J=4.1 Hz, 1H), 4.32-4.22 (m, 1H), 3.62 (dd, J=12.7, 4.3 Hz, 1H), 3.30-3.20 (m, 2H), 3.05 (dd, J=14.6, 9.5 Hz, 1H), 2.23-2.07 (m, 2H), 1.16 (t, J=7.5 Hz, 3H). MS obsd. ($ESI^+$): 339.2 $[(M+H)]^+$.

Example 103: (3S,4S,5R)-5-(4-(benzo[d]isoxazol-5-yl)benzyl)-4-ethoxypyrrolidin-3-ol Scheme 95

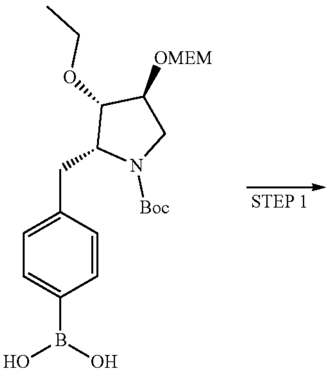

75-3

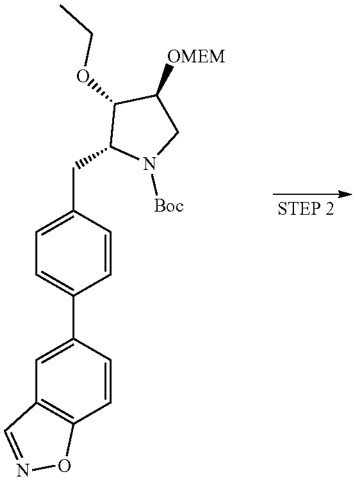

95-2

-continued

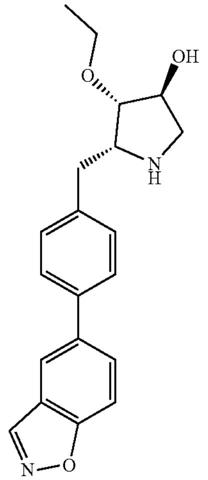

Step 1: tert-butyl (2R,3S,4S)-2-(4-(benzo[d]isoxazol-5-yl)benzyl)-3-ethoxy-4-((2-methoxyethoxy)methoxy)pyrrolidine-1-carboxylate (95-2). Under a nitrogen atmosphere, Pd(dppf)$Cl_2$ (8 mg) and $Na_2CO_3$ (35 mg) were added to a stirred solution of (4-(((2R,3S,4S)-1-(tert-butoxycarbonyl)-3-ethoxy-4-((2-methoxyethoxy)methoxy)pyrrolidin-2-yl) methyl)phenyl) boronic acid (50 mg) and 5-bromo-1,2-benzoxazole (43 mg) in 1,4-dioxane (5 mL) and $H_2O$ (1 mL) at room temperature. The resulting mixture was stirred at 80° C. overnight, then it was diluted with water and extracted with EtOAc. The organic extracts were washed with brine, dried over $Na_2SO_4$, filtered, and concentrated. The residue was purified by reversed-phase flash chromatography to afford the title compound as a yellow solid (35 mg). MS obsd. ($ESI^+$): 527.3 $[(M+H)]^+$.

\Step 2: (3S,4S,5R)-5-(4-(benzo[d]isoxazol-5-yl)benzyl)-4-ethoxypyrrolidin-3-ol. The title compound was prepared in 56.2% yield as a white solid according to General Procedure VIII in DCM. $^1H$ NMR (400 MHz, MeOD) δ 7.64-7.56 (m, 2H), 7.55-7.48 (m, 2H), 7.37-7.31 (m, 2H), 6.85 (d, J=8.6 Hz, 1H), 4.88 (s, 1H), 4.40-4.33 (m, 1H), 3.80-3.67 (m, 2H), 3.58-3.44 (m, 3H), 3.12 (dd, J=13.6, 8.0 Hz, 1H), 3.02-2.90 (m, 2H), 1.33-1.22 (m, 3H). MS obsd. ($ESI^+$): 339.2 $[(M+H)]^+$.

Example 104: (3S,4S,5R)-4-(1,1-difluoropropoxy)-5-(4-(1-(oxetan-3-yl)-1H-1,2,3-triazol-4-yl)benzyl)pyrrolidin-3-ol Scheme 96

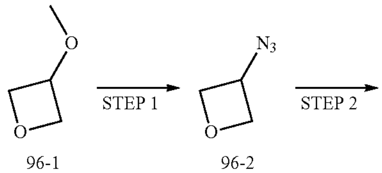

96-1 96-2

-continued

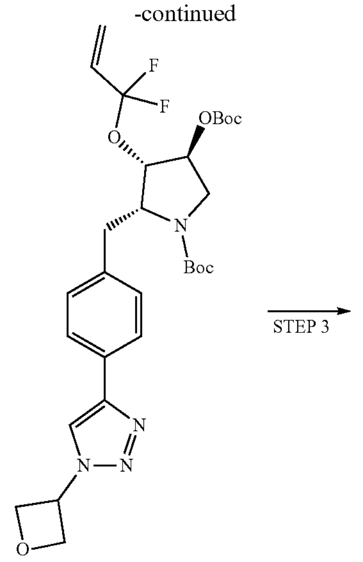

96-3

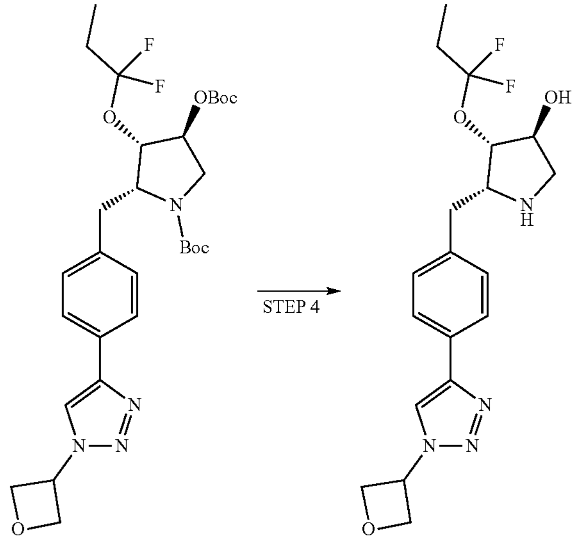

96-4

Step 1: 3-azidooxetane (96-2). NaN3 (769 mg) was added in portions to a stirred solution of oxetan-3-yl methanesulfonate (600 mg) in DMSO (5 mL) at room temperature. The resulting mixture was stirred over night at 100° C. under a nitrogen atmosphere, then it was diluted with water and extracted with EtOAc. The organic extracts were washed with brine, dried over $Na_2SO_4$, filtered, and concentrated. The crude product was used in the next step directly without further purification.

Step 2: tert-butyl (2R,3S,4S)-4-((tert-butoxycarbonyl)oxy)-3-((1,1-difluoroallyl)oxy)-2-(4-(1-(oxetan-3-yl)-1H-1,2,3-triazol-4-yl)benzyl)pyrrolidine-1-carboxylate (96-3). $CuSO_4 \cdot 5H_2O$ (91 mg) and sodium (2S)-2-[(1S)-1,2-dihydroxyethyl]-4-hydroxy-5-oxooxolan-3-olate (72 mg) were added to a stirred solution of tert-butyl (2R,3S,4S)-4-[(tert-butoxycarbonyl)oxy]-3-[(1,1-difluoroprop-2-en-1-yl)oxy]-2-[(4-ethynylphenyl)methyl]pyrrolidine-1-carboxylate (60 mg) and 3-azidooxetane (24 mg) in methanol (5 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (40 mg). MS obsd. ($ESI^+$): 593.3 $[(M+H)]^+$.

Step 3-4: (3S,4S,5R)-4-(1,1-difluoropropoxy)-5-(4-(1-(oxetan-3-yl)-1H-1,2,3-triazol-4-yl)benzyl)pyrrolidin-3-ol. The title compound was prepared in 67.6% overall yield as a white solid according to General Procedure VI using 96-3 (40 mg) in MeOH in STEP 3, and General Procedure VIII in STEP 4. $^1H$ NMR (400 MHz, MeOD) δ 8.61 (s, 1H), 7.91 (d, J=8.0 Hz, 2H), 7.48 (d, J=7.8 Hz, 2H), 5.96-5.85 (m, 1H), 5.24-5.03 (m, 4H), 4.79-4.73 (m, 1H), 4.52 (d, J=4.2 Hz, 1H), 4.32-4.23 (m, 1H), 3.63 (dd, J=12.7, 4.3 Hz, 1H), 3.25 (dd, J=17.5, 13.4 Hz, 2H), 3.06 (dd, J=14.6, 9.5 Hz, 1H), 2.23-2.03 (m, 2H), 1.20-1.01 (m, 3H); MS obsd. ($ESI^+$): 395.2 $[(M+H)]^+$.

Example 105: (3S,4S,5R)-4-(1,1-difluoropropoxy)-5-(4-(1-isopropyl-1H-pyrazol-4-yl)benzyl)pyrrolidin-3-ol Scheme 97

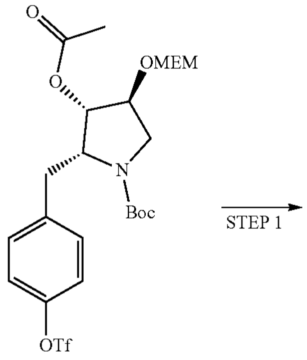

3-1

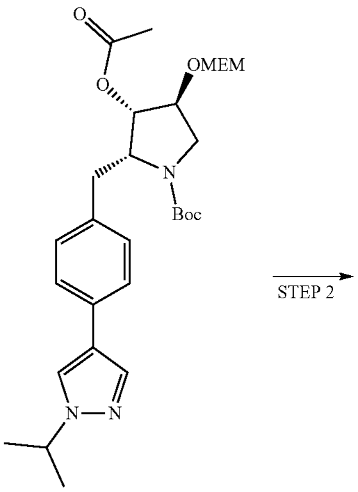

97-2

-continued

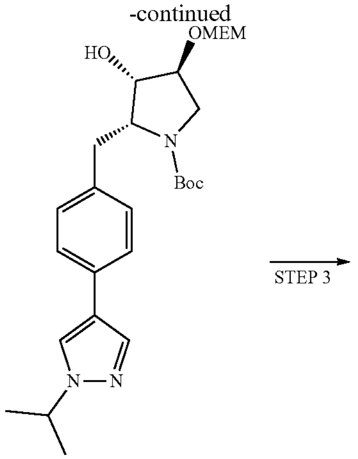

97-3

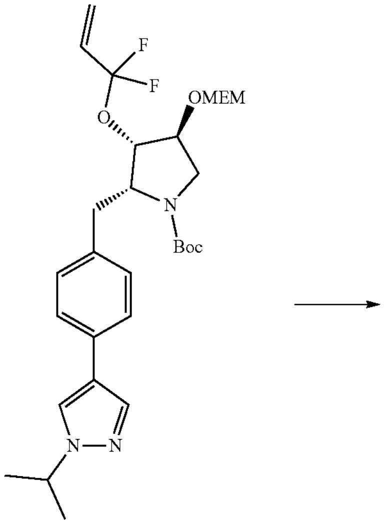

97-4

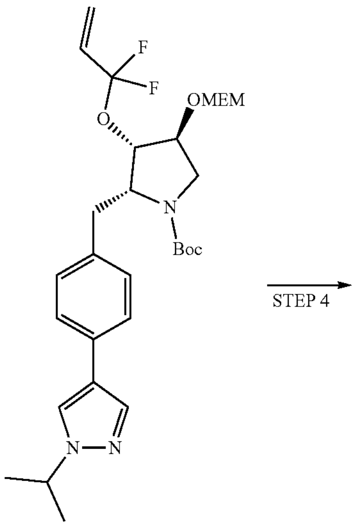

97-4

-continued

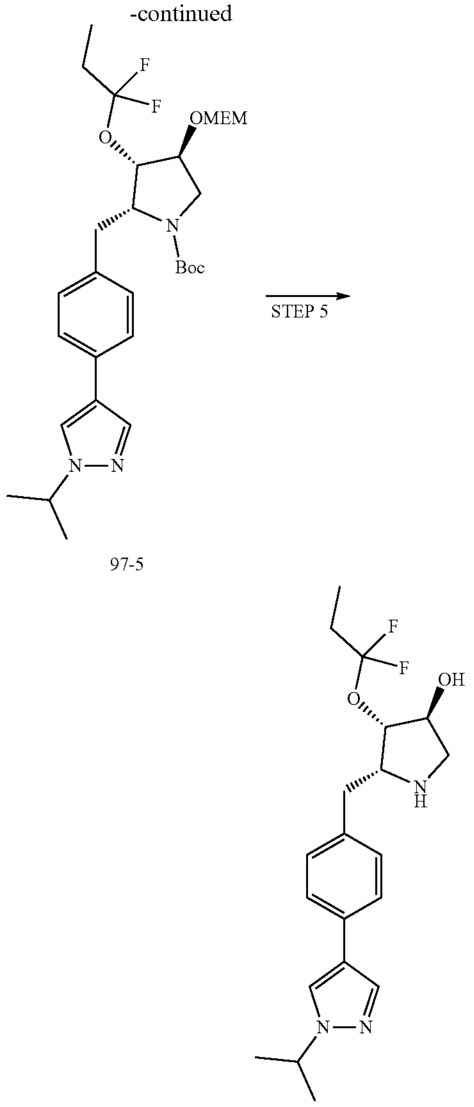

97-5

Step 1: tert-butyl (2R,3S,4S)-3-acetoxy-2-(4-(1-isopropyl-1H-pyrazol-4-yl)benzyl)-4-((2-methoxyethoxy)methoxy)pyrrolidine-1-carboxylate (97-2). Under a nitrogen atmosphere, XPhos (16 mg), XPhos Pd $G_3$ (59 mg) and $NaHCO_3$ (88 mg) was added to a stirred solution of tert-butyl (2R,3S,4S)-3-acetoxy-4-((2-methoxyethoxy)methoxy)-2-(4-(((trifluoromethyl) sulfonyl)oxy)benzyl)pyrrolidine-1-carboxylate (200 mg) and (1-isopropyl-1H-pyrazol-4-yl) boronic acid (64 mg) in 1,4-dixoane (5 mL) and $H_2O$ (1 mL) at room temperature. The resulting mixture was stirred at 80° C. overnight, then it was diluted with water and extracted with EtOAc. The organic extracts were washed with brine, dried over $Na_2SO_4$, filtered and concentrated. The residue was purified by reversed-phase flash chromatography to afford the title compound as a light-yellow oil (150 mg). MS obsd. ($ESI^+$): 532.3 $[(M+H)]^+$.

Step 2: tert-butyl (2R,3S,4S)-3-hydroxy-2-(4-(1-isopropyl-1H-pyrazol-4-yl)benzyl)-4-((2-methoxyethoxy)methoxy)pyrrolidine-1-carboxylate (97-3). LiOH (20 mg) was added to a stirred solution of tert-butyl (2R,3S,4S)-3-acetoxy-2-(4-(1-isopropyl-1H-pyrazol-4-yl)benzyl)-4-((2-methoxyethoxy)methoxy)pyrrolidine-1-carboxylate (150 mg) in THF (10 mL) and $H_2O$ (3 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a light-yellow oil (100 mg). MS obsd. ($ESI^+$): 490.3 $[(M+H)]^+$.

Step 3-5: (3S,4S,5R)-4-(1,1-difluoropropoxy)-5-(4-(1-isopropyl-1H-pyrazol-4-yl)benzyl)pyrrolidin-3-ol. The title compound was prepared in 38.9% overall yield as a white solid according to General Procedure I using 97-3 (60 mg) and 1-(3,3-difluoroprop-2-en-1-yl)-1-methylpiperidin-1-ium triflate (79 mg) in DMF in STEP 3, and General Procedure VI using tert-butyl (2R,3S,4S)-3-((1,1-difluoroallyl)oxy)-2-(4-(1-isopropyl-1H-pyrazol-4-yl)benzyl)-4-((2-methoxyethoxy)methoxy)pyrrolidine-1-carboxylate in MeOH in STEP 4, and General Procedure VIII in STEP 5. $^1H$ NMR (400 MHz, MeOD) δ 8.06 (d, J=0.8 Hz, 1H), 7.84 (d, J=0.8 Hz, 1H), 7.64-7.56 (m, 2H), 7.40-7.33 (m, 2H), 4.77-4.71 (m, 1H), 4.64-4.53 (m, 1H), 4.53-4.48 (m, 1H), 4.28-4.19 (m, 1H), 3.62 (dd, J=12.7, 4.3 Hz, 1H), 3.26-3.16 (m, 2H), 3.01 (dd, J=14.6, 9.4 Hz, 1H), 2.23-2.07 (m, 2H), 1.54 (d, J=6.7 Hz, 6H), 1.19-1.11 (m, 3H). MS obsd. ($ESI^+$): 380.2 $[(M+H)]^+$.

Example 106: (3S,4S,5R)-4-(3,3-difluoropropoxy)-5-(2-fluoro-4-(thiazol-5-yl)benzyl)pyrrolidin-3-ol Scheme 98

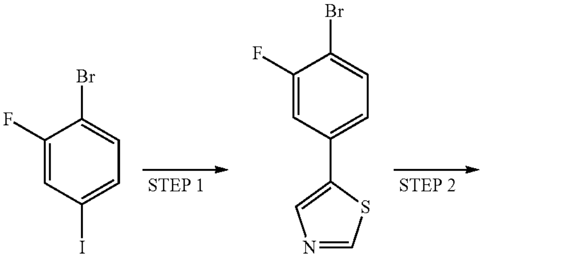

98-1 98-2

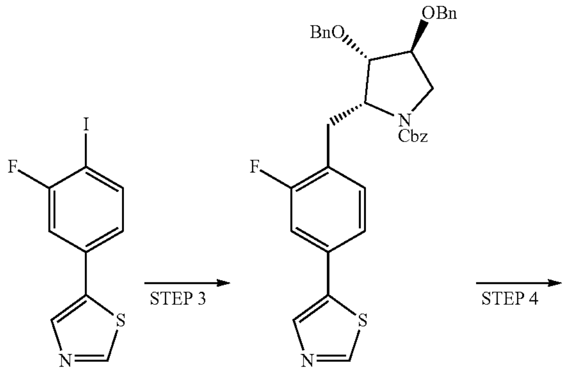

98-3 98-4

-continued

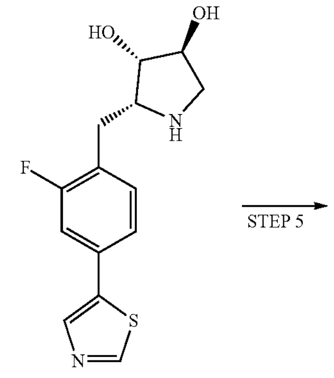

98-5

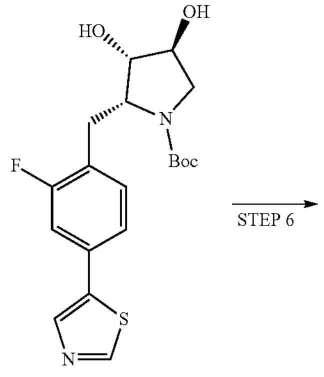

98-6

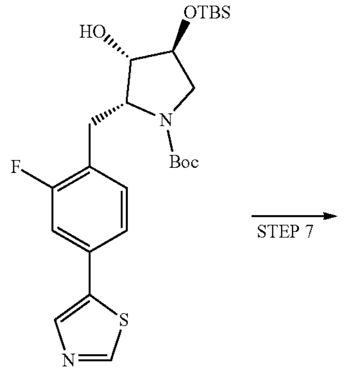

98-7

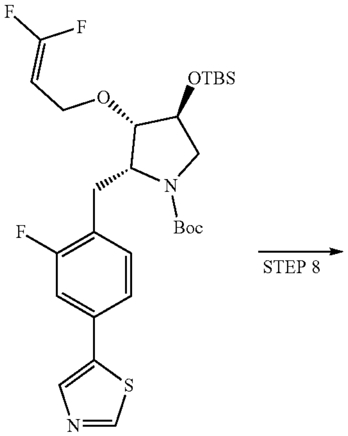

98-8

-continued

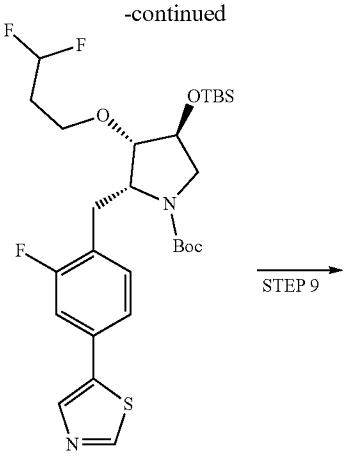

98-9

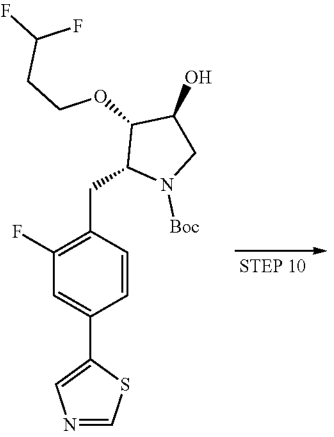

98-9

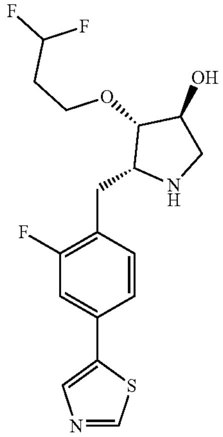 [SMILES: O[C@H]1CN[C@H](Cc2ccc(-c3cncs3)cc2F)[C@@H]1OCCC(F)F]

Step 1: 5-(4-bromo-3-fluorophenyl)thiazole (98-2). Under a nitrogen atmosphere, $Pd(PPh_3)_4$ (7.2 g) and $K_3PO_4$ (19.7 g) were added to a stirred solution of 1,3-thiazol-5-ylboronic acid (4 g) and 1-bromo-2-fluoro-4-iodobenzene (10.2 g) in DMF (40 mL) at room temperature. The resulting mixture was stirred at 80° C. overnight, then diluted with water and extracted with EtOAc. The organic extracts were washed with brine, dried over $Na_2SO_4$, filtered, and concentrated. The residue was purified by silica gel column chromatography to afford the title compound as a yellow solid (3.8 g). MS obsd. ($ESI^+$): 257.9 $[(M+H)]^+$.

Step 2: 5-(3-fluoro-4-iodophenyl)thiazole (98-3). 1,2-Bis (methylamino) ethane (0.3 g) was added to a stirred solution of 5-(4-bromo-3-fluorophenyl)thiazole (3.8 g). NaI (4.4 g) and CuI (0.3 g) in 1,4-dioxane (15 mL) at room temperature. The resulting mixture was stirred at 80° C. for 3 h, then diluted with water and extracted with EA. The organic extracts were washed with brine, dried over $Na_2SO_4$, filtered, and concentrated. The residue was purified by silica gel column chromatography to afford the title compound as a yellow solid (3.8 g). MS obsd. ($ESI^+$): 305.9 $[(M+H)]^+$.

Step 3: benzyl (2R,3S,4S)-3,4-bis(benzyloxy)-2-(2-fluoro-4-(thiazol-5-yl)benzyl)pyrrolidine-1-carboxylate (98-4). Under a nitrogen atmosphere, Iodine (50 mg) was added to a stirred solution of benzyl (2S,3S,4S)-3,4-bis(benzyloxy)-2-(iodomethyl)pyrrolidine-1-carboxylate (2 g) and Zinc (2.3 g) in DMF (20 mL) at room temperature. The resulting mixture was stirred at room temperature for 1 h. then the supernatant was added to a stirred solution of 5-(3-fluoro-4-iodophenyl)thiazole (2.2 g), $Pd_2(dba)_3$ (0.6 g) and Q-Phos (0.5 g) in THF (20 mL) at room temperature. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (600 mg). MS obsd. ($ESI^+$): 609.2 $[(M+H)]^+$.

Step 4: (2R,3S,4S)-2-(2-fluoro-4-(thiazol-5-yl)benzyl)pyrrolidine-3,4-diol (98-5). Boron trichloride (1154 mg) was added to a stirred solution of benzyl (2R,3S,4S)-3,4-bis(benzyloxy)-2-(2-fluoro-4-(thiazol-5-yl)benzyl)pyrrolidine-1-carboxylate (600 mg) in DCM (20 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (300 mg). MS obsd. ($ESI^+$): 295.1 $[(M+H)]^+$.

Step 5: tert-butyl (2R,3S,4S)-2-(2-fluoro-4-(thiazol-5-yl)benzyl)-3,4-dihydroxypyrrolidine-1-carboxylate (98-6). $Boc_2O$ (444 mg) was added to a stirred solution of (2R,3S,4S)-2-(2-fluoro-4-(thiazol-5-yl)benzyl)pyrrolidine-3,4-diol (300 mg) and $Et_3N$ (309 mg) in DCM (10 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (200 mg). MS obsd. ($ESI^+$): 395.1 $[(M+H)]^+$.

Step 6: tert-butyl (2R,3S,4S)-4-((tert-butyldimethylsilyl)oxy)-2-(2-fluoro-4-(thiazol-5-yl)benzyl)-3-hydroxypyrrolidine-1-carboxylate (98-7). Tert-butyl(chloro)dimethylsilane (114 mg) was added to a stirred solution of tert-butyl (2R,3S,4S)-2-(2-fluoro-4-(thiazol-5-yl)benzyl)-3,4-dihydroxypyrrolidine-1-carboxylate (200 mg) and Imidazole (103 mg) in DCM (10 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a white solid (120 mg). MS obsd. ($ESI^+$): 509.2 $[(M+H)]^+$.

Step 7: tert-butyl (2R,3S,4S)-4-((tert-butyldimethylsilyl)oxy)-3-((3,3-difluoroallyl)oxy)-2-(2-fluoro-4-(thiazol-5-yl)benzyl)pyrrolidine-1-carboxylate (98-8). $Cs_2CO_3$ (230 mg) and $Ag_2O$ (163 mg) were added to a stirred solution of 3-bromo-3,3-difluoroprop-1-ene (74 mg) and tert-butyl (2R,3S,4S)-4-((tert-butyldimethylsilyl)oxy)-2-(2-fluoro-4-(thiazol-5-yl)benzyl)-3-hydroxypyrrolidine-1-carboxylate (120 mg) in DMF (10 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a white solid (50 mg). MS obsd. ($ESI^+$): 585.2 $[(M+H)]^+$.

Step 8: tert-butyl (2R,3S,4S)-4-((tert-butyldimethylsilyl)oxy)-3-(3,3-difluoropropoxy)-2-(2-fluoro-4-(thiazol-5-yl)benzyl)pyrrolidine-1-carboxylate (98-9). The title compound was prepared in 73.6% yield as a yellow oil according to General Procedure VI using 98-8 (30 mg) in MeOH. MS obsd. ($ESI^+$): 587.3 $[(M+H)]^+$.

Step 9: tert-butyl (2R,3S,4S)-3-(3,3-difluoropropoxy)-2-(2-fluoro-4-(thiazol-5-yl)benzyl)-4-hydroxypyrrolidine-1-carboxylate (98-10). Pyridine hydrofluoride (3 mL) was added to a stirred solution of tert-butyl (2R,3S,4S)-4-((tert-butyldimethylsilyl)oxy)-3-(3,3-difluoropropoxy)-2-(2-fluoro-4-(thiazol-5-yl)benzyl)pyrrolidine-1-carboxylate (25 mg) in THF (3 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow oil (15 mg). MS obsd. ($ESI^+$): 473.2 $[(M+H)]^+$.

Step 10: (3S,4S,5R)-4-(3,3-difluoropropoxy)-5-(2-fluoro-4-(thiazol-5-yl)benzyl)pyrrolidin-3-ol The title compound was prepared in 42.1% yield as a white solid according to General Procedure VIII using 98-10 (15 mg) in DCM. $^1H$ NMR (400 MHz, MeOD) δ 8.99 (d, J=0.7 Hz, 1H), 8.21 (d, J=0.7 Hz, 1H), 7.48-7.37 (m, 3H), 6.26-5.90 (m, 1H), 4.28-4.21 (m, 1H), 3.82-3.73 (m, 1H), 3.56-3.47 (m, 2H), 3.50 (d, J=1.6 Hz, 2H), 3.04 (dd, J=13.6, 8.1 Hz, 1H), 2.93 (dd, J=13.8, 6.7 Hz, 1H), 2.69 (dd, J=12.3, 2.6 Hz, 1H), 2.15 (d, J=9.7 Hz, 2H). MS obsd. ($ESI^+$): 373.1 $[(M+H)]^+$.

Example 107: (3S,4S,5R)-4-(1,1-difluoropropoxy)-5-(2-fluoro-4-(thiazol-5-yl)benzyl)pyrrolidin-3-ol Scheme 99

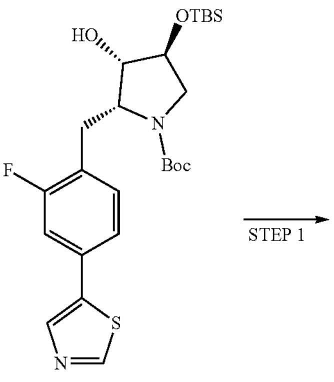

98-7

-continued

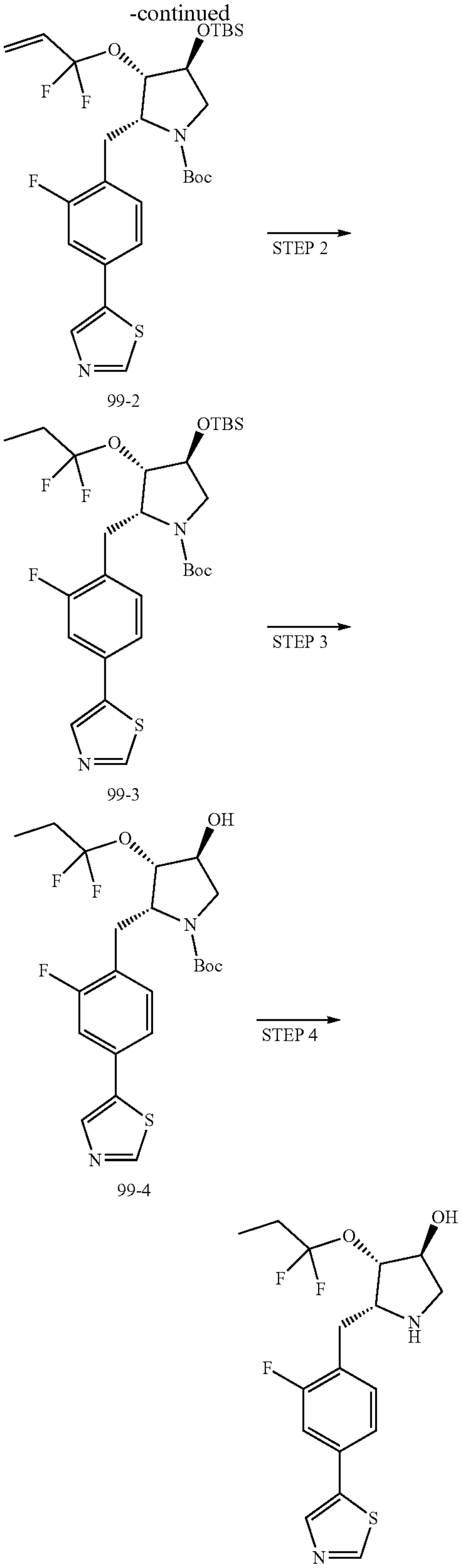

99-2

99-3

99-4

Step 1: tert-butyl (2R,3S,4S)-4-((tert-butyldimethylsilyl)oxy)-3-((1,1-difluoroallyl)oxy)-2-(2-fluoro-4-(thiazol-5-yl)benzyl)pyrrolidine-1-carboxylate (99-2). Under a nitrogen atmosphere, $Cs_2CO_3$ (230 mg) and $Ag_2O$ (163 mg) were added to a stirred solution of 3-bromo-3,3-difluoroprop-1-ene (74 mg) and tert-butyl (2R,3S,4S)-4-((tert-butyldimethylsilyl)oxy)-2-(2-fluoro-4-(thiazol-5-yl)benzyl)-3-hydroxypyrrolidine-1-carboxylate (120 mg) in DMF (10 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a yellow solid (30 mg). MS obsd. ($ESI^+$): 585.2 $[(M+H)]^+$.

Step 2: tert-butyl (2R,3S,4S)-4-((tert-butyldimethylsilyl)oxy)-3-(1,1-difluoropropoxy)-2-(2-fluoro-4-(thiazol-5-yl)benzyl)pyrrolidine-1-carboxylate (99-3). The title compound was prepared in 75.3% yield as a yellow oil according to General Procedure VI using 99-2 (20 mg) in MeOH. MS obsd. ($ESI^+$): 587.3 $[(M+H)]^+$.

Step 3: tert-butyl (2R,3S,4S)-3-(1,1-difluoropropoxy)-2-(2-fluoro-4-(thiazol-5-yl)benzyl)-4-hydroxypyrrolidine-1-carboxylate (99-4). Pyridine hydrofluoride (3 mL) was added to a stirred solution of tert-butyl (2R,3S,4S)-4-((tert-butyldimethylsilyl)oxy)-3-(1,1-difluoropropoxy)-2-(2-fluoro-4-(thiazol-5-yl)benzyl)pyrrolidine-1-carboxylate (20 mg) in THF (3 mL) at 0° C. The resulting mixture was stirred at room temperature overnight, then diluted with water and extracted with EtOAc. The organic extracts were washed with brine, dried over $Na_2SO_4$, filtered, and concentrated. The residue was purified by reversed-phase flash chromatography to afford the title compound as a white solid (10 mg). MS obsd. ($ESI^+$): 473.2 $[(M+H)]^+$.

Step 4: (3S,4S,5R)-4-(1,1-difluoropropoxy)-5-(2-fluoro-4-(thiazol-5-yl)benzyl)pyrrolidin-3-ol The title compound was prepared in 11.1% yield as a white solid according to General Procedure VIII using 99-4 (10 mg) in DCM. $^1H$ NMR (400 MHz, MeOD) δ 8.99 (s, 1H), 8.21 (s, 1H), 7.47-7.38 (m, 3H), 4.41 (d, J=3.6 Hz, 1H), 4.31 (d, J=5.4 Hz, 1H), 3.70-3.57 (m, 2H), 3.02 (dd, J=14.2, 6.1 Hz, 1H), 2.86 (dd, J=14.2, 8.2 Hz, 1H), 2.75-2.65 (m, 1H), 2.14-1.99 (m, 2H), 1.15-1.07 (m, 3H). MS obsd. ($ESI^+$): 373.1 $[(M+H)]^+$.

Example 108: (3S,4S,5R)-4-ethoxy-5-((5-(1-methyl-1H-indazol-5-yl)pyridin-2-yl)methyl)pyrrolidin-3-ol Scheme 100

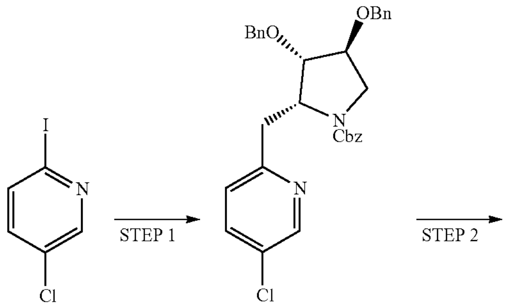

100-1

100-2

-continued

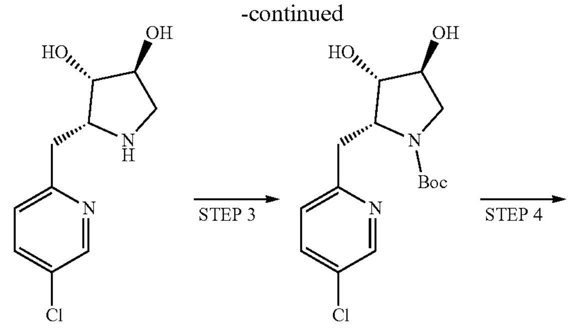

100-3 100-4

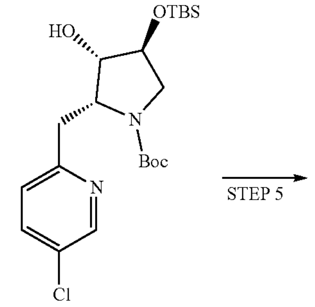

100-5

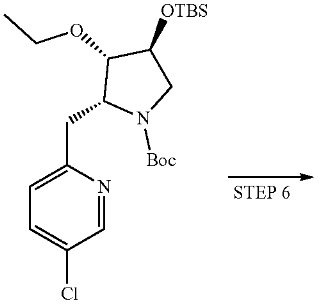

100-6

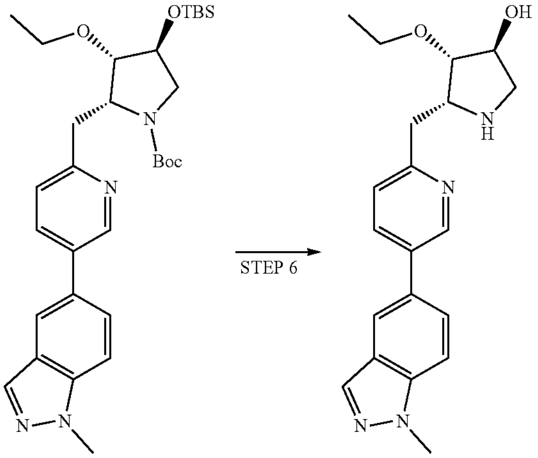

100-7

Step 1: benzyl (2R,3S,4S)-3,4-bis(benzyloxy)-2-((5-chloropyridin-2-yl)methyl)pyrrolidine-1-carboxylate (100-2). N4,N4,N4',N4'-tetramethyl-[2,2'-bipyridine]-4,4'-diamine (174 mg), 4-methylpyridine (1336 mg), Dibromo (glyme) nickel (442 mg), LiI (960 mg), Zinc (1876 mg) and TFA (82 mg) was added to a stirred solution of benzyl (2S,3S,4S)-3,4-bis(benzyloxy)-2-(iodomethyl)pyrrolidine-1-carboxylate (4000 mg) and 5-chloro-2-iodopyridine (3436 mg) in MeCN (60 mL). The resulting mixture was subsequently degassed by bubbling nitrogen through the solution for 5 minutes and then stirred at 60° C. overnight. The reaction mixture was diluted with water and extracted with EtOAc. The organic extracts were washed with brine, dried over $Na_2SO_4$, filtered, and concentrated. The residue was purified by reversed-phase flash chromatography to afford the title compound as a yellow solid (1300 mg). MS obsd. ($ESI^+$): 543.2 $[(M+H)]^+$.

Step 2: (2R,3S,4S)-2-((5-chloropyridin-2-yl)methyl)pyrrolidine-3,4-diol (100-3). Boron trichloride (24 mL) was slowly added to a stirred solution of benzyl (2R,3S,4S)-3,4-bis(benzyloxy)-2-[(5-chloropyridin-2-yl)methyl]pyrrolidine-1-carboxylate (1300 mg) in DCM (20 mL) at 0° C. and the mixture was stirred at room temperature overnight. The reaction was quenched with MeOH (30 mL) at 0° C. and concentrated to obtain the title compound as a black solid. MS obsd. ($ESI^+$): 229.1 $[(M+H)]^+$.

Step 3: tert-butyl (2R,3S,4S)-2-((5-chloropyridin-2-yl)methyl)-3,4-dihydroxypyrrolidine-1-carboxylate (100-4). $(Boc)_2O$ (1145 mg) and $NaHCO_3$ (881 mg) were added to a stirred solution of (2R,3S,4S)-2-[(5-chloropyridin-2-yl)methyl]pyrrolidine-3,4-diol (600 mg) in 1,4-dioxane (10 mL) and $H_2O$ (10 mL) at 0° C. The mixture was stirred at room temperature for 2 h, then it was diluted with water and extracted with EtOAc. The organic extracts were washed with brine, dried over $Na_2SO_4$, filtered, and concentrated. The residue was purified by reversed-phase flash chromatography to afford the title compound as a yellow oil (400 mg). MS obsd. ($ESI^+$): 329.1 $[(M+H)]^+$.

Step 4: tert-butyl (2R,3S,4S)-4-((tert-butyldimethylsilyl)oxy)-2-((5-chloropyridin-2-yl)methyl)-3-hydroxypyrrolidine-1-carboxylate (100-5). Imidazole (331 mg) and tert-butyl(chloro)dimethylsilane (366 mg) were added to a stirred solution of tert-butyl (2R,3S,4S)-2-[(5-chloropyridin-2-yl)methyl]-3,4-dihydroxypyrrolidine-1-carboxylate (400 mg) in DCM (10 mL) at room temperature. The resulting mixture was stirred at overnight, then it was diluted with water and extracted with EtOAc. The organic extracts were washed with brine, dried over $Na_2SO_4$, filtered, and concentrated. The residue was purified by reversed-phase flash chromatography to afford the title compound as a yellow solid (300 mg). MS obsd. ($ESI^+$): 443.2 $[(M+H)]^+$.

Step 5: tert-butyl (2R,3S,4S)-4-((tert-butyldimethylsilyl)oxy)-2-((5-chloropyridin-2-yl)methyl)-3-ethoxypyrrolidine-1-carboxylate (100-6). The title compound was prepared in 70.5% yield as a yellow solid according to General Procedure II using 100-5 (300 mg) in DMF. MS obsd. ($ESI^+$): 471.2 $[(M+H)]^+$.

Step 6: tert-butyl (2R,3S,4S)-4-((tert-butyldimethylsilyl)oxy)-3-ethoxy-2-((5-(1-methyl-1H-indazol-5-yl)pyridin-2-yl)methyl)pyrrolidine-1-carboxylate (100-7). Under a nitrogen atmosphere. XPhos Pd $G_3$ (14 mg) and XPhos (8 mg) were added to a stirred solution of 1-methyl-5-(4,4,5,5-tetramethyl-1,3,2-dioxaborolan-2-yl)-1H-indazole (66 mg), tert-butyl (2R,3S,4S)-4-((tert-butyldimethylsilyl)oxy)-2-((5-chloropyridin-2-yl)methyl)-3-ethoxypyrrolidine-1-carboxylate (80 mg), and $NaHCO_3$ (43 mg) in DMF (5 mL) at room temperature. The resulting mixture was stirred at 80° C. overnight, then it was diluted with water and extracted with EtOAc. The organic extracts were washed with brine, dried over $Na_2SO_4$, filtered, and concentrated. The residue was purified by silica gel column chromatography to afford the title compound as a light-yellow oil (80 mg). MS obsd. ($ESI^+$): 567.3 $[(M+H)]^+$.

Step 7: (3S,4S,5R)-4-ethoxy-5-((5-(1-methyl-1H-indazol-5-yl)pyridin-2-yl)methyl)pyrrolidin-3-ol. 4N HCl-1,4- dioxane (4 mL) was added to a stirred solution of tert-butyl (2R,3S,4S)-4-((tert-butyldimethylsilyl)oxy)-3-ethoxy-2-((5-(1-methyl-1H-indazol-5-yl)pyridin-2-yl)methyl)pyrrolidine-1-carboxylate (105 mg) in 1,4-dioxane (2 mL) at 0° C. The resulting mixture was stirred at room temperature for 2 h. then concentrated, and the resulting residue was purified by Prep-HPLC to afford the title compound as a white solid. $^1$H NMR (400 MHz, MeOD) δ 8.78 (d, J=2.4 Hz, 1H), 8.10-7.99 (m, 3H), 7.77-7.62 (m, 2H), 7.44 (d, J=8.1 Hz, 1H), 4.30-4.22 (m, 1H), 4.10 (s, 3H), 3.72-3.63 (m, 1H), 3.73-3.65 (m, 1H), 3.55 (d, J=3.9 Hz, 1H), 3.47-3.36 (m, 2H), 3.26-3.02 (m, 2H), 2.75 (dd, J=12.2, 2.4 Hz, 1H), 1.21 (t, J=7.0 Hz, 3H). MS obsd. (ESI$^+$): 353.2 [(M+H)]$^+$.

Example 109: (3S,4S,5R)-5-(4-(1-methyl-1H-indazol-5-yl)benzyl)-4-(pyridin-2-ylmethoxy)pyrrolidin-3-ol Scheme 101

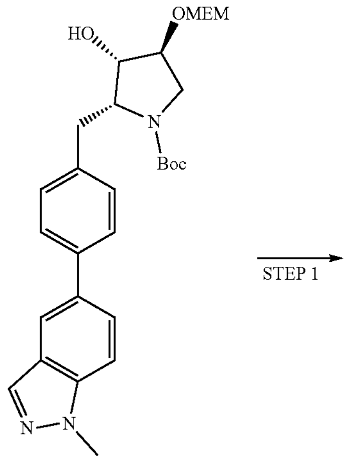

74-3

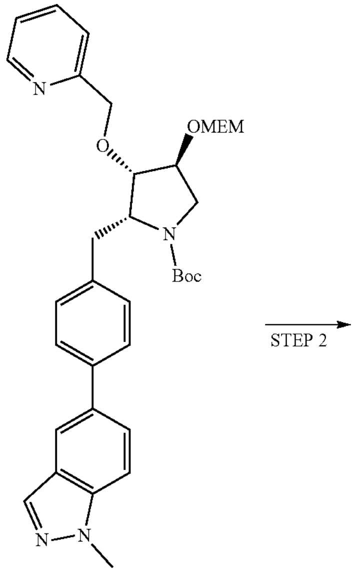

101-2

-continued

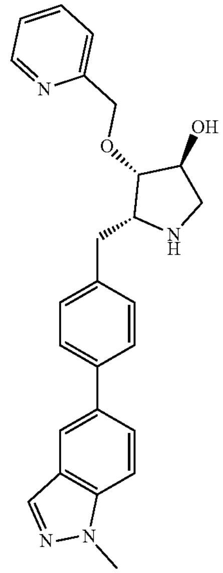

Step 1-2: (3S,4S,5R)-5-(4-(1-methyl-1H-indazol-5-yl)benzyl)-4-(pyridin-2-ylmethoxy)pyrrolidin-3-ol. The title compound was prepared in 40.2% overall yield as a white solid according to General Procedure I using 74-3 (70 mg) and 2-(bromomethyl)pyridine (72 mg) in DMF in STEP 1, and General Procedure VIII in STEP 2. $^1$H NMR (400 MHz, MeOD) δ 8.56-8.50 (m, 1H), 8.06 (d, J=0.9 Hz, 1H), 7.96 (dd, J=1.7, 0.8 Hz, 1H), 7.90 (m, J=7.7, 1.8 Hz, 1H), 7.72 (dd, J=8.8, 1.7 Hz, 1H), 7.63 (t, J=8.2 Hz, 2H), 7.60-7.56 (m, 2H), 7.38 (m, J=7.7, 4.9, 1.2 Hz, 1H), 7.35-7.31 (m, 2H), 4.79 (d, J=12.9 Hz, 1H), 4.58 (d, J=13.0 Hz, 1H), 4.38 (dd, J=6.3, 2.6 Hz, 1H), 4.11 (s, 3H), 3.63 (d, J=3.7 Hz, 1H), 3.54 (m, J=8.9, 6.7, 3.5 Hz, 1H), 3.48 (dd, J=12.3, 5.9 Hz, 1H), 3.09 (dd, J=13.4, 8.7 Hz, 1H), 2.98 (dd, J=13.4, 6.4 Hz, 1H), 2.75 (dd, J=12.3, 2.6 Hz, 1H). MS obsd. (ESI$^+$): 415.2 [(M+H)]$^+$.

Example 110: (3S,4S,5R)-5-(4-(1-methyl-1H-indazol-5-yl)benzyl)-4-((1-methyl-1H-pyrazol-3-yl)methoxy)pyrrolidin-3-ol Scheme 102

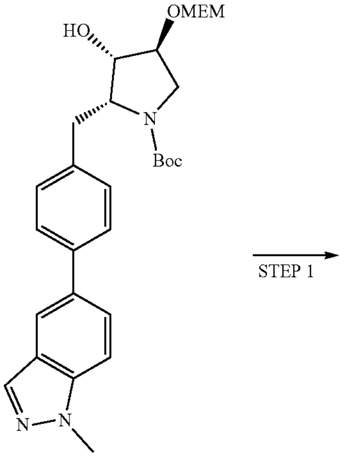

74-3

-continued

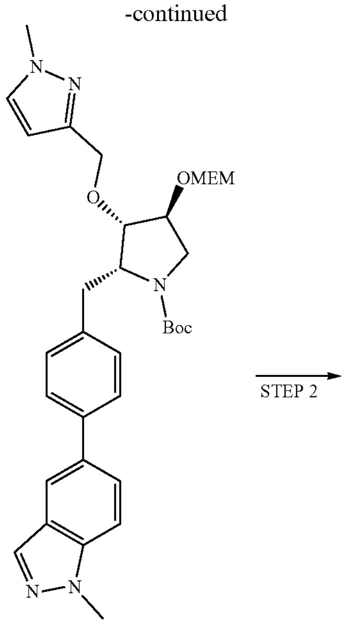

102-2

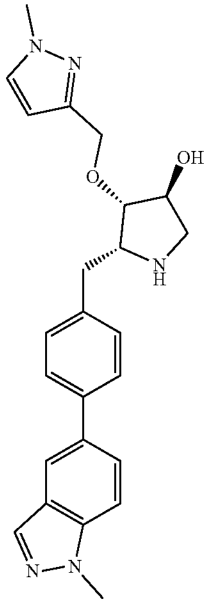

Step 1-2: (3S,4S,5R)-5-(4-(1-methyl-1H-indazol-5-yl) benzyl)-4-((1-methyl-1H-pyrazol-3-yl)methoxy)pyrrolidin-3-ol. The title compound was prepared in 45.2% overall yield as a white solid according to General Procedure I using 74-2 (100 mg) and 3-(bromomethyl)-1-methylpyrazole (137 mg) in DMF in STEP 1, and General Procedure VIII in STEP 2. $^{1}$H NMR (400 MHz, MeOD) δ 8.06 (d, J=1.0 Hz, 1H), 7.96 (d, J=1.7 Hz, 1H), 7.72 (dd, J=8.8, 1.7 Hz, 1H), 7.65-7.56 (m, 2H), 7.60-7.54 (m, 2H), 7.30 (d, J=8.1 Hz, 2H), 6.35 (d, J=2.2 Hz, 1H), 4.63 (d, J=11.8 Hz, 1H), 4.46 (d, J=11.8 Hz, 1H), 4.34 (dd, J=5.9, 2.3 Hz, 1H), 4.10 (d, J=1.4 Hz, 3H), 3.89 (s, 3H), 3.58 (d, J=3.6 Hz, 1H), 3.50-3.39 (m, 2H), 2.99 (dd, J=13.3, 8.7 Hz, 1H), 2.88 (dd, J=13.3, 6.3 Hz, 1H), 2.72 (dd, J=12.3, 2.4 Hz, 1H). MS obsd. (ESI$^{+}$): 418.2 $[(M+H)]^{+}$.

Example 111: (3S,4S,5R)-5-(4-(1-methyl-1H-indazol-5-yl)benzyl)-4-((1-methyl-1H-pyrazol-4-yl) methoxy)pyrrolidin-3-ol Scheme 103

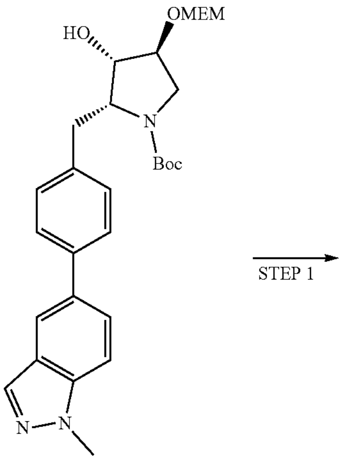

74-3

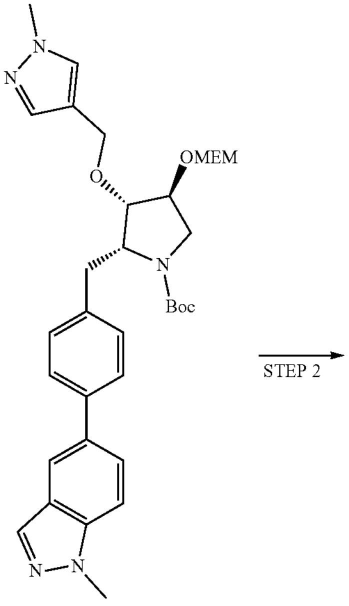

103-2

-continued

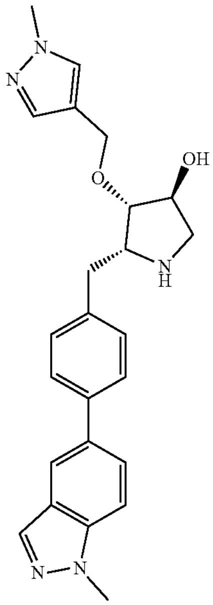

Step 1-2: (3S,4S,5R)-5-(4-(1-methyl-1H-indazol-5-yl)benzyl)-4-((1-methyl-1H-pyrazol-4-yl)methoxy)pyrrolidin-3-ol. The title compound was prepared in 45.5% overall yield as a white solid according to General Procedure I using 74-3 (70 mg) and 4-(chloromethyl)-1-methyl-1H-pyrazole (69 mg) in DMF in STEP 1, and General Procedure VIII in STEP 2. $^1$H NMR (400 MHz, MeOD) δ 8.06 (s, 1H), 8.00-7.95 (m, 1H), 7.73 (m, J=8.8, 1.4 Hz, 1H), 7.66-7.57 (m, 4H), 7.52 (s, 1H), 7.31 (d, J=8.0 Hz, 2H), 4.61 (d, J=11.8 Hz, 1H), 4.44-4.34 (m, 2H), 4.10 (d, J=1.0 Hz, 3H), 3.86 (s, 3H), 3.60 (s, 2H), 3.46 (dd, J=12.3, 5.5 Hz, 1H), 3.02 (dd, J=13.5, 8.2 Hz, 1H), 2.92 (dd, J=13.4, 5.7 Hz, 1H), 2.82 (dd, J=12.3, 2.1 Hz, 1H). MS obsd (ESI$^+$): 418.2 $[M+H]^+$.

Example 112: (3S,4S,5R)-4-(benzyloxy)-5-(4-(1-methyl-1H-indazol-5-yl)benzyl)pyrrolidin-3-ol Scheme 104

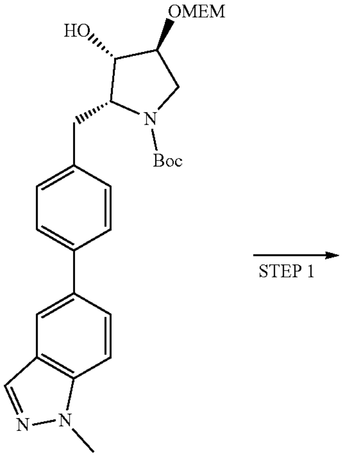

74-3

-continued

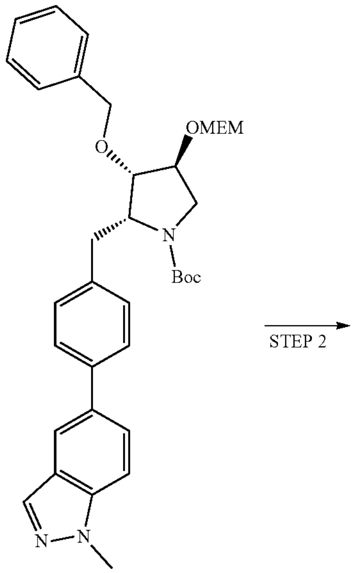

104-2

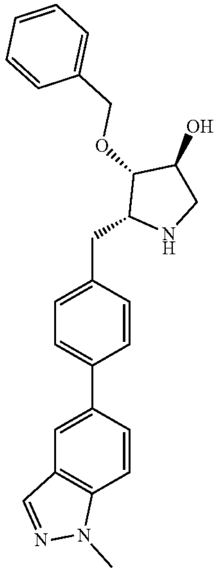

Step 1-2: (3S,4S,5R)-4-(benzyloxy)-5-(4-(1-methyl-1H-indazol-5-yl)benzyl)pyrrolidin-3-ol. The title compound was prepared in 38.5% overall yield as a white solid according to General Procedure I using 74-3 (50 mg) and benzyl bromide (50 mg) in DMF in STEP 1, and General Procedure VIII in STEP 2. $^1$H NMR (400 MHz, MeOD) δ 8.03 (s, 1H), 7.96-7.91 (m, 1H), 7.70 (dd, J=8.8, 1.7 Hz, 1H), 7.58 (dd, J=14.8, 8.5 Hz, 3H), 7.47-7.24 (m, 7H), 4.68 (d, J=11.6 Hz, 1H), 4.46 (d, J=11.5 Hz, 1H), 4.36 (dd, J=6.1, 2.3 Hz, 1H), 4.08 (s, 3H), 3.58 (d, J=3.7 Hz, 1H), 3.55-3.37 (m, 2H), 3.03 (dd, J=13.4, 8.6 Hz, 1H), 2.92 (dd, J=13.4, 6.5 Hz, 1H), 2.74 (dd, J=12.3, 2.4 Hz, 1H). MS obsd (ESI$^+$): 414.2 $[M+H]^+$.

Example 113: (3S,4S,5R)-4-methoxy-5-(4-(1-methyl-1H-pyrazol-4-yl)benzyl)pyrrolidin-3-ol Scheme 105

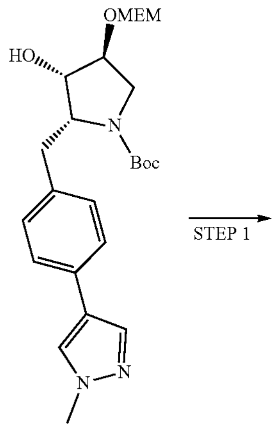

47-3

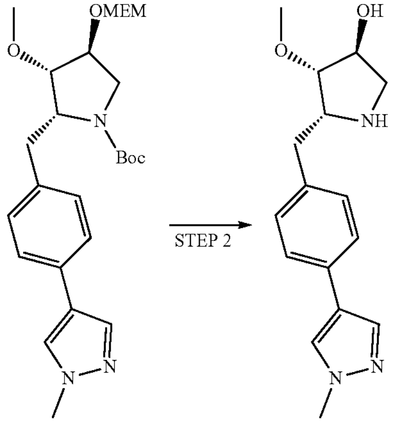

105-2

Step 1-2: (3S,4S,5R)-4-methoxy-5-(4-(1-methyl-1H-pyrazol-4-yl)benzyl)pyrrolidin-3-ol. The title compound was prepared in 35.1% overall yield as an off-white solid according to General Procedure I using 105-2 (70 mg) and iodomethane (46 mg) in DMF in STEP 1, and General Procedure VIII in STEP 2. $^1$H NMR (400 MHz, MeOD) δ 7.92 (s, 1H), 7.78 (s, 1H), 7.50 (dd, J=8.3, 2.0 Hz, 2H), 7.27 (d, J=7.9 Hz, 2H), 4.32 (d, J=5.1 Hz, 1H), 3.91 (s, 3H), 3.62-3.53 (m, 1H), 3.47-3.35 (m, 1H), 3.40 (s, 3H), 3.35 (d, J=3.7 Hz, 1H), 3.01 (dd, J=13.4, 8.6 Hz, 1H), 2.92-2.79 (m, 2H). MS obsd. (ESI$^+$): 288.2 [(M+H)]$^+$.

Example 114: (3S,4S,5R)-4-(benzyloxy)-5-((5-(1-methyl-1H-indazol-5-yl)pyridin-2-yl)methyl)pyrrolidin-3-ol Scheme 106

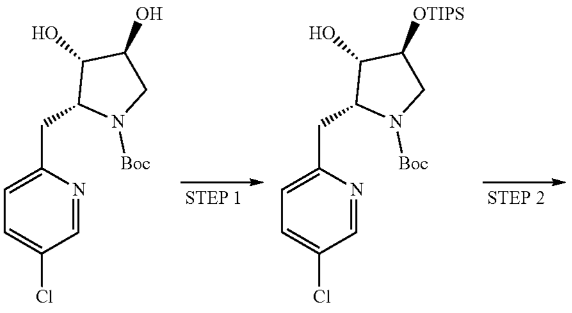

100-4 106-2

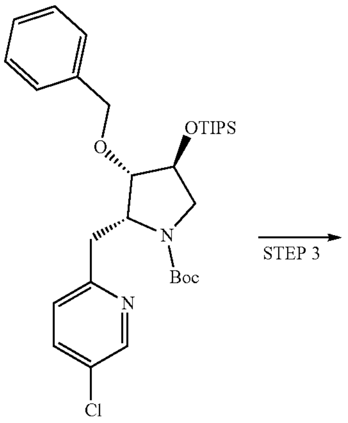

106-3

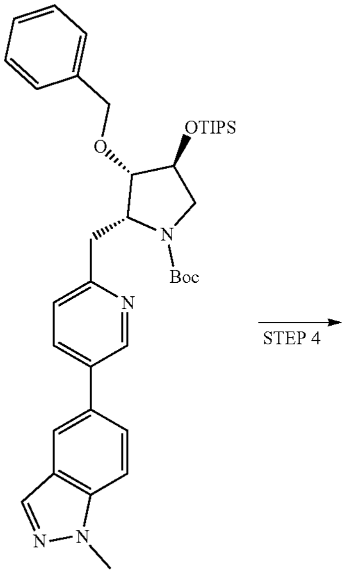

106-4

-continued

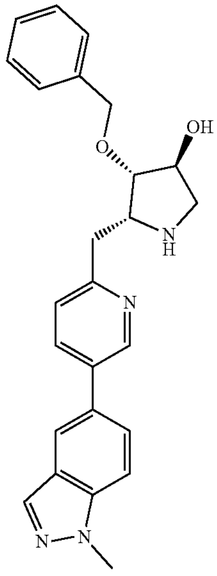 [SMILES: Cn1ncc2cc(-c3ccc(C[C@H]4NC[C@H](O)[C@H]4OCc4ccccc4)nc3)ccc21]

Step 1: tert-butyl (2R,3S,4S)-2-((5-chloropyridin-2-yl)methyl)-3-hydroxy-4-((triisopropylsilyl)oxy)pyrrolidine-1-carboxylate (106-2). Imidazole (362 mg) and chlorotris(propan-2-yl)silane (440 mg) were added to a stirred solution of tert-butyl (2R,3S,4S)-2-((5-chloropyridin-2-yl)methyl)-3,4-dihydroxypyrrolidine-1-carboxylate (250 mg) in DCM (5 mL) at 0° C. The resulting mixture was stirred at room temperature for 12 h, then diluted with water, and extracted with EtOAc. The organic extracts were washed with brine, dried over $Na_2SO_4$, filtered, and concentrated. The residue was purified by reversed-phase flash chromatography to afford the title compound as a yellow oil (150 mg). MS obsd ($ESI^+$): 485.3 $[M+H]^+$.

Step 2: tert-butyl (2R,3S,4S)-3-(benzyloxy)-2-((5-chloropyridin-2-yl)methyl)-4-((triisopropylsilyl)oxy)pyrrolidine-1-carboxylate (106-3). The title compound was prepared in 52.7% yield as a yellow oil according to General Procedure I using 106-2 (100 mg) and (bromomethyl)benzene (106 mg) in DMF. MS obsd ($ESI^+$): 575.3 $[M+H]^+$.

Step 3: tert-butyl (2R,3S,4S)-3-(benzyloxy)-2-((5-(1-methyl-1H-indazol-5-yl)pyridin-2-yl)methyl)-4-((triisopropylsilyl)oxy)pyrrolidine-1-carboxylate (106-4). Under a nitrogen atmosphere, $NaHCO_3$ (24 mg), XPhos Pd $G_3$ (8 mg) and XPhos (9 mg) were added to a stirred solution of tert-butyl (2R,3S,4S)-3-(benzyloxy)-2-((5-chloropyridin-2-yl)methyl)-4-((triisopropylsilyl)oxy)pyrrolidine-1-carboxylate (55 mg) and 1-methyl-5-(4,4,5,5-tetramethyl-1,3,2-dioxaborolan-2-yl)-1H-indazole (37 mg) in DMF (5 mL) at room temperature. The resulting mixture was stirred at 80° C. for 12 h, then diluted with water and extracted with EtOAc. The organic extracts were washed with brine, dried over $Na_2SO_4$, filtered, and concentrated. The residue was purified by reversed-phase flash chromatography to afford the title compound as a yellow oil (55 mg). MS obsd ($ESI^+$): 671.4 $[M+H]^+$.

Step 4: (3S,4S,5R)-4-(benzyloxy)-5-((5-(1-methyl-1H-indazol-5-yl)pyridin-2-yl)methyl)pyrrolidin-3-ol. The title compound was prepared in 62.7% yield as a white solid according to General Procedure VIII using 106-4 (50 mg) and TFA in DCM. $^1H$ NMR (400 MHz, MeOD) δ 8.78 (d, J=2.3 Hz, 1H), 8.10 (s, 1H), 8.07-7.97 (m, 2H), 7.78-7.66 (m, 2H), 7.38 (d, J=5.6 Hz, 2H), 7.39-7.31 (m, 3H), 7.34-7.25 (m, 1H), 4.72 (d, J=11.7 Hz, 1H), 4.51 (d, J=11.6 Hz, 1H), 4.46-4.38 (m, 1H), 4.12 (s, 3H), 3.86 (m, J=7.3, 3.8 Hz, 1H), 3.76 (d, J=3.9 Hz, 1H), 3.47 (dd, J=12.3, 5.5 Hz, 1H), 3.29-3.07 (m, 2H), 2.83 (dd, J=12.2, 2.3 Hz, 1H). MS obsd ($ESI^+$): 415.2 $[M+H]^+$.

Example 115: rac-(3S,4S,5R)-4-(1,1-difluoropropoxy)-5-[(4-methoxyphenyl)methyl]pyrrolidin-3-ol

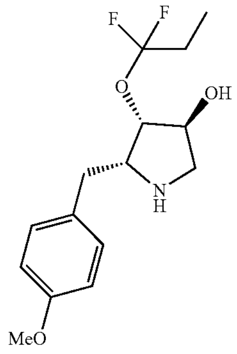 [SMILES: CCC(F)(F)O[C@@H]1[C@@H](O)CN[C@@H]1Cc1ccc(OC)cc1]

Step 1-3: rac-(3S,4S,5R)-4-(1,1-difluoropropoxy)-5-[(4-methoxyphenyl)methyl]pyrrolidin-3-ol. The title compound was prepared in 36.2% overall yield as a white solid according to O-alkylation reaction with $Cs_2CO_3$, $Ag_2O$ for synthesis of ether; General Procedure II using 3-bromo-3,3-difluoro-prop-1-ene in STEP 1; Reduction reaction with Pd/C, hydrogen; General Procedure VI in STEP 2; Boc Deprotection; General Procedure III in STEP 3. MS: m/z: Calc'd for $C_{15}H_{21}F_2NO_3$ $[M+H]^+$ 302, found 302. $^1H$ NMR (400 MHz, DMSO-$d_6$) δ 7.15 (d, J=8.1 Hz, 2H), 6.83 (d, J=8.2 Hz, 2H), 5.08 (d, J=4.3 Hz, 1H), 4.20 (d, J=3.7 Hz, 1H), 4.06 (s, 1H), 3.72 (s, 3H), 3.16 (dd, J=11.7, 5.7 Hz, 2H), 2.68 (dd, J=13.8, 5.7 Hz, 1H), 2.60-2.52 (m, 1H), 2.01-1.95 (m, 2H), 1.01 (t, J=7.5 Hz, 3H).

Example 116: (3S,4S,5R)-4-(1,1-difluoro-3-(3-(trifluoromethoxy)phenyl)propoxy)-5-(4-(thiazol-5-yl)benzyl)pyrrolidin-3-ol

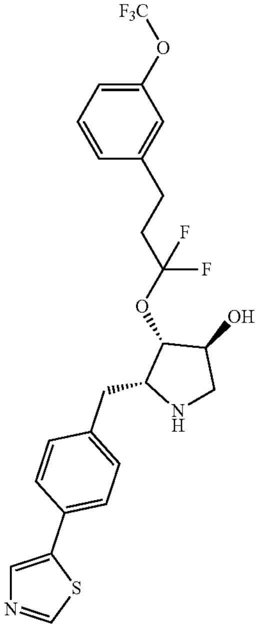 [SMILES: O[C@H]1CN[C@H](Cc2ccc(-c3cncs3)cc2)[C@@H]1OC(F)(F)CCc1cccc(OC(F)(F)F)c1]

Step 1-3: (3S,4S,5R)-4-(1,1-difluoro-3-(3-(trifluoromethoxy)phenyl)propoxy)-5-(4-(thiazol-5-yl)benzyl)pyrrolidin-3-ol. The title compound was prepared in 24.1% overall light yellow semi-solid according to Heck Coupling with $Pd_2(dba)_3$, tris(2-methylphenyl)phosphate, TEA; General Procedure V using tert-butyl (2R,3S,4S)-4-[(tert-butoxycarbonyl)oxy]-3-[(1,1-difluoroprop-2-en-1-yl)oxy]2-{[4-(1,3-thiazol-5-yl)phenyl]methyl}pyrrolidine-1-carboxylate (Int-19) instead of tert-butyl (2R,3S,4S)-4-[(tert-butoxycarbonyl)oxy]-3-(prop-2-en-1-yloxy)-2-{[4-(1,3-thiazol-5-yl)phenyl]methyl}pyrrolidine-1-carboxylate (Int-14), (3-(trifluoromethoxy)phenyl) boronic acid in STEP 1; Reduction reaction with Pd/C, hydrogen; General Procedure VI in STEP 2; Boc Deprotection; General Procedure III in STEP 3. MS: m/z: Calc'd for $C_{24}H_{23}F_5N_2O_3S$ $[M+H]^+$ 515; Found, 515. $^1H$ NMR (400 MHz, Methanol-$d_4$) δ 9.00 (s, 1H), 8.20 (s, 1H), 7.72 (d, J=8.0 Hz, 2H), 7.45 (dd, J=16.4, 8.0 Hz, 3H), 7.31 (d, J=7.7 Hz, 1H), 7.22 (s, 1H), 7.20-7.14 (m, 1H), 4.80 (d, J=3.3 Hz, 1H), 4.52 (d, J=4.2 Hz, 1H), 4.34-4.25 (m, 1H), 3.63 (dd, J=12.7, 4.3 Hz, 1H), 3.31-3.20 (m, 2H), 3.07 (dd, J=14.7, 9.6 Hz, 1H), 2.99 (dd, J=10.4, 6.3 Hz, 2H), 2.56-2.42 (m, 2H).

Example 117: rac-(3S,4S,5R)-4-(1,1-difluoroallyloxy)-5-[(4-methoxyphenyl)methyl]pyrrolidin-3-ol

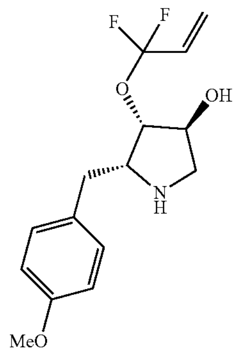 [SMILES: C=CC(F)(F)O[C@@H]1[C@@H](O)CN[C@@H]1Cc1ccc(OC)cc1]

Step 1: rac-(3S,4S,5R)-4-(1,1-difluoroallyloxy)-5-[(4-methoxyphenyl)methyl]pyrrolidin-3-ol. The title compound was prepared in 9.8% yield as a white solid according to Boc Deprotection; General Procedure III using tert-butyl rac-(2R,3S,4S)-4-tert-butoxycarbonyloxy-3-(1,1-difluoroallyloxy)-2-[(4-methoxyphenyl)methyl]pyrrolidine-1-carboxylate. MS: m/z: Calc'd for $C_{15}H_{19}F_2NO_3$ $[M+H]^+$ 300, found 300. $^1H$ NMR (400 MHz, DMSO-$d_6$) δ 7.14 (d, J=8.4 Hz, 2H), 6.86-6.78 (m, 2H), 6.08-6.05 (m, 1H), 5.89-5.79 (m, 1H), 5.61 (d, J=10.8 Hz, 1H), 5.11 (d, J=4.4 Hz, 1H), 4.24 (d, J=3.9 Hz, 1H), 4.10 (s, 1H), 3.71 (s, 3H), 3.19 (dd, J=11.7, 5.8 Hz, 2H), 2.68 (dd, J=13.8, 6.0 Hz, 1H), 2.57 (d, J=5.8 Hz, 1H).

Example 118: (3S,4S,5R)-4-(2-(azetidin-3-yl)ethoxy)-5-(4-methoxybenzyl)pyrrolidin-3-ol

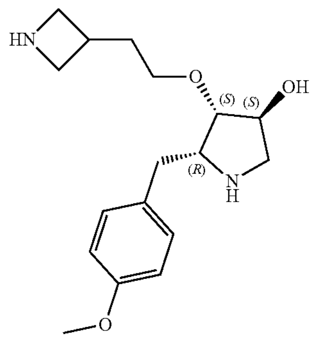

Step 1-2: (3S,4S,5R)-4-(2-(azetidin-3-yl)ethoxy)-5-(4-methoxybenzyl)pyrrolidin-3-ol. The title compound was prepared in 32.4% overall yield as a yellow oil according to O-Alkylation reaction with $Cs_2CO_3$, $Ag_2O$ for synthesis of ether; General Procedure II using tert-butyl (2R,3S,4S)-4-((tert-butoxycarbonyl)oxy)-3-hydroxy-2-(4-methoxybenzyl)pyrrolidine-1-carboxylate (Int-1) instead tert-butyl (2R,3S,4S)-3-hydroxy-4-[(2-methoxyethoxy)methoxy]-2-{[4-(1,3-thiazol-5-yl)phenyl]methyl}pyrrolidine-1-carboxylate (Int-16) and tert-butyl 3-(2-bromoethyl) azetidine-1-carboxylate in STEP 1; Boc Deprotection, General Procedure III in STEP 2. MS: m/z: Calc'd for $C_{17}H_{26}N_2O_3$ $[M+H]^+$ 307, Found 307. $^1H$ NMR (400 MHz, Methanol-$d_4$) δ 7.31-7.21 (m, 2H), 6.99-6.90 (m, 2H), 4.46 (d, J=4.2 Hz, 1H), 4.22-4.13 (m, 2H), 4.01 (dd, J=7.8, 3.4 Hz, 1H), 3.91 (dd, J=10.8, 7.8 Hz, 2H), 3.80 (s, 3H), 3.76-3.66 (m, 2H), 3.55-3.48 (dd, J=9.5, 5.9 Hz, 2H), 3.21-3.03 (m, 3H), 2.97 (dd, J=14.0, 8.3 Hz, 1H), 2.09-1.93 (m, 2H).

Example 47: 2,2-difluoro-2-(((2R,3S,4S)-4-hydroxy-2-(4-(thiazol-5-yl)benzyl)pyrrolidin-3-yl)oxy) acetic Acid Scheme 107

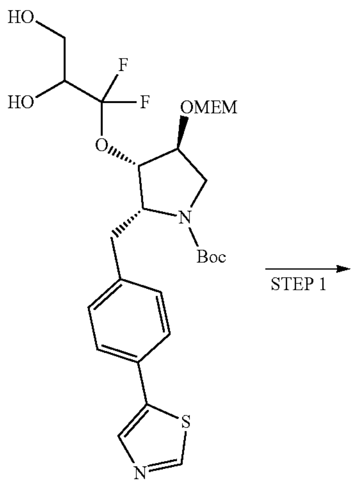

44-2

-continued

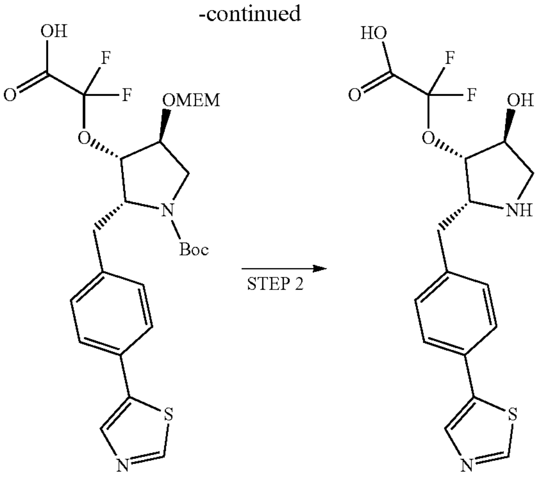

107-2

Step 1: 2-(((2R,3S,4S)-1-(tert-butoxycarbonyl)-4-((2-methoxyethoxy)methoxy)-2-(4-(thiazol-5-yl)benzyl)pyrrolidin-3-yl)oxy)-2,2-difluoroacetic Acid (107-2)

$Pb(OAc)_4$ (493.8 mg, 1.12 mmol, 8 eq.) and $Na_2CO_3$ (44.3 mg, 0.42 mmol, 3 eq.) were added to a stirred solution of tert-butyl (2R,3S,4S)-3-(1,1-difluoro-2,3-dihydroxy-propoxy)-4-[(2-methoxyethoxy)methoxy]-2-{[4-(1,3-thiazol-5-yl)phenyl]methyl}pyrrolidine-1-carboxylate (24-1, 80 mg, 0.14 mmol, 1 eq) in DCM (6 mL) at 0° C. and the mixture was stirred at room temperature overnight. The mixture was filtered and washed with DCM. Filtrate was concentrated and purified by reverse-phase column to obtain {[(2R,3S,4S)-1-(tert-butoxycarbonyl)-4-[(2-methoxyethoxy)methoxy]-2-{[4-(1,3-thiazol-5-yl)phenyl]methyl}pyrrolidin-3-yl]oxy}difluoroacetic acid (50 mg, 64.3% yield) as a brown oil. MS: m/z: Calc'd for $C_{25}H_{32}F_2N_2O_8S$ $[M+H]^+$ 559; Found, 559.

Step 2: 2,2-difluoro-2-(((2R,3S,4S)-4-hydroxy-2-(4-(thiazol-5-yl)benzyl)pyrrolidin-3-yl)oxy)acetic Acid The title compound was prepared in 22.3% yield as a white solid according to Boc Deprotection; General Procedure III in STEP 2. MS: m/z: Calc'd for $C_{16}H_{16}F_2N_{204}S$ $[M+H]^+$ 371; Found, 371. $^1H$ NMR (400 MHz, Methanol-$d_4$) δ 8.98 (s, 1H), 8.19 (s, 1H), 7.71 (d, J=8.1 Hz, 2H), 7.48 (d, J=8.0 Hz, 2H), 4.73-4.68 (m, 1H), 4.56 (d, J=4.5 Hz, 1H), 4.25-4.16 (m, 1H), 3.72 (dd, J=12.7, 4.6 Hz, 1H), 3.28 (dd, J=14.4, 5.8 Hz, 1H), 3.22-3.08 (m, 2H).

Example 120: (3S,4S,5R)-4-((1H-1,2,3-triazol-4-yl)methoxy)-5-(4-methoxybenzyl)pyrrolidin-3-ol Scheme 108

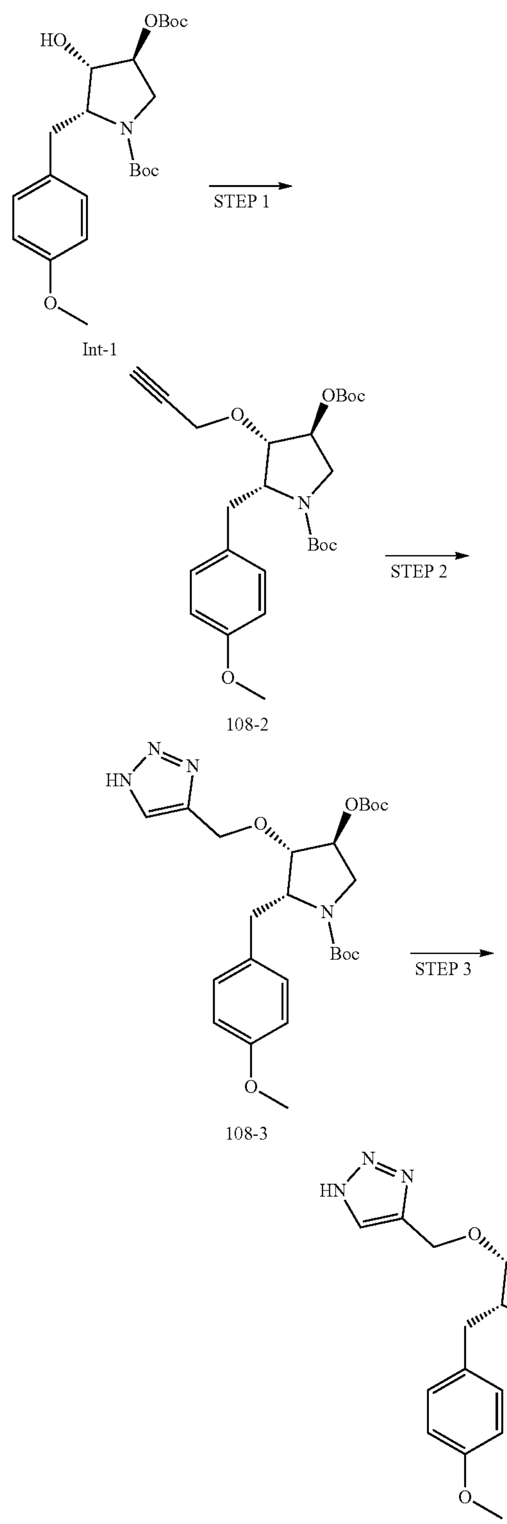

Step 1: tert-butyl (2R,3S,4S)-4-((tert-butoxycarbonyl)oxy)-2-(4-methoxybenzyl)-3-(prop-2-yn-1-yloxy)pyrrolidine-1-carboxylate (108-2). $Cs_2CO_3$ (1538.7 mg, 4.72 mmol, 2 eq.) were added to a stirred solution of tert-butyl (2R,3S,4S)-4-[(tert-butoxycarbonyl)oxy]-3-hydroxy-2-[(4-methoxyphenyl)methyl]pyrrolidine-1-carboxylate (Int-1, 1 g, 2.36 mmol, 1 eq.) and propargyl bromide (561.8 mg, 4.72 mmol, 2 eq.) in DMF (20 mL). The mixture was stirred at r.t. for 2 days. The mixture was filtered and the filtrate was purified by reverse phase flash column to obtain tert-butyl (2R,3S,4S)-4-[(tert-butoxycarbonyl)oxy]-2-[(4-methoxyphenyl)methyl]-3-(prop-2-yn-1-yloxy)pyrrolidine-1-carboxylate (660 mg, 60.6%) as a brown oil. MS: m/z: Calc'd for $C_{25}H_{35}NO_7$ $[M+H-56-56]^+$ 350, found $[M+H-56-56]^+$ 350.

Step 2-3: (3S,4S,5R)-4-((1H-1,2,3-triazol-4-yl)methoxy)-5-(4-methoxybenzyl)pyrrolidin-3-ol. The title compound was prepared in 8.9% overall yield as an off-white solid according to Cyclization reaction for synthesis of Substituted triazoles; General Procedure IX using trimethylsilyl azide in STEP 2; Boc Deprotection, General Procedure III in STEP 3. MS: m/z: Calc'd for $C_{15}H_{20}N_4O_5$ $[M+H]^+$ 305, found 305. $^1H$ NMR (400 MHz, Methanol-$d_4$) δ 7.78 (s, 1H), 7.12 (d, J=8.6, 2H), 6.85 (d, J=8.6, 2H), 4.80 (d, J=12.1 Hz, 1H), 4.63 (d, J=12.2 Hz, 1H), 4.40 (d, J=5.3 Hz, 1H), 3.78 (s, 3H), 3.64 (d, J=3.4 Hz, 1H), 3.60-3.56 (m, 1H), 3.53-3.44 (m, 1H), 2.99-2.78 (m, 3H).

Example 121: (3S,4S,5R)-4-(2-hydroxyethoxy)-5-(4-methoxybenzyl)pyrrolidin-3-ol Scheme 109

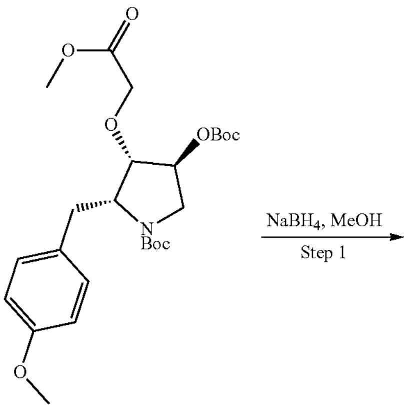

16-1

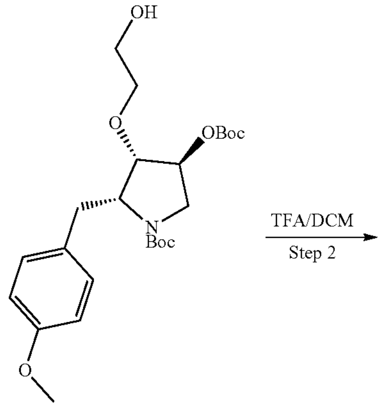

17-1

-continued

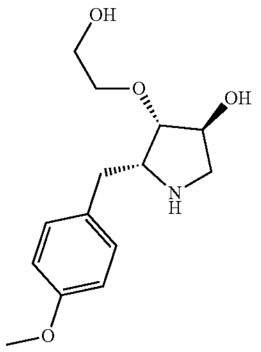

Step 1: To a stirred solution of tert-butyl (2R,3S,4S)-4-[(tert-butoxycarbonyl)oxy]-3-(2-methoxy-2-oxoethoxy)-2-[(4-methoxyphenyl)methyl]pyrrolidine-1-carboxylate (16-1, 120 mg, 0.24 mmol, 1 eq.) in MeOH (5 mL) was added $NaBH_4$ (18 mg, 0.48 mmol, 2 eq.) at 0° C. and the resulting mixture was stirred at room temperature for 1 h. The reaction mixture was quenched with water and extracted with EA. The extracts were washed with brine, dried over anhydrous sodium sulfate, filtered and concentrated. The residue was purified by Prep-HPLC to obtain tert-butyl (2R,3S,4S)-4-[(tert-butoxycarbonyl)oxy]-3-(2-hydroxyethoxy)-2-[(4-methoxyphenyl)methyl]pyrrolidine-1-carboxylate (100 mg, 88.3%) as a white solid. MS: m/z: Calc'd for $C_{24}H_{37}NO_8$ $[M+Na]^+$ 490, found 490.

Step 2: The title compound was prepared in 18.8% yield as a white solid according to Boc Deprotection; General Procedure III in STEP 2. MS: m/z: Calc'd for $C_{1-4}H_{21}NO_4$ $[M+H]^+$ 268, found 268. $^1H$ NMR (400 MHz, Methanol-$d_4$) δ 7.23 (d, J=8.3 Hz, 2H), 6.88 (d, J=8.5 Hz, 2H), 4.31 (d, J=5.6 Hz, 1H), 3.79 (s, 3H), 3.77-3.64 (m, 3H), 3.54-3.41 (m, 4H), 3.05-2.97 (m, 1H), 2.90-2.74 (m, 2H).

Example 122: (3S,4S,5R)-5-(4-(1-(azetidin-3-yl)-1H-1,2,3-triazol-4-yl)benzyl)-4-(1,1-difluoropropoxy)pyrrolidin-3-ol Scheme 110

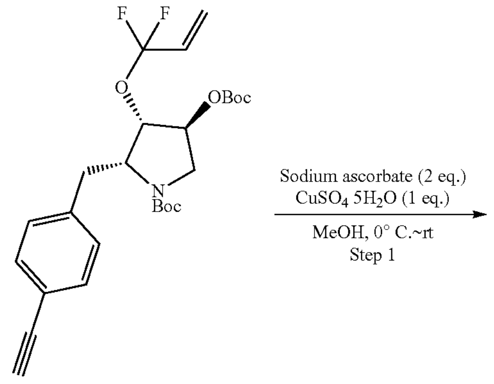

Int-18

-continued

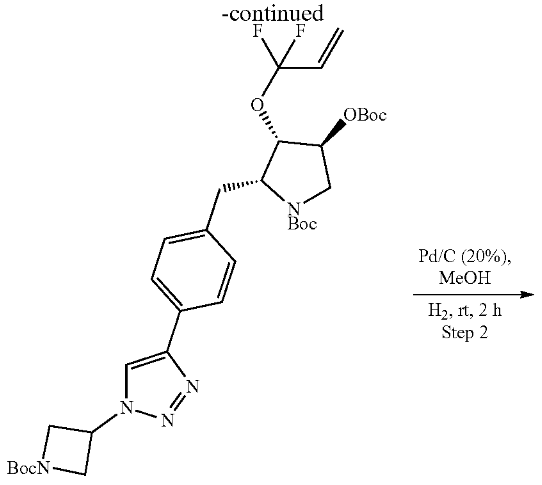

29-1

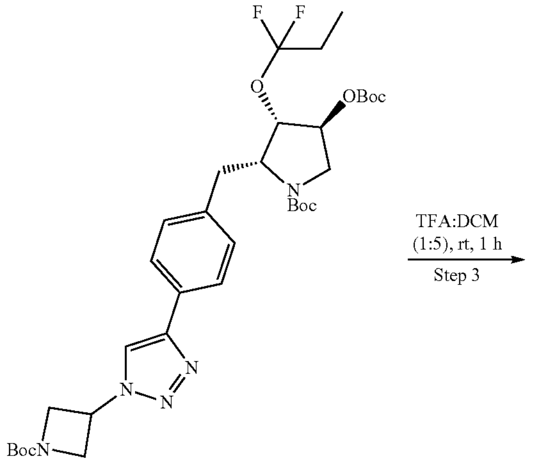

29-2

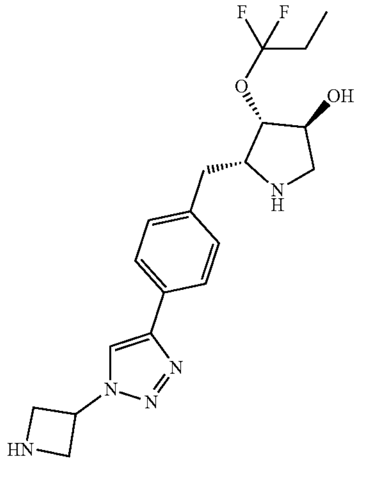 [SMILES: CCC(F)(F)O[C@@H]1[C@@H](O)CN[C@@H]1Cc1ccc(-c2cn(C3CNC3)nn2)cc1]

Step 1: To a stirred solution of tert-butyl (2R,3S,4S)-4-[(tert-butoxycarbonyl)oxy]-3-[(1,1-difluoroprop-2-en-1-yl)oxy]-2-[(4-ethynylphenyl)methyl]pyrrolidine-1-carboxylate (Int-18, 100 mg, 0.21 mmol, 1 eq.) and tert-butyl 3-azido-azetidine-1-carboxylate (48.2 mg, 0.24 mmol, 1.2 eq.) in methanol (5 mL) were added $CuSO_4 \cdot 5H_2O$ (50.6 mg, 0.21 mmol, 1 eq.) and sodium (2S)-2-[(1S)-1,2-dihydroxyethyl]-4-hydroxy-5-oxooxolan-3-olate (80.3 mg, 0.41 mmol, 2 eq.) at 0° C. The resulting mixture was stirred at room temperature for 4 h. The residue was purified by reversed flash to obtain tert-butyl (2R,3S,4S)-2-[(4-{1-[1-(tert-butoxycarbonyl) azetidin-3-yl]-1,2,3-triazol-4-yl}phenyl)methyl]-4-[(tert-butoxycarbonyl)oxy]-3-[(1,1-difluoroprop-2-en-1-yl)oxy]pyrrolidine-1-carboxylate (150 mg, 107.1% yield) as a light yellow oil. MS: m/z: Calc'd for $C_{34}H_{47}F_2N_5O_8$ $[M+H]^+$ 692, found 692.

Step 2 & 3: The title compound was prepared in 28.5% overall yield as a light yellow solid according to Reduction reaction with Pd/C, hydrogen; General Procedure VI using tert-butyl (2R,3S,4S)-2-(4-(1-(1-(tert-butoxycarbonyl) azetidin-3-yl)-1H-1,2,3-triazol-4-yl)benzyl)-4-((tert-butoxycarbonyl)oxy)-3-((1,1-difluoroallyl)oxy)pyrrolidine-1-carboxylate (29-1) in STEP 2; Boc Deprotection; General Procedure III using tert-butyl (2R,3S,4S)-2-(4-(1-(1-(tert-butoxycarbonyl) azetidin-3-yl)-1H-1,2,3-triazol-4-yl)benzyl)-4-((tert-butoxycarbonyl)oxy)-3-(1,1-difluoropropoxy) pyrrolidine-1-carboxylate (29-2) in STEP 3. MS: m/z: Calc'd for $C_{19}H_{25}F_2N_5O_2$ $[M+H]^+$ 394, found 394. $^1H$ NMR (400 MHz, MeOD) δ 8.47 (s, 1H), 7.94-7.87 (m, 2H), 7.49 (d, J=8.2 Hz, 2H), 5.79-5.71 (m, 1H), 4.75 (s, 1H), 4.71 (d, J=7.4 Hz, 4H), 4.52 (d, J=4.2 Hz, 1H), 4.30-4.25 (m, 1H), 3.63 (dd, J=12.7, 4.3 Hz, 1H), 3.30-3.22 (m, 2H), 3.08 (dd, J=14.6, 9.3 Hz, 1H), 2.21-2.10 (m, 2H), 1.15 (t, J=7.5 Hz, 3H).

In Vitro Transcription/Translation Data

All reporter constructs were cloned into the pT7CFE1-CHis plasmid (ThermoFisher #88860) using Gibson assembly procedures (NEB #E2611L). The parental pT7CFE1-CHis plasmid contained an EMCV IRES at the 5'UTR for translation initiation, a multiple-cloning site (MCS) for gene insertion, an optional C-terminal His-epitope tag, and polyA sequence in the 3'UTR to regulate mRNA stability. All reporters were designed to be inserted at the MCS to include a red fluorescent protein (mCherry), P2A self-cleaving peptide which releases the preceding mCherry protein product, and a fusion open reading frame containing a 3×FLAG epitope, a peptide sequence of interest (TEST), and green fluorescent protein (sfGFP).

Construct Plasmid Preparation: All plasmids were isolated from MACH1 cells (ThermoFisher) grown overnight in ampicillin-containing luria broth, and purified using ZymoPure Express Plasmid Midiprep Kit (Zymo Research). Constructs were sequenced verified and diluted to a working concentration of 110 ng/μL.

HeLa S3 Lysate Preparation: HeLa S3 cell pellets were acquired from Ipracell/Ipratech (Belgium) and shipped as 4 mL frozen cell pellets on dry ice for storage at −80° C. until use. The procedure for lysate preparation is as follows. 1× Lysis Buffer was prepared, cold and stored on ice:

| Hela S3 Lysis Buffer (1X) | Vol. for 40 mL of buffer |
|---|---|
| 20 mM Hepes pH 7.4 | 800 μL of 1M stock |
| 10 mM KOAc pH 7.6 | 133.2 μL of 3M stock |
| 1.8 mM $Mg(OAc)_2$ | 72 μL of 1M stock |
| 1 mM DTT | 40 μL of 1M stock |
| 500 nM ISRIB | 20 μL of 1 mM stock |
| $H_2O$ (cold nuclease free) | |

Each preparation takes 8 cell pellets (4 ml packed volume each, approximately $1.0 \times 10^9$ cells per pellet). Cell pellets were thawed from −80° C. on ice for 90 mins. Pellets were laid horizontally on top of the ice and rotated every 30 mins to ensure even thawing. Once thawed, 4 mL of cold lysis buffer was added to each pellet, and, using a serological pipet, gently pipeted up and down to break up clumps. Resuspended cells were incubated in ice for an additional 30 mins (plunged into ice). During 30 min incubation, glass dounces (use loose pestle "A") were rinsed and RNase-zapped (Ambion), gently dried and placed on ice until needed. RNase-free Eppendorf tubes were prepared for spinning and for batch storage. Batch labels were added to 1.5-1.7 mL RNase-free microcentrifuge tubes (labeling scheme below). Each batch had an extra 1.5-1.7 mL RNase-free microcentrifuge tube for 40 μL of lysate; the top of this tube was labeled (labeling scheme below). After 30 min incubation, all 8 mL of cell pellet were transferred to dounce. Cell lysis was complete after douncing 100 times. Cell lysis were aliquoted into 1.5-1.7 mL temporary-microcentrifuge tubes. Tubes were placed in centrifuge with "fins" out, and spun at 1,200×g for 5 mins. After the first spin, a 1 mL pipet was used to resuspend each tube and spin was repeated as an additional more vigorous lysis step that increased lysate yield. During second spin, liquid $N_2$ was obtained and a fresh conical tube was placed on ice. After spin was complete, supernatant (lysate) was transferred from microcentrifuge tubes into the 50 mL conical tube and kept on ice. The steps beginning with aliquoting cell lysis into 1.5-1.7 mL temporary-microcentrifuge tubes were repeated for all other cell pellets until completed. Once all cell lysate were transferred to the 50 mL conical tube, they were pipetted to mix so the solution was homogenous. 1 mL of lysate was transferred into batch-labeled microcentrifuge tubes and flash frozen in liquid nitrogen, taking care to pipet up and down to mix throughout transfer step. All tubes were placed in the 80° C. oven for long-term storage.

Lysate batch quality control: IDB-PL005 & IDB-PL055 reporters (highest & lowest signal generators) were used as controls. Reaction Set-Up included 5 μL Lysate (Previous preparation or new preparation), 1 μL TF accessory proteins, 2 μL TF reaction mix, 1 μL $H_2O$, and 1 μL of 110 ng/μL plasmid DNA. A 96-well plate was set up as seen below, and reactions were incubated at 30° C. for 2 hours:

| | Control lysate reactions | | | Batch #00X Rxns | | |
|---|---|---|---|---|---|---|
| | 1 | 2 | 3 | 4 | 5 | 6 |
| A | Lysate Only | PL005 | PL055 | Lysate Only | PL005 | PL055 |

After 2 hrs, the assay was quenched using 45 μL of PBS, and 50 μL was transferred to a flat-bottom black microplate. Fluorescent signals were compared between the previous lysate batch and the new batch to confirm activity.

In vitro transcription-translation assay setup: Each assay included a master mix containing lysate and shared components, a 96-well plate containing compound titrations for testing, a 96-well DNA plate with reporter constructs to be tested, 96-well skirted PCR plates, and 96-well flat-bottom, black, fluorescent assay plates. Reaction materials setup: (A) Master mix-15 ml conical tube (3 mL of HeLa S3 Lysate described above; 0.6 mL of ThermoFisher Accessory Proteins (#88882); 1.2 ml of ThermoFisher Reaction Mix (#88882); 0.54 mL of nuclease-free Water); (B) 96-Well Master Mix+Compound Plate (Half-log dilutions (30 μM-0.1 μM) of 4 compounds of interest were prepared in 100% DMSO); 96-Well DNA Plate (Five DNA constructs were plated into single columns within the plate. Row 1 of the column contained nuclease free $H_2O$, all other wells contained 110 ng/μL plasmid DNA). Reactions were started by mixing 155 μL of master mix and 3.5 μL of compound serial dilutions, then 9.1 μL of master mix+compound mixture was aliquoted across 5 96-well plates. Reactions began with final addition of 2 μL of DNA for a 11.1 μL reaction volume in each well. The entire plate was scaled, and incubated for 2 hrs at 30° C. After 2 hrs, the assay was quenched using 45 μL of PBS, and 50 μL was transferred to a flat-bottom black microplate. The sfGFP and mCherry signals from each well on each plate were quantified (3 reads), and data analysis was performed as described below.

In vitro transcription-translation assay data analysis: Each plate was read three times in channels for both sfGFP and mCherry signals. The average signal across these 3 reads was then calculated for further analysis. Control wells containing no DNA reporter were subtracted from reporter wells in the same column to remove auto-fluorescence of the lysate. Then, the ratio of sfGFP/mCherry was calculated per well, and these ratios were averaged across the triplicate experiments on the same plate. Finally, the ratio of each titration concentration was normalized to the no drug control to create the normalized stalling metric. The error on this measurement was determined by propagating error through the averaging and normalization steps. Values were plotted and fit for $IC_{50}$ determination for each test sequence and titration of compound.

TABLE 3

In Vitro Transcription-Translation (IVTT) Data

| Example Number | MYC IVTT IC50 (μM) |
|---|---|
| 1 | B |
| 2 | A |
| 3 | A |
| 4 | B |
| 5 | B |
| 6 | B |
| 7 | A |
| 8 | B |
| 9 | A |
| 10 | B |
| 11 | B |
| 12 | B |
| 14 | B |
| 15 | B |
| 16 | A |
| 17 | B |
| 18 | B |
| 19 | B |
| 20 | C |
| 21 | A |
| 22 | A |
| 23 | A |
| 24 | B |
| 25 | A |
| 26 | A |
| 27 | A |
| 28 | A |
| 29 | B |
| 30 | A |
| 31 | A |
| 32 | B |
| 33 | A |
| 34 | A |
| 35 | B |
| 36 | A |
| 37 | B |
| 38 | B |
| 39 | B |
| 40 | B |
| 41 | A |
| 42 | A |
| 43 | B |
| 44 | B |
| 45 | B |
| 46 | B |
| 47 | A |
| 48 | A |

TABLE 3-continued

In Vitro Transcription-Translation (IVTT) Data

| Example Number | MYC IVTT IC50 (μM) |
|---|---|
| 49 | B |
| 50 | A |
| 51 | A |
| 52 | A |
| 53 | B |
| 54 | A |
| 55 | B |
| 56 | B |
| 57 | A |
| 58 | A |
| 59 | B |
| 60 | A |
| 61 | A |
| 62 | B |
| 63 | A |
| 64 | A |
| 65 | B |
| 66 | A |
| 67 | A |
| 68 | A |
| 69 | B |
| 70 | B |
| 71 | A |
| 72 | B |
| 73 | B |
| 74 | A |
| 75 | B |
| 76 | A |
| 77 | A |
| 78 | B |
| 79 | A |
| 80 | A |
| 81 | A |
| 82 | A |
| 83 | A |
| 84 | B |
| 85 | B |
| 86 | B |
| 87 | A |
| 88 | A |
| 89 | B |
| 90 | B |
| 91 | B |
| 92 | B |
| 93 | B |
| 94 | B |
| 95 | B |
| 96 | A |
| 97 | B |
| 98 | B |
| 99 | A |
| 100 | B |
| 101 | B |
| 102 | B |
| 103 | A |
| 104 | B |
| 105 | B |
| 106 | B |
| 107 | B |
| 108 | B |
| 109 | A |
| 110 | A |
| 111 | A |
| 112 | A |
| 113 | A |
| 114 | B |
| 115 | B |
| 116 | C |
| 117 | D |
| 119 | C |
| 122 | B |
| — | — |
| — | — |

A ≥0 μM to <1 μM; B ≥1 μM to <10 μM; C ≥10 μM to <20 μM; D ≥20 μM to ≤30 μM.

Cell Viability Assays

HCC-1143, LS411N, and MCF-7 cell lines were purchased from ATCC (American Type Culture Collection) and cultured using recommended protocols. Indicated cell lines were plated in black Bio-One CELLSTAR 96-well, cell culture-treated, flat-bottom microplates (Greiner) at concentrations between 2,000-10,000 cells/well in tissue culture media and incubated overnight in standard tissue culture incubator (37° C., 5% $CO_2$). Once cells adhered, compounds resuspended in 10% DMSO were added to each well containing 100 μL of media for a final concentration of 0.5% DMSO. After 72 h of incubation, viability was assessed using established protocols for CellTiter-Fluor assay (Promega). Briefly, the media was removed from the plates, cells gently rinsed with PBS, and a 1:1 mix of PBS and fluorescent substrate is added to the plates before incubating for 60 min at room temperature with orbital shaking. Finally, viability was quantified per kit instructions using an Envision fluorescent plate reader (Revvity). To calculate $IC_{50}$ values, each plate is background subtracted and normalized to DMSO only control wells for a % viability compared to control. Non-linear regressions for each compound and cell line were performed to obtain the $IC_{50}$ value.

TABLE 4

Cell Viability Assay Data

| Example Number | HCC1143 IC50 (μM) | LS411N IC50 (μM) | MCF7 IC50 (μM) |
|---|---|---|---|
| 1 | C | C | C |
| 2 | B | C | B |
| 3 | B | B | B |
| 4 | C | C | C |
| 5 | C | C | C |
| 6 | C | C | C |
| 7 | B | B | B |
| 8 | C | C | C |
| 9 | C | B | B |
| 10 | C | B | C |
| 11 | C | C | C |
| 12 | C | C | C |
| 13 | C | C | C |
| 14 | C | C | C |
| 15 | C | C | C |
| 16 | B | B | B |
| 17 | C | C | C |
| 18 | B | B | B |
| 19 | C | C | C |
| 20 | C | C | C |
| 21 | B | A | A |
| 22 | B | B | B |
| 23 | B | A | B |
| 24 | B | B | B |
| 25 | B | C | B |
| 26 | A | A | A |
| 27 | C | B | C |
| 28 | B | B | B |
| 29 | B | B | B |
| 30 | B | B | B |
| 31 | A | A | A |
| 32 | C | B | C |
| 33 | B | B | B |
| 34 | C | C | B |
| 35 | C | C | C |
| 36 | B | B | C |
| 37 | B | B | B |
| 38 | C | C | C |
| 39 | C | C | C |
| 40 | C | C | C |
| 41 | C | B | C |
| 42 | B | A | B |
| 43 | C | C | C |
| 44 | B | B | B |
| 45 | C | C | C |

TABLE 4-continued

Cell Viability Assay Data

| Example Number | HCC1143 IC50 (μM) | LS411N IC50 (μM) | MCF7 IC50 (μM) |
|---|---|---|---|
| 46 | C | B | C |
| 47 | B | B | B |
| 48 | A | A | A |
| 49 | C | B | C |
| 50 | B | B | B |
| 51 | C | B | B |
| 52 | C | B | B |
| 53 | C | B | C |
| 54 | B | A | B |
| 55 | B | B | B |
| 56 | B | B | C |
| 57 | B | A | B |
| 58 | B | A | C |
| 59 | B | A | B |
| 60 | C | C | C |
| 61 | B | B | B |
| 62 | C | B | C |
| 63 | C | C | B |
| 64 | B | B | B |
| 65 | B | B | B |
| 66 | B | A | B |
| 67 | B | B | B |
| 68 | B | A | B |
| 69 | B | B | B |
| 70 | B | B | B |
| 71 | B | B | B |
| 72 | C | B | C |
| 73 | B | B | B |
| 74 | A | A | A |
| 75 | B | B | B |
| 76 | A | A | A |
| 77 | A | A | A |
| 78 | C | C | B |
| 79 | A | A | A |
| 80 | B | B | A |
| 81 | A | A | A |
| 82 | A | A | A |
| 83 | A | A | A |
| 84 | C | B | B |
| 85 | B | B | B |
| 86 | B | B | B |
| 87 | B | A | B |
| 88 | C | B | C |
| 89 | C | B | C |
| 90 | B | B | B |
| 91 | B | B | B |
| 92 | C | B | C |
| 93 | C | B | C |
| 94 | B | B | B |
| 95 | C | B | C |
| 96 | A | A | A |
| 97 | B | B | C |
| 98 | B | B | B |
| 99 | A | A | A |
| 100 | C | B | C |
| 101 | C | B | C |
| 102 | B | B | C |
| 103 | B | B | B |
| 104 | C | B | C |
| 105 | C | B | C |
| 106 | B | B | C |
| 107 | C | C | C |
| 108 | C | B | C |
| 109 | B | A | B |
| 110 | B | A | B |
| 111 | B | A | B |
| 112 | B | A | B |
| 113 | B | A | B |
| 114 | B | B | C |
| 115 | C | B | — |
| 116 | C | C | C |
| 117 | C | C | C |
| 118 | C | C | — |
| 119 | C | C | C |
| 120 | C | — | C |

TABLE 4-continued

Cell Viability Assay Data

| Example Number | HCC1143 IC50 (μM) | LS411N IC50 (μM) | MCF7 IC50 (μM) |
|---|---|---|---|
| 121 | C | C | — |
| 122 | C | C | C |

A ≥0 μM to <0.05 μM; B ≥0.05 μM to <0.5 μM; C ≥0.5 μM to ≤10 μM.

INCORPORATION BY REFERENCE

The present application refers to various issued patent, published patent applications, scientific journal articles, and other publications, all of which are incorporated herein by reference. The details of one or more embodiments of the present disclosure are set forth herein. Other features, objects, and advantages of the present disclosure will be apparent from the Detailed Description, the FIGURES, the Examples, and the Claims.

EQUIVALENTS AND SCOPE

In the articles such as "a," "an," and "the" may mean one or more than one unless indicated to the contrary or otherwise evident from the context. Embodiments or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claims that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the embodiments. Because such embodiments are deemed to be known to one of ordinary skill in the art, they may be excluded even if the exclusion is not set forth explicitly herein. Any particular embodiment of the present disclosure can be excluded from any embodiment, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended embodiments. Those of ordinary skill in the art will appreciate that various changes and modifications to this description may be made without departing from the spirit or scope of the present disclosure, as defined in the following claims.

What is claimed is:

1. A compound selected from the group consisting of:

(EXAMPLE 22)

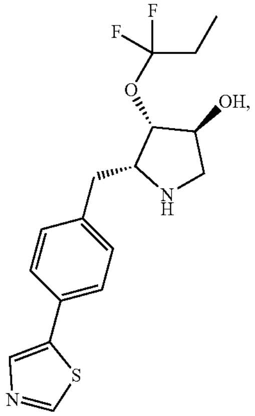

(EXAMPLE 24)

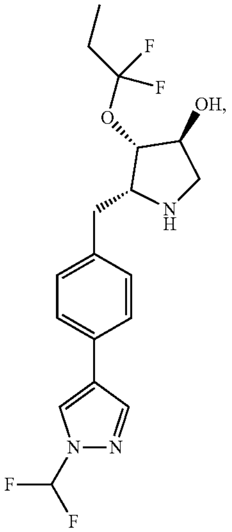

-continued (EXAMPLE 55)

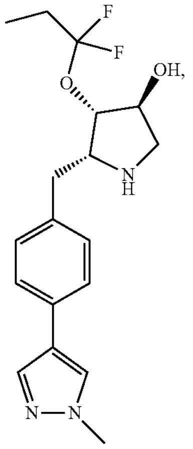

(EXAMPLE 58)

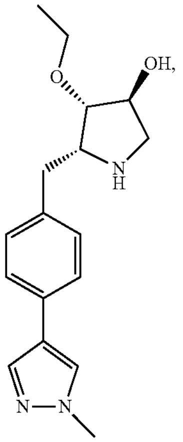

(EXAMPLE 59)

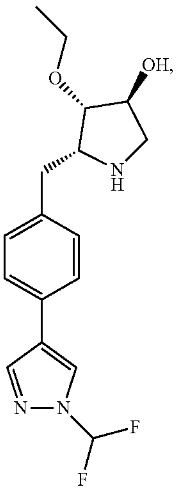

and

-continued (EXAMPLE 71)

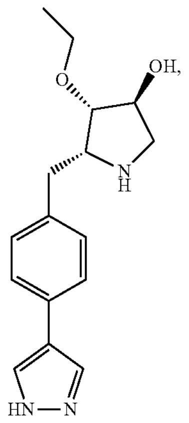

or a pharmaceutically acceptable salt thereof.

2. The compound of claim 1, wherein the compound is:

(EXAMPLE 22)

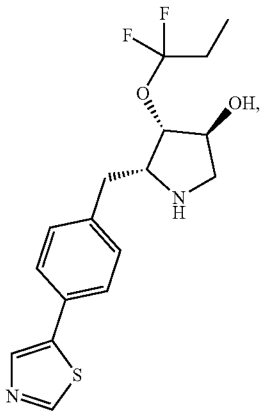

or a pharmaceutically acceptable salt thereof.

3. The compound of claim 1, wherein the compound is:

(EXAMPLE 24)

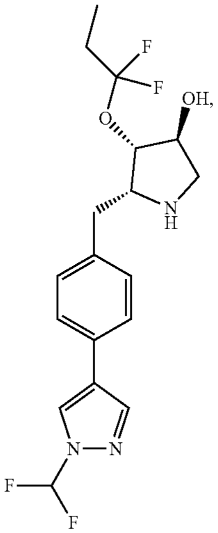

or a pharmaceutically acceptable salt thereof.

4. The compound of claim 1, wherein the compound is:

(EXAMPLE 55)

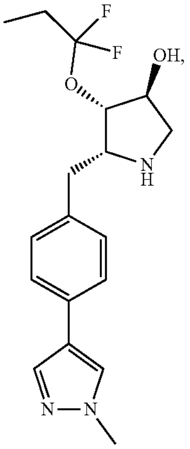

or a pharmaceutically acceptable salt thereof.

5. The compound of claim 1, wherein the compound is:

(EXAMPLE 58)

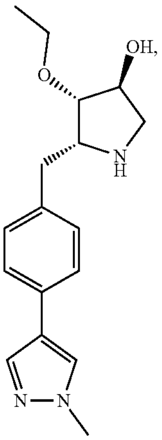

or a pharmaceutically acceptable salt thereof.

6. The compound of claim 1, wherein the compound is:

(EXAMPLE 59)

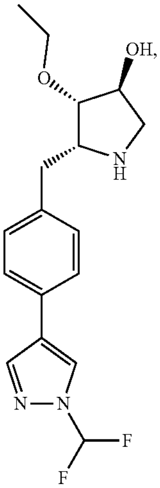

or a pharmaceutically acceptable salt thereof.

7. The compound of claim 1, wherein the compound is:

(EXAMPLE 71)

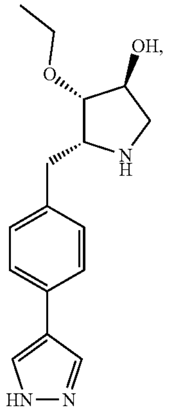

or a pharmaceutically acceptable salt thereof.

8. The compound of claim 1, wherein the compound is:

(EXAMPLE 22)

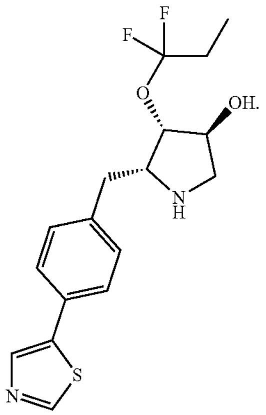

9. The compound of claim 1, wherein the compound is:

(EXAMPLE 24)

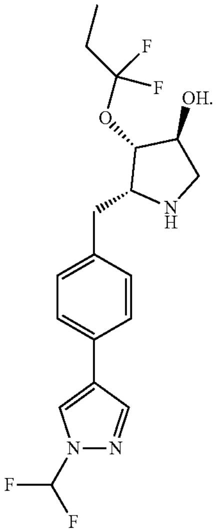

10. The compound of claim 1, wherein the compound is:

(EXAMPLE 55)

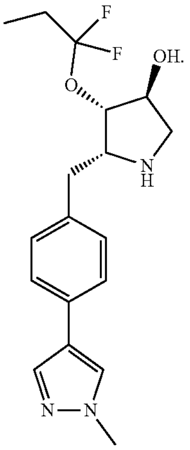

11. The compound of claim 1, wherein the compound is:

(EXAMPLE 58)

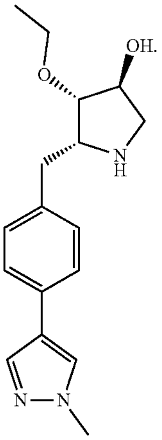

12. The compound of claim 1, wherein the compound is:

(EXAMPLE 59)

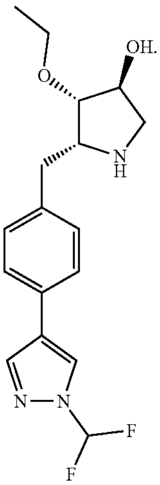

13. The compound of claim 1, wherein the compound is:

(EXAMPLE 71)

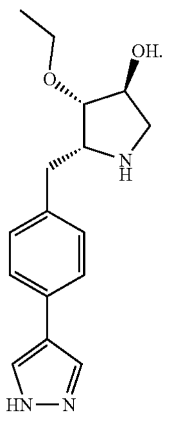

14. A pharmaceutical composition comprising the compound of claim 1, or a pharmaceutically acceptable salt thereof, and a pharmaceutically acceptable excipient.

15. A method of modulating protein synthesis in a subject in need thereof or in a cell, tissue, or biological sample, comprising administering to the subject in need thereof or contacting the cell, tissue, or biological sample with an effective amount of the compound of claim 1, or a pharmaceutically acceptable salt thereof.

16. A method of decreasing protein synthesis in a subject in need thereof or in a cell, tissue, or biological sample, comprising administering to the subject in need thereof or contacting the cell, tissue, or biological sample with an effective amount of the compound of claim 1, or a pharmaceutically acceptable salt thereof.

17. A method comprising administering to a subject the compound of claim 1, or a pharmaceutically acceptable salt thereof.

18. A method of treating a disease in a subject in need thereof, comprising administering to the subject in need thereof an effective amount of the compound of claim 1, or a pharmaceutically acceptable salt thereof, wherein the disease is:

a. associated with B-cell lymphoma 2 (BCL-2), MYC proto-oncogene bHLH transcription factor (MYC), cyclin D1 (CCND1), myeloid cell leukemia 1 (MCL-1), anaplastic lymphoma kinase (ALK), or GTPase KRas G12D mutant (KRAS-G12D);

b. a cancer selected from prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, and neuroblastoma;

c. a neurological disease selected from cerebellar ataxia and a neurodegenerative disease; or d. an immune disorder selected from psoriasis, lupus, and rheumatoid arthritis.

19. The method of claim 18, wherein the disease is associated with B-cell lymphoma 2 (BCL-2), MYC proto-oncogene bHLH transcription factor (MYC), cyclin D1 (CCND1), myeloid cell leukemia 1 (MCL-1), anaplastic lymphoma kinase (ALK), or GTPase KRas G12D mutant (KRAS-G12D).

20. The method of claim 18, wherein the disease is:

a cancer selected from prostate cancer, pancreatic cancer, lung cancer, breast cancer, colorectal cancer, endometrial cancer, ovarian cancer, cervical cancer, esophageal cancer, bladder cancer, biliary cancer, hematopoietic cancer, and neuroblastoma;

a neurological disease selected from cerebellar ataxia and a neurodegenerative disease; or an immune disorder selected from psoriasis, lupus, and rheumatoid arthritis.

21. A kit comprising:

the compound of claim 1, or a pharmaceutically acceptable salt thereof; and instructions for use of the compound, or pharmaceutically acceptable salt thereof.

* * * * *